US008389557B2

(12) United States Patent
Singh et al.

(10) Patent No.: US 8,389,557 B2
(45) Date of Patent: Mar. 5, 2013

(54) TRIAZOLE DERIVATIVES USEFUL AS AXL INHIBITORS

(75) Inventors: Rajinder Singh, Belmont, CA (US); Catherine Sylvain, San Mateo, CA (US); Sacha Holland, San Francisco, CA (US); Jing Zhang, Foster City, CA (US); John J. Partridge, Chapel Hill, NC (US); Jeffrey Clough, Redwood City, CA (US); Ankush Argade, Foster City, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 12/965,545

(22) Filed: Dec. 10, 2010

(65) Prior Publication Data

US 2011/0082131 A1 Apr. 7, 2011

Related U.S. Application Data

(62) Division of application No. 11/518,550, filed on Sep. 7, 2006, now Pat. No. 7,884,119.

(60) Provisional application No. 60/714,673, filed on Sep. 7, 2005, provisional application No. 60/780,166, filed on Mar. 7, 2006, provisional application No. 60/813,143, filed on Jun. 12, 2006.

(51) Int. Cl.
*A61K 31/41* (2006.01)
*C07D 249/00* (2006.01)

(52) U.S. Cl. ..................... 514/383; 548/262.2

(58) Field of Classification Search ............. 514/383; 548/262.2
See application file for complete search history.

(56) References Cited

U.S. PATENT DOCUMENTS

| | | | |
|---|---|---|---|
| 3,813,400 A | 5/1974 | Boyle et al. | 260/295 |
| 6,924,302 B2 * | 8/2005 | Lin et al. | 514/383 |
| 7,709,482 B2 | 5/2010 | Goff et al. | 514/248 |
| 7,872,000 B2 | 1/2011 | Goff et al. | 514/210.21 |
| 2004/0077699 A1 | 4/2004 | Lin et al. | 514/383 |
| 2004/0214817 A1 | 10/2004 | Pierce et al. | 514/217.09 |
| 2005/0118604 A1 | 6/2005 | Lorens et al. | 435/6 |
| 2008/0176847 A1 | 7/2008 | Goff et al. | 514/234.5 |
| 2008/0182862 A1 | 7/2008 | Ding et al. | 514/260.1 |
| 2008/0188474 A1 | 8/2008 | Goff et al. | 514/236.2 |
| 2009/0111816 A1 | 4/2009 | Singh et al. | 514/248 |
| 2010/0168416 A1 | 7/2010 | Goff et al. | 540/551 |
| 2010/0196511 A1 | 8/2010 | Hitoshi et al. | 424/649 |
| 2011/0071133 A1 | 3/2011 | Goff et al. | 514/210.21 |
| 2011/0098274 A1 | 4/2011 | Goff et al. | 514/211.08 |
| 2011/0105511 A1 | 5/2011 | Singh | 514/248 |
| 2011/0105512 A1 | 5/2011 | Singh | 514/248 |
| 2011/0183986 A1 | 7/2011 | Singh et al. | 514/248 |
| 2011/0281846 A1 | 11/2011 | Goff et al. | 514/214.02 |

FOREIGN PATENT DOCUMENTS

| | | |
|---|---|---|
| EP | 0 710 654 A1 | 5/1996 |
| WO | WO 01/09106 A1 | 2/2001 |
| WO | WO 01/09106 * | 8/2001 |
| WO | WO 02/057240 * | 7/2002 |
| WO | WO 02/057240 A1 | 7/2002 |
| WO | WO 03/027275 A1 | 4/2003 |
| WO | WO 03/093344 A1 | 11/2003 |
| WO | WO 2004/017997 A1 | 3/2004 |
| WO | WO 2004/039955 A2 | 5/2004 |
| WO | WO 2004/046120 A2 | 6/2004 |
| WO | WO 2005/013982 A1 | 2/2005 |
| WO | WO 2005/077922 A2 | 8/2005 |
| WO | WO 2008/157131 A1 | 12/2008 |

OTHER PUBLICATIONS

Patani et al., Chem Rev, 1996, 98(8), pp. 3147-3176.*
Agrafiotis et al., "SAR Maps: A New SAR Visualization Technique for Medicinal Chemists," *J. Med. Chem.* 50(24): 5926-5937, 2007.
Alexander et al., "Human Parathyroid Hormone 1-34 Reverses Bone Loss in Ovariectomized Mice," *Journal of Bone and Mineral Research* 16(9): 1665-1673, 2001.
Angelillo-Scherrer et al., "Role of Gas6 receptors in platelet signaling during thrombus stabilization and implications for antithrombotic therapy," *Journal of Clinical Investigation* 115(2): 237-246, Feb. 2005.
Bora et al., "Immunotherapy for choroidal neovascularization in a laser-induced mouse model simulating exudative (wet) macular degeneration," *Proc. Natl. Acad. Sci U.S.A.* 100(5): 2679-2684, Mar. 4, 2003.
Brewster et al., "Ro 32/3555, an orally active collagenase selective inhibitor, prevents structural damage in the STR/ORT mouse model of osteoarthritis," *Arthritis & Rheumatism* 41(9): 1639-1644, Sep. 1998.
Fujioka et al., "Equol, a Metabolite of Daidzein, Inhibits Bone Loss in Ovariectomized Mice," *Journal of Nutrition* 134: 2623-2627, 2004.
Holland et al., "Multiple Roles for the Receptor Tyrosine Kinase Axl in Tumor Formation," *Cancer Res.* 65(20): 9294-9303, Oct. 15, 2005.
Holland et al., "Requirement for the Receptor Tyrosine Kinase Axl in Angiogenesis and Tumor Growth", 7th Annual Symposium on Anti-Angiogenic Agents, Feb. 10-13, 2005, San Diego, California, 1 page.
Kadoya et al., "Role of calpain in hydrogen peroxide induced cataract," *Current Eye Research* 12(4): 341-346, 1993.
Katritzky et al., "Syntheses of 5-(2-arylazeny1)-1,2,4-triazoles and 2-amino-5-aryl-1,3,4-oxadiazoles," *ARKIVOC* 6: 82-90, 2002.
Kim et al., "Novel Oral Formulation of Paclitaxel Inhibits Neointimal Hyperplasia in a Rat Carotid Artery Injury Model," *Circulation* 109: 1558-1563, Mar. 8, 2004.
Kurzer and Douraghi-Zadeh, "Heterocyclic Compounds from Urea Derivatives. Part VI. Synthesis and Cyclisation of 1-Amino-3-(NN'-diarylamidino)guanidines and Some Analogues," *J. Chem. Soc.* 932-937, 1965.
Lebovic et al., "Peroxisome proliferator-activated receptor-gamma induces regression of endometrial explants in a rat model of endometriosis," *Fertility and Sterility* 82(Suppl 3): 1008-1013, Oct. 2004.
Nakashima et al., "ApoE-Deficient Mice Develop Lesions of All Phases of Atherosclerosis Throughout the Arterial Tree," *Arterioscler. Thromb. Vasc. Biol.* 14(1): 133-140, Jan. 1994.
Nickoloff et al., "Severe Combined Immunodeficiency Mouse and Human Psoriatic Skin Chimeras. Validation of a New Animal Model," *American Journal of Pathology* 146(3): 580-588, Mar. 1995.
Patani and LaVoie, "Bioisosterism: A Rational Approach in Drug Design," *Chem. Rev.* 96: 3147-3176, 1996.

(Continued)

*Primary Examiner* — Susannah Chung

(74) *Attorney, Agent, or Firm* — Seed IP Law Group PLLC; Travis Young

(57) ABSTRACT

Methods of using triazole derivatives in treating diseases or conditions associated with Axl catalytic activity are disclosed.

6 Claims, No Drawings

OTHER PUBLICATIONS

Phadke et al., "Evaluation of the Effects of Various Anti-Arthritic Drugs on Type II Collagen-Induced Mouse Arthritis Model," *Immunopharmacology 10*: 51-60, 1985.

Reiter and Pongó, "On Triazoles. VI [1]. The Acylation of 5-Amino-1,2,4-triazoles," *J. Heterocyclic Chem.* 24: 127-142, Jan.-Feb. 1987.

Sarayba et al, "Inhibition of corneal neovascularization by a peroxisome proliferator-activated receptor-γ ligand," *Experimental Eye Research 80*: 435-442, 2005.

Sheets et al., "Cataract- and Lens-Specific Upregulation of ARK Receptor Tyrosine Kinase in Emory Mouse Cataract," *Investigative Ophthalmology & Visual Science 43*(6): 1870-1875, Jun. 2002.

Smith et al., "Oxygen-Induced Retinopathy in the Mouse," *Investigative Ophthalmology & Visual Science 35*(1): 101-111, Jan. 1994.

Somigliana et al., "Endometrial ability to implant in ectopic sites can be prevented by interleukin-12 in a murine model of endometriosis," *Human Reproduction 14*(12): 2944-2950, 1999.

Von Der Thüsen et al., "Adenoviral Transfer of Endothelial Nitric Oxide Synthase Attenuates Lesion Formation in a Novel Murine Model of Postangioplasty Restenosis," *Arterioscler. Thromb. Vasc. Biol.* 24: 357-362, Feb. 2004.

Wronski et al., "Endocrine and Pharmacological Suppressors of Bone Turnover Protect against Osteopenia in Ovariectomized Rats," *Endocrinology 125*(2): 810-816, 1989.

Xu et al., "Requirement for the tyrosine kinase Axl in angiogenesis and tumor growth," *Proc. Amer. Assoc. Cancer Res. 46*, 2005. Tumor Biology 14: Signaling and Angiogenesis; Abstract #2019 of observations disclosed at American Association Cancer Research General Meeting, Apr. 16-20, 2005, Anaheim, California, 1 page.

Yin et al., "Expression of growth arrest-specific gene 6 and its receptors in a rat model of chronic renal transplant rejection," *Transplantation 73*(4): 657-660, Feb. 27, 2002.

Beilstein Database, Beilstein Registry No. 886094, 1965, 2 pages.

Chung et al., "Expression of the proto-oncogene Axl in renal cell carcinoma," *DNA Cell Biol. 22*(8): 533-540, Aug. 2003 (abstract only).

Daouti et al., "Development of comprehensive functional genomic screens to identify novel mediators of osteoarthritis," *Osteoarthritis Cartilage 13*(6): 508-518, Jun. 2005 (abstract only).

Goswami et al., "Spectrum and Range of Oxidative Stress Responses of Human Lens Epithelial Cells to $H_2O_2$ Insult," *Invest Ophthalmol Vis Sci. 44*(5): 2084-2093, May 2003.

Hafizi and Dahlbäck, "Signalling and functional diversity within the Axl subfamily of receptor tyrosine kinases," *Cytokine Growth Factor Rev. 17*(4): 295-304, Aug. 2006 (abstract only).

Holland et al., "R428, a Selective Small Molecule Inhibitor of Axl Kinase, Blocks Tumor Spread and Prolongs Survival in Models of Metastatic Breast Cancer," *Cancer Res 70*(4): 1544-1554, Feb. 15, 2010.

McCloskey et al., "Activation of the Axl Receptor Tyrosine Kinase Induces Mitogenesis and Transformation in 32D Cells," *Cell Growth & Differentiation 5*: 1105-1117, Oct. 1994.

O'Donnell et al., "Expression of Receptor Tyrosine Kinase Axl and its Ligand Gas6 in Rheumatoid Arthritis," *American Journal of Pathology 154*(4): 1171-80, Apr. 1999.

Sun et al., "Coexpression of growth arrest-specific gene 6 and receptor tyrosine kinases, Axl and Sky, in human uterine endometrium and ovarian endometriosis," *Molecular Human Reproduction 8* (6): 552-8, 2002.

\* cited by examiner

TRIAZOLE DERIVATIVES USEFUL AS AXL INHIBITORS

CROSS-REFERENCE(S) TO RELATED APPLICATION(S)

This application is a divisional of U.S. patent application Ser. No. 11/518,550, filed Sep. 7, 2006 (now allowed); which claims the benefit under 35 U.S.C. §119(e) of U.S. Provisional Patent Application No. 60/714,673, filed Sep. 7, 2005; U.S. Provisional Patent Application No. 60/780,166, filed Mar. 7, 2006; and U.S. Provisional Patent Application No. 60/813,143, filed Jun. 12, 2006. These applications are incorporated herein by reference in their entireties.

FIELD OF THE INVENTION

This invention is directed to triazole derivatives and pharmaceutical compositions thereof which are useful as inhibitors of the receptor protein tyrosine kinase known as Axl. This invention is also directed to methods of using the derivatives and compositions in treating diseases and conditions associated with Axl activity, particularly in treating diseases and conditions associated with angiogenesis and/or cell proliferation.

BACKGROUND OF THE INVENTION

All of the protein kinases that have been identified to date in the human genome share a highly conserved catalytic domain of around 300 aa. This domain folds into a bi-lobed structure in which reside ATP-binding and catalytic sites. The complexity of protein kinase regulation allows many potential mechanisms of inhibition including competition with activating ligands, modulation of positive and negative regulators, interference with protein dimerization, and allosteric or competitive inhibition at the substrate or ATP binding sites.

Axl (also known as UFO, ARK, and Tyro7; nucleotide accession numbers NM_021913 and NM_001699; protein accession numbers NP_068713 and NP_001690) is a receptor protein tyrosine kinase (RTK) that comprises a C-terminal extracellular ligand-binding domain and N-terminal cytoplasmic region containing the catalytic domain. The extracellular domain of Axl has a unique structure that juxtaposes immunoglobulin and fibronectin Type III repeats and is reminiscent of the structure of neural cell adhesion molecules. Axl and its two close relatives, Mer/Nyk and Sky (Tyro3/Rse/Dtk), collectively known as the Tyro3 family of RTKs, all bind and are stimulated to varying degrees by the same ligand, Gas6 (growth arrest specific-6), a ~76 kDa secreted protein with significant homology to the coagulation cascade regulator, Protein S. In addition to binding to ligands, the Axl extracellular domain has been shown to undergo homophilic interactions that mediate cell aggregation, suggesting that one important function of Axl may be to mediate cell-cell adhesion.

Axl is predominantly expressed in the vasculature in both endothelial cells (ECs) and vascular smooth muscle cells (VSMCs) and in cells of the myeloid lineage and is also detected in breast epithelial cells, chondrocytes, Sertoli cells and neurons. Several functions including protection from apoptosis induced by serum starvation, TNF-α or the viral protein E1A, as well as migration and cell differentiation have been ascribed to Axl signaling in cell culture. However, Axl−/− mice exhibit no overt developmental phenotype and the physiological function of Axl in vivo is not clearly established in the literature.

Angiogenesis (the formation of new blood vessels) is limited to functions such as wound healing and the female reproductive cycle in healthy adults. This physiological process has been co-opted by tumors, thus securing an adequate blood supply that feeds tumor growth and facilitates metastasis. Deregulated angiogenesis is also a feature of many other diseases (for example, psoriasis, rheumatoid arthritis, endometriosis and blindness due to age-related macular degeneration (AMD), retinopathy of prematurity and diabetes) and often contributes to the progression or pathology of the condition.

The overexpression of Axl and/or its ligand has also been reported in a wide variety of solid tumor types including, but not limited to, breast, renal, endometrial, ovarian, thyroid, non-small cell lung carcinoma, and uveal melanoma as well as in myeloid leukemias. Furthermore, it possesses transforming activity in NIH3T3 and 32D cells. It has been demonstrated that loss of Axl expression in tumor cells blocks the growth of solid human neoplasms in an in vivo MDA-MB-231 breast carcinoma xenograft model. Taken together, these data suggest Axl signaling can independently regulate EC angiogenesis and tumor growth and thus represents a novel target class for tumor therapeutic development.

The expression of Axl and Gas6 proteins is upregulated in a variety of other disease states including endometriosis, vascular injury and kidney disease and Axl signaling is functionally implicated in the latter two indications. Axl-Gas6 signaling amplifies platelet responses and is implicated in thrombus formation. Axl may thus potentially represent a therapeutic target for a number of diverse pathological conditions including solid tumors, including, but not limited to, breast, renal, endometrial, ovarian, thyroid, non-small cell lung carcinoma and uveal melanoma; liquid tumors, including but not limited to, leukemias (particularly myeloid leukemias) and lymphomas; endometriosis, vascular disease/injury (including but not limited to restenosis, atherosclerosis and thrombosis), psoriasis; visual impairment due to macular degeneration; diabetic retinopathy and retinopathy of prematurity; kidney disease (including but not limited to glomerulonephritis, diabetic nephropathy and renal transplant rejection), rheumatoid arthritis; osteoarthritis and cataracts.

SUMMARY OF THE INVENTION

This invention is directed to certain triazole derivatives which are useful as Axl inhibitors, methods of using such derivatives in treating diseases and conditions associated with Axl activity and pharmaceutical compositions comprising such derivatives.

Accordingly, in one aspect this invention is directed to compounds of formula (Ia) or formula (Ib):

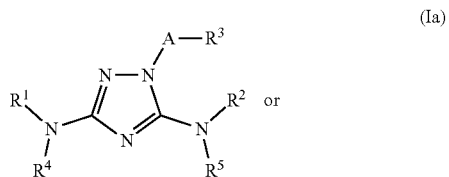

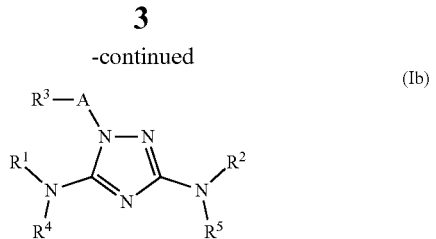

wherein, independently at each occurrence:

A is —C(O)—;

or A is selected from the group consisting of —C(S)—, —C(NR$^{11}$)—, —C(O)O—, —C(S)O—, —C(O)S—, —C(S)S—, —C(S)S—, —C(NR$^{11}$)S—, —C(NR$^{11}$)O—, —C(S)N(R$^6$), —C(O)N(R$^6$)— and —C(NR$^{11}$)N(R$^6$)—;

R$^1$ is one of the following:
- a) aryl optionally substituted with one or more substituents selected from the group consisting of halo, haloalkyl, alkyl, optionally substituted heteroaryl, optionally substituted heterocyclyl, —R$^8$—OR$^{10}$, —R$^8$—O—R$^9$—OR$^{10}$, —R$^8$—O—R$^9$—O—R$^9$—OR$^{10}$, —R$^8$—O—R$^9$—C(O)OR$^{10}$, —R$^8$—O—R$^9$—C(O)N(R$^6$)R$^7$, —R$^8$—O—R$^9$—S(O)$_p$R$^6$ (where p is 0, 1 or 2), —R$^8$—O—R$^9$—N(R$^6$)R$^7$, —R$^8$—O—R$^9$—C(NR$^{11}$)N(R$^{11}$)H, and —R$^8$—N(R$^6$)C(O)R$^{10}$; or
- b) heteroaryl optionally substituted with one or more substituents selected from the group consisting of alkyl, halo, oxo, —R$^8$—OR$^{10}$, —R$^8$—C(O)OR$^{10}$, —R$^8$—C(O)N(R$^6$)R$^7$ and —R$^8$—N(R$^6$)R$^7$; or
- c) heterocyclyl optionally substituted with one or more substituents selected from the group consisting of halo, haloalkyl, alkyl, oxo, —R$^8$—OR$^{10}$, —R$^8$—C(O)OR$^{10}$, —R$^8$—C(O)N(R$^6$)R$^7$, —R$^8$—S(O)$_p$R$^{10}$ (where p is 0, 1 or 2) and —R$^8$—N(R$^6$)R$^7$;
- d) heterocyclylalkyl optionally substituted with one or more substitutents selected from the group consisting of halo, haloalkyl, alkyl, optionally substituted aryl, optionally substituted aralkyl, —R$^8$—OR$^{10}$, —R$^8$—C(O)OR$^{10}$, —R$^8$—C(O)N(R$^6$)R$^7$ and —R$^8$—N(R$^6$)R$^7$; or
- e) cycloalkyl optionally substituted with one or more substituents selected from the group consisting of halo, haloalkyl, alkyl, oxo, —R$^8$—OR$^{10}$, —R$^8$—C(O)OR$^{10}$, —R$^8$—C(O)N(R$^6$)R$^7$, —R$^8$—S(O)$_p$R$^{10}$ (where p is 0, 1 or 2) and —R$^8$—N(R$^6$)R$^7$;

R$^2$, R$^4$ and R$^5$ are each independently hydrogen, alkyl, aryl, aralkyl, —C(O)R$^{10}$ or —C(O)N(R$^6$)R$^7$;

R$^3$ is one of the following:
- a) alkyl optionally substituted with one or more substituents selected from the group consisting of halo, cyano, nitro, oxo, thioxo, trimethylsilanyl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{14}$, —N(R$^{14}$)C(O)R$^{14}$, —N(R$^{14}$)S(O)$_t$R$^{14}$ (where t is 1 or 2), —S(O)$_t$OR$^{14}$ (where t is 1 or 2), —S(O)$_p$R$^{14}$ (where p is 0, 1 or 2), and —S(O)$_t$N(R$^{14}$)$_2$ (where t is 1 or 2) where each R$^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl;
- b) cycloalkyl optionally substituted with one or more substituents selected from the group consisting of —R$^8$—OR$^{10}$, alkyl, halo, haloalkyl, aryl, and aralkyl;
- c) aryl optionally substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, —R$^8$—OR$^{10}$, —R$^8$—C(O)OR$^{10}$, —R$^8$—OC(O)R$^{10}$, —R$^8$—O—R$^6$—C(O)OR$^{10}$, —R$^8$—O—R$^6$—C(O)N(R$^6$)R$^7$, —S(O)$_p$R$^6$ (where p is 0, 1 or 2), —S(O)$_t$N(R$^6$)R$^7$ (where t is 1 or 2), —R$^8$—N(R$^6$)R$^7$, —R$^8$—N(R$^6$)C(O)R$^{10}$, —R$^8$—N(R$^8$)C(O)OR$^{10}$ and —R$^8$—CN;
- d) aralkyl, wherein:
  - (1) the alkyl part of the aralkyl radical is optionally substituted with one or more substituents selected from the group consisting of halo, cyano, nitro, oxo, thioxo, trimethylsilanyl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{14}$, —N(R$^{14}$)C(O)R$^{14}$, —N(R$^{14}$)S(O)$_t$R$^{14}$ (where t is 1 or 2), —S(O)$_t$OR$^{14}$ (where t is 1 or 2), —S(O)$_p$R$^{14}$ (where p is 0, 1 or 2), and —S(O)$_t$N(R$^{14}$)$_2$ (where t is 1 or 2) where each R$^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl; and
  - (2) the aryl part of the aralkyl radical is optionally substituted with one or more substituents selected from the group consisting of alkyl, alkenyl, alkynyl, halo, haloalkyl, haloalkenyl, haloalkynyl, cyano, nitro, aryl, aralkyl, aralkenyl, aralkynyl, cycloalkyl, cycloalkylalkyl, cycloalkylalkenyl, cycloalkylalkynyl, heterocyclyl, heterocyclylalkyl, heterocyclylalkenyl, heterocyclylalkynyl, heteroaryl, heteroarylalkyl, heteroarylalkenyl, heteroarylalkynyl, —R$^{15}$—OR$^{14}$, —R$^{15}$—OC(O)—R$^{14}$, —R$^{15}$—N(R$^{14}$)$_2$, —R$^{15}$—C(O)R$^{14}$, —R$^{15}$—C(O)OR$^{14}$, —R$^{15}$—C(O)N(R$^{14}$)$_2$, —R$^{15}$—O—R$^{16}$—C(O)N(R$^{14}$)$_2$, —R$^{15}$—N(R$^{14}$)C(O)OR$^{14}$, —R$^{15}$—N(R$^{14}$)C(O)R$^{14}$, —R$^{15}$—N(R$^{14}$)S(O)$_t$R$^{14}$ (where t is 1 or 2), —R$^{15}$—S(O)$_t$OR$^{14}$ (where t is 1 or 2), —R$^{15}$—S(O)$_p$R$^{14}$ (where p is 0, 1 or 2), and —R$^{15}$—S(O)$_t$N(R$^{14}$)$_2$ (where t is 1 or 2), where each R$^{14}$ is independently hydrogen, alkyl, haloalkyl, cycloalkyl, cycloalkylalkyl, aryl, aralkyl, heterocyclyl, heterocylylalkyl, heteroaryl or heteroarylalkyl, each R$^{15}$ is independently a direct bond or a straight or branched alkylene or alkenylene chain, and R$^{16}$ is a straight or branched alkylene or alkenylene chain;
- e) optionally substituted aralkenyl;
- f) optionally substituted aralkynyl;
- g) optionally substituted heteroaryl;
- h) optionally substituted heteroarylalkenyl; or
- i) optionally substituted heteroarylalkynyl;

R$^6$ and R$^7$ are each independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R$^9$—OR$^{10}$, —R$^9$—CN, —R$^9$—NO$_2$, —R$^9$—N(R$^{10}$)$_2$, —R$^9$—C(O)OR$^{10}$ and —R$^9$—C(O)N(R$^{10}$)$_2$;

optionally, $R^6$ and $R^7$, together with the nitrogen to which they are attached, form an optionally substituted N-heteroaryl or an optionally substituted N-heterocyclyl;

each $R^8$ is independently selected from the group consisting of a direct bond, an optionally substituted straight or branched alkylene chain, an optionally substituted straight or branched alkenylene chain and an optionally substituted straight or branched alkynylene chain;

each $R^9$ is independently selected from the group consisting of an optionally substituted straight or branched alkylene chain, an optionally substituted straight or branched alkenylene chain and an optionally substituted straight or branched alkynylene chain; and each $R^{10}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl; and each $R^{11}$ is hydrogen, alkyl, cyano, nitro or —$OR^{10}$;

as an isolated stereoisomer or tautomer thereof or mixtures thereof, or a pharmaceutically acceptable salt, hydrate, solvate, N-oxide or prodrug thereof;

provided that for compounds of formula (Ia):
a) when A is —C(O)—, $R^2$, $R^4$ and $R^5$ are all hydrogen, and $R^3$ is 3,4,5-trimethoxyphenyl, $R^1$ is not pyridin-3-yl;
b) when A is —C(O)—, $R^2$, $R^4$ and $R^5$ are all hydrogen, and $R^1$ is unsubstituted phenyl, $R^3$ is not unsubstituted phenyl, unsubstituted 1,3-benzodioxol-5-yl, 2-(furan-2-yl)ethenyl, 4-chlorophenyl, unsubstituted naphthyl, 3-bromophenyl, 4-phenylphenyl, 4-trifluoromethylphenyl, 3-nitrophenyl, 3-(phenylcarbonyl)phenyl, 4-phenylbenzyl, 3-phenoxyphenyl, unsubstituted cyclohexyl, unsubstituted benzyl, unsubstituted pyridin-3-yl, 3,5-dichlorophenyl, 4-acetylphenyl, 4-nitrophenyl, 4-fluorobenzyl, 2,6-difluorophenyl, 2-phenoxyphenyl, 3-methoxyphenyl, 2-methoxyphenyl, 4-methylphenyl or unsubstituted furan-2-yl;
c) when A is —C(O)—, $R^2$, $R^4$ and $R^5$ are all hydrogen, and $R^3$ is unsubstituted phenyl, $R^1$ is not 2-methyl-5-chlorophenyl, 3-chlorophenyl, or 3,4,5-trimethoxyphenyl;
d) when A is —C(O)—, $R^2$, $R^4$ and $R^5$ are all hydrogen, and $R^3$ is 2,6-difluorophenyl, is not 3-chlorophenyl, 4-(4-methylpiperidin-1-yl)phenyl, 4-(imidazol-1-yl)phenyl, 4-(1,2,4-triazol-1-yl)phenyl, 4-(1,2,4-triazol-4-yl)phenyl, 4-(imidazolidin-2-on-1-yl)phenyl, or 4-(1,1-dioxidoisothiazolidin-2-yl)phenyl;
e) when A is —C(O)—, $R^2$, $R^4$ and $R^5$ are all hydrogen, and $R^1$ is 4-(4-methylpiperidin-1-yl)phenyl, $R^3$ is not 2,6-difluoro-3-methylphenyl, 3-methylthien-2-yl, 2,4-dimethylthien-2-yl, or 2-ethylthien-2-yl;
f) when A is —C(O)—, $R^2$, $R^4$ and $R^5$ are all hydrogen, and $R^1$ is 4-(imidazol-1-yl)phenyl, $R^3$ is not 5-ethylthien-2-yl, 3-methylthien-2-yl, 2,5-dimethylthien-2-yl, or 2,6-difluoro-3-methylphenyl;
g) when A is —C(O)—, $R^2$, $R^4$ and $R^5$ are all hydrogen, and $R^1$ is 3-chlorophenyl, $R^3$ is not 2-(phenylcarbonyl)ethyl, 3-phenylpropyl, 2-phenylethyl, naphth-2-ylmethyl or 2-(phenylcarbonyl)propyl;
h) when A is —C(O)—, $R^2$, $R^4$ and $R^5$ are all hydrogen, and $R^1$ is 4-(1,2,4-triazol-1-yl)phenyl, $R^3$ is not 2,6-difluoro-3-methylphenyl, 3-methylthien-2-yl, 3,5-dimethylthien-2-yl, or 5-ethylthien-2-yl;
i) when A is —C(O)—, $R^2$, $R^4$ and $R^5$ are all hydrogen, and $R^1$ is 4-(1,2,4-triazol-4-yl)phenyl, $R^3$ is not 3-methylthien-2-yl or 2,6-difluoro-3-methylphenyl;
j) when A is —C(O)—, $R^2$, $R^4$ and $R^5$ are all hydrogen, and $R^1$ is 4-(imidazolidin-2-on-1-yl)phenyl, $R^3$ is not 3-methylthien-2-yl or 2,6-difluoro-3-methylphenyl;
k) when A is —C(O)—, $R^2$, $R^4$ and $R^5$ are all hydrogen, and $R^1$ is 4-(1,1-dioxidoisothiazolidin-2-yl)phenyl, $R^3$ is not 3-methylthien-2-yl;
l) when A is —C(O)—, $R^2$, $R^4$ and $R^5$ are all hydrogen, and $R^3$ is 2-chlorophenyl, $R^1$ is not 6-methoxypyridin-3-yl or 4-methoxyphenyl;
m) when A is —C(O)—, $R^2$, $R^4$ and $R^5$ are all hydrogen, and $R^3$ is unsubstituted pyridin-3-yl, $R^1$ is not 6-methoxypyridin-3-yl;
m) when A is —C(O)—, $R^2$, $R^4$ and $R^5$ are all hydrogen, and $R^3$ is 4-nitrophenyl, $R^1$ is not 4-methyl-2,4-dihydrothiazol-2-yl;
o) when A is —C(O)—, $R^2$, $R^4$ and $R^5$ are all hydrogen, and $R^1$ is 4-methoxyphenyl, $R^3$ is not thien-2-yl or furan-2-yl;
p) when A is —C(O)N(H)—, $R^2$, $R^4$ and $R^5$ are all hydrogen, and $R^1$ is unsubstituted phenyl, $R^3$ is not unsubstituted phenyl, unsubstituted cyclohexyl, 4-phenylphenyl, 4-phenoxyphenyl, 2-methyl-4-bromophenyl, unsubstituted naphth-1-yl, 3-nitrophenyl, or 3-methoxyphenyl;
q) when A is —C(O)N(H)—, $R^2$, $R^4$ and $R^5$ are all hydrogen, and $R^1$ is 4-chlorophenyl, $R^3$ is not 4-methoxyphenyl;
r) when A is —C(O)N(H)—, $R^2$, $R^4$ and $R^5$ are all hydrogen, and $R^3$ is unsubstituted phenyl, $R^1$ is not unsubstituted pyridin-3-yl or 3,4,5-trimethoxyphenyl; or
s) when A is —C(O)N(H)—, $R^2$, $R^4$ and $R^5$ are all hydrogen, and $R^1$ is unsubstituted pyridin-3-yl, $R^3$ is not unsubstituted benzyl, 2-chlorophenyl, 3-chlorophenyl, or 4-methylphenyl;

and provided that for compounds of formula (Ib):
t) when A is —C(O)—, $R^2$, $R^4$ and $R^5$ are all hydrogen, and $R^1$ is unsubstituted phenyl, $R^3$ is not 2-(furan-2-yl)ethenyl, unsubstituted phenyl, or 2,6-difluorophenyl;
u) when A is —C(O)—, $R^2$, $R^4$ and $R^5$ are all hydrogen, and $R^1$ is 3-chlorophenyl, $R^3$ is not unsubstituted phenyl or 2,6-difluorophenyl;
v) when A is —C(O)N(H)—, $R^2$, $R^4$ and $R^5$ are all hydrogen, $R^1$ is unsubstituted phenyl, $R^3$ is not 3,4,5-trimethoxyphenyl; or
w) when A is —C(O)N(H)—, $R^2$, $R^4$ and $R^5$ are all hydrogen, $R^1$ is 4-methylphenyl, $R^3$ is not pyridin-3-yl.

In another aspect, this invention provides assays to determine a compound of the invention effectiveness in inhibiting Axl activity in a cell-based assay.

In another aspect, the following compounds, as identified by their unique Chemical Abstracts Service (CAS) registry numbers, are not meant to be included within the scope of the invention: 110984-61-7; 324074-12-6; 324074-13-7; 324074-14-8; 324074-15-9; 324074-16-0; 324074-17-1; 324074-18-2; 324074-19-3; 324074-20-6; 324074-21-7; 324074-22-8; 324074-23-9; 324074-24-0; 324074-25-1; 324074-28-4; 324074-29-5; 324074-30-8; 324074-31-9;

324074-32-0; 324074-33-1; 324074-34-2; 324074-35-3; 324074-36-4; 324074-38-6; 324074-39-7; 324074-41-1; 324074-42-2; 324074-43-3; 324074-44-4; 324074-45-5; 324074-46-6; 324074-47-7; 324074-48-8; 324074-50-2; 324074-51-3; 324074-52-4; 443798-64-9; 443798-65-0; 443798-66-1; 443798-67-2; 443798-68-3; 443798-69-4; 443798-70-7; 443798-71-8; 443798-72-9; 443798-73-0; 443798-74-1; 443798-87-6; 443798-88-7; 443798-89-8; 443798-90-1; 443798-91-2; 443798-92-3; 443798-93-4; 443798-96-7; 443798-95-6; 443798-94-5; 443798-97-8; 443798-98-9; 443798-99-0; 443799-10-8; 443799-12-0; 443799-14-2; 443799-16-4; 443799-18-6; 503546-63-2; 503546-65-4; 700811-45-6; 700812-30-2; 700812-68-6; 700812-69-7; 863030-86-8; 863030-85-7; 863030-84-6; 863030-77-7; 863030-76-6; 863030-74-4; 863030-87-9; 863030-83-5; 863030-81-3; and 863030-79-9.

In another aspect, the scope of the invention is not meant to include any compounds disclosed or claimed in the following publications, patents and patent applications:
U.S. Pat. No. 3,813,400;
PCT Published Patent Application No. WO 01/09106;
PCT Published Patent Application No. WO 02/057240;
PCT Published Patent Application No. WO 03/027275;
PCT Published Patent Application No. WO 03/093344
PCT Published Patent Application No. WO 2004/017997;
PCT Published Patent Application No. WO 2004/046120;
PCT Published Patent Application No. WO 2005/077922;
Katrizky, A. R. et al., "Synthesis of 5-(2-arylazenyl)-1,2,4-triazoles and 2-amino-5-aryl-1,3,4-oxadiazoles", *ARKIVOC* (2002), vi, pp. 82-90; and
Reiter, J. et al., "On triazoles. VI. The acylation of 5-amino-1,2,4-triazoles", *Journal of Heterocyclic Chemistry* (1987), 24(1), pp. 127-42.

DETAILED DESCRIPTION OF THE INVENTION

Definitions

As used in the specification and appended claims, unless specified to the contrary, the following terms have the meaning indicated:

"Amino" refers to the $-NH_2$ radical.
"Cyano" refers to the $-CN$ radical.
"Nitro" refers to the $-NO_2$ radical.
"Oxa" refers to the $-O-$ radical.
"Oxo" refers to the $=O$ radical.
"Thioxo" refers to the $=S$ radical.
"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms, and which is attached to the rest of the molecule by a single bond, for example, methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group may be optionally substituted by one or more of the following substituents: halo, cyano, nitro, oxo, thioxo, trimethylsilanyl, $-OR^{14}$, $-OC(O)-R^{14}$, $-N(R^{14})_2$, $-C(O)R^{14}$, $-C(O)OR^{14}$, $-C(O)N(R^{14})_2$, $-N(R^{14})C(O)OR^{14}$, $-N(R^{14})C(O)R^{14}$, $-N(R^{14})S(O)_tR^{14}$ (where t is 1 or 2), $-S(O)_tOR^{14}$ (where t is 1 or 2), $-S(O)_pR^{14}$ (where p is 0, 1 or 2), and $-S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl, and where each of the above substituents is unsubstituted unless otherwise indicated.

"Alkenyl" refers to a straight or branched hydrocarbon chain radical group consisting solely of carbon and hydrogen atoms, containing at least one double bond, having from two to twelve carbon atoms, preferably one to eight carbon atoms and which is attached to the rest of the molecule by a single bond, for example, ethenyl, prop-1-enyl, but-1-enyl, pent-1-enyl, penta-1,4-dienyl, and the like. Unless stated otherwise specifically in the specification, an alkenyl group may be optionally substituted by one or more of the following substituents: halo, cyano, nitro, oxo, thioxo, trimethylsilanyl, $-OR^{14}$, $-OC(O)-R^{14}$, $-N(R^{14})_2$, $-C(O)R^{14}$, $C(O)OR^{14}$, $-C(O)N(R^{14})_2$, $-N(R^{14})C(O)OR^{14}$, $-N(R^{14})C(O)R^{14}$, $N(R^{14})S(O)_tR^{14}$ (where t is 1 or 2), $-S(O)_tOR^{14}$ (where t is 1 or 2), $-S(O)_pR^{14}$ (where p is 0, 1 or 2), and $-S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl, and where each of the above substituents is unsubstituted unless otherwise indicated.

"Alkynyl" refers to a straight or branched hydrocarbon chain radical group consisting solely of carbon and hydrogen atoms, containing at least one triple bond, optionally containing at least one double bond, having from two to twelve carbon atoms, preferably one to eight carbon atoms and which is attached to the rest of the molecule by a single bond, for example, ethynyl, propynyl, butynyl, pentynyl, hexynyl, and the like. Unless stated otherwise specifically in the specification, an alkynyl group may be optionally substituted by one or more of the following substituents: halo, cyano, nitro, oxo, thioxo, trimethylsilanyl, $-OR^{14}$, $-OC(O)-R^{14}$, $-N(R^{14})_2$, $-C(O)R^{14}$, $-C(O)OR^{14}$, $-C(O)N(R^{14})_2$, $-N(R^{14})C(O)OR^{14}$, $-N(R^{14})C(O)R^{14}$, $-N(R^{14})S(O)_tR^{14}$ (where t is 1 or 2), $-S(O)_tOR^{14}$ (where t is 1 or 2), $-S(O)_pR^{14}$ (where p is 0, 1 or 2), and $-S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl, and where each of the above substituents is unsubstituted unless otherwise indicated.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain may be optionally substituted by one or more of the following substituents: halo, cyano, nitro, aryl, cycloalkyl, heterocyclyl, heteroaryl, oxo, thioxo, trimethylsilanyl, $-OR^{14}$, $-OC(O)-R^{14}$, $-N(R^{14})_2$, $C(O)R^{14}$, $-C(O)OR^{14}$, $-C(O)N(R^{14})_2$, $-N(R^{14})C(O)OR^{14}$, $-N(R^{14})C(O)R^{14}$, $-N(R^{14})S(O)_tR^{14}$ (where t is 1 or 2), $-S(O)_tOR^{14}$ (where t is 1 or 2), $-S(O)_pR^{14}$ (where p is 0, 1 or 2), and $-S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl, and where each of the above substituents is unsubstituted unless otherwise indicated.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain may be optionally substituted by one or more of the following substituents: halo, cyano, nitro, aryl, cycloalkyl, heterocyclyl, heteroaryl, oxo, thioxo, trimethylsilanyl, —$OR^{14}$, —$OC(O)$—$R^{14}$, —$N(R^{14})_2$, —$C(O)R^{14}$, —$C(O)OR^{14}$, —$C(O)N(R^{14})_2$, —$N(R^{14})C(O)OR^{14}$, —$N(R^{14})C(O)R^{14}$, $N(R^{14})S(O)_tR^{14}$ (where t is 1 or 2), —$S(O)_tOR^{14}$ (where t is 1 or 2), —$S(O)_pR^{14}$ (where p is 0, 1 or 2), and —$S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl, and where each of the above substituents is unsubstituted unless otherwise indicated.

"Alkynylene" or "alkynylene chain" refers to a straight or branched divalent hydrocarbon chain linking the rest of the molecule to a radical group, consisting solely of carbon and hydrogen, containing at least one triple bond and having from two to twelve carbon atoms, for example, propynylene, n-butynylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, an alkynylene chain may be optionally substituted by one or more of the following substituents: alkyl, alkenyl, halo, haloalkenyl, cyano, nitro, aryl, cycloalkyl, heterocyclyl, heteroaryl, oxo, thioxo, trimethylsilanyl, —$OR^{14}$, —$OC(O)$—$R^{14}$, —$N(R^{14})_2$, —$C(O)R^{14}$, —$C(O)OR^{14}$, —$C(O)N(R^{14})_2$, $N(R^{14})C(O)OR^{14}$, —$N(R^{14})C(O)R^{14}$, —$N(R^{14})S(O)_tR^{14}$ (where t is 1 or 2), —$S(O)_tOR^{14}$ (where t is 1 or 2), —$S(O)_pR^{14}$ (where p is 0, 1 or 2), and —$S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl, and where each of the above substituents is unsubstituted unless otherwise indicated.

"Alkoxy" refers to a radical of the formula —$OR_a$ where $R_a$ is an alkyl radical as defined above containing one to twelve carbon atoms. The alkyl part of the alkoxy radical may be optionally substituted as defined above for an alkyl radical.

"Alkoxyalkyl" refers to a radical of the formula —$R_a$—O—$R_a$ where each $R_a$ is independently an alkyl radical as defined above. The oxygen atom may be bonded to any carbon in either alkyl radical. Each alkyl part of the alkoxyalkyl radical may be optionally substituted as defined above for an alkyl group.

"Aryl" refers to aromatic monocyclic or multicyclic hydrocarbon ring system consisting only of hydrogen and carbon and containing from 6 to 19 carbon atoms, where the ring system may be partially or fully saturated. Aryl groups include, but are not limited to, groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents independently selected from the group consisting of alkyl, alkenyl, alkynyl, halo, haloalkyl, haloalkenyl, haloalkynyl, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—O—$R^{16}$—$C(O)N(R^{14})_2$, —$R^{15}$—$N(R^{14})C(O)OR^{14}$, —$R^{15}$—$N(R^{14})C(O)R^{14}$, —$R^{15}$—$N(R^{14})S(O)_tR^{14}$ (where t is 1 or 2), —$R^{15}$—$S(O)_tOR^{14}$ (where t is 1 or 2), —$R^{15}$—$S(O)_pR^{14}$ (where p is 0, 1 or 2), and —$R^{15}$—$S(O)_tN(R^{14})_2$ (where t is 1 or 2), where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl, each $R^{15}$ is independently a direct bond or a straight or branched alkylene or alkenylene chain, and $R^{16}$ is a straight or branched alkylene or alkenylene chain, and where each of the above substituents is unsubstituted unless otherwise indicated.

"Aralkyl" refers to a radical of the formula —$R_aR_b$ where $R_a$ is an alkyl radical as defined above and $R_b$ is one or more aryl radicals as defined above, for example, benzyl, diphenylmethyl and the like. The alkyl part of the aralkyl radical may be optionally substituted as described above for an alkyl group. The aryl part of the aralkyl radical may be optionally substituted as described above for an aryl group.

"Aralkenyl" refers to a radical of the formula —$R_cR_b$ where $R_c$ is an alkenyl radical as defined above and $R_b$ is one or more aryl radicals as defined above. The aryl part of the aralkenyl radical may be optionally substituted as described above for an aryl group. The alkenyl part of the aralkenyl radical may be optionally substituted as defined above for an alkenyl group.

"Aralkynyl" refers to a radical of the formula —$R_dR_b$ where $R_d$ is an alkynyl radical as defined above and $R_b$ is one or more aryl radicals as defined above. The aryl part of the aralkynyl radical may be optionally substituted as described above for an aryl group. The alkynyl part of the aralkynyl radical may be optionally substituted as defined above for an alkynyl group.

"Aryloxy" refers to a radical of the formula —$OR_b$ where $R_b$ is an aryl group as defined above. The aryl part of the aryloxy radical may be optionally substituted as defined above.

"Aralkyloxy" refers to a radical of the formula —$OR_b$ where $R_b$ is an aralkyl group as defined above. The aralkyl part of the aralkyloxy radical may be optionally substituted as defined above.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantine, norbornane, norbornene, decalinyl, 7,7-dimethyl-bicyclo[2.2.1]heptanyl, and the like. Unless otherwise stated specifically in the specification, the term "cycloalkyl" is meant to include cycloalkyl radicals which are optionally substituted by one or more substituents independently selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-N(R^{14})C(O)OR^{14}$, $-R^{15}-N(R^{14})C(O)R^{14}$, $-R^{15}-N(R^{14})S(O)_tR^{14}$ (where t is 1 or 2), $-R^{15}-S(O)_tOR^{14}$ (where t is 1 or 2), $-R^{15}-S(O)_pR^{14}$ (where p is 0, 1 or 2), and $-R^{15}-S(O)_tN(R^{14})_2$ (where t is 1 or 2), where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{15}$ is independently a direct bond or a straight or branched alkylene or alkenylene chain, and where each of the above substituents is unsubstituted unless otherwise indicated.

"Cycloalkylalkyl" refers to a radical of the formula $-R_aR_e$ where $R_a$ is an alkyl radical as defined above and $R_e$ is a cycloalkyl radical as defined above. The alkyl radical and the cycloalkyl radical may be optionally substituted as defined above.

"Cycloalkylalkenyl" refers to a radical of the formula $-R_cR_e$ where $R_c$ is an alkenyl radical as defined above and $R_e$ is a cycloalkyl radical as defined above. The alkenyl radical and the cycloalkyl radical may be optionally substituted as defined above.

"Cycloalkylalkynyl" refers to a radical of the formula $-R_dR_e$ where $R_d$ is an alkynyl radical as defined above and $R_e$ is a cycloalkyl radical as defined above. The alkynyl radical and the cycloalkyl radical may be optionally substituted as defined above.

"Halo" refers to bromo, chloro, fluoro or iodo.

"Haloalkyl" refers to an alkyl radical, as defined above, that is substituted by one or more halo radicals, as defined above, for example, trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Haloalkenyl" refers to an alkenyl radical, as defined above, that is substituted by one or more halo radicals, as defined above. The alkenyl part of the haloalkyl radical may be optionally substituted as defined above for an alkenyl group.

"Haloalkynyl" refers to an alkynyl radical, as defined above, that is substituted by one or more halo radicals, as defined above. The alkynyl part of the haloalkyl radical may be optionally substituted as defined above for an alkynyl group.

"Heterocyclyl" refers to a stable 3- to 18-membered non-aromatic ring radical which consists of one to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above which are optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-N(R^{14})C(O)OR^{14}$, $-R^{15}-N(R^{14})C(O)R^{14}$, $-R^{15}-N(R^{14})S(O)_tR^{14}$ (where t is 1 or 2), $-R^{15}-S(O)_tOR^{14}$ (where t is 1 or 2), $-R^{15}-S(O)_pR^{14}$ (where p is 0, 1 or 2), and $-R^{15}-S(O)_tN(R^{14})_2$ (where t is 1 or 2), where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{15}$ is independently a direct bond or a straight or branched alkylene or alkenylene chain, and where each of the above substituents is unsubstituted unless otherwise indicated.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical may be optionally substituted as described above for heterocyclyl radicals.

"Heterocyclylalkyl" refers to a radical of the formula $-R_aR_f$ where $R_a$ is an alkyl radical as defined above and $R_f$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"Heterocyclylalkenyl" refers to a radical of the formula $-R_cR_f$ where $R_c$ is an alkenyl radical as defined above and $R_f$ is a heterocyclyl radical as defined above, and if the heterocyclyl is a nitrogen-containing heterocyclyl, the heterocyclyl may be attached to the alkenyl radical at the nitrogen atom. The alkenyl part of the heterocyclylalkenyl radical may be optionally substituted as defined above for an alkenyl group.

The heterocyclyl part of the heterocyclylalkenyl radical may be optionally substituted as defined above for a heterocyclyl group.

"Heterocyclylalkynyl" refers to a radical of the formula —$R_dR_f$ where $R_d$ is an alkynyl radical as defined above and $R_f$ is a heterocyclyl radical as defined above, and if the heterocyclyl is a nitrogen-containing heterocyclyl, the heterocyclyl may be attached to the alkynyl radical at the nitrogen atom. The alkynyl part of the heterocyclylalkynyl radical may be optionally substituted as defined above for an alkynyl group. The heterocyclyl part of the heterocyclylalkynyl radical may be optionally substituted as defined above for a heterocyclyl group.

"Heteroaryl" refers to a 3- to 18-membered partially or fully aromatic ring radical which consists of one to thirteen carbon atoms and from one to six heteroatoms selected from the group consisting of nitrogen, oxygen and sulfur. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, 1,3-benzodioxolyl, benzofuranyl, benzooxazolyl, benzothiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyl, naphthyridinyl, oxadiazolyl, 2-oxoazepinyl, oxazolyl, oxiranyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, pyrrolyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, the term "heteroaryl" is meant to include heteroaryl radicals as defined above which are optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{14}$, —$R^{15}$—$N(R^{14})C(O)R^{14}$, —$R^{15}$—$N(R^{14})S(O)_tR^{14}$ (where t is 1 or 2), —$R^{15}$—$S(O)_tOR^{14}$ (where t is 1 or 2), —$R^{15}$—$S(O)_pR^{14}$ (where p is 0, 1 or 2), and —$R^{15}$—$S(O)_tN(R^{14})_2$ (where t is 1 or 2), where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{15}$ is independently a direct bond or a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical may be optionally substituted as described above for heteroaryl radicals.

"Heteroarylalkyl" refers to a radical of the formula —$R_aR_g$ where $R_a$ is an alkyl radical as defined above and $R_g$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"Heteroarylalkenyl" refers to a radical of the formula —$R_cR_g$ where $R_c$ is an alkenyl radical as defined above and $R_g$ is a heteroaryl radical as defined above. The heteroaryl part of the heteroarylalkenyl radical may be optionally substituted as defined above for a heteroaryl group. The alkenyl part of the heteroarylalkenyl radical may be optionally substituted as defined above for an alkenyl group.

"Heteroarylalkynyl" refers to a radical of the formula —$R_dR_g$ where $R_d$ is an alkynyl radical as defined above and $R_g$ is a heteroaryl radical as defined above. The heteroaryl part of the heteroarylalkynyl radical may be optionally substituted as defined above for a heteroaryl group. The alkynyl part of the heteroarylalkynyl radical may be optionally substituted as defined above for an alkynyl group.

"Hydroxyalkyl" refers to an alkyl radical as defined above which is substituted by one or more hydroxy groups (—OH).

"Hydroxyalkenyl" refers to an alkenyl radical as defined above which is substituted by one or more hydroxy groups (—OH).

"Hydroxyalkenyl" refers to an alkynyl radical as defined above which is substituted by one or more hydroxy groups (—OH).

Certain chemical groups named herein may be preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

"Prodrugs" is meant to indicate a compound that may be converted under physiological conditions or by solvolysis to a biologically active compound of the invention. Thus, the term "prodrug" refers to a precursor of a compound of the invention that is pharmaceutically acceptable. A prodrug may be inactive when administered to a subject in need thereof, but is converted in vivo to an active compound of the invention for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like. Preferably, for purposes of this invention, the mammal is a human.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfonic acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, for example, humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of a disease or condition of interest in the mammal, preferably a human. The amount of a compound of the invention which constitutes a "therapeutically effective amount" will vary depending on the compound, the disease or condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) stabilizing the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

"Atropisomers" are stereoisomers resulting from hindered rotation about single bonds where the barrier to rotation is high enough to allow for the isolation of the conformers (Eliel, E. L.; Wilen, S. H. *Stereochemistry of Organic Compounds*; Wiley & Sons: New York, 1994; Chapter 14). Atropisomerism is significant because it introduces an element of chirality in the absence of stereogenic atoms. The invention is meant to encompass atropisomers, for example in cases of limited rotation around the single bonds emanating from the core triazole structure, atropisomers are also possible and are also specifically included in the compounds and/or prodrugs of the invention.

The chemical naming protocol and structure diagrams used herein are a modified form of the I.U.P.A.C. nomenclature system wherein the compounds of the invention are named herein as derivatives of the central core structure, i.e., the triazole structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

The numbering system of the ring atoms in compounds of formula (Ia) and (Ib) is shown below:

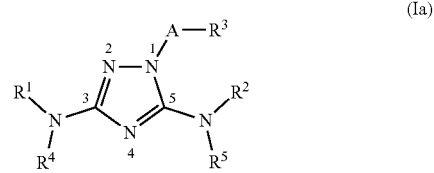

(Ia)

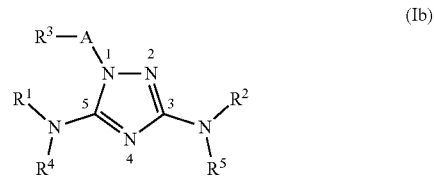

(Ib)

For example, a compound of formula (Ia) wherein A is —C(O)—, $R^1$ is phenyl substituted at the 4-position by —$R^8$—$OR^{10}$ (where $R^8$ is a direct bond and $R^{10}$ is 2-pyrrolidin-1-ylethyl); $R^2$, $R^4$ and $R^5$ are each hydrogen and $R^3$ is 1H-indol-5-yl; i.e., a compound of the following formula:

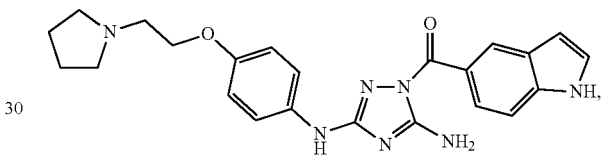

is named herein as 5-amino-1-(1H-indol-5-yl)carbonyl-3-[4-[2-(pyrrolidin-1-yl)ethoxy]phenylamino]-1H-1,2,4-triazole.

EMBODIMENTS OF THE INVENTION

One embodiment of the various aspects of the invention set forth above in the Summary of the Invention are compounds of formula (Ia):

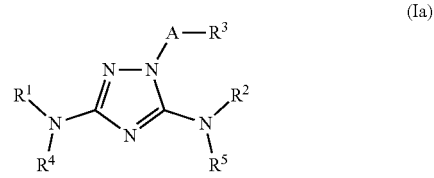

(Ia)

wherein:
A is —C(O)—;
$R^1$ is one of the following:
  a) aryl substituted with one or more substituents selected from the group consisting of halo, haloalkyl, alkyl, optionally substituted heteroaryl, optionally substituted heterocyclyl, —$R^8$—$OR^{10}$, —$R^8$—O—$R^9$—$OR^{10}$, —$R^8$—O—$R^9$—O—$R^9$—$OR^{10}$, —$R^8$—O—$R^9$—CN, —$R^8$—O—$R^9$—C(O)$OR^{10}$, —$R^8$—O—$R^9$—C(O)N($R^6$)$R^7$, —$R^8$—O—$R^9$—S(O)$_p$$R^6$ (where p is 0, 1 or 2), —$R^8$—O—$R^9$—N($R^6$)$R^7$, —$R^6$—O—$R^9$—C(N$R^{11}$)N($R^{11}$)H, and —$R^8$—N($R^6$)C(O)$R^{10}$; or
  b) heteroaryl optionally substituted with one or more substituents selected from the group consisting of alkyl, halo, oxo, —$R^8$—$OR^{10}$, —$R^8$—C(O)$OR^{10}$, —$R^8$—C(O)N($R^6$)$R^7$ and —$R^8$—N($R^6$)$R^7$; or
  c) heterocyclyl optionally substituted with one or more substituents selected from the group consisting of halo, haloalkyl, alkyl, oxo, $-R^8-OR^{10}$, $-R^8-C(O)OR^{10}$, $-R^8-C(O)N(R^6)R^7$, $-R^8-S(O)_pR^{10}$ (where p is 0, 1 or 2) and $-R^8-N(R^6)R^7$;

d) heterocyclylalkyl optionally substituted with one or more substituents selected from the group consisting of halo, haloalkyl, alkyl, optionally substituted aryl, optionally substituted aralkyl, $-R^8-OR^{10}$, $-R^8-C(O)OR^{10}$, $-R^8-C(O)N(R^6)R^7$ and $-R^8-N(R^6)R^7$; or e) cycloalkyl optionally substituted with one or more substituents selected from the group consisting of halo, haloalkyl, alkyl, oxo, $-R^6-OR^{10}$, $-R^8-C(O)OR^{10}$, $-R^8-C(O)N(R^6)R^7$, $-R^8-S(O)_pR^{10}$ (where p is 0, 1 or 2) and $-R^8-N(R^6)R^7$;

$R^2$ is hydrogen, alkyl or $-C(O)R^{10}$;

$R^4$ and $R^5$ are each hydrogen or alkyl;

$R^3$ is one of the following:

a) alkyl optionally substituted with one or more substituents selected from the group consisting of halo, cyano, nitro, oxo, thioxo, trimethylsilanyl, $-OR^{14}$, $-OC(O)-R^{14}$, $-N(R^{14})_2$, $-C(O)R^{14}$, $-C(O)OR^{14}$, $-C(O)N(R^{14})_2$, $-N(R^{14})C(O)OR^{14}$, $-N(R^{14})C(O)R^{14}$, $-N(R^{14})S(O)_tR^{14}$ (where t is 1 or 2), $-S(O)_tOR^{14}$ (where t is 1 or 2), $-S(O)_pR^{14}$ (where p is 0, 1 or 2), and $-S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl;

b) cycloalkyl optionally substituted with one or more substituents selected from the group consisting of $-R^8-OR^{10}$, alkyl, halo, haloalkyl, aryl, and aralkyl;

c) aryl substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, $-R^8-OR^{10}$, $-R^8-C(O)OR^{10}$, $-R^8-OC(O)R^{10}$, $-R^8-O-R^9-C(O)OR^{10}$, $-R^8-O-R^9-C(O)N(R^6)R^7$, $-S(O)_pR^6$ (where p is 0, 1 or 2), $-S(O)_tN(R^6)R^7$ (where t is 1 or 2), $-R^8-N(R^6)R^7$, $-R^8-N(R^6)C(O)R^{10}$, $-R^8-N(R^6)C(O)OR^{10}$ and $-R^8-CN$;

d) aralkyl, wherein:

(1) the alkyl part of the aralkyl radical is optionally substituted with one or more substituents selected from the group consisting of halo, cyano, nitro, oxo, thioxo, trimethylsilanyl, $-OC(O)-R^{14}$, $-N(R^{14})_2$, $-C(O)R^{14}$, $-C(O)OR^{14}$, $-C(O)N(R^{14})_2$, $-N(R^{14})C(O)OR^{14}$, $-N(R^{14})C(O)R^{14}$, $-N(R^{14})S(O)_tR^{14}$ (where t is 1 or 2), $-S(O)_tOR^{14}$ (where t is 1 or 2), $-S(O)_pR^{14}$ (where p is 0, 1 or 2), and $-S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl; and (2) the aryl part of the aralkyl radical is optionally substituted with one or more substituents selected from the group consisting of alkyl, alkenyl, alkynyl, halo, haloalkyl, haloalkenyl, haloalkynyl, cyano, nitro, aryl, aralkyl, aralkenyl, aralkynyl, cycloalkyl, cycloalkylalkyl, cycloalkylalkenyl, cycloalkylalkynyl, heterocyclyl, heterocyclylalkyl, heterocyclylalkenyl, heterocyclylalkynyl, heteroaryl, heteroarylalkyl, heteroarylalkenyl, heteroarylalkynyl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-O-R^{16}-C(O)N(R^{14})_2$, $-R^{15}-N(R^{14})C(O)OR^{14}$, $-R^{15}-N(R^{14})C(O)R^{14}$, $-R^{15}-N(R^{14})S(O)_tR^{14}$ (where t is 1 or 2), $-R^{15}-S(O)_tOR^{14}$ (where t is 1 or 2), $-R^{15}-S(O)_pR^{14}$ (where p is 0, 1 or 2), and $-R^{15}-S(O)_tN(R^{14})_2$ (where t is 1 or 2), where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl, each $R^{15}$ is independently a direct bond or a straight or branched alkylene or alkenylene chain, and $R^{16}$ is a straight or branched alkylene or alkenylene chain;

e) heteroaryl optionally substituted with one or more substituents selected from the group consisting of alkyl, oxo, and $-R^9-OR^{10}$; or f) heteroarylalkenyl where the heteroaryl part of the heteroarylakyl radical is optionally substituted with one or more substituents selected from the group consisting of alkyl, halo, haloalkyl, aryl and aralkyl;

$R^6$ and $R^7$ are each independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^9-OR^{10}$, $-R^9-CN$, $-R^9-NO_2$, $-R^9-N(R^{10})_2$, $-R^9-C(O)OR^{10}$ and $-R^9-C(O)N(R^{10})_2$;

optionally, $R^6$ and $R^7$, together with the nitrogen to which they are attached, form an optionally substituted N-heteroaryl or an optionally substituted N-heterocyclyl;

each $R^8$ is independently selected from the group consisting of a direct bond, an optionally substituted straight or branched alkylene chain, an optionally substituted straight or branched alkenylene chain and an optionally substituted straight or branched alkynylene chain;

each $R^9$ is independently selected from the group consisting of an optionally substituted straight or branched alkylene chain, an optionally substituted straight or branched alkenylene chain and an optionally substituted straight or branched alkynylene chain; and each $R^{10}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl; and each $R^{11}$ is hydrogen, alkyl, cyano, nitro or —$OR^{10}$.

Another embodiment of the compounds of formula (Ia) are compounds of formula (Ia) wherein:

A is —C(O)—;

$R^1$ is one of the following:
  a) aryl substituted with one or more substituents selected from the group consisting of halo, haloalkyl, alkyl, optionally substituted heteroaryl, optionally substituted heterocyclyl, —$R^8$—$OR^{10}$, —$R^8$—O—$R^9$—$OR^{10}$, —$R^8$—O—$R^9$—O—$R^3$—$OR^{10}$, —$R^8$—O—$R^9$—CN, —$R^8$—O—$R^9$—C(O)$OR^{10}$, —$R^8$—O—$R^9$—C(O)N($R^6$)$R^7$, —$R^8$—O—$R^9$—S(O)$_p R^6$ (where p is 0, 1 or 2), —$R^8$—O—$R^9$—N($R^6$)$R^7$, —$R^8$—O—$R^9$—C(N$R^{11}$)N($R^{11}$)H, and —$R^8$—N($R^6$)C(O)$OR^{10}$; or
  b) heteroaryl optionally substituted with one or more substituents selected from the group consisting of alkyl, halo, oxo, —$R^8$—$OR^{10}$, —$R^8$—C(O)$OR^{13}$, —$R^8$—C(O)N($R^6$)$R^7$ and —$R^8$—N($R^6$)$R^7$;
  c) heterocyclyl optionally substituted with one or more substituents selected from the group consisting of halo, haloalkyl, alkyl, oxo, —$R^8$—$OR^{10}$, —$R^8$—C(O)$OR^{10}$, —$R^B$—C(O)N($R^6$)$R^7$, —$R^3$—S(O)$_p R^{10}$ (where p is 0, 1 or 2) and —$R^8$—N($R^6$)$R^7$; or
  d) heterocyclylalkyl optionally substituted with one or more substituents selected from the group consisting of halo, haloalkyl, alkyl, optionally substituted aryl, optionally substituted aralkyl, —$R^8$—$OR^{10}$, —$R^8$—C(O)$OR^{10}$, —$R^8$—C(O)N($R^6$)$R^7$ and —$R^8$—N($R^6$)$R^7$;

$R^2$ is hydrogen, alkyl or —C(O)$R^{10}$;

$R^4$ and $R^5$ are each hydrogen or alkyl;

$R^3$ is one of the following:
  a) alkyl optionally substituted with one or more substituents selected from the group consisting of halo, cyano, nitro, oxo, thioxo, trimethylsilanyl, —$OR^{14}$, —OC(O)—$R^{14}$, —N($R^{14}$)$_2$, —C(O)$R^{14}$, —C(O)$OR^{14}$, —C(O)N($R^{14}$)$_2$, —N($R^{14}$)C(O)$OR^{14}$, —N($R^{14}$)C(O)$R^{14}$, —N($R^{14}$)S(O)$_t R^{14}$ (where t is 1 or 2), —S(O)$_t OR^{14}$ (where t is 1 or 2), —S(O)$_p R^{14}$ (where p is 0, 1 or 2), and —S(O)$_t N(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl;
  b) cycloalkyl optionally substituted with one or more substituents selected from the group consisting of —$R^8$—$OR^{10}$, alkyl, halo, haloalkyl, aryl, and aralkyl;
  c) aryl substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, —$R^8$—$OR^{10}$, —$R^8$—C(O)$OR^{10}$, —$R^8$—OC(O)$R^{10}$, —$R^8$—O—$R^9$—C(O)$OR^{10}$, —$R^8$—O—$R^9$—C(O)N($R^6$)$R^7$, —S(O)$_p R^6$ (where p is 0, 1 or 2), —S(O)$_t N(R^6)R^7$ (where t is 1 or 2), —$R^8$—N($R^6$)$R^7$, —$R^8$—N($R^6$)C(O)$R^{10}$, —$R^8$—N($R^6$)C(O)$OR^{10}$ and —$R^8$—CN;
  d) aralkyl, wherein:
    (1) the alkyl part of the aralkyl radical is optionally substituted with one or more substituents selected from the group consisting of halo, cyano, nitro, oxo, thioxo, trimethylsilanyl, —$OR^{14}$, —OC(O)—$R^{14}$, —N($R^{14}$)$_2$, —C(O)$R^{14}$, —C(O)$OR^{14}$, —C(O)N($R^{14}$)$_2$, —N($R^{14}$)C(O)$OR^{14}$, —N($R^{14}$)C(O)$R^{14}$, —N($R^{14}$)S(O)$_t R^{14}$ (where t is 1 or 2), —S(O)$_t OR^{14}$ (where t is 1 or 2), —S(O)$_p R^{14}$ (where p is 0, 1 or 2), and —S(O)$_t N(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl; and
    (2) the aryl part of the aralkyl radical is optionally substituted with one or more substituents selected from the group consisting of alkyl, alkenyl, alkynyl, halo, haloalkyl, haloalkenyl, haloalkynyl, cyano, nitro, aryl, aralkyl, aralkenyl, aralkynyl, cycloalkyl, cycloalkylalkyl, cycloalkylalkenyl, cycloalkylalkynyl, heterocyclyl, heterocyclylalkyl, heterocyclylalkenyl, heterocyclylalkynyl, heteroaryl, heteroarylalkyl, heteroarylalkenyl, heteroarylalkynyl, —$R^{15}$—$OR^{14}$, —$R^{15}$—OC(O)—$R^{14}$, —$R^{15}$—N($R^{14}$)$_2$, —$R^{15}$—C(O)$R^{14}$, —$R^{15}$—C(O)$OR^{14}$, —$R^{15}$—C(O)N($R^{14}$)$_2$, —$R^{15}$—O—$R^{16}$—C(O)N($R^{14}$)$_2$, —$R^{15}$—N($R^{14}$)C(O)$OR^{14}$, —$R^{15}$—N($R^{14}$)C(O)$R^{14}$, —$R^{15}$—N($R^{14}$)S(O)$_t R^{14}$ (where t is 1 or 2), —$R^{15}$—S(O)$_t OR^{14}$ (where t is 1 or 2), —$R^{15}$—S(O)$_p R^{14}$ (where p is 0, 1 or 2), and —$R^{15}$—S(O)$_t N(R^{14})_2$ (where t is 1 or 2), where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl, each $R^{15}$ is independently a direct bond or a straight or branched alkylene or alkenylene chain, and $R^{16}$ is a straight or branched alkylene or alkenylene chain;
  e) heteroaryl optionally substituted with one or more substituents selected from the group consisting of alkyl, oxo, and —$R^8$—$OR^{10}$; or
  f) heteroarylalkenyl where the heteroaryl part of the heteroarylakyl radical is optionally substituted with one or more substituents selected from the group consisting of alkyl, halo, haloalkyl, aryl and aralkyl;

$R^6$ and $R^7$ are each independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocylylalkynyl, optionally substituted heteroaryl, optionally substituted heteroarylalkyl, optionally substituted heteroarylalkenyl, optionally substituted heteroarylalkynyl, —$R^9$—$OR^{10}$, —$R^9$—$NO_2$, —$R^9$—N($R^{10}$)$_2$, —$R^9$—C(O)$OR^{10}$ and —$R^9$—C(O)N($R^{10}$)$_2$;

optionally, $R^6$ and $R^7$, together with the nitrogen to which they are attached, form an optionally substituted N-heteroaryl or an optionally substituted N-heterocyclyl;

each $R^8$ is independently selected from the group consisting of a direct bond, an optionally substituted straight or branched alkylene chain, an optionally substituted straight or branched alkenylene chain and an optionally substituted straight or branched alkynylene chain;

each $R^9$ is independently selected from the group consisting of an optionally substituted straight or branched alkylene chain, an optionally substituted straight or branched alkenylene chain and an optionally substituted straight or branched alkynylene chain; and each $R^{10}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl; and each $R^{11}$ is hydrogen, alkyl, cyano, nitro or $-OR^{10}$.

Another embodiment of the compounds of formula (Ia) are compounds of formula (Ia) wherein:

A is $-C(O)-$;

$R^1$ is aryl substituted with one or more substituents selected from the group consisting of halo, haloalkyl, alkyl, optionally substituted heteroaryl, optionally substituted heterocyclyl, $-R^8-OR^{10}$, $-R^8-O-R^9-OR^{10}$, $-R^8-O-R^9-O-R^8-OR^{10}$, $-R^8-O-R^9-CN$, $-R^8-O-R^9-C(O)OR^{10}$, $-R^8-O-R^9-C(O)N(R^6)R^7$, $-R^8-O-R^8-S(O)_pR^6$ (where p is 0, 1 or 2), $-R^8-O-R^8-N(R^6)R^7$, $-R^8-O-R^9-C(NR^{11})N(R^{11})H$, and $-R^8-N(R^6)C(O)R^{10}$;

$R^2$, $R^4$ and $R^5$ are each hydrogen or alkyl;

$R^3$ is one of the following:

a) alkyl optionally substituted with one or more substituents selected from the group consisting of halo, cyano, nitro, oxo, thioxo, trimethylsilanyl, $-OR^{14}$, $-OC(O)-R^{14}$, $-N(R^{14})_2$, $-C(O)R^{14}$, $-C(O)OR^{14}$, $-C(O)N(R^{14})_2$, $-N(R^{14})C(O)OR^{14}$, $-N(R^{14})C(O)R^{14}$, $-N(R^{14})S(O)_tR^{14}$ (where t is 1 or 2), $-S(O)_tOR^{14}$ (where t is 1 or 2), $-S(O)_pR^{14}$ (where p is 0, 1 or 2), and $-S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl;

b) cycloalkyl optionally substituted with one or more substituents selected from the group consisting of $-R^8-OR^{10}$, alkyl, halo, haloalkyl, aryl, and aralkyl;

c) aryl substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, $-R^8-OR^{10}$, $-R^8-C(O)OR^{10}$, $-R^8-OC(O)R^{10}$, $-R^8-O-R^9-C(O)OR^{10}$, $-R^8-O-R^9-C(O)N(R^6)R^7$, $-S(O)_pR^6$ (where p is 0, 1 or 2), $-S(O)_tN(R^6)R^7$ (where t is 1 or 2), $-R^8-N(R^6)R^7$, $-R^8-N(R^6)C(O)R^{10}$, $-R^8-N(R^8)C(O)OR^{10}$ and $-R^6-CN$;

d) aralkyl, wherein:
  (1) the alkyl part of the aralkyl radical is optionally substituted with one or more substituents selected from the group consisting of halo, cyano, nitro, oxo, thioxo, trimethylsilanyl, $-OR^{14}$, $-OC(O)-R^{14}$, $-N(R^{14})_2$, $-C(O)R^{14}$, $-C(O)OR^{14}$, $-C(O)N(R^{14})_2$, $-N(R^{14})C(O)OR^{14}$, $-N(R^{14})C(O)R^{14}$, $-N(R^{14})S(O)_tR^{14}$ (where t is 1 or 2), $-S(O)_tOR^{14}$ (where t is 1 or 2), $-S(O)_pR^{14}$ (where p is 0, 1 or 2), and $-S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl; and
  (2) the aryl part of the aralkyl radical is optionally substituted with one or more substituents selected from the group consisting of alkyl, alkenyl, alkynyl, halo, haloalkyl, haloalkenyl, haloalkynyl, cyano, nitro, aryl, aralkyl, aralkenyl, aralkynyl, cycloalkyl, cycloalkylalkyl, cycloalkylalkenyl, cycloalkylalkynyl, heterocyclyl, heterocyclylalkyl, heterocyclylalkenyl, heterocyclylalkynyl, heteroaryl, heteroarylalkyl, heteroarylalkenyl, heteroarylalkynyl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-O-R^{16}-C(O)N(R^{14})_2$, $-R^{15}-N(R^{14})C(O)OR^{14}$, $-R^{15}-N(R^{14})C(O)R^{14}$, $-R^{15}-N(R^{14})S(O)_tR^{14}$ (where t is 1 or 2), $-R^{15}-S(O)_tOR^{14}$ (where t is 1 or 2), $-R^{15}-S(O)_pR^{14}$ (where p is 0, 1 or 2), and $-R^{15}-S(O)_tN(R^{14})_2$ (where t is 1 or 2), where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl, each $R^{15}$ is independently a direct bond or a straight or branched alkylene or alkenylene chain, and $R^{16}$ is a straight or branched alkylene or alkenylene chain;

e) heteroaryl optionally substituted with one or more substituents selected from the group consisting of alkyl, oxo, and $-R^8-OR^{10}$; or f) heteroarylalkenyl where the heteroaryl part of the heteroarylakyl radical is optionally substituted with one or more substituents selected from the group consisting of alkyl, halo, haloalkyl, aryl and aralkyl;

$R^6$ and $R^7$ are each independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^9-OR^{10}$, $-R^9-CN$, $-R^9-NO_2$, $-R^9-N(R^{10})_2$, $-R^9-C(O)OR^{10}$ and $-R^9-C(O)N(R^{10})_2$;

optionally, $R^6$ and $R^7$, together with the nitrogen to which they are attached, form an optionally substituted N-heteroaryl or an optionally substituted N-heterocyclyl;

each $R^8$ is independently selected from the group consisting of a direct bond, an optionally substituted straight or branched alkylene chain, an optionally substituted straight or branched alkenylene chain and an optionally substituted straight or branched alkynylene chain;

each $R^9$ is independently selected from the group consisting of an optionally substituted straight or branched alkylene chain, an optionally substituted straight or branched alkenylene chain and an optionally substituted straight or branched alkynylene chain; and each $R^{10}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl; and each $R^{11}$ is hydrogen, alkyl, cyano, nitro or —$OR^{10}$.

Another embodiment of the compounds of formula (Ia) are compounds of formula (Ia) wherein:

A is —C(O)—;
$R^1$ is aryl substituted with one or more substituents selected from the group consisting of halo, haloalkyl, alkyl, optionally substituted heteroaryl, optionally substituted heterocyclyl, —$R^8$—$OR^{10}$, —$R^8$—O—$R^9$—$OR^{10}$, —$R^8$—O—$R^9$—O—$R^9$—$OR^{10}$, —$R^8$—O—$R^9$—CN, —$R^8$—O—$R^9$—C(O)$OR^{10}$, —$R^8$—O—$R^9$—C(O)N($R^6$)$R^7$, —$R^8$—O—$R^9$—S(O)$_p R^6$ (where p is 0, 1 or 2), —$R^8$—O—$R^9$—N($R^6$)$R^7$, —$R^8$—O—$R^9$—C(N$R^{11}$)N($R^{11}$)H, and —$R^8$—N($R^6$)C(O)$R^{10}$;
$R^2$, $R^4$ and $R^5$ are each hydrogen or alkyl;
$R^3$ is cycloalkyl optionally substituted with —$R^8$—$OR^{10}$; or
$R^3$ is aryl substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, —$R^6$—$OR^{10}$, —$R^8$—C(O)$OR^{10}$, —$R^8$—OC(O)$R^{10}$, —$R^8$—O—$R^9$—C(O)$OR^{10}$, —$R^8$—O—$R^9$—C(O)N($R^6$)$R^7$, —S(O)$_p R^6$ (where p is 0, 1 or 2), —S(O)$_t$N($R^6$)$R^7$ (where t is 1 or 2), —$R^8$—N($R^6$)$R^7$, —$R^8$—N($R^6$)C(O)$R^{10}$, —$R^8$—N($R^6$)C(O)$OR^{10}$ and —$R^8$—CN;
$R^6$ and $R^7$ are each independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^9$—$OR^{10}$, —$R^9$—CN, —$R^9$—$NO_2$, —$R^9$—N($R^{10}$)$_2$, —$R^9$—C(O)$OR^{10}$ and —$R^9$—C(O)N($R^{10}$)$_2$;
optionally, $R^6$ and $R^7$, together with the nitrogen to which they are attached, form an optionally substituted N-heteroaryl or an optionally substituted N-heterocyclyl;
each $R^8$ is independently selected from the group consisting of a direct bond, an optionally substituted straight or branched alkylene chain, an optionally substituted straight or branched alkenylene chain and an optionally substituted straight or branched alkynylene chain;
each $R^9$ is independently selected from the group consisting of an optionally substituted straight or branched alkylene chain, an optionally substituted straight or branched alkenylene chain and an optionally substituted straight or branched alkynylene chain; and
each $R^{10}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl; and each $R^{11}$ is hydrogen, alkyl, cyano, nitro or —$OR^1$.

Another embodiment of the compounds of formula (Ia) are compounds of formula (Ia) wherein:

A is —C(O)—;
$R^1$ is phenyl substituted with one or more substituents selected from the group consisting of halo, haloalkyl, alkyl, optionally substituted heteroaryl, optionally substituted heterocyclyl, —$R^8$—$OR^{10}$, —$R^8$—O—$R^9$—$OR^{10}$, —$R^8$—O—$R^9$—O—$R^9$—$OR^{10}$, —$R^8$—O—$R^9$—CN, —$R^8$—O—$R^9$—C(O)$OR^{10}$, —$R^8$—O—$R^9$—C(O)N($R^8$)$R^7$, —$R^8$—O—$R^9$—S(O)$_p R^8$ (where p is 0, 1 or 2), —$R^8$—O—$R^9$—N($R^8$)$R^7$, —$R^8$—O—$R^9$—C(N$R^{11}$)N($R^{11}$)H, and —$R^8$—N($R^8$)C(O)$R^{10}$;
$R^2$, $R^4$ and $R^5$ are each hydrogen or alkyl;
$R^3$ is cycloalkyl optionally substituted with —$R^8$—$OR^{10}$; or
$R^3$ is phenyl substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, —$R^8$—$OR^{10}$, —$R^8$—C(O)$OR^{10}$, —$R^8$—OC(O)$R^{10}$, —$R^8$—O—$R^9$—C(O)$OR^{10}$, —$R^8$—O—$R^9$—C(O)N($R^6$)$R^7$, —S(O)$_p R^6$ (where p is 0, 1 or 2), —S(O)$_t$N($R^6$)$R^7$ (where t is 1 or 2), —$R^8$—N($R^6$)$R^7$, —$R^8$—N($R^6$)C(O)$R^{10}$, —$R^8$—N($R^6$)C(O)$OR^{10}$, and —$R^8$—CN;
$R^6$ and $R^7$ are each independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^9$—$OR^{10}$, —$R^9$—CN, —$R^9$—$NO_2$, —$R^9$—N($R^{10}$)$_2$, —$R^9$—C(O)$OR^{10}$ and —$R^9$—C(O)N($R^{10}$)$_2$;
optionally, $R^8$ and $R^7$, together with the nitrogen to which they are attached, form an optionally substituted N-heteroaryl or an optionally substituted N-heterocyclyl;
each $R^8$ is independently selected from the group consisting of a direct bond, an optionally substituted straight or branched alkylene chain, an optionally substituted straight or branched alkenylene chain and an optionally substituted straight or branched alkynylene chain;
each $R^9$ is independently selected from the group consisting of an optionally substituted straight or branched alkylene chain, an optionally substituted straight or branched alkenylene chain and an optionally substituted straight or branched alkynylene chain; and
each $R^{10}$ is independently selected from the group consisting of hydrogen, alkyl, alkenyl, alkynyl, haloalkyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl; and each $R^{11}$ is hydrogen, alkyl, cyano, nitro or —$OR^{10}$.

Another embodiment of the compounds of formula (Ia) are compounds of formula (Ia) wherein:

A is —C(O)—;

$R^1$ is phenyl substituted with one or two substituents selected from the group consisting of halo, haloalkyl, alkyl, optionally substituted heteroaryl, optionally substituted heterocyclyl, —$R^8$—$OR^{10}$, —$R^8$—O—$R^8$—$OR^{10}$, —$R^8$—O—$R^8$—O—$R^8$—$OR^{10}$, —$R^8$—O—$R^8$—CN, —$R^8$—O—$R^8$—C(O)$OR^{10}$, —$R^8$—O—$R^8$—C(O)N($R^6$)$R^7$, —$R^8$—O—$R^8$—S(O)$_p$$R^6$ (where p is 0, 1 or 2), —$R^8$—O—$R^8$—N($R^6$)$R^7$, —$R^8$—O—$R^9$—C(N$R^{11}$)N($R^{11}$)H, and —$R^8$—N($R^6$)C(O)$R^{10}$;

$R^2$, $R^4$ and $R^5$ are each hydrogen or alkyl;

$R^3$ is cycloalkyl optionally substituted with —$R^8$—$OR^{10}$; or $R^3$ is phenyl substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, —$R^8$—$OR^{10}$, —$R^8$—C(O)$OR^{10}$, —$R^8$—OC(O)$R^{10}$, —$R^8$—O—$R^8$—C(O)$OR^{10}$, —$R^8$—O—$R^9$—C(O)N($R^6$)$R^7$, —S(O)$_p$$R^6$ (where p is 0, 1 or 2), —S(O)$_t$N($R^6$)$R^7$ (where t is 1 or 2), —$R^8$—N($R^6$)$R^7$, —$R^8$—N($R^6$)C(O)$R^{10}$, —$R^8$—N($R^6$)C(O)$OR^{10}$ and —$R^8$—CN;

$R^6$ and $R^7$ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^8$—$OR^{10}$, —$R^9$—CN, —$R^9$—$NO_2$, —$R^8$—N($R^{10}$)$_2$, —$R^8$—C(O)$OR^{10}$ and —$R^8$—C(O)N($R^{10}$)$_2$;

optionally, $R^6$ and $R^7$, together with the nitrogen to which they are attached, form an optionally substituted N-heteroaryl or an optionally substituted N-heterocyclyl;

each $R^8$ is independently selected from the group consisting of a direct bond, an optionally substituted straight or branched alkylene chain, and an optionally substituted straight or branched alkenylene chain;

each $R^9$ is independently selected from the group consisting of an optionally substituted straight or branched alkylene chain, or an optionally substituted straight or branched alkenylene chain; and each $R^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl; and each $R^{11}$ is hydrogen, alkyl, cyano, nitro or —$OR^{10}$.

Another embodiment of the compounds of formula (Ia) are compounds of formula (Ia) wherein:

A is —C(O)—;

$R^1$ is phenyl substituted with one or more substituents selected from the group consisting of halo, haloalkyl, alkyl, —$R^8$—$OR^{10}$, —$R^8$—O—$R^9$—$OR^{10}$, and —$R^8$—O—$R^9$—O—$R^9$—$OR^{10}$;

$R^2$, $R^4$ and $R^5$ are each hydrogen or alkyl;

$R^3$ is cycloalkyl optionally substituted with —$R^8$—$OR^{10}$; or $R^3$ is phenyl substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, —$R^8$—$OR^{13}$, —$R^8$—C(O)$OR^{10}$, —$R^8$—OC(O)$R^{10}$, —$R^8$—O—$R^8$—C(O)$OR^{10}$, —$R^8$—O—$R^9$—C(O)N($R^6$)$R^7$, —S(O)$_p$$R^6$ (where p is 0, 1 or 2), —S(O)$_t$N($R^6$)$R^7$ (where t is 1 or 2), —$R^8$—N($R^6$)$R^7$, —$R^8$—N($R^6$)C(O)$R^{10}$, —$R^8$—N($R^6$)C(O)$OR^{10}$ and —$R^8$—CN;

$R^6$ and $R^7$ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^9$—$OR^{10}$, —$R^9$—CN, —$R^9$—$NO_2$, —$R^9$—N($R^{10}$)$_2$, —$R^9$—C(O)$OR^{10}$ and —$R^9$—C(O)N($R^{10}$)$_2$;

optionally, $R^6$ and $R^7$, together with the nitrogen to which they are attached, form an optionally substituted N-heteroaryl or an optionally substituted N-heterocyclyl;

each $R^8$ is independently selected from the group consisting of a direct bond, an optionally substituted straight or branched alkylene chain, and an optionally substituted straight or branched alkenylene chain;

each $R^9$ is independently selected from the group consisting of an optionally substituted straight or branched alkylene chain, or an optionally substituted straight or branched alkenylene chain; and each $R^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl.

Another embodiment of the compounds of formula (Ia) are compounds of formula (Ia) wherein:

A is —C(O)—;

$R^1$ is phenyl substituted with one or more substituents selected from the group consisting of halo, haloalkyl, alkyl, —$R^8$—$OR^{10}$, —$R^8$—O—$R^9$—$OR^{10}$, and —$R^8$—O—$R^9$—O—$R^9$—$OR^{10}$;

$R^2$, $R^4$ and $R^5$ are each hydrogen or alkyl;

$R^3$ is cycloalkyl optionally substituted with —$R^8$—$OR^{10}$;

each $R^8$ is independently selected from the group consisting of a direct bond, an optionally substituted straight or branched alkylene chain, and an optionally substituted straight or branched alkenylene chain;

each $R^9$ is independently selected from the group consisting of an optionally substituted straight or branched alkylene chain, or an optionally substituted straight or branched alkenylene chain; and each $R^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl.

Of this embodiment, a specific embodiment is a compound of formula (Ia) selected from the group consisting of:

5-amino-1-[2-(bicyclo[2.2.1]hept-5-ene)carbonyl]-3-[4-[2-(pyrrolidin-1-yl)ethoxy]phenylamino]-1H-1,2,4-triazole;

5-amino-1-(4-(methoxy)cyclohexyl)carbonyl-3-[4-[2-(piperidin-1-yl)ethoxy]phenylamino]-1H-1,2,4-triazole;

5-amino-1-[2-(bicyclo[2.2.1]heptane)carbonyl]-3-[4-[2-(pyrrolidin-1-yl)ethoxy]phenylamino]-1H-1,2,4-triazole; and 5-amino-1-(bicyclo[2.2.1]heptan-2-yl)carbonyl-3-[4-(4-methylpiperazin-1-yl)phenylamino]-1H-1,2,4-triazole.

Another embodiment of the compounds of formula (Ia) are compounds of formula (Ia) wherein:

A is —C(O)—;

$R^1$ is phenyl substituted with one or more substituents selected from the group consisting of halo, haloalkyl, alkyl, —$R^8$—$OR^{10}$, —$R^8$—O—$R^9$—$OR^{10}$, and —$R^8$—O—$R^9$—O—$R^9$—$OR^{10}$;

$R^2$, $R^4$ and $R^5$ are each hydrogen or alkyl;

$R^3$ is phenyl substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, —$R^8$—$OR^{10}$, —$R^8$—$C(O)OR^{10}$, —$R^8$—$OC(O)R^{10}$, —$R^8$—O—$R^9$—$C(O)OR^{10}$, —$R^8$—O—$R^9$—$C(O)N(R^6)R^7$, —$S(O)_pR^6$ (where p is 0, 1 or 2), —$S(O)_tN(R^6)R^7$ (where t is 1 or 2), —$R^8$—$N(R^6)R^7$, —$R^8$—$N(R^6)C(O)R^{10}$, —$R^8$—$N(R^6)C(O)OR^{10}$ and —$R^8$—CN;

$R^6$ and $R^7$ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^9$—$OR^{10}$, —$R^9$—CN, —$R^9$—$NO_2$, —$R^9$—$N(R^{10})_2$, —$R^9$—$C(O)OR^{10}$ and —$R^9$—$C(O)N(R^{10})_2$;

optionally, $R^6$ and $R^7$, together with the nitrogen to which they are attached, form an optionally substituted N-heteroaryl or an optionally substituted N-heterocyclyl;

each $R^8$ is independently selected from the group consisting of a direct bond, an optionally substituted straight or branched alkylene chain, and an optionally substituted straight or branched alkenylene chain;

each $R^9$ is independently selected from the group consisting of an optionally substituted straight or branched alkylene chain, or an optionally substituted straight or branched alkenylene chain; and each $R^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl.

Another embodiment of the compounds of formula (Ia) are compounds of formula (Ia) wherein:

A is —C(O)—;

$R^1$ is phenyl substituted with one or more substituents selected from the group consisting of halo, haloalkyl, alkyl, —$R^8$—$OR^{10}$, —$R^9$—O—$R^9$—$OR^{10}$, and —$R^8$—O—$R^9$—O—$R^9$—$OR^{10}$;

$R^2$, $R^4$ and $R^5$ are each hydrogen or alkyl;

$R^3$ is phenyl substituted with one or more substituents selected from the group consisting of alkyl, halo, haloalkyl, nitro, —$R^8$—$OR^{10}$, —$R^8$—$C(O)OR^{10}$, —$R^8$—$OC(O)R^{10}$, —$R^8$—O—$R^9$—$C(O)OR^{10}$, —$R^8$—O—$R^9$—$C(O)N(R^6)R^7$, —$S(O)_pR^6$ (where p is 0, 1 or 2), —$S(O)_tN(R^6)R^7$ (where t is 1 or 2), —$R^8$—$N(R^6)R^7$, —$R^8$—$N(R^6)C(O)R^{10}$, —$R^8$—$N(R^6)C(O)OR^{10}$ and —$R^8$—CN;

$R^6$ and $R^7$ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^9$—$OR^{10}$, —$R^9$—CN, —$R^9$—$NO_2$, —$R^9$—$N(R^{10})_2$, —$R^9$—$C(O)OR^{10}$ and —$R^9$—$C(O)N(R^{10})_2$;

optionally, $R^6$ and $R^7$, together with the nitrogen to which they are attached, form an optionally substituted N-heteroaryl or an optionally substituted N-heterocyclyl;

each $R^8$ is independently selected from the group consisting of a direct bond, an optionally substituted straight or branched alkylene chain, and an optionally substituted straight or branched alkenylene chain;

each $R^9$ is independently selected from the group consisting of an optionally substituted straight or branched alkylene chain, or an optionally substituted straight or branched alkenylene chain; and each $R^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl.

Another embodiment of the compounds of formula (Ia) are compounds of formula (Ia) wherein:

A is —C(O)—;

$R^1$ is phenyl substituted with —$R^8$—$OR^{10}$ and optionally substituted with halo or alkoxy, where $R^8$ is a direct bond and $R^{10}$ is selected from the group consisting of 2-(pyrrolidin-1-yl)ethyl, 2-(piperidin-1-yl)ethyl, 2-(morpholin-4-yl)ethyl, 2-(1,3-dioxolan-2-yl)ethyl, 2-(thiomorpholin-4-yl)ethyl, 3-(pyrrolidin-1-yl)propyl, 2-(azepan-1-yl)ethyl, 2-(isoindolin-1-yl)ethyl, 2-(imidazol-1-yl)ethyl, 2-(pyrrolidin-2-on-1-yl)ethyl, and 2-(3-fluoropyrrolidin-1-yl)ethyl;

$R^2$, $R^4$ and $R^5$ are each hydrogen or alkyl; and $R^3$ is phenyl substituted with one or more substituents selected from the group consisting of alkyl, halo, haloalkyl, nitro, —$R^8$—$OR^{10}$, $C(O)OR^{10}$, —$R^8$—$OC(O)R^{10}$, —$R^8$—O—$R^9$—$C(O)OR^{10}$, —$R^8$—O—$R^9$—$C(O)N(R)R^7$, —$S(O)_pR^6$ (where p is 0, 1 or 2), —$S(O)_tN(R^6)R^7$ (where t is 1 or 2), —$R^6$—$N(R^6)R^7$, —$R^8$—$N(R^6)C(O)R^{10}$, —$R^8$—$N(R^6)C(O)OR^{10}$ and —$R^8$—CN, where:

$R^6$ and $R^7$ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^9$—$OR^{10}$, —$R^9$—CN, —$R^9$—$NO_2$, —$R^9$—$N(R^{10})_2$, —$R^9$—$C(O)OR^{10}$ and —$R^9$—$C(O)N(R^{10})_2$;

optionally, $R^6$ and $R^7$, together with the nitrogen to which they are attached, form an optionally substituted N-heteroaryl or an optionally substituted N-heterocyclyl;

each $R^8$ is independently selected from the group consisting of a direct bond, an optionally substituted straight or branched alkylene chain, and an optionally substituted straight or branched alkenylene chain;

each $R^9$ is independently selected from the group consisting of an optionally substituted straight or branched alkylene chain, or an optionally substituted straight or each $R^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl.

Of this embodiment, a specific embodiment is a compound of formula (Ia) selected from the group consisting of:

5-amino-1-(3-(iso-propoxy)phenyl)carbonyl-3-[4-[2-(piperidin-1-yl)ethoxy]phenylamino]-1H-1,2,4-triazole;
5-amino-1-(3-(iso-propoxy)phenyl)carbonyl-3-[4-[2-(morpholin-4-yl)ethoxy]phenylamino]-1H-1,2,4-triazole;
5-amino-1-(3-(methyl)phenylcarbonyl-3-[3-[2-(morpholin-4-yl)ethoxy]phenylamino]-1H-1,2,4-triazole;
5-amino-1-(4-(iso-propoxy)phenylcarbonyl-3-[3-[2-(morpholin-4-yl)ethoxy]phenylamino]-1H-1,2,4-triazole;
5-amino-3-[3-[2-(1,3-dioxolan-2-yl)ethoxy]phenylamino]-1-(4-(iso-propoxy)phenyl)carbonyl-1H-1,2,4-triazole;
5-amino-3-[4-[2-(1,3-dioxolan-2-yl)ethoxy]phenylamino]-1-(4-(iso-propoxy)phenyl)carbonyl-1H-1,2,4-triazole;
5-amino-1-(4-(iso-propoxy)phenylcarbonyl-3-[4-[2-(morpholin-4-yl)ethoxy]phenylamino]-1H-1,2,4-triazole;
5-amino-1-(4-(iso-propoxy)phenylcarbonyl-3-[4-[2-(piperidin-1-yl)ethoxy]phenylamino]-1H-1,2,4-triazole;
5-amino-3-[4-[2-(piperidin-1-yl)ethoxy]phenylamino]-1-(4-(tert-butoxy)phenyl)carbonyl-1H-1,2,4-triazole;
5-amino-1-(4-(iso-propyl)phenyl)carbonyl-3-[4-[2-(piperidin-1-yl)ethoxy]phenylamino]-1H-1,2,4-triazole;
5-amino-1-(4-(methyl)phenyl)carbonyl-3-[4-[2-(piperidin-1-yl)ethoxy]phenylamino]-1H-1,2,4-triazole;
5-amino-1-(3-(methyl)phenyl)carbonyl-3-[4-[2-(piperidin-1-yl)ethoxy]phenylamino]-1H-1,2,4-triazole;
5-amino-1-(4-(iso-propoxy)phenylcarbonyl-3-[4-[2-(thiomorpholin-4-yl)ethoxy]phenylamino]-1H-1,2,4-triazole;
5-amino-1-(3-(methyl)phenylcarbonyl-3-[4-[2-(thiomorpholin-4-yl)ethoxy]phenylamino]-1H-1,2,4-triazole;
5-amino-1-(4-(cyclohexyl)phenyl)carbonyl-3-[4-[2-(piperidin-1-yl)ethoxy]phenylamino]-1H-1,2,4-triazole;
5-amino-1-(3-(methoxycarbonyl)phenyl)carbonyl-3-[4-[2-(piperidin-1-yl)ethoxy]phenylamino]-1H-1,2,4-triazole;
5-amino-1-(3-(methoxy)phenyl)carbonyl-3-[4-[2-(piperidin-1-yl)ethoxy]phenylamino]-1H-1,2,4-triazole;
5-amino-1-(4-(iso-propoxy)phenyl)carbonyl-3-[4-[2-(pyrrolidin-1-yl)ethoxy]phenylamino]-1H-1,2,4-triazole;
5-amino-1-(3,4-(dimethoxy)phenyl)carbonyl-3-[4-[2-(piperidin-1-yl)ethoxy]phenylamino]-1H-1,2,4-triazole;
5-amino-1-(3,5-(dimethoxy)phenyl)carbonyl-3-[4-[2-(piperidin-1-yl)ethoxy]phenylamino]-1H-1,2,4-triazole;
5-amino-1-(3-(dimethylamino)phenyl)carbonyl-3-[4-[2-(piperidin-1-yl)ethoxy]phenylamino]-1H-1,2,4-triazole;
5-amino-1-(4-(dimethylamino)phenyl)carbonyl-3-[4-[2-(piperidin-1-yl)ethoxy]phenylamino]-1H-1,2,4-triazole;
5-amino-1-(3-methylphenyl)carbonyl-3-[4-[2-(pyrrolidin-1-yl)ethoxy]phenylamino]-1H-1,2,4-triazole;
5-amino-1-(3,5-(dimethoxy)phenyl)carbonyl-3-[4-[2-(pyrrolidin-1-yl)ethoxy]phenylamino]-1H-1,2,4-triazole;
5-amino-1-(4-methylphenyl)carbonyl-3-[4-[2-(pyrrolidin-1-yl)ethoxy]phenylamino]-1H-1,2,4-triazole;
5-amino-3-[4-[2-(pyrrolidin-1-yl)ethoxy]phenylamino]-1-(4-(tert-butoxy)phenyl)carbonyl-1H-1,2,4-triazole;
5-amino-1-(3-methoxyphenyl)carbonyl-3-[4-[2-(pyrrolidin-1-yl)ethoxy]phenylamino]-1H-1,2,4-triazole;
5-amino-1-(4-(dimethylamino)phenyl)carbonyl-3-[4-[2-(pyrrolidin-1-yl)ethoxy]phenylamino]-1H-1,2,4-triazole;
5-amino-1-(3-(dimethylamino)phenyl)carbonyl-3-[4-[2-(pyrrolidin-1-yl)ethoxy]phenylamino]-1H-1,2,4-triazole;
5-amino-1-(3,4-(dimethoxy)phenyl)carbonyl-3-[4-[2-(pyrrolidin-1-yl)ethoxy]phenylamino]-1H-1,2,4-triazole;
5-amino-3-[4-[2-(pyrrolidin-1-yl)ethoxy]phenylamino]-1-(3-(tert-butoxy)phenyl)carbonyl-1H-1,2,4-triazole;
5-amino-3-[4-[2-(pyrrolidin-1-yl)ethoxy]phenylamino]-1-(3-(trifluoromethoxy)phenyl)carbonyl-1H-1,2,4-triazole;
5-amino-3-[4-[2-(pyrrolidin-1-yl)ethoxy]phenylamino]-1-(4-(trifluoromethoxy)phenyl)carbonyl-1H-1,2,4-triazole;
5-amino-3-[4-[3-(pyrrolidin-1-yl)propoxy]phenylamino]-1-(4-(tert-butoxy)phenyl)carbonyl-1H-1,2,4-triazole;
5-amino-3-[4-[3-(pyrrolidin-1-yl)propoxy]phenylamino]-1-(3-(tert-butoxy)phenyl)carbonyl-1H-1,2,4-triazole;
5-amino-1-(4-(iso-propoxy)phenyl)carbonyl-3-[4-[3-(pyrrolidin-1-yl)propoxy]phenylamino]-1H-1,2,4-triazole;
5-amino-1-(4-(dimethylamino)phenyl)carbonyl-3-[4-[3-(pyrrolidin-1-yl)propoxy]phenylamino]-1H-1,2,4-triazole;
5-amino-1-(3-(dimethylamino)phenyl)carbonyl-3-[4-[3-(pyrrolidin-1-yl)propoxy]phenylamino]-1H-1,2,4-triazole;
5-amino-1-(4-(tert-butyl)phenyl)carbonyl-3-[4-[2-(morpholin-4-yl)ethoxy]phenylamino]-1H-1,2,4-triazole;
5-amino-1-(4-(tert-butoxy)phenyl)carbonyl-3-[4-[2-(morpholin-4-yl)ethoxy]phenylamino]-1H-1,2,4-triazole;
5-amino-1-(4-(phenoxy)phenyl)carbonyl-3-[4-[2-(pyrrolidin-1-yl)ethoxy]phenylamino]-1H-1,2,4-triazole;
5-amino-1-(4-(tert-butoxycarbonylamino)phenyl)carbonyl-3-[4-[2-(pyrrolidin-1-yl)ethoxy]phenylamino]-1H-1,2,4-triazole;
5-amino-1-(4-(tert-butoxy)phenyl)carbonyl-3-[4-[2-(pyrrolidin-1-yl)ethoxy]phenyl][methyl]amino-1H-1,2,4-triazole;
5-amino-1-[4-((tert-butoxycarbonyl)aminomethyl)phenyl]carbonyl-3-[4-[2-(pyrrolidin-1-yl)ethoxy]phenylamino]-1H-1,2,4-triazole;
5-amino-1-(4-(methylamino)phenyl)carbonyl-3-[4-[2-(pyrrolidin-1-yl)ethoxy]phenylamino]-1H-1,2,4-triazole;
5-amino-1-(4-(methylthio)phenyl)carbonyl-3-[4-[2-(pyrrolidin-1-yl)ethoxy]phenylamino]-1H-1,2,4-triazole;
5-amino-1-(2,6-difluorophenyl)carbonyl-3-[4-[2-(pyrrolidin-1-yl)ethoxy]phenylamino]-1H-1,2,4-triazole;
5-amino-1-(4-(tert-butylcarbonylamino)phenyl)carbonyl-3-[4-[2-(pyrrolidin-1-yl)ethoxy]phenylamino]-1H-1,2,4-triazole;
5-amino-1-(4-(tert-butyl)phenyl)carbonyl-3-[4-[2-(pyrrolidin-1-yl)ethoxy]phenylamino]-1H-1,2,4-triazole;
5-amino-1-(4-(tert-butoxy)phenyl)carbonyl-3-[3-fluoro-4-[2-(pyrrolidin-1-yl)ethoxy]phenylamino]-1H-1,2,4-triazole;
5-amino-1-(4-(iso-propoxy)phenyl)carbonyl-3-[3-fluoro-4-[2-(pyrrolidin-1-yl)ethoxy]phenylamino]-1H-1,2,4-triazole;
5-amino-1-(4-(tert-butyl)phenyl)carbonyl-3-[3-methoxy-4-[2-(pyrrolidin-1-yl)ethoxy]phenylamino]-1H-1,2,4-triazole;
5-amino-1-(4-(iso-propoxy)phenyl)carbonyl-3-[3-methoxy-4-[2-(pyrrolidin-1-yl)ethoxy]phenylamino]-1H-1,2,4-triazole;
5-amino-1-(4-(tert-butoxy)phenyl)carbonyl-3-[3-methoxy-4-[2-(pyrrolidin-1-yl)ethoxy]phenylamino]-1H-1,2,4-triazole;
5-amino-1-(4-(tert-butyl)phenyl)carbonyl-3-[4-[2-(azepan-1-yl)ethoxy]phenylamino]-1H-1,2,4-triazole;
5-amino-1-(4-(iso-propoxy)phenyl)carbonyl-3-[4-[2-(azepan-1-yl)ethoxy]phenylamino]-1H-1,2,4-triazole;
5-amino-1-(4-(tert-butoxy)phenyl)carbonyl-3-[4-[2-(azepan-1-yl)ethoxy]phenylamino]-1H-1,2,4-triazole;

5-amino-1-(4-(iso-propoxy)phenyl)carbonyl-3-[4-[2-(isoindolin-1-yl)ethoxy]phenylamino]-1H-1,2,4-triazole;
5-amino-1-(4-(tert-butoxy)phenyl)carbonyl-3-[4-[2-(isoindolin-1-yl)ethoxy]phenylamino]-1H-1,2,4-triazole;
5-amino-1-[4-(2-(morpholin-4-yl)ethoxy)phenyl]carbonyl-3-[4-[2-(pyrrolidin-1-yl)ethoxy]phenylamino]-1H-1,2,4-triazole;
5-amino-1-(4-(iso-propoxy)phenyl)carbonyl-3-[4-[2-(pyrrolidin-2-on-1-yl)ethoxy]phenylamino]-1H-1,2,4-triazole;
5-amino-1-(4-(tert-butoxy)phenyl)carbonyl-3-[4-[2-(pyrrolidin-2-on-1-yl)ethoxy]phenylamino]-1H-1,2,4-triazole;
5-amino-1-(4-(tert-butoxy)phenyl)carbonyl-3-[4-[2-(imidazol-1-yl)ethoxy]phenylamino]-1H-1,2,4-triazole;
5-amino-1-(3-(tert-butoxy)phenyl)carbonyl-3-[4-[2-(imidazol-1-yl)ethoxy]phenylamino]-1H-1,2,4-triazole;
5-amino-1-(4-(iso-propoxy)phenyl)carbonyl-3-[4-[2-(imidazol-1-yl)ethoxy]phenylamino]-1H-1,2,4-triazole;
5-amino-1-(4-(dimethylamino)phenyl)carbonyl-3-[4-[2-(imidazol-1-yl)ethoxy]phenylamino]-1H-1,2,4-triazole;
5-amino-1-(3-(dimethylamino)phenyl)carbonyl-3-[4-[2-(imidazol-1-yl)ethoxy]phenylamino]-1H-1,2,4-triazole;
5-amino-1-(4-(tert-butoxy)phenyl)carbonyl-3-[4-[2-(pyrrolidin-1-yl)ethoxy]phenylamino]-1H-1,2,4-triazole;
5-amino-1-(3-fluoro-4-methoxyphenyl)carbonyl-3-[4-[2-(pyrrolidin-1-yl)ethoxy]phenylamino]-1H-1,2,4-triazole;
5-amino-1-(4-(tert-butoxy)phenyl)carbonyl-3-[4-[2-((S)-3-fluoropyrrolidin-1-yl)ethoxy]phenylamino]-1H-1,2,4-triazole;
5-amino-1-(4-(dimethylamino)phenyl)carbonyl-3-[4-[2-((S)-3-fluoropyrrolidin-1-yl)ethoxy]phenylamino]-1H-1,2,4-triazole;
5-amino-1-(3,5-difluoro-4-methoxyphenyl)carbonyl-3-[4-[2-(pyrrolidin-1-yl)ethoxy]phenylamino]-1H-1,2,4-triazole; and
5-amino-3-[3-chloro-4-[2-(pyrrolidin-1-yl)ethoxy]phenylamino]-1-(3,5-dichlorophenyl)carbonyl-1H-1,2,4-triazole.

Another embodiment of the compounds of formula (Ia) are compounds of formula (Ia) wherein:
A is —C(O)—;
$R^1$ is phenyl substituted with one or more substituents selected from the group consisting of halo, haloalkyl, alkyl, —$R^8$—O—$R^6$—$OR^{10}$, —$R^8$—O—$R^9$—O—$R^6$—$OR^{10}$, and —$R^8$—$OR^{10}$ (where $R^{10}$ for —$R^8$—$OR^{10}$ is hydrogen, alkyl, haloalkyl, optionally substituted aryl, optionally substituted aralkyl, optionally substituted cycloalkyl, optionally substituted cycloalkylalkyl, optionally substituted heterocyclyl, or optionally substituted heteroaryl);
$R^2$, $R^4$ and $R^5$ are each hydrogen or alkyl;
$R^3$ is phenyl substituted with one or more substituents selected from the group consisting of alkyl, halo, haloalkyl, nitro, —$R^8$—$OR^{10}$, —$R^8$—$C(O)OR^{10}$, —$R^8$—$OC(O)R^{10}$, —$R^8$—O—$R^9$—$C(O)OR^{10}$, —$R^8$—O—$R^9$—$C(O)N(R^6)R^7$, —$S(O)_p R^6$ (where p is 0, 1 or 2), —$S(O)_t N(R^6)R^7$ (where t is 1 or 2), —$R^8$—$N(R^6)R^7$, —$R^8$—$N(R^6)C(O)R^{10}$, —$R^8$—$N(R^6)C(O)OR^{10}$ and —$R^8$—CN;
$R^6$ and $R^7$ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^9$—$OR^{10}$, —$R^9$—CN, —$R^9$—$NO_2$, —$R^9$—$N(R^{10})_2$, —$R^9$—$C(O)OR^{10}$ and —$R^6$—$C(O)N(R^{10})_2$;

optionally, $R^6$ and $R^7$, together with the nitrogen to which they are attached, form an optionally substituted N-heteroaryl or an optionally substituted N-heterocyclyl;
each $R^8$ is independently selected from the group consisting of a direct bond, an optionally substituted straight or branched alkylene chain, and an optionally substituted straight or branched alkenylene chain;
each $R^9$ is independently selected from the group consisting of an optionally substituted straight or branched alkylene chain, or an optionally substituted straight or branched alkenylene chain; and
each $R^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl.

Of this embodiment, a specific embodiment is a compound of formula (Ia) selected from the group consisting of:
5-amino-3-[3-(benzyloxy)phenylamino]-1-(4-(methyl)phenyl)carbonyl-1H-1,2,4-triazole;
5-amino-3-[3-(hydroxy)phenylamino]-1-(4-(methyl)phenyl)carbonyl-1H-1,2,4-triazole;
5-amino-3-[4-(benzyloxy)phenylamino]-1-(4-methylphenyl)carbonyl-1H-1,2,4-triazole;
5-amino-3-[4-(hydroxy)phenylamino]-1-(4-methylphenyl)carbonyl-1H-1,2,4-triazole;
5-amino-3-[3-(hydroxy)phenylamino]-1-(2-(methyl)phenyl)carbonyl-1H-1,2,4-triazole;
5-amino-3-[3-(hydroxy)phenylamino]-1-(3-(methyl)phenyl)carbonyl-1H-1,2,4-triazole;
5-amino-3-[4-(benzyloxy)phenylamino]-1-(4-(iso-propoxy)phenyl)carbonyl-1H-1,2,4-triazole;
5-amino-3-[3-(benzyloxy)phenylamino]-1-(3-(iso-propoxy)phenyl)carbonyl-1H-1,2,4-triazole;
5-amino-3-[4-(iso-propoxy)phenylamino]-1-(4-(iso-propoxy)phenyl)carbonyl-1H-1,2,4-triazole;
5-amino-3-[3-(hydroxy)phenylamino]-1-4-(iso-propoxy)phenyl)carbonyl-1H-1,2,4-triazole;
5-amino-3-[3-(hydroxy)phenylamino]-1-(3-(iso-propoxy)phenyl)carbonyl-1H-1,2,4-triazole;
5-amino-3-[3-(benzyloxy)phenylamino]-1-(4-(iso-propoxy)phenyl)carbonyl-1H-1,2,4-triazole;
5-amino-3-[3-(cyclopentoxy)phenylamino]-1-(4-(iso-propoxy)phenyl)carbonyl-1H-1,2,4-triazole;
5-amino-3-[4-(hydroxy)phenylamino]-1-(4-(iso-propoxy)phenyl)carbonyl-1H-1,2,4-triazole;
5-amino-1-(4-(iso-propoxy)phenyl)carbonyl-3-[4-(methoxy)phenylamino]-1H-1,2,4-triazole;
5-amino-3-[4-(ethoxy)phenylamino]-1-(4-(iso-propoxy)phenyl)carbonyl-1H-1,2,4-triazole;
5-amino-1-(4-(iso-propoxy)phenyl)carbonyl-3-[3-(methoxy)phenylamino]-1H-1,2,4-triazole;
5-amino-3-[3-(iso-propoxy)phenylamino]-1-(4-(iso-propoxy)phenyl)carbonyl-1H-1,2,4-triazole;
5-amino-3-[4-(fluoro)phenylamino]-1-(4-(methyl)phenyl)carbonyl-1H-1,2,4-triazole;
5-amino-3-[3-(fluoro)phenylamino]-1-(4-(methyl)phenyl)carbonyl-1H-1,2,4-triazole;
5-amino-3-[3-(ethoxy)phenylamino]-1-(4-(iso-propoxy)phenyl)carbonyl-1H-1,2,4-triazole;
5-amino-3-[2-(fluoro)phenylamino]-1-(4-(methyl)phenyl)carbonyl-1H-1,2,4-triazole;
5-amino-3-[4-(methyl)phenylamino]-1-(4-(methyl)phenyl)carbonyl-1H-1,2,4-triazole;

5-amino-3-[4-(methoxy)phenylamino]-1-(4-(methyl)phenyl)carbonyl-1H-1,2,4-triazole;
5-amino-3-[3-(methyl)phenylamino]-1-(4-(methyl)phenyl)carbonyl-1H-1,2,4-triazole;
5-amino-3-[3-(methoxy)phenylamino]-1-(4-(methyl)phenyl)carbonyl-1H-1,2,4-triazole;
5-amino-1-(4-(iso-propoxy)phenyl)carbonyl-3-[3-(2,2,2-trifluoroethoxy)phenylamino]-1H-1,2,4-triazole;
5-amino-3-[2-(methoxy)phenylamino]-1-(4-(methyl)phenyl)carbonyl-1H-1,2,4-triazole;
5-amino-3-[2-(methyl)phenylamino]-1-(4-(methyl)phenyl)carbonyl-1H-1,2,4-triazole;
5-amino-3-[-[2-(hydroxyl)ethoxy]phenylamino]-1-(3-(methyl)phenyl)carbonyl-1H-1,2,4-triazole;
5-amino-3-[4-(cyclopentoxy)phenylamino]-1-(4-(iso-propoxy)phenyl)carbonyl-1H-1,2,4-triazole;
5-amino-1-(4-(iso-propoxy)phenyl)carbonyl-3-[4-(2,2,2-trifluoroethoxy)phenylamino]-1H-1,2,4-triazole;
5-amino-3-[2-(hydroxyl)phenylamino]-1-(4-methylphenyl)carbonyl-1H-1,2,4-triazole;
5-amino-1-(3-methylphenyl)carbonyl-3-[3-[(2-methoxyethoxy)methoxy]phenylamino]-1H-1,2,4-triazole;
5-amino-3-(3-methoxymethoxy)phenylamino-1-(3-methylphenyl)carbonyl-1H-1,2,4-triazole;
5-amino-3-(4-chlorophenyl)amino-1-(4-chlorophenyl)carbonyl-1H-1,2,4-triazole;
5-amino-3-(4-bromophenyl)amino-1-(4-chlorophenyl)carbonyl-1H-1,2,4-triazole;
5-amino-3-[4-(iso-propoxy)phenylamino]-1-(4-(methyl)phenyl)carbonyl-1H-1,2,4-triazole;
5-amino-3-[4-(iso-propoxy)phenylamino]-1-(3-(nitro)phenyl)carbonyl-1H-1,2,4-triazole;
5-amino-1-(3-(hydroxy)phenyl)carbonyl-3-[4-(iso-propoxy)phenylamino]-1H-1,2,4-triazole;
5-amino-1-(3-(chloro)phenyl)carbonyl-3-[4-(iso-propoxy)phenylamino]-1H-1,2,4-triazole; and
5-amino-3-[4-(iso-propoxy)phenylamino]-1-[4-[2-(piperidin-1-yl)ethoxy]phenyl)carbonyl-1H-1,2,4-triazole.

Another embodiment of the compounds of formula (Ia) are compounds of formula (Ia) wherein:

A is —C(O)—;
$R^1$ is phenyl substituted with one or more substituents selected from the group consisting of halo, haloalkyl, alkyl, —$R^8$—$OR^{10}$, —$R^8$—O—$R^9$—$OR^{10}$, and —$R^8$—O—$R^9$—O—$R^9$—$OR^{10}$;
$R^2$, $R^4$ and $R^5$ are each hydrogen or alkyl;
$R^3$ is phenyl substituted with one or more substituents selected from the group consisting of cycloalkyl, cycloalkylalkyl, optionally substituted aryl, optionally substituted heteroaryl, and optionally substituted heterocyclyl;
each $R^8$ is independently selected from the group consisting of a direct bond, an optionally substituted straight or branched alkylene chain, and an optionally substituted straight or branched alkenylene chain;
each $R^9$ is independently selected from the group consisting of an optionally substituted straight or branched alkylene chain, or an optionally substituted straight or branched alkenylene chain; and
each $R^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl.

Another embodiment of the compounds of formula (Ia) are compounds of formula (Ia) wherein:
A is —C(O)—;
$R^1$ is phenyl substituted with —$R^8$—$OR^{10}$ and optionally substituted with halo, alkyl or alkoxy, where $R^8$ is a direct bond and $R^{10}$ is selected from the group consisting of 2-(pyrrolidin-1-yl)ethyl, 2-(piperidin-1-yl)ethyl, 2-(morpholin-4-yl)ethyl, 2-(1,3-dioxolan-2-yl)ethyl, 2-(thiomorpholin-4-yl)ethyl, 3-(pyrrolidin-1-yl)propyl, 2-(azepan-1-yl)ethyl, 2-(isoindolin-1-yl)ethyl, 2-(imidazol-1-yl)ethyl, 2-(pyrrolidin-2-on-1-yl)ethyl, and 2-(3-fluoropyrrolidin-1-yl)ethyl;
$R^2$, $R^4$ and $R^5$ are each hydrogen or alkyl; and
$R^3$ is phenyl substituted with one or more substituents selected from the group consisting of cycloalkyl, cycloalkylalkyl, optionally substituted aryl, optionally substituted heteroaryl, and optionally substituted heterocyclyl.

Of this embodiment, a specific embodiment is a compound of formula (Ia) selected from the group consisting of:
5-amino-3-[4-[2-(pyrrolidin-1-yl)ethoxy]-3-fluorophenyl]amino-1-[4-(morpholin-4-yl)phenyl]carbonyl-1H-1,2,4-triazole
5-amino-1-(4-(imidazol-1-yl)phenyl)carbonyl-3-[4-[2-(pyrrolidin-1-yl)ethoxy]phenylamino]-1H-1,2,4-triazole;
5-amino-1-(4-(phenyl)phenyl)carbonyl-3-[4-[2-(pyrrolidin-1-yl)ethoxy]phenylamino]-1H-1,2,4-triazole;
5-amino-1-(4-(1,2,3-thiadiazol-4-yl)phenyl)carbonyl-3-[4-[2-(pyrrolidin-1-yl)ethoxy]phenylamino]-1H-1,2,4-triazole;
5-amino-1-(4-(pyrrol-1-yl)phenyl)carbonyl-3-[4-[2-(pyrrolidin-1-yl)ethoxy]phenylamino]-1H-1,2,4-triazole;
5-amino-1-(4-(1,2,3-thiadiazol-4-yl)phenyl)carbonyl-3-[3-fluoro-4-[2-(pyrrolidin-1-yl)ethoxy]phenylamino]-1H-1,2,4-triazole;
5-amino-1-(3-(thiazol-2-yl)phenyl)carbonyl-3-[4-[2-(pyrrolidin-1-yl)ethoxy]phenylamino]-1H-1,2,4-triazole;
5-amino-1-(4-(thien-2-yl)phenyl)carbonyl-3-[4-[2-(pyrrolidin-1-yl)ethoxy]phenylamino]-1H-1,2,4-triazole;
5-amino-1-(3-(thien-2-yl)phenyl)carbonyl-3-[4-[2-(pyrrolidin-1-yl)ethoxy]phenylamino]-1H-1,2,4-triazole;
5-amino-1-(4-(thien-3-yl)phenyl)carbonyl-3-[4-[2-(pyrrolidin-1-yl)ethoxy]phenylamino]-1H-1,2,4-triazole;
5-amino-1-(4-(1,2,3-thiadiazol-4-yl)phenyl)carbonyl-3-[3-methoxy-4-[2-(pyrrolidin-1-yl)ethoxy]phenylamino]-1H-1,2,4-triazole;
5-amino-1-(4-(1,2,3-thiadiazol-4-yl)phenyl)carbonyl-3-[4-[2-(azepan-1-yl)ethoxy]phenylamino]-1H-1,2,4-triazole;
5-amino-1-(4-(morpholin-4-yl)phenyl)carbonyl-3-[4-[2-(isoindolin-1-yl)ethoxy]phenylamino]-1H-1,2,4-triazole;
5-amino-1-(3-(morpholin-4-yl)phenyl)carbonyl-3-[4-[2-(pyrrolidin-1-yl)ethoxy]phenylamino]-1H-1,2,4-triazole;
5-amino-1-(4-(1,2,3-thiadiazol-4-yl)phenyl)carbonyl-3-[4-[2-(pyrrolidin-2-on-1-yl)ethoxy]phenylamino]-1H-1,2,4-triazole;
5-amino-1-(4-(morpholin-4-yl)phenyl)carbonyl-3-[4-[2-(pyrrolidin-2-on-1-yl)ethoxy]phenylamino]-1H-1,2,4-triazole;
5-amino-1-(3-(morpholin-4-yl)phenyl)carbonyl-3-[4-[2-(pyrrolidin-2-on-1-yl)ethoxy]phenylamino]-1H-1,2,4-triazole;
5-amino-1-(4-(morpholin-4-yl)phenyl)carbonyl-3-[3-methoxy-4-[2-(pyrrolidin-1-yl)ethoxy]phenylamino]-1H-1,2,4-triazole;
5-amino-1-(3-(morpholin-4-yl)phenyl)carbonyl-3-[3-methoxy-4-[2-(pyrrolidin-1-yl)ethoxy]phenylamino]-1H-1,2,4-triazole;

5-amino-1-(4-(morpholin-4-yl)phenyl)carbonyl-3-[4-[2-(pyrrolidin-1-yl)ethoxy]phenylamino]-1H-1,2,4-triazole;

5-amino-1-(4-(4-methylpiperazin-1-yl)phenyl)carbonyl-3-[4-[2-(pyrrolidin-1-yl)ethoxy]phenylamino]-1H-1,2,4-triazole;

5-amino-1-(4-(1,1-dioxo-thiomorpholin-4-yl)phenyl)carbonyl-3-[4-[2-(pyrrolidin-1-yl)ethoxy]phenylamino]-1H-1,2,4-triazole; and 5-amino-1-(4-(piperidin-1-yl)phenyl)carbonyl-3-[4-[2-(pyrrolidin-1-yl)ethoxy]phenylamino]-1H-1,2,4-triazole.

Another embodiment of the compounds of formula (Ia) are compounds of formula (Ia) wherein:

A is —C(O)—;

$R^1$ is phenyl substituted with optionally substituted heteroaryl or optionally substituted heterocyclyl;

$R^2$, $R^4$ and $R^5$ are each hydrogen;

$R^3$ is phenyl substituted with one or more substituents selected from the group consisting of alkyl, halo, haloalkyl, nitro, cycloalkyl, cycloalkylalkyl, —$R^8$—$OR^{10}$, —$R^8$—C(O)$OR^{10}$, —$R^8$—OC(O)$R^{10}$, —$R^8$—O—$R^9$—C(O)$OR^{10}$, —$R^8$—O—$R^9$—C(O)N($R^6$)$R^7$, —S(O)$_p R^6$ (where p is 0, 1 or 2), —S(O)$_t$N($R^6$)$R^7$ (where t is 1 or 2), —$R^8$—N($R^6$)$R^7$, —$R^8$—N($R^6$)C(O)$R^{10}$, and —$R^8$—CN;

$R^6$ and $R^7$ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^9$—$OR^{10}$, —$R^9$—CN, —$R^9$—$NO_2$, —$R^9$—N($R^{10}$)$_2$, —$R^9$—C(O)$OR^{10}$ and —$R^9$—C(O)N($R^{10}$)$_2$;

each $R^8$ is independently selected from the group consisting of a direct bond, an optionally substituted straight or branched alkylene chain, and an optionally substituted straight or branched alkenylene chain;

each $R^9$ is independently selected from the group consisting of an optionally substituted straight or branched alkylene chain, or an optionally substituted straight or branched alkenylene chain; and each $R^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl.

Another embodiment of the compounds of formula (Ia) are compounds of formula (Ia) wherein:

A is —C(O)—;

$R^1$ is phenyl substituted with optionally substituted heteroaryl or optionally substituted heterocyclyl;

$R^2$, $R^4$ and $R^5$ are each hydrogen;

$R^3$ is phenyl substituted with one or more substituents selected from the group consisting of alkyl, halo, haloalkyl, cycloalkyl, and cycloalkylalkyl.

Of this embodiment, a specific embodiment is a compound of formula (Ia) selected from the group consisting of:

5-amino-1-(4-(iso-propyl)phenyl)carbonyl-3-(4-(morpholin-4-yl)phenylamino]-1H-1,2,4-triazole;

5-amino-1-(4-(methyl)phenyl)carbonyl-3-(4-(morpholin-4-yl)phenylamino)-1H-1,2,4-triazole;

5-amino-1-(3-(chloro)phenyl)carbonyl-3-(4-(morpholin-4-yl)phenylamino)-1H-1,2,4-triazole;

5-amino-1-(4-(tert-butyl)phenyl)carbonyl-3-[3-(1,3-oxazol-5-yl)phenylamino]-1H-1,2,4-triazole;

5-amino-1-(4-(tert-butyl)phenyl)carbonyl-3-[4-(pyrrolidin-1-yl)phenylamino]-1H-1,2,4-triazole; and 5-amino-1-(4-(methyl)phenyl)carbonyl-3-[4-(pyrrolidin-1-yl)phenylamino]-1H-1,2,4-triazole.

Another embodiment of the compounds of formula (Ia) are compounds of formula (Ia) wherein:

A is —C(O)—;

$R^1$ is phenyl substituted with optionally substituted heteroaryl or optionally substituted heterocyclyl;

$R^2$, $R^4$ and $R^5$ are each hydrogen;

$R^3$ is phenyl substituted with one or more substituents selected from the group consisting of —$R^8$—$OR^{10}$, —$R^8$—C(O)$OR^{10}$, —$R^8$—OC(O)$R^{10}$, —$R^8$—O—$R^9$—C(O)$OR^{10}$, —$R^8$—O—$R^9$—C(O)N($R^6$)$R^7$, —S(O)$_p R^6$ (where p is 0, 1 or 2), and —S(O)$_t$N($R^6$)$R^7$ (where t is 1 or 2);

$R^6$ and $R^7$ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^9$—$OR^{10}$, —$R^9$—CN, —$R^9$—$NO_2$, —$R^9$—N($R^{10}$)$_2$, —$R^9$—C(O)$OR^{10}$ and —$R^9$—C(O)N($R^{10}$)$_2$;

each $R^8$ is independently selected from the group consisting of a direct bond, an optionally substituted straight or branched alkylene chain, and an optionally substituted straight or branched alkenylene chain;

each $R^9$ is independently selected from the group consisting of an optionally substituted straight or branched alkylene chain, or an optionally substituted straight or branched alkenylene chain; and each $R^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl.

Of this embodiment, a specific embodiment is a compound of formula (Ia) selected from the group consisting of:

5-amino-1-(4-(iso-propoxy)phenyl)carbonyl-3-[3-(piperidin-1-yl)phenylamino]-1H-1,2,4-triazole;

5-amino-1-(3-(iso-propoxy)phenyl)carbonyl-3-[3-(1,3-oxazol-5-yl)phenylamino]-1H-1,2,4-triazole;

5-amino-1-(4-(iso-propoxy)phenyl)carbonyl-3-(4-(morpholin-4-yl)phenylamino]-1H-1,2,4-triazole;

5-amino-3-(4-(morpholin-4-yl)phenylamino)-1-(4-(tert-butoxy)phenyl)carbonyl-1H-1,2,4-triazole;

5-amino-1-(3-(hydroxy)phenyl)carbonyl-3-(4-(morpholin-4-yl)phenylamino)-1H-1,2,4-triazole;

5-amino-1-(4-(aminosulfonyl)phenyl)carbonyl-3-(4-(morpholin-4-yl)phenylamino)-1H-1,2,4-triazole;

5-amino-1-(3-(methoxy)phenyl)carbonyl-3-(4-(morpholin-4-yl)phenylamino)-1H-1,2,4-triazole;

5-amino-1-(4-(iso-propoxy)phenyl)carbonyl-3-[4-(piperidin-1-yl)phenylamino]-1H-1,2,4-triazole;

5-amino-1-(4-(tert-butoxy)phenyl)carbonyl-3-[3-(1,3-oxazol-5-yl)phenylamino]-1H-1,2,4-triazole;

5-amino-1-(4-(tert-butoxy)phenyl)carbonyl-3-[4-(pyrrolidin-1-yl)phenylamino]-1H-1,2,4-triazole;

5-amino-1-(4-(iso-propoxy)phenyl)carbonyl-3-[4-(pyrrolidin-1-yl)phenylamino]-1H-1,2,4-triazole;

5-amino-1-(4-(tert-butoxy)phenyl)carbonyl-3-[4-(4-methylpiperazin-1-yl)phenylamino]-1H-1,2,4-triazole;

5-amino-1-(3-(tert-butoxy)phenyl)carbonyl-3-[4-(4-methylpiperazin-1-yl)phenylamino]-1H-1,2,4-triazole; and 5-amino-1-(4-(iso-propoxy)phenyl)carbonyl-3-[4-(4-methylpiperazin-1-yl)phenylamino]-1H-1,2,4-triazole.

Another embodiment of the compounds of formula (Ia) are compounds of formula (Ia) wherein:

A is —C(O)—;

$R^1$ is phenyl substituted with optionally substituted heteroaryl or optionally substituted heterocyclyl;

$R^2$, $R^4$ and $R^5$ are each hydrogen;

$R^3$ is phenyl substituted with one or more substituents selected from the group consisting of alkyl, halo, haloalkyl, nitro, cycloalkyl, cycloalkylalkyl, —$R^8$—$OR^{10}$, —$R^8$—C(O)$R^{10}$, —$R^8$—OC(O)$R^{10}$, —$R^8$—O—$R^9$—C(O)$OR^{10}$, —$R^8$—O—$R^9$—C(O)N($R^6$)$R^7$, —S(O)$_p R^6$ (where p is 0, 1 or 2), —S(O)$_t$N($R^6$)$R^7$ (where t is 1 or 2), —$R^8$—N($R^6$)$R^7$, —$R^8$—N($R^6$)C(O)$R^{10}$, and —$R^8$—CN;

$R^6$ and $R^7$ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^9$—$OR^{10}$, —$R^9$—CN, —$R^9$—$NO_2$, —$R^9$—N($R^{10}$)$_2$, —$R^9$—C(O)$OR^{10}$ and —$R^8$—C(O)N($R^{10}$)$_2$;

each $R^8$ is independently selected from the group consisting of a direct bond, an optionally substituted straight or branched alkylene chain, and an optionally substituted straight or branched alkenylene chain;

each $R^9$ is independently selected from the group consisting of an optionally substituted straight or branched alkylene chain, or an optionally substituted straight or branched alkenylene chain; and each $R^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl.

Of this embodiment, a specific embodiment is a compound of formula (Ia) selected from the group consisting of:

5-amino-3-(4-(morpholin-4-yl)phenylamino)-1-(3-(nitro)phenyl)carbonyl-1H-1,2,4-triazole;

5-amino-1-(4-(dimethylamino)phenyl)carbonyl-3-[4-(pyrrolidin-1-yl)phenylamino]-1H-1,2,4-triazole;

5-amino-1-(4-(dimethylamino)phenyl)carbonyl-3-[4-(4-methylpiperazin-1-yl)phenylamino]-1H-1,2,4-triazole; and 5-amino-1-(3-(dimethylamino)phenyl)carbonyl-3-[4-(4-methylpiperazin-1-yl)phenylamino]-1H-1,2,4-triazole.

Another embodiment of the compounds of formula (Ia) are compounds of formula (Ia) wherein:

A is —C(O)—;

$R^1$ is phenyl substituted with —$R^8$—O—$R^9$—CN, —$R^8$—O—$R^9$—C(O)$OR^{10}$, —$R^8$—O—$R^9$—C(O)N($R^6$)$R^7$, —$R^8$—O—$R^9$—S(O)$_p R^6$ (where p is 0, 1 or 2), —$R^8$—O—$R^9$—N($R^6$)$R^7$, —$R^8$—O—$R^9$—C(N$R^{11}$)N($R^{11}$)H, and —$R^8$—N($R^6$)C(O)$R^{10}$;

$R^2$, $R^4$ and $R^5$ are each hydrogen;

$R^3$ is phenyl substituted with one or more substituents selected from the group consisting of alkyl, halo, haloalkyl, nitro, cycloalkyl, cycloalkylalkyl, —$R^8$—$OR^{10}$, —$R^8$—C(O)$OR^{10}$, —$R^8$—OC(O)$R^{10}$, —$R^8$—O—$R^9$—C(O)$OR^{10}$, —$R^8$—O—$R^9$—C(O)N($R^6$)$R^7$, —S(O)$_p R^6$ (where p is 0, 1 or 2), —S(O)$_t$N($R^6$)$R^7$ (where t is 1 or 2), —$R^8$—N($R^6$)$R^7$, —$R^8$—N($R^6$)C(O)$R^{10}$, and —$R^8$—CN;

$R^6$ and $R^7$ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^9$—$OR^{10}$, —$R^9$—CN, —$R^9$—$NO_2$, —$R^9$—N($R^{10}$)$_2$, —$R^9$—C(O)$OR^{10}$ and —$R^9$—C(O)N($R^{10}$)$_2$;

each $R^8$ is independently selected from the group consisting of a direct bond, an optionally substituted straight or branched alkylene chain, and an optionally substituted straight or branched alkenylene chain;

each $R^9$ is independently selected from the group consisting of an optionally substituted straight or branched alkylene chain, or an optionally substituted straight or branched alkenylene chain; and each $R^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl; and each $R^{11}$ is hydrogen, alkyl, cyano, nitro or —$OR^{10}$.

Another embodiment of the compounds of formula (Ia) are compounds of formula (Ia) wherein:

A is —C(O)—;

$R^1$ is phenyl substituted with —$R^8$—O—$R^9$—CN, —$R^8$—O—$R^9$—C(O)$OR^{10}$, —$R^8$—O—$R^9$—C(O)N($R^6$)$R^7$, —$R^8$—O—$R^9$—S(O)$_p R^6$ (where p is 0, 1 or 2), —$R^8$—O—$R^9$—N($R^6$)$R^7$, —$R^8$—O—$R^9$—C(N$R^{11}$)N($R^{11}$)H, and —$R^8$—N($R^6$)C(O)$R^{10}$;

$R^2$, $R^4$ and $R^5$ are each hydrogen;

$R^3$ is phenyl substituted with one or more substituents selected from the group consisting of nitro, —$R^8$—$OR^{10}$, —$R^8$—C(O)$OR^{10}$, —$R^8$—OC(O)$R^{10}$, —$R^8$—O—$R^9$—C(O)$OR^{10}$, —$R^8$—O—$R^9$—C(O)N($R^6$)$R^7$, —S(O)$_p R^6$ (where p is 0, 1 or 2), —S(O)$_t$N($R^6$)$R^7$ (where t is 1 or 2), —$R^8$—N($R^6$)$R^7$, —$R^8$—N($R^6$)C(O)$R^{10}$, and —$R^B$—CN;

$R^6$ and $R^7$ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^9$—$OR^{10}$, —$R^9$—CN, —$R^9$—$NO_2$, —$R^9$—N($R^{10}$)$_2$, —$R^9$—C(O)$OR^{10}$ and —$R^9$—C(O)N($R^{10}$)$_2$;

each $R^8$ is independently selected from the group consisting of a direct bond, an optionally substituted straight or branched alkylene chain, and an optionally substituted straight or branched alkenylene chain;

each $R^9$ is independently selected from the group consisting of an optionally substituted straight or branched alkylene chain, or an optionally substituted straight or branched alkenylene chain; and each $R^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl; and each $R^{11}$ is hydrogen, alkyl, cyano, nitro or —$OR^{10}$.

Of this embodiment, a specific embodiment is a compound of formula (Ia) selected from the group consisting of:

5-amino-1-(4-(iso-propoxy)phenyl)carbonyl-3-[3-(methoxycarbonylmethoxy)phenylamino]-1H-1,2,4-triazole;
5-amino-3-[4-(cyanomethoxy)phenylamino]-1-(4-(iso-propoxy)phenyl)carbonyl-1H-1,2,4-triazole;
5-amino-3-[3-(cyanomethoxy)phenylamino]-1-(4-(iso-propoxy)phenyl)carbonyl-1H-1,2,4-triazole;
5-amino-1-(4-(iso-propoxy)phenyl)carbonyl-3-[4-(methoxycarbonylmethoxy)phenylamino]-1H-1,2,4-triazole;
5-amino-3-[4-[2-(dimethylamino)ethoxy]phenylamino]-1-(4-(tert-butoxy)phenyl)carbonyl-1H-1,2,4-triazole;
5-amino-3-[4-[2-(dimethylamino)propoxy]phenylamino]-1-(4-(iso-propoxy)phenyl)carbonyl-1H-1,2,4-triazole;
5-amino-3-[4-[2-(dimethylamino)ethoxy]phenylamino]-1-(4-(iso-propoxy)phenyl)carbonyl-1H-1,2,4-triazole;
5-amino-3-[4-[2-(dimethylamino)ethoxy]phenylamino]-1-(4-(dimethylamino)phenyl)carbonyl-1H-1,2,4-triazole;
5-amino-1-(4-(dimethylamino)phenyl)carbonyl-3-[4-[2-(dimethylamino)propoxy]phenylamino]-1H-1,2,4-triazole; and
5-amino-3-[4-[2-(dimethylamino)propoxy]phenylamino]-1-(4-(tert-butoxy)phenyl)carbonyl-1H-1,2,4-triazole.

Another embodiment of the compounds of formula (Ia) are compounds of formula (Ia) wherein:

A is —C(O)—;
$R^1$ is phenyl substituted with —$R^8$—O—$R^9$—CN, —$R^8$—O—$R^9$—C(O)O$R^{10}$, —$R^8$—O—$R^9$—C(O)N($R^6$)$R^7$, —$R^8$—O—$R^9$—S(O)$_p$$R^6$ (where p is 0, 1 or 2), —$R^8$—O—$R^9$—N($R^6$)$R^7$, —$R^8$—O—$R^9$—C(N$R^{11}$)N($R^{11}$)H, and —$R^8$—N($R^6$)C(O)$R^{10}$;
$R^2$, $R^4$ and $R^5$ are each hydrogen;
$R^3$ is phenyl substituted with one or more substituents selected from the group consisting of alkyl, halo, haloalkyl, cycloalkyl, and cycloalkylalkyl;
$R^6$ and $R^7$ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^9$—O$R^{10}$, —$R^9$—CN, —$R^9$—NO$_2$, —$R^9$—N($R^{10}$)$_2$, —$R^9$—C(O)O$R^{10}$ and —$R^9$—C(O)N($R^{10}$)$_2$;
each $R^8$ is independently selected from the group consisting of a direct bond, an optionally substituted straight or branched alkylene chain, and an optionally substituted straight or branched alkenylene chain;
each $R^9$ is independently selected from the group consisting of an optionally substituted straight or branched alkylene chain, or an optionally substituted straight or branched alkenylene chain; and
each $R^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl; and
each $R^{11}$ is hydrogen, alkyl, cyano, nitro or —O$R^{10}$.

Of this embodiment, a specific embodiment is a compound of formula (Ia) selected from the group consisting of:
5-amino-3-[3-(cyanomethoxy)phenylamino]-1-(4-(methyl)phenyl)carbonyl-1H-1,2,4-triazole;
5-amino-3-[3-(cyanomethoxy)phenylamino]-1-(2-(methyl)phenyl)carbonyl-1H-1,2,4-triazole;
5-amino-3-[3-(cyanomethoxy)phenylamino]-1-(3-(methyl)phenyl)carbonyl-1H-1,2,4-triazole;
5-amino-3-[3-(methylaminocarbonylmethoxy)phenylamino]-1-(3-(methyl)phenyl)carbonyl-1H-1,2,4-triazole;
5-amino-3-[3-(methoxycarbonylmethoxy)phenylamino]-1-(3-(methyl)phenyl)carbonyl-1H-1,2,4-triazole;
5-amino-3-[3-(N-(2,2-dimethyl-1,3-dioxolan-4-yl)methyl)aminocarbonylmethoxy)phenylamino]-1-(3-(methyl)phenyl)carbonyl-1H-1,2,4-triazole;
5-amino-3-[3-(N-(2,3-dihydroxypropyl)amino)carbonylmethoxy]-phenylamino-1-(3-(methyl)phenyl)carbonyl-1H-1,2,4-triazole;
5-amino-3-[3-[cyclohexylaminocarbonylmethoxy]phenylamino]-1-(3-(methyl)phenyl)carbonyl-1H-1,2,4-triazole;
5-amino-1-(3-methylphenyl)carbonyl-3-[(3-tert-butoxycarbonylmethoxy)phenyl]amino-1H-1,2,4-triazole;
5-amino-1-(3-methylphenyl)carbonyl-3-[3-[2-(tetrahydropyran-2-yl)ethoxyaminocarbonyl]methoxy]phenylamino-1H-1,2,4-triazole;
5-amino-3-(3-hydroxycarbonylmethoxy)phenylamino-1-(3-methylphenyl)carbonyl-1H-1,2,4-triazole;
5-amino-3-[3-((2-hydroxyethyl)aminocarbonylmethoxy)phenyl]amino-1-(3-methylphenyl)carbonyl-1H-1,2,4-triazole;
5-amino-1-(3-methylphenyl)carbonyl-3-[3-[2-(4-morpholinyl)ethylaminocarbonylmethoxy]phenyl]amino-1H-1,2,4-triazole;
5-amino-1-(3-methylphenyl)carbonyl-3-[3-(N-tert-butoxycarbonyl)piperazin-4-ylcarbonylmethoxy)phenyl]amino-1H-1,2,4-triazole;
5-amino-1-(3-methylphenyl)carbonyl-3-[3-(piperazin-4-ylcarbonylmethoxy)phenyl]amino-1H-1,2,4-triazole;
5-amino-1-(3-methylphenyl)carbonyl-3-[3-(methylsulfonylmethoxy)phenyl]amino-1H-1,2,4-triazole;
5-amino-3-[4-[2-(dimethylamino)ethoxy]phenylamino]-1-(4-(methyl)phenyl)carbonyl-1H-1,2,4-triazole; and
5-amino-3-[4-[3-(dimethylamino)propoxy]phenylamino]-1-(4-(methyl)phenyl)carbonyl-1H-1,2,4-triazole.

Another embodiment of the compounds of formula (Ia) are compounds of formula (Ia) wherein:

A is —C(O)—;
$R^1$ is aryl substituted with one or more substituents selected from the group consisting of halo, haloalkyl, alkyl, optionally substituted heteroaryl, optionally substituted heterocyclyl, $R^8$—O$R^{10}$, —$R^8$—O—$R^9$—O$R^{10}$, —$R^8$—O—$R^9$—O—$R^9$—O$R^{10}$, —$R^8$—O—$R^9$—CN, —$R^8$—O—$R^9$—C(O)O$R^{10}$, —$R^8$—O—$R^9$—C(O)N($R^6$)$R^7$, —$R^8$—O—$R^9$—S(O)$_p$$R^6$ (where p is 0, 1 or 2), —$R^8$—O—$R^9$—N($R^6$)$R^7$, —$R^8$—O—$R^9$—C(N$R^{11}$)N($R^{11}$)H, and —$R^8$—N($R^6$)C(O)$R^{10}$;
$R^2$, $R^4$ and $R^5$ are each hydrogen;
$R^3$ is heteroaryl optionally substituted with one or more substituents selected from the group consisting of alkyl, oxo, and —$R^8$—O$R^{10}$;
$R^6$ and $R^7$ are each independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^9$—$OR^{10}$, —$R^9$—CN, —$R^9$—$NO_2$, —$R^9$—$N(R^{10})_2$, —$R^9$—$C(O)OR^{10}$ and —$R^9$—$C(O)N(R^{10})_2$;

optionally, $R^6$ and $R^7$, together with the nitrogen to which they are attached, form an optionally substituted N-heteroaryl or an optionally substituted N-heterocyclyl;

each $R^8$ is independently selected from the group consisting of a direct bond, an optionally substituted straight or branched alkylene chain, an optionally substituted straight or branched alkenylene chain and an optionally substituted straight or branched alkynylene chain;

each $R^9$ is independently selected from the group consisting of an optionally substituted straight or branched alkylene chain, an optionally substituted straight or branched alkenylene chain and an optionally substituted straight or branched alkynylene chain; and each $R^{10}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl; and each $R^{11}$ is hydrogen, alkyl, cyano, nitro or —$OR^{10}$.

Another embodiment of the compounds of formula (Ia) are compounds of formula (Ia) wherein:

A is —C(O)—;

$R^1$ is phenyl substituted with one or more substituents selected from the group consisting of halo, haloalkyl, alkyl, optionally substituted heteroaryl, optionally substituted heterocyclyl, —$R^9$—$OR^{10}$, —$R^9$—O—$R^9$—$OR^{10}$, —$R^8$—O—$R^9$—O—$R^9$—$OR^{10}$, —$R^8$—O—$R^9$—$C(O)OR^{10}$, —$R^8$—O—$R^9$—$C(O)N(R^6)R^7$, —$R^8$—O—$R^9$—$S(O)_pR^6$ (where p is 0, 1 or 2), —$R^3$—O—$R^9$—$N(R^6)R^7$, —$R^8$—O—$R^9$—$C(NR^{11})N(R^{11})H$, and —$R^8$—$N(R^6)C(O)R^{10}$;

$R^2$, $R^4$ and $R^5$ are each hydrogen;

$R^3$ is heteroaryl optionally substituted with one or more substituents selected from the group consisting of alkyl, oxo, and —$R^8$—$OR^{10}$;

$R^6$ and $R^7$ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally optionally substituted heterocyclyl, optionally substituted heterocyclylalkyl, optionally substituted heteroaryl, optionally substituted heteroarylalkyl, —$R^9$—$OR^{10}$, —$R^9$—CN, —$R^9$—$NO_2$, —$R^9$—$N(R^{10})_2$, —$R^9$—$C(O)OR^{10}$ and —$R^9$—$C(O)N(R^{10})_2$;

each $R^8$ is independently selected from the group consisting of a direct bond, an optionally substituted straight or branched alkylene chain or an optionally substituted straight or branched alkenylene chain;

each $R^9$ is independently selected from the group consisting of an optionally substituted straight or branched alkylene chain or an optionally substituted straight or branched alkenylene chain; and each $R^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, or optionally substituted heteroarylalkyl; and each $R^{11}$ is hydrogen, alkyl, cyano, nitro or —$OR^{10}$.

Another embodiment of the compounds of formula (Ia) are compounds of formula (Ia) wherein:

A is —C(O)—;

$R^1$ is phenyl substituted with —$R^8$—$OR^{10}$ and optionally substituted with halo or alkoxy, where $R^8$ is a direct bond and $R^{10}$ is selected from the group consisting of 2-(pyrrolidin-1-yl)ethyl, 2-(piperidin-1-yl)ethyl, 2-(morpholin-4-yl)ethyl, 2-(1,3-dioxolan-2-yl)ethyl, 2-(thiomorpholin-4-yl)ethyl, 3-(pyrrolidin-1-yl)propyl, 2-(azepan-1-yl)ethyl, 2-(isoindolin-1-yl)ethyl, 2-(imidazol-1-yl)ethyl, 2-(pyrrolidin-2-on-1-yl)ethyl, and 2-(3-fluoropyrrolidin-1-yl)ethyl;

$R^2$, $R^4$ and $R^5$ are each hydrogen;

$R^3$ is heteroaryl optionally substituted with one or more substituents selected from the group consisting of alkyl, oxo, and —$R^8$—$OR^{10}$;

$R^6$ and $R^7$ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally optionally substituted heterocyclyl, optionally substituted heterocyclylalkyl, optionally substituted heteroaryl, optionally substituted heteroarylalkyl, —$R^9$—$OR^{10}$, —$R^9$—CN, —$R^9$—$NO_2$, —$R^9$—$N(R^{10})_2$, —$R^9$—$C(O)OR^{10}$ and —$R^9$—$C(O)N(R^{10})_2$;

each $R^8$ is independently selected from the group consisting of a direct bond, an optionally substituted straight or branched alkylene chain or an optionally substituted straight or branched alkenylene chain;

each $R^9$ is independently selected from the group consisting of an optionally substituted straight or branched alkylene chain or an optionally substituted straight or branched alkenylene chain; and each $R^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, or optionally substituted heteroarylalkyl; and each $R^{11}$ is hydrogen, alkyl, cyano, nitro or —$OR^{10}$.

Of this embodiment, a specific embodiment is a compound of formula (Ia) selected from the group consisting of:

5-amino-1-(3-(iso-propoxy)pyridin-5-yl)carbonyl-3-[4-[2-(morpholin-4-yl)ethoxy]phenylamino]-1H-1,2,4-triazole;

5-amino-1-(2,2-dimethyl-2H-benzo[b][1,4]oxazin-3(4H)-on-6-yl)carbonyl-3-[4-[2-(piperidin-1-yl)ethoxy]phenylamino]-1H-1,2,4-triazole;

5-amino-1-(1,3-benzodioxol-5-yl)carbonyl-3-[4-[2-(piperidin-1-yl)ethoxy]phenylamino]-1H-1,2,4-triazole;

5-amino-1-(1,3-benzodioxol-5-yl)carbonyl-3-[4-[2-(pyrrolidin-1-yl)ethoxy]phenylamino]-1H-1,2,4-triazole;

5-amino-1-(1,4-benzodioxan-6-yl)carbonyl-3-[4-[2-(pyrrolidin-1-yl)ethoxy]phenylamino]-1H-1,2,4-triazole;

5-amino-1-(1H-indol-5-yl)carbonyl-3-[4-[2-(pyrrolidin-1-yl)ethoxy]phenylamino]-1H-1,2,4-triazole;

5-amino-1-(1H-indol-6-yl)carbonyl-3-[4-[2-(pyrrolidin-1-yl)ethoxy]phenylamino]-1H-1,2,4-triazole;

5-amino-1-(1H-indol-2-yl)carbonyl-3-[4-[2-(pyrrolidin-1-yl)ethoxy]phenylamino]-1H-1,2,4-triazole;

5-amino-1-(benzimidazol-6-yl)carbonyl-3-[4-[2-(pyrrolidin-1-yl)ethoxy]phenylamino]-1H-1,2,4-triazole;

5-amino-1-(6-(methyl)pyridin-3-yl)carbonyl-3-[4-[2-(pyr-rolidin-1-yl)ethoxy]phenylamino]-1H-1,2,4-triazole;
5-amino-1-(pyridin-2-yl)carbonyl-3-[4-[2-(pyrrolidin-1-yl)ethoxy]phenylamino]-1H-1,2,4-triazole;
5-amino-1-(pyridin-4-yl)carbonyl-3-[4-[2-(pyrrolidin-1-yl)ethoxy]phenylamino]-1H-1,2,4-triazole;
5-amino-1-(1H-indol-6-yl)carbonyl-3-[4-[2-(morpholin-4-yl)ethoxy]phenylamino]-1H-1,2,4-triazole;
5-amino-1-(benzo[d]thiazol-6-yl)carbonyl-3-[4-[2-(pyrrolidin-1-yl)ethoxy]phenylamino]-1H-1,2,4-triazole;
5-amino-1-(2,3-dihydrobenzofuran-5-yl)carbonyl-3-[4-[2-(pyrrolidin-1-yl)ethoxy]phenylamino]-1H-1,2,4-triazole;
5-amino-1-(1H-benzo[d][1,2,3]triazol-5-yl)carbonyl-3-[4-[2-(pyrrolidin-1-yl)ethoxy]phenylamino]-1H-1,2,4-triazole;
5-amino-1-(3-methylthien-2-yl)carbonyl-3-[4-[2-(pyrrolidin-1-yl)ethoxy]phenylamino]-1H-1,2,4-triazole;
5-amino-1-(5-methylthien-2-yl)carbonyl-3-[4-[2-(pyrrolidin-1-yl)ethoxy]phenylamino]-1H-1,2,4-triazole;
5-amino-1-(thien-2-yl)carbonyl-3-[4-[2-(pyrrolidin-1-yl)ethoxy]phenylamino]-1H-1,2,4-triazole;
5-amino-1-(quinolin-6-yl)carbonyl-3-[4-[2-(pyrrolidin-1-yl)ethoxy]phenylamino]-1H-1,2,4-triazole;
5-amino-1-(1H-indol-6-yl)carbonyl-3-[3-fluoro-4-[2-(pyrrolidin-1-yl)ethoxy]phenylamino]-1H-1,2,4-triazole;
5-amino-1-(1,2,3-thiadiazol-4-yl)carbonyl-3-[4-[2-(pyrrolidin-1-yl)ethoxy]phenylamino]-1H-1,2,4-triazole;
5-amino-1-(1H-indol-6-yl)carbonyl-3-[3-methoxy-4-[2-(pyrrolidin-1-yl)ethoxy]phenylamino]-1H-1,2,4-triazole;
5-amino-1-(1H-indol-6-yl)carbonyl-3-[4-[2-(azepan-1-yl)ethoxy]phenylamino]-1H-1,2,4-triazole;
5-amino-1-(1H-indol-6-yl)carbonyl-3-[4-[2-(isoindolin-1-yl)ethoxy]phenylamino]-1H-1,2,4-triazole;
5-amino-1-(1H-indol-3-yl)carbonyl-3-[4-[2-(pyrrolidin-1-yl)ethoxy]phenylamino]-1H-1,2,4-triazole;
5-amino-1-(benzo[b]thiophen-2-yl)carbonyl-3-[4-[2-(pyrrolidin-1-yl)ethoxy]phenylamino]-1H-1,2,4-triazole;
5-amino-1-(benzo[b]thiophen-5-yl)carbonyl-3-[4-[2-(pyrrolidin-1-yl)ethoxy]phenylamino]-1H-1,2,4-triazole;
5-amino-1-(1H-indol-6-yl)carbonyl-3-[4-[2-(imidazol-1-yl)ethoxy]phenylamino]-1H-1,2,4-triazole;
5-amino-1-(benzo[b]thiophen-5-yl)carbonyl-3-[4-[2-(imidazol-1-yl)ethoxy]phenylamino]-1H-1,2,4-triazole;
5-amino-1-(benzo[b]thiophen-2-yl)carbonyl-3-[4-[2-(imidazol-1-yl)ethoxy]phenylamino]-1H-1,2,4-triazole;
5-amino-1-(1,4-benzodioxan-6-yl)carbonyl-3-[4-[2-((S)-3-fluoropyrrolidin-1-yl)ethoxy]phenylamino]-1H-1,2,4-triazole; and
5-amino-1-(1H-indol-6-yl)carbonyl-3-[4-[2-((S)-3-fluoropyrrolidin-1-yl)ethoxy]phenylamino]-1H-1,2,4-triazole.

Another embodiment of the compounds of formula (Ia) are compounds of formula (Ia) wherein:

A is —C(O)—;

$R^1$ is phenyl substituted with one or more substituents selected from the group consisting of halo, haloalkyl, alkyl, optionally substituted heteroaryl, optionally substituted heterocyclyl, —$R^8$—O—$R^9$—$OR^{10}$, —$R^8$—O—$R^9$—O—$R^9$—$OR^{10}$, —$R^8$—O—$R^9$—$C(O)OR^{10}$, —$R^8$—O—$R^9$—$C(O)N(R^6)R^7$, —$R^8$—O—$R^9$—$S(O)_pR^6$ (where p is 0, 1 or 2), —$R^8$—O—$R^9$—$N(R^6)R^7$, —$R^8$—O—$R^9$—$C(NR^{11})N(R^{11})H$, —$R^8$—$N(R^6)C(O)R^{10}$, and —$R^8$—$OR^{10}$ (where $R^{10}$ for —$R^8$—$OR^{10}$ is hydrogen, alkyl, haloalkyl, optionally substituted aryl, optionally substituted aralkyl, optionally substituted cycloalkyl, optionally substituted cycloalkylalkyl, optionally substituted heterocyclyl, or optionally substituted heteroaryl);

$R^2$, $R^4$ and $R^5$ are each hydrogen;

$R^3$ is heteroaryl optionally substituted with one or more substituents selected from the group consisting of alkyl, oxo, and —$R^8$—$OR^{10}$;

$R^6$ and $R^7$ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally optionally substituted heterocyclyl, optionally substituted heterocyclylalkyl, optionally substituted heteroaryl, optionally substituted heteroarylalkyl, —$R^9$—$OR^{10}$, —$R^9$—CN, —$R^9$—$NO_2$, —$R^9$—N($R^{10}$)$_2$, —$R^9$—$C(O)OR^{10}$ and —$R^9$—$C(O)N(R^{10})_2$;

each $R^8$ is independently selected from the group consisting of a direct bond, an optionally substituted straight or branched alkylene chain or an optionally substituted straight or branched alkenylene chain;

each $R^9$ is independently selected from the group consisting of an optionally substituted straight or branched alkylene chain or an optionally substituted straight or branched alkenylene chain; and each $R^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, or optionally substituted heteroarylalkyl; and each $R^{11}$ is hydrogen, alkyl, cyano, nitro or —$OR^{10}$.

Of this embodiment, a specific embodiment is a compound of formula (Ia) selected from the group consisting of:

5-amino-1-(2,2-dimethyl-2H-benzo[b][1,4]oxazin-3(4H)-on-6-yl)carbonyl-3-(4-(iso-propoxy)phenyl)amino-1H-1,2,4-triazole;
5-amino-1-(2,2-dimethyl-2H-benzo[b][1,4]oxazin-3(4H)-on-6-yl)carbonyl-3-(4-(morpholin-4-yl)phenylamino)-1H-1,2,4-triazole;
5-amino-3-[4-[2-(dimethylamino)ethoxy]phenylamino]-1-(2,2-dimethyl-2H-benzo[b][1,4]oxazin-3(4H)-on-6-yl)carbonyl-1H-1,2,4-triazole;
5-amino-3-[4-[2-(dimethylamino)propoxy]phenylamino]-1-(2,2-dimethyl-2H-benzo[b][1,4]oxazin-3(4H)-on-6-yl)carbonyl-1H-1,2,4-triazole; and
5-amino-1-(2,2-dimethyl-2H-benzo[b][1,4]oxazin-3(4H)-on-6-yl)carbonyl-3-[4-(pyrrolidin-1-yl)phenylamino]-1H-1,2,4-triazole.

Another embodiment of the compounds of formula (Ia) are compounds of formula (Ia) wherein:

A is —C(O)—;

$R^1$ is heteroaryl optionally substituted with one or more substituents selected from the group consisting of alkyl, halo, oxo, —$R^8$—$OR^{10}$, —$R^8$—$C(O)OR^{10}$, —$R^8$—$C(O)N(R^6)R^7$ and —$R^8$—$N(R^6)R^7$;

or $R^1$ is heterocyclyl optionally substituted with one or more substituents selected from the group consisting of halo, haloalkyl, alkyl, oxo, —$R^8$—$OR^{10}$, —$R^8$—$C(O)OR^{10}$, —$R^8$—$C(O)N(R^6)R^7$, —$R^9$—$S(O)_pR^{10}$ (where p is 0, 1 or 2) and —$R^8$—$N(R^6)R^7$;

or $R^1$ is heterocyclylalkyl optionally substituted with one or more substitutents selected from the group consisting of halo, haloalkyl, alkyl, optionally substituted aryl, optionally substituted aralkyl, —$R^8$—$OR^{10}$, —$R^8$—$C(O)OR^{10}$, —$R^8$—$C(O)N(R^6)R^7$ and —$R^8$—$N(R^6)R^7$;

$R^2$ is hydrogen, alkyl or —$C(O)R^{10}$;

$R^4$ and $R^5$ are each hydrogen or alkyl;

$R^3$ is one of the following:

a) alkyl optionally substituted with one or more substituents selected from the group consisting of halo, cyano, nitro, oxo, thioxo, trimethylsilanyl, —OC(O)—$R^{14}$, —N($R^{14}$)$_2$, —C(O)$R^{14}$, —C(O)O$R^{14}$, —C(O)N($R^{14}$)$_2$, —N($R^{14}$)C(O)O$R^{14}$, —N($R^{14}$)C(O)$R^{14}$, —N($R^{14}$)S(O)$_t$$R^{14}$ (where t is 1 or 2), —S(O)$_t$O$R^{14}$ (where t is 1 or 2), —S(O)$_p$$R^{14}$ (where p is 0, 1 or 2), and —S(O)$_t$N($R^{14}$)$_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl;

b) cycloalkyl optionally substituted with one or more substituents selected from the group consisting of —$R^8$—O$R^{10}$, alkyl, halo, haloalkyl, aryl, and aralkyl;

c) aryl substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, —$R^8$—O$R^{10}$, —$R^8$—C(O)O$R^{10}$, —$R^8$—OC(O)$R^{10}$, —$R^8$—O—$R^9$—C(O)O$R^{10}$, —$R^8$—O—$R^9$—C(O)N($R^8$)$R^7$, —S(O)$_p$$R^8$ (where p is 0, 1 or 2), —S(O)$_t$N($R^8$)$R^7$ (where t is 1 or 2), —$R^8$—N($R^6$)$R^7$, —$R^8$—N($R^8$)C(O)$R^{10}$ and —$R^8$—CN;

d) aralkyl, wherein:
  (1) the alkyl part of the aralkyl radical is optionally substituted with one or more substituents selected from the group consisting of halo, cyano, nitro, oxo, thioxo, trimethylsilanyl, —O$R^{14}$, —OC(O)—$R^{14}$, —N($R^{14}$)$_2$, —C(O)$R^{14}$, —C(O)O$R^{14}$, —C(O)N($R^{14}$)$_2$, —N($R^{14}$)C(O)O$R^{14}$, —N($R^{14}$)C(O)$R^{14}$, —N($R^{14}$)S(O)$_t$$R^{14}$ (where t is 1 or 2), —S(O)$_t$O$R^{14}$ (where t is 1 or 2), —S(O)$_p$$R^{14}$ (where p is 0, 1 or 2), and —S(O)$_t$N($R^{14}$)$_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl; and
  (2) the aryl part of the aralkyl radical is optionally substituted with one or more substituents selected from the group consisting of alkyl, alkenyl, alkynyl, halo, haloalkyl, haloalkenyl, haloalkynyl, cyano, nitro, aryl, aralkyl, aralkenyl, aralkynyl, cycloalkyl, cycloalkylalkyl, cycloalkylalkenyl, cycloalkylalkynyl, heterocyclyl, heterocyclylalkyl, heterocyclylalkenyl, heterocyclylalkynyl, heteroaryl, heteroarylalkyl, heteroarylalkenyl, heteroarylalkynyl, —$R^{15}$—O$R^{14}$, —$R^{15}$—OC(O)—$R^{14}$, —$R^{15}$—N($R^{14}$)$_2$, —$R^{15}$—C(O)$R^{14}$, —$R^{15}$—C(O)O$R^{14}$, —$R^{15}$—C(O)N($R^{14}$)$_2$, —$R^{15}$—O—$R^{10}$—C(O)N($R^{14}$)$_2$, —$R^{15}$—N($R^{14}$)C(O)O$R^{14}$, —$R^{15}$—N($R^{14}$)C(O)$R^{14}$, —$R^{15}$—N($R^{14}$)S(O)$_t$$R^{14}$ (where t is 1 or 2), —$R^{15}$—S(O)$_t$O$R^{14}$ (where t is 1 or 2), —$R^{15}$—S(O)$_p$$R^{14}$ (where p is 0, 1 or 2), and —$R^{15}$—S(O)$_t$N($R^{14}$)$_2$ (where t is 1 or 2), where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl, each $R^{15}$ is independently a direct bond or a straight or branched alkylene or alkenylene chain, and $R^{16}$ is a straight or branched alkylene or alkenylene chain;

e) heteroaryl optionally substituted with one or more substituents selected from the group consisting of alkyl, oxo, and —$R^8$—O$R^{10}$; or f) heteroarylalkenyl where the heteroaryl part of the heteroarylalkyl radical is optionally substituted with one or more substituents selected from the group consisting of alkyl, halo, haloalkyl, aryl and aralkyl;

$R^6$ and $R^7$ are each independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^9$—O$R^{15}$, —$R^9$—CN, —$R^9$—NO$_2$, —$R^9$—N($R^{10}$)$_2$, —$R^9$—C(O)O$R^{15}$ and —$R^9$—C(O)N($R^{10}$)$_2$;

optionally, $R^6$ and $R^7$, together with the nitrogen to which they are attached, form an optionally substituted N-heteroaryl or an optionally substituted N-heterocyclyl;

each $R^8$ is independently selected from the group consisting of a direct bond, an optionally substituted straight or branched alkylene chain, an optionally substituted straight or branched alkenylene chain and an optionally substituted straight or branched alkynylene chain;

each $R^9$ is independently selected from the group consisting of an optionally substituted straight or branched alkylene chain, an optionally substituted straight or branched alkenylene chain and an optionally substituted straight or branched alkynylene chain; and each $R^{10}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl.

Another embodiment of the compounds of formula (Ia) are compounds of formula (Ia) wherein:

A is —C(O)—;

$R^1$ is heteroaryl optionally substituted with one or more substituents selected from the group consisting of alkyl, halo, oxo, —$R^8$—O$R^{10}$, —$R^8$—C(O)O$R^{10}$, —$R^8$—C(O)N($R^6$)$R^7$ and —$R^8$—N($R^8$)$R^7$;

or $R^1$ is heterocyclyl optionally substituted with one or more substituents selected from the group consisting of halo, haloalkyl, alkyl, oxo, —$R^8$—O$R^{10}$, —$R^8$—C(O)O$R^{10}$, —$R^8$—C(O)N($R^6$)$R^7$, —$R^8$—S(O)$_p$$R^{10}$ (where p is 0, 1 or 2) and —$R^8$—N($R^6$)$R^7$;

or $R^1$ is heterocyclylalkyl optionally substituted with one or more substitutents selected from the group consisting of halo, haloalkyl, alkyl, optionally substituted aryl, optionally substituted aralkyl, —$R^8$—O$R^{10}$, —$R^8$—C(O)O$R^{10}$, —$R^8$—C(O)N($R^6$)$R^7$ and —$R^8$—N($R^6$)$R^7$;

$R^2$ is hydrogen, alkyl or —C(O)$R^{10}$, $R^4$ and $R^5$ are each hydrogen or alkyl;

$R^3$ is alkyl optionally substituted with one or more substituents selected from the group consisting of halo, cyano, nitro, oxo, thioxo, trimethylsilanyl, —O$R^{14}$, —OC(O)—$R^{14}$, —N($R^{14}$)$_2$, —C(O)$R^{14}$, —C(O)O$R^{14}$, —C(O)N($R^{14}$)$_2$, —N($R^{14}$)C(O)O$R^{14}$, —N($R^{14}$)C(O)$R^{14}$, —N($R^{14}$)S(O)$_t$$R^{14}$ (where t is 1 or 2), —S(O)$_t$O$R^{14}$ (where t is 1 or 2), —S(O)$_p$R$^{14}$ (where p is 0, 1 or 2), and —S(O)$_t$N(R$^{14}$)$_2$ (where t is 1 or 2) where each R$^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl;

or R$^3$ is phenyl substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, —R$^8$—OR$^{10}$, —R$^8$—C(O)OR$^{10}$, —R$^8$—OC(O)R$^{10}$, —R$^8$—O—R$^9$—C(O)OR$^{10}$, —R$^8$—O—R$^9$—C(O)N(R$^6$)R$^7$, —S(O)$_p$R$^6$ (where p is 0, 1 or 2), —S(O)$_t$N(R$^6$)R$^7$ (where t is 1 or 2), —R$^8$—N(R$^6$)R$^7$, —R$^8$—N(R$^6$)C(O)R$^{10}$ and —R$^8$—CN;

or R$^3$ is heteroaryl optionally substituted with one or more substituents selected from the group consisting of alkyl, oxo, and —R$^8$—OR$^{10}$;

R$^6$ and R$^7$ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally optionally substituted heterocyclyl, optionally substituted heterocyclylalkyl, optionally substituted heteroaryl, optionally substituted heteroarylalkyl, —R$^9$—OR$^{10}$, —R$^9$—CN, —R$^9$—NO$_2$, —R$^9$—N(R$^{10}$)$_2$, —R$^9$—C(O)OR$^{10}$ and —R$^9$—C(O)N(R$^{10}$)$_2$;

each R$^8$ is independently selected from the group consisting of a direct bond, an optionally substituted straight or branched alkylene chain or an optionally substituted straight or branched alkenylene chain;

each R$^9$ is independently selected from the group consisting of an optionally substituted straight or branched alkylene chain or an optionally substituted straight or branched alkenylene chain; and each R$^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, or optionally substituted heteroarylalkyl.

Another embodiment of the compounds of formula (Ia) are compounds of formula (Ia) wherein:

A is —C(O)—;

R$^1$ is heterocyclyl optionally substituted with one or more substituents selected from the group consisting of halo, haloalkyl, alkyl, oxo, —R$^8$—OR$^{10}$, —R$^8$—C(O)OR$^{10}$, —R$^8$—C(O)N(R$^6$)R$^7$, —R$^8$—S(O)$_p$R$^{10}$ (where p is 0, 1 or 2) and —R$^8$—N(R$^6$)R$^7$;

or R$^1$ is heterocyclylalkyl optionally substituted with one or more substitutents selected from the group consisting of halo, haloalkyl, alkyl, optionally substituted aryl, optionally substituted aralkyl, —R$^8$—OR$^{10}$, —R$^8$—C(O)OR$^{10}$, —R$^8$—C(O)N(R$^6$)R$^7$ and —R$^8$—N(R$^6$)R$^7$;

R$^2$ is hydrogen, alkyl or —C(O)R$^{10}$;

R$^4$ and R$^5$ are each hydrogen or alkyl;

R$^3$ is phenyl substituted with one or more substituents selected from the group consisting of alkyl, halo, haloalkyl, optionally substituted heterocyclyl, —R$^8$—OR$^{10}$, and —R$^8$—N(R$^6$)R$^7$;

or R$^3$ is heteroaryl optionally substituted with one or more substituents selected from the group consisting of alkyl, oxo, and —R$^8$—OR$^{10}$;

R$^6$ and R$^7$ are each independently selected from the group consisting of hydrogen, alkyl, haloalkyl, hydroxyalkyl, optionally substituted aryl, and optionally substituted aralkyl;

each R$^8$ is independently selected from the group consisting of a direct bond and an optionally substituted straight or branched alkylene chain;

each R$^{10}$ is independently selected from the group consisting of hydrogen, alkyl, haloalkyl, optionally substituted aryl, and optionally substituted aralkyl.

Of this embodiment, a specific embodiment is a compound of formula (Ia) selected from the group consisting of:

5-amino-1-(2,6-difluorophenyl)carbonyl-3-(1-methylsulfonylpiperidin-4-yl)amino-1H-1,2,4-triazole;

5-amino-1-(4-(tert-butoxy)phenyl)carbonyl-3-(1-methylsulfonylpiperidin-4-yl)amino-1H-1,2,4-triazole;

5-amino-1-(4-(iso-propoxy)phenyl)carbonyl-3-(1-methylsulfonylpiperidin-4-yl)-amino-1H-1,2,4-triazole;

5-amino-1-(4-(dimethylamino)phenyl)carbonyl-3-(1-methylsulfonylpiperidin-4-yl)amino-1H-1,2,4-triazole;

5-amino-1-(1,4-benzodioxan-6-yl)carbonyl-3-(1-methylsulfonylpiperidin-4-yl)amino-1H-1,2,4-triazole;

5-amino-1-(1H-indol-6-yl)carbonyl-3-(1-methylsulfonylpiperidin-4-yl)amino-1H-1,2,4-triazole;

5-amino-1-(4-(morpholin-4-yl)phenyl)carbonyl-3-(1-methylsulfonylpiperidin-4-yl)amino-1H-1,2,4-triazole;

5-amino-3-[N-(3-(4-(2-chloro-6-fluorophenyl)piperazin-1-yl)prop-1-yl)-N-((3-methylphenyl)carbonyl)amino]-1-(3-methylphenyl)carbonyl-1H-1,2,4-triazole; and 5-amino-3-[3-(4-(2-chloro-6-fluorophenyl)piperazin-1-yl)prop-1-yl]amino-1-(3-methylphenyl)carbonyl-1H-1,2,4-triazole.

Another embodiment of the compounds of formula (Ia) are compounds of formula (Ia) wherein:

A is —C(O)—;

R$^1$ is heteroaryl optionally substituted with one or more substituents selected from the group consisting of alkyl, halo, oxo, —R$^8$—OR$^{10}$, —R$^8$—C(O)OR$^{10}$, —R$^8$—C(O)N(R$^6$)R$^7$ and —R$^6$—N(R$^6$)R$^7$;

R$^2$, R$^4$ and R$^5$ are each hydrogen;

R$^3$ is alkyl optionally substituted with one or more substituents selected from the group consisting of halo, cyano, nitro, oxo, thioxo, trimethylsilanyl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{14}$, —N(R$^{14}$)C(O)R$^{14}$, —N(R$^{14}$)S(O)$_t$R$^{14}$ (where t is 1 or 2), —S(O)$_t$OR$^{14}$ (where t is 1 or 2), —S(O)$_p$R$^{14}$ (where p is 0, 1 or 2), and —S(O)$_t$N(R$^{14}$)$_2$ (where t is 1 or 2) where each R$^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl;

or R$^3$ is phenyl substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, —R$^8$—OR$^{10}$, —R$^8$—C(O)OR$^{10}$, —R$^8$—OC(O)R$^{10}$, —R$^8$—O—R$^9$—C(O)OR$^{10}$, —R$^8$—O—R$^9$—C(O)N(R$^6$)R$^7$, —S(O)$_p$R$^6$ (where p is 0, 1 or 2), —S(O)$_t$N(R$^6$)R$^7$ (where t is 1 or 2), —R$^8$—N(R$^6$)R$^7$, —R$^8$—N(R$^6$)C(O)R$^{13}$ and —R$^8$—CN;

or R$^3$ is heteroaryl optionally substituted with one or more substituents selected from the group consisting of alkyl, oxo, and —R$^8$—OR$^{10}$;

R$^6$ and R$^7$ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally optionally substituted heterocyclyl, optionally substituted heterocyclylalkyl, optionally substituted heteroaryl, optionally substituted heteroarylalkyl, —$R^9$—$OR^{10}$, —$R^9$—CN, —$R^9$—$NO_2$, —$R^9$—N$(R^{10})_2$, —$R^9$—C(O)$OR^{10}$ and —$R^9$—C(O)N$(R^{10})_2$;

each $R^8$ is independently selected from the group consisting of a direct bond, an optionally substituted straight or branched alkylene chain or an optionally substituted straight or branched alkenylene chain;

each $R^9$ is independently selected from the group consisting of an optionally substituted straight or branched alkylene chain or an optionally substituted straight or branched alkenylene chain; and each $R^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, or optionally substituted heteroarylalkyl.

Another embodiment of the compounds of formula (Ia) are compounds of formula (Ia) wherein:

A is —C(O)—;

$R^1$ is heteroaryl optionally substituted with one or more substituents selected from the group consisting of alkyl, halo, oxo, —$R^8$—$OR^{10}$, —$R^8$—C(O)$OR^{10}$, —$R^8$—C(O)N($R^6$)$R^7$ and —$R^6$—N($R^6$)$R^7$;

$R^2$, $R^4$ and $R^5$ are each hydrogen;

$R^3$ is alkyl optionally substituted with one or more substituents selected from the group consisting of halo, cyano, nitro, oxo, thioxo, trimethylsilanyl, —$OR^{14}$, —OC(O)—$R^{14}$, —N$(R^{14})_2$, —C(O)$R^{14}$, —C(O)$OR^{14}$, —C(O)N$(R^{14})_2$, —N$(R^{14})$C(O)$OR^{14}$, —N$(R^{14})$C(O)$R^{14}$, —N$(R^{14})$S(O)$_t R^{14}$ (where t is 1 or 2), —S(O)$_t OR^{14}$ (where t is 1 or 2), —S(O)$_p R^{14}$ (where p is 0, 1 or 2), and —S(O)$_t$N$(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl;

or $R^3$ is heteroaryl optionally substituted with one or more substituents selected from the group consisting of alkyl, oxo, and —$R^8$—$OR^{10}$;

$R^6$ and $R^7$ are each independently selected from the group consisting of hydrogen, alkyl, haloalkyl, hydroxyalkyl, optionally substituted aryl, and optionally substituted aralkyl;

each $R^8$ is independently selected from the group consisting of a direct bond and an optionally substituted straight or branched alkylene chain;

each $R^{10}$ is independently selected from the group consisting of hydrogen, alkyl, haloalkyl, optionally substituted aryl, and optionally substituted aralkyl.

Of this embodiment, a specific embodiment is a compound of formula (Ia) selected from the group consisting of:

1-acetyl-5-amino-3-(1,4-benzodioxan-6-yl)amino-1H-1,2,4-triazole; and 5-amino-1-(1H-indol-6-yl)carbonyl-3-[4-((tert-butoxycarbonyl)aminochroman-6-yl]amino-1H-1,2,4-triazole.

Another embodiment of the compounds of formula (Ia) are compounds of formula (Ia) wherein:

A is —C(O)—;

$R^1$ is heteroaryl optionally substituted with one or more substituents selected from the group consisting of alkyl, halo, oxo, —$R^8$—$OR^{10}$, —$R^8$—C(O)$OR^{10}$, —$R^8$—C(O)N($R^6$)$R^7$ and —$R^8$—N($R^6$)$R^7$;

$R^2$, $R^4$ and $R^5$ are each hydrogen;

$R^3$ is phenyl substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, —$R^8$—$OR^{10}$, —$R^8$—C(O)$OR^{10}$, —$R^8$—OC(O)$R^{10}$, —$R^8$—O—$R^9$—C(O)$OR^{10}$, —$R^8$—O—$R^9$—C(O)N($R^8$)$R^7$, —S(O)$_p R^6$ (where p is 0, 1 or 2), —S(O)$_t$N($R^6$)$R^7$ (where t is 1 or 2), —$R^8$—N($R^6$)$R^7$, —$R^8$—N($R^8$)C(O)$R^{10}$ and —$R^8$—CN;

$R^6$ and $R^7$ are each independently selected from the group consisting of hydrogen, alkyl, haloalkyl, hydroxyalkyl, optionally substituted aryl, and optionally substituted aralkyl;

each $R^8$ is independently selected from the group consisting of a direct bond and an optionally substituted straight or branched alkylene chain;

each $R^9$ is an optionally substituted straight or branched alkylene chain; and each $R^{10}$ is independently selected from the group consisting of hydrogen, alkyl, haloalkyl, optionally substituted aryl, and optionally substituted aralkyl.

Of this embodiment, a specific embodiment is a compound of formula (Ia) selected from the group consisting of:

5-amino-3-[N-(2-(tetrahydropyran-2-yloxy)methylbenzofuran-5-yl)-amino]-1-(3-(methyl)phenyl)carbonyl-1H-1,2,4-triazole;

5-amino-1-(2-(chloro)phenyl)carbonyl-3-(1,4-benzodioxan-6-yl)amino-1H-1,2,4-triazole;

5-amino-1-(4-(chloro)phenyl)carbonyl-3-(1,4-benzodioxan-6-yl)amino-1H-1,2,4-triazole;

5-amino-3-(1,4-benzodioxan-6-yl)amino-1-(3-(methyl)phenyl)carbonyl-1H-1,2,4-triazole;

5-amino-3-(1,4-benzodioxan-6-yl)amino-1-(2-(methyl)phenyl)carbonyl-1H-1,2,4-triazole;

5-amino-3-(1,4-benzodioxan-6-yl)amino-1-(3-(methoxy)phenyl)carbonyl-1H-1,2,4-triazole;

5-amino-3-(1,4-benzodioxan-6-yl)amino-1-(2-(fluoro)phenyl)carbonyl-1H-1,2,4-triazole;

5-amino-3-(1,4-benzodioxan-6-yl)amino-1-(4-(fluoro)phenyl)carbonyl-1H-1,2,4-triazole;

5-amino-1-(3-(chloro)phenyl)carbonyl-3-(1,4-benzodioxan-6-yl)amino-1H-1,2,4-triazole;

5-amino-3-(1,4-benzodioxan-6-yl)amino-1-(4-(methyloxy)phenyl)carbonyl-1H-1,2,4-triazole;

5-amino-3-(2-(ethoxycarbonyl)benzofuran-5-yl)amino-1-(3-(iso-propoxy)phenyl)carbonyl-1H-1,2,4-triazole;

5-amino-3-(1,4-benzodioxan-6-yl)amino-1-(4-(methyl)phenyl)carbonyl-1H-1,2,4-triazole;

5-amino-3-(1,4-benzodioxan-6-yl)amino-1-(3-(fluoro)phenyl)carbonyl-1H-1,2,4-triazole;

5-amino-3-(1,4-benzodioxan-6-yl)amino-1-(2-(methyloxy)phenyl)carbonyl-1H-1,2,4-triazole;

1-(4-(acetoxy)phenyl)carbonyl-5-amino-3-(1,4-benzodioxan-6-yl)amino-1H-1,2,4-triazole;

1-(3-(acetoxy)phenyl)carbonyl-5-amino-3-(1,4-benzodioxan-6-yl)amino-1H-1,2,4-triazole;

5-amino-3-(1,4-benzodioxan-6-yl)amino-1-(3-(iso-propoxy)phenyl)carbonyl-1H-1,2,4-triazole;

5-amino-3-(1,4-benzodioxan-6-yl)-amino-1-(4-(iso-propoxy)phenyl)carbonyl-1H-1,2,4-triazole;

5-amino-1-(4-(ethoxyphenyl)carbonyl-3-(1,4-benzodioxan-6-yl)amino-1H-1,2,4-triazole;

1-(2-(acetoxy)phenyl)carbonyl-5-amino-3-(1,4-benzodioxan-6-yl)amino-1H-1,2,4-triazole;

5-amino-1-(4-(cyclopentoxy)phenylcarbonyl-3-(1,4-benzodioxan-6-yl)amino-1H-1,2,4-triazole;

5-amino-3-(1,4-benzodioxan-6-yl)amino-1-[4-(methoxycarbonylmethoxy)phenyl)carbonyl-1H-1,2,4-triazole;
5-amino-1-(3-(cyclopentoxy)phenyl)carbonyl-3-(1,4-benzodioxan-6-yl)amino-1H-1,2,4-triazole;
5-amino-1-(3-(ethoxy)phenyl)carbonyl-3-(1,4-benzodioxan-6-yl)amino-1H-1,2,4-triazole;
5-amino-3-(2-(hydroxymethyl)benzofuran-5-yl)amino-1-(3-(methyl)phenyl)carbonyl-1H-1,2,4-triazole;
5-amino-3-(1,4-benzodioxan-6-yl)amino-1-[3-(methoxycarbonylmethoxy)phenyl)carbonyl-1H-1,2,4-triazole;
5-amino-1-(4-(benzyloxy)phenyl)carbonyl-3-(1,4-benzodioxan-6-yl)amino-1H-1,2,4-triazole;
5-amino-3-(1,4-benzodioxan-6-yl)amino-1-[4-[2-(morpholin-4-yl)ethoxy]phenyl]carbonyl-1H-1,2,4-triazole;
5-amino-3-(1,4-benzodioxan-6-yl)amino-1-[3-[2-(morpholin-4-yl)ethoxy]phenyl]carbonyl-1H-1,2,4-triazole;
5-amino-3-(indazol-5-yl)amino-1-(3-(methyl)phenyl)carbonyl-1H-1,2,4-triazole;
5-amino-1-(3-(benzyloxy)phenyl)carbonyl-3-(1,4-benzodioxan-6-yl)amino-1H-1,2,4-triazole;
5-amino-3-(indazol-6-yl)amino-1-(3-(methyl)phenyl)carbonyl-1H-1,2,4-triazole;
5-amino-3-(benzo[b][1,4]oxazin-3(4H)-on-6-yl)amino-1-(3-(methyl)phenyl)carbonyl-1H-1,2,4-triazole;
5-amino-3-(1,4-benzodioxan-6-yl)amino-1-(4-(hydroxy)phenyl)carbonyl-1H-1,2,4-triazole;
5-amino-3-(1,4-benzodioxan-6-yl)amino-1-(3-(hydroxy)phenyl)carbonyl-1H-1,2,4-triazole;
5-amino-3-[(2H,3H-4-tert-butoxycarbonylbenzo[1,4]oxazin-6-yl)amino]-1-(3-methylphenyl)carbonyl-1,2,4-triazole;
5-amino-1-(3-methylphenyl)carbonyl-3-[2-[N-[2-(tetrahydropyran-2-yloxy)ethyl]amino]carbonylbenzofuran-5-yl]amino-1H-1,2,4-triazole;
5-amino-3-[2-[2-hydroxyethylaminocarbonyl]benzofuran-5-yl]amino-1-(3-methylphenyl)carbonyl-1H-1,2,4-triazole;
5-amino-1-[3-[2-(1,3-dioxolan-2-yl)ethoxy]phenylcarbonyl-3-(1,4-benzodioxan-6-yl)amino-1H-1,2,4-triazole;
5-amino-1-[4-[2-(1,3-dioxolan-2-yl)ethoxy]phenylcarbonyl-3-(1,4-benzodioxan-6-yl)amino-1H-1,2,4-triazole;
5-amino-3-[(3,4-dihydrobenzo[1,4]oxazin-6-yl)amino]-1-(3-methylphenyl)carbonyl-1H-1,2,4-triazole;
5-amino-3-[2-(ethoxycarbonyl)benzofuran-5-yl]amino-1-(3-methylphenyl)carbonyl-1H-1,2,4-triazole;
5-amino-1-(3-methylphenyl)carbonyl-3-(pyridin-3-yl)amino-1H-1,2,4-triazole;
5-amino-3-(2-methyl-2H-indazol-5-yl)-amino-1-(3-methylphenyl)carbonyl-1H-1,2,4-triazole;
5-amino-3-(1,4-benzodioxan-6-yl)amino-1-[4-[2-(piperidin-1-yl)ethoxy]phenylcarbonyl-1H-1,2,4-triazole;
5-amino-3-(2-((allyl(methyl)amino)methyl)benzofuran-5-yl)amino-1-(3-methylphenyl)carbonyl-1H-1,2,4-triazole;
5-amino-3-[1-methyl-1H-indazol-5-yl]amino-1-(3-methylphenyl)carbonyl-1H-1,2,4-triazole;
5-amino-3-(2-((methylamino)methyl)benzofuran-5-yl)-amino-1-(3-methylphenyl)carbonyl-1H-1,2,4-triazole;
5-amino-3-(1,4-benzodioxan-6-yl)amino-1-(3-(2,2,2-trifluoroethoxy)phenyl)carbonyl-1H-1,2,4-triazole;
5-amino-3-(benzofuran-5-yl)amino-1-(3-methylphenyl)carbonyl-1H-1,2,4-triazole;
5-amino-3-(1,4-benzodioxan-6-yl)amino-1-(4-(2,2,2-trifluoroethoxy)phenyl)carbonyl-1H-1,2,4-triazole;
5-amino-1-(3-aminocarbonylmethoxy)phenylcarbonyl-3-(1,4-benzodioxan-6-yl)amino-1H-1,2,4-triazole;
5-amino-3-(1,4-benzodioxan-6-yl)amino-1-(4-iso-propylphenyl)carbonyl-1H-1,2,4-triazole;
5-amino-1-(3,4-dimethylphenyl)carbonyl-3-(1,4-benzodioxan-6-yl)amino-1H-1,2,4-triazole;
5-amino-3-(1,4-benzodioxan-6-yl)amino-1-(4-thiomethylphenyl)carbonyl-1H-1,2,4-triazole;
5-amino-3-(1,4-benzodioxan-6-yl)amino-1-(3,5-dimethylphenyl)carbonyl-1H-1,2,4-triazole;
5-amino-3-(1,4-benzodioxan-6-yl)amino-1-(4-nitrophenyl)carbonyl-1H-1,2,4-triazole;
5-amino-3-(1,4-benzodioxan-6-yl)amino-1-[(4-fluoro-3-methyl)phenyl]carbonyl-1H-1,2,4-triazole;
5-amino-1-(4-aminophenyl)carbonyl-3-(1,4-benzodioxan-6-yl)amino-1H-1,2,4-triazole;
5-amino-3-(1,4-benzodioxan-6-yl)amino-1-[(4-trifluoromethyl)phenyl]carbonyl-1H-1,2,4-triazole;
5-amino-1-(4-cyanophenyl)carbonyl-3-(1,4-benzodioxan-6-yl)amino-1H-1,2,4-triazole;
1-[(4-acetylamino)phenyl]carbonyl-5-amino-3-(1,4-benzodioxan-6-yl)amino-1H-1,2,4-triazole;
5-amino-1-[(4-dimethylamino)phenyl]carbonyl-3-(1,4-benzodioxan-6-yl)amino-1H-1,2,4-triazole;
5-amino-3-(1,4-benzodioxan-6-yl)amino-1-[(4-methylsulfonyl)phenyl]carbonyl-1H-1,2,4-triazole;
5-amino-1-[(3-chloro-4-methyl)phenyl]carbonyl-3-(1,4-benzodioxan-6-yl)amino-1H-1,2,4-triazole;
5-amino-3-(benzothiazol-6-yl)amino-1-(3-methylphenyl)carbonyl-1H-1,2,4-triazole;
5-amino-1-(3-methylphenyl)carbonyl-3-(6-quinolinyl)amino-1H-1,2,4-triazole;
5-amino-3-(1H-indol-5-yl)amino-1-(3-methylphenyl)carbonyl-1H-1,2,4-triazole;
5-amino-3-(1H-2-methyl-indazol-6-yl)amino-1-(3-methylphenyl)carbonyl-1H-1,2,4-triazole;
5-amino-3-(1H-1-methyl-indazol-6-yl)amino-1-(3-methylphenyl)carbonyl-1H-1,2,4-triazole;
5-amino-3-(1H-2-methyl-indol-5-yl)amino-1-(3-methylphenyl)carbonyl-1H-1,2,4-triazole;
5-amino-3-(benzothiazol-2-yl)amino-1-(3-methylphenyl)carbonyl-1H-1,2,4-triazole;
5-amino-3-(1,4-benzodioxan-6-yl)amino-1-(3-methyl-4-methoxy)phenylcarbonyl-1H-1,2,4-triazole;
5-amino-3-(1,4-benzodioxan-6-yl)amino-1-(3-methyl-4-iso-propoxy)phenylcarbonyl-1H-1,2,4-triazole;
5-amino-3-(1,2-benzisothiazol-5-yl)amino-1-(3-methylphenyl)carbonyl-1H-1,2,4-triazole;
5-amino-3-(3-methyl-1,2-benzisothiazol-5-yl)amino-1-(3-methylphenyl)carbonyl-1H-1,2,4-triazole;
5-amino-3-(2,2-difluoro-2H-benzo[b][1,4]oxazin-3(4H)-on-6-yl)amino-1-(4-(iso-propoxy)phenyl)carbonyl-1H-1,2,4-triazole;
5-amino-3-(2,2-difluoro-2H-benzo[b][1,4]oxazin-3(4H)-on-6-yl)amino-1-(3-(methyl)phenyl)carbonyl-1H-1,2,4-triazole;
5-amino-1-(4-(tert-butyl)phenyl)carbonyl-3-[4-((tert-butoxycarbonyl)aminochroman-6-yl]amino-1H-1,2,4-triazole;
5-amino-1-(4-(iso-propoxy)phenyl)carbonyl-3-[4-((tert-butoxycarbonyl)aminochroman-6-yl]amino-1H-1,2,4-triazole;
5-amino-1-(4-(tert-butoxy)phenyl)carbonyl-3-[4-((tert-butoxycarbonyl)aminochroman-6-yl]amino-1H-1,2,4-triazole;

Another embodiment of the compounds of formula (Ia) are compounds of formula (Ia) wherein:

A is —C(O)—;

$R^1$ is cycloalkyl optionally substituted with one or more substituents selected from the group consisting of halo, haloalkyl, alkyl, oxo, —$R^8$—$OR^{10}$, —$R^8$—$C(O)OR^{10}$, —$R^8$—$C(O)N(R^6)R^7$, —$R^8$—$S(O)_pR^{10}$ (where p is 0, 1 or 2) and —$R^8$—$N(R^6)R^7$;

$R^2$, $R^4$ and $R^5$ are each hydrogen;

$R^3$ is one of the following:
a) alkyl optionally substituted with one or more substituents selected from the group consisting of halo, cyano, nitro, oxo, thioxo, trimethylsilanyl, —$OR^{14}$, —$OC(O)$—$R^{14}$, —$N(R^{14})_2$, —$C(O)R^{14}$, —$C(O)OR^{14}$, —$C(O)N(R^{14})_2$, —$N(R^{14})C(O)OR^{14}$, —$N(R^{14})C(O)R^{14}$, —$N(R^{14})S(O)_tR^{14}$ (where t is 1 or 2), —$S(O)_tOR^{14}$ (where t is 1 or 2), —$S(O)_pR^{14}$ (where p is 0, 1 or 2), and —$S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl;
b) cycloalkyl optionally substituted with one or more substituents selected from the group consisting of —$R^8$—$OR^{10}$, alkyl, halo, haloalkyl, aryl, and aralkyl;
c) aryl substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, —$R^8$—$OR^{10}$, —$R^8$—$C(O)OR^{10}$, —$R^8$—$OC(O)R^{10}$, —$R^8$—$O$—$R^9$—$C(O)OR^{10}$, —$R^8$—$O$—$R^9$—$C(O)N(R^8)R^7$, —$S(O)_pR^8$ (where p is 0, 1 or 2), —$S(O)_tN(R^8)R^7$ (where t is 1 or 2), —$R^8$—$N(R^6)R^7$, —$R^8$—$N(R^6)C(O)R^{10}$ and —$R^8$—CN;
d) aralkyl, wherein:
(1) the alkyl part of the aralkyl radical is optionally substituted with one or more substituents selected from the group consisting of halo, cyano, nitro, oxo, thioxo, trimethylsilanyl, —$OR^{14}$, —$OC(O)$—$R^{14}$, —$N(R^{14})_2$, —$C(O)R^{14}$, —$C(O)OR^{14}$, —$C(O)N(R^{14})_2$, —$N(R^{14})C(O)OR^{14}$, —$N(R^{14})C(O)R^{14}$, —$N(R^{14})S(O)_tR^{14}$ (where t is 1 or 2), —$S(O)_tOR^{14}$ (where t is 1 or 2), —$S(O)_pR^{14}$ (where p is 0, 1 or 2), and —$S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl; and
(2) the aryl part of the aralkyl radical is optionally substituted with one or more substituents selected from the group consisting of alkyl, alkenyl, alkynyl, halo, haloalkyl, haloalkenyl, haloalkynyl, cyano, nitro, aryl, aralkyl, aralkenyl, aralkynyl, cycloalkyl, cycloalkylalkyl, cycloalkylalkenyl, cycloalkylalkynyl, heterocyclyl, heterocyclylalkyl, heterocyclylalkenyl, heterocyclylalkynyl, heteroaryl, heteroarylalkyl, heteroarylalkenyl, heteroarylalkynyl, —$R^{15}$—$OC(O)$—$R^{14}$, —$R^{16}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$O$—$R^{16}$—$C(O)N(R^{14})_2$, —$R^{15}$—$N(R^{14})C(O)OR^{14}$, —$R^{15}$—$N(R^{14})C(O)R^{14}$, —$R^{15}$—$N(R^{14})S(O)_tR^{14}$ (where t is 1 or 2), —$R^{15}$—$S(O)_tOR^{14}$ (where t is 1 or 2), —$R^{15}$—$S(O)_pR^{14}$ (where p is 0, 1 or 2), and —$R^{15}$—$S(O)_tN(R^{14})_2$ (where t is 1 or 2), where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl, each $R^{15}$ is independently a direct bond or a straight or branched alkylene or alkenylene chain, and $R^{16}$ is a straight or branched alkylene or alkenylene chain;

e) heteroaryl optionally substituted with one or more substituents selected from the group consisting of alkyl, oxo, and —$R^8$—$OR^{10}$; or
f) heteroarylalkenyl where the heteroaryl part of the heteroarylakyl radical is optionally substituted with one or more substituents selected from the group consisting of alkyl, halo, haloalkyl, aryl and aralkyl;

$R^6$ and $R^7$ are each independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^9$—$OR^{10}$, —$R^9$—CN, —$R^9$—$NO_2$, —$R^9$—$N(R^{10})_2$, —$R^9$—$C(O)OR^{10}$ and —$R^9$—$C(O)N(R^{10})_2$;

optionally, $R^6$ and $R^7$, together with the nitrogen to which they are attached, form an optionally substituted N-heteroaryl or an optionally substituted N-heterocyclyl;

each $R^8$ is independently selected from the group consisting of a direct bond, an optionally substituted straight or branched alkylene chain, an optionally substituted straight or branched alkenylene chain and an optionally substituted straight or branched alkynylene chain;

each $R^9$ is independently selected from the group consisting of an optionally substituted straight or branched alkylene chain, an optionally substituted straight or branched alkenylene chain and an optionally substituted straight or branched alkynylene chain; and each $R^{10}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl.

Another embodiment of the compounds of formula (Ia) are compounds of formula (Ia) wherein:

A is —C(O)—;

$R^1$ is cycloalkyl optionally substituted with one or more substituents selected from the group consisting of halo, haloalkyl, alkyl, oxo, —$R^8$—$OR^{10}$, —$R^8$—$C(O)OR^{10}$, —$R^8$—$C(O)N(R^6)R^7$, —$R^8$—$S(O)_pR^{13}$ (where p is 0, 1 or 2) and —$R^8$—$N(R^6)R^7$; $R^2$, $R^4$ and $R^5$ are each hydrogen;

$R^3$ is alkyl optionally substituted with one or more substituents selected from the group consisting of halo, cyano, nitro, oxo, thioxo, trimethylsilanyl, —$OR^{14}$, —$OC(O)$—$R^{14}$, —$N(R^{14})_2$, —$C(O)R^{14}$, —$C(O)OR^{14}$, —$C(O)N(R^{14})_2$, —$N(R^{14})C(O)OR^{14}$, —$N(R^{14})C(O)R^{14}$, —$N(R^{14})S(O)_tR^{14}$ (where t is 1 or 2), —$S(O)_tOR^{14}$ (where t is 1 or 2), —$S(O)_pR^{14}$ (where p is 0, 1 or 2), and —$S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl;

or R³ is phenyl substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, —R⁸—OR¹⁰, —R⁸—C(O)OR¹⁰, —R⁸—OC(O)R¹⁰, —R⁸—O—R⁹—C(O)OR¹⁰, —R⁸—O—R⁹—C(O)N(R⁶)R⁷, —S(O)$_p$R⁶ (where p is 0, 1 or 2), —S(O)$_t$N(R⁶)R⁷ (where t is 1 or 2), —R⁸—N(R⁶)R⁷, —R⁸—N(R⁶)C(O)R¹⁰ and —R⁸—CN;

or R³ is heteroaryl optionally substituted with one or more substituents selected from the group consisting of alkyl, oxo, and —R⁸—OR¹⁰;

R⁶ and R⁷ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally optionally substituted heterocyclyl, optionally substituted heterocyclylalkyl, optionally substituted heteroaryl, optionally substituted heteroarylalkyl, —R⁹—OR¹⁰, —R⁹—CN, —R⁹—NO₂, —R⁹—N(R¹⁰)₂, —R⁹—C(O)OR¹⁰ and —R⁹—C(O)N(R¹⁰)₂;

each R⁸ is independently selected from the group consisting of a direct bond, an optionally substituted straight or branched alkylene chain or an optionally substituted straight or branched alkenylene chain;

each R⁹ is independently selected from the group consisting of an optionally substituted straight or branched alkylene chain or an optionally substituted straight or branched alkenylene chain; and each R¹⁰ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, or optionally substituted heteroarylalkyl.

Of this embodiment, a specific embodiment is a compound of formula (Ia) selected from the group consisting of:

5-amino-1-(4-(tert-butoxy)phenyl)carbonyl-3-[(5-(aminocarbonyl)bicyclo[2.2.1]hept-2-en-6-yl)amino]-1H-1,2,4-triazole;

5-amino-1-(3-(tert-butoxy)phenyl)carbonyl-3-[(5-(aminocarbonyl)bicyclo[2.2.1]hept-2-en-6-yl)amino]-1H-1,2,4-triazole;

5-amino-1-(4-(dimethylamino)phenyl)carbonyl-3-[(5-(aminocarbonyl)bicyclo[2.2.1]hept-2-en-6-yl)amino]-1H-1,2,4-triazole;

5-amino-1-(3-(dimethylamino)phenyl)carbonyl-3-[(5-(aminocarbonyl)bicyclo[2.2.1]hept-2-en-6-yl)amino]-1H-1,2,4-triazole;

5-amino-1-(4-(iso-propoxy)phenyl)carbonyl-3-[(5-(aminocarbonyl)bicyclo[2.2.1]hept-2-en-6-yl)-amino]-1H-1,2,4-triazole; and 5-amino-1-(1H-indol-6-yl)carbonyl-3-[(5-(aminocarbonyl)bicyclo[2.2.1]hept-2-en-6-yl)amino]-1H-1,2,4-triazole.

Another embodiment of the various aspects of the invention set forth above in the Summary of the Invention are compounds of formula (Ia):

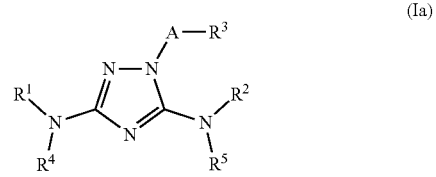

(Ia)

wherein:

A is —C(O)O—, —C(O)N(R⁶)— or —C(S)N(R⁶)—;

R¹ is one of the following:

a) aryl substituted with one or more substituents selected from the group consisting of halo, haloalkyl, alkyl, optionally substituted heteroaryl, optionally substituted heterocyclyl, —R⁸—OR¹⁰, —R⁸—O—R⁹—OR¹⁰, —R⁸—O—R⁹—O—R⁹—OR¹⁰, —R⁸—O—R⁹—C(O)OR¹⁰, —R⁸—O—R⁹—C(O)N(R⁶)R⁷, —R⁸—O—R⁶—S(O)$_p$R⁶ (where p is 0, 1 or 2), —R⁸—O—R⁹—N(R⁶)R⁷, —R⁸—O—R⁹—C(NR¹¹)N(R¹¹)H, and —R⁸—N(R⁶)C(O)R¹⁰; or b) heteroaryl optionally substituted with one or more substituents selected from the group consisting of alkyl, halo, oxo, —R⁸—OR¹⁰, —R⁸—C(O)OR¹⁰, —R⁸—C(O)N(R⁶)R⁷ and —R⁸—N(R⁶)R⁷;

R², R⁴ and R⁵ are each hydrogen;

R³ is one of the following:

a) alkyl optionally substituted with one or more substituents selected from the group consisting of halo, cyano, nitro, oxo, thioxo, trimethylsilanyl, —OR¹⁴, —OC(O)—R¹⁴, —N(R¹⁴)₂, —C(O)R¹⁴, —C(O)OR¹⁴, —C(O)N(R¹⁴)₂, —N(R¹⁴)C(O)OR¹⁴, —N(R¹⁴)C(O)R¹⁴, —N(R¹⁴)S(O)$_t$R¹⁴ (where t is 1 or 2), —S(O)$_t$OR¹⁴ (where t is 1 or 2), —S(O)$_p$R¹⁴ (where p is 0, 1 or 2), and —S(O)$_t$N(R¹⁴)₂ (where t is 1 or 2) where each R¹⁴ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl;

b) cycloalkyl optionally substituted with one or more substituents selected from the group consisting of —R⁸—OR¹⁰, alkyl, halo, haloalkyl, aryl, and aralkyl;

c) aryl substituted with one or more substituents selected from the group consisting of alkyl, halo, haloalkyl, nitro, cycloalkyl, cycloalkylalkyl, —R⁸—OR¹⁰, —R⁸—C(O)OR¹⁰, —R⁸—OC(O)R¹⁰, —R⁸—O—R⁹—C(O)OR¹⁰, —R⁸—O—R⁹—C(O)N(R⁶)R⁷, —S(O)$_p$R⁶ (where p is 0, 1 or 2), —S(O)$_t$N(R⁶)R⁷ (where t is 1 or 2), —R⁸—N(R⁶)R⁷, —R⁸—N(R⁶)C(O)R¹⁰ and —R⁸—CN;

d) aralkyl, wherein:
(1) the alkyl part of the aralkyl radical is optionally substituted with one or more substituents selected from the group consisting of halo, cyano, nitro, oxo, thioxo, trimethylsilanyl, —OR¹⁴, —OC(O)—R¹⁴, —N(R¹⁴)₂, —C(O)R¹⁴, —C(O)OR¹⁴, —C(O)N(R¹⁴)₂, —N(R¹⁴)C(O)OR¹⁴, —N(R¹⁴)C(O)R¹⁴, —N(R¹⁴)S(O)$_t$R¹⁴ (where t is 1 or 2), —S(O)$_t$OR¹⁴ (where t is 1 or 2), —S(O)$_p$R¹⁴ (where p is 0, 1 or 2), and —S(O)$_t$N(R¹⁴)₂ (where t is 1 or 2) where each R¹⁴ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl; and
  (2) the aryl part of the aralkyl radical is optionally substituted with one or more substituents selected from the group consisting of alkyl, alkenyl, alkynyl, halo, haloalkyl, haloalkenyl, haloalkynyl, cyano, nitro, aryl, aralkyl, aralkenyl, aralkynyl, cycloalkyl, cycloalkylalkyl, cycloalkylalkenyl, cycloalkylalkynyl, heterocyclyl, heterocyclylalkyl, heterocyclylalkenyl, heterocyclylalkynyl, heteroaryl, heteroarylalkyl, heteroarylalkenyl, heteroarylalkynyl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-O-R^{16}-C(O)N(R^{14})_2$, $-R^{15}-N(R^{14})C(O)OR^{14}$, $-R^{15}-N(R^{14})C(O)R^{14}$, $-R^{15}-N(R^{14})S(O)_tR^{14}$ (where t is 1 or 2), $-R^{15}-S(O)_tOR^{14}$ (where t is 1 or 2), $-R^{15}-S(O)_pR^{14}$ (where p is 0, 1 or 2), and $-R^{15}-S(O)_tN(R^{14})_2$ (where t is 1 or 2), where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl, each $R^{15}$ is independently a direct bond or a straight or branched alkylene or alkenylene chain, and $R^{16}$ is a straight or branched alkylene or alkenylene chain;
  e) heteroaryl optionally substituted with one or more substituents selected from the group consisting of alkyl, oxo, and $-R^8-OR^{10}$; or
  f) heteroarylalkenyl where the heteroaryl part of the heteroarylakyl radical is optionally substituted with one or more substituents selected from the group consisting of alkyl, halo, haloalkyl, aryl and aralkyl;
$R^6$ and $R^7$ are each independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^9-OR^{10}$, $-R^9-NO_2$, $-R^9-N(R^{10})_2$, $-R^9-C(O)OR^{10}$ and $-R^9-C(O)N(R^{10})_2$;
each $R^8$ is independently selected from the group consisting of a direct bond, an optionally substituted straight or branched alkylene chain, an optionally substituted straight or branched alkenylene chain and an optionally substituted straight or branched alkynylene chain;
each $R^9$ is independently selected from the group consisting of an optionally substituted straight or branched alkylene chain, an optionally substituted straight or branched alkenylene chain and an optionally substituted straight or branched alkynylene chain; and
each $R^{10}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl; and
each $R^{11}$ is hydrogen, alkyl, cyano, nitro or $-OR^{10}$.

Another embodiment of the compounds of formula (Ia) are compounds of formula (Ia) wherein:
A is $-C(O)O-$, $-C(O)N(R^6)-$ or $-C(S)N(R^6)-$;
$R^1$ is aryl substituted with one or more substituents selected from the group consisting of halo, haloalkyl, alkyl, optionally substituted heteroaryl, optionally substituted heterocyclyl, $-R^8-OR^{10}$, $-R^8-O-R^9-OR^{10}$, $-R^8-O-R^9-O-R^9-OR^{10}$, $-R^8-O-R^9-CN$, $-R^8-O-R^9-C(O)OR^{10}$, $-R^8-O-R^9-C(O)N(R^6)R^7$, $-R^8-O-R^9-S(O)_pR^6$ (where p is 0, 1 or 2), $-R^8-O-R^9-N(R^6)R^7$, $-R^8-O-R^9-C(NR^{11})N(R^{11})H$, and $-R^8-N(R^6)C(O)R^{10}$;
$R^2$, $R^4$ and $R^5$ are each hydrogen;
$R^3$ is cycloalkyl optionally substituted with one or more substituents selected from the group consisting of $-R^8-OR^{10}$, alkyl, halo, haloalkyl, aryl, and aralkyl;
or $R^3$ is phenyl substituted with one or more substituents selected from the group consisting of alkyl, halo, haloalkyl, nitro, cycloalkyl, cycloalkylalkyl, $-R^8-OR^{10}$, $-R^8-C(O)OR^{10}$, $-R^8-OC(O)R^{10}$, $-R^8-O-R^9-C(O)OR^{10}$, $-R^8-O-R^9-C(O)N(R^6)R^7$, $-S(O)_pR^6$ (where p is 0, 1 or 2), $-S(O)_tN(R^6)R^7$ (where t is 1 or 2), $-R^8-N(R^6)R^7$, $-R^8-N(R^6)C(O)R^{10}$, and $-R^8-CN$;
or $R^3$ is heteroaryl optionally substituted with one or more substituents selected from the group consisting of alkyl, oxo, and $-R^8-OR^{10}$;
$R^6$ and $R^7$ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, $-R^9-OR^{10}$, $-R^9-CN$, $-R^9-NO_2$, $-R^9-N(R^{10})_2$, $-R^9-C(O)OR^{10}$ and $-R^9-C(O)N(R^{10})_2$;
each $R^8$ is independently selected from the group consisting of a direct bond, an optionally substituted straight or branched alkylene chain or an optionally substituted straight or branched alkenylene chain;
each $R^9$ is independently selected from the group consisting of an optionally substituted straight or branched alkylene chain or an optionally substituted straight or branched alkenylene chain;
each $R^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, or optionally substituted heteroarylalkyl; and
each $R^{11}$ is hydrogen, alkyl, cyano, nitro or $-OR^{10}$.

Of this embodiment, a specific embodiment is a compound of formula (Ia) selected from the group consisting of:
5-amino-N-(4-chlorophenyl)-3-[4-(methoxy)phenylamino]-1H-1,2,4-triazole-1-carboxamide;
5-amino-N-(3,5-(dimethyl)phenyl)-3-[4-[2-(piperidin-1-yl)ethoxy]phenylamino]-1H-1,2,4-triazole-1-carboxamide;
5-amino-N-(4-(dimethylamino)phenyl)-3-[4-[2-(piperidin-1-yl)ethoxy]phenylamino]-1H-1,2,4-triazole-1-carboxamide;

5-amino-3-(4-methoxyphenyl)amino-1-(tert-butoxycarbo-
nyl)-1H-1,2,4-triazole;

3-[4-(acetyl(methyl)amino)phenyl]amino-5-amino-N-(4-
chlorophenyl)-1H-1,2,4-triazole-1-carboxamide;

3-[4-(acetyl(methyl)amino)phenyl]amino-5-amino-N-(1,3-
benzodioxol-5-yl)-1H-1,2,4-triazole-1-carboxamide;

3-[4-(acetyl(methyl)amino)phenyl]amino-5-amino-N-cy-
clopentyl-1H-1,2,4-triazole-1-carboxamide;

3-[4-(acetyl(methyl)amino)phenyl]amino-5-amino-N-(4-
(iso-propyl)phenyl)-1H-1,2,4-triazole-1-carboxamide;

3-[4-(acetyl(methyl)amino)phenyl]amino-5-amino-N-(4-
(butoxy)phenyl)-1H-1,2,4-triazole-1-carboxamide;

5-amino-N-(4-(iso-propyl)phenyl)-3-[4-[2-(piperidin-1-yl)
ethoxy]phenylamino]-1H-1,2,4-triazole-1-carboxamide;

5-amino-N-(4-butoxyphenyl)-3-[4-[2-(piperidin-1-yl)
ethoxy]phenylamino]-1H-1,2,4-triazole-1-carboxamide;

5-amino-N-(4-methylphenyl)-3-[4-[2-(piperidin-1-yl)
ethoxy]phenylamino]-1H-1,2,4-triazole-1-carboxamide;

5-amino-N-(4-(methoxy)phenyl)-3-[4-[2-(piperidin-1-yl)
ethoxy]phenylamino]-1H-1,2,4-triazole-1-carboxamide;

3-[4-(acetyl(methyl)amino)phenyl]amino-5-amino-N-cy-
clohexyl-1H-1,2,4-triazole-1-carboxamide;

5-amino-N-(1,3-benzodioxol-5-yl)-3-[4-[2-(piperidin-1-yl)
ethoxy]phenylamino]-1H-1,2,4-triazole-1-carboxamide;

5-amino-N-(3-methylphenyl)-3-[4-[2-(piperidin-1-yl)
ethoxy]phenylamino]-1H-1,2,4-triazole-1-carboxamide;

5-amino-N-(3-methoxyphenyl)-3-[4-[2-(piperidin-1-yl)
ethoxy]phenylamino]-1H-1,2,4-triazole-1-carboxamide;

5-amino-N-(3,5-(dimethoxy)phenyl)-3-[4-[2-(piperidin-1-
yl)ethoxy]phenylamino]-1H-1,2,4-triazole-1-carboxam-
ide;

5-amino-N-cyclohexyl-3-[4-[2-(piperidin-1-yl)ethoxy]phe-
nylamino]-1H-1,2,4-triazole-1-carboxamide;

5-amino-N-cyclopentyl-3-[4-[2-(piperidin-1-yl)ethoxy]phe-
nylamino]-1H-1,2,4-triazole-1-carboxamide;

5-amino-N-(4-methylphenyl)-3-[4-[2-(pyrrolidin-1-yl)
ethoxy]phenylamino]-1H-1,2,4-triazole-1-carboxamide;

5-amino-N-(3-methoxyphenyl)-3-[4-[2-(pyrrolidin-1-yl)
ethoxy]phenylamino]-1H-1,2,4-triazole-1-carboxamide;

5-amino-N-(4-cyanophenyl)-3-[4-[2-(piperidin-1-yl)
ethoxy]phenylamino]-1H-1,2,4-triazole-1-carboxamide;

5-amino-N-(1,3-benzodioxol-5-yl)-3-[4-[2-(pyrrolidin-1-yl)
ethoxy]phenylamino]-1H-1,2,4-triazole-1-carboxamide;

5-amino-N-(3-methylphenyl)-3-[4-[2-(pyrrolidin-1-yl)
ethoxy]phenylamino]-1H-1,2,4-triazole-1-carboxamide;

5-amino-N-(3,5-(dimethoxy)phenyl)-3-[4-[2-(pyrrolidin-1-
yl)ethoxy]phenylamino]-1H-1,2,4-triazole-1-carboxam-
ide;

5-amino-N-(3,4-(dimethoxy)phenyl)-3-[4-[2-(piperidin-1-
yl)ethoxy]phenylamino]-1H-1,2,4-triazole-1-carboxam-
ide;

5-amino-N-(3,4-(dimethyl)phenyl)-3-[4-[2-(piperidin-1-yl)
ethoxy]phenylamino]-1H-1,2,4-triazole-1-carboxamide;

5-amino-3-[4-(piperidin-1-yl)phenylamino]-1-(tert-butoxy-
carbonyl)-1H-1,2,4-triazole;

5-amino-N-(2,4,6-trifluorophenyl)-3-[4-[2-(pyrrolidin-1-yl)
ethoxy]phenylamino]-1H-1,2,4-triazole-1-carbothioam-
ide; and 5-amino-N-(2,6-difluorophenyl)-3-[4-[2-(pyrrolidin-1-yl)
ethoxy]phenylamino]-1H-1,2,4-triazole-1-carbothioam-
ide.

Another embodiment of the various aspects of the invention set forth above in the Summary of the Invention are compounds of formula (Ib):

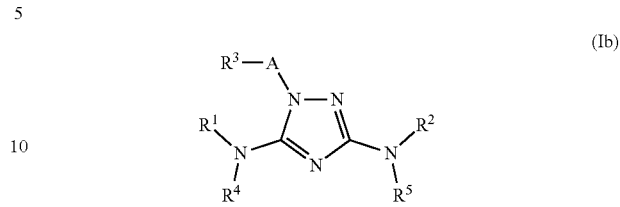

wherein:
A is —C(O)—;
$R^1$ is one of the following:
  a) aryl substituted with one or more substituents selected from the group consisting of halo, haloalkyl, alkyl, optionally substituted heteroaryl, optionally substituted heterocyclyl, —$R^8$—$OR^{10}$, $R^9$—$OR^{10}$, —$R^8$—O—$R^9$—O—$R^9$—$OR^{10}$, —$R^8$—O—$R^9$—CN, —$R^8$—O—$R^9$—C(O)$OR^{10}$, —$R^8$—O—$R^9$—C(O)N($R^8$)$R^7$, —$R^8$—O—$R^9$—S(O)$_p$$R^6$ (where p is 0, 1 or 2), —$R^8$—O—$R^9$—N($R^8$)$R^7$, —$R^8$—O—$R^9$—C(N$R^{11}$)N($R^{11}$)H, and —$R^8$—N($R^6$)C(O)$R^{10}$; or
  b) heteroaryl optionally substituted with one or more substituents selected from the group consisting of alkyl, halo, oxo, —$R^8$—$OR^{10}$, —$R^8$—C(O)$OR^{10}$, —$R^8$—C(O)N($R^6$)$R^7$ and —$R^8$—N($R^6$)$R^7$; or
  c) heterocyclyl optionally substituted with one or more substituents selected from the group consisting of halo, haloalkyl, alkyl, oxo, —$R^8$—$OR^{10}$, —$R^8$—C(O)$OR^{10}$, —$R^8$—C(O)N($R^6$)$R^7$, —$R^8$—S(O)$_p$$R^{10}$ (where p is 0, 1 or 2) and —$R^8$—N($R^6$)$R^7$;
  d) heterocyclylalkyl optionally substituted with one or more substitutents selected from the group consisting of halo, haloalkyl, alkyl, optionally substituted aryl, optionally substituted aralkyl, —$R^8$—$OR^{10}$, —$R^8$—C(O)$OR^{10}$, —$R^8$—C(O)N($R^6$)$R^7$ and —$R^8$—N($R^6$)$R^7$; or
  e) cycloalkyl optionally substituted with one or more substituents selected from the group consisting of halo, haloalkyl, alkyl, oxo, —$R^8$—$OR^{10}$, —$R^8$—C(O)$OR^{10}$, —$R^8$—C(O)N($R^6$)$R^7$, —$R^8$—S(O)$_p$$R^{10}$ (where p is 0, 1 or 2) and —$R^8$—N($R^8$)$R^7$;
$R^2$ is hydrogen, alkyl or —C(O)$R^{10}$;
$R^4$ and $R^5$ are each hydrogen or alkyl;
$R^3$ is one of the following:
  a) alkyl optionally substituted with one or more substituents selected from the group consisting of halo, cyano, nitro, oxo, thioxo, trimethylsilanyl, —$OR^{14}$, —OC(O)—$R^{14}$, —N($R^{14}$)$_2$, —C(O)$R^{14}$, —C(O)$OR^{14}$, —C(O)N($R^{14}$)$_2$, —N($R^{14}$)C(O)$OR^{14}$, —N($R^{14}$)C(O)$R^{14}$, —N($R^{14}$)S(O)$_t$$R^{14}$ (where t is 1 or 2), —S(O)$_t$$OR^{14}$ (where t is 1 or 2), S(O)$_p$$R^{14}$ (where p is 0, 1 or 2), and —S(O)$_t$N($R^{14}$)$_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl;
  b) cycloalkyl optionally substituted with one or more substituents selected from the group consisting of —$R^8$—$OR^{10}$, alkyl, halo, haloalkyl, aryl, and aralkyl;
  c) aryl substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, —$R^8$—$OR^{10}$, —$R^8$—$C(O)OR^{10}$, —$R^8$—$OC(O)R^{10}$, —$R^8$—O—$R^8$—$OR^{10}$, —$R^8$—O—$R^8$—$C(O)N(R^6)R^7$, —$S(O)_pR^6$ (where p is 0, 1 or 2), —$S(O)_tN(R^6)R^7$ (where t is 1 or 2), —$R^8$—$N(R^6)R^7$, —$R^8$—$N(R^6)C(O)R^{10}$ and —$R^8$—CN;

d) aralkyl, wherein:
  (1) the alkyl part of the aralkyl radical is optionally substituted with one or more substituents selected from the group consisting of halo, cyano, nitro, oxo, thioxo, trimethylsilanyl, —$OR^{14}$, —$OC(O)$—$R^{14}$, —$N(R^{14})_2$, —$C(O)R^{14}$, —$C(O)OR^{14}$, —$C(O)N(R^{14})_2$, —$N(R^{14})C(O)OR^{14}$, —$N(R^{14})C(O)R^{14}$, —$N(R^{14})S(O)_tR^{14}$ (where t is 1 or 2), —$S(O)_tOR^{14}$ (where t is 1 or 2), —$S(O)_pR^{14}$ (where p is 0, 1 or 2), and —$S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl; and
  (2) the aryl part of the aralkyl radical is optionally substituted with one or more substituents selected from the group consisting of alkyl, alkenyl, alkynyl, halo, haloalkyl, haloalkenyl, haloalkynyl, cyano, nitro, aryl, aralkyl, aralkenyl, aralkynyl, cycloalkyl, cycloalkylalkyl, cycloalkylalkenyl, cycloalkylalkynyl, heterocyclyl, heterocyclylalkyl, heterocyclylalkenyl, heterocyclylalkynyl, heteroaryl, heteroarylalkyl, heteroarylalkenyl, heteroarylalkynyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—O—$R^{16}$—$C(O)N(R^{14})_2$, —$R^{15}$—$N(R^{14})C(O)OR^{14}$, —$R^{15}$—$N(R^{14})C(O)R^{14}$, —$R^{15}$—$N(R^{14})S(O)_tR^{14}$ (where t is 1 or 2), —$R^{15}$—$S(O)_tOR^{14}$ (where t is 1 or 2), —$R^{15}$—$S(O)_pR^{14}$ (where p is 0, 1 or 2), and —$R^{15}$—$S(O)_tN(R^{14})_2$ (where t is 1 or 2), where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl, each $R^{15}$ is independently a direct bond or a straight or branched alkylene or alkenylene chain, and $R^{16}$ is a straight or branched alkylene or alkenylene chain;

e) heteroaryl optionally substituted with one or more substituents selected from the group consisting of alkyl, oxo, and —$R^8$—$OR^{10}$; or f) heteroarylalkenyl where the heteroaryl part of the heteroarylakyl radical is optionally substituted with one or more substituents selected from the group consisting of alkyl, halo, haloalkyl, aryl and aralkyl;

$R^6$ and $R^7$ are each independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^9$—$OR^{10}$, —$R^9$—CN, —$R^9$—$NO_2$, —$R^9$—$N(R^{10})_2$, —$R^9$—$C(O)OR^{10}$ and —$R^9$—$C(O)N(R^{10})_2$;

optionally, $R^6$ and $R^7$, together with the nitrogen to which they are attached, form an optionally substituted N-heteroaryl or an optionally substituted N-heterocyclyl;

each $R^8$ is independently selected from the group consisting of a direct bond, an optionally substituted straight or branched alkylene chain, an optionally substituted straight or branched alkenylene chain and an optionally substituted straight or branched alkynylene chain;

each $R^9$ is independently selected from the group consisting of an optionally substituted straight or branched alkylene chain, an optionally substituted straight or branched alkenylene chain and an optionally substituted straight or branched alkynylene chain; and each $R^{10}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl; and each $R^{11}$ is hydrogen, alkyl, cyano, nitro or —$OR^{10}$.

Another embodiment of the compounds of formula (Ib) are compounds of formula (Ib) wherein:

A is —C(O)—;

$R^1$ is one of the following:
  a) aryl substituted with one or more substituents selected from the group consisting of halo, haloalkyl, alkyl, optionally substituted heteroaryl, optionally substituted heterocyclyl, —$R^8$—$OR^{10}$, —$R^8$—O—$R^8$—$OR^{10}$, —$R^8$—O—$R^9$—O—$R^9$—$OR^{10}$, —$R^8$—O—$R^9$—CN, —$R^8$—O—$R^9$—$C(O)OR^{10}$, —$R^8$—O—$R^9$—$C(O)N(R^6)R^7$, —$R^8$—O—$R^9$—$S(O)_pR^6$ (where p is 0, 1 or 2), —$R^8$—O—$R^9$—$N(R^6)R^7$, —$R^8$—O—$R^9$—$C(NR^{11})N(R^{11})H$, and —$R^8$—$N(R^6)C(O)R^{10}$; or
  b) heteroaryl optionally substituted with one or more substituents selected from the group consisting of alkyl, halo, oxo, —$R^8$—$OR^{10}$, —$R^8$—$C(O)OR^{10}$, —$R^8$—$C(O)N(R^6)R^7$ and —$R^8$—$N(R^6)R^7$; or
  c) heterocyclyl optionally substituted with one or more substituents selected from the group consisting of halo, haloalkyl, alkyl, oxo, —$R^8$—$OR^{10}$, —$R^8$—$C(O)OR^{10}$, —$R^8$—$C(O)N(R^6)R^7$, —$R^8$—$S(O)_pR^{10}$ (where p is 0, 1 or 2) and —$R^8$—$N(R^6)R^7$;
  d) heterocyclylalkyl optionally substituted with one or more substitutents selected from the group consisting of halo, haloalkyl, alkyl, optionally substituted aryl, optionally substituted aralkyl, —$R^8$—$OR^{10}$, —$R^8$—$C(O)OR^{10}$, —$R^8$—$C(O)N(R^6)R^7$ and —$R^8$—$N(R^6)R^7$; or
  e) cycloalkyl optionally substituted with one or more substituents selected from the group consisting of halo, haloalkyl, alkyl, oxo, —$R^8$—$OR^{10}$, —$R^8$—$C(O)OR^{10}$, —$R^8$—$C(O)N(R^6)R^7$, —$R^8$—$S(O)_pR^{10}$ (where p is 0, 1 or 2) and —$R^8$—$N(R^6)R^7$;

$R^2$ is hydrogen, alkyl or —$C(O)R^{10}$;

$R^4$ and $R^5$ are each hydrogen or alkyl;

$R^3$ is one of the following:
  a) alkyl optionally substituted with one or more substituents selected from the group consisting of halo, cyano, nitro, oxo, thioxo, trimethylsilanyl, —$OR^{14}$, —OC (O)—$R^{14}$, —$N(R^{14})_2$, —$C(O)R^{14}$, —$C(O)OR^{14}$, —$C(O)N(R^{14})_2$, —$N(R^{14})C(O)OR^{14}$, —$N(R^{14})C(O)R^{14}$, —$N(R^{14})S(O)_tR^{14}$ (where t is 1 or 2), —$S(O)_tOR^{14}$ (where t is 1 or 2), —$S(O)_pR^{14}$ (where p is 0, 1 or 2), and —$S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl;
b) cycloalkyl optionally substituted with one or more substituents selected from the group consisting of —$R^8$—$OR^{10}$, alkyl, halo, haloalkyl, aryl, and aralkyl;
c) aryl substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, —$R^8$—$OR^{10}$, —$R^8$—$C(O)OR^{10}$, —$R^8$—$OC(O)R^{10}$, —$R^8$—$O$—$R^9$—$C(O)OR^{10}$, —$R^8$—$O$—$R^9$—$C(O)N(R^6)R^7$, —$S(O)_pR^6$ (where p is 0, 1 or 2), —$S(O)_tN(R^6)R^7$ (where t is 1 or 2), —$R^8$—$N(R^6)R^7$, —$R^8$—$N(R^6)C(O)R^{10}$ and —$R^8$—$CN$;
d) aralkyl, wherein:
 (1) the alkyl part of the aralkyl radical is optionally substituted with one or more substituents selected from the group consisting of halo, cyano, nitro, oxo, thioxo, trimethylsilanyl, —$OC(O)$—$R^{14}$, —$N(R^{14})_2$, —$C(O)R^{14}$, —$C(O)OR^{14}$, —$C(O)N(R^{14})_2$, —$N(R^{14})C(O)OR^{14}$, —$N(R^{14})C(O)R^{14}$, —$N(R^{14})S(O)_tR^{14}$ (where t is 1 or 2), —$S(O)_tOR^{14}$ (where t is 1 or 2), —$S(O)_pR^{14}$ (where p is 0, 1 or 2), and —$S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl; and
 (2) the aryl part of the aralkyl radical is optionally substituted with one or more substituents selected from the group consisting of alkyl, alkenyl, alkynyl, halo, haloalkyl, haloalkenyl, haloalkynyl, cyano, nitro, aryl, aralkyl, aralkenyl, aralkynyl, cycloalkyl, cycloalkylalkyl, cycloalkylalkenyl, cycloalkylalkynyl, heterocyclyl, heterocyclylalkyl, heterocyclylalkenyl, heterocyclylalkynyl, heteroaryl, heteroarylalkyl, heteroarylalkenyl, heteroarylalkynyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$O$—$R^{16}$—$C(O)N(R^{14})_2$, —$R^{15}$—$N(R^{14})C(O)OR^{14}$, —$R^{15}$—$N(R^{14})C(O)R^{14}$, —$R^{15}$—$N(R^{14})S(O)_tR^{14}$ (where t is 1 or 2), —$R^{15}$—$S(O)_tOR^{14}$ (where t is 1 or 2), —$R^{15}$—$S(O)_pR^{14}$ (where p is 0, 1 or 2), and —$R^{15}$—$S(O)_tN(R^{14})_2$ (where t is 1 or 2), where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl, each $R^{15}$ is independently a direct bond or a straight or branched alkylene or alkenylene chain, and $R^{16}$ is a straight or branched alkylene or alkenylene chain;
e) heteroaryl optionally substituted with one or more substituents selected from the group consisting of alkyl, oxo, and —$R^8$—$OR^{10}$; or
f) heteroarylalkenyl where the heteroaryl part of the heteroarylakyl radical is optionally substituted with one or more substituents selected from the group consisting of alkyl, halo, haloalkyl, aryl and aralkyl;
$R^6$ and $R^7$ are each independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^9$—$OR^{10}$, —$R^9$—$CN$, —$R^9$—$NO_2$, —$R^9$—$N(R^{10})_2$, —$R^9$—$C(O)OR^{10}$ and —$R^9$—$C(O)N(R^{10})_2$;
optionally, $R^6$ and $R^7$, together with the nitrogen to which they are attached, form an optionally substituted N-heteroaryl or an optionally substituted N-heterocyclyl;
each $R^8$ is independently selected from the group consisting of a direct bond, an optionally substituted straight or branched alkylene chain, an optionally substituted straight or branched alkenylene chain and an optionally substituted straight or branched alkynylene chain;
each $R^9$ is independently selected from the group consisting of an optionally substituted straight or branched alkylene chain, an optionally substituted straight or branched alkenylene chain and an optionally substituted straight or branched alkynylene chain; and
each $R^{10}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl; and
each $R^{11}$ is hydrogen, alkyl, cyano, nitro or —$OR^{10}$.

Another embodiment of the compounds of formula (Ib) are compounds of formula (Ib) wherein:
A is —$C(O)$—;
$R^1$ is aryl substituted with one or more substituents selected from the group consisting of halo, haloalkyl, alkyl, optionally substituted heteroaryl, optionally substituted heterocyclyl, —$R^8$—$OR^{10}$, —$R^8$—$O$—$R^9$—$OR^{10}$, —$R^8$—$O$—$R^9$—$O$—$R^9$—$OR^{10}$, —$R^8$—$O$—$R^9$—$C(O)OR^{10}$, —$R^8$—$O$—$R^9$—$C(O)N(R^8)R^7$, —$R^8$—$O$—$R^9$—$S(O)_pR^6$ (where p is 0, 1 or 2), —$R^8$—$O$—$R^9$—$N(R^6)R^7$, —$R^8$—$O$—$R^9$—$C(NR^{11})N(R^{11})H$, and —$R^8$—$N(R^6)C(O)R^{10}$;
$R^2$, $R^4$ and $R^5$ are each hydrogen;
$R^3$ is one of the following:
 a) alkyl optionally substituted with one or more substituents selected from the group consisting of halo, cyano, nitro, oxo, thioxo, trimethylsilanyl, —$OR^{14}$, —$OC(O)$—$R^{14}$, —$N(R^{14})_2$, —$C(O)R^{14}$, —$C(O)OR^{14}$, —$C(O)N(R^{14})_2$, —$N(R^{14})C(O)OR^{14}$, —$N(R^{14})C(O)R^{14}$, —$N(R^{14})S(O)_tR^{14}$ (where t is 1 or 2), —$S(O)_tOR^{14}$ (where t is 1 or 2), —$S(O)_pR^{14}$ (where p is 0, 1 or 2), and —$S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl;

b) cycloalkyl optionally substituted with one or more substituents selected from the group consisting of —$R^8$—$OR^{10}$, alkyl, halo, haloalkyl, aryl, and aralkyl;

c) aryl substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, —$R^8$—$OR^{10}$, —$R^8$—$C(O)OR^{10}$, —$R^8$—$OC(O)R^{10}$, —$R^8$—O—$R^9$—$C(O)OR^{10}$, —$R^8$—O—$R^9$—$C(O)N(R^6)R^7$, —$S(O)_pR^6$ (where p is 0, 1 or 2), —$S(O)_tN(R^6)R^7$ (where t is 1 or 2), —$R^8$—$N(R^6)R^7$, —$R^8$—$N(R^6)C(O)R^{10}$ and —$R^8$—CN;

d) aralkyl, wherein:
  (1) the alkyl part of the aralkyl radical is optionally substituted with one or more substituents selected from the group consisting of halo, cyano, nitro, oxo, thioxo, trimethylsilanyl, —$OR^{14}$, —$OC(O)$—$R^{14}$, —$N(R^{14})_2$, —$C(O)R^{14}$, —$C(O)OR^{14}$, —$C(O)N(R^{14})_2$, —$N(R^{14})C(O)OR^{14}$, —$N(R^{14})C(O)R^{14}$, —$N(R^{14})S(O)_tR^{14}$, (where t is 1 or 2), —$S(O)_tOR^{14}$ (where t is 1 or 2), —$S(O)_pR^{14}$ (where p is 0, 1 or 2), and —$S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl; and
  (2) the aryl part of the aralkyl radical is optionally substituted with one or more substituents selected from the group consisting of alkyl, alkenyl, alkynyl, halo, haloalkyl, haloalkenyl, haloalkynyl, cyano, nitro, aryl, aralkyl, aralkenyl, aralkynyl, cycloalkyl, cycloalkylalkyl, cycloalkylalkenyl, cycloalkylalkynyl, heterocyclyl, heterocyclylalkyl, heterocyclylalkenyl, heterocyclylalkynyl, heteroaryl, heteroarylalkyl, heteroarylalkenyl, heteroarylalkynyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—O—$R^{16}$—$C(O)N(R^{14})_2$, —$R^{15}$—$N(R^{14})C(O)OR^{14}$, —$R^{15}$—$N(R^{14})C(O)R^{14}$, —$R^{15}$—$N(R^{14})S(O)_tR^{14}$ (where t is 1 or 2), —$R^{15}$—$S(O)_tOR^{14}$ (where t is 1 or 2), —$R^{15}$—$S(O)_pR^{14}$ (where p is 0, 1 or 2), and —$R^{15}$—$S(O)_tN(R^{14})_2$ (where t is 1 or 2), where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl, each $R^{15}$ is independently a direct bond or a straight or branched alkylene or alkenylene chain, and $R^{16}$ is a straight or branched alkylene or alkenylene chain;

e) heteroaryl optionally substituted with one or more substituents selected from the group consisting of alkyl, oxo, and —$R^8$—$OR^{10}$; or f) heteroarylalkenyl where the heteroaryl part of the heteroarylakyl radical is optionally substituted with one or more substituents selected from the group consisting of alkyl, halo, haloalkyl, aryl and aralkyl;

$R^6$ and $R^7$ are each independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^9$—$OR^{10}$, —$R^9$—CN, —$R^9$—$NO_2$, —$R^9$—$N(R^{10})_2$, —$R^9$—$C(O)OR^{10}$ and —$R^9$—$C(O)N(R^{10})_2$;

optionally, $R^6$ and $R^7$, together with the nitrogen to which they are attached, form an optionally substituted N-heteroaryl or an optionally substituted N-heterocyclyl;

each $R^8$ is independently selected from the group consisting of a direct bond, an optionally substituted straight or branched alkylene chain, an optionally substituted straight or branched alkenylene chain and an optionally substituted straight or branched alkynylene chain;

each $R^9$ is independently selected from the group consisting of an optionally substituted straight or branched alkylene chain, an optionally substituted straight or branched alkenylene chain and an optionally substituted straight or branched alkynylene chain; and each $R^{10}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl; and each $R^{11}$ is hydrogen, alkyl, cyano, nitro or —$OR^{10}$.

Another embodiment of the compounds of formula (Ib) are compounds of formula (Ib) wherein:

A is —C(O)—;

$R^1$ is aryl substituted with one or more substituents selected from the group consisting of halo, haloalkyl, alkyl, optionally substituted heteroaryl, optionally substituted heterocyclyl, —$R^8$—$OR^{10}$, —$R^8$—O—$R^9$—$OR^{10}$, —$R^8$—O—$R^9$—O—$R^9$—$OR^{10}$, —$R^8$—O—$R^9$—CN, —$R^8$—O—$R^9$—$C(O)OR^{10}$, —$R^8$—O—$R^9$—$C(O)N(R^8)R^7$, —$R^8$—O—$R^9$—$S(O)_pR^8$ (where p is 0, 1 or 2), —$R^8$—O—$R^9$—$N(R^6)R^7$, —$R^8$—O—$R^9$—$C(NR^{11})N(R^{11})H$, and —$R^8$—$N(R^6)C(O)R^{10}$;

$R^2$, $R^4$ and $R^5$ are each hydrogen;

$R^3$ is cycloalkyl optionally substituted with —$R^8$—$OR^{10}$;

or $R^3$ is aryl substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, —$R^8$—$OR^{10}$, —$R^8$—$C(O)OR^{10}$, —$R^8$—$OC(O)R^{10}$, —$R^8$—O—$R^9$—$C(O)OR^{10}$, —$R^8$—O—$R^9$—$C(O)N(R^6)R^7$, —$S(O)_pR^6$ (where p is 0, 1 or 2), —$S(O)_tN(R^6)R^7$ (where t is 1 or 2), —$R^8$—$N(R^6)R^7$, —$R^8$—$N(R^6)C(O)R^{10}$, and —$R^8$—CN;

$R^6$ and $R^7$ are each independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^9$—$OR^{10}$, —$R^9$—CN, —$R^9$—$NO_2$, —$R^9$—$N(R^{10})_2$, —$R^9$—$C(O)OR^{10}$ and —$R^9$—$C(O)N(R^{10})_2$;

optionally, $R^6$ and $R^7$, together with the nitrogen to which they are attached, form an optionally substituted N-heteroaryl or an optionally substituted N-heterocyclyl;

each $R^8$ is independently selected from the group consisting of a direct bond, an optionally substituted straight or branched alkylene chain, an optionally substituted straight or branched alkenylene chain and an optionally substituted straight or branched alkynylene chain;

each $R^9$ is independently selected from the group consisting of an optionally substituted straight or branched alkylene chain, an optionally substituted straight or branched alkenylene chain and an optionally substituted straight or branched alkynylene chain; and each $R^{10}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl; and each $R^{11}$ is hydrogen, alkyl, cyano, nitro or —$OR^{10}$.

Another embodiment of the compounds of formula (Ib) are compounds of formula (Ib) wherein:

A is —C(O)—;

$R^1$ is phenyl substituted with one or more substituents selected from the group consisting of halo, haloalkyl, alkyl, optionally substituted heteroaryl, optionally substituted heterocyclyl, —$R^6$—$OR^{10}$, —$R^8$—O—$R^9$—$OR^{10}$, —$R^8$—O—$R^9$—O—$R^8$—$OR^{10}$, —$R^8$—O—$R^9$—CN, —$R^8$—O—$R^9$—$C(O)OR^{10}$, —$R^8$—O—$R^9$—$C(O)N(R^6)R^7$, —$R^8$—O—$R^9$—$S(O)_pR^6$ (where p is 0, 1 or 2), —$R^8$—O—$R^9$—$N(R^6)R^7$, —$R^8$—O—$R^9$—$C(NR^{11})N(R^{11})H$, and —$R^8$—$N(R^6)C(O)R^{10}$;

$R^2$, $R^4$ and $R^5$ are each hydrogen;

$R^3$ is cycloalkyl optionally substituted with —$R^8$—$OR^{10}$; or $R^3$ is phenyl substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, —$R^8$—$OR^{10}$, —$R^8$—$C(O)OR^{10}$, —$R^8$—$OC(O)R^{10}$, —$R^8$—O—$R^9$—$C(O)OR^{10}$, —$R^8$—O—$R^9$—$C(O)N(R^6)R^7$, —$S(O)_pR^6$ (where p is 0, 1 or 2), —$S(O)_tN(R^6)R^7$ (where t is 1 or 2), —$R^8$—$N(R^6)R^7$, —$R^8$—$N(R^6)C(O)R^{10}$, and —$R^8$—CN;

$R^6$ and $R^7$ are each independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^9$—$OR^{10}$, —$R^9$—CN, —$R^9$—$NO_2$, —$R^9$—$N(R^{10})_2$, —$R^9$—$C(O)OR^{10}$ and —$R^9$—$C(O)N(R^{10})_2$;

optionally, $R^6$ and $R^7$, together with the nitrogen to which they are attached, form an optionally substituted N-heteroaryl or an optionally substituted N-heterocyclyl;

each $R^8$ is independently selected from the group consisting of a direct bond, an optionally substituted straight or branched alkylene chain, an optionally substituted straight or branched alkenylene chain and an optionally substituted straight or branched alkynylene chain;

each $R^9$ is independently selected from the group consisting of an optionally substituted straight or branched alkylene chain, an optionally substituted straight or branched alkenylene chain and an optionally substituted straight or branched alkynylene chain; and each $R^{10}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl; and each $R^{11}$ is hydrogen, alkyl, cyano, nitro or —$OR^{10}$.

Another embodiment of the compounds of formula (Ib) are compounds of formula (Ib) wherein:

A is —C(O)—;

$R^1$ is phenyl substituted with one or two substituents selected from the group consisting of halo, haloalkyl, alkyl, optionally substituted heteroaryl, optionally substituted heterocyclyl, —$R^8$—$OR^{10}$, —$R^8$—O—$R^9$—$OR^{10}$, —$R^8$—O—$R^9$—O—$R^9$—$OR^{10}$, —$R^8$—O—$R^9$—CN, —$R^8$—O—$R^9$—$C(O)OR^{10}$, —$R^8$—O—$R^9$—$C(O)N(R^6)R^7$, —$R^8$—O—$R^9$—$S(O)_pR^6$ (where p is 0, 1 or 2), —$R^8$—O—$R^9$—$N(R^6)R^7$, —$R^8$—O—$R^9$—$C(NR^{11})N(R^{11})H$, and —$R^8$—$N(R^6)C(O)R^{10}$;

$R^2$, $R^4$ and $R^5$ are each hydrogen;

$R^3$ is cycloalkyl optionally substituted with —$R^8$—$OR^{10}$;

or $R^3$ is phenyl substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, —$R^8$—$OR^{10}$, —$R^8$—$C(O)OR^{10}$, —$R^8$—$OC(O)R^{10}$, —$R^8$—O—$R^9$—$C(O)OR^{10}$, —$R^8$—O—$R^9$—$C(O)N(R^6)R^7$, —$S(O)_pR^6$ (where p is 0, 1 or 2), —$S(O)_tN(R^6)R^7$ (where t is 1 or 2), —$R^8$—$N(R^6)R^7$, —$R^8$—$N(R^6)C(O)R^{10}$, and —$R^8$—CN;

$R^6$ and $R^7$ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^9$—$OR^{10}$, —$R^9$—CN, —$R^9$—$NO_2$, —$R^9$—$N(R^{10})_2$, —$R^9$—$C(O)OR^{10}$ and —$R^9$—$C(O)N(R^{10})_2$;

each R⁸ is independently selected from the group consisting of a direct bond, an optionally substituted straight or branched alkylene chain, and an optionally substituted straight or branched alkenylene chain;

each R⁹ is independently selected from the group consisting of an optionally substituted straight or branched alkylene chain, or an optionally substituted straight or branched alkenylene chain; and each R¹⁰ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl; and each R¹¹ is hydrogen, alkyl, cyano, nitro or —OR¹⁰.

Another embodiment of the compounds of formula (Ib) are compounds of formula (Ib) wherein:

A is —C(O)—;

R¹ is phenyl substituted with one or more substituents selected from the group consisting of halo, haloalkyl, alkyl, —R⁸—OR¹⁰, —R⁸—O—R⁹—OR¹⁰, and —R⁸—O—R⁹—O—R⁹—OR¹⁰;

R², R⁴ and R⁵ are each hydrogen;

R³ is cycloalkyl optionally substituted with —R⁸—OR¹⁰;

or R³ is phenyl substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, —R⁸—OR¹⁰, —R⁸—C(O)OR¹⁰, —R⁸—OC(O)R¹⁰, —R⁸—O—R⁹—C(O)OR¹⁰, —R⁸—O—R⁹—C(O)N(R⁶)R⁷, —S(O)ₚR⁶ (where p is 0, 1 or 2), —S(O)ₜN(R⁶)R⁷ (where t is 1 or 2), —R⁸—N(R⁶)R⁷, —R⁸—N(R⁶)C(O)R¹⁰, and —R⁸—CN;

R⁶ and R⁷ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally, substituted heteroaryl, optionally substituted heteroarylalkyl, —R⁹—OR¹⁰, —R⁹—CN, —R⁹—NO₂, —R⁹—N(R¹⁰)₂, —R⁹—C(O)OR¹⁰ and —R⁹—C(O)N(R¹⁰)₂;

each R⁸ is independently selected from the group consisting of a direct bond, an optionally substituted straight or branched alkylene chain, and an optionally substituted straight or branched alkenylene chain;

each R⁹ is independently selected from the group consisting of an optionally substituted straight or branched alkylene chain, or an optionally substituted straight or branched alkenylene chain; and each R¹⁰ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl.

Of this embodiment, a specific embodiment is a compound of formula (Ib) selected from the group consisting of:
3-amino-1-(4-(iso-propoxy)phenyl)carbonyl-5-[4-[2-(piperidin-1-yl)ethoxy]phenylamino]-1H-1,2,4-triazole;
3-amino-5-[4-(iso-propoxy)phenylamino]-1-(4-(methyl)phenyl)carbonyl-1H-1,2,4-triazole;
3-amino-1-(4-iso-propoxyphenyl)carbonyl-5-[4-[2-(pyrrolidin-1-yl)ethoxy]phenylamino]-1H-1,2,4-triazole;
3-amino-1-(4-(tert-butyl)phenyl)carbonyl-5-[4-[2-(pyrrolidin-1-yl)ethoxy]phenylamino]-1H-1,2,4-triazole; and
3-amino-1-(4-(morpholin-4-yl)phenyl)carbonyl-5-[3-fluoro-4-[2-(pyrrolidin-1-yl)ethoxy]phenylamino]-1H-1,2,4-triazole.

Another embodiment of the compounds of formula (Ib) are compounds of formula (Ib) wherein:

A is —C(O)—;

R¹ is phenyl substituted with optionally substituted heteroaryl or optionally substituted heterocyclyl;

R², R⁴ and R⁵ are each hydrogen;

R³ is phenyl substituted with one or more substituents selected from the group consisting of alkyl, halo, haloalkyl, nitro, cycloalkyl, cycloalkylalkyl, optionally substituted aryl, optionally substituted heteroaryl, optionally substituted heterocyclyl, —R⁸—OR¹⁰, —R⁸—C(O)OR¹⁰, —R⁸—OC(O)R¹⁰, —R⁸—O—R⁹—C(O)OR¹⁰, —R⁸—O—R⁹—C(O)N(R⁶)R⁷, —S(O)ₚR⁶ (where p is 0, 1 or 2), —S(O)ₜN(R⁶)R⁷ (where t is 1 or 2), —R⁸—N(R⁶)R⁷, —R⁸—N(R⁶)C(O)R¹⁰, and —R⁸—CN;

R⁶ and R⁷ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —R⁹—OR¹⁰, —R⁹—CN, —R⁹—NO₂, —R⁹—N(R¹⁰)₂, —R⁹—C(O)OR¹⁰ and —R⁹—C(O)N(R¹⁰)₂;

each R⁸ is independently selected from the group consisting of a direct bond, an optionally substituted straight or branched alkylene chain, and an optionally substituted straight or branched alkenylene chain;

each R⁹ is independently selected from the group consisting of an optionally substituted straight or branched alkylene chain, or an optionally substituted straight or branched alkenylene chain; and each R¹⁰ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl.

Of this embodiment, a specific embodiment is a compound of formula (Ib) selected from the group consisting of:
3-amino-1-(4-(iso-propoxy)phenyl)carbonyl-5-(4-(morpholin-4-yl)phenylamino]-1H-1,2,4-triazole;
3-amino-5-(4-(morpholin-4-yl)phenylamino)-1-(4-(tert-butoxy)phenyl)carbonyl-1H-1,2,4-triazole;
3-amino-1-(3-(chloro)phenyl)carbonyl-5-(4-(morpholin-4-yl)phenylamino)-1H-1,2,4-triazole;
3-amino-1-(4-(iso-propoxy)phenyl)carbonyl-5-[4-(piperidin-1-yl)phenylamino]-1H-1,2,4-triazole;
3-amino-1-(4-(tert-butoxy)phenyl)carbonyl-5-(4-(pyrrolidin-1-yl)phenylamino]-1H-1,2,4-triazole;
3-amino-1-(4-(iso-propoxy)phenyl)carbonyl-5-(4-(pyrrolidin-1-yl)phenylamino]-1H-1,2,4-triazole;
3-amino-1-(4-(tert-butyl)phenyl)carbonyl-5-[4-(pyrrolidin-1-yl)phenylamino]-1H-1,2,4-triazole;
3-amino-1-(4-methylphenyl)carbonyl-5-(4-(pyrrolidin-1-yl)phenylamino]-1H-1,2,4-triazole;
3-amino-1-(4-(iso-propoxy)phenyl)carbonyl-5-(4-(4-methylpiperazin-1-yl)phenylamino]-1H-1,2,4-triazole;
3-amino-1-(4-(dimethylamino)phenyl)carbonyl-5-(4-(4-methylpiperazin-1-yl)phenylamino]-1H-1,2,4-triazole; and 3-amino-1-(3-(dimethylamino)phenyl)carbonyl-5-(4-(4-methylpiperazin-1-yl)phenylamino]-1H-1,2,4-triazole.

Another embodiment of the compounds of formula (Ib) are compounds of formula (Ib) wherein:

A is —C(O)—;

$R^1$ is phenyl substituted with —$R^8$—O—$R^9$—CN, —$R^8$—O—$R^9$—C(O)O$R^{10}$, —$R^8$—O—$R^9$—C(O)N($R^6$)$R^7$, —$R^8$—O—$R^9$—S(O)$_p R^6$ (where p is 0, 1 or 2), —$R^8$—O—$R^9$—N($R^6$)$R^7$, —$R^8$—O—$R^9$—C(N$R^{11}$)N($R^{11}$)H, and —$R^8$—N($R^6$)C(O)$R^{10}$;

$R^2$, $R^4$ and $R^5$ are each hydrogen;

$R^3$ is phenyl substituted with one or more substituents selected from the group consisting of alkyl, halo, haloalkyl, nitro, cycloalkyl, cycloalkylalkyl, —$R^8$—O$R^{10}$, —$R^8$—C(O)O$R^{10}$, —$R^8$—OC(O)$R^{10}$, —$R^8$—O—$R^9$—C(O)O$R^{10}$, —$R^8$—O—$R^9$—C(O)N($R^6$)$R^7$, —S(O)$_p R^6$ (where p is 0, 1 or 2), —S(O)$_t$N($R^8$)$R^7$ (where t is 1 or 2), —$R^8$—N($R^6$)$R^7$, —$R^8$—N($R^6$)C(O)$R^{10}$, and —$R^8$—CN;

$R^6$ and $R^7$ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^9$—O$R^{10}$, —$R^9$—CN, —$R^9$—NO$_2$, —$R^9$—N($R^{10}$)$_2$, —$R^9$—C(O)O$R^{10}$ and —$R^9$—C(O)N($R^{10}$)$_2$;

each $R^8$ is independently selected from the group consisting of a direct bond, an optionally substituted straight or branched alkylene chain, and an optionally substituted straight or branched alkenylene chain;

each $R^9$ is independently selected from the group consisting of an optionally substituted straight or branched alkylene chain, or an optionally substituted straight or branched alkenylene chain; and each $R^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl; and each $R^{11}$ is hydrogen, alkyl, cyano, nitro or —O$R^{10}$.

Of this embodiment, a specific embodiment is the following compound of formula (Ib), i.e., 3-amino-5-[3-[cyclohexylaminocarbonylmethoxy]phenylamino]-1-(3-(methyl)phenyl)carbonyl-1H-1,2,4-triazole.

Another embodiment of the compounds of formula (Ib) are compounds of formula (Ib) wherein:

A is —C(O)—;

$R^1$ is aryl substituted with one or more substituents selected from the group consisting of halo, haloalkyl, alkyl, optionally substituted heteroaryl, optionally substituted heterocyclyl, —$R^8$—O$R^{10}$, —$R^8$—O—$R^9$—O$R^{10}$, —$R^8$—O—$R^9$—O—$R^9$—O$R^{10}$, —$R^8$—O—$R^9$—CN, —$R^8$—O—$R^9$—C(O)O$R^{10}$, —$R^8$—O—$R^9$—C(O)N($R^6$)$R^7$, —$R^8$—O—$R^9$—S(O)$_p R^6$ (where p is 0, 1 or 2), —$R^8$—O—$R^9$—N($R^6$)$R^7$, —$R^8$—O—$R^9$—C(N$R^{11}$)N($R^{11}$)H, and —$R^8$—N($R^6$)C(O)$R^{10}$;

$R^2$, $R^4$ and $R^5$ are each hydrogen;

$R^3$ is heteroaryl optionally substituted with one or more substituents selected from the group consisting of alkyl, oxo, and —$R^8$—O$R^{10}$;

$R^6$ and $R^7$ are each independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^9$—O$R^{10}$, —$R^9$—CN, —$R^9$—NO$_2$, —$R^9$—N($R^{10}$)$_2$, —$R^9$—C(O)O$R^{10}$ and —$R^9$—C(O)N($R^{10}$)$_2$;

optionally, $R^6$ and $R^7$, together with the nitrogen to which they are attached, form an optionally substituted N-heteroaryl or an optionally substituted N-heterocyclyl;

each $R^8$ is independently selected from the group consisting of a direct bond, an optionally substituted straight or branched alkylene chain, an optionally substituted straight or branched alkenylene chain and an optionally substituted straight or branched alkynylene chain;

each $R^9$ is independently selected from the group consisting of an optionally substituted straight or branched alkylene chain, an optionally substituted straight or branched alkenylene chain and an optionally substituted straight or branched alkynylene chain; and each $R^{10}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl; and each $R^{11}$ is hydrogen, alkyl, cyano, nitro or —O$R^{10}$.

Another embodiment of the compounds of formula (Ib) are compounds of formula (Ib) wherein:

A is —C(O)—;

$R^1$ is phenyl substituted with one or more substituents selected from the group consisting of halo, haloalkyl, alkyl, optionally substituted heteroaryl, optionally substituted heterocyclyl, —$R^8$—O$R^{10}$, —$R^8$—O—$R^9$—O$R^{10}$, —$R^6$—O—$R^9$—O—$R^9$—O$R^{10}$, —$R^8$—O—$R^9$—CN, —$R^8$—O—$R^9$—C(O)O$R^{10}$, —$R^8$—O—$R^9$—C(O)N($R^6$)$R^7$, —$R^8$—O—$R^9$—S(O)$_p R^6$ (where p is 0, 1 or 2), —$R^8$—O—$R^9$—N($R^6$)$R^7$, —$R^8$—O—$R^9$—C(N$R^{11}$)N($R^{11}$)H, and —$R^8$—N($R^6$)C(O)$R^{10}$;

$R^2$, $R^4$ and $R^5$ are each hydrogen;

$R^3$ is heteroaryl optionally substituted with one or more substituents selected from the group consisting of alkyl, oxo, and —$R^8$—O$R^{10}$;

$R^6$ and $R^7$ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally optionally substituted heterocyclyl, optionally substituted heterocyclylalkyl, optionally substituted heteroaryl, optionally substituted heteroarylalkyl, —$R^9$—O$R^{10}$, —$R^9$—CN, —$R^9$—NO$_2$, —$R^9$—N($R^{10}$)$_2$, —$R^9$—C(O)O$R^{10}$ and —$R^9$—C(O)N($R^{10}$)$_2$;

each $R^8$ is independently selected from the group consisting of a direct bond, an optionally substituted straight or branched alkylene chain or an optionally substituted straight or branched alkenylene chain;

each $R^9$ is independently selected from the group consisting of an optionally substituted straight or branched alkylene chain or an optionally substituted straight or branched alkenylene chain; and each $R^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, or optionally substituted heteroarylalkyl; and each $R^{11}$ is hydrogen, alkyl, cyano, nitro or —$OR^{10}$.

Of this embodiment, a specific embodiment is a compound of formula (Ib) selected from the group consisting of:

3-amino-1-(2,2-dimethyl-2H-benzo[b][1,4]oxazin-3(4H)-on-6-yl)carbonyl-5-(4-(iso-propoxy)phenyl)amino-1H-1,2,4-triazole;

3-amino-1-(2,2-dimethyl-2H-benzo[b][1,4]oxazin-3(4H)-on-6-yl)carbonyl-5-(4-(morpholin-4-yl)phenylamino)-1H-1,2,4-triazole;

3-amino-1-(1H-indol-5-yl)carbonyl-5-[4-[2-(pyrrolidin-1-yl)ethoxy]phenylamino]-1H-1,2,4-triazole;

3-amino-1-(2,2-dimethyl-2H-benzo[b][1,4]oxazin-3(4H)-on-6-yl)carbonyl-5-[4-(pyrrolidin-1-yl)phenylamino]-1H-1,2,4-triazole;

3-amino-1-(benzo[b]thiophen-2-yl)carbonyl-5-[4-[2-(pyrrolidin-1-yl)ethoxy]phenylamino]-1H-1,2,4-triazole;

3-amino-1-(1H-indol-6-yl)carbonyl-5-[4-[2-(imidazol-1-yl)ethoxy]phenylamino]-1H-1,2,4-triazole;

3-amino-1-(benzo[b]thiophen-5-yl)carbonyl-5-[4-[2-(imidazol-1-yl)ethoxy]phenylamino]-1H-1,2,4-triazole;

3-amino-1-(1,4-benzodioxan-6-yl)carbonyl-5-[4-[2-((S)-3-fluoropyrrolidin-1-yl)ethoxy]phenylamino]-1H-1,2,4-triazole; and 3-amino-1-(1H-indol-6-yl)carbonyl-5-[4-[2-((S)-3-fluoropyrrolidin-1-yl)ethoxy]phenylamino]-1H-1,2,4-triazole.

Another embodiment of the compounds of formula (Ib) are compounds of formula (Ib) wherein:

A is —C(O)—;

$R^1$ is heteroaryl optionally substituted with one or more substituents selected from the group consisting of alkyl, halo, oxo, —$R^8$—$OR^{10}$, —$R^8$—$C(O)OR^{10}$, —$R^8$—$C(O)N(R^6)R^7$ and —$R^8$—$N(R^6)R^7$;

or $R^1$ is heterocyclylalkyl optionally substituted with one or more substituents selected from the group consisting of halo, haloalkyl, alkyl, optionally substituted aryl, optionally substituted aralkyl, —$R^8$—$OR^{10}$, —$R^8$—$C(O)OR^{10}$, —$R^8$—$C(O)N(R^6)R^7$ and —$R^8$—$N(R^6)R^7$;

or $R^1$ is cycloalkyl optionally substituted with one or more substituents selected from the group consisting of halo, haloalkyl, alkyl, oxo, —$R^8$—$OR^{10}$, —$R^8$—$C(O)OR^{10}$, —$R^8$—$C(O)N(R^6)R^7$, —$R^8$—$S(O)_pR^{10}$ (where p is 0, 1 or 2) and —$R^8$—$N(R^6)R^7$;

$R^2$ is hydrogen, alkyl or —$C(O)R^{10}$;

$R^4$ and $R^5$ are each hydrogen or alkyl;

$R^3$ is one of the following:

a) alkyl optionally substituted with one or more substituents selected from the group consisting of halo, cyano, nitro, oxo, thioxo, trimethylsilanyl, —$OR^{14}$, —$OC(O)$—$R^{14}$, —$N(R^{14})_2$, —$C(O)R^{14}$, —$C(O)OR^{14}$, —$C(O)N(R^{14})_2$, —$N(R^{14})C(O)OR^{14}$, —$N(R^{14})C(O)R^{14}$, —$N(R^{14})S(O)_tR^{14}$ (where t is 1 or 2), —$S(O)_tOR^{14}$ (where t is 1 or 2), —$S(O)_pR^{14}$ (where p is 0, 1 or 2), and —$S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl;

b) cycloalkyl optionally substituted with one or more substituents selected from the group consisting of —$R^8$—$OR^{10}$, alkyl, halo, haloalkyl, aryl, and aralkyl;

c) aryl substituted with one or more substituents selected from the group consisting of alkyl, halo, haloalkyl, nitro, cycloalkyl, cycloalkylalkyl, —$R^8$—$OR^{10}$, —$R^8$—$C(O)$ $OR^{10}$, —$R^8$—$OC(O)R^{10}$, —$R^8$—$O$—$R^8$—$C(O)OR^{10}$, —$R^8$—$O$—$R^8$—$C(O)N(R^6)R^7$, —$S(O)_pR^6$ (where p is 0, 1 or 2), —$S(O)_tN(R^6)R^7$ (where t is 1 or 2), —$R^8$—$N(R^6)R^7$, —$R^8$—$N(R^6)C(O)R^{10}$ and —$R^8$—$CN$;

d) aralkyl, wherein:
   (1) the alkyl part of the aralkyl radical is optionally substituted with one or more substituents selected from the group consisting of halo, cyano, nitro, oxo, thioxo, trimethylsilanyl, —$OR^{14}$, —$OC(O)$—$R^{14}$, —$N(R^{14})_2$, —$C(O)R^{14}$, —$C(O)OR^{14}$, —$C(O)N(R^{14})_2$, —$N(R^{14})C(O)OR^{14}$, —$N(R^{14})C(O)R^{14}$, —$N(R^{14})S(O)_tR^{14}$ (where t is 1 or 2), —$S(O)_tOR^{14}$ (where t is 1 or 2), —$S(O)_pR^{14}$ (where p is 0, 1 or 2), and —$S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl; and
   (2) the aryl part of the aralkyl radical is optionally substituted with one or more substituents selected from the group consisting of alkyl, alkenyl, alkynyl, halo, haloalkyl, haloalkenyl, haloalkynyl, cyano, nitro, aryl, aralkyl, aralkenyl, aralkynyl, cycloalkyl, cycloalkylalkyl, cycloalkylalkenyl, cycloalkylalkynyl, heterocyclyl, heterocyclylalkyl, heterocyclylalkenyl, heterocyclylalkynyl, heteroaryl, heteroarylalkyl, heteroarylalkenyl, heteroarylalkynyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$O$—$R^{16}$—$C(O)N(R^{14})_2$, —$R^{15}$—$N(R^{14})C(O)OR^{14}$, —$R^{15}$—$N(R^{14})C(O)R^{14}$, —$R^{15}$—$N(R^{14})S(O)_tR^{14}$ (where t is 1 or 2), —$R^{15}$—$S(O)_tOR^{14}$ (where t is 1 or 2), —$R^{15}$—$S(O)_pR^{14}$ (where p is 0, 1 or 2), and —$R^{15}$—$S(O)_tN(R^{14})_2$ (where t is 1 or 2), where each $R^{14}$ is independently hydrogen, alkyl, haloalkyl, cycloalkyl, cycloalkylalkyl, aryl, aralkyl, heterocyclyl, heterocylylalkyl, heteroaryl or heteroarylalkyl, each $R^{15}$ is independently a direct bond or a straight or branched alkylene or alkenylene chain, and $R^{16}$ is a straight or branched alkylene or alkenylene chain;

e) heteroaryl optionally substituted with one or more substituents selected from the group consisting of alkyl, oxo, and —$R^8$—$OR^{10}$; or f) heteroarylalkenyl where the heteroaryl part of the heteroarylakyl radical is optionally substituted with one or more substituents selected from the group consisting of alkyl, halo, haloalkyl, aryl and aralkyl;

$R^6$ and $R^7$ are each independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R$^9$—OR$^{10}$, —R$^9$—CN, —R$^9$—NO$_2$, —R$^9$—N(R$^{10}$)$_2$, —R$^9$—C(O)OR$^{10}$ and —R$^9$—C(O)N(R$^{10}$)$_2$;

optionally, R$^6$ and R$^7$, together with the nitrogen to which they are attached, form an optionally substituted N-heteroaryl or an optionally substituted N-heterocyclyl;

each R$^8$ is independently selected from the group consisting of a direct bond, an optionally substituted straight or branched alkylene chain, an optionally substituted straight or branched alkenylene chain and an optionally substituted straight or branched alkynylene chain;

each R$^9$ is independently selected from the group consisting of an optionally substituted straight or branched alkylene chain, an optionally substituted straight or branched alkenylene chain and an optionally substituted straight or branched alkynylene chain; and each R$^{10}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl.

Another embodiment of the compounds of formula (Ib) are compounds of formula (Ib) wherein:

A is —C(O)—;

R$^1$ is heteroaryl optionally substituted with one or more substituents selected from the group consisting of alkyl, halo, oxo, —R$^8$—OR$^{10}$, —R$^8$—C(O)OR$^{10}$, —R$^8$—C(O)N(R$^6$)R$^7$ and —R$^8$—N(R$^6$)R$^7$;

or R$^1$ is heterocyclylalkyl optionally substituted with one or more substituents selected from the group consisting of halo, haloalkyl, alkyl, optionally substituted aryl, optionally substituted aralkyl, —R$^8$—OR$^{10}$, —R$^8$—C(O)OR$^{10}$, —R$^8$—C(O)N(R$^6$)R$^7$ and —R$^8$—N(R$^6$)R$^7$;

or R$^1$ is cycloalkyl optionally substituted with one or more substituents selected from the group consisting of halo, haloalkyl, alkyl, oxo, —R$^8$—OR$^{10}$, —R$^8$—C(O)OR$^{10}$, —R$^8$—C(O)N(R$^6$)R$^7$, —R$^8$—S(O)$_p$R$^{10}$ (where p is 0, 1 or 2) and —R$^8$—N(R$^6$)R$^7$;

R$^2$ is hydrogen, alkyl or —C(O)R$^{10}$;

R$^4$ and R$^5$ are each hydrogen or alkyl;

R$^3$ is alkyl optionally substituted with one or more substituents selected from the group consisting of halo, cyano, nitro, oxo, thioxo, trimethylsilanyl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{14}$, —N(R$^{14}$)C(O)R$^{14}$, —N(R$^{14}$)S(O)$_t$R$^{14}$ (where t is 1 or 2), —S(O)$_t$OR$^{14}$ (where t is 1 or 2), —S(O)$_p$R$^{14}$ (where p is 0, 1 or 2), and —S(O)$_t$N(R$^{14}$)$_2$ (where t is 1 or 2) where each R$^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl;

or R$^3$ is phenyl substituted with one or more substituents selected from the group consisting of alkyl, halo, haloalkyl, nitro, cycloalkyl, cycloalkylalkyl, —R$^8$—OR$^{10}$, —R$^8$—C(O)OR$^{10}$, —R$^8$—OC(O)R$^{15}$, —R$^8$—O—R$^3$—C(O)OR$^{10}$, —R$^8$—O—R$^9$—C(O)N(R$^6$)R$^7$, —S(O)$_p$R$^6$ (where p is 0, 1 or 2), —S(O)$_t$N(R$^6$)R$^7$ (where t is 1 or 2), —R$^8$—N(R$^6$)R$^7$, —R$^8$—N(R$^6$)C(O)R$^{10}$ and —R$^8$—CN;

or R$^3$ is heteroaryl optionally substituted with one or more substituents selected from the group consisting of alkyl, oxo, and —R$^8$—OR$^{10}$;

each R$^6$ and R$^7$ is independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally optionally substituted heterocyclyl, optionally substituted heterocyclylalkyl, optionally substituted heteroaryl, optionally substituted heteroarylalkyl, —R$^9$—OR$^{10}$, —R$^9$—CN, —R$^9$—NO$_2$, —R$^9$—N(R$^{10}$)$_2$, —R$^9$—C(O)OR$^{10}$ and —R$^9$—C(O)N(R$^{10}$)$_2$;

each R$^8$ is independently selected from the group consisting of a direct bond, an optionally substituted straight or branched alkylene chain or an optionally substituted straight or branched alkenylene chain;

each R$^9$ is independently selected from the group consisting of an optionally substituted straight or branched alkylene chain or an optionally substituted straight or branched alkenylene chain; and each R$^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, or optionally substituted heteroarylalkyl.

Of this embodiment, a specific embodiment is a compound of formula (Ib) selected from the group consisting of:

3-amino-5-[(2H,3H-4-tert-butoxycarbonylbenzo[1,4]oxazin-6-yl)-[(2H,3H-4-tert-butoxycarbonylbenzo[1,4]oxazin-6-yl)amino]-1-(3-(methyl)phenyl)carbonyl-1H-1,2,4-triazole;

3-amino-1-[3-[2-(1,3-dioxolan-2-yl)ethoxy]phenylcarbonyl-5-(1,4-benzodioxan-6-yl)amino-1H-1,2,4-triazole;

3-amino-1-[4-[2-(1,3-dioxolan-2-yl)ethoxy]phenylcarbonyl-5-(1,4-benzodioxan-6-yl)amino-1H-1,2,4-triazole;

3-amino-5-(1,4-benzodioxan-6-yl)amino-1-(4-iso-propylphenyl)carbonyl-1H-1,2,4-triazole;

3-amino-1-(3,4-dimethylphenyl)carbonyl-5-(1,4-benzodioxan-6-yl)amino-1H-1,2,4-triazole;

3-amino-1-(3-(benzyloxy)phenyl)carbonyl-5-(1,4-benzodioxan-6-yl)amino-1H-1,2,4-triazole;

3-amino-5-(1,4-benzodioxan-6-yl)amino-1-(4-thiomethylphenyl)carbonyl-1H-1,2,4-triazole;

3-amino-5-(1,4-benzodioxan-6-yl)amino-1-[(4-fluoro-3-methyl)phenyl]carbonyl-1H-1,2,4-triazole 3-amino-1-(2,6-difluorophenyl)carbonyl-5-(1-methylsulfonylpiperidin-4-yl)amino-1H-1,2,4-triazole;

3-amino-1-(4-(dimethylamino)phenyl)carbonyl-5-(1-methylsulfonylpiperidin-4-yl)amino-1H-1,2,4-triazole; and 3-amino-5-[3-(4-(2-chloro-6-fluorophenyl)piperazin-1-yl)prop-1-yl]amino-1-(3-methylphenyl)carbonyl-1H-1,2,4-triazole.

Another embodiment of the compounds of formula (Ib) are compounds of formula (Ib) wherein:

A is —C(O)—;

R$^1$ is cycloalkyl optionally substituted with one or more substituents selected from the group consisting of halo, haloalkyl, alkyl, oxo, —R$^8$—OR$^{10}$, —R$^8$—C(O)OR$^{10}$, —R$^8$—C(O)N(R$^6$)R$^7$, —R$^8$—S(O)$_p$R$^{10}$ (where p is 0, 1 or 2) and —R$^8$—N(R$^6$)R$^7$;

$R^2$, $R^4$ and $R^5$ are each hydrogen;

$R^3$ is one of the following:

a) alkyl optionally substituted with one or more substituents selected from the group consisting of halo, cyano, nitro, oxo, thioxo, trimethylsilanyl, —$OR^{14}$, —OC(O)—$R^{14}$, —$N(R^{14})_2$, —$C(O)R^{14}$—$C(O)N(R^{14})_2$, —$N(R^{14})C(O)OR^{14}$, —$N(R^{14})C(O)R^{14}$, —$N(R^{14})S(O)_tR^{14}$ (where t is 1 or 2), —$S(O)_tOR^{14}$ (where t is 1 or 2), —$S(O)_pR^{14}$ (where p is 0, 1 or 2), and —$S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl;

b) cycloalkyl optionally substituted with one or more substituents selected from the group consisting of —$R^8$—$OR^{10}$, alkyl, halo, haloalkyl, aryl, and aralkyl;

c) aryl substituted with one or more substituents selected from the group consisting of alkyl, halo, haloalkyl, nitro, cycloalkyl, cycloalkylalkyl, —$R^8$—$OR^{10}$, —$R^8$—$C(O)OR^{10}$, —$R^8$—$OC(O)R^{10}$, —$R^8$—O—$R^9$—$C(O)OR^{10}$, —$R^8$—O—$R^8$—$C(O)N(R^8)R^7$, —$S(O)_pR^8$ (where p is 0, 1 or 2), —$S(O)_tN(R^8)R^7$ (where t is 1 or 2), —$R^8$—$N(R^6)R^7$, —$R^8$—$N(R^8)C(O)R^{10}$ and —$R^8$—CN;

d) aralkyl, wherein:
  (1) the alkyl part of the aralkyl radical is optionally substituted with one or more substituents selected from the group consisting of halo, cyano, nitro, oxo, thioxo, trimethylsilanyl, —$OR^{14}$, —$OC(O)$—$R^{14}$, —$N(R^{14})^2$, —$C(O)R^{14}$, —$C(O)OR^{14}$, —$C(O)N(R^{14})_2$, —$N(R^{14})C(O)OR^{14}$, —$N(R^{14})C(O)R^{14}$, —$N(R^{14})S(O)_tR^{14}$ (where t is 1 or 2), —$S(O)_tOR^{14}$ (where t is 1 or 2), —$S(O)_pR^{14}$ (where p is 0, 1 or 2), and —$S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl; and
  (2) the aryl part of the aralkyl radical is optionally substituted with one or more substituents selected from the group consisting of alkyl, alkenyl, alkynyl, halo, haloalkyl, haloalkenyl, haloalkynyl, cyano, nitro, aryl, aralkyl, aralkenyl, aralkynyl, cycloalkyl, cycloalkylalkyl, cycloalkylalkenyl, cycloalkylalkynyl, heterocyclyl, heterocyclylalkyl, heterocyclylalkenyl, heterocyclylalkynyl, heteroaryl, heteroarylalkyl, heteroarylalkenyl, heteroarylalkynyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—O—$R^{16}$—$C(O)N(R^{14})_2$, —$R^{15}$—$N(R^{14})C(O)OR^{14}$, —$R^{15}$—$N(R^{14})C(O)R^{14}$, —$R^{15}$—$N(R^{14})S(O)_tR^{14}$ (where t is 1 or 2), —$R^{15}$—$S(O)_tOR^{14}$ (where t is 1 or 2), —$R^{15}$—$S(O)_pR^{14}$ (where p is 0, 1 or 2), and —$R^{15}$—$S(O)_tN(R^{14})_2$ (where t is 1 or 2), where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl, each $R^{15}$ is independently a direct bond or a straight or branched alkylene or alkenylene chain, and $R^{16}$ is a straight or branched alkylene or alkenylene chain;

e) heteroaryl optionally substituted with one or more substituents selected from the group consisting of alkyl, oxo, and —$R^8$—$OR^{10}$; or f) heteroarylalkenyl where the heteroaryl part of the heteroarylalkyl radical is optionally substituted with one or more substituents selected from the group consisting of alkyl, halo, haloalkyl, aryl and aralkyl;

$R^6$ and $R^7$ are each independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^9$—$OR^{10}$, —$R^9$—CN, —$R^9$—$NO_2$, —$R^9$—$N(R^{10})_2$, —$R^9$—$C(O)OR^{10}$ and —$R^9$—$C(O)N(R^{10})_2$;

optionally, $R^6$ and $R^7$, together with the nitrogen to which they are attached, form an optionally substituted N-heteroaryl or an optionally substituted N-heterocyclyl;

each $R^8$ is independently selected from the group consisting of a direct bond, an optionally substituted straight or branched alkylene chain, an optionally substituted straight or branched alkenylene chain and an optionally substituted straight or branched alkynylene chain;

each $R^9$ is independently selected from the group consisting of an optionally substituted straight or branched alkylene chain, an optionally substituted straight or branched alkenylene chain and an optionally substituted straight or branched alkynylene chain; and each $R^{10}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl.

Another embodiment of the compounds of formula (Ib) are compounds of formula (Ib) wherein:

A is —C(O)—;

$R^1$ is cycloalkyl optionally substituted with one or more substituents selected from the group consisting of halo, haloalkyl, alkyl, oxo, —$R^8$—$OR^{10}$, —$R^8$—$C(O)OR^{10}$, —$R^8$—$C(O)N(R^6)R^7$, —$R^8$—$S(O)_pR^{10}$ (where p is 0, 1 or 2) and —$R^8$—$N(R^6)R^7$;

$R^2$, $R^4$ and $R^5$ are each hydrogen;

$R^3$ is alkyl optionally substituted with one or more substituents selected from the group consisting of halo, cyano, nitro, oxo, thioxo, trimethylsilanyl, —$OR^{14}$, —OC(O)—$R^{14}$, —$N(R^{14})_2$, —$C(O)R^{14}$, —$C(O)OR^{14}$, —$C(O)N(R^{14})_2$, —$N(R^{14})C(O)OR^{14}$, —$N(R^{14})C(O)R^{14}$, —$N(R^{14})S(O)_tR^{14}$ (where t is 1 or 2), —$S(O)_tOR^{14}$ (where t is 1 or 2), —$S(O)_pR^{14}$ (where p is 0, 1 or 2), and —$S(O)_tN(R^{14})_2$ (where t is 1 or 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl;

or $R^3$ is phenyl substituted with one or more substituents selected from the group consisting of alkyl, halo, haloalkyl, nitro, cycloalkyl, cycloalkylalkyl, —R$^8$—OR$^{10}$, —R$^8$—C(O)OR$^{10}$, —R$^8$—OC(O)R$^{10}$, —R$^8$—O—R$^8$—C(O)OR$^{10}$, —R$^8$—O—R$^9$—C(O)N(R$^6$)R$^7$, —S(O)$_p$R$^6$ (where p is 0, 1 or 2), —S(O)$_t$N(R$^6$)R$^7$ (where t is 1 or 2), —R$^8$—N(R$^6$)R$^7$, —R$^8$—N(R$^6$)C(O)R$^{10}$ and —R$^8$—CN;

or R$^3$ is heteroaryl optionally substituted with one or more substituents selected from the group consisting of alkyl, oxo, and —R$^8$—OR$^{10}$;

each R$^6$ and R$^7$ is independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally optionally substituted heterocyclyl, optionally substituted heterocyclylalkyl, optionally substituted heteroaryl, optionally substituted heteroarylalkyl, —R$^9$—OR$^{10}$, —R$^9$—NO$_2$, —R$^9$—N(R$^{13}$)$_2$, —R$^9$—C(O)OR$^{13}$ and —R$^9$—C(O)N(R$^{10}$)$_2$;

each R$^8$ is independently selected from the group consisting of a direct bond, an optionally substituted straight or branched alkylene chain or an optionally substituted straight or branched alkenylene chain;

each R$^9$ is independently selected from the group consisting of an optionally substituted straight or branched alkylene chain or an optionally substituted straight or branched alkenylene chain; and each R$^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, or optionally substituted heteroarylalkyl.

Of this embodiment, a specific embodiment is a compound of formula (Ib) selected from the group consisting of:
3-amino-1-(4-(tert-butoxy)phenyl)carbonyl-5-[(3-(aminocarbonyl)bicyclo[2.2.1]hept-5-en-2-yl)amino]-1H-1,2,4-triazole;
3-amino-1-(3-(tert-butoxy)phenyl)carbonyl-5-[(3-(aminocarbonyl)bicyclo[2.2.1]hept-5-en-2-yl)amino]-1H-1,2,4-triazole;
3-amino-1-(4-(dimethylamino)phenyl)carbonyl-5-[(3-(aminocarbonyl)bicyclo[2.2.1]hept-5-en-2-yl)amino]-1H-1,2,4-triazole;
3-amino-1-(3-(dimethylamino)phenyl)carbonyl-5-[(3-(aminocarbonyl)bicyclo[2.2.1]hept-5-en-2-yl)amino]-1H-1,2,4-triazole;
3-amino-1-(4-(iso-propoxy)phenyl)carbonyl-5-[(3-(aminocarbonyl)bicyclo[2.2.1]hept-5-en-2-yl)amino]-1H-1,2,4-triazole; and
3-amino-1-(1H-indol-6-yl)carbonyl-5-[(3-(aminocarbonyl)bicyclo[2.2.1]hept-5-en-2-yl)amino]-1H-1,2,4-triazole.

Another embodiment of the various aspects of the invention set forth above in the Summary of the Invention are compounds of formula (Ib):

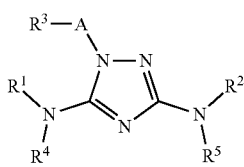

(Ib)

wherein:
A is —C(O)O—, or —C(O)N(R$^6$)—;
R$^1$ is one of the following:
  a) aryl substituted with one or more substituents selected from the group consisting of halo, haloalkyl, alkyl, optionally substituted heteroaryl, optionally substituted heterocyclyl, —R$^8$—OR$^{10}$, —R$^6$—O—R$^8$—OR$^{10}$, —R$^8$—O—R$^8$—O—R$^8$—OR$^{10}$, —R$^8$—O—R$^8$—CN, —R$^8$—O—R$^8$—C(O)OR$^{10}$, —R$^8$—O—R$^8$—C(O)N(R$^6$)R$^7$, —R$^8$—O—R$^8$—S(O)$_p$R$^6$ (where p is 0, 1 or 2), —R$^8$—O—R$^8$—N(R$^6$)R$^7$, —R$^8$—O—R$^8$—C(NR$^{11}$)N(R$^{11}$)H, and —R$^8$—N(R$^6$)C(O)R$^{10}$; or
  b) heteroaryl optionally substituted with one or more substituents selected from the group consisting of alkyl, halo, oxo, —R$^8$—OR$^{10}$, —R$^8$—C(O)OR$^{10}$, —R$^8$—C(O)N(R$^6$)R$^7$ and —R$^8$—N(R$^6$)R$^7$;
R$^2$, R$^4$ and R$^5$ are each hydrogen;
R$^3$ is one of the following:
  a) alkyl optionally substituted with one or more substituents selected from the group consisting of halo, cyano, nitro, oxo, thioxo, trimethylsilanyl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{14}$, —N(R$^{14}$)C(O)R$^{14}$, —N(R$^{14}$)S(O)$_t$R$^{14}$ (where t is 1 or 2), —S(O)$_t$OR$^{14}$ (where t is 1 or 2), —S(O)$_p$R$^{14}$ (where p is 0, 1 or 2), and —S(O)$_t$N(R$^{14}$)$_2$ (where t is 1 or 2) where each R$^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl;
  b) cycloalkyl optionally substituted with one or more substituents selected from the group consisting of —R$^8$—OR$^{10}$, alkyl, halo, haloalkyl, aryl, and aralkyl;
  c) aryl substituted with one or more substituents selected from the group consisting of alkyl, halo, haloalkyl, nitro, cycloalkyl, cycloalkylalkyl, —R$^8$—OR$^{10}$, —R$^8$—C(O)OR$^{10}$, —R$^8$—OC(O)R$^{10}$, —R$^8$—O—R$^9$—C(O)OR$^{10}$, —R$^8$—O—R$^9$—C(O)N(R$^6$)R$^7$, —S(O)$_p$R$^6$ (where p is 0, 1 or 2), —S(O)$_t$N(R$^6$)R$^7$ (where t is 1 or 2), —R$^8$—N(R$^6$)R$^7$, —R$^8$—N(R$^6$)C(O)R$^{10}$ and —R$^8$—CN;
  d) aralkyl, wherein:
    (1) the alkyl part of the aralkyl radical is optionally substituted with one or more substituents selected from the group consisting of halo, cyano, nitro, oxo, thioxo, trimethylsilanyl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{14}$, —N(R$^{14}$)C(O)$_R$R$^{14}$, —N(R$^{14}$)S(O)$_t$R$^{14}$ (where t is 1 or 2), —S(O)$_t$OR$^{14}$ (where t is 1 or 2), —S(O)$_p$R$^{14}$ (where p is 0, 1 or 2), and —S(O)$_t$N(R$^{14}$)$_2$ (where t is 1 or 2) where each R$^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl; and
    (2) the aryl part of the aralkyl radical is optionally substituted with one or more substituents selected from the group consisting of alkyl, alkenyl, alkynyl, halo, haloalkyl, haloalkenyl, haloalkynyl, cyano, nitro, aryl, aralkyl, aralkenyl, aralkynyl, cycloalkyl, cycloalkylalkyl, cycloalkylalkenyl, cycloalkylalkynyl, heterocyclyl, heterocyclylalkyl, heterocyclylalkenyl, heterocyclylalkynyl, heteroaryl, heteroarylalkyl, heteroarylalkenyl, heteroarylalkynyl, —R$^{15}$—OR$^{14}$, —R$^{15}$—OC(O)—R$^{14}$, —R$^{15}$—N(R$^{14}$)$_2$, —R$^{15}$—C(O)R$^{14}$, —R$^{15}$—C(O)OR$^{14}$, —R$^{15}$—C(O)N(R$^{14}$)$_2$, —R$^{15}$—O—R$^{16}$—C(O)N(R$^{14}$)$_2$, —R$^{15}$—

N($R^{14}$)C(O)O$R^{14}$, —$R^{15}$—N($R^{14}$)C(O)$R^{14}$, —$R^{15}$—N($R^{14}$)S(O)$_t$$R^{14}$ (where t is 1 or 2), —$R^{15}$—S(O)$_t$O$R^{14}$ (where t is 1 or 2), —$R^{15}$—S(O)$_p$$R^{14}$ (where p is 0, 1 or 2), and —$R^{15}$—S(O)$_t$N($R^{14}$)$_2$ (where t is 1 or 2), where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl, each $R^{15}$ is independently a direct bond or a straight or branched alkylene or alkenylene chain, and $R^{16}$ is a straight or branched alkylene or alkenylene chain;

e) heteroaryl optionally substituted with one or more substituents selected from the group consisting of alkyl, oxo, and —$R^8$—O$R^{10}$; or f) heteroarylalkenyl where the heteroaryl part of the heteroarylakyl radical is optionally substituted with one or more substituents selected from the group consisting of alkyl, halo, haloalkyl, aryl and aralkyl;

$R^6$ and $R^7$ are each independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^9$—O$R^{10}$, —$R^9$—CN, —$R^9$—NO$_2$, —$R^9$—N($R^{10}$)$_2$, —$R^9$—C(O)O$R^{10}$ and —$R^9$—C(O)N($R^{10}$)$_2$;

each $R^8$ is independently selected from the group consisting of a direct bond, an optionally substituted straight or branched alkylene chain, an optionally substituted straight or branched alkenylene chain and an optionally substituted straight or branched alkynylene chain;

each $R^9$ is independently selected from the group consisting of an optionally substituted straight or branched alkylene chain, an optionally substituted straight or branched alkenylene chain and an optionally substituted straight or branched alkynylene chain; and each $R^{10}$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl; and each $R^{11}$ is hydrogen, alkyl, cyano, nitro or —O$R^{10}$.

Another embodiment of the compounds of formula (Ib) are compounds of formula (Ib) wherein:

A is —C(O)O—, or —C(O)N($R^6$)—;

$R^1$ is one of the following:

a) aryl substituted with one or more substituents selected from the group consisting of halo, haloalkyl, alkyl, optionally substituted heteroaryl, optionally substituted heterocyclyl, —$R^8$—O$R^{10}$, —$R^8$—O—$R^9$—O$R^{10}$, —$R^8$—O—$R^9$—O—$R^9$—O$R^{10}$, —$R^8$—O—$R^9$—CN, —$R^8$—O—$R^9$—C(O)O$R^{10}$, —$R^8$—O—$R^9$—C(O)N($R^6$)$R^7$, —$R^8$—O—$R^9$—S(O)$_p$$R^6$ (where p is 0, 1 or 2), —$R^8$—O—$R^9$—N($R^6$)$R^7$, —$R^8$—O—$R^9$—C(N$R^{11}$)N($R^{11}$)H, and —$R^8$—N($R^6$)C(O)$R^{10}$; or b) heteroaryl optionally substituted with one or more substituents selected from the group consisting of alkyl, halo, oxo, —$R^6$—O$R^{10}$, —$R^8$—C(O)O$R^{10}$, —$R^8$—C(O)N($R^6$)$R^7$ and —$R^8$—N($R^6$)$R^7$;

$R^2$, $R^4$ and $R^5$ are each hydrogen;

$R^3$ is cycloalkyl optionally substituted with one or more substituents selected from the group consisting of —$R^8$—O$R^{10}$, alkyl, halo, haloalkyl, aryl, and aralkyl;

or $R^3$ is phenyl substituted with one or more substituents selected from the group consisting of alkyl, halo, haloalkyl, nitro, cycloalkyl, cycloalkylalkyl, —$R^8$—O$R^{10}$, —$R^8$—C(O)O$R^{10}$, —$R^8$—OC(O)$R^{10}$, —$R^8$—O—$R^9$—C(O)O$R^{10}$, —$R^8$—O—$R^9$—C(O)N($R^6$)$R^7$, —S(O)$_p$$R^6$ (where p is 0, 1 or 2), —S(O)$_t$N($R^6$)$R^7$ (where t is 1 or 2), —$R^8$—N($R^6$)$R^7$, —$R^8$—N($R^6$)C(O)$R^{10}$, and —$R^8$—CN;

or $R^3$ is heteroaryl optionally substituted with one or more substituents selected from the group consisting of alkyl, oxo, and —$R^8$—O$R^{10}$;

$R^6$ and $R^7$ are each independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^9$—O$R^{10}$, —$R^9$—CN, —$R^9$—NO$_2$, —$R^9$—N($R^{10}$)$_2$, —$R^9$—C(O)O$R^{13}$ and —$R^9$—C(O)N($R^{10}$)$_2$;

each $R^8$ is independently selected from the group consisting of a direct bond, an optionally substituted straight or branched alkylene chain or an optionally substituted straight or branched alkenylene chain;

each $R^9$ is independently selected from the group consisting of an optionally substituted straight or branched alkylene chain or an optionally substituted straight or branched alkenylene chain;

each $R^{10}$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, or optionally substituted heteroarylalkyl; and each $R^{11}$ is hydrogen, alkyl, cyano, nitro or —O$R^{10}$.

Of this embodiment, a specific embodiment is a compound of formula (Ib) selected from the group consisting of:

3-amino-5-(1,4-benzodioxan-6-yl)amino-1-methoxycarbonyl-1H-1,2,4-triazole;

5-[4-(acetyl(methyl)amino)phenyl]amino-3-amino-N-(1,3-benzodioxol-5-yl)-1H-1,2,4-triazole-1-carboxamide;

5-[4-(acetyl(methyl)amino)phenyl]amino-3-amino-N-cyclopentyl-1H-1,2,4-triazole-1-carboxamide;

3-amino-N-(4-(butoxy)phenyl)-5-[4-[2-(piperidin-1-yl)ethoxy]phenylamino]-1H-1,2,4-triazole-1-carboxamide;

3-amino-N-(4-(methyl)phenyl)-5-[4-[2-(piperidin-1-yl)ethoxy]phenylamino]-1H-1,2,4-triazole-1-carboxamide;

3-amino-N-(4-(methoxy)phenyl)-5-[4-[2-(piperidin-1-yl)ethoxy]phenylamino]-1H-1,2,4-triazole-1-carboxamide;

3-[4-(acetyl(methyl)amino)phenyl]amino-3-amino-N-cyclohexyl-1H-1,2,4-triazole-1-carboxamide;

3-amino-N-(3-(methyl)phenyl)-5-[4-[2-(piperidin-1-yl)ethoxy]phenylamino]-1H-1,2,4-triazole-1-carboxamide;

3-amino-N-(3,5-dimethoxyphenyl)-5-[4-[2-(piperidin-1-yl)ethoxy]phenylamino]-1H-1,2,4-triazole-1-carboxamide;
3-amino-N-cyclohexyl-5-[4-[2-(piperidin-1-yl)ethoxy]phenylamino]-1H-1,2,4-triazole-1-carboxamide;
3-amino-N-cyclopentyl-5-[4-[2-(piperidin-1-yl)ethoxy]phenylamino]-1H-1,2,4-triazole-1-carboxamide; and
3-amino-N-(1,3-benzodioxol-5-yl)-5-[4-[2-(piperidin-1-yl)ethoxy]phenylamino]-1H-1,2,4-triazole-1-carboxamide.

Another embodiment of the various aspects of the invention set forth above in the Summary of the Invention is the group of compounds of formula (Ia) and compounds of formula (Ib) which does not include the following compounds (identified by their unique Chemical Abstracts Registry number:

110984-61-7; 324074-12-6; 324074-13-7; 324074-14-8; 324074-15-9; 324074-16-0; 324074-17-1; 324074-18-2; 324074-19-3; 324074-20-6; 324074-21-7; 324074-22-8; 324074-23-9; 324074-24-0; 324074-25-1; 324074-28-4; 324074-29-5; 324074-30-8; 324074-31-9; 324074-32-0; 324074-33-1; 324074-34-2; 324074-35-3; 324074-36-4; 324074-38-6; 324074-39-7; 324074-41-1; 324074-42-2; 324074-43-3; 324074-44-4; 324074-45-5; 324074-46-6; 324074-47-7; 324074-48-8; 324074-50-2; 324074-51-3; 324074-52-4; 443798-64-9; 443798-65-0; 443798-66-1; 443798-67-2; 443798-68-3; 443798-69-4; 443798-70-7; 443798-71-8; 443798-72-9; 443798-73-0; 443798-74-1; 443798-87-6; 443798-88-7; 443798-89-8; 443798-90-1; 443798-91-2; 443798-92-3; 443798-93-4; 443798-96-7; 443798-95-6; 443798-94-5; 443798-97-8; 443798-98-9; 443798-99-0; 443799-10-8; 443799-12-0; 443799-14-2; 443799-16-4; 443799-18-6; 503546-63-2; 503546-65-4; 700811-45-6; 700812-30-2; 700812-68-6; 700812-69-7; 863030-86-8; 863030-85-7; 863030-84-6; 863030-77-7; 863030-76-6; 863030-74-4; 863030-87-9; 863030-83-5; 863030-81-3; and 863030-79-9.

Another embodiment of the various aspects of the invention set forth above in the Summary of the Invention is the group of compounds of formula (Ia) and compounds of formula (Ib) which does not include the following compounds:

5-amino-N-benzyl-3-(pyridin-3-ylamino)-1H-1,2,4-triazole-1-carboxamide; 5-amino-N-(2-chlorophenyl)-3-(pyridin-3-ylamino)-1H-1,2,4-triazole-1-carboxamide; 5-amino-N-(3-chlorophenyl)-3-(pyridin-3-ylamino)-1H-1,2,4-triazole-1-carboxamide; 3-amino-N-(2-chlorophenyl)-5-(pyridin-3-ylamino)-1H-1,2,4-triazole-1-carboxamide; and 5-amino-N-(4-methylphenyl)-3-(pyridin-3-ylamino)-1H-1,2,4-triazole-1-carboxamide.

Other embodiments of the invention are the pharmaceutical compositions, as set forth above in the Summary of the Invention, wherein the compounds of formula (Ia) or the compounds of formula (Ib) therein are as set forth above in the embodiments of the compound of formula (Ia) or the compound of formula (Ib).

Other embodiments of the invention are the methods of treating a disease or condition associated with Axl catalytic activity in a mammal, as set forth above in the Summary of the Invention, wherein the compounds of formula (Ia) or the compounds of formula (Ib) therein are as set forth above in the embodiments of the compound of formula (Ia) or the compound of formula (Ib).

Another embodiment of the invention are those methods of treating a disease or condition associated with Axl catalytic activity by administering to the mammal a therapeutically effective amount of a compound of formula (I), as set forth above in the Summary of the Invention, wherein the disease or condition is selected from the group consisting of rheumatoid arthritis, vascular disease/injury (including but not limited to restenosis, atherosclerosis and thrombosis), psoriasis, visual impairment due to macular degeneration, diabetic retinopathy or retinopathy of prematurity, kidney disease (including but not limited to glomerulonephritis, diabetic nephropathy and renal transplant rejection), osteoarthritis and cataracts.

Another embodiment of the invention are those methods of treating a disease or condition associated with Axl catalytic activity by administering to the mammal a therapeutically effective amount of a compound of formula (I), as set forth above in the Summary of the Invention, wherein the disease or condition is selected from the group consisting of breast carcinoma, renal carcinoma, endometrial carcinoma, ovarian carcinoma, thyroid carcinoma, non-small cell lung carcinoma, uveal melanoma, myeloid leukemia and lymphoma.

Another embodiment of the invention are those methods of treating a disease or condition associated with Axl catalytic activity by administering to the mammal of therapeutically effective amount of a compound of formula (I), as set forth above in the Summary of the Invention, wherein the disease or condition is endometriosis.

Specific embodiments of the invention are described in more detail below in the following sections.

Utility and Testing of the Compounds of the Invention

The oncogenic RTK, Axl, was recently identified, using a retroviral-based functional genetic screening protocol, as a regulator of haptotactic migration, which is a key event in angiogenesis. Axl inhibition by RNAi-mediated silencing blocked endothelial cell migration, proliferation and in vitro tube formation. These observations, which were disclosed at the American Association Cancer Research General Meeting, Apr. 16-20, 2005, Anaheim, Calif., and The 7th Annual Symposium on Anti-Angiogenic Agents, Feb. 10-13, 2005, San Diego, Calif.; (*Requirement for The Receptor Tyrosine Kinase Axl in Angiogenesis and Tumor Growth*, Holland, S. J. Powell, M. J., Franci, C., Chan, E., Friera, A. M., Atchison, R., Xu, W., McLaughlin, J., Swift, S. E., Pali, E., Yam, G., Wong, S., Xu, X., Hu, Y., Lasaga, J., Shen, M., Yu, S., Daniel, R., Hitoshi, Y., Bogenberger, J., Nor, J. E., Payan, D. G and Lorens, J. B), were substantiated by an in vivo study which demonstrated that stable, shRNAi-mediated Axl knockdown impaired formation of functional human blood vessels in a mouse model of human angiogenesis. These observations were published in a peer reviewed journal (Holland S J, Powell M J, Franci C, Chan E W, Friera A M, Atchison R E, McLaughlin J, Swift S E, Pali E S, Yam G, Wong S, Lasaga J, Shen M R, Yu S, Xu W, Hitoshi Y, Bogenberger J, Nor J E, Payan D G, Lorens J B. "Multiple roles for the receptor tyrosine kinase axl in tumor formation." *Cancer Res*. (2005) Vol 65 pp 9294-303. These observations are also disclosed in U.S. Published Patent Application 2005/0118604 and European Patent Application 1 563 094, the disclosures of which are incorporated in full by reference. Axl signaling, therefore, impacts multiple functions required for neovascularization in vitro, and regulates angiogenesis in vivo. Regulation of these pro-angiogenic processes required the catalytic activity of Axl. Thus, Axl-mediated angiogenic stimulation would be amenable to modulation by a small molecule inhibitor of Axl catalytic activity.

The compounds of the invention are small molecule inhibitors of Axl catalytic activity, and are therefore useful in treating diseases and conditions which are associated with Axl catalytic activity including those diseases and conditions which are characterized by angiogenesis and/or cell proliferation. Such diseases and conditions include, but are not limited to, solid tumors, including, but not limited to, breast, renal, endometrial, ovarian, thyroid, non-small cell lung carcinoma and uveal melanoma; liquid tumors, including but not limited to, leukemias (particularly myeloid leukemias) and lymphomas; endometriosis, vascular disease/injury (including but not limited to restenosis, atherosclerosis and thrombosis), psoriasis; visual impairment due to macular degeneration; diabetic retinopathy and retinopathy of prematurity; kidney disease (including but not limited to glomerulonephritis, diabetic nephropathy and renal transplant rejection), rheumatoid arthritis; osteoarthritis and cataracts.

The following animal models provide guidance to one of ordinary skill in the art in testing the compounds of the invention for their use in treating the disease or condition indicated.

The compounds of the invention may be tested for their use in treating leukemias and lymphomas by testing the compounds in the xenograft in SCID mouse model using human Axl-expressing cancer cell lines including, but not limited to, HeLa, MDA-MB-231, SK-OV-3, OVCAR-8, DU145 and H1299.

The compounds of the invention may be tested for their use in treating leukemias in the xenograft in SCID mouse model using human Axl-expressing AML and CML leukemia cell lines.

The compounds of the invention may be tested for their use in treating endometriosis by using the syngenic mouse model of endometriosis (see Somigliana, E. et al., "Endometrial ability to implant in ectopic sites can be prevented by interleukin-12 in a murine model of endometriosis", *Hum. Reprod.* (1999), Vol. 14, NO. 12, pp. 2944-50). The compounds may also be tested for their use in treating endometriosis by using the rat model of endometriosis (see Lebovic, D. I. et al., "Peroxisome proliferator-activated receptor-gamma induces regression of endometrial explants in a rat model of endometriosis", *Fertil. Steril.* (2004), 82 Suppl 3, pp. 1008-13).

The compounds of the invention may be tested for their use in treating restenosis by using the balloon-injured rate carotid artery model (see Kim, D. W. et al., "Novel oral formulation of paclitaxel inhibits neointimal hyperplasia in a rat carotid artery injury model", *Circulation* (2004), Vol. 109, No. 12, pp. 1558-63, Epub 2004 Mar. 8).

The compounds of the invention may also be tested for their use in treating restenosis by using the percutaneous transluminal coronary angioplasty in apoE deficient mouse model (see von der Thusen, J. H. et al., "Adenoviral transfer of endothelial nitric oxide synthase attenuates lesion formation in a novel murine model of postangioplasty restenosis", *Arterioscler. Thromb. Vasc. Biol.* (2004), Vol. 24, No. 2, pp. 357-62).

The compounds of the invention may be tested for their use in treating atherosclerosis/thrombosis in the ApoE deficient mouse model (see Nakashima, Y. et al., "ApoE-deficient mice develop lesions of all phases of atherosclerosis throughout the arterial tree", *Arterioscler. Thromb.* (1994), Vol. 14, No. 1, pp. 133-40).

The compounds of the invention may also be tested for their use in treating thrombosis using the collagen-epinephrin-induced pulmonary thromboembolism model and the stasis induced venous thrombosis model (see Angelillo-Scherrer A. et al., "Role of Gas6 receptors in platelet signaling during thrombus stabilization and implications for antithrombotic therapy", *J Clin Invest.* (2005) Vol 115 pp 237-46).

The compounds of the invention may be tested for their use in treating psoriasis by using the SCID mouse model or the human skin model of psoriasis (see Nickoloff, B. J. et al., "Severe combined immunodeficiency mouse and human psoriatic skin chimeras. Validation of a new animal model", *Am. J. Pathol.* (1995), Vol. 146, No. 3, pp. 580-8).

The compounds of the invention may be tested for their use in treating age-related macular degeneration or diabetic retinopathy by using the rat corneal angiogenesis model (see Sarayba M A, Li L, Tungsiripat T, Liu N H, Sweet P M, Patel A J, Osann K E, Chittiboyina A, Benson S C, Pershadsingh H A, Chuck R S. Inhibition of corneal neovascularization by a peroxisome proliferator-activated receptor-gamma ligand. Exp Eye Res. 2005 March; 80(3):435-42) or the laser-induced mouse choroidal neovasculation model (see Bora, P. S., et al., "Immunotherapy for choroidal neovascularization in a laser-induced mouse model simulating exudative (wet) macular degeneration", *Proc. Natl. Acad. Sci. U.S.A.* (2003), Vol. 100, No. 5, pp. 2679-84, Epub 2003 Feb. 14).

The compounds of the invention may be tested for their use in treating retinopathy of prematurity in the mouse retinopathy of prematurity model (see Smith, L. E. et al., "Oxygen-induced retinopathy in the mouse", *Invest. Ophthalmol. Vis. Sci.* (1994), Vol. 35, No. 1, pp. 101-11).

The compounds of the invention may be tested for their use in treating glomerulonephritis or diabetic nephropathy in the rat anti-Thy1.1-induced experimental mesengial proliferative glomerulonephritis model (see Smith, L. E. et al, cited above).

The compounds of the invention may be tested for their use in treating renal transplant rejection by using a rat model of chronic renal transplant rejection (see Yin, J. L. et al., "Expression of growth arrest-specific gene 6 and its receptors in a rat model of chronic renal transplant rejection", *Transplantation* (2002), Vol. 73, No. 4, pp. 657-60).

The compounds of the invention may be tested for their use in treating rheumatoid arthritis by using the CAIA mouse model (see Phadke, K. et al., "Evaluation of the effects of various anti-arthritic drugs on type II collagen-induced mouse arthritis model", *Immunopharmacology* (1985) Vol. 10, No. 1, pp. 51-60).

The compounds of the invention may be tested for their use in treating osteoarthritis by using the STR/ORT mouse model (see Brewster, M. et al., "Ro 32-3555, an orally active collagenase selective inhibitor, prevents structural damage in the STR/ORT mouse model of osteoarthritis", *Arthritis. Rheum.* (1998), Vol. 41, No. 9, pp. 1639-44).

The compounds of the invention may be tested for their use in treating cataracts by using the $H_2O_2$-induced model (see Kadoya, K. et al., "Role of calpain in hydrogen peroxide induced cataract", *Curr. Eye Res.* (1993), Vol. 12, No. 4, pp. 341-6) or the Emory mouse model (see Sheets, N. L. et al., "Cataract- and lens-specific upregulation of ARK receptor tyrosine kinase in Emory mouse cataract", *Invest. Ophthalmol. Vis. Sci.* (2002), Vol. 43, No. 6, pp. 1870-5).

Pharmaceutical Compositions of the Invention and Administration

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 75% of the compound of the invention. Preferred pharmaceutical compositions and preparations according to the present invention are prepared so that a parenteral dosage unit contains between 0.01 to 10% by weight of the compound prior to dilution of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.7 mg) to about 100 mg/kg (i.e., 7.0 gm); preferably a therapeutically effective dose is (for a 70 kg mammal) from about 0.01 mg/kg (i.e., 7 mg) to about 50 mg/kg (i.e., 3.5 gm); more preferably a therapeutically effective dose is (for a 70 kg mammal) from about 1 mg/kg (i.e., 70 mg) to about 25 mg/kg (i.e., 1.75 gm).

Compounds of the invention, or pharmaceutically acceptable derivatives thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

Preparation of the Compounds of the Invention

The following Reaction Schemes illustrate methods to make compounds of this invention, i.e., compounds of formula (Ia) and compounds of formula (Ib):

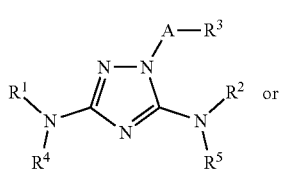

(Ia)

-continued

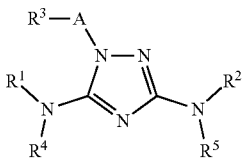

(Ib)

where A, $R^1$, $R^2$, $R^3$, $R^4$ and $R^5$ are described above in the Summary of the Invention, as isolated stereoisomers or tautomers thereof or mixtures thereof, or as pharmaceutically acceptable salts, hydrates, solvates, N-oxides or prodrugs thereof. It is understood that in the following Reaction Schemes, combinations of substituents and/or variables of the depicted formulae are permissible only if such contributions result in stable compounds.

It will also be appreciated by those skilled in the art that in the processes described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are known to one of ordinary skill in the art and as described herein.

The use of protecting groups is described in detail in Green, T. W. and P. G. M. Wuts, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

It is understood that one of ordinary skill in the art would be able to make the compounds of the invention by methods similar to the methods described herein or by methods known to one of ordinary skill in the art. It is also understood that one of ordinary skill in the art would be able to make in a similar manner as described below other compounds of formula (Ia) and formula (Ib) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc, or synthesized according to sources known to those skilled in the art (see, for example, Advanced Organic Chemistry: Reactions, Mechanisms, and Structure, 5th edition (Wiley, December 2000)) or prepared as described in this invention. $^1$H NMR spectra were recorded in CDCl$_3$, DMSO-d$_6$, CD$_3$OD, Acetone-d$_6$ with trimethylsilane (TMS) as internal reference using Gemini 300 MHz instrument. Reagents and solvents were purchased from commercial sources and used without further purification. Flash column chromatography was conducted using silica gel (230-400 mesh) under a positive pressure of nitrogen. LCMS spectra for purity and mass were recorded using Waters LCMS instruments. Deionized water was used to dilute the reactions and wash the products. Brine used was prepared by dissolving sodium chloride into deionized water to saturation point.

In the following Reaction Schemes, the following common abbreviations are used:

HOAt for 1-hydroxy-7-azabenzotriazole

Bn for benzyl

EDCl.HCl for 1-ethyl-3-(3-dimethylaminopropyl)carbodiimide hydrochloride $^i$Pr$_2$NEt for N,N-diisopropylethylamine DMF for N,N-Dimethylformamide rt for ambient temperature MeOH for methanol THF for tetrahydrofuran TFA for trifluoroacetic acid THP for tetrahydropyran BOC for benzyloxycarbonyl Pd(dba)$_2$ for bis(dibenzylideneacetone)palladium EtOAc for ethyl acetate 2-PrOH for iso-propylalcohol, isopropanol or 2-propanol Ph$_2$P(CH$_2$)$_4$PPh$_2$ for 1,4-bis(diphenylphosphino)butane HOAc for acetic acid Compounds (Ia-1) and (Ib-1), as set forth below in Reaction Scheme 1, are compounds of formula (Ia) and (Ib), as set forth above in the Summary of the Invention, and are prepared as illustrated below in Reaction Scheme 1 where R$^{1a}$ is one or more substituents selected from the group consisting of halo, haloalkyl, alkyl, optionally substituted heteroaryl, optionally substituted heterocyclyl, —R$^8$—OR$^{10}$, —R$^8$—O—R$^9$—OR$^{10}$, —R$^8$—O—R$^9$—O—R$^9$—OR$^{10}$, —R$^8$—O—R$^9$—CN, —R$^8$—O—R$^9$—C(O)OR$^{10}$, —R$^8$—O—R$^9$—C(O)N(R$^6$)R$^7$, —R$^8$—O—R$^9$—S(O)$_p$R$^6$ (where p is 0, 1 or 2), —R$^8$—O—R$^9$—N(R$^6$)R$^7$, —R$^8$—O—R$^9$—C(NR$^{11}$)N(R$^{11}$)H, and —R$^8$—N(R$^6$)C(O)R$^{10}$, wherein each R$^6$, R$^7$, R$^8$, R$^9$, R$^{10}$ and R$^{11}$ are as defined above in the Summary of the Invention and R$^{38}$ is one or more substituents selected from the group consisting of halo, haloalkyl, alkyl, optionally substituted heteroaryl, optionally substituted heterocyclyl, —R$^8$—OR$^{10}$, —R$^8$—O—R$^9$—OR$^{10}$—R$^8$—O—R$^9$—O—R$^9$—OR$^{10}$, —R$^8$—O—R$^9$—C(O)OR$^{10}$, —R$^8$—O—R$^9$—C(O)N(R$^6$)R$^7$, —R$^8$—O—R$^9$—S(O)$_p$R$^6$ (where p is 0, 1 or 2), —R$^8$—O—R$^9$—N(R$^6$)R$^7$, —R$^8$—O—R$^9$—C(NR$^{11}$)N(R$^{11}$)H, and —R$^8$—N(R$^6$)C(O)R$^{10}$ where each R$^6$, R$^7$, R$^8$, R$^9$, R$^{10}$ and R$^{11}$ is as defined above in the Summary of the Invention:

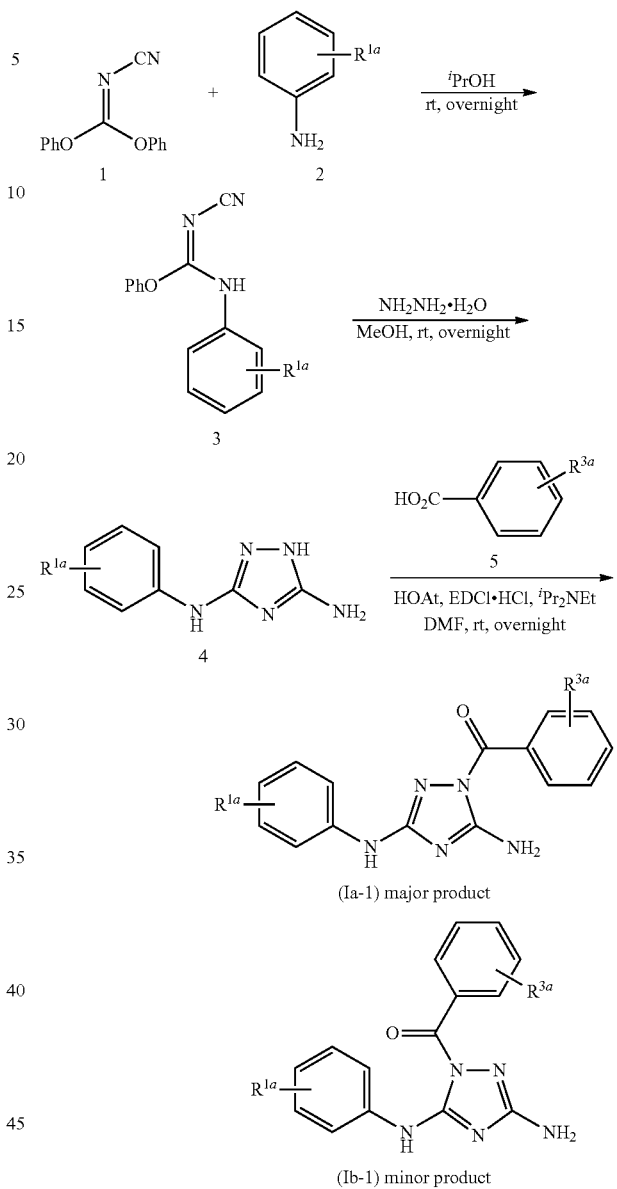

REACTION SCHEME 1

In general, diphenylcyanocarbonimidate 1 (1.1 equiv) and appropriately substituted aniline 2 (1 equiv) are stirred in isopropyl alcohol at ambient temperature overnight. The diarylisourea product, 3, generally precipitates and isolation can be accomplished via filtration, washing with an appropriate solvent, and drying. Hydrazine hydrate (2 equiv) is added to a slurry of 3 in an alcohol or other appropriate solvent. Generally, the ring formation reaction occurs at ambient temperature and the product triazole, 4, can be isolated by standard isolation techniques. The 3,5-diamino-1,2,4-triazole, 4, is then acylated with an appropriately substituted benzoic acid 5 to provide a mixture of the acylated products, (Ia-1) and (Ib-1), which can be separated and isolated by standard separation and isolation techniques, such as chromatography.

Compounds (Ia-2), as set forth below in Reaction Scheme 1A, are compounds of formula (Ia), as set forth above in the Summary of the Invention, and are prepared as illustrated below in Reaction Scheme 1A. For purposes of convenience, the minor product, i.e., the corresponding compound of formula (Ib), is not illustrated in Reaction Scheme 1A, but it is understood that the compound is prepared as well by the method disclosed therein and is isolated and separated from compound (Ia-2) by standard isolation and separation techniques.

Hz, 2H), 4.78 (m, 1H), 3.98 (br. s, 2H), 2.77 (br. s, 2H), 2.48 (m, 4H), 1.67 (m, 4H), 1.30 (d, J=6.0 Hz, 6H) ppm; MS (ES) 451.4 (M+H), 449.0 (M−H).

In a similar manner as described above in Reaction Scheme 1 and Reaction Scheme 1A, the following compounds of formula (Ia) and formula (Ib) were made with the appropri- REACTION SCHEME 1A
Preparation of 5-Amino-1-(4-(iso-propoxy)phenyl)carbonyl-3-[4-[2-(pyrrolidin-1-yl)ethoxy]phenylamino]-1H-1,2,4-triazole (Ia-2)

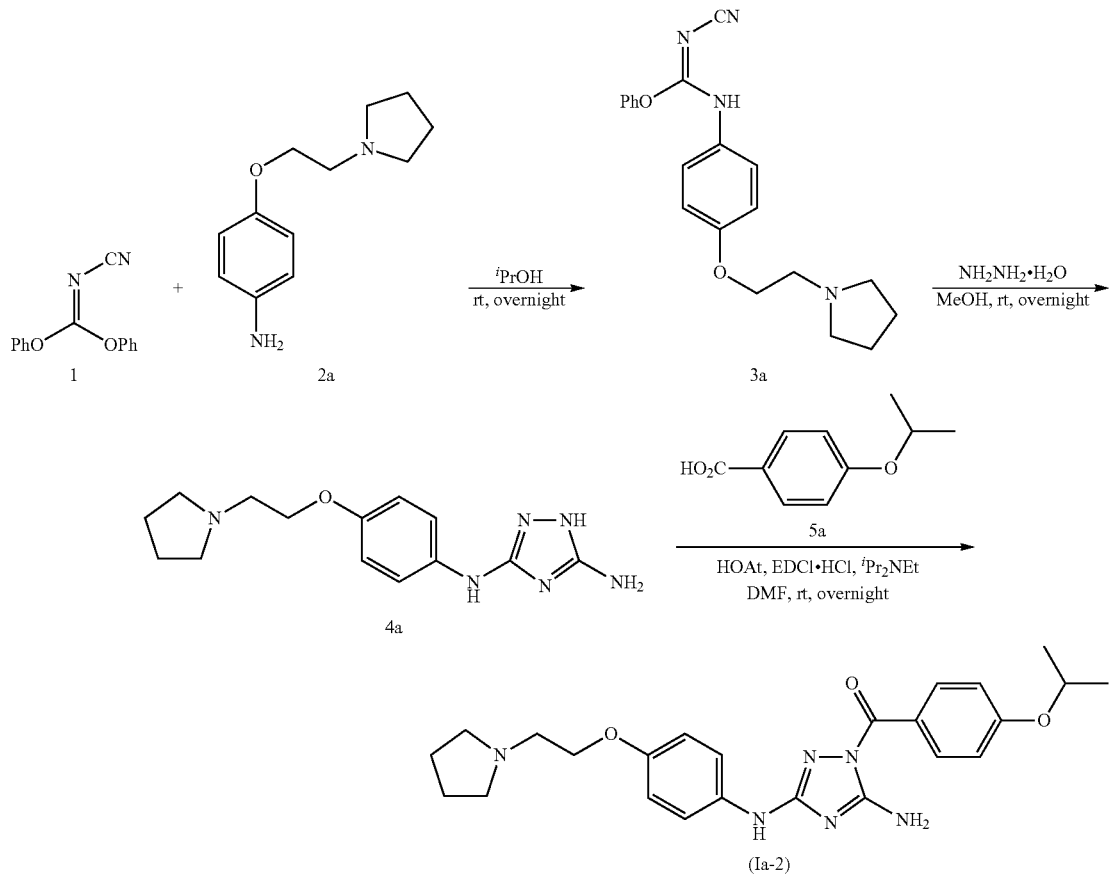

Specifically, diphenylcyanocarbonimidate 1 (1.1 equiv) and aniline 2a (1 equiv) were stirred in iso-propyl alcohol at ambient temperature overnight. The white precipitate was filtered and washed with iso-propyl alcohol and dried to yield 3a. Then hydrazine hydrate (2 equiv) was added to a slurry of 3a in methanol. After stirring at ambient temperature overnight the solution was concentrated and the oily residue was triturated with diethyl ether to remove impurities and give 4a as a white solid. The 3,5-diamino-1,2,4-triazole compound 4a was then acylated with benzoic acid 5a mediated by HOAt/EDCl·HCl and $^i$Pr$_2$NEt in anhydrous DMF. The reaction mixture was diluted with ethyl acetate and washed with aqueous sodium bicarbonate. The organic layer was separated and concentrated. Purification of the residue by silica gel column chromatography in 5% triethylamine/ethyl acetate gave 5-amino-1-(4-(iso-propoxy)phenyl)carbonyl-3-[4-[2-(pyrrolidin-1-yl)ethoxy]phenylamino]-1H-1,2,4-triazole (Ia-2), as a yellow solid (38% yield); $^1$H-NMR (DMSO-d$_6$, 300 MHz) 9.01 (s, 1H), 8.22 (d, J=8.7 Hz, 2H), 7.69 (br. s, 2H), 7.41 (d, J=8.7 Hz, 2H), 7.04 (d, J=8.7 Hz, 2H), 6.82 (d, J=8.7 ately substituted starting materials. The number following each compound below refers to its number in Tables 1-10, as discussed in more detail below.

5-Amino-3-[4-[2-(pyrrolidin-1-yl)ethoxy]phenylamino]-1-(4-(tert-butoxy)phenyl)carbonyl-1H-1,2,4-triazole (compound #1), as a yellow solid (52% yield); $^1$H-NMR (DMSO-d$_6$, 300 MHz) 9.03 (s, 1H), 8.17 (d, J=9.0 Hz, 2H), 7.72 (br. s, 2H), 7.41 (d, J=9.0 Hz, 2H), 7.12 (d, J=9.0 Hz, 2H), 6.81 (d, J=9.0 Hz, 2H), 3.99 (t, J=5.6 Hz, 2H), 2.80 (br. s, 2H), 2.55 (m, 4H), 1.69 (m, 4H), 1.41 (s, 9H) ppm; MS (ES) 465.2 (M+H), 463.3 (M−H).

5-Amino-1-(4-(dimethylamino)phenyl)carbonyl-3-[4-[2-(piperidin-1-yl)ethoxy]phenylamino]-1H-1,2,4-triazole (compound #2), as a yellow solid (65% yield); $^1$H-NMR (DMSO-d$_6$, 300 MHz) 8.97 (s, 1H), 8.25 (d, J=9.0 Hz, 2H), 7.63 (br. s, 2H), 7.44 (d, J=9.0 Hz, 2H), 6.84 (d, J=9.3 Hz, 2H), 6.77 (d, J=9.3 Hz, 2H), 3.98 (t, J=6.1 Hz, 2H), 2.60 (t, J=6.1 Hz, 2H), 2.42 (m, 4H), 1.49 (m, 4H), 1.38 (m, 2H) ppm; MS (ES) 450.2 (M+H), 448.0 (M−H).

5-Amino-1-(1H-indol-5-yl)carbonyl-3-[4-[2-(pyrrolidin-1-yl)ethoxy]phenylamino]-1H-1,2,4-triazole (compound

3), ¹H-NMR (DMSO-d₆, 300 MHz) 11.48 (s, 1H), 9.03 (s, 1H), 8.69 (s, 1H), 8.14 (s, 1H), 7.95 (d, J=8.4 Hz, 1H), 7.71 (s, 2H), 7.49 (d, J=9.0 Hz, 2H), 7.46 (d, J=8.1 Hz, 1H), 6.81 (d, J=8.7 Hz, 2H), 6.62 (s, 1H), 4.02 (t, J=5.6 Hz, 2H), 2.91 (t, J=5.6 Hz, 2H), 2.68 (m, 4H), 1.72 (m, 4H) ppm; MS (ES) 432.9 (M+H), 430.5 (M−H).

5-Amino-1-(4-(dimethylamino)phenyl)carbonyl-3-[4-[2-(pyrrolidin-1-yl)ethoxy]phenylamino]-1H-1,2,4-triazole (compound #4), ¹H-NMR (DMSO-d₆, 300 MHz) 8.96 (s, 1H), 8.24 (d, J=7.8 Hz, 2H), 7.62 (s, 2H), 7.44 (d, J=7.8 Hz, 2H), 6.83 (d, J=7.8 Hz, 2H), 6.76 (d, J=8.1 Hz, 2H), 3.99 (t, J=5.7 Hz, 2H), 3.03 (s, 6H), 2.81 (m, 2H), 2.55 (m, 4H), 1.68 (m, 4H) ppm; MS (ES) 436.2 (M+H), 434.1 (M−H).

5-Amino-1-(1H-indol-6-yl)carbonyl-3-[4-[2-(pyrrolidin-1-yl)ethoxy]phenylamino]-1H-1,2,4-triazole (compound #5), ¹H-NMR (DMSO-d₆, 300 MHz) 11.6 (s, 1H), 9.04 (s, 1H), 8.50 (s, 1H), 8.13 (s, 1H), 7.85 (d, J=8.7 Hz, 1H), 7.73 (s, 2H), 7.63 (d, J=8.7 Hz, 2H), 7.47 (d, J=8.7 Hz, 2H), 6.84 (d, J=8.4 Hz, 2H), 6.54 (s, 1H), 4.02 (t, J=5.6 Hz, 2H), 2.93 (t, J=5.6 Hz, 2H), 2.69 (m, 4H), 1.73 (m, 4H) ppm; MS (ES) 432.9 (M+H), 430.5 (M−H).

5-Amino-1-(1H-indol-2-yl)carbonyl-3-[4-[2-(pyrrolidin-1-yl)ethoxy]phenylamino]-1H-1,2,4-triazole (compound #6), ¹H-NMR (DMSO-d₆, 300 MHz) 11.91 (s, 1H), 9.15 (s, 1H), 8.15 (s, 1H), 8.00 (s, 1H), 7.81 (s, 1H), 7.55 (d, J=8.4 Hz, 2H), 7.51 (d, J=11.7 Hz, 1H), 7.29 (t, J=8.1 Hz, 1H), 7.10 (t, J=7.8 Hz, 1H), 6.95 (d, J=8.7 Hz, 2H), 4.06 (t, J=5.6 Hz, 2H), 2.85 (t, J=5.6 Hz, 2H), 2.60 (m, 4H), 1.71 (m, 4H) ppm; MS (ES) 432.9 (M+H), 430.5 (M−H).

5-Amino-3-[4-[2-(pyrrolidin-1-yl)ethoxy]phenylamino]-1-(3-(trifluoromethoxy)phenyl)carbonyl-1H-1,2,4-triazole (compound #7), ¹H-NMR (DMSO-d₆, 300 MHz) 9.11 (s, 1H), 8.21 (s, 1H), 8.09 (d, J=7.2 Hz, 1H), 7.80 (s, 2H), 7.68 (m, 2H), 7.38 (d, J=9.0 Hz, 2H), 6.75 (d, J=8.7 Hz, 2H), 3.96 (t, J=5.8 Hz, 2H), 2.75 (m, 2H), 2.49 (m, 4H), 1.67 (m, 4H) ppm; MS (ES) 477.2 (M+H), 475.0 (M−H).

5-Amino-1-(4-(dimethylamino)phenyl)carbonyl-3-[4-[3-(pyrrolidin-1-yl)propoxy]phenylamino]-1H-1,2,4-triazole (compound #8), ¹H-NMR (DMSO-d₆, 300 MHz) 8.96 (s, 1H), 8.25 (d, J=9.0 Hz, 1H), 7.62 (s, 2H), 7.44 (d, J=9.0 Hz, 2H), 6.82 (d, J=9.3 Hz, 2H), 6.77 (d, J=9.0 Hz, 2H), 3.93 (t, J=6.3 Hz, 2H), 3.30 (t, J=6.3 Hz, 2H), 3.04 (s, 6H), 2.49 (m, 4H), 1.85 (quint, 2H), 1.68 (m, 4H) ppm; MS (ES) 450.3 (M+H), 448.3 (M−H).

5-Amino-1-(3-methylphenyl)carbonyl-3-[4-[2-(pyrrolidin-1-yl)ethoxy]phenylamino]-1H-1,2,4-triazole (compound #9), ¹H-NMR (DMSO-d₆, 300 MHz) 9.05 (s, 1H), 8.04 (s, 1H), 7.90 (d, J=7.2 Hz, 1H), 7.75 (s, 2H), 7.43 (m, 4H), 6.79 (d, J=8.4 Hz, 2H), 3.96 (t, J=5.7 Hz, 2H), 2.72 (t, J=5.7 Hz, 2H), 2.49 (m, 4H), 2.42 (s, 3H), 1.67 (m, 4H) ppm; MS (ES) 407.2 (M+H), 405.2 (M−H).

5-Amino-1-(4-(iso-propoxy)phenyl)carbonyl-3-[4-[3-(pyrrolidin-1-yl)propoxy]phenylamino]-1H-1,2,4-triazole (compound #10), ¹H-NMR (DMSO-d₆, 300 MHz) 9.02 (s, 1H), 8.24 (d, J=9.0 Hz, 1H), 7.71 (s, 2H), 7.42 (d, J=9.3 Hz, 2H), 7.05 (d, J=9.0 Hz, 2H), 6.82 (d, J=9.0 Hz, 2H), 4.78 (m, 1H), 3.93 (t, J=6.0 Hz, 2H), 3.31 (m, 2H), 2.49 (m, 4H), 1.87 (m, 2H), 1.70 (m, 4H) 1.32 (d, J=5.7 Hz, 6H) ppm; MS (ES) 465.4 (M+H), 463.0 (M−H).

5-Amino-1-(3-(dimethylamino)phenyl)carbonyl-3-[4-[2-(piperidin-1-yl)ethoxy]phenylamino]-1H-1,2,4-triazole (compound #11), ¹H-NMR (DMSO-d₆, 300 MHz) 9.04 (s, 1H), 7.74 (s, 2H), 7.57 (m, 1H), 7.42 (d, J=9.0 Hz, 2H), 7.35 (m, 2H), 6.98 (dm, J=9.0 Hz, 1H), 6.76 (d, J=9.0 Hz, 2H), 3.96 (t, J=6.0 Hz, 2H), 2.95 (s, 6H), 2.58 (t, J=6.0 Hz, 2H), 2.42 (m, 4H), 1.48 (m, 4H), 1.38 (m, 2H) ppm; MS (ES) 450.3 (M+H), 448.2 (M−H).

5-Amino-1-(4-methylphenyl)carbonyl-3-[4-[2-(pyrrolidin-1-yl)ethoxy]phenylamino]-1H-1,2,4-triazole (compound #12), ¹H-NMR (DMSO-d₆, 300 MHz) 9.03 (s, 1H), 8.09 (d, J=8.1 Hz, 2H), 7.73 (s, 2H), 7.40 (d, J=9.0 Hz, 2H), 7.35 (d, J=−8.4 Hz, 2H), 6.80 (d, J=8.4 Hz, 2H), 3.97 (t, J=5.7 Hz, 2H), 2.73 (t, J=5.7 Hz, 2H), 2.49 (m, 4H), 2.41 (s, 3H), 1.66 (m, 4H) ppm; MS (ES) 407.3 (M+H), 405.1 (M−H).

5-Amino-1-(1,3-benzodioxol-5-yl)carbonyl-3-[4-[2-(piperidin-1-yl)ethoxy]phenylamino]-1H-1,2,4-triazole (compound #13), ¹H-NMR (DMSO-d₆, 300 MHz) 9.03 (s, 1H), 7.89 (d, J=7.5 Hz, 1H), 7.73 (d, J=7.5 Hz, 1H), 7.72 (s, 2H), 7.39 (d, J=8.7 Hz, 2H), 7.08 (d, J=8.1 Hz, 1H), 6.80 (d, J=8.4 Hz, 2H), 6.15 (s, 2H), 3.96 (t, J=5.4 Hz, 2H), 2.59 (t, J=5.4 Hz, 2H), 2.39 (m, 4H), 1.48 (m, 4H), 1.36 (m, 2H) ppm; MS (ES) 451.3 (M+H), 449.5 (M−H).

5-Amino-1-(3-methoxyphenyl)carbonyl-3-[4-[2-(pyrrolidin-1-yl)ethoxy]phenylamino]-1H-1,2,4-triazole (compound #14), ¹H-NMR (DMSO-d₆, 300 MHz) 9.06 (s, 1H), 7.77 (s, 2H), 7.68 (d, J=6.6 Hz, 1H), 7.46 (t, J=7.8 Hz, 2H), 7.40 (d, J=9.3 Hz, 2H), 7.19 (d, J=7.5 Hz, 1H), 6.77 (d, J=9.0 Hz, 2H), 3.96 (t, J=5.4 Hz, 2H), 2.75 (t, J=5.4 Hz, 2H), 2.49 (m, 4H), 1.67 (m, 4H) ppm; MS (ES) 423.2 (M+H), 421.2 (M−H).

5-Amino-3-[4-[3-(pyrrolidin-1-yl)propoxy]phenylamino]-1-(4-(tert-butoxy)phenyl)carbonyl-1H-1,2,4-triazole (compound #15), ¹H-NMR (DMSO-d₆, 300 MHz) 9.02 (s, 1H), 8.17 (d, J=8.7 Hz, 1H), 7.72 (s, 2H), 7.40 (d, J=8.7 Hz, 2H), 7.12 (d, J=8.7 Hz, 2H), 6.79 (d, J=8.7 Hz, 2H), 3.91 (t, J=6.3 Hz, 2H), 2.49 (m, 2H), 2.41 (m, 4H), 1.83 (quint, J=6.6 Hz, 2H), 1.66 (m, 4H) 1.41 (s, 9H) ppm; MS (ES) 479.2 (M+H), 477.6 (M−H).

5-Amino-1-(1,3-benzodioxol-5-yl)carbonyl-3-[4-[2-(pyrrolidin-1-yl)ethoxy]phenylamino]-1H-1,2,4-triazole (compound #16), ¹H-NMR (DMSO-d₆, 300 MHz) 9.03 (s, 1H), 7.89 (dd, J=8.1, 1.8 Hz, 1H), 7.74 (d, J=9.0 Hz, 1H), 7.72 (s, 2H), 7.40 (d, J=8.7 Hz, 2H), 7.08 (d, J=8.4 Hz, 1H), 6.80 (d, J=8.7 Hz, 2H), 6.15 (s, 2H), 3.97 (t, J=5.4 Hz, 2H), 2.75 (t, J=5.4 Hz, 2H), 2.43 (m, 4H), 1.67 (m, 4H) ppm; MS (ES) 437.2 (M+H), 435.1 (M−H).

5-Amino-1-(1,4-benzodioxan-6-yl)carbonyl-3-[4-[2-(pyrrolidin-1-yl)ethoxy]phenylamino]-1H-1,2,4-triazole (compound #17), ¹H-NMR (DMSO-d₆, 300 MHz) 9.03 (s, 1H), 7.80 (m, 2H), 7.72 (s, 2H), 7.41 (d, J=7.2 Hz, 2H), 7.00 (d, J=8.1 Hz, 1H), 6.80 (d, J=8.1 Hz, 2H), 4.33 (s, 2H), 4.31 (s, 2H), 3.97 (t, J=5.4 Hz, 2H), 2.74 (t, J=5.4 Hz, 2H), 2.43 (m, 4H), 1.66 (m, 4H) ppm; MS (ES) 451.3 (M+H), 449.2 (M−H.

5-Amino-3-[4-[2-(pyrrolidin-1-yl)ethoxy]phenylamino]-1-(3-(tert-butoxy)phenyl)carbonyl-1H-1,2,4-triazole (compound #18), ¹H-NMR (DMSO-d₆, 300 MHz) 9.05 (s, 1H), 7.82 (d, J=7.5 Hz, 1H), 7.77 (m, 3H), 7.47 (t, J=7.8 Hz, 1H), 7.39 (d, J=9.0 Hz, 2H), 7.24 (dm, J=7.5 Hz, 1H), 6.76 (d, J=8.7 Hz, 2H), 3.97 (t, J=6.0 Hz, 2H), 2.75 (t, J=6.0 Hz, 2H), 2.49 (m, 4H), 1.67 (m, 4H), 1.32 (s, 9H) ppm; MS (ES) 465.4 (M+H), 463.2 (M−H).

5-Amino-1-(3,5-(dimethoxy)phenyl)carbonyl-3-[4-[2-(piperidin-1-yl)ethoxy]phenylamino]-1H-1,2,4-triazole (compound #19), ¹H-NMR (DMSO-d₆, 300 MHz) 9.07 (s, 1H), 7.77 (s, 2H), 7.42 (d, J=8.7 Hz, 1H), 7.36 (s, 1H), 7.35 (s, 1H), 6.77 (d, J=8.7 Hz, 2H), 6.75 (s, 1H), 3.97 (t, J=5.4 Hz, 2H), 3.80 (s, 6H), 2.61 (m, 2H), 2.42 (m, 4H), 1.49 (m, 4H), 1.37 (m, 2H) ppm; MS (ES) 467.2 (M+H), 465.2 (M−H).

5-Amino-1-(3-(dimethylamino)phenyl)carbonyl-3-[4-[3-(pyrrolidin-1-yl)propoxy]phenylamino]-1H-1,2,4-triazole (compound #20), ¹H-NMR (DMSO-d₆, 300 MHz) 9.03 (s, 1H), 7.74 (s, 2H), 7.57 (s, 1H), 7.42 (d, J=9.0 Hz, 2H), 7.33 (m, 2H), 6.97 (dm, J=7.8 Hz, 1H), 6.75 (d, J=9.0 Hz, 2H), 3.91 (t, J=6.3 Hz, 2H), 2.95 (s, 6H), 2.54 (m, 2H), 2.49 (m, 4H), 1.84 (quint, J=6.3 Hz, 2H), 1.68 (m, 4H) ppm; MS (ES) 450.2 (M+H), 448.6 (M−H).

5-Amino-1-(3,4-(dimethoxy)phenyl)carbonyl-3-[4-[2-(piperidin-1-yl)ethoxy]phenylamino]-1H-1,2,4-triazole (compound #21), $^1$H-NMR (DMSO-$d_6$, 300 MHz) 9.06 (s, 1H), 7.99 (s, 1H), 7.89 (d, J=7.6 Hz, 1H), 7.73 (s, 2H), 7.44 (d, J=8.7 Hz, 2H), 7.12 (d, J=7.6 Hz, 1H), 6.80 (d, J=8.7 Hz, 2H), 3.97 (t, J=5.4 Hz, 2H), 3.87 (s, 3H), 3.82 (s, 3H), 2.59 (t, J=5.4 Hz, 2H), 2.40 (m, 4H), 1.48 (m, 4H), 1.36 (m, 2H) ppm; MS (ES) 467.3 (M+H), 465.1 (M−H).

5-Amino-1-(3,5-(dimethoxy)phenyl)carbonyl-3-[4-[2-(pyrrolidin-1-yl)ethoxy]phenylamino]-1H-1,2,4-triazole (compound #22), $^1$H-NMR (DMSO-$d_6$, 300 MHz) 9.07 (s, 1H), 7.77 (s, 1H), 7.42 (d, J=8.1 Hz, 2H), 7.35 (s, 2H), 6.76 (d, J=7.8 Hz, 2H), 6.75 (s, 1H), 3.96 (t, J=5.7 Hz, 2H), 3.80 (s, 6H), 2.72 (t, J=5.7 Hz, 2H), 2.49 (m, 4H), 1.66 (m, 4H) ppm; MS (ES) 453.2 (M+H), 451.4 (M−H).

5-Amino-3-[4-[2-(pyrrolidin-1-yl)ethoxy]phenylamino]-1-(4-(trifluoromethoxy)phenyl)carbonyl-1H-1,2,4-triazole (compound #23), $^1$H-NMR (DMSO-$d_6$, 300 MHz) 9.06 (s, 1H), 8.27 (d, J=8.4 Hz, 2H), 7.78 (s, 2H), 7.54 (d, J=7.5 Hz, 2H), 7.37 (d, J=8.4 Hz, 2H), 6.80 (d, J=8.7 Hz, 2H), 3.97 (m, 2H), 2.76 (m, 3H), 2.49 (m, 4H), 1.68 (m, 4H) ppm; MS (ES) 477.4 (M+H), 475.4 (M−H).

5-Amino-3-[4-[3-(pyrrolidin-1-yl)propoxy]phenylamino]-1-(3-(tert-butoxy)phenyl)carbonyl-1H-1,2,4-triazole (compound #24), $^1$H-NMR (DMSO-$d_6$, 300 MHz) 9.04 (s, 1H), 7.82 (d, J=7.8 Hz, 1H), 7.78 (s, 1H), 7.76 (s, 2H), 7.46 (t, J=7.8 Hz, 1H), 7.38 (d, J=8.7 Hz, 2H), 7.23 (d, J=7.2 Hz, 1H), 6.75 (d, J=9.0 Hz, 2H), 3.90 (t, J=6.3 Hz, 2H), 2.46 (m, 2H), 2.40 (m, 4H), 1.82 (quint, J=6.3 Hz, 2H), 1.66 (m, 4H), 1.32 (s, 9H) ppm; MS (ES) 479.4 (M+H), 477.4 (M−H).

5-Amino-1-(benzimidazol-6-yl)carbonyl-3-[4-[2-(pyrrolidin-1-yl)ethoxy]phenylamino]-1H-1,2,4-triazole (compound #25), $^1$H-NMR (DMSO-$d_6$, 300 MHz) 9.07 (s, 1H), 8.63 (s, 1H), 8.40 (s, 1H), 8.34 (s, 1H), 8.02 (d, J=8.7 Hz, 1H), 7.76 (s, 2H), 7.70 (d, J=8.7 Hz, 1H), 7.45 (d, J=9.0 Hz, 2H), 6.81 (d, J=9.0 Hz, 2H), 4.04 (t, J=5.7 Hz, 2H), 2.99 (t, J=5.7 Hz, 2H), 2.77 (m, 4H), 1.75 (m, 4H) ppm; MS (ES) 433.5 (M+H), 431.5 (M−H).

5-Amino-1-(4-(iso-propoxy)phenyl)carbonyl-3-[4-(piperidin-1-yl)phenylamino]-1H-1,2,4-triazole (compound #26), $^1$H-NMR (DMSO-$d_6$, 300 MHz) 8.93 (s, 1H), 8.24 (d, J=8.7 Hz, 2H), 7.69 (s, 2H), 7.36 (d, J=8.7 Hz, 1H), 7.05 (d, J=8.7 Hz, 1H), 6.82 (d, J=8.7 Hz, 2H), 4.78 (m, 1H), 2.97 (t, J=5.7 Hz, 4H), 1.60 (m, 4H), 1.48 (m, 2H), 1.31 (d, J=5.7 Hz, 6H) ppm; MS (ES) 421.2 (M+H), 419.3 (M−H).

5-Amino-1-(4-(methoxy)cyclohexyl)carbonyl-3-[4-[2-(piperidin-1-yl)ethoxy]phenylamino]-1H-1,2,4-triazole (compound #27), $^1$H-NMR (DMSO-$d_6$, 300 MHz) 8.97 (s, 1H), 7.52 (s, 2H), 7.44 (d, J=8.7 Hz, 2H), 6.82 (d, J=8.7 Hz, 2H), 3.98 (t, J=5.1 Hz, 2H), 3.39 (s, 3H), 3.22 (m, 1H), 2.73 (t, J=5.1 Hz, 2H), 2.49 (m, 4H), 2.07-1.45 (m, 13H) ppm; MS (ES) 429.3 (M+H), 427.2 (M−H); and 5-Amino-1-(6-(methyl)pyridin-3-yl)carbonyl-3-[4-[2-(pyrrolidin-1-yl)ethoxy]phenylamino]-1H-1,2,4-triazole (compound #28), $^1$H-NMR (DMSO-$d_6$, 300 MHz) 8.88 (s, 1H), 8.32 (s, 1H), 8.16 (s, 2H), 8.08 (d, J=6.6 Hz, 1H), 7.37 (d, J=8.7 Hz, 2H), 7.32 (d, J=7.5 Hz, 1H), 6.75 (d, J=9.0 Hz, 2H), 3.97 (t, J=5.7 Hz, 2H), 2.81 (t, J=5.7 Hz, 2H), 2.58 (s, 3H), 2.49 (m, 4H), 1.69 (m, 4H) ppm; MS (ES) 408.5 (M+H), 406.5 (M−H).

In the following reaction schemes and examples, unless otherwise noted, reagents and solvents were used as received from commercial suppliers. Proton and carbon nuclear magnetic resonance spectra were obtained on a Bruker AC 300 or a Bruker AV-300 spectrometer at 300 MHz for proton and 75 MHz for carbon. Spectra are given in ppm (δ) and coupling constants, J, are reported in Hertz. Tetramethylsilane was used as an internal standard for proton spectra and the solvent peak was used as the reference peak for carbon spectra. Infrared spectra were obtained on a Nicolet Nexus 470 (ATR) spectrometer. Mass spectra were obtained on a Perkin Elmer Sciex 100 atmospheric pressure ionization (APCI) mass spectrometer, or a Finnigan LCQ Duo LCMS ion trap electrospray ionization (ESI) mass spectrometer. Thin-layer chromatography (TLC) was performed using Analtech silica gel plates and visualized by ultraviolet (UV) light, iodine, or 20 wt % phosphomolybdic acid in ethanol. HPLC analyses were obtained using a YMC J'Sphere ODS-M80 column (150×4.6 mm) with UV detection at 254 nm using a standard solvent gradient program (Method A). Elemental analyses were performed by Quantitative Technologies, Inc. (Whitehouse, N.J.).

| Method 1: | | | |
|---|---|---|---|
| Time (min) | Flow (mL/min) | % A | % B |
| 0 | 1 | 90 | 10 |
| 15 | 1 | 0 | 100 |
| 25 | 1 | 0 | 100 |
| 30 | 1 | 90 | 10 |

A = Water with 0.03 v/v Trifluoroacetic Acid

B = Acetonitrile with 0.03 v/v Trifluoroacetic acid

| Method 2: | | | |
|---|---|---|---|
| Time (min) | Flow (mL/min) | % A | % B |
| 0 | 1 | 90 | 10 |
| 15 | 1 | 0 | 100 |
| 25 | 1 | 0 | 100 |
| 30 | 1 | 90 | 10 |

A = Water + 5% Acetonitrile (v/v) with 0.03 v/v Trifluoroacetic Acid

B = Acetonitrile + 5% Water (v/v) with 0.03 v/v Trifluoroacetic Acid

Compounds (Ia-3), (Ia-4) and (Ia-5), as set forth below in Reaction Scheme 1B, are compounds of formula (Ia), as set forth above in the Summary of the Invention, and are prepared as illustrated below in Reaction Scheme 1B. For purposes of convenience, the minor products, i.e., the corresponding compounds of formula (Ib), are not illustrated in Reaction Scheme 1B, but it is understood that these compounds are prepared as well by the method disclosed therein and can be isolated and separated from compounds (Ia-3), (Ia-4) and (Ia-5) by standard isolation and separation techniques.

REACTION SCHEME 1B

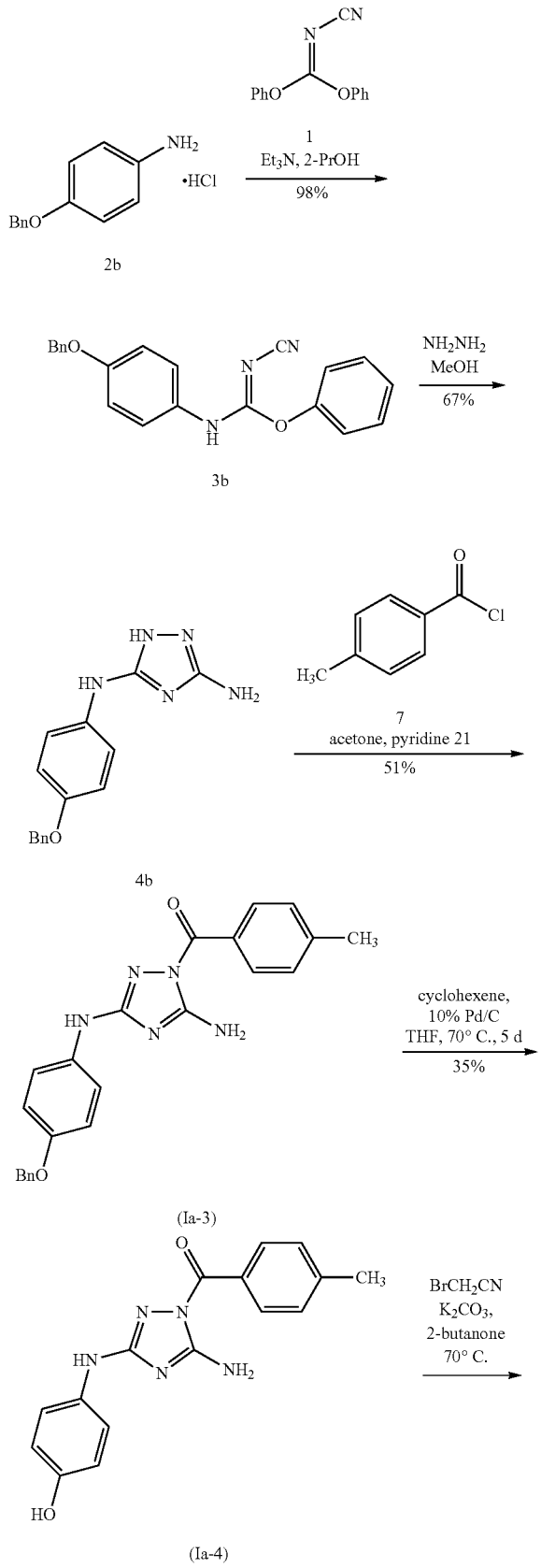

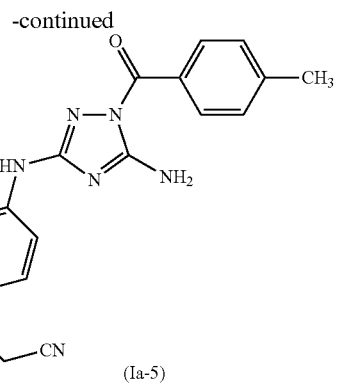

(Ia-5)

Preparation of 5-Amino-3-[4-(hydroxy)phenylamino]-1-(4-methylphenyl)carbonyl-1H-1,2,4-triazole (Ia-4) and 5-Amino-3-[3-cyanomethoxy)phenylamino]-1-(4-(methyl)phenyl)carbonyl-1H-1,2,4-triazole (Ia-5)

In general, compound (Ia-3) was prepared by methods similar to those described in Reaction Scheme 1, Reaction Scheme 1A, and as described below. Successful debenzylation of (Ia3) was accomplished by heating for 5 days in cyclohexene in the presence of Pd/C. The alkylation of (Ia-4) with bromoacetonitrile gave (Ia-5).

Specifically, a mixture of 4-benzyloxyaniline hydrochloride 2b (10.26 g, 43.5 mmol) and triethylamine (4.40 g, 43.5 mmol) in 2-propanol (100 mL) was stirred at ambient temperature. After 10 min, diphenylcyanocarbimidate 1 (10.37 g, 43.5 mmol) was added and stirring continued at ambient temperature. After 3.5 h the solids that formed were collected by filtration, washing with 2-propanol, to afford 3b (14.64 g, 98%) as an off-white solid: $^1$H NMR (300 MHz, DMSO-$d_6$) δ 10.68 (br s, 1H), 7.47-7.02 (m, 14H), 5.11 (s, 2H).

A mixture of 3b (14.60 g, 42.5 mmol) and hydrazine hydrate (2.55 g, 51.0 mmol) in MeOH (150 mL) was stirred at ambient temperature. After 2.25 h, additional hydrazine hydrate (1.28 g, 25.6 mmol) was added and stirring continued at ambient temperature for 1.5 h. The present solids were collected by filtration, washing with 2-propanol, to afford 4b (8.0 g, 67%) as a yellow solid: $^1$H NMR (300 MHz, DMSO-$d_6$) δ 11.00 (br s, 1H), 8.35 (br s, 1H), 7.43-7.24 (m, 7H), 6.83 (d, J=8.9 Hz, 2H), 5.78 (br s, 2H), 5.01 (s, 2H).

To a stirred mixture of 4b (1.0 g, 3.57 mmol) and pyridine (0.28 g, 3.57 mmol) in acetone (20 mL) at ice bath temperature was added p-toluoyl chloride 7 (0.55 g, 3.57 mmol). After stirring for 1 h at ice bath temperature and an additional 3 h at ambient temperature the reaction mixture was poured onto water (100 mL) and stirred vigorously. The solids that formed were collected by filtration and triturated with 2-propanol (100 mL) to give 1.1 g of a yellow solid. Purification by flash chromatography (98:2 methylene chloride/methanol) afforded 5-amino-3-[4-(benzyloxy)phenylamino]-1-(4-methylphenyl)carbonyl-1H-1,2,4-triazole (Ia-3) (0.72 g, 51%) as a yellow solid: $^1$H NMR (300 MHz, DMSO-$d_6$) δ 9.10 (br s, 1H), 8.13 (d, J=8.2 Hz, 2H), 7.78 (br s, 2H), 7.47-7.21 (m, 9H), 6.92 (d, J=9.0 Hz, 2H), 5.03 (s, 2H), 2.42 (s, 3H).

A mixture of 5-amino-3-[4-(benzyloxy)phenylamino]-1-(4-methylphenyl)carbonyl-1H-1,2,4-triazole (Ia-3) (3.95 g, 9.89 mmol) and 10% Pd/C (0.80 g) in cyclohexene (64 mL) and THF (128 mL) was stirred and heated at 70° C. After 2 d, additional 10% Pd/C (0.80 g) was added and heating and stirring at 70° C. was continued for an additional 3 d. After cooling to ambient temperature, the mixture was filtered through diatomaceous earth and concentrated to give a yellow-brown residue. Purification by flash chromatography (95:5 methylene chloride/methanol) followed by trituration with methylene chloride afforded 5-amino-3-[4-(hydroxy)phenylamino]-1-(4-methylphenyl)carbonyl-1H-1,2,4-triazole (Ia-4) (1.08 g, 35%) as a pale yellow solid: $R_f$ 0.36 (95:5 methylene chloride/methanol); mp 221-223° C.; $^1$H NMR (300 MHz, DMSO-$d_6$) δ 8.92 (s, 1H), 8.88 (s, 1H), 8.13 (d, J=8.2 Hz, 2H), 7.74 (br s, 2H), 7.38-7.32 (m, 4H), 6.64 (d, J=8.8 Hz, 2H), 2.42 (s, 3H); $^{13}$C NMR (75 MHz, DMSO-$d_6$) δ 166.1, 158.4, 157.3, 151.0, 142.9, 132.9, 130.6, 129.8, 128.4, 118.1, 115.1, 21.1; IR (ATR) 1697 cm$^{-1}$; ESI MS m/z 310 $[C_{16}H_{16}N_6O_2+H]^+$; HPLC (Method A) >99% (AUC), $t_R$=11.22 min. Anal. Calcd for $C_{16}H_{16}N_6O_2 \cdot 0.5H_2O$: C, 60.47; H, 4.92; N, 22.04. Found: C, 60.27; H, 4.70; N, 21.51.

A mixture of (Ia-4) (0.50 g, 1.62 mmol), potassium carbonate (0.25 g, 1.78 mmol) and bromoacetonitrile (0.21 g, 1.78 mmol) in 2-butanone (5 mL) was stirred at 75° C. After 18 h the reaction was cooled to ambient temperature, diluted with ethyl acetate (100 mL), washed with water, brine, dried over magnesium sulfate and concentrated to afford 0.55 g of a tan solid. Purification by flash chromatography (1:1 ethyl acetate/hexanes), followed by recrystallization from acetonitrile afforded 5-amino-3-[3-(cyanomethoxy)phenylamino]-1-(4-(methyl)phenyl)carbonyl-1H-1,2,4-triazole (Ia-5) (0.08 g, 14%) as a yellow solid: $R_f$ 0.46 (95:5 methylene chloride/methanol); mp 236-241° C.; $^1$H NMR (300 MHz, DMSO-$d_6$) δ 9.23 (s, 1H), 8.12 (d, J=8.0 Hz; 2H), 7.79 (br s, 2H), 7.50 (d, J=8.9 Hz, 2H), 7.39 (d, J=8.0 Hz, 2H), 6.98 (d, J=8.9 Hz, 2H), 5.08 (s, 2H), 2.43 (s, 3H); $^{13}$C NMR (75 MHz, DMSO-$d_5$) δ 166.6, 158.5, 157.7, 150.4, 143.3, 136.5, 130.9, 130.1, 128.8, 118.0, 117.2, 115.9, 54.4, 21.5; IR (ATR) 1687 cm$^{-1}$; APCI MS m/z 349 $[C_{18}H_{16}N_6O_2+H]^+$; HPLC (Method A) 96.4% (AUC), $t_R$=13.31 min. Anal. Calcd for $C_{18}H_{16}N_6O_2 \cdot 0.25H_2O$: C, 61.31; H, 4.65; N, 23.82. Found: C, 61.51; H, 4.41; N, 23.69.

Compounds (Ia-8) and (Ia-9), as set forth below in Reaction Scheme 1C, are compounds of formula (Ia), as set forth above in the Summary of the Invention, and are prepared as illustrated below in Reaction Scheme 10 from compounds (Ia-6) and (Ia-7), which are both compounds of the invention as well. The corresponding compounds of formula (Ib) of these compounds may be prepared in a similar manner.

REACTION SCHEME 1C

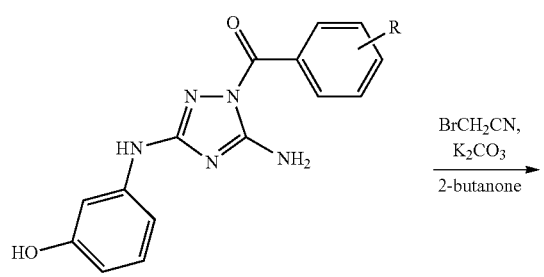

(Ia-6): R is 2-methyl
(Ia-7): R is 3-methyl

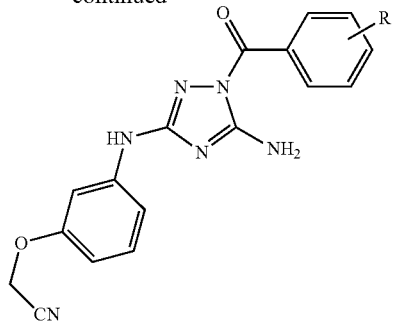

(Ia-8): R is 2-methyl
(Ia-9): R is 3-methyl

Preparation of 5-Amino-3-[3-(cyanomethoxy)phenylamino]-1-(2-methyl)phenyl)carbonyl-1H-1,2,4-triazole (Ia-8) and 5-Amino-3-[3-(cyanomethoxy)phenylamino]-1-(3-(methyl)phenyl)carbonyl-1H-1,2,4-triazole (Ia-9)

In general, alkylation of compounds (Ia-6) and (Ia-7) with 2-bromoacetonitrile in the presence of $K_2CO_3$ afforded compounds (Ia-8) and (Ia-9). Compounds (Ia-6) and (Ia-7) can be prepared according to methods similar to those described above using the appropriately substituted starting materials or by methods known to one skilled in the art.

In particular, to a solution of 5-amino-3-[3-(hydroxy)phenylamino]-1-(2-(methyl)phenyl)carbonyl-1H-1,2,4-triazole (Ia-6) (0.23 g, 0.75 mmol) in 2-butanone (3 mL) was added $K_2CO_3$ (0.11 g, 0.83 mmol) and $BrCH_2CN$ (0.10 g, 0.83 mmol). After stirring the mixture at 75° C. for 20 h, the 2-butanone was removed under reduced pressure. The residue was dissolved in EtOAc (50 mL), washed with water (50 mL), brine (30 mL), dried ($Na_2SO_4$) and concentrated to afford the crude product. Purification by flash chromatography (1:1 hexanes/EtOAc) gave 5-amino-3-[3-(cyanomethoxy)phenylamino]-1-(2-(methyl)phenyl)carbonyl-1H-1,2,4-triazole (Ia-8) (0.09 g, 35%) as a white solid: $R_f$ 0.29 (1:1 hexanes/ethyl acetate); mp (DSC) 204.5-207.9° C.; $^1$H NMR (300 MHz, DMSO-$d_6$) δ 9.43 (s, 1H), 7.84 (s, 2H), 7.56 (d, J=7.6 Hz, 1H), 7.46-7.41 (m, 1H), 7.35-7.22 (m, 3H), 7.11 (t, J=8.1 Hz, 1H), 6.96-6.93 (m, 1H), 6.48 (dd, J=8.0, 2.2 Hz, 1H), 4.80 (s, 2H), 2.31 (s, 3H); $^{13}$C NMR (75 MHz, DMSO-$d_6$) δ 168.8, 158.5, 157.0, 156.9, 142.7, 135.5, 134.7, 130.5, 130.4, 129.8, 128.1, 125.5, 116.7, 111.2, 106.3, 103.3, 53.3, 19.5; IR (ATR) 3448, 3368, 2325, 1689 cm$^{-1}$; APCI MS m/z 349 $[C_{18}H_{16}N_6O_2+H]^+$; HPLC (Method A) 91.3% (AUC), $t_R$=12.46 min.

Alternatively, to a solution of 5-amino-3-[3-(hydroxy)phenylamino]-1-(3-(methyl)phenyl)carbonyl-1H-1,2,4-triazole (Ia-7) (0.84 g, 2.7 mmol) in 2-butanone (9 mL) was added $K_2CO_3$ (0.41 g, 3.0 mmol) and $BrCH_2CN$ (0.36 g, 3.0 mmol). After stirring the mixture at 75° C. for 20 h, the 2-butanone was removed under reduced pressure. The residue was dissolved in EtOAc (50 mL), washed with water (50 mL), brine (30 mL), dried ($Na_2SO_4$) and concentrated to afford the crude product. Recrystallization from $CH_3CN$ afforded 5-amino-3-[3-(cyanomethoxy)phenylamino]-1-(3-(methyl)phenyl)carbonyl-1H-1,2,4-triazole (Ia-9) (0.12 g, 13%) as a white solid: $R_f$ 0.22 (1:1 hexanes/ethyl acetate); mp (DSC) 220.0-224.4° C.; $^1$H NMR (300 MHz, DMSO-$d_6$) δ 9.45 (s, 1H), 8.05 (s, 1H), 7.91 (d, J=7.1 Hz, 1H), 7.83 (s, 2H), 7.50-7.39 (m, 3H), 7.20 (t, J=8.1 Hz, 1H), 7.12-7.09 (m, 1H), 6.56 (dd, J=7.9, 2.2 Hz, 1H), 5.04 (s, 2H), 2.43 (s, 3H); $^{13}$C NMR (75 MHz, DMSO-$d_6$) δ 166.6, 157.9, 157.2, 156.9, 142.3, 137.2, 133.0, 132.6, 130.8, 129.5, 127.8, 127.4, 116.5, 111.1, 105.2, 104.0, 53.3, 20.8; IR (ATR) 3449, 3367, 2325, 1684 cm$^{-1}$; APCI MS m/z 349 [C$_{18}$H$_{16}$N$_6$O$_2$+H]$^+$; HPLC (Method A) 96.8% (AUC), t$_R$=12.81 min.

Compounds (Ia-10) and (Ia-11), as set forth below in Reaction Scheme 1D, are compounds of formula (Ia), as set forth above in the Summary of the Invention, and are prepared as illustrated below in Reaction Scheme 1D. For purposes of convenience, the minor products, i.e., the corresponding compounds of formula (Ib), are not illustrated in Reaction Scheme 1D, but it is understood that these compounds are prepared as well by the method disclosed therein and can be isolated and separated from compounds (Ia-10) and (Ia-11) by standard isolation and separation techniques.

REACTION SCHEME 1D

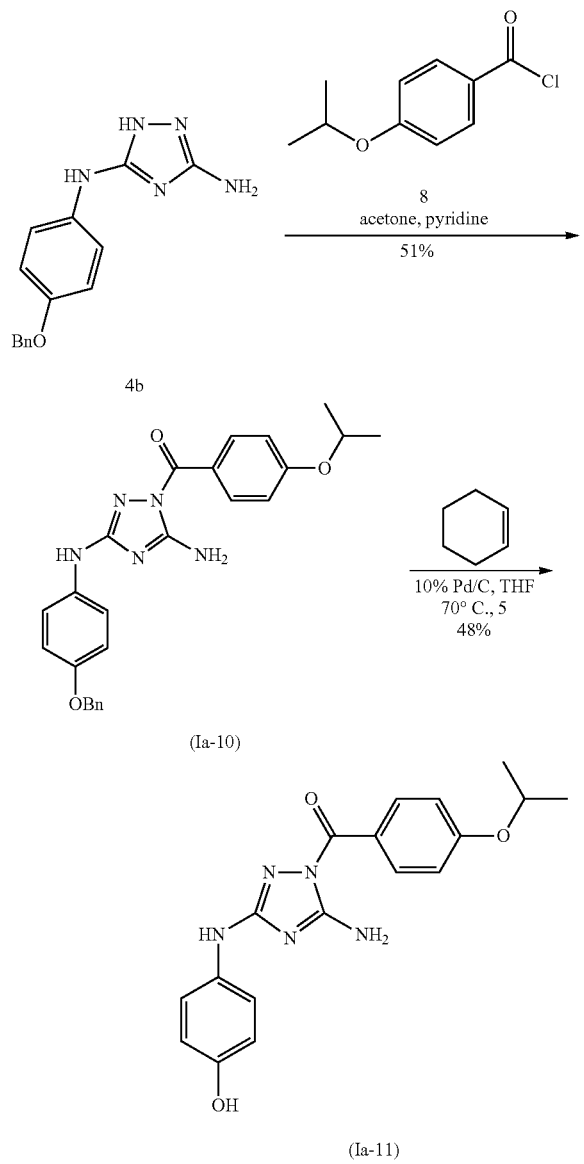

Preparation of 5-Amino-3-[3-(benzyloxy)phenylamino]-1-(4-(iso-propoxy)phenyl)carbonyl-1H-1,2,4-triazole (Ia-10) and 5-Amino-3-[4-(hydroxy)phenylamino]-1-(4-iso-propoxy)phenyl)carbonyl-1H-1,2,4-triazole (Ia-11)

In general, compound (Ia-11) is prepared by the acylation of compound 4b with the compound 8, followed by removal of the benzyl group. Compound 4b can be prepared by methods similar to those described herein or by methods known to one skilled in the art.

Specifically, to a stirred mixture of 4-isopropoxy benzoic acid (10.0 g, 55.5 mmol) and DMF (1 drop) in methylene chloride (80 mL) was added dropwise over a period of 15 min, a solution of oxalyl chloride (7.40 g, 58.2 mmol) in methylene chloride (20 mL). After stirring for 2.45 h at ambient temperature the reaction mixture was concentrated, taken up into a small amount of methylene chloride, filtered to remove insolubles and again concentrated to afford 8 (10.38 g, 94%) as a yellow liquid: $^1$H NMR (300 MHz, CDCl$_3$) δ 8.05 (d, 2H), 6.94 (d, 2H), 4.68 (m, 1H), 1.44 (d, 6H).

To a stirred mixture of 8 (0.50 g, 1.78 mmol) and pyridine (0.14 g, 1.78 mmol) in acetone (15 mL) at ice bath temperature was added 31 (0.35 g, 1.78 mmol). After stirring for 1 h at ice bath temperature and an additional 21.5 h at ambient temperature the reaction mixture was poured onto water (150 mL) and stirred vigorously. The aqueous mixture was extracted with ethyl acetate and the organic layer was separated, washed with brine, dried over magnesium sulfate and concentrated to give 0.74 g of a yellow foam. Purification by flash chromatography (97:3 methylene chloride/methanol) afforded 5-amino-3-[4-(benzyloxy)phenylamino]-1-(4-(iso-propoxy)phenyl)carbonyl-1H-1,2,4-triazole (Ia-10) (0.52 g, 51%) as a yellow solid: R$_f$ 0.51 (95:5 methylene chloride/methanol); mp 79-81° C.; $^1$H NMR (300 MHz, DMSO-d$_6$) δ 9.08 (s, 1H), 8.26 (d, J=8.9 Hz, 2H), 7.75 (br s, 2H), 7.60-7.20 (m, 7H), 7.08 (d, J=9.0 Hz, 2H), 6.93 (d, J=9.0 Hz, 2H), 5.26 (s, 2H), 4.80 (m, 1H), 1.33 (d, J=6.0 Hz, 6H); $^{13}$C NMR (75 MHz, DMSO-d$_6$) δ 165.8, 161.4, 158.6, 157.8, 152.5, 137.7, 135.1, 133.5, 128.7, 128.0, 127.9, 124.4, 118.1, 115.4, 114.8, 69.9, 69.8, 22.0; IR (ATR) 1669, 1581, 1544, 1506 cm$^{-1}$; ESI MS m/z 444 [C$_{25}$H$_{25}$N$_5$O$_3$+H]$^+$; HPLC (Method A)>99% (AUC), t$_R$=16.27 min. Anal. Calcd for C$_{25}$H$_{25}$N$_5$O$_3$: C, 67.70; H, 5.68; N, 15.79. Found: C, 67.73; H, 5.63; N, 15.79.

A mixture of (Ia-10) (0.36 g, 0.812 mmol) and 10% Pd/C (0.072 g) in cyclohexene (6 mL) and THF (12 mL) was stirred and heated at 70° C. After 2 d, additional 10% Pd/C (0.036 g) was added and heating and stirring at 70° C. was continued for an additional 3 d. After cooling to ambient temperature, the mixture was filtered through diatomaceous earth and concentrated to give a yellow-brown residue. Purification by flash chromatography (95:5 methylene chloride/methanol) afforded 5-amino-3-[4-(hydroxy)phenylamino]-1-(4-(iso-propoxy)phenyl)carbonyl-1H-1,2,4-triazole (Ia-11) (0.14 g, 48%) as a tan solid: R$_f$ 0.37 (95:5 methylene chloride/methanol); mp 229-234° C.; $^1$H NMR (300 MHz, DMSO-d$_6$) δ 8.91 (s, 1H), 8.88 (s, 1H), 8.26 (d, J=8.9 Hz, 2H), 7.72 (br s, 2H), 7.34 (d, J=8.8 Hz, 2H), 7.07 (d, J=8.9 Hz, 2H), 6.65 (d, J=8.8 Hz, 2H), 4.79 (m, 1H), 1.32 (d, J=6.0 Hz, 6H); $^{13}$C NMR (75 MHz, DMSO-d$_6$) δ 165.8, 161.4, 158.7, 157.8, 151.4, 133.5, 133.4, 124.4, 118.5, 115.5, 114.8, 70.0, 55.3, 22.0; IR (ATR) 1652, 1607, 1573, 1505 cm$^{-1}$; ESI MS m/z 354 [C$_{18}$H$_{19}$N$_5$O$_3$+H]$^+$; HPLC (Method A)>99% (AUC), t$_R$=11.74 min. Anal. Calcd for C$_{18}$H$_{19}$N$_5$O$_3$.0.5H$_2$O: C, 59.74; H, 5.43; N, 19.32. Found: C, 59.94; H, 5.08; N, 19.00.

Compound (Ia-12), as set forth below in Reaction Scheme 1E, is a compound of formula (Ia), as set forth above in the Summary of the Invention, and is prepared as illustrated below in Reaction Scheme 1E. For purposes of convenience, the minor product, i.e., the corresponding compound of formula (Ib), is not illustrated in Reaction Scheme 1E, but it is understood that this compound is prepared as well by the method disclosed therein and can be isolated and separated from compound (Ia-12) by standard isolation and separation techniques.

REACTION SCHEME 1E

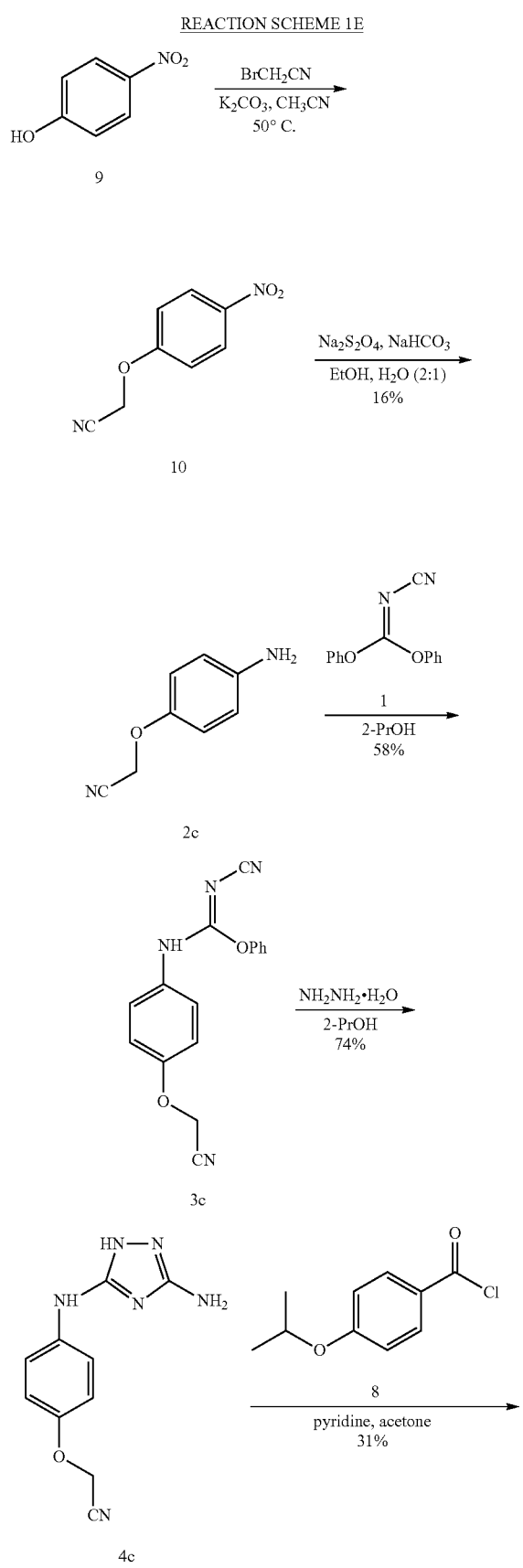

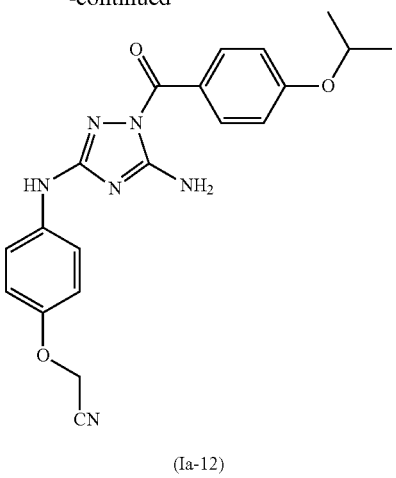

(Ia-12)

Preparation of 5-Amino-3-[4-(cyanomethoxy)phenylamino]-1-(4-(isopropoxy)phenyl)carbonyl-1H-1,2,4-triazole In general, compound (Ia-12) was prepared as shown above in Reaction Scheme 1E from commercially available 4-nitrophenol 9.

Specifically, a mixture of 4-nitrophenol 9 (6.00 g, 43.1 mmol), bromoacetonitrile (5.05 g, 47.4 mmol) and potassium carbonate (6.56 g, 47.4 mmol) in acetonitrile (120 mL) was heated to 50° C. for 5 h. The reaction was concentrated to remove most of the acetonitrile, extracted with ethyl acetate (25 mL), washed with water (25 mL), 1 N aqueous sodium hydroxide (25 mL), brine, dried (MgSO$_4$) and concentrated to afford 10 (7.49 g, 97%) as a tan-yellow solid: $^1$H NMR (300 MHz, DMSO-d$_6$) δ 8.29 (dd, J=2.1, 7.2 Hz, 2H), 7.29 (dd, J=7.2, 2.1 Hz, 2H), 5.36 (s, 2H).

A mixture of 10 (5.42 g, 30.4 mmol), sodium dithionite (15.89 g, 91.2 mmol) and sodium bicarbonate (15.30 g, 182.0 mmol) in 1:2 ethanol/water (75 mL) was stirred at ambient temperature for 20 h. Water (25 mL) was added and the pH of the resultant solution was adjusted to pH 10 with 1 N aqueous sodium hydroxide. The aqueous solution was extracted with methylene chloride (3×200 mL), the combined organic layers were separated, dried (MgSO$_4$) and concentrated to afford crude product 2c (0.73 g, 16%) as a yellow oil: $^1$H NMR (300 MHz, DMSO-d$_6$) δ 6.78 (dd, J=7.5, 3.0 Hz, 2H), 6.55 (dd, J=7.5, 3.0 Hz, 2H), 4.96 (s, 2H), 4.83 (br s, 2H).

A mixture of 2c (0.86 g, 5.79 mmol) and diphenylcyanocarbimidate 1 (1.38 g, 5.79 mmol) in 2-propanol (20 mL) was stirred at ambient temperature for 17 h. The solids that formed were collected by filtration and washed with 2-propanol, to afford 3c (0.99 g, 58%) as an off-white solid: $^1$H NMR (300 MHz, CDCl$_3$) δ 8.90 (br s, 1H), 7.44-7.33 (m, 5H), 7.52 (d, J=7.9 Hz, 2H), 7.12 (dd, J=3.0, 7.9 Hz, 2H), 4.77 (s, 2H); ESI MS m/z 293 [C$_{16}$H$_{12}$N$_4$O$_2$+H]$^+$.

A mixture of 3c (0.99 g, 3.38 mmol) and hydrazine hydrate (0.16 g, 3.38 mmol) in 2-propanol (20 mL) was stirred at ambient temperature for 24 h. The solids that formed were collected by filtration and washed with 2-propanol, to afford 4c (0.58 g, 74%) as an off-white solid: $^1$H NMR (300 MHz, DMSO-d$_6$) δ 11.09 (s, 1H), 8.53 (s, 1H), 7.48 (dd, J=3.0, 9.0 Hz, 2H), 6.91 (dd, J=3.0, 9.0 Hz, 2H), 5.83 (br s, 2H), 5.04 (s, 2H); ESI MS m/z 231 [C$_{10}$H$_{10}$N$_6$O+H]$^+$.

To a stirred ice-cold mixture of 4c (0.50 g, 2.17 mmol) and pyridine (0.17 g, 2.17 mmol) in acetone (35 mL) was added 4-isopropoxybenzoyl chloride 8 (0.43 g, 2.17 mmol). After stirring for 1 h at ice bath temperature and an additional 16 h at ambient temperature, the reaction mixture was slowly added to a vigorously stirred solution of water (100 mL). The crude product formed a yellow precipitate, which was collected by filtration. Purification by flash chromatography (98:2 methylene chloride/methanol) afforded 5-amino-3-[4-(cyanomethoxy)phenylamino]-1-(4-(iso-propoxy)phenyl) carbonyl-1H-1,2,4-triazole (Ia-12) (0.27 g, 31%) as a beige solid: $R_f$ 0.72 (97:3 methylene chloride/methanol); mp (DSC) 182.9-186.1° C.; $^1$H NMR (300 MHz, DMSO-$d_6$) δ 9.22 (s, 1H), 8.25 (d, J=9.0 Hz, 2H), 7.77 (br s, 2H), 7.52 (d, J=9.0 Hz, 2H), 7.09 (d, J=9.0 Hz, 2H), 7.00 (d, J=9.0 Hz, 2H), 5.09 (s, 2H), 4.94-4.78 (m, 1H), 1.33 (d, J=6.0 Hz, 6H); $^{13}$C NMR (75 MHz, DMSO-$d_6$) 165.5, 161.0, 158.1, 157.4, 150.0, 136.2, 133.0, 123.9, 117.7, 116.7, 115.5, 114.4, 69.5, 54.0, 21.6; IR (ATR) 3353, 3098, 1678, 1585, 1506 cm$^{-1}$; ESI MS m/z 393 $[C_{20}H_{20}N_6O_3+H]^+$; HPLC (Method A) 94.3% (AUC), $t_R$=14.00 min.

Compound (Ia-13), as set forth below in Reaction Scheme 1F, is a compound of formula (Ia), as set forth above in the Summary of the Invention, and is prepared as illustrated below in Reaction Scheme 1F. For purposes of convenience, the minor product, i.e., the corresponding compound of formula (Ib), is not illustrated in Reaction Scheme 1F, but it is understood that this compound is prepared as well by the method disclosed therein and can be isolated and separated from compound (Ia-13) by standard isolation and separation techniques.

REACTION SCHEME 1F

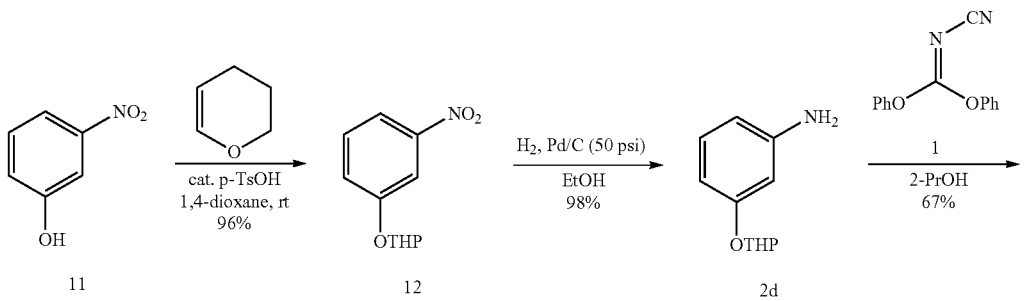

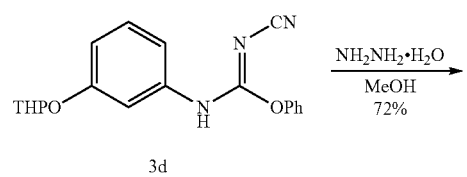

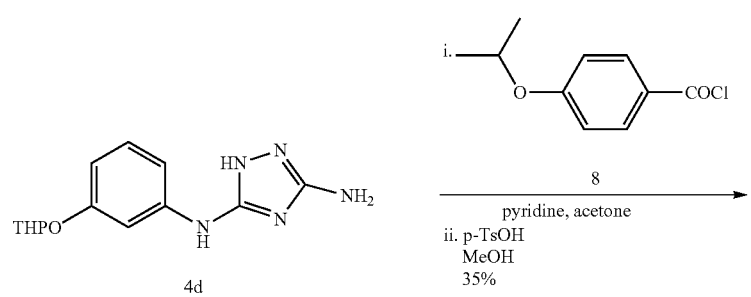

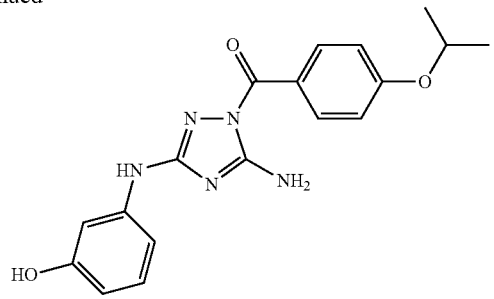

(Ia-13)

Preparation of 5-Amino-3-[3-(hydroxy)phenylamino]-1-(4-(iso-propoxy)phenyl)carbonyl-1H-1,2,4-triazole In general, compound (Ia-13) is prepared as shown above in Reaction Scheme 1F starting from commercially available 3-nitrophenol 11.

Specifically, to a solution of 3-nitrophenol 11 (2.00 g, 14.4 mmol) in 1,4-dioxane (40 mL) was added tetrahydro-2H-pyran (4.84 g, 57.5 mmol) and p-TsOH (a few crystals). The reaction mixture was stirred at ambient temperature under $N_2$ for 60 h. The dioxane was removed under reduced pressure and the crude oil obtained was diluted with EtOAc (100 mL). The organic layer was washed with 1 N NaOH (2×50 mL), brine (30 mL), dried ($Na_2SO_4$) and concentrated to afford 12 (3.08 g, 96%) as a yellow oil: $^1$H NMR (300 MHz, $CDCl_3$) δ 7.92-7.90 (m, 1H), 7.86-7.82 (m, 1H), 7.45-7.34 (m, 2H), 5.50 (t, J=2.7 Hz, 1H), 3.89-3.81 (m, 1H), 3.68-3.61 (m, 1H), 2.01-1.95 (m, 1H), 1.92-1.87 (m, 2H), 1.75-1.58 (m, 3H).

A mixture of 12 (3.08 g, 13.8 mmol) and 10% Pd/C (0.30 g) in EtOH (150 mL) at ambient temperature was shaken in an atmosphere of hydrogen at 50 psi. After 1 h, the reaction mixture was filtered through diatomaceons earth and the solids washed with EtOH. The filtrate was concentrated to afford 2d (2.62 g, 98%) as a yellow oil: $^1$H NMR (300 MHz, $CDCl_3$) δ 7.04 (t, J=8.0 Hz, 1H), 6.47-6.41 (m, 2H), 6.34-6.30 (m, 1H), 5.37 (t, J=3.2 Hz, 1H), 3.95-3.87 (m, 1H), 3.72-3.56 (m, 3H), 2.02-1.89 (m, 1H), 1.85-1.80 (m, 2H), 1.75-1.54 (m, 3H).

A mixture of 2d (2.62 g, 13.6 mmol) and diphenylcyanocarbimidate (3.23 g, 13.6 mmol) in 2-PrOH (40 mL) was stirred at ambient temperature under $N_2$ for 20 h. The solids that formed were collected by filtration and washed with 2-PrOH to afford 3d (3.08 g, 67%) as a white solid: $^1$H NMR (300 MHz, $CDCl_3$) δ 7.90 (br s, 1H), 7.47-7.40 (m, 2H), 7.36-7.28 (m, 2H), 7.21-7.14 (m, 2H), 7.10 (t, J=2.1 Hz, 1H), 6.97 (dt, J=7.6, 1.6 Hz, 2H), 5.40 (t, J=3.2 Hz, 1H), 3.87 (dt, J=11.7, 3.0 Hz, 1H), 3.63-3.58 (m, 1H), 2.05-1.91 (m, 1H), 1.88-1.83 (m, 2H), 1.74-1.62 (m, 3H).

A mixture of 3d (3.08 g, 9.16 mmol) and hydrazine monohydrate (0.46 g, 9.16 mmol) in MeOH (40 mL) was stirred at ambient temperature for 20 h. The MeOH was removed under reduced pressure and the crude oil obtained was partitioned between EtOAc (100 mL) and water (100 mL). The aqueous layer was extracted with EtOAc (100 mL) and the combined organic extracts were washed with brine (30 mL), dried ($Na_2SO_4$) and concentrated to give the crude product. Purification by flash chromatography ($CH_2Cl_2$ then 9:1 $CH_2Cl_2$/MeOH) afforded 4d (1.81 g, 72%) as a white foam: $^1$H NMR (300 MHz, DMSO-$d_6$) δ 11.12 (s, 1H), 7.38 (s, 1H), 7.03-7.01 (m, 2H), 6.42-6.38 (m, 1H), 5.86 (s, 2H), 5.35 (t, J=3.0 Hz, 1H), 3.81-3.73 (m, 1H), 3.55-3.48 (m, 1H), 1.88-1.53 (m, 6H).

To a ice-cold mixture of 4d (0.50 g, 1.80 mmol) and pyridine (0.14 g, 1.80 mmol) in acetone (25 mL) was added dropwise a solution of 4-isopropoxybenzoyl chloride (8) (0.36 g, 1.80 mmol) in acetone (5 mL) over 2 min and the resulting solution was stirred at ambient temperature for 20 h. The acetone was removed under reduced pressure and the crude yellow foam obtained was dissolved in MeOH and p-TsOH (a few crystals) was added. After stirring for 7 d at ambient temperature, the MeOH was removed under reduced pressure and the residue partitioned between EtOAc (100 mL) and water (100 mL). The organic layer was washed with brine (30 mL), dried ($Na_2SO_4$), and concentrated to give the crude product. Purification by flash chromatography (95:5 $CH_2Cl_2$/MeOH) gave 5-amino-3-[3-(hydroxy)phenylamino]-1-(4-(iso-propoxy)phenyl)carbonyl-1H-1,2,4-triazole (Ia-13) (0.22 g, 35%) as a yellow solid: $R_f$ 0.53 (9:1 $CH_2Cl_2$/MeOH); mp (DSC) 204.2-211.9° C.; $^1$H NMR (300 MHz, DMSO-$d_6$) δ 9.17 (s, 1H), 9.13 (s, 1H), 8.26 (d, J=8.8 Hz, 2H), 7.75 (s, 2H), 7.07-6.96 (m, 5H), 6.29-6.26 (m, 1H), 4.82-4.74 (m, 1H), 1.32 (d, J=5.9 Hz, 6H); $^{13}$C NMR (75 MHz, DMSO-$d_6$) δ 165.9, 161.4, 158.4, 158.0, 157.7, 142.4, 133.5, 129.6, 124.3, 114.8, 108.2, 107.8, 104.4, 70.0, 22.0; IR (ATR) 3426, 3305, 1661 cm$^{-1}$; APCI MS m/z 354 $[C_{18}H_{19}N_6O_3+H]^+$; HPLC (Method A) >99% (AUC), $t_R$=12.24 min. Anal. Calcd for $C_{16}H_{19}N_6O_3$: C, 61.18; H, 5.42; N, 19.82. Found: C, 61.10; H, 5.29; N, 19.69.

Compounds (Ia-14) and (Ia-15), as set forth below in Reaction Scheme 1G, are compounds of formula (Ia), as set forth above in the Summary of the Invention, and are prepared as illustrated below in Reaction Scheme 1G. For purposes of convenience, the minor products, i.e., the corresponding compounds of formula (Ib), are not illustrated in Reaction Scheme 1G, but it is understood that these compounds are prepared as well by the method disclosed therein and can be isolated and separated from compounds (Ia-14) and (Ia-15) by standard isolation and separation techniques.

REACTION SCHEME 1G

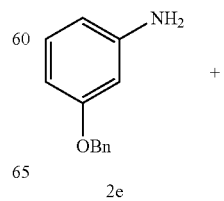

2e

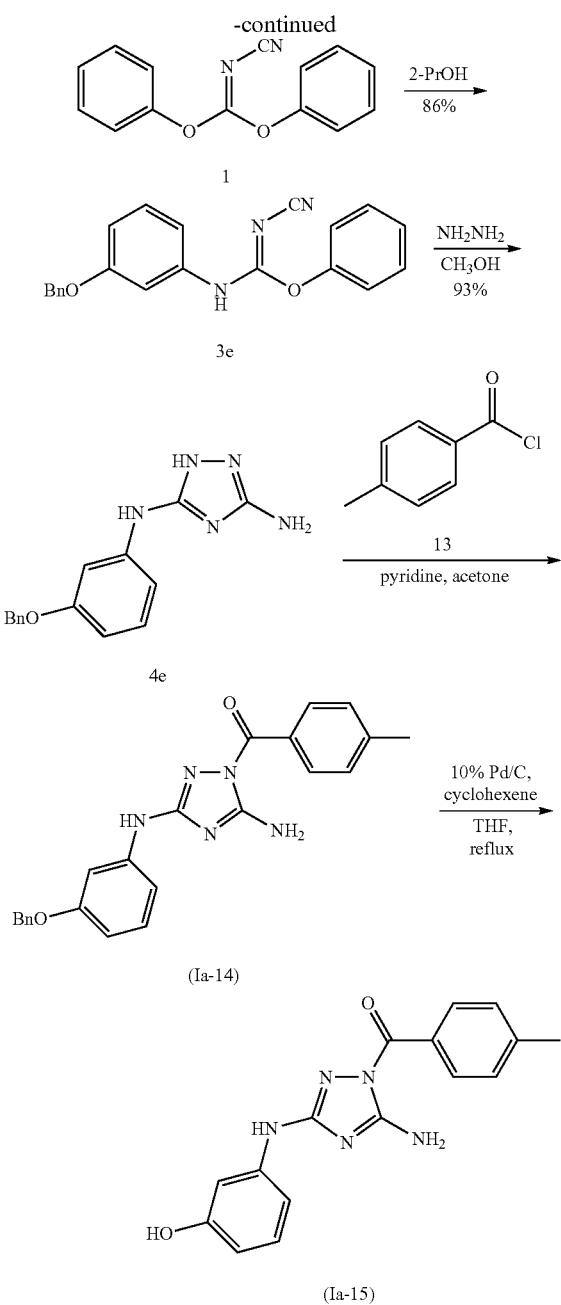

Preparation of 5-Amino-3-[3-(hydroxy)phenylamino]-1-(4-(methyl)phenyl)carbonyl-1H-1,2,4-triazole In general, condensation of benzyloxyaniline and diphenylcyanocarbonimidate afforded intermediate 3e, which was then treated with hydrazine to give triazole 4e. Acylation of 4e with p-toluoyl chloride (13) in the presence of pyridine afforded compound (Ia-14) in good yield. Initial attempts to remove the benzyl protecting group by hydrogenolysis with Pd/C (50 psi) were unsuccessful. Deprotection of compound (Ia-14) was achieved with cyclohexene in the presence of 10% Pd/C and refluxing THF to provide (Ia-15).

Specifically, a solution of 3-benzyloxyaniline 2e (0.84 g, 4.2 mmol) and diphenylcyanocarbonimidate 1 (1.0 g, 4.2 mmol) in 2-PrOH (15 mL) was stirred at ambient temperature under $N_2$. After 5 h, the solids were collected by filtration washing with cold 2-PrOH to afford 3e (1.25 g, 86%) as a white solid: $^1$H NMR (300 MHz, DMSO-$d_6$) δ 7.47-7.26 (m, 12H), 7.17 (s, 1H), 7.05 (d, J=7.9 Hz, 1H), 6.90 (d, J=8.3 Hz, 1H), 5.10 (s, 2H).

To a mixture of 3e (1.25 g, 3.6 mmol) in $CH_3OH$ (20 mL) was added $NH_2NH_2.H_2O$ (0.2 g, 3.8 mmol) dropwise. Once the addition was completed, the reaction was stirred at ambient temperature. After 2 h, the methanol was removed under reduced pressure and the residue partitioned between water (50 mL) and EtOAc (50 mL). The organic layer was washed with brine (20 mL), dried ($Na_2SO_4$), filtered, and concentrated. The crude foam obtained was purified by flash chromatography (9:1 $CH_2Cl_2/CH_3OH$) to afford 4e (0.93 g, 93%) as a white solid: $^1$H NMR (300 MHz, DMSO-$d_6$) δ 11.13 (s, 1H), 8.61 (s, 1H), 7.46-7.32 (m, 6H), 7.04-6.97 (m, 2H), 6.37 (d, J=7.1 Hz, 1H), 5.86 (s, 2H), 5.02 (s, 2H).

Pyridine (0.56 g, 7.1 mmol) was added to a mixture of 4e (2.0 g, 7.1 mmol) and acetone (60 mL) at ambient temperature under $N_2$. The reaction was cooled to 0° C. and p-toluoyl chloride (1.1 g, 7.1 mmol) was added dropwise over 2 min. Once the addition was complete, the reaction was stirred at ambient temperature for 1 h. The acetone was removed under reduced pressure and the residue diluted in water (150 mL). Solids were collected by filtration, washing with water, and then purified by flash chromatography (95:5 $CH_2Cl_2/CH_3OH$) to afford 5-amino-3-[3-(benzyloxy)phenylamino]-1-(4-(methyl)phenyl)carbonyl-1H-1,2,4-triazole (Ia-14) (2.12 g, 75%) as a pale-yellow solid: $^1$H NMR (300 MHz, DMSO-$d_6$) δ 9.35 (s, 1H), 8.10 (d, J=8.1 Hz, 2H), 7.79 (br s, 2H), 7.59 (t, J=2.1 Hz, 1H), 7.41-7.34 (m, 5H), 7.27 (d, J=8.1 Hz, 2H), 7.11 (t, J=8.1 Hz, 1H), 6.89 (dd, J=1.3, 8.0 Hz, 1H), 6.47 (dd, J=2.3, 7.9 Hz, 1H), 4.91 (s, 2H), 2.20 (s, 3H).

To a solution of 5-amino-3-[3-(benzyloxy)phenylamino]-1-(4-(methyl)phenyl)carbonyl-1H-1,2,4-triazole (Ia-14) (0.50 g, 1.3 mmol) in THF (20 mL) was added cyclohexene (10 mL) and 10% Pd/C (0.10 g). The reaction was stirred at 90° C. under $N_2$ for 48 h, then filtered through diatomaceous earth, washing with THF, and concentrated to give a yellow-orange solid. Purification by flash chromatography (95:5 $CH_2Cl_2/CH_3OH$) followed by triturated in $CH_2Cl_2$ afforded 5-amino-3-[3-(hydroxy)phenylamino]-1-(4-(methyl)phenyl)carbonyl-1H-1,2,4-triazole (Ia-15) (0.05 g, 14%) as a yellow solid: $R_f$ 0.22 (95:5 $CH_2Cl_2/CH_3OH$); mp (DSC) 2 endothermic events, 214.7-217.5° C., 322.1-329.8° C., 1 exothermic event, 226.8-228.8° C.; $^1$H NMR (300 MHz, DMSO-$d_6$) δ 9.14 (d, J=8.1 Hz, 2H), 8.13 (d, J=8.2 Hz, 2H), 7.77 (s, 2H), 7.36 (d, J=8.1 Hz, 2H), 6.99-6.94 (m, 3H), 6.29-6.25 (m, 1H), 2.45 (s, 3H); $^{13}$C NMR (75 MHz, DMSO-$d_6$) δ 166.2, 158.2, 157.6, 157.3, 142.9, 142.0, 130.6, 129.7, 129.1, 128.5, 107.8, 107.4, 104.0, 21.0; IR (ATR) 3363, 1668 $cm^{-1}$; APCI MS m/z 310 $[C_{16}H_{15}N_5O_2+H]^+$; HPLC (Method A) 96.9% (AUC), $t_R$=11.5 min. Anal. Calcd for $C_{16}H_{16}N_6O_2.0.50H_2O$: C, 60.47; H, 4.92; N, 22.03. Found: C, 60.87; H, 4.65; N, 21.75.

Compounds (Ia-16) and (Ia-17), as set forth below in Reaction Scheme 1H, are compounds of formula (Ia), as set forth above in the Summary of the Invention, and are prepared as illustrated below in Reaction Scheme 1H. For purposes of convenience, the minor products, i.e., the corresponding compounds of formula (Ib), are not illustrated in Reaction Scheme 1H, but it is understood that these compounds are prepared as well by the method disclosed therein and can be isolated and separated from compounds (Ia-16) and (Ia-17) by standard isolation and separation techniques.

REACTION SCHEME 1H

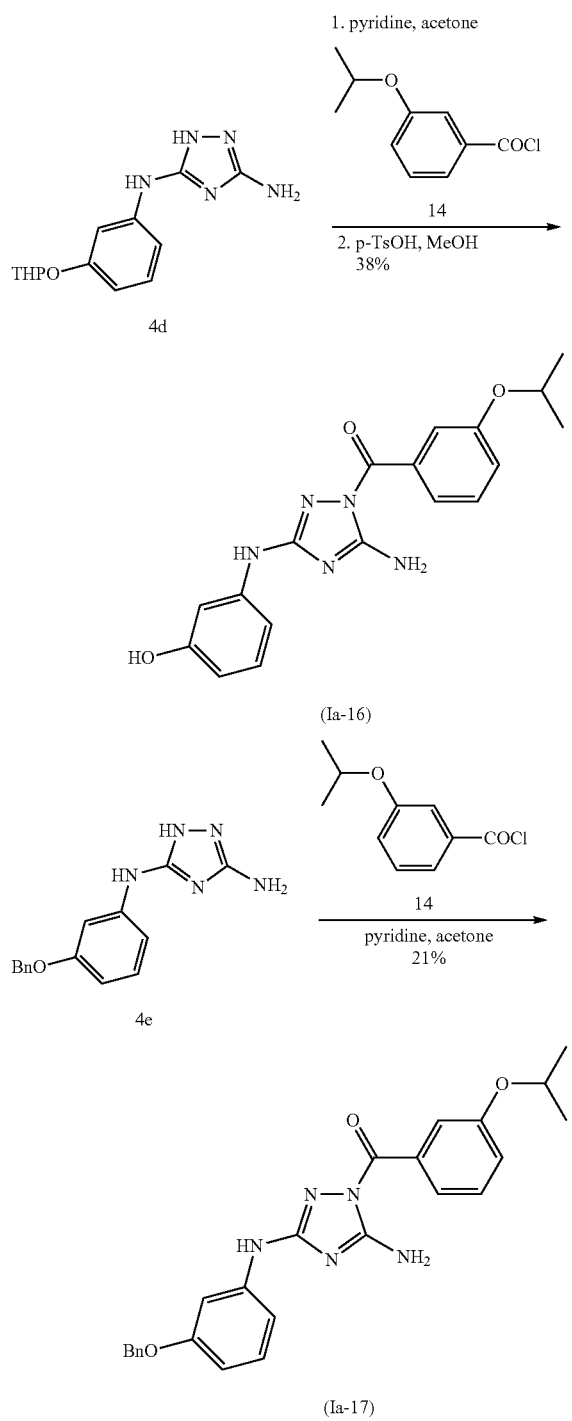

Preparation of 5-Amino-3-[3-(hydroxy)phenylamino]-1-(3-(iso-propoxy)phenyl)carbonyl-1H-1,2,4-triazole and 5-Amino-3-[3-(benzyloxy)phenylamino]-1-(3-(iso-propoxy)phenyl)carbonyl-1H-1,2,4-triazole In general, compounds of (Ia-16) and (Ia-17) are prepared from the acylation of compounds 4d and 4e, respectively, with compound 14. Compounds 4d and 4e can be prepared by methods disclosed herein or by methods known to one skilled in the art.

Specifically, to an ice-cold mixture of 4d (0.50 g, 1.80 mmol) and pyridine (0.28 g, 3.60 mmol) in acetone (10 mL) placed under $N_2$ was added dropwise a solution of 3-isopropoxybenzoyl chloride 14 (0.36 g, 1.80 mmol) in acetone (5 mL) over 2 min and the resulting solution was stirred at ambient temperature for 20 h. The acetone was concentrated to a small volume (5 mL) and diluted in water (15 mL). The resulting precipitate was collected by filtration, dissolved in acetone and the organic solution dried ($Na_2SO_4$) and concentrated to afford a yellow foam. The yellow foam and p-TsOH (a few crystals) in MeOH (15 mL) was stirred at 50° C. for 24 h then at ambient temperature for 6 d. The MeOH was removed under reduced pressure and the residue was partitioned between EtOAc (30 mL) and water (30 mL). The aqueous layer was extracted with EtOAc (20 mL) and the combined organics were dried ($Na_2SO_4$), and concentrated to give the crude product. Purification by flash chromatography (95:5 $CH_2Cl_2$/MeOH) followed by trituration with $CH_2Cl_2$ afforded 5-amino-3-[3-(hydroxy)phenylamino]-1-(3-(isopropoxy)phenyl)carbonyl-1H-1,2,4-triazole (Ia-16) (0.36 g, 38%) as a yellow solid: $R_f$ 0.55 (9:1 $CH_2Cl_2$/MeOH); mp (DSC) 211.3-214.8° C.; $^1$H NMR (300 MHz, DMSO-$d_6$) δ 9.16 (d, J=3.1 Hz, 2H), 7.80-7.74 (m, 3H), 7.67 (d, J=7.7 Hz, 1H), 7.44 (t, J=8.0 Hz, 1H), 7.19 (dd, J=8.0, 2.2 Hz, 1H), 7.04-6.89 (m, 3H), 6.27 (dd, J=7.8, 1.4 Hz, 1H), 4.72-4.64 (m, 1H), 1.29 (d, J=6.0 Hz, 6H); $^{13}$C NMR (75 MHz, DMSO-$d_6$) δ 166.5, 158.6, 158.0, 157.7, 157.1, 142.3, 134.2, 129.5, 129.4, 122.7, 120.5, 117.5, 108.1, 107.9, 104.4, 70.0, 22.1; IR (ATR) 3424, 3365, 1689 cm$^{-1}$; APCI MS m/z 354 $[C_{18}H_{19}N_5O_3+H]^+$; HPLC (Method A) 97.9% (AUC), $t_R$=12.10 min. Anal. Calcd for $C_{15}H_{13}N_5O_3$: C, 61.18; H, 5.42; N, 19.82. Found: C, 61.11; H, 5.33; N, 19.68.

Alternatively, to an ice cold mixture of 4e (0.30 g, 1.07 mmol) and pyridine (0.08 g, 1.07 mmol) in acetone (25 mL) under $N_2$ was added dropwise a solution of 3-isopropoxybenzoyl chloride 14 (0.21 g, 1.07 mmol) in acetone (5 mL) over 2 min and the resulting solution was stirred at ambient temperature for 20 h. The acetone was concentrated to a small volume (5 mL) and diluted in water (15 mL). The resulting precipitate was collected by filtration, dissolved in acetone and the organic solution dried ($Na_2SO_4$) and concentrated to afford 5-amino-3-[3-(benzyloxy)phenylamino]-1-(3-(isopropoxy)phenyl)carbonyl-1H-1,2,4-triazole (Ia-17) (0.10 g, 21%) as a yellow solid: $R_f$ 0.63 (9:1 $CH_2Cl_2$/MeOH); mp (DSC) 131.1-132.4° C.; $^1$H NMR (300 MHz, DMSO-$d_6$) δ 9.31 (s, 1H), 7.80 (s, 2H), 7.70-7.63 (m, 2H), 7.40-7.31 (m, 7H), 7.14-7.01 (m, 3H), 6.48-6.47 (m, 1H), 4.92 (s, 2H), 4.66-4.58 (m, 1H), 1.24 (d, J=6.0 Hz, 6H); $^{13}$C NMR (75 MHz, DMSO-$d_6$) δ 165.1, 157.5, 156.8, 155.9, 155.5, 140.8, 135.7, 132.9, 127.9, 127.7, 127.0, 126.4, 126.2, 120.9, 118.4, 115.7, 108.1, 105.3, 101.9, 68.3, 67.5, 20.4; IR (ATR) 3685, 3434, 3343, 1674 cm$^{-1}$; APCI MS m/z 444 $[C_{25}H_{25}N_5O_3+H]^+$; HPLC (Method A)>99% (AUC), $t_R$=16.29 min. Anal. Calcd for $C_{25}H_{25}N_5O_3$·0.25$H_2O$: C, 66.70; H, 5.68; N, 15.79. Found: C, 67.42; H, 5.71; N, 15.63.

Compounds 2f, 2g and 2h, as set forth below in Reaction Scheme 1I, are intermediates in the preparation of compounds of the invention and are prepared as illustrated below in Reaction Scheme 1I. In Scheme 1I, "X" represents, e.g., an appropriate leaving group on the R as represented. Typical leaving groups include halides, such as bromide, chloride, iodide and the like.

REACTION SCHEME 1I

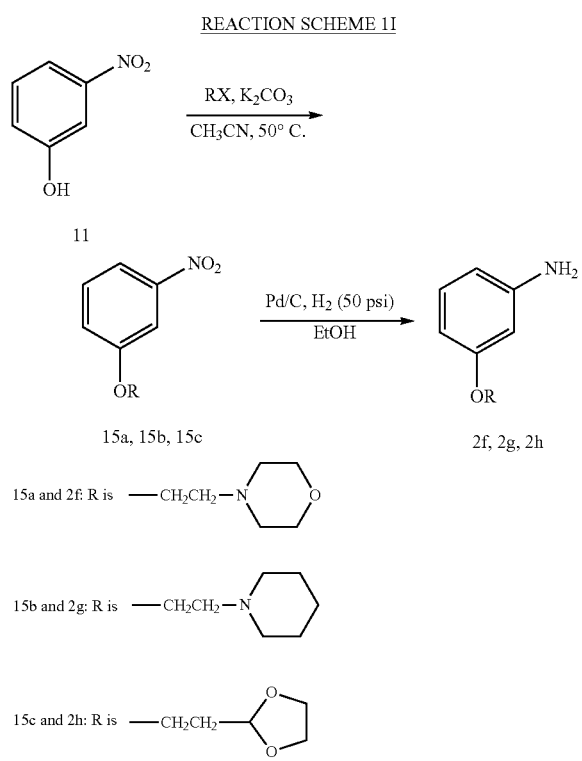

Specifically, a mixture of 3-nitrophenol 11 (2.0 g, 14.3 mmol), K$_2$CO$_3$ (4.17 g, 30.2 mmol), and N-(2-chloroethyl)morpholine hydrochloride (2.94 g, 15.8 mmol) in DMF (20 mL) was stirred under N$_2$ at 50° C. for 5 h. The DMF was removed under reduced pressure and the residue was partitioned between EtOAc (50 mL) and water (50 mL). The aqueous layer was extracted with EtOAc (50 mL) and the combined organics were dried (Na$_2$SO$_4$) and concentrated to give 15a (3.39 g, 94%) as a brown oil: $^1$H NMR (300 MHz, CDCl$_3$) δ 7.85-7.81 (m, 1H), 7.76-7.74 (m, 1H), 7.45-7.40 (m, 1H), 7.25-7.24 (m, 1H), 4.18 (t, J=5.5 Hz, 2H), 3.76-3.71 (m, 4H), 2.84 (t, J=5.5 Hz, 2H), 2.61-2.50 (m, 4H).

A mixture of 15a (3.39 g, 13.4 mmol) and 10% Pd/C (0.17 g) in EtOH (100 mL) at ambient temperature was shaken in an atmosphere of hydrogen at 50 psi. After 1 h, the reaction was filtered through diatomaceous earth, the solids washed with EtOAc and the filtrate concentrated to give the crude product. Purification by flash chromatography (95:5 CH$_2$Cl$_2$/MeOH) afforded 2f (1.68 g, 56%) as a brown oil: $^1$H NMR (300 MHz, CDCl$_3$) δ 7.04 (t, J=8.0 Hz, 1H), 6.33-6.24 (m, 3H), 4.07 (t, J=5.7 Hz, 2H), 3.75-3.72 (m, 4H), 3.65 (s, 2H), 2.78 (t, J=5.7 Hz, 2H), 2.59-2.56 (m, 4H).

Alternatively, a mixture of 3-nitrophenol 11 (3.0 g, 21.6 mmol), K$_2$CO$_3$ (6.56 g, 47.4 mmol), and 1-(2-chloroethyl)piperidine hydrochloride (4.80 g, 25.9 mmol) in DMF (30 mL) was stirred at 50° C. under N$_2$ for 48 h. The DMF was removed under reduced pressure and the residue was partitioned between EtOAc (100 mL) and water (100 mL). The organic layer was washed with water (2×50 mL), dried (Na$_2$SO$_4$) and concentrated to give the crude product. Purification by flash chromatography (95:5 CH$_2$Cl$_2$/MeOH) gave 15b (2.90 g, 54%) as a brown oil: ESI MS m/z 251 [C$_{13}$H$_{18}$N$_2$O$_3$+H]$^+$.

A mixture of 15b (2.90 g, 11.6 mmol) and 10% Pd/C (0.22 g) in EtOH (150 mL) at ambient temperature was shaken in an atmosphere of hydrogen at 50 psi. After 30 min, the reaction was filtered through diatomaceous earth, the solids washed with EtOAc and the filtrate was concentrated to afford 2g (2.57 g, quantitative) as a brown oil: $^1$H NMR (300 MHz, CDCl$_3$) δ 6.86 (t, J=8.3 Hz, 1H), 6.13-6.11 (m, 2H), 6.07-6.04 (m, 1H), 5.01 (s, 2H), 3.92 (t, J=6.0 Hz, 2H), 2.95 (t, J=6.0 Hz, 2H), 2.40-2.38 (m, 4H), 1.52-1.36 (m, 6H).

Alternatively, a mixture of 3-nitrophenol 11 (3.0 g, 21.6 mmol), K$_2$CO$_3$ (3.40 g, 24.8 mmol), and 2-(2-bromoethyl)-1,3-dioxolane (4.49 g, 24.8 mmol) in CH$_3$CN (30 mL) was stirred under N$_2$ at 50° C. for 24 h. The CH$_3$CN was removed under reduced pressure and the residue was partitioned between EtOAc (75 mL) and water (75 mL). The aqueous layer was extracted with EtOAc (75 mL) and the combined organic extracts were washed with 1 N NaOH (2×30 mL), water (30 mL), dried (Na$_2$SO$_4$), and concentrated to afford 15c (5.11 g, 99%) as a yellow oil: $^1$H NMR (300 MHz, DMSO-d$_6$) δ 7.83-7.80 (m, 1H), 7.71-7.69 (m, 1H), 7.58 (t, J=8.2 Hz, 1H), 7.44-7.40 (m, 1H), 5.00 (t, J=4.9 Hz, 1H), 4.20 (t, J=6.5 Hz, 2H), 3.95-3.76 (m, 4H), 2.13-2.03 (m, 2H).

A mixture of 15c (5.11 g, 21.4 mmol) and 10% Pd/C (0.30 g) in EtOH (175 mL) at ambient temperature was shaken in an atmosphere of hydrogen at 50 psi. After 30 min, the reaction was filtered through diatomaceous earth, the solids washed with EtOAc and the filtrate was concentrated to afford 2h (4.51 g, quantitative) as a brown oil: ESI MS m/z 210 [C$_{11}$H$_{15}$NO$_3$+H]$^+$.

Compounds (Ia-18) and (Ia-19), as set forth below in Reaction Scheme 1J, are compounds of formula (Ia), as set forth above in the Summary of the Invention, and are prepared as illustrated below in Reaction Scheme 1J. For purposes of convenience, the minor products, i.e., the corresponding compounds of formula (Ib), are not illustrated in Reaction Scheme 1J, but it is understood that these compounds are prepared as well by the method disclosed therein and can be isolated and separated from compounds (Ia-18) and (Ia-19) by standard isolation and separation techniques.

REACTION SCHEME 1J

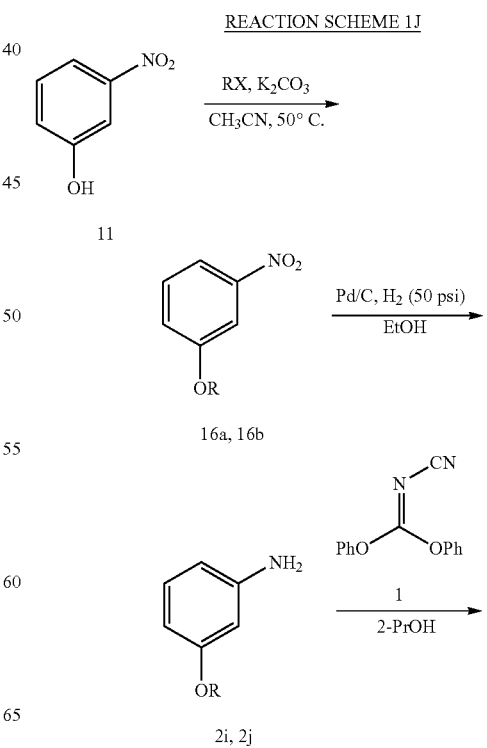

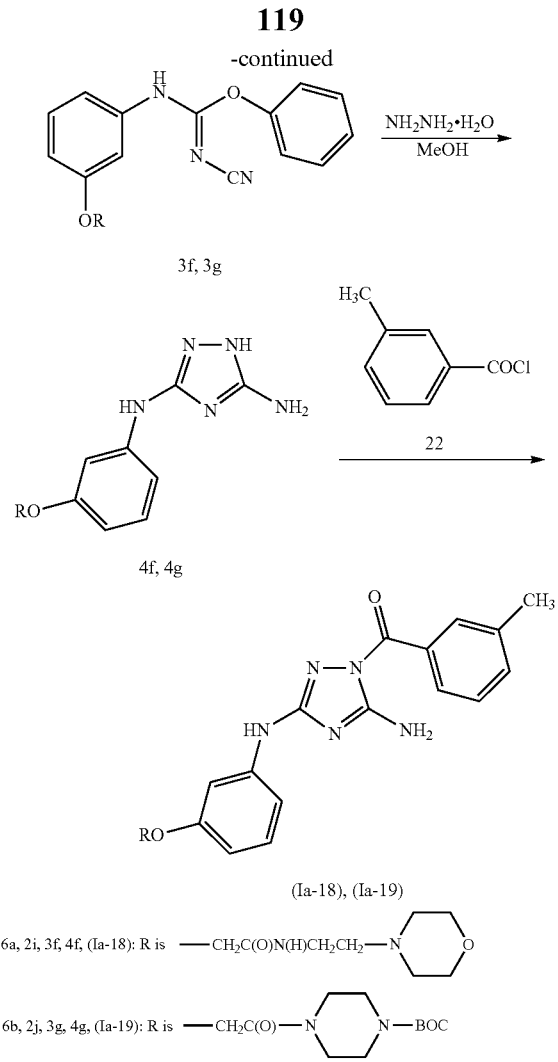

Preparation of 5-Amino-1-(3-methylphenyl)carbonyl-3-[3-[2-(4-morpholinyl)ethylaminocarbonylmethoxy]phenyl]amino-1H-1,2,4-triazole and 5-Amino-1-(3-methylphenyl)carbonyl-3-[3-(N-tert-butoxycarbonyl)piperazin-4-ylcarbonylmethoxy)phenyl]amino-1H-1,2,4-triazole In general, alkylation of 3-nitrophenol 11 was performed using reagents RX which are commercially available or prepared by methods disclosed herein to afford intermediates (Ia-18) and (Ia-19). In Reaction Scheme 1J, "X" represents, e.g., an appropriate leaving group on the R as represented. Typical leaving groups include halides, such as bromide, chloride, iodide and the like.

Specifically, the alkylation of 3-nitrophenol 11 was performed as described above in Reaction Scheme 1I using 18, prepared as described below in Reaction Scheme 1K, to afford 16a (3.02 g, 34%) as a yellow-orange solid: $^1$H NMR (300 MHz, DMSO-d$_6$) δ 8.14-8.10 (m, 1H), 7.87-7.83 (m, 1H), 7.76 (t, J=2.3 Hz, 1H), 7.60 (t, J=8.2 Hz, 1H), 7.46-7.42 (m, 1H), 4.64 (s, 2H), 3.53 (t, J=4.6 Hz, 4H), 3.26 (q, J=6.6 Hz, 2H), 2.38-2.33 (m, 6H).

The reduction of 16a was performed as described above in Reaction Scheme to afford 21 (2.81 g, quantitative) as a yellow oil: $^1$H NMR (300 MHz, DMSO-d$_6$) δ 7.83-7.79 (m, 1H), 6.89 (t, J=7.9 Hz, 1H), 6.19-6.06 (m, 3H), 5.10 (s, 2H), 4.33 (s, 2H), 3.53 (t, J=4.6 Hz, 4H), 3.24 (q, J=6.5 Hz, 2H), 2.38-2.32 (m, 6H).

The condensation of 2i was performed as described above in Reaction Scheme 1G. The reaction mixture was concentrated almost to dryness and Et$_2$O (100 mL) was added. The mixture was vigorously stirred for 0.5 h. The solids which formed were collected by filtration to afford 3f (6.14 g, quantitative) as a pale yellow solid: $^1$H NMR (300 MHz, DMSO-d$_6$) δ 10.86 (br s, 1H), 7.98-7.94 (m, 1H), 7.48-7.42 (m, 2H), 7.34-7.20 (m, 4H), 7.11-7.02 (m, 2H), 6.85-6.81 (m, 1H), 4.48 (s, 2H), 3.52 (t, J=4.6 Hz, 4H), 3.23 (q, J=6.5 Hz, 2H), 2.35-2.34 (m, 6H).

The cyclization of 3f was performed as described above in Reaction Scheme 1G to afford 4f (0.90 g, 45%) as an off-white solid: $^1$H NMR (300 MHz, DMSO-d$_6$) δ 11.15 (s, 1H), 8.65 (s, 1H), 7.88-7.84 (m, 1H), 7.28 (s, 1H), 7.08-7.01 (m, 2H), 6.33-6.30 (m, 1H), 5.85 (s, 2H), 4.38 (s, 2H), 3.52 (t, J=4.5 Hz, 4H), 3.30-3.21 (m, 2H), 2.38-2.32 (m, 6H).

The acylation of 4f was performed as described above in Reaction Scheme 1G. The mixture was concentrated to approximately 15 mL and poured into a mixture of water (50 mL) and saturated NaHCO$_3$ (50 mL). The aqueous mixture was extracted with EtOAc (2×75 mL) and the combine organics were washed with brine (30 mL), dried (Na$_2$SO$_4$), and concentrated under reduced pressure. The crude product was slurried in acetone and filtered to afford 5-amino-1-(3-methylphenyl)carbonyl-3-[3-[2-(4-morpholinyl)ethylaminocarbonylmethoxy]phenyl]amino-1H-1,2,4-triazole (Ia-18) (0.28 g, 42%) as a yellow solid: R$_f$ 0.51 (9:1 methylene chloride/methanol); mp 145-147° C.; $^1$H NMR (300 MHz, DMSO-d$_6$) δ 9.35 (s, 1H), 8.02 (s, 1H), 7.98-7.95 (m, 1H), 7.85-7.82 (m, 3H), 7.50-7.46 (m, 2H), 7.29-7.28 (m, 1H), 7.15-7.07 (m, 2H), 6.46-6.42 (m, 1H), 4.36 (s, 2H), 3.52 (t, J=4.5 Hz, 4H), 3.25 (q, J=6.5 Hz, 2H), 2.41 (s, 3H), 2.38-2.32 (m, 6H); $^{13}$C NMR (75 MHz, DMSO-d$_6$) δ 165.8, 164.9, 156.5, 156.4, 155.6, 140.5, 135.6, 131.4, 130.9, 129.2, 127.6, 126.2, 125.8, 108.4, 104.3, 102.0, 65.3, 64.5, 55.3, 51.4, 33.7, 19.2; IR (ATR) 3433, 3249, 3197, 1667 cm$^{-1}$; APCI MS m/z 480 [C$_{24}$H$_{29}$N$_7$O$_4$+H]$^+$; HPLC (Method 2) 97.6% (AUC), t$_R$=8.99 min. Anal. Calcd for C$_{24}$H$_{29}$N$_7$O$_4$: C, 60.11; H, 6.10; N, 20.45. Found: C, 60.22; H, 5.92; N, 20.41.

Alternatively, the alkylation of 3-nitrophenol 11 was performed as described above in Reaction Scheme 1I using 20, as prepared below in Reaction Scheme 1K, to afford 16b (6.20 g, 99%) as a brown, gummy solid: $^1$H NMR (300 MHz, DMSO-d$_6$) δ 7.83-7.80 (m, 1H), 7.73 (t, J=2.3 Hz, 1H), 7.57 (t, J=8.2 Hz, 1H), 7.42-7.39 (m, 1H), 5.04 (s, 2H), 3.43-3.32 (m, 8H), 1.41 (s, 9H).

The reduction of 16b was performed as described as described above in Reaction Scheme 1I to afford 2j (5.79 g, quantitative) as an off-white, gummy solid: $^1$H NMR (300 MHz, DMSO-d$_6$) δ 6.87 (t, J=8.0 Hz, 1H), 6.17-6.05 (m, 3H), 5.05 (s, 2H), 4.67 (s, 2H), 3.45-3.31 (m, 8H), 1.41 (s, 9H).

The condensation of 2j was performed as described above in Reaction Scheme 1G to afford 3g (7.00 g, 86%) as a white solid: $^1$H NMR (300 MHz, DMSO-d$_6$) δ 10.85 (s, 1H), 7.46-7.41 (m, 2H), 7.31-7.26 (m, 4H), 7.06-7.03 (m, 2H), 6.81-6.78 (m, 1H), 4.84 (s, 2H), 3.40-3.28 (m, 8H), 1.41 (s, 9H).

The cyclization of 3g was performed as described above in Reaction Scheme 1G. The mixture was concentrated almost to dryness and Et$_2$O (100 mL) was added. The mixture was stirred vigorously at 0° C. for 1 h and the solids were collected by filtration to afford 4g (5.67 g, 93%) as a white solid: $^1$H NMR (300 MHz, DMSO-d$_6$) δ 11.12 (s, 1H), 8.60 (s, 1H), 7.19 (s, 1H), 7.06-7.02 (m, 2H), 6.31-6.29 (m, 1H), 5.85 (s, 2H), 4.71 (s, 2H), 3.45-3.26 (m, 8H), 1.41 (s, 9H).

The acylation of 4g was performed as described above in Reaction Scheme 1G with m-toluoyl chloride 22. The mixture was concentrated almost to dryness and water (50 mL) was added. The mixture was stirred vigorously for 1 h, the solids that formed were collected by filtration and purified by trituration with acetonitrile to afford 5-amino-1-(3-methylphenyl)carbonyl-3-[3-(N-tert-butoxycarbonyl)piperazin-4-ylcarbonylmethoxy)phenyl]amino-1H-1,2,4-triazole (Ia-19) (0.68 g, 75%) as a yellow solid: $R_f$ 0.56 (9:1 methylene chloride/methanol); mp 206-208° C.; $^1$H NMR (300 MHz, DMSO-$d_6$) δ 9.32 (s, 1H), 8.04 (s, 1H), 7.95-7.93 (m, 1H), 7.81 (s, 2H), 7.48-7.40 (m, 2H), 7.23 (s, 1H), 7.13-7.04 (m, 2H), 6.43-6.40 (m, 1H), 4.69 (s, 2H), 3.43-3.27 (m, 8H), 2.41 (s, 3H), 1.41 (s, 9H); $^{13}$C NMR (75 MHz, DMSO-$d_6$) δ 166.9, 166.3, 158.7, 158.4, 157.6, 154.0, 142.3, 137.5, 133.3, 132.9, 131.2, 129.5, 128.1, 127.8, 110.2, 105.9, 104.1, 79.5, 66.3, 44.3, 41.3, 28.3, 21.1; IR (ATR) 3421, 3128, 1694, 1654 cm$^{-1}$; APCI MS m/z 536 $[C_{27}H_{33}N_7O_5+H]^+$; HPLC (Method 2) 99.0% (AUC), $t_R$=13.72 min. Anal. Calcd for $C_{27}H_{33}N_7O_5$: C, 60.55; H, 6.21; N, 18.31. Found: C, 60.52; H, 6.03; N, 18.35.

Compounds 18 and 20, as set forth below in Reaction Scheme 1K, are alkylating agents used above in Reaction Scheme 1J for compounds of RX and are prepared as illustrated below in Reaction Scheme 1K.

REACTION SCHEME 1K

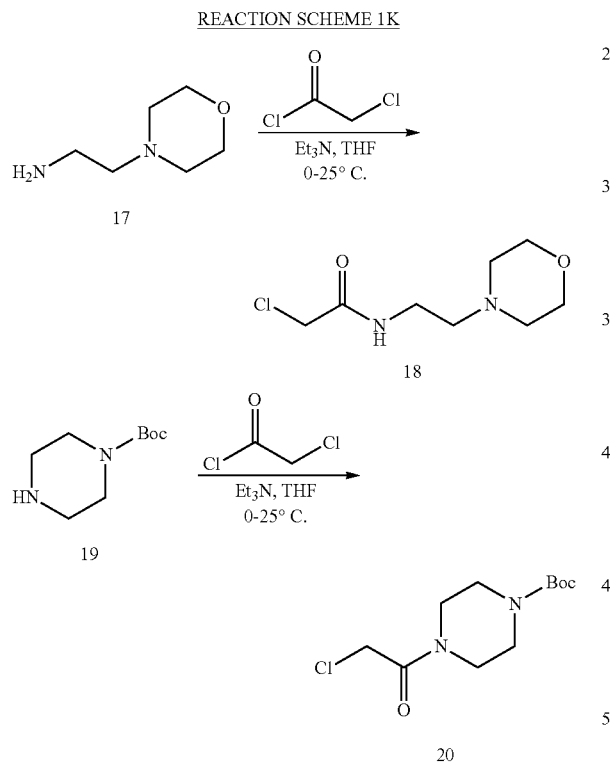

In particular, a mixture of 2-morpholin-4-yl-ethylamine hydrochloride 17 (5.0 g, 38.4 mmol) and Et$_3$N (4.31 g, 42.2 mmol) in THF (60 mL) was cooled to 0° C. and chloroacetyl chloride (4.34 g, 38.4 mmol) was added dropwise over 2-3 min. The reaction mixture was stirred at 0° C. for 1 h and then at ambient temperature for 20 h. The mixture was filtered, concentrated, and the residue partitioned between EtOAc (75 mL) and water (25 mL). The organic solution was dried (Na$_2$SO$_4$) and concentrated to afford 18 (5.92, 72%) as a brown oil: $^1$H NMR (300 MHz, DMSO-$d_6$) δ 8.14 (br s, 1H), 4.06 (s, 2H), 3.56 (t, J=4.6 Hz, 4H), 3.21 (q, J=6.6 Hz, 2H), 2.38-2.33 (m, 6H).

Alternatively, a mixture of piperazine-1-carboxylic acid tert-butyl ester 19 (3.10 g, 16.6 mmol) and Et$_3$N (1.76 g, 17.4 mmol) in THF (40 mL) was cooled to 0° C. and chloroacetyl chloride (1.87 g, 16.6 mmol) was added dropwise over 2-3 min. The reaction mixture was stirred at 0° C. for 1 h and then at ambient temperature for 20 h. The mixture was filtered, concentrated and the residue was partitioned between EtOAc (75 mL) and water (25 mL). The organic extract was dried (Na$_2$SO$_4$) and concentrated to afford 20 (4.80 g, quantitative) as a brown oil: $^1$H NMR (300 MHz, DMSO-$d_6$) δ 4.39 (s, 2H), 3.43-3.42 (m, 4H), 3.35-3.30 (m, 4H), 1.41 (s, 9H).

Compound (Ia-20), as set forth below in Reaction Scheme 1L, is a compound of formula (Ia), as set forth above in the Summary of the Invention, and is prepared as illustrated below in Reaction Scheme 1L. The corresponding compound of formula (Ib) of this compound may be prepared in a similar manner.

REACTION SCHEME 1L

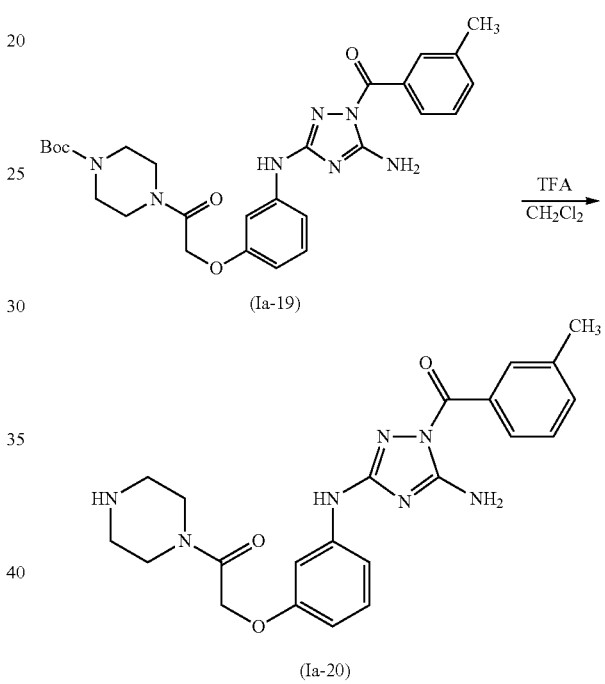

Preparation of 5-Amino-1-(3-methylphenyl)carbonyl-3-[3-(piperazin-4-ylcarbonylmethoxy)phenyl]amino-1H-1,2,4-triazole Compound (Ia-19) was prepared by the method disclosed above in Reaction Scheme 1J.

In particular, the deprotection of 5-amino-1-(3-methylphenyl)carbonyl-3-[3-(N-tert-butoxycarbonyl)piperazin-4-yl-carbonylmethoxy)phenyl]amino-1H-1,2,4-triazole (Ia-19) was performed under standard acidic conditions, such as TFA and methylene chloride. The solvents were removed under reduced pressure and the residue was dissolved in CH$_2$Cl$_2$ (20 mL) and evaporated to dryness (3×). The crude solid was partitioned between EtOAc (35 mL) and saturated NaHCO$_3$ (15 mL). The organic layer was separated, washed with brine (20 mL), dried, and concentrated to afford 5-amino-1-(3-methylphenyl)carbonyl-3-[3-(piperazin-4-ylcarbonylmethoxy)phenyl]amino-1H-1,2,4-triazole (Ia-20) (0.19 g, 93%) as a yellow solid: $R_f$ 0.35 (9:1 methylene chloride/methanol); mp 169-171° C.; $^1$H NMR (300 MHz, DMSO-$d_6$) δ 9.32 (s, 1H), 8.04 (s, 1H), 7.95-7.92 (m, 1H), 7.82 (s, 2H), 7.46-7.43 (m, 2H), 7.24 (s, 1H), 7.12-7.03 (m, 2H), 6.42-6.39 (m, 1H), 4.65 (s, 2H), 3.37-3.29 (m, 5H), 2.64 (br s, 4H), 2.41 (s, 3H); $^{13}$C NMR (75 MHz, DMSO-$d_6$) δ 164.7, 163.7, 156.6, 156.2, 155.4, 140.1, 135.3, 131.2, 130.7, 129.0, 127.3, 125.9, 125.6, 108.0, 103.7, 101.9, 64.2, 43.8, 43.4, 40.5, 19.0; IR (ATR) 3427, 3127, 1680, 1647 cm$^{-1}$; APCI MS m/z 436 $[C_{22}H_{25}N_7O_3+H]^+$; HPLC (Method 1) 97.8% (AUC), $t_R$=8.65 min.

Compounds (Ia-21), (Ia-22), (Ia-23) and (Ia-24), as set forth below in Reaction Scheme 1M, are compounds of formula (Ia), as set forth above in the Summary of the Invention, and are prepared as illustrated below in Reaction Scheme 1M. For purposes of convenience, the minor products, i.e., the corresponding compounds of formula (Ib), are not illustrated in Reaction Scheme 1M, but it is understood that these compounds are prepared as well by the method disclosed therein and can be isolated and separated from compounds (Ia-21), (Ia-22), (Ia-23) and (Ia-24) by standard isolation and separation techniques.

REACTION SCHEME 1M

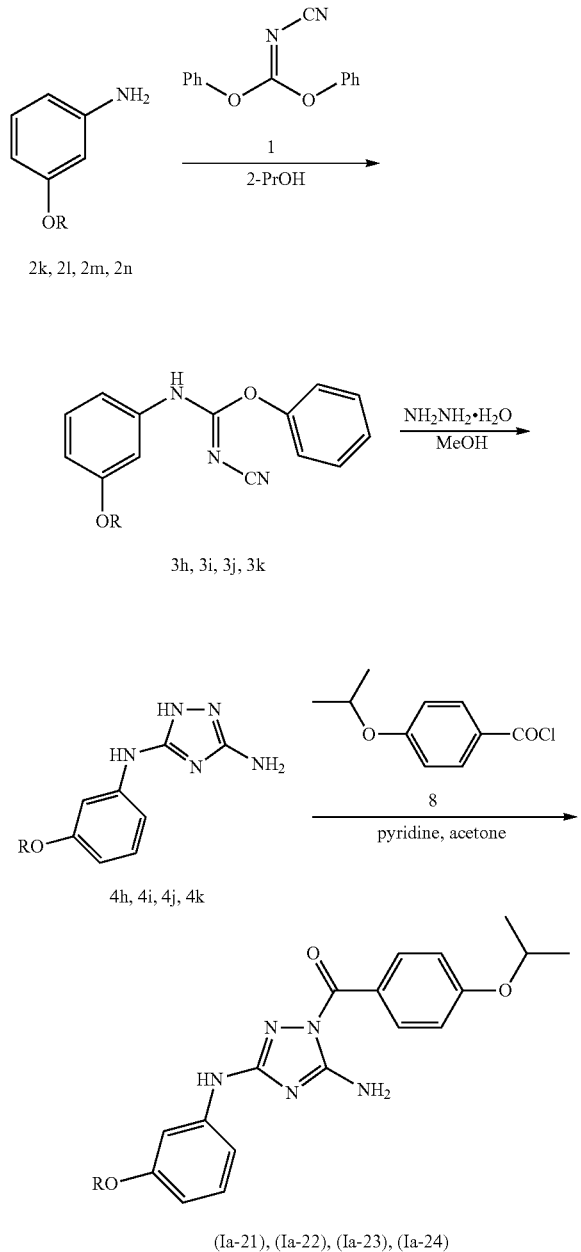

(Ia-21), (Ia-22), (Ia-23), (Ia-24)

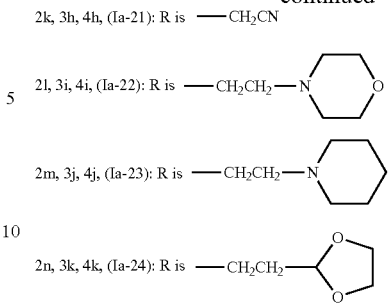

Preparation of 5-Amino-3-[3-(cyanomethoxy)phenylamino]-1-(4-(iso-propoxy)phenyl)carbonyl-1H-1,2,4-triazole, 5-Amino-1-(4-(iso-propoxy)phenylcarbonyl-3-[3-[2-(morpholin-4-yl)ethoxy]phenylamino]-1H-1,2,4-triazole, 5-Amino-1-(4-(iso-propoxy)phenyl)carbonyl-3-[3-(piperidin-1-yl)phenylamino]-1H-1,2,4-triazole, and 5-Amino-3-[3-[2-(1,3-dioxolan-2-yl)ethoxy]phenylamino]-1-(4-(iso-propoxy)phenyl)carbonyl-1H-1,2,4-triazole In general, compounds (Ia-21), (Ia-22), (Ia-23) and (Ia-24) are prepared from compound 1 and compounds 2k, 2l, 2m and 2n, as set forth above in Reaction Scheme 1M. Compound 1 and compounds 2k, 2l, 2m and 2n are commercially available or can be prepared by the methods disclosed herein or by methods known to one skilled in the art. Compound 8 is commercially available or can be prepared by methods known to one skilled in the art.

Specifically, a mixture of (3-aminophenoxy)acetonitrile 2k (1.0 g, 6.70 mmol) and diphenylcyanocarbimidate 1 (1.64 g, 6.90 mmol) in 2-PrOH (20 mL) was stirred at ambient temperature under N$_2$ for 8 h. The solids that formed were collected by filtration and washed with 2-PrOH, to afford 3h (1.76 g, 88%) as a white solid: $^1$H NMR (300 MHz, DMSO-d$_6$) δ 10.94 (s, 1H), 7.50-7.37 (m, 3H), 7.34-7.27 (m, 3H), 7.23-7.17 (m, 2H), 6.99-6.95 (m, 1H), 5.18 (s, 2H).

A mixture of 3h (1.76 g, 6.00 mmol) and hydrazine monohydrate (0.30 g, 6.00 mmol) in MeOH (30 mL) was stirred at ambient temperature for 20 h. The MeOH was removed under reduced pressure and the crude material was partitioned between EtOAc (75 mL) and water (75 mL). The aqueous layer was extracted with EtOAc (50 mL) and the combined organics were washed with brine (40 mL), dried (Na$_2$SO$_4$) and concentrated to give the crude product. Purification by trituration with CH$_2$Cl$_2$ afforded 4h (1.28 g, 93%) as a white solid: $^1$H NMR (300 MHz, DMSO-d$_6$) δ 11.18 (s, 1H), 8.75 (s, 1H), 7.37-7.32 (m, 1H), 7.13-7.11 (m, 2H), 6.45-6.41 (m, 1H), 5.89 (s, 2H), 5.06 (s, 2H).

To an ice-cold mixture of 4h (0.50 g, 2.17 mmol) and pyridine (0.18 g, 2.28 mmol) in acetone (35 mL) under N$_2$ was added dropwise a solution of 4-isopropoxybenzoyl chloride 8 (0.45 g, 2.28 mmol) in acetone (5 mL) over 2 min and the resulting solution was stirred at ambient temperature for 20 h. The acetone was removed under reduced pressure and the residue was partitioned between EtOAc (100 mL) and water (100 mL). The aqueous layer was extracted with EtOAc (30 mL) and the combined organic extracts were washed with brine (50 mL), dried (Na$_2$SO$_4$), and concentrated to give the crude product. Purification by trituration with CH$_3$CN afforded 5-amino-3-[3-(cyanomethoxy)phenylamino]-1-(4-(iso-propoxy)phenyl)carbonyl-1H-1,2,4-triazole (Ia-21) (0.62 g, 71%) as a white solid: R$_f$ 0.65 (9:1 CH$_2$Cl$_2$/MeOH); mp (DSC) 210.6-211.7° C.; $^1$H NMR (300 MHz, DMSO-d$_6$) δ 9.45 (s, 1H), 8.25 (d, J=8.9 Hz, 2H), 7.80 (s, 2H), 7.42-7.40 (m, 1H), 7.25-7.13 (m, 2H), 7.07 (d, J=8.9 Hz, 2H), 6.59-6.55 (m, 1H), 5.08 (s, 2H), 4.83-4.75 (m, 1H), 1.33 (d, J=6.0 Hz, 6H); $^{13}$C NMR (75 MHz, DMSO-d$_6$) δ 165.6, 161.0, 157.8, 157.3, 156.8, 142.3, 133.0, 129.5, 123.9, 116.5, 114.3, 111.0, 105.5, 103.5, 69.6, 53.3, 21.5; IR (ATR) 3421, 3357, 3103, 1676 cm$^{-1}$; APCI MS m/z 393 [C$_{20}$H$_{20}$N$_6$O$_3$+H]$^+$; HPLC (Method A) 98.8% (AUC), t$_R$=13.99 min. Anal. Calcd for C$_{20}$H$_{20}$N$_6$O$_3$: C, 61.21; H, 5.14; N, 21.42. Found: C, 61.17; H, 4.88; N, 21.19.

Alternatively, a mixture of 2l (1.68 g, 7.56 mmol) and diphenylcyanocarbimidate 1 (1.80 g, 7.56 mmol) in 2-PrOH (20 mL) was stirred at ambient temperature under N$_2$ for 20 h. The solids that formed were collected by filtration and washed with 2-PrOH, to afford 3i (2.04 g, 74%) as a yellow-white solid: $^1$H NMR (300 MHz, DMSO-d$_6$) δ 10.82 (br s, 1H), 7.50-7.26 (m, 6H), 7.09-7.01 (m, 2H), 6.85-6.73 (m, 1H), 4.08 (t, J=5.7 Hz, 2H), 3.58-3.55 (m, 4H), 2.70 (t, J=5.7 Hz, 2H), 2.50-2.46 (m, 4H).

A mixture of 3i (2.03 g, 5.50 mmol) and hydrazine monohydrate (0.28 g, 5.50 mmol) in MeOH (30 mL) was stirred at ambient temperature for 4 h. The MeOH was removed under reduced pressure and the residue was slurried in EtOAc and filtered to afford 4i (1.35 g, 81%) as a white solid: $^1$H NMR (300 MHz, DMSO-d$_6$) δ 11.13 (s, 1H), 8.58 (s, 1H), 7.24 (s, 1H), 7.05-6.85 (m, 2H), 6.30 (d, J=7.5 Hz, 1H), 5.86 (s, 2H), 4.00 (t, J=5.7 Hz, 2H), 3.70-3.47 (m, 4H), 2.67 (t, J=5.7 Hz, 2H), 2.50-2.22 (m, 4H).

To an ice-cold mixture of 4i (0.30 g, 0.98 mmol) and Et$_3$N (0.10 g, 1.00 mmol) in acetone (15 mL) under N$_2$ was added dropwise a solution of 4-isopropoxy benzoyl chloride 8 (0.20 g, 0.98 mmol) in acetone (5 mL) over 2 min and the resulting solution was stirred at ambient temperature for 20 h. The acetone was removed under reduced pressure and the residue was partitioned between EtOAc (50 mL) and water (50 mL). The aqueous layer was extracted with EtOAc (50 mL) and the combined organics were washed with brine (50 mL), dried (Na$_2$SO$_4$), and concentrated to give the crude product. Purification by flash chromatography (95:5 CH$_2$Cl$_2$/MeOH) afforded 5-amino-1-(4-(iso-propoxy)phenylcarbonyl-3-[3-[2-(morpholin-4-yl)ethoxy]phenylamino]-1H-1,2,4-triazole (Ia-22) (0.23 g, 50%) as a white solid: R$_f$ 0.50 (9:1 CH$_2$Cl$_2$/MeOH); mp (DSC) 152-153.7° C.; $^1$H NMR (300 MHz, DMSO-d$_6$) δ 9.29 (s, 1H), 8.25 (d, J=8.9 Hz, 2H), 7.77 (s, 2H), 7.42-7.41 (m, 1H), 7.13-7.05 (m, 3H), 6.92 (dd, J=8.0, 1.0 Hz, 1H), 6.41 (dd, J=7.9, 2.0 Hz, 1H), 4.82-4.74 (m, 1H), 3.99 (t, J=5.5 Hz, 2H), 3.58-3.55 (m, 4H), 2.64 (t, J=5.5 Hz, 2H), 2.45-2.42 (m, 4H), 1.32 (d, J=6.0 Hz, 6H); $^{13}$C NMR (75 MHz, DMSO-d$_6$) δ 166.0, 161.4, 159.3, 158.3, 157.7, 142.4, 133.4, 129.6, 124.4, 114.8, 109.6, 106.5, 103.0, 69.9, 66.4, 65.4, 57.5, 54.0, 22.0; IR (ATR) 3664, 1692 cm$^{-1}$; APCI MS m/z 467 [C$_{24}$H$_{30}$N$_6$O$_4$+H]$^+$; HPLC (Method A) 98.0% (AUC), t$_R$=9.54 min.

Alternatively, a mixture of 2m (2.56 g, 11.6 mmol) and diphenylcyanocarbimidate 1 (2.77 g, 11.6 mmol) in 2-PrOH (70 mL) was stirred at ambient temperature under N$_2$ for 20 h. The 2-PrOH was removed under reduced pressure and the residue was partitioned between EtOAc (75 mL) and water (75 mL). The aqueous layer was extracted with EtOAc (75 mL) and the combined organics were dried (Na$_2$SO$_4$), and concentrated to give the crude product. Purification by flash chromatography (CH$_2$Cl$_2$ then 95:5 CH$_2$Cl$_2$/MeOH) afforded 3j (3.68 g, 87%) as a beige foam: $^1$H NMR (300 MHz, DMSO-d$_6$) δ 10.36 (br s, 1H), 7.50-7.41 (m, 2H), 7.29-7.23 (m, 4H), 7.12-6.96 (m, 2H), 6.80-6.73 (m, 1H), 4.09-4.05 (m, 2H), 2.73-2.69 (m, 2H), 2.49-2.42 (m, 4H), 1.54-1.37 (m, 6H).

A mixture of 3j (3.0 g, 8.20 mmol) and hydrazine monohydrate (0.41 g, 8.40 mmol) in MeOH (30 mL) was stirred at ambient temperature for 20 h. The MeOH was removed under reduced pressure and the residue was partitioned between EtOAc (75 mL) and water (75 mL). The aqueous layer was extracted with EtOAc (75 mL) and the organic layer concentrated to afford 4j (2.00 g, 81%) as a beige foam: $^1$H NMR (300 MHz, DMSO-d$_6$) δ 11.16 (s, 1H), 8.58 (s, 1H), 7.24 (s, 1H), 7.05-6.94 (m, 2H), 6.30-6.28 (m, 1H), 5.87 (s, 2H), 3.97 (t, J=6.0 Hz, 2H), 2.62 (t, J=6.0 Hz, 2H), 2.41-2.39 (m, 4H), 1.53-1.36 (m, 6H).

To an ice-cold mixture of 4j (0.35 g, 1.16 mmol) and Et$_3$N (0.12 g, 1.18 mmol) in acetone (20 mL) under N$_2$ was added dropwise a solution of 4-isopropoxyl benzoylchloride 8 (0.23 g, 1.16 mmol) in acetone (5 mL) over 2 min and the resulting solution was stirred at ambient temperature for 20 h. The acetone was removed under reduced pressure and the residue was partitioned between EtOAc (75 mL) and saturated aqueous NaHCO$_3$. The aqueous layer was separated, extracted with EtOAc (75 mL) and the combined organics were dried (Na$_2$SO$_4$) and concentrated to give the crude product. Purification by flash chromatography (95:5 CH$_2$Cl$_2$/MeOH) afforded 5-amino-1-(4-(iso-propoxy)phenyl)carbonyl-3-[3-(piperidin-1-yl)phenylamino]-1H-1,2,4-triazole (Ia-23) (0.19 g, 35%) as a yellow solid: R$_f$ 0.25 (9:1 CH$_2$Cl$_2$/MeOH); mp 121-124° C.; $^1$H NMR (300 MHz, DMSO-d$_6$) δ 9.29 (s, 1H), 8.25 (d, J=8.8 Hz, 2H), 7.77 (s, 2H), 7.40 (s, 1H), 7.13-7.05 (m, 3H), 6.94-6.91 (m, 1H), 6.42-6.40 (m, 1H), 4.79-4.75 (m, 1H), 3.99 (br s, 2H), 2.63 (br s, 2H), 2.41 (br s, 4H), 1.50 (br s, 4H), 1.38-1.30 (m, 8H); $^{13}$C NMR (75 MHz, DMSO-d$_6$) δ 166.0, 161.4, 159.3, 158.3, 157.7, 142.4, 133.4, 129.6, 124.3, 114.8, 109.7, 106.5, 103.1, 69.9, 65.5, 57.6, 54.6, 25.6, 24.1, 22.0; IR (ATR) 3329, 1671 cm$^{-1}$; APCI MS m/z 465 [C$_{25}$H$_{32}$N$_6$O$_3$+H]$^+$; HPLC (Method A) 97.7% (AUC), t$_R$=10.19 min.

Alternatively, a mixture of 2n (4.46 g, 21.3 mmol) and diphenylcyanocarbimidate (5.07 g, 21.3 mmol) in 2-PrOH (100 mL) was stirred at ambient temperature under N$_2$ for 20 h. The solids that formed were collected by filtration and washed with 2-PrOH to afford 3k (5.90 g, 78%) as an off-white solid: $^1$H NMR (300 MHz, DMSO-d$_6$) δ 10.82 (s, 1H), 7.50-7.37 (m, 2H), 7.32-7.26 (m, 4H), 7.08-7.03 (m, 2H), 6.82 (dd, J=7.9, 1.9 Hz, 1H), 4.98 (t, J=4.9 Hz, 1H), 4.07 (t, J=6.5 Hz, 2H), 3.93-3.76 (m, 4H), 2.06-2.00 (m, 2H).

A mixture of 3k (3.0 g, 8.50 mmol) and hydrazine monohydrate (0.43 g, 8.67 mmol) in MeOH (40 mL) was stirred at ambient temperature for 20 h. The MeOH was removed under reduced pressure and the residue was partitioned between EtOAc (75 mL) and water (75 mL). The aqueous layer was extracted with EtOAc (75 mL) and the combined organics were washed with brine (50 mL), dried (Na$_2$SO$_4$), and concentrated. Purification by flash chromatography (CH$_2$Cl$_2$ to 95:5 CH$_2$Cl$_2$/MeOH) afforded 4k (1.90 g, 65%) as a white solid: $^1$H NMR (300 MHz, DMSO-d$_6$) δ 11.13 (s, 1H), 8.78 (s, 1H), 7.58 (s, 1H), 7.05-6.95 (m, 2H), 6.30-6.27 (m, 1H), 5.86 (s, 2H), 4.97 (t, J=4.9 Hz, 1H), 3.99 (t, J=6.5 Hz, 2H), 3.93-3.76 (m, 4H), 2.04-1.98 (m, 2H).

To an ice-cold mixture of 4k (0.50 g, 1.70 mmol) and pyridine (0.16 g, 2.05 mmol) in acetone (35 mL) under N$_2$ was added dropwise a solution of 4-isopropoxybenzoyl chloride 8 (0.37 g, 1.87 mmol) in acetone (5 mL) over 2 min and the resulting solution was stirred at ambient temperature for 20 h. The acetone was removed under reduced pressure and the residue was partitioned between EtOAc (75 mL) and water (75 mL). The aqueous layer was extracted with EtOAc (75 mL) and the combined organics were washed with brine (40 mL), dried (Na$_2$SO$_4$), and concentrated to give the crude product. Purification by trituration with CH$_3$CN afforded 5-amino-3-[3-[2-(1,3-dioxolan-2-yl)ethoxy]phenylamino]-1-(4-(iso-propoxy)phenyl)carbonyl-1H-1,2,4-triazole (Ia-24) (0.51 g, 35%) as an off-white solid: R$_f$ 0.61 (9:1 CH$_2$Cl$_2$/

MeOH); mp (DSC) 144.4-145.4° C.; $^1$H NMR (300 MHz, DMSO-d$_6$) δ 9.31 (s, 1H), 8.25 (d, J=8.8 Hz, 2H), 7.78 (s, 2H), 7.40 (s, 1H), 7.14-7.03 (m, 3H), 6.95 (dd, J=8.1, 1.0 Hz, 1H), 6.41 (dd, J=7.9, 2.1 Hz, 1H), 4.97 (t, J=5.1 Hz, 1H), 4.81-4.73 (m, 1H), 3.98 (t, J=6.3 Hz, 2H), 3.93-3.76 (m, 4H), 2.02-1.96 (m, 2H), 1.32 (d, J=6.0 Hz, 6H); $^{13}$C NMR (75 MHz, DMSO-d$_6$) δ 166.0, 161.4, 159.3, 158.3, 157.7, 142.5, 133.4, 129.6, 124.3, 114.8, 109.7, 106.5, 103.0, 101.5, 70.0, 64.6, 63.5, 33.8, 22.0; IR (ATR) 3417, 3355, 3115, 1678 cm$^{-1}$; APCI MS m/z 454 [C$_{23}$H$_{27}$N$_6$O$_6$+H]$^+$; HPLC (Method A)>99% (AUC), t$_R$=14.59 min. Anal. Calcd for C$_{23}$H$_{27}$N$_6$O$_5$: C, 60.92; H, 6.00; N, 15.44. Found: C, 60.71; H, 5.89; N, 15.32.

In a manner similar to that described above in the preparation of (Ia-21), (Ia-22), (Ia-23), and (Ia-24), a solution of 4-isopropoxybenzoyl chloride 8 (0.37 g, 1.86 mmol) in acetone (5 mL) was added dropwise over 2 min under N$_2$ to an ice-cold mixture of triazole 2i (0.26 g, 0.92 mmol), prepared as described above in Reaction Scheme 1J, and pyridine (0.08 g, 0.92 mmol) in acetone (15 mL) and the resulting solution was stirred at ambient temperature for 40 h. The solids that formed were collected by filtration and triturated with acetone to afford 5-amino-3-[3-(benzyloxy)phenylamino]-1-(4-(iso-propoxy)phenyl)carbonyl-1H-1,2,4-triazole (Ia-25) (0.10 g, 24%) as a white solid: R$_f$ 0.57 (9:1 CH$_2$Cl$_2$/MeOH); mp (DSC) 188.7-189.9° C.; $^1$H NMR (300 MHz, DMSO-d$_6$) δ 9.35 (s, 1H), 8.27 (d, J=8.8 Hz, 2H), 7.78 (s, 1H), 7.43-7.33 (m, 5H), 7.12 (t, J=8.1 Hz, 1H), 6.99-6.91 (m, 3H), 6.50-6.47 (m, 1H), 4.98 (s, 2H), 4.52-4.42 (m, 1H), 1.19 (d, J=6.0 Hz, 6H); $^{13}$C NMR (75 MHz, DMSO-d$_6$) δ 166.0, 161.4, 159.3, 158.3, 157.7, 142.5, 137.3, 133.4, 129.6, 128.7, 128.3, 128.1, 124.3, 114.8, 109.8, 106.9, 103.1, 69.8, 69.3, 21.9; IR (ATR) 3364, 1671 cm$^{-1}$; APCI MS m/z 444 [C$_{25}$H$_{25}$N$_5$O$_3$+H]$^+$; HPLC (Method A)>99% (AUC), t$_R$=16.51 min. Anal. Calcd for C$_{25}$H$_{25}$N$_5$O$_3$: C, 66.70; H, 5.68; N, 15.79. Found: C, 67.42; H, 5.71; N, 15.63.

Compounds (Ia-26) and (Ia-27), as set forth below in Reaction Scheme 1N, are compounds of formula (Ia), as set forth above in the Summary of the Invention, and are prepared as illustrated below in Reaction Scheme 1N. For purposes of convenience, the minor products, i.e., the corresponding compounds of formula (Pb), are not illustrated in Reaction Scheme 1N, but it is understood that these compounds are prepared as well by the method disclosed therein and can be isolated and separated from compounds (Ia-26) and (Ia-27) by standard isolation and separation techniques.

REACTION SCHEME 1N

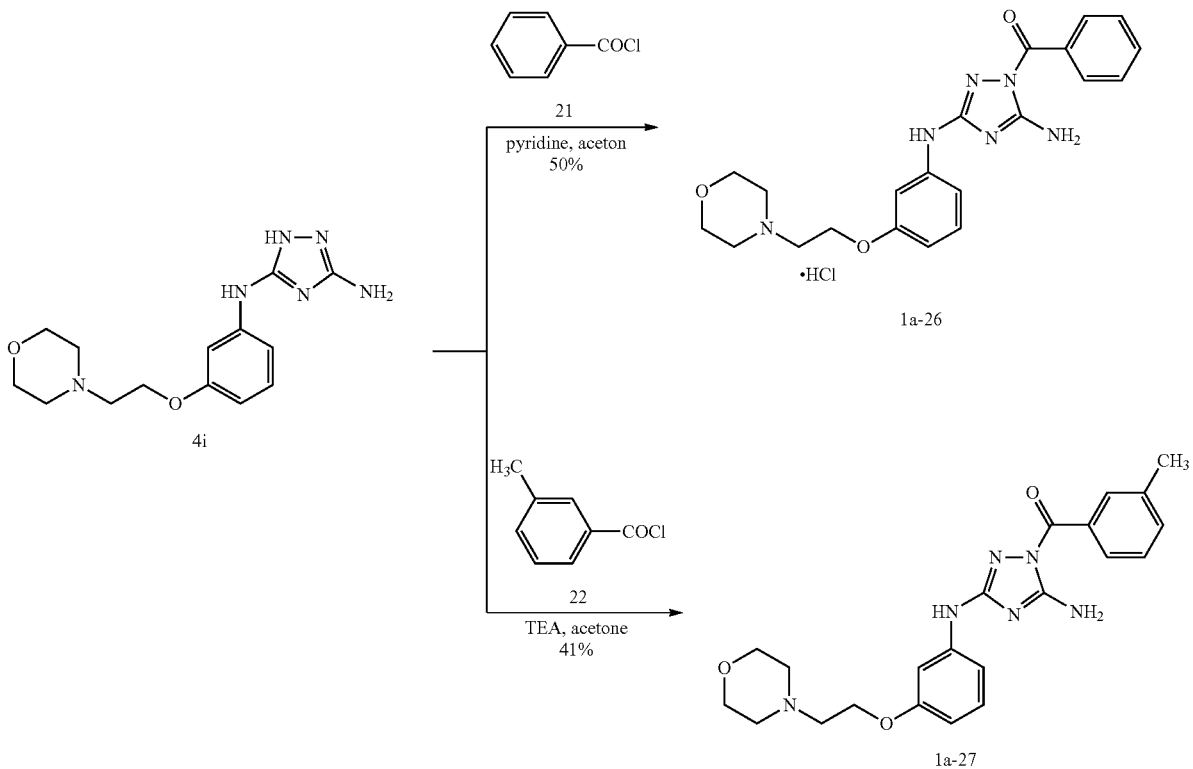

Preparation of 5-Amino-3-[3-[2-(morpholin-4-yl)ethoxy]phenylamino]-1-phenylcarbonyl-1H-1,2,4-triazole and 5-Amino-1-(3-(methyl)phenylcarbonyl-3-[3-[2-(morpholin-4-yl)ethoxy]phenylamino]-1H-1,2,4-triazole In general, compounds (Ia-26) and (Ia-27) are prepared from compounds 4i and compounds 21 and 22, respectively. Compound 4i can be prepared by methods described herein or by methods known to one skilled in the art. Compounds 21 and 22 are commercially available or can be prepared by methods known to one skilled in the art.

Specifically, to an ice-cold mixture of 4i (0.30 g, 0.98 mmol) and pyridine (0.08 g, 1.00 mmol) in acetone (25 mL) under N$_2$ was added dropwise benzoyl chloride 21 (0.14 g, 0.98 mmol) over 2 min and the resulting solution was stirred at ambient temperature for 4 h. The acetone was removed under reduced pressure and the residue was partitioned between EtOAc (50 mL) and water (50 mL). The organic layer was washed with brine (50 mL), dried (Na$_2$SO$_4$), and concentrated to give the crude product which was triturated with EtOAc to afford 5-amino-3-[3-[2-(morpholin-4-yl)ethoxy]phenylamino]-1-phenylcarbonyl-1H-1,2,4-triazole, hydrogen chloride salt (Ia-26) (0.23 g, 50%) as a yellow solid: $R_f$ 0.54 (9:1 $CH_2Cl_2$/MeOH); mp (DSC) 236.6-242.1° C.; $^1H$ NMR (300 MHz, DMSO-$d_6$) δ 9.39 (s, 1H), 8.15-8.12 (m, 2H), 7.84 (s, 2H), 7.69-7.66 (m, 1H), 7.59 (t, J=7.7 Hz, 2H), 7.32 (s, 1H), 7.13 (t, J=8.1 Hz, 1H), 7.04-7.01 (m, 1H), 6.48 (dd, J=7.7, 1.7 Hz, 1H), 4.29 (s, 2H), 3.96-3.79 (m, 4H), 3.48-3.38 (m, 5H), 3.21-3.16 (m, 2H); $^{13}C$ NMR (75 MHz, DMSO-$d_6$) δ 164.9, 156.3, 156.2, 155.5, 140.4, 131.1, 130.7, 128.4, 127.6, 126.2, 108.3, 104.5, 101.1, 61.3, 60.2, 53.2, 49.9; IR (ATR) 3685, 3393, 1678 cm$^{-1}$; APCI MS m/z 409 $[C_{21}H_{24}N_6O_3+H]^+$; HPLC (Method A) 98.6% (AUC), $t_R$=8.55 min. Anal. Calcd for $C_{21}H_{24}N_6O_3$·HCl: C, 56.69; H, 5.66; N, 18.89. Found: C, 56.51; H, 5.62; N, 18.68.

Alternatively, to an ice-cold mixture of 4i (0.30 g, 0.98 mmol) and pyridine (0.08 g, 1.00 mmol) in acetone (15 mL) under $N_2$ was added dropwise m-toluoyl chloride 22 (0.15 g, 0.98 mmol) over 2 min and the resulting solution was stirred at ambient temperature for 4 h. The acetone was removed under reduced pressure and the residue was partitioned between EtOAc (50 mL) and water (50 mL). The organic layer was washed with brine (50 mL), dried ($Na_2SO_4$), and concentrated to give the crude product which was purified by flash chromatography (95:5 $CH_2Cl_2$/MeOH) followed by trituration with $CH_2Cl_2$ to afford 5-amino-1-(3-(methyl)phenylcarbonyl-3-[2-(morpholin-4-yl)ethoxy]phenylamino]-1H-1,2,4-triazole (Ia-27) (0.17 g, 41%) as a yellow solid: $R_f$ 0.50 (9:1 $CH_2Cl_2$/MeOH); mp 60-63° C.; $^1H$ NMR (300 MHz, DMSO-$d_6$) δ 9.30 (s, 1H), 7.99-7.93 (m, 2H), 7.81 (s, 2H), 7.49-7.37 (m, 2H), 7.32 (s, 1H), 7.08 (t, J=8.1 Hz, 1H), 6.96-6.93 (m, 1H), 6.41 (dd, J=7.9, 1.7 Hz, 1H), 3.93 (t, J=5.5 Hz, 2H), 3.57-3.54 (m, 4H), 2.62 (t, J=5.5 Hz, 2H), 2.42 (s, 7H); $^{13}C$ NMR (75 MHz, DMSO-$d_6$) δ 167.0, 159.3, 158.4, 157.6, 142.4, 137.5, 133.3, 133.0, 131.1, 129.5, 128.1, 127.7, 109.7, 106.3, 103.4, 66.5, 65.3, 57.4, 53.9, 21.2; IR (ATR) 3706, 3680, 3428, 3291, 1676 cm$^{-1}$; APCI MS m/z 423 $[C_{22}H_{26}N_6O_3+H]^+$; HPLC (Method A) 98.2% (AUC), $t_R$=8.96 min.

Compounds (Ia-28) and (Ia-29), as set forth below in Reaction Scheme 2, are compounds of formula (Ia), as set forth above in the Summary of the Invention, and are prepared as illustrated below in Reaction Scheme 2. For purposes of convenience, the minor products, i.e., the corresponding compounds of formula (Ib), are not illustrated in Reaction Scheme 2, but it is understood that these compounds are prepared as well by the method disclosed therein and can be isolated and separated from compounds (Ia-28) and (Ia-29) by standard isolation and separation techniques.

REACTION SCHEME 2

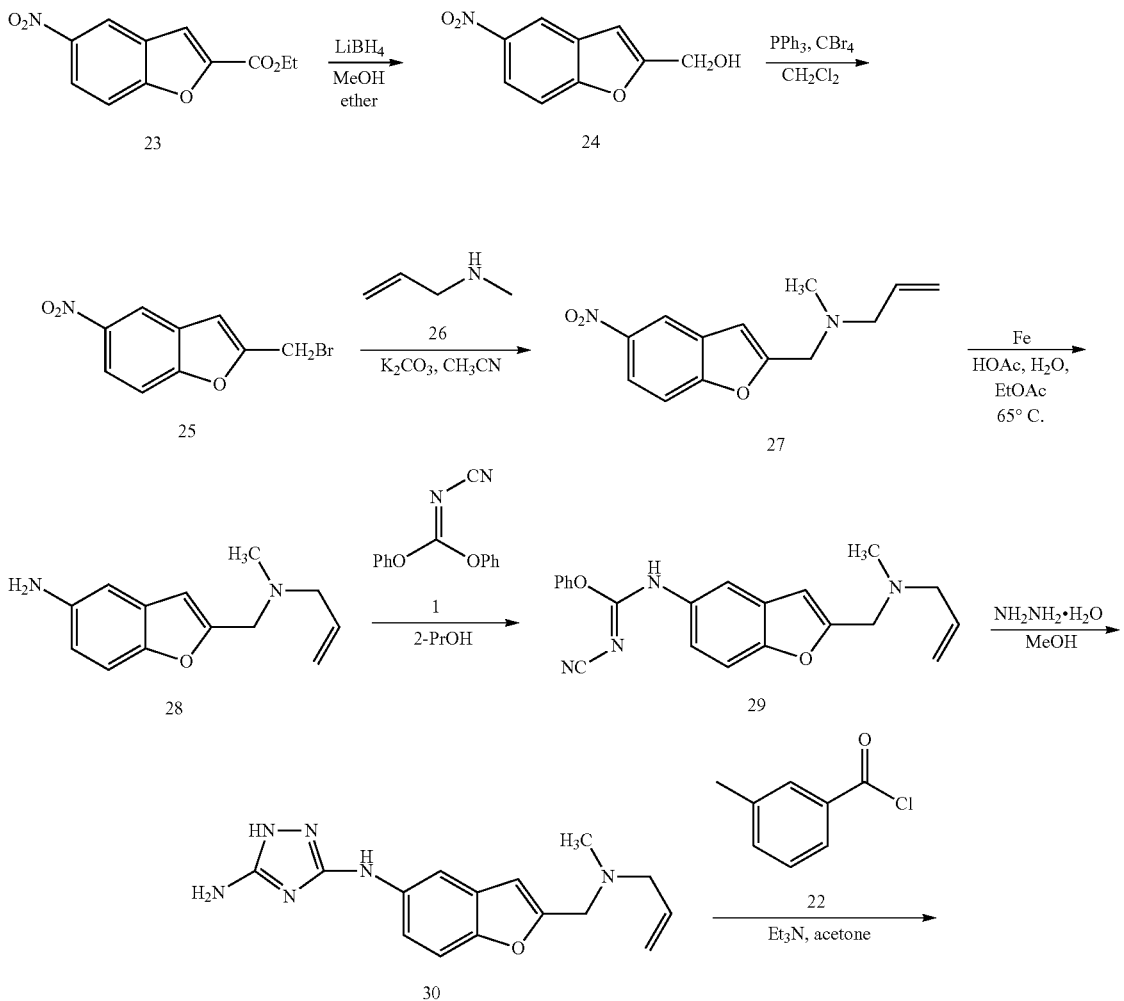

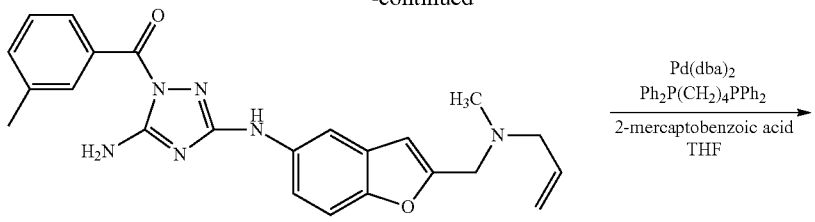

(Ia-28)

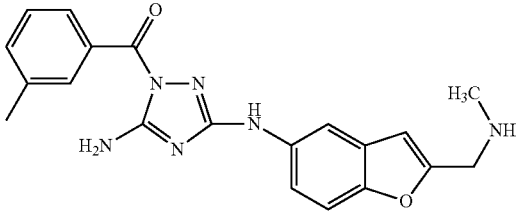

(Ia-29)

Preparation of 5-Amino-3-(2-((allyl(methyl)amino)methyl)benzofuran-5-yl)amino-1-(3-methylphenyl)carbonyl-1H-1,2,4-triazole and 5-Amino-3-(2-((methylamino)metnyl)benzofuran-5-yl)amino-1-(3-methylphenyl)carbonyl-1H-1,2,4-triazole In general, compounds (Ia-28) and (Ia-29) are prepared from compounds 23, 26, 1 and 22, as described above in Reaction Scheme 2. Compounds 23, 26, 1 and 22 are commercially available or can be prepared by methods known to one skilled in the art.

Specifically, a mixture of 23 (4.0 g, 17.0 mmol), MeOH (0.82 g, 25.5 mmol) and lithium borohydride (0.56 g, 25.5 mmol) in ether (80 mL) was stirred at ambient temperature for 4 h. The mixture was diluted with ethyl acetate and washed with 1 N HCl and brine, dried (MgSO$_4$), and concentrated to afford 24 (3.08 g, 87%) as a yellow solid: $^1$H NMR (300 MHz, DMSO-d$_6$) δ 8.59 (d, J=2.4 Hz, 1H), 8.19 (dd, J=9.0, 2.5 Hz, 1H), 7.80 (d, J=9.0 Hz, 1H), 7.00 (s, 1H), 5.65 (t, J=5.9 Hz, 1H), 4.63 (d, J=5.6 Hz, 2H).

A mixture of 24 (3.85 g, 19.9 mmol), carbon tetrabromide (9.25 g, 27.9 mmol) and triphenylphosphine (7.32 g, 27.9 mmol) in CH$_2$Cl$_2$ was stirred at ambient temperature for 1.5 h. The reaction mixture was concentrated to afford a residue which was purified by flash chromatography (silica, 1:10 ethyl acetate/hexanes) to afford 25 (4.24 g, 83%) as a white solid: $^1$H NMR (300 MHz, DMSO-d$_6$) δ 8.64 (d, J=2.4 Hz, 1H), 8.25 (dd, J=9.1, 2.5 Hz, 1H), 7.85 (d, J=9.1 Hz, 1H), 7.26 (s, 1H), 4.97 (s, 2H).

To a stirred ice cold mixture of N-methylallylamine 26 (2.09 g, 29.4 mmol) and potassium carbonate (2.43 g, 17.6 mmol) in acetonitrile (37 mL) was added dropwise a solution of 25 (3.76 g, 14.7 mmol) in acetonitrile (37 mL) over a period of 30 min. After stirring for 1.5 h in an ice-bath and an additional 22 h at ambient temperature, the reaction mixture was partitioned between methylene chloride and water. The organic layer was separated washed with brine, dried (MgSO$_4$), and concentrated to afford 27 (3.11 g, 86%) as a yellow oil: $^1$H NMR (300 MHz, DMSO-d$_6$) δ 8.58 (d, J=2.3 Hz, 1H), 8.18 (dd, J=9.0, 2.4 Hz, 1H), 7.81 (d, J=9.0 Hz, 1H), 7.02 (s, 1H), 5.90-5.80 (m, 1H), 5.30-5.10 (m, 2H), 3.74 (s, 2H), 3.08 (d, J=6.3 Hz, 2H), 2.21 (s, 3H).

To a solution of 27 (1.81 g, 7.35 mmol) in 10:1 HOAc/water (22 mL) at 55° C. was added iron powder (2.46 g, 44.1 mmol) portionwise over 5 min and the mixture stirred at 55° C. for 3 h. The reaction mixture was diluted with ethyl acetate (100 mL), filtered through diatomaceous earth and the filtrate concentrated. The residue was taken up into ethyl acetate, the ethyl acetate solution washed with water, brine, dried (MgSO$_4$), and concentrated to afford 28 (0.56 g, 35%) as an amber oil: ESI MS m/z 217 [C$_{13}$H$_{16}$N$_2$O+H]$^+$.

A mixture of 28 (0.66 g, 3.05 mmol) and diphenylcyanocarbimidate 1 (0.73 g, 3.05 mmol) in 2-PrOH (7 mL) was stirred at ambient temperature under N$_2$ for 22 h. The solids that formed were collected by filtration and washed with 2-PrOH to afford 29 (0.59 g, 54%) as a tan solid: $^1$H NMR (300 MHz, DMSO-d$_6$) δ 10.83 (br s, 1H), 7.70-7.20 (m, 8H), 6.81 (s, 1H), 5.90-5.80 (m, 1H), 5.30-5.10 (m, 2H), 3.68 (s, 1H), 3.06 (d, J=6.3 Hz, 2H), 2.19 (s, 3H).

A mixture of 29 (0.59 g, 1.64 mmol) and hydrazine monohydrate (0.12 g, 2.45 mmol) in MeOH (6 mL) was stirred at ambient temperature for 20 h. The reaction mixture was concentrated and the residue obtained was purified by flash chromatography (silica, 9:1 methylene chloride/methanol) to afford 30 (0.40 g, 82%) as an off-white foam: $^1$H NMR (300 MHz, DMSO-d$_6$) δ 11.06 (br s, 1H), 8.51 (br s, 1H), 7.83 (d, J=1.2 Hz, 1H), 7.35-7.20 (m, 2H), 6.62 (s, 1H), 6.0-5.57 (m, 3H), 5.30-5.10 (m, 2H), 3.61 (s, 2H), 3.04 (d, J=6.4 Hz, 2H), 2.18 (s, 3H).

To a stirred, ice-cold mixture of 30 (0.40 g, 1.34 mmol) and triethylamine (0.14 g, 1.34 mmol) in acetone (8 mL) was added m-toluoyl chloride 22 (0.21 g, 1.34 mmol). After stirring for 1 h in an ice-bath and an additional 20 h at ambient temperature, the reaction mixture was partitioned between saturated Na$_2$CO$_3$ (40 mL) and ethyl acetate (40 mL). The organic layer was separated, washed with brine, dried (MgSO$_4$), and concentrated to afford a yellow oil. Purification by flash chromatography (silica, 1:1 ethyl acetate/hexanes then 2:1 ethyl acetate/hexanes) gave 5-amino-3-(2-((allyl(methyl)amino)methyl)benzofuran-5-yl)amino-1-(3-methylphenyl)carbonyl-1H-1,2,4-triazole (Ia-28) (0.192 g, 34%) as a yellow solid: R$_f$ 0.36 (95:5 methylene chloride/ methanol); mp 128-131° C.; $^1$H NMR (300 MHz, DMSO-d$_6$) δ 9.27 (s, 1H), 8.12 (s, 1H), 7.97 (d, J=5.8 Hz, 1H), 7.86-7.80 (m, 3H), 7.50-7.30 (m, 4H), 6.58 (s, 1H), 5.90-5.81 (m, 1H), 5.24-5.14 (m, 2H), 3.64 (s, 2H), 3.04 (d, J=6.2 Hz, 2H), 2.45 (s, 3H), 2.18 (s, 3H); $^{13}$C NMR (75 MHz, DMSO-d$_6$) δ 166.6, 158.6, 157.5, 156.2, 149.3, 137.2, 136.8, 135.9, 133.3, 132.8, 131.2, 128.3, 128.0, 127.6, 117.7, 114.6, 110.8, 107.8, 105.3, 59.6, 53.2, 41.6, 21.1; IR (ATR) 1672, 1584, 1558 cm$^1$; ESI MS m/z 417 [C$_{23}$H$_{24}$N$_6$O$_2$+H]$^+$; HPLC (Method 2) 96.9% (AUC), t$_R$=9.59 min.

A mixture of bis(dibenzylideneacetone)palladium(0) (0.0061 g, 0.011 mmol) and 1,4-bis(diphenylphosphino)butane (0.0045 g, 0.011 mmol) in THF (2 mL) was stirred at ambient temperature for 15 minutes, then added to a stirred solution of (Ia-28) (0.088 g, 0.211 mmol) and thiosalicyclic acid (0.036 g, 0.232 mmol) in THF (4 mL). After stirring for 30 h at ambient temperature, additional bis(dibenzylideneacetone)palladium (0.012 g, 0.022 mmol) and 1,4-bis(diphenylphosphino)butane (0.009 g, 0.022 mmol) in THF (2 mL) was added. The reaction was stirred an additional 20 h at ambient temperature, then diluted with ethyl acetate. The organic solution was washed with 1 N NaOH, and brine, dried (MgSO4), and concentrated to afford a yellow-orange residue. Purification by flash chromatography (silica, 95:5 methylene chloride/methanol) followed by preparative TLC (silica, 9:1 methylene chloride/methanol) gave 5-amino-3-(2-((methylamino)methyl)benzofuran-5-yl)amino-1-(3-methylphenyl)carbonyl-1H-1,2,4-triazole (Ia-29) (0.019 g, 19%) as a pale yellow solid: R$_f$ 0.35 (9:1 methylene chloride/methanol); mp 128-131° C.; $^1$H NMR (300 MHz, DMSO-d$_6$) δ 9.26 (s, 1H), 8.11 (s, 1H), 7.96 (d, J=6.3 Hz, 1H), 7.85 (d, J=2.0 Hz, 1H), 7.80 (br s, 2H), 7.50-7.48 (m, 2H), 7.37-7.47 (m, 2H), 6.53 (s, 1H), 3.74 (s, 2H), 2.46 (s, 3H), 2.30 (s, 3H); IR (ATR) 1675, 1561, 1350 cm$^1$; ESI MS m/z 377 [C$_{20}$H$_{20}$N$_6$O$_2$+H]$^+$; HPLC (Method 2) 90.4% (AUC), t$_R$=8.79 min.

Compounds (Ia-30), as set forth below in Reaction Scheme 3, are compounds of formula (Ia), as set forth above in the Summary of the Invention, and are prepared as illustrated below in Reaction Scheme 3 wherein R$^{1a}$ is one or more substituents selected from the group consisting of halo, haloalkyl, alkyl, optionally substituted heteroaryl, optionally substituted heterocyclyl, —R$^8$—OR$^{10}$, —R$^8$—O—R$^9$—OR$^{10}$, —R$^8$—O—R$^9$—O—R$^9$—OR$^{10}$, —R$^8$—O—R$^9$—C(O)OR$^{10}$, —R$^8$—O—R$^9$—C(O)N(R$^6$)R$^7$, —R$^8$—O—R$^9$—S(O)$_p$R$^6$ (where p is 0, 1 or 2), —R$^8$—O—R$^9$—N(R$^6$)R$^7$, —R$^8$—O—R$^9$—C(NR$^{11}$)N(R$^{11}$)H, and —R$^8$—N(R$^6$)C(O)R$^{10}$, wherein each R$^6$, R$^7$, R$^8$, R$^9$, R$^{10}$ and R$^{11}$ are as defined above in the Summary of the Invention and R$^{3a}$ is one or more substituents selected from the group consisting of halo, haloalkyl, alkyl, optionally substituted heteroaryl, optionally substituted heterocyclyl, —R$^8$—OR$^{10}$, —R$^8$—O—R$^9$—OR$^{10}$, —R$^8$—O—R$^9$—O—R$^9$—OR$^{10}$, —R$^8$—O—R$^9$—CN, —R$^8$—O—R$^9$—C(O)OR$^{10}$, —R$^8$—O—R$^9$—C(O)N(R$^6$)R$^7$, —R$^8$—O—R$^9$—S(O)$_p$R$^6$ (where p is 0, 1 or 2), —R$^8$—O—R$^9$—N(R$^6$)R$^7$, —R$^8$—O—R$^9$—C(NR$^{11}$)N(R$^{11}$)H, and —R$^8$—N(R$^6$)C(O)R$^{10}$ where each R$^6$, R$^7$, R$^8$, R$^9$, R$^{10}$ and R$^{11}$ is as defined above in the Summary of the Invention. For purposes of convenience, the minor products, i.e., the corresponding compounds of formula (Ib), are not illustrated in Reaction Scheme 3, but it is understood that these compounds are prepared as well by the method disclosed therein and can be isolated and separated from compounds (Ia-30) by standard isolation and separation techniques.

REACTION SCHEME 3

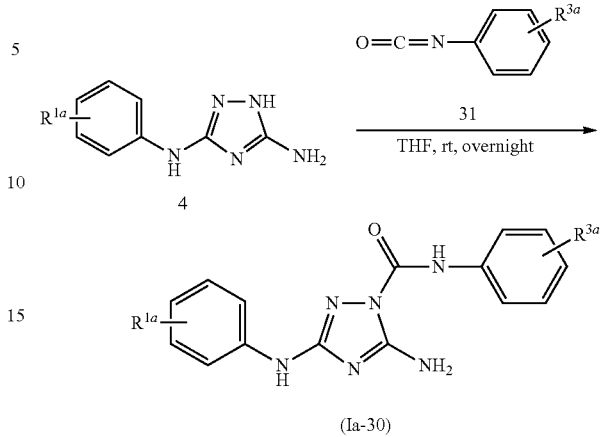

In general, compounds (Ia-30) are prepared from compounds 4 and 31 as set forth above in Reaction Scheme 3. Compounds 4 can be prepared by methods disclosed herein or by methods known to one skilled in the art. Compounds 31 are commercially available or can be prepared by methods known to one skilled in the art.

Specifically, a mixture of 3-amino-5-anilino-1,2,4-triazole 4 (1 equiv) and isocyanate 31 (1.5 equiv) in dry THF was stirred at ambient temperature overnight. The reaction was then quenched with methanol and concentrated in vacuo. The residue was purified by silica gel column chromatography in 5% triethylamine/ethyl acetate gave the product (Ia-30).

The method disclosed above in Reaction Scheme 3 can be used to prepare the following compounds, using the appropriately substituted starting materials:

5-amino-N-(3-methylphenyl)-3-[4-[2-(piperidin-1-yl)ethoxy]phenylamino]-1H-1,2,4-triazole-1-carboxamide (compound #29), as a white solid (33% yield); $^1$H-NMR (DMSO-d$_6$, 300 MHz) 9.33 (s, 1H), 8.92 (s, 1H), 7.55 (d, J=9.0 Hz, 2H), 7.46 (s, 1H), 7.42 (d, J=7.8 Hz, 1H), 7.29 (s, 2H), 7.23 (t, J=7.8 Hz, 1H), 6.94 (d, J=7.5 Hz, 1H), 6.81 (d, J=9.0 Hz, 2H), 3.98 (t, J=6.0 Hz, 2H), 2.60 (t, J=6.0 Hz, 2H), 2.41 (m, 4H), 2.31 (s, 3H), 1.47 (m, 4H), 1.37 (m, 2H) ppm; MS (ES) 436.8 (M+H).

5-amino-N-(3-methoxyphenyl)-3-[4-[2-(piperidin-1-yl)ethoxy]phenylamino]-1H-1,2,4-triazole-1-carboxamide (compound #30), $^1$H-NMR (DMSO-d$_6$, 300 MHz) 9.37 (s, 1H), 8.92 (s, 1H), 7.55 (d, J=9.0 Hz, 2H), 7.27 (m, 5H), 6.81 (d, J=8.4 Hz, 2H), 6.71 (m, 1H), 3.98 (t, J=6.0 Hz, 2H), 3.75 (s, 3H), 2.60 (t, J=6.0 Hz, 2H), 2.41 (m, 4H), 1.48 (m, 4H), 1.37 (m, 2H) ppm; MS (ES) 452.8 (M+H).

5-amino-N-(3-methylphenyl)-3-[4-[2-(pyrrolidin-1-yl)ethoxy]phenylamino]-1H-1,2,4-triazole-1-carboxamide (compound #31), $^1$H-NMR (DMSO-d$_6$, 300 MHz) 9.32 (s, 1H), 8.91 (s, 1H), 7.56 (d, J=9.0 Hz, 2H), 7.46 (s, 1H), 7.42 (d, J=7.5 Hz, 1H), 7.28 (s, 2H), 7.23 (t, J=7.8 Hz, 1H), 6.94 (d, J=7.5 Hz, 1H), 6.82 (d, J=8.7 Hz, 2H), 3.99 (t, J=6.0 Hz, 2H), 2.78 (m, 2H), 2.55 (m, 4H), 2.31 (s, 3H), 1.68 (m, 4H) ppm; MS (ES) 422.2 (M+H).

5-amino-N-(3-methoxyphenyl)-3-[4-[2-(pyrrolidin-1-yl)ethoxy]phenylamino]-1H-1,2,4-triazole-1-carboxamide (compound #32); $^1$H-NMR (DMSO-d$_6$, 300 MHz) 9.37 (s, 1H), 8.92 (s, 1H), 7.55 (d, J=9.0 Hz, 2H), 7.30 (s, 2H), 7.24 (d, J=6.3 Hz, 1H), 7.23 (s, 1H), 6.81 (d, J=9.3 Hz, 2H), 6.70 (d, J=6.3 Hz, 1H), 3.98 (t, J=6.0 Hz, 2H), 3.75 (s, 3H), 2.74 (t, J=6.0 Hz, 2H), 2.48 (m, 4H), 1.67 (m, 4H) ppm; MS (ES) 438.1 (M+H).

5-amino-N-(3,5-(dimethoxy)phenyl)-3-[4-[2-(piperidin-1-yl)ethoxy]phenylamino]-1H-1,2,4-triazole-1-carboxamide (compound #33), $^1$H-NMR (DMSO-d$_6$, 300 MHz) 9.31 (s, 1H), 8.92 (s, 1H), 7.54 (d, J=8.7 Hz, 2H), 7.31 (s, 2H), 6.93 (s, 2H), 6.81 (d, J=8.4 Hz, 2H), 6.28 (s, 1H), 3.99 (t, J=6.0 Hz, 2H), 3.73 (s, 6H), 2.60 (t, J=6.0 Hz, 2H), 2.42 (m, 4H), 1.48 (m, 4H), 1.37 (m, 2H) ppm; MS (ES) 482.8 (M+H).

5-amino-N-(3,5-(dimethoxy)phenyl)-3-[4-[2-(pyrrolidin-1-yl)ethoxy]phenylamino]-1H-1,2,4-triazole-1-carboxamide (compound #34), $^1$H-NMR (DMSO-d$_6$, 300 MHz) 9.31 (s, 1H), 8.93 (s, 1H), 7.54 (d, J=8.7 Hz, 2H), 7.31 (s, 2H), 6.94 (s, 1H), 6.93 (s, 1H), 6.81 (d, J=9.0 Hz, 2H), 6.28 (t, J=2.4 Hz, 1H), 3.98 (t, J=6.0 Hz, 2H), 3.73 (s, 6H), 2.75 (t, J=6.0 Hz, 2H), 2.42 (m, 4H), 1.67 (m, 4H) ppm; MS (ES) 468.3 (M+H).

5-amino-N-(1,3-benzodioxol-5-yl)-3-[4-[2-(piperidin-1-yl)ethoxy]phenylamino]-1H-1,2,4-triazole-1-carboxamide (compound #35), $^1$H-NMR (DMSO-d$_6$, 300 MHz) 9.34 (s, 1H), 8.90 (s, 1H), 7.55 (d, J=9.0 Hz, 2H), 7.26 (s, 2H), 7.24 (d, J=2.4 Hz, 1H), 7.04 (dd, J=8.1, 2.1 Hz, 1H), 6.89 (d, J=8.4 Hz, 1H), 6.80 (d, J=9.0 Hz, 2H), 6.00 (s, 2H), 3.97 (t, J=6.0 Hz, 2H), 2.61 (t, J=6.0 Hz, 2H), 2.41 (m, 4H), 1.48 (m, 4H), 1.37 (m, 2H) ppm; MS (ES) 466.1 (M+H).

5-amino-N-(1,3-benzodioxol-5-yl)-3-[4-[2-(pyrrolidin-1-yl)ethoxy]phenylamino]-1H-1,2,4-triazole-1-carboxamide (compound #36), $^1$H-NMR (DMSO-d$_6$, 300 MHz) 9.34 (s, 1H), 8.91 (s, 1H), 8.14 (s, 1H), 7.55 (d, J=8.7 Hz, 2H), 7.24 (s, 2H), 7.03 (d, J=8.4 Hz, 1H), 6.89 (d, J=8.4 Hz, 1H), 6.80 (d, J=8.7 Hz, 2H), 6.01 (s, 2H), 3.99 (t, J=6.0 Hz, 2H), 2.81 (t, J=6.0 Hz, 2H), 2.57 (m, 4H), 1.69 (m, 4H) ppm; MS (ES) 452.2 (M+H).

5-amino-N-(4-methylphenyl)-3-[4-[2-(pyrrolidin-1-yl)ethoxy]phenylamino]-1H-1,2,4-triazole-1-carboxamide (compound #37), $^1$H-NMR (DMSO-d$_6$, 300 MHz) 9.34 (s, 1H), 8.91 (s, 1H), 7.56 (d, J=8.4 Hz, 2H), 7.49 (d, J=8.4 Hz, 1H), 7.27 (s, 2H), 7.15 (d, J=8.4 Hz, 1H), 6.81 (d, J=8.7 Hz, 2H), 3.99 (t, J=5.4 Hz, 2H), 2.77 (t, J=5.4 Hz, 2H), 2.49 (m, 4H), 2.28 (s, 3H), 1.68 (m, 4H) ppm; MS (ES) 422.2 (M+H).

5-amino-N-(3,4-(dimethyl)phenyl)-3-[4-[2-(piperidin-1-yl)ethoxy]phenylamino]-1H-1,2,4-triazole-1-carboxamide (compound #38), $^1$H-NMR (DMSO-d$_6$, 300 MHz) 9.26 (s, 1H), 8.91 (s, 1H), 7.55 (d, J=9.0 Hz, 2H), 7.41 (s, 1H), 7.34 (d, J=8.4 Hz, 1H), 7.27 (s, 2H), 7.10 (d, J=8.1 Hz, 1H), 6.81 (d, J=9.0 Hz, 2H), 3.98 (t, J=6.0 Hz, 2H), 2.61 (t, J=6.0 Hz, 2H), 2.41 (m, 4H), 2.22 (s, 3H), 2.20 (s, 3H), 1.49 (m, 4H), 1.37 (s, 2H) ppm; MS (ES) 452.2 (M+H).

5-amino-N-(4-methylphenyl)-3-[4-[2-(piperidin-1-yl)ethoxy]phenylamino]-1H-1,2,4-triazole-1-carboxamide (compound #39), $^1$H-NMR (DMSO-d$_6$, 300 MHz) 9.34 (s, 1H), 8.91 (s, 1H), 7.55 (d, J=9.0 Hz, 2H), 7.49 (d, J=8.4 Hz, 2H), 7.27 (s, 2H), 7.15 (d, J=8.4 Hz, 2H), 6.81 (d, J=9.0 Hz, 2H), 3.98 (t, J=6.0 Hz, 2H), 2.61 (t, J=6.0 Hz, 2H), 2.42 (m, 4H), 2.28 (s, 3H), 1.49 (m, 4H) 1.38 (m, 2H) ppm; MS (ES) 452.2 (M+H).

5-amino-N-(4-(methoxy)phenyl)-3-[4-[2-(piperidin-1-yl)ethoxy]phenylamino]-1H-1,2,4-triazole-1-carboxamide (compound #40), $^1$H-NMR (DMSO-d$_6$, 300 MHz) 9.34 (s, 1H), 8.90 (s, 1H), 7.56 (d, J=9.0 Hz, 2H), 7.49 (d, J=8.4 Hz, 2H), 7.25 (s, 2H), 6.92 (d, J=8.7 Hz, 2H), 6.80 (d, J=9.0 Hz, 2H), 3.98 (t, J=5.4 Hz, 2H), 3.74 (s, 3H) 2.61 (m, 2H), 2.42 (m, 4H), 1.49 (m, 4H), 1.36 (m, 2H) ppm; MS (ES) 452.8 (M+H).

5-amino-N-(4-(iso-propyl)phenyl)-3-[4-[2-(piperidin-1-yl)ethoxy]phenylamino]-1H-1,2,4-triazole-1-carboxamide (compound #41), $^1$H-NMR (DMSO-d$_6$, 300 MHz) 9.35 (s, 1H), 8.91 (s, 1H), 7.55 (d, J=9.0 Hz, 2H), 7.52 (d, J=9.0 Hz, 2H), 7.28 (s, 2H), 7.22 (d, J=8.1 Hz, 2H), 6.81 (d, J=7.8 Hz, 2H), 3.98 (t, J=6.0 Hz, 2H), 2.61 (t, J=6.0 Hz, 2H), 2.56 (m, 1H), 2.41 (m, 4H), 1.49 (m, 4H), 1.37 (m, 2H), 1.20 (d, J=6.3 Hz, 6H) ppm; MS (ES) 464.9 (M+H).

5-amino-N-cyclohexyl-3-[4-[2-(piperidin-1-yl)ethoxy]phenylamino]-1H-1,2,4-triazole-1-carboxamide (compound #42), $^1$H-NMR (DMSO-d$_6$, 300 MHz) 8.81 (s, 1H), 7.45 (d, J=9.0 Hz, 2H), 7.21 (d, J=7.8 Hz, 1H), 7.15 (s, 2H), 6.79 (d, J=9.3 Hz, 2H), 3.97 (m, 2H), 3.56 (m, 1H), 2.60 (m, 2H), 2.42 (m, 4H), 1.47 (m, 16H) ppm; MS (ES) 428.7 (M+H).

5-amino-N-(3,4-(dimethoxy)phenyl)-3-[4-[2-(piperidin-1-yl)ethoxy]phenylamino]-1H-1,2,4-triazole-1-carboxamide (compound #43), $^1$H-NMR (DMSO-d$_6$, 300 MHz) 9.30 (s, 1H), 8.90 (s, 1H), 7.56 (d, J=8.7 Hz, 2H), 7.285 (d, J=2.1 Hz, 1H), 7.278 (s, 2H), 7.14 (dd, J=8.4, 2.1 Hz, 1H), 6.92 (d, J=9.0 Hz, 1H), 6.81 (d, J=9.0 Hz, 2H), 3.98 (t, J=5.7 Hz, 2H), 3.75 (s, 3H), 3.74 (s, 3H), 2.60 (t, J=5.7 Hz, 2H), 2.43 (m, 4H), 1.49 (m, 4H), 1.37 (s, 2H) ppm; MS (ES) 482.2 (M+H).

5-amino-N-(4-(dimethylamino)phenyl)-3-[4-[2-(piperidin-1-yl)ethoxy]phenylamino]-1H-1,2,4-triazole-1-carboxamide (compound #44), $^1$H-NMR (DMSO-d$_6$, 300 MHz) 9.17 (s, 1H), 8.89 (s, 1H), 7.56 (d, J=8.7 Hz, 2H), 7.36 (d, J=8.7 Hz, 2H), 7.22 (s, 2H), 6.81 (d, J=8.7 Hz, 2H), 6.70 (d, J=8.7 Hz, 2H), 4.01 (t, J=6.6 Hz, 2H), 2.86 (s, 3H), 2.80 (s, 3H), 2.48 (m, 2H), 1.97 (m, 4H), 1.50-1.14 (m, 6H) ppm; MS (ES) 465.2 (M+H), 463.3 (M−H).

5-amino-N-cyclopentyl-3-[4-[2-(piperidin-1-yl)ethoxy]phenylamino]-1H-1,2,4-triazole-1-carboxamide (compound #45), $^1$H-NMR (DMSO-d$_6$, 300 MHz) 8.79 (s, 1H), 7.45 (d, J=8.7 Hz, 2H), 7.28 (d, J=7.8 Hz, 1H), 7.15 (s, 2H), 6.79 (d, J=9.0 Hz, 2H), 3.97 (m, 3H), 2.60 (m, 2H), 2.41 (m, 4H), 1.89-1.38 (m, 14H) ppm; MS (ES) 414.2 (M+H); and 5-amino-N-(4-butoxyphenyl)-3-[4-[2-(piperidin-1-yl)ethoxy]phenylamino]-1H-1,2,4-triazole-1-carboxamide (compound #46), $^1$H-NMR (CDCl$_3$, 300 MHz) 8.37 (s, 1H), 7.39 (d, J=8.7 Hz, 2H), 7.32 (d, J=8.7 Hz, 2H), 6.90 (d, J=8.7 Hz, 2H), 6.88 (d, J=8.7 Hz, 2H), 6.57 (s, 1H), 6.23 (s, 2H), 4.09 (t, J=6.0 Hz, 2H), 3.96 (t, J=6.3 Hz, 2H), 2.77 (t, J=6.0 Hz, 2H), 2.50 (m, 4H), 1.80-1.26 (m, 12H), 0.99 (t, J=7.2 Hz, 3H) ppm; MS (ES) 494.8 (M+H).

In addition to the preparation of the compounds of the invention as disclosed above, the following compounds of the invention were prepared by methods similar to those disclosed herein utilizing appropriately substituted starting materials and reagents. The number following each compound below refers to its number in Tables 1-10, as discussed in more detail below.

3-amino-1-(4-(iso-propoxy)phenyl)carbonyl-5-[4-[2-(piperidin-1-yl)ethoxy]phenylamino]-1H-1,2,4-triazole (compound #47);

5-amino-1-(4-(iso-propoxy)phenyl)carbonyl-3-(4-(morpholin-4-yl)phenylamino]-1H-1,2,4-triazole (compound #48), yellow solid. $^1$H-NMR (DMSO-d$_6$, 300 MHz) 8.97 (s, 1H), 8.23 (d, J=8.1 Hz, 2H), 7.69 (br. s, 2H), 7.40 (d, J=8.4 Hz, 2H), 7.05 (d, J=8.4 Hz, 2H), 6.84 (d, J=9.0 Hz, 2H), 4.77 (quint., J=6.3 Hz, 1H), 3.70 (t, J=4.35 Hz, 4H), 2.98 (t, J=4.65 Hz, 4H), 1.31 (d, J=5.7 Hz, 6H) ppm; MS (ES) 423.10 (M+H), 421.20 (M−H).

3-amino-1-(4-(iso-propoxy)phenyl)carbonyl-5-(4-(morpholin-4-yl)phenylamino]-1H-1,2,4-triazole (compound #49);

5-amino-3-[4-[2-(piperidin-1-yl)ethoxy]phenylamino]-1-(4-(tert-butoxy)phenyl)carbonyl-1H-1,2,4-triazole (compound #50), yellow solid, $^1$H-NMR (DMSO-d$_6$, 300 MHz) 9.02 (s, 1H), 8.19 (d, J=9.0 Hz, 2H), 7.72 (br. s, 2H), 7.40 (d, J=7.5 Hz, 2H), 7.12 (d, J=8.7 Hz, 2H), 6.80 (d, J=8.1 Hz, 2H), 3.96 (t, J=5.7 Hz, 2H), 2.59 (t, J=5.7 Hz, 2H), 2.39 (m, 4H), 1.47 (m, 4H), 1.41 (s, 9H), 1.37-1.34 (m, 2H) ppm; MS (ES) 479.92 (M+H), 477.58 (M−H).

5-amino-1-(4-(iso-propyl)phenyl)carbonyl-3-[4-[2-(piperidin-1-yl)ethoxy]phenylamino]-1H-1,2,4-triazole (compound #51), yellow solid, $^1$H-NMR (DMSO-$d_6$, 300 MHz) 9.03 (s, 1H), 8.12 (d, J=8.4 Hz, 2H), 7.74 (br. s, 2H), 7.43-7.38 (m, 4H), 6.81 (d, J=9 Hz, 2H), 3.98 (t, J=5.85 Hz, 2H), 2.99 (quint., J=7 Hz, 1H), 2.66 (m, 2H), 2.55-2.4 (m, 4H), 1.56-1.45 (m, 4H), 1.40-1.35 (m, 2H), 1.25 (d, J=6.9 Hz, 6H) ppm; MS (ES) 449.50 (M+H), 447.48 (M−H).

5-amino-1-(4-(iso-propyl)phenyl)carbonyl-3-(4-(morpholin-4-yl)phenylamino]-1H-1,2,4-triazole (compound #52), yellow solid, $^1$H-NMR (DMSO-$d_6$, 300 MHz) 8.97 (s, 1H), 8.13 (d, J=8.4 Hz, 2H), 7.73 (br. s, 2H), 7.41 (d, J=8.7 Hz, 2H), 7.38 (d, J=9.0 Hz, 2H), 6.82 (d, J=9.3 Hz, 2H), 3.70 (m, 4H), 2.97 (m, 5H), 1.25 (d, J=6.9 Hz, 6H) ppm; MS (ES) 407.14 (M+H), 405.24 (M−H).

5-amino-1-(4-(methyl)phenyl)carbonyl-3-[4-[2-(piperidin-1-yl)ethoxy]phenylamino]-1H-1,2,4-triazole (compound #53), yellow solid, $^1$H-NMR (DMSO-$d_6$, 300 MHz) 9.03 (s, 1H), 8.09 (d, J=8.4 Hz, 2H), 7.73 (br. s, 2H), 7.41-7.33 (m, 4H), 6.80 (d, J=8.7 Hz, 2H), 3.99 (m, 2H), 2.52 (m, 2H), 2.41 (s, 4H), 1.82 (s, 3H), 1.50 (br. s, 4H), 1.39 (br. s, 2H) ppm; MS (ES) 421.47 (M+H), 419.42 (M−H).

5-amino-1-(4-(methyl)phenyl)carbonyl-3-(4-(morpholin-4-yl)phenylamino)-1H-1,2,4-triazole (compound #54), yellow solid, $^1$H-NMR (DMSO-$d_6$, 300 MHz) 8.98 (s, 1H), 8.10 (d, J=8.1 Hz, 2H), 7.72 (br. s, 2H), 7.38 (d, J=8.7 Hz, 2H), 7.35 (d, J=8.7 Hz, 2H), 6.82 (d, J=8.7 Hz, 2H), 3.70 (m, 4H), 2.97 (m, 4H), 2.41 (s, 3H) ppm; MS (ES) 379.13 (M+H), 377.16 (M−H).

5-amino-3-[4-(iso-propoxy)phenylamino]-1-(4-(methyl)phenyl)carbonyl-1H-1,2,4-triazole (compound #55), yellow solid, $^1$H-NMR (DMSO-$d_6$, 300 MHz) 9.01 (s, 1H), 8.09 (d, J=8.4 Hz, 2H), 7.73 (br. s, 2H), 7.38 (d, J=9.3 Hz, 2H), 7.35 (d, J=8.4 Hz, 2H), 6.77 (d, J=8.7 Hz, 2H), 4.45 (quint., J=5.9 Hz, 1H), 2.40 (s, 3H), 1.20 (d, J=6.0 Hz, 6H) ppm; MS (ES) 352.11 (M+H), 350.19 (M−H).

3-amino-5-[4-(iso-propoxy)phenylamino]-1-(4-(methyl)phenyl)carbonyl-1H-1,2,4-triazole (compound #56);

5-amino-3-(4-morpholin-4-yl)phenylamino)-1-(4-(tert-butoxy)phenyl)carbonyl-1H-1,2,4-triazole (compound #57); yellow solid, $^1$H-NMR (DMSO-$d_6$, 300 MHz) 8.97 (s, 1H), 8.17 (d, J=9 Hz, 2H), 7.71 (br. s, 2H), 7.38 (d, J=9 Hz, 2H), 7.11 (d, J=8.7 Hz, 2H), 6.82 (d, J=9.0 Hz, 2H), 3.70 (m, 4H), 2.97 (m, 4H), 1.41 (s, 9H) ppm; MS (ES) 437.17 (M+H), 435.26 (M−H).

3-amino-5-(4-(morpholin-4-yl)phenylamino)-1-(4-(tert-butoxy)phenyl)carbonyl-1H-1,2,4-triazole (compound #58);

5-amino-1-(3-(methyl)phenyl)carbonyl-3-[4-[2-(piperidin-1-yl)ethoxy]phenylamino]-1H-1,2,4-triazole (compound #59); yellow solid, $^1$H-NMR (DMSO-$d_6$, 300 MHz) 9.04 (s, 1H), 8.15 (s, 1H), 8.02 (br. s, 1H), 7.90 (d, J=6 Hz, 1H), 7.74 (br. s, 2H), 7.44-7.38 (m, 4H), 6.78 (d, J=9.3 Hz, 2H), 3.96 (t, J=5.85 Hz, 2H), 2.59 (t, J=6 Hz, 2H), 2.42 (m, 4H), 2.41 (s, 3H), 1.48 (m, 4H), 1.37 (m, 2H) ppm; MS (ES) 421.47 (M+H), 419.44 (M−H).

5-amino-1-(4-(iso-propoxy)phenylcarbonyl-3-[4-[2-(thiomorpholin-4-yl)ethoxy]phenylamino]-1H-1,2,4-triazole (compound #60); yellow solid, $^1$H-NMR (DMSO-$d_6$, 300 MHz) 9.02 (s, 1H), 8.23 (d, J=9.0 Hz, 2H), 7.70 (br. s, 2H), 7.41 (d, J=9.0 Hz, 2H), 7.05 (d, J=9.0 Hz, 2H), 6.82 (d, J=9.0 Hz, 2H), 4.78 (quint., J=5.9 Hz, 1H), 3.97 (t, J=6.0 Hz, 2H), 2.74-2.67 (m, 6H), 2.59-2.56 (m, 4H), 1.31 (d, J=5.7 Hz, 6H) ppm; MS (ES) 483.47 (M+H), 481.36 (M−H).

5-amino-1-(3-(methyl)phenylcarbonyl-3-[4-[2-(thiomorpholin-4-yl)ethoxy]phenylamino]-1H-1,2,4-triazole (compound #61); yellow solid, $^1$H-NMR (DMSO-$d_6$, 300 MHz) 9.03 (s, 1H), 8.02 (br. s, 1H), 7.90 (d, J=6.3 Hz, 1H), 7.73 (br. s, 2H), 7.44-7.39 (m, 4H), 6.78 (d, J=8.7 Hz, 2H), 3.96 (t, J=5.8 Hz, 2H), 2.74-2.71 (m, 4H), 2.68 (t, J=5.7 Hz, 2H), 2.59-2.56 (m, 4H), 2.41 (s, 3H) ppm; MS (ES) 439.41 (M+H), 437.33 (M−H).

5-amino-1-(4-(cyclohexyl)phenyl)carbonyl-3-[4-[2-(piperidin-1-yl)ethoxy]phenylamino]-1H-1,2,4-triazole (compound #62);

5-amino-3-(2,2-difluoro-2H-benzo[b][1,4]oxazin-3(4H)-on-6-yl)amino-1-(4-(iso-propoxy)phenyl)carbonyl-1H-1,2,4-triazole (compound #63);

5-amino-3-(2,2-difluoro-2H-benzo[b][1,4]oxazin-3(4H)-on-6-yl)amino-1-(3-(methyl)phenyl)carbonyl-1H-1,2,4-triazole (compound #64);

5-amino-1-(2,2-dimethyl-2H-benzo[b][1,4]oxazin-3(4H)-on-6-yl)carbonyl-3-(4-(iso-propoxy)phenyl)amino-1H-1,2,4-triazole (compound #65); yellow solid, $^1$H-NMR (DMSO-$d_6$, 300 MHz) 10.87 (s, 1H), 9.02 (s, 1H), 7.94 (dd, J=8.1 Hz, J=1.8 Hz, 1H), 7.72 (br. s, 2H), 7.69 (d, J=1.8 Hz, 1H), 7.39 (d, J=9.0 Hz, 2H), 7.08 (d, J=8.4 Hz, 1H), 6.77 (d, J=9.0 Hz, 2H), 4.45 (quint., J=6.0 Hz, 1H), 1.46 (s, 6H), 1.21 (d, J=6.0 Hz, 6H) ppm; MS (ES) 437.46 (M+H), 435.38 (M−H).

3-amino-1-(2,2-dimethyl-2H-benzo[b][1,4]oxazin-3(4H)-on-6-yl)carbonyl-5-(4-(iso-propoxy)phenyl)amino-1H-1,2,4-triazole (compound #66);

5-amino-1-(3-(hydroxy)phenyl)carbonyl-3-(4-(morpholin-4-yl)phenylamino)-1H-1,2,4-triazole (compound #67); yellow solid, $^1$H-NMR (DMSO-$d_6$, 300 MHz) 9.77 (s, 1H), 8.97 (s, 1H), 7.72 (br. s, 2H), 7.59 (d, J=7.8 Hz, 1H), 7.49 (t, J=1.95 Hz, 1H), 7.38 (d, J=8.7 Hz, 2H), 7.32 (t, J=7.8 Hz, 1H), 7.00 (dd, J=7.8 Hz, J=1.8 Hz, 1H), 6.80 (d, J=9.0 Hz, 2H), 3.70 (m, 4H), 2.96 (m, 4H) ppm; MS (ES) 381.08 (M+H), 379.16 (M−H).

5-amino-1-(2,2-dimethyl-2H-benzo[b][1,4]oxazin-3(4H)-on-6-yl)carbonyl-3-(4-(morpholin-4-yl)phenylamino)-1H-1,2,4-triazole (compound #68); yellow solid, $^1$H-NMR (DMSO-$d_6$, 300 MHz) 10.86 (s, 1H), 8.96 (s, 1H), 7.98 (dd, J=8.4 Hz, J=2.1 Hz, 1H), 7.70 (br. s, 2H), 7.66 (d, J=2.1 Hz, 1H), 7.38 (d, J=9.0 Hz, 2H), 7.08 (d, J=8.4 Hz, 1H), 6.82 (d, J=9.0 Hz, 2H), 3.70 (m, 4H), 2.97 (m, 4H), 1.45 (s, 6H) ppm; MS (ES) 464.46 (M+H), 462.41 (M−H).

3-amino-1-(2,2-dimethyl-2H-benzo[b][1,4]oxazin-3(4H)-on-6-yl)carbonyl-5-(4-(morpholin-4-yl)phenylamino)-1H-1,2,4-triazole (compound #69);

5-amino-1-(4-(aminosulfonyl)phenyl)carbonyl-3-(4-(morpholin-4-yl)phenylamino)-1H-1,2,4-triazole (compound #70);

5-amino-3-[4-(iso-propoxy)phenylamino]-1-(3-(nitro)phenyl)carbonyl-1H-1,2,4-triazole (compound #71); yellow solid, $^1$H-NMR (DMSO-$d_6$, 300 MHz) 9.25 (t, J=2.1 Hz, 1H), 9.12 (s, 1H), 8.49-8.45 (m, 2H), 7.87-7.81 (m, 3H), 7.42 (d, J=8.7 Hz, 2H), 6.76 (d, J=9.0 Hz, 2H), 4.43 (quint., J=6.0 Hz, 1H), 1.21 (d, J=6.0 Hz, 6H) ppm; MS (ES) 383.39 (M+H), 381.36 (M−H).

5-amino-3-(4-(morpholin-4-yl)phenylamino)-1-(3-(nitro)phenyl)carbonyl-1H-1,2,4-triazole (compound #72); yellow solid, $^1$H-NMR (DMSO-$d_6$, 300 MHz) 9.22 (s, 1H), 9.08 (s, 1H), 8.48 (m, 2H), 7.84 (m, 3H), 7.40 (d, J=8.1 Hz, 2H), 6.80 (d, J=8.7 Hz, 2H), 3.70 (m, 4H), 2.96 (m, 4H) ppm; MS (ES) 410.42 (M+H), 408.38 (M−H).

5-amino-1-(3-(hydroxy)phenyl)carbonyl-3-[4-(iso-propoxy)phenylamino]-1H-1,2,4-triazole (compound #73); yellow solid, $^1$H-NMR (DMSO-$d_6$, 300 MHz) 9.74 (s, 1H), 8.99

(s, 1H), 7.71 (br. s, 2H), 7.58 (d, J=8.1 Hz, 1H), 7.50 (t, J=2.4 Hz, 1H), 7.38 (d, J=9.3 Hz, 2H), 7.32 (t, J=7.9 Hz, 1H), 6.99 (dd, J=8.1 Hz, J=2.7 Hz, 1H), 6.74 (d, J=9.3 Hz, 2H), 4.44 (quint., J=6.0 Hz, 1H), 1.20 (d, J=5.7 Hz, 6H) ppm; MS (ES) 354.41 (M+H), 352.38 (M−H).

5-amino-1-(3-(chloro)phenyl)carbonyl-3-(4-(morpholin-4-yl)phenylamino)-1H-1,2,4-triazole (compound #74); yellow solid, $^1$H-NMR (DMSO-$d_6$, 300 MHz) 9.03 (s, 1H), 8.29 (t, J=1.8 Hz, 1H), 8.02 (d, J=7.8 Hz, 1H), 7.77 (br. s, 2H), 7.72-7.69 (m, 1H), 7.57 (t, J=7.95 Hz, 1H), 7.37 (d, J=9.3 Hz, 2H), 6.80 (d, J=9.3 Hz, 2H), 3.70 (m, 4H), 2.96 (m, 4H) ppm; MS (ES) 399.38 (M+H), 397.34 (M−H).

3-amino-1-(3-(chloro)phenyl)carbonyl-5-(4-(morpholin-4-yl)phenylamino)-1H-1,2,4-triazole (compound #75);

5-amino-1-(3-(chloro)phenyl)carbonyl-3-[4-(iso-propoxy)phenylamino]-1H-1,2,4-triazole (compound #76);

5-amino-3-[4-(iso-propoxy)phenylamino]-1-[4-[2-(piperidin-1-yl)ethoxy]phenyl)carbonyl-1H-1,2,4-triazole (compound #77); yellow solid, $^1$H-NMR (DMSO-$d_6$, 300 MHz) 9.01 (s, 1H), 8.24 (d, J=9.0 Hz, 2H), 7.70 (br. s, 2H), 7.40 (d, J=9.0 Hz, 2H), 7.08 (d, J=9.3 Hz, 2H), 6.80 (d, J=9.0 Hz, 2H), 4.45 (quint., J=6.0 Hz, 1H), 4.18 (t, J=5.7 Hz, 2H), 2.70 (t, J=5.7 Hz, 2H), 2.60 (m, 4H), 1.56-1.47 (m, 4H), 1.38 (m, 2H), 1.21 (d, J=6.0 Hz, 6H) ppm; MS (ES) 465.59 (M+H), 463.55 (M−H).

5-amino-1-(2,2-dimethyl-2H-benzo[b][1,4]oxazin-3(4H)-on-6-yl)carbonyl-3-[4-[2-(piperidin-1-yl)ethoxy]phenylamino]-1H-1,2,4-triazole (compound #78); yellow solid, 1H-NMR (DMSO-$d_6$, 300 MHz) 10.86 (s, 1H), 9.02 (s, 1H), 7.96 (dd, J=8.4 Hz, J=1.8 Hz, 1H), 7.71 (br. s, 2H), 7.67 (d, J=1.8 Hz, 1H), 7.40 (d, J=8.7 Hz, 2H), 7.08 (d, J=8.1 Hz, 1H), 6.79 (d, J=8.4 Hz, 2H), 3.97 (t, J=5.85 Hz, 2H), 2.62 (t, J=5.7 Hz, 2H), 2.43 (m, 4H), 1.54-1.44 (m, 4H), 1.45 (s, 6H), 1.42-1.32 (m, 2H) ppm; MS (ES) 506.14 (M+H), 504.33 (M−H).

5-amino-1-(3-(methoxycarbonyl)phenyl)carbonyl-3-[4-[2-(piperidin-1-yl)ethoxy]phenylamino]-1H-1,2,4-triazole (compound #79); yellow solid, $^1$H-NMR (DMSO-$d_6$, 300 MHz) 9.09 (s, 1H), 8.90 (t, J=1.2 Hz, 1H), 8.34 (dt, J=7.8 Hz, J=1.8 Hz, 1H), 8.19 (dt, J=7.5 Hz, J=1.5 Hz, 1H), 7.80 (br. s, 2H), 7.70 (t, J=7.5 Hz, 1H), 7.41 (d, J=9.0 Hz, 2H), 6.77 (d, J=9.0 Hz, 2H), 3.96 (t, J=6.0 Hz, 2H), 3.89 (s, 3H), 2.59 (t, J=6.0 Hz, 2H), 2.39 (m, 4H), 1.49-1.22 (m, 6H) ppm; MS (ES) 465.95 (M+H), 463.52 (M−H).

5-amino-1-(3-(methoxy)phenyl)carbonyl-3-[4-[2-(piperidin-1-yl)ethoxy]phenylamino]-1H-1,2,4-triazole (compound #80); yellow solid, $^1$H-NMR (DMSO-$d_6$, 300 MHz) 9.05 (s, 1H), 7.77 (br. s, 2H), 7.70-7.66 (m 2H), 7.46 (d, J=7.8 Hz, 1H), 7.40 (d, J=8.7 Hz, 2H), 7.19 (dd, J=8.4 Hz, J=3.0 Hz, 1H), 6.77 (d, J=9.0 Hz, 2H), 3.95 (t, J=5.85 Hz, 2H), 3.82 (s, 3H), 2.58 (t, J=6 Hz, 2H), 2.39 (m, 4H), 1.46 (m, 4H), 1.37 (m, 2H) ppm; MS (ES) 437.89 (M+H), 435.53 (M−H).

5-amino-1-(3-(methoxy)phenyl)carbonyl-3-(4-(morpholin-4-yl)phenylamino)-1H-1,2,4-triazole (compound #81); yellow solid, $^1$H-NMR (DMSO-$d_6$, 300 MHz) 9.01 (s, 1H), 7.78 (t, J=1.9 Hz, 1H), 7.75 (br. s, 2H), 7.69 (d, J=7.8 Hz, 1H), 7.45 (t, J=8.1 Hz, 1H), 7.39 (d, J=9.0 Hz, 2H), 7.19 (dd, J=8.1 Hz, J=2.4 Hz, 1H), 6.79 (d, J=9.0 Hz, 2H), 3.82 (s, 3H), 3.70 (m, 4H), 2.97 (m, 4H) ppm; MS (ES) 395.09 (M+H), 393.22 (M−H).

5-amino-3-[4-[2-(dimethylamino)ethoxy]phenylamino]-1-(4-(methyl)phenyl)carbonyl-1H-1,2,4-triazole (compound #82);

5-amino-3-[4-[2-(dimethylamino)ethoxy]phenylamino]-1-(4-(tert-butoxy)phenyl)carbonyl-1H-1,2,4-triazole (compound #83); yellow solid, $^1$H-NMR (DMSO-$d_6$, 300 MHz) 9.02 (s, 1H), 8.17 (d, J=8.7 Hz, 2H), 7.71 (br. s, 2H), 7.41 (d, J=9.0 Hz, 2H), 7.11 (d, J=8.7 Hz, 2H), 6.81 (d, J=9.0 Hz, 2H), 3.98 (t, J=5.85 Hz, 2H), 2.68 (t, J=5.85 Hz, 2H), 2.27 (s, 6H), 1.41 (s, 9H) ppm; MS (ES) 439.61 (M+H), 437.61 (M−H).

5-amino-3-[4-[2-(dimethylamino)propoxy]phenylamino]-1-(4-(iso-propoxy)phenyl)carbonyl-1H-1,2,4-triazole (compound #84); yellow solid, $^1$H-NMR (DMSO-$d_6$, 300 MHz) 9.02 (s, 1H), 8.23 (d, J=9.0 Hz, 2H), 7.70 (br. s, 2H), 7.42 (d, J=9.0 Hz, 2H), 7.05 (d, J=9.3 Hz, 2H), 6.01 (d, J=9.0 Hz, 2H), 4.78 (quint., J=6.0 Hz, 1H), 3.91 (t, J=6.1 Hz, 2H), 2.53 (m, 2H), 2.28 (s, 6H), 1.85 (quint., J=6.9 Hz, 2H), 1.31 (d, J=5.7 Hz, 6H) ppm; MS (ES) 439.61 (M+H), 437.64 (M−H).

5-amino-3-[4-[2-(dimethylamino)ethoxy]phenylamino]-1-(4-(iso-propoxy)phenyl)carbonyl-1H-1,2,4-triazole (compound #85); yellow solid, $^1$H-NMR (DMSO-$d_6$, 300 MHz) 9.03 (s, 1H), 8.23 (d, J=9.0 Hz, 2H), 7.70 (br. s, 2H), 7.42 (d, J=9.0 Hz, 2H), 7.05 (d, J=9.3 Hz, 2H), 6.83 (d, J=9.0 Hz, 2H), 4.78 (quint., J=6.0 Hz, 1H), 3.97 (t, J=5.85 Hz, 2H), 2.65 (t, J=5.7 Hz, 2H), 2.24 (s, 6H), 1.31 (d, J=6.0 Hz, 6H) ppm; MS (ES) 425.18 (M+H), 423.23 (M−H).

5-amino-3-[4-[2-(dimethylamino)ethoxy]phenylamino]-1-(2,2-dimethyl-2H-benzo[b][1,4]oxazin-3(4H)-on-6-yl)carbonyl-1H-1,2,4-triazole (compound #86); yellow solid, $^1$H-NMR (DMSO-$d_6$, 300 MHz) 10.87 (s, 1H), 9.03 (s, 1H), 7.95 (dd, J=8.4 Hz, J=2.1 Hz, 1H), 7.72 (br. s, 2H), 7.68 (d, J=2.1 Hz, 1H), 7.40 (dd, J=6.9 Hz, J=2.4 Hz, 2H), 7.08 (d, J=8.4 Hz, 1H), 6.80 (d, J=9.3 Hz, 2H), 3.95 (t, J=5.85 Hz, 2H), 2.60 (t, J=5.7 Hz, 2H), 2.21 (s, 6H), 1.45 (s, 6H) ppm; MS (ES) 466.15 (M+H), 464.22 (M−H).

5-amino-3-[4-[2-(dimethylamino)ethoxy]phenylamino]-1-(4-(dimethylamino)phenyl)carbonyl-1H-1,2,4-triazole (compound #87); yellow solid, $^1$H-NMR (DMSO-$d_6$, 300 MHz) 8.97 (s, 1H), 8.24 (d, J=9.3 Hz, 2H), 7.63 (br. s, 2H), 7.44 (d, J=9.0 Hz, 2H), 6.84 (d, J=9.0 Hz, 2H), 6.76 (d, J=9.6 Hz, 2H), 3.96 (t, J=5.85 Hz, 2H), 3.04 (s, 6H), 2.58 (t, J=6 Hz, 2H), 2.20 (s, 6H) ppm; MS (ES) 410.18 (M+H), 408.22 (M−H).

5-amino-1-(4-(dimethylamino)phenyl)carbonyl-3-[4-[2-(dimethylamino)propoxy]phenylamino]-1H-1,2,4-triazole (compound #88); yellow solid, $^1$H-NMR (DMSO-$d_6$, 300 MHz) 8.97 (s, 1H), 8.25 (d, J=9.3 Hz, 2H), 7.63 (br. s, 2H), 7.44 (d, J=9.0 Hz, 2H), 6.82 (d, J=9.0 Hz, 2H), 6.77 (d, J=9.6 Hz, 2H), 3.19 (t, J=6.3 Hz, 2H), 3.04 (s, 6H), 2.39 (t, J=5.4 Hz, 2H), 2.17 (d, J=1.5 Hz, 6H), 1.81 (Quint., J=6.75 Hz, 2H) ppm; MS (ES) 424.19 (M+H), 422.29 (M−H).

5-amino-3-[4-[2-(dimethylamino)propoxy]phenylamino]-1-(4-(tert-butoxy)phenyl)carbonyl-1H-1,2,4-triazole (compound #89); yellow solid, $^1$H-NMR (DMSO-$d_6$, 300 MHz) 9.01 (s, 1H), 8.17 (d, J=8.7 Hz, 2H), 7.71 (br. s, 2H), 7.40 (d, J=9.0 Hz, 2H), 7.11 (d, J=8.7 Hz, 2H), 6.78 (d, J=8.7 Hz, 2H), 3.89 (t, J=6.3 Hz, 2H), 2.31 (t, J=6.9 Hz, 2H), 2.11 (s, 6H) 1.78 (m, 2H), 1.41 (s, 9H) ppm; MS (ES) 453.19 (M+H), 451.33 (M−H).

5-amino-3-[4-[2-(dimethylamino)propoxy]phenylamino]-1-(2,2-dimethyl-2H-benzo[b][1,4]oxazin-3(4H)-on-6-yl)carbonyl-1H-1,2,4-triazole (compound #90); yellow solid, $^1$H-NMR (DMSO-$d_6$, 300 MHz) 10.87 (s, 1H), 9.02 (s, 1H), 7.95 (dd, J=9.0 Hz, J=2.1 Hz, 1H), 7.72 (br. s, 2H), 7.68 (d, J=1.8 Hz, 1H), 7.40 (d, J=9.0 Hz, 2H), 7.08 (d, J=8.4 Hz, 1H), 6.78 (d, J=9.3 Hz, 2H), 3.89 (t, J=6.4 Hz, 2H), 2.31 (t, J=7.0 Hz, 2H), 2.11 (s, 6H) 1.78 (m, 2H), 1.45 (s, 9H) ppm; MS (ES) 480.14 (M+H), 478.31 (M−H).

5-amino-3-[4-[3-(dimethylamino)propoxy]phenylamino]-1-(4-(methyl)phenyl)carbonyl-1H-1,2,4-triazole (compound #91); yellow solid, $^1$H-NMR (DMSO-$d_6$, 300 MHz) 9.02 (s, 1H), 8.09 (d, J=8.4 Hz, 2H), 7.73 (br. s, 2H), 7.39 (d, J=9.3 Hz, 2H), 7.35 (d, J=8.7 Hz, 2H), 6.78 (d, J=9.0

Hz, 2H), 3.89 (t, J=6.4 Hz, 2H), 2.40 (s, 3H), 2.32 (t, J=7.2 Hz, 2H), 2.12 (s, 6H) 1.78 (quint., J=6.9 Hz, 2H) ppm; MS (ES) 395.16 (M+H), 393.28 (M−H).

3-amino-5-(1,4-benzodioxan-6-yl)amino-1-phenylcarbonyl-1H-1,2,4-triazole (compound #92);

3-amino-5-(1,4-benzodioxan-6-yl)amino-1-methoxycarbonyl-1H-1,2,4-triazole (compound #93);

5-amino-1-(2-(chloro)phenyl)carbonyl-3-(1,4-benzodioxan-6-yl)amino-1H-1,2,4-triazole (compound #94);

5-amino-1-(4-(chloro)phenyl)carbonyl-3-(1,4-benzodioxan-6-yl)amino-1H-1,2,4-triazole (compound #95);

5-amino-3-(1,4-benzodioxan-6-yl)amino-1-(3-(methyl)phenyl)carbonyl-1H-1,2,4-triazole (compound #96);

5-amino-3-(1,4-benzodioxan-6-yl)amino-1-(2-(methyl)phenyl)carbonyl-1H-1,2,4-triazole (compound #97);

5-amino-3-(1,4-benzodioxan-6-yl)amino-1-(3-(methoxy)phenyl)carbonyl-1H-1,2,4-triazole (compound #98);

5-amino-3-(1,4-benzodioxan-6-yl)amino-1-(2-(fluoro)phenyl)carbonyl-1H-1,2,4-triazole (compound #99);

5-amino-3-(1,4-benzodioxan-6-yl)amino-1-(4-(fluoro)phenyl)carbonyl-1H-1,2,4-triazole (compound #100);

5-amino-1-(3-(chloro)phenyl)carbonyl-3-(1,4-benzodioxan-6-yl)amino-1H-1,2,4-triazole (compound #101);

5-amino-3-(1,4-benzodioxan-6-yl)amino-1-(4-(methyloxy)phenyl)carbonyl-1H-1,2,4-triazole (compound #102);

5-amino-3-(2-(ethoxycarbonyl)benzofuran-5-yl)amino-1-(3-(iso-propoxy)phenyl)carbonyl-1H-1,2,4-triazole (compound #103);

5-amino-3-(1,4-benzodioxan-6-yl)amino-1-(4-(methyl)phenyl)carbonyl-1H-1,2,4-triazole (compound #104);

5-amino-3-(1,4-benzodioxan-6-yl)amino-1-(3-(fluoro)phenyl)carbonyl-1H-1,2,4-triazole (compound #105);

5-amino-3-(1,4-benzodioxan-6-yl)amino-1-(2-(methyloxy)phenyl)carbonyl-1H-1,2,4-triazole (compound #106);

5-amino-3-[3-(hydroxy)phenylamino]-1-(2-(methyl)phenyl)carbonyl-1H-1,2,4-triazole (compound #107, (Ia-6));

5-amino-3-[3-(hydroxy)phenylamino]-1-(3-(methyl)phenyl)carbonyl-1H-1,2,4-triazole (compound #108, (Ia-7));

1-(4-(Acetoxy)phenyl)carbonyl-5-amino-3-(1,4-benzodioxan-6-yl)amino-1H-1,2,4-triazole (compound #109);

1-(3-(Acetoxy)phenyl)carbonyl-5-amino-3-(1,4-benzodioxan-6-yl)amino-1H-1,2,4-triazole (compound #110);

5-amino-3-[4-(iso-propoxy)phenylamino]-1-(4-(iso-propoxy)phenyl)carbonyl-1H-1,2,4-triazole (compound #111);

5-amino-3-(1,4-benzodioxan-6-yl)amino-1-(3-(iso-propoxy)phenyl)carbonyl-1H-1,2,4-triazole (compound #112);

5-amino-3-(1,4-benzodioxan-6-yl)amino-1-(4-(iso-propoxy)phenyl)carbonyl-1H-1,2,4-triazole (compound #113);

5-amino-1-(4-(ethoxyphenyl)carbonyl-3-(1,4-benzodioxan-6-yl)amino-1H-1,2,4-triazole (compound #114);

5-amino-3-[3-(cyclopentoxy)phenylamino]-1-(4-(iso-propoxy)phenyl)carbonyl-1H-1,2,4-triazole (compound #116);

5-amino-1-(4-(iso-propoxy)phenyl)carbonyl-3-[4-(methoxy)phenylamino]-1H-1,2,4-triazole (compound #117);

5-amino-3-[4-(ethoxy)phenylamino]-1-(4-(iso-propoxy)phenyl)carbonyl-1H-1,2,4-triazole (compound #118);

1-(2-(acetoxy)phenyl)carbonyl-5-amino-3-(1,4-benzodioxan-6-yl)amino-1H-1,2,4-triazole (compound #119);

5-amino-1-(4-(cyclopentoxy)phenylcarbonyl-3-(1,4-benzodioxan-6-yl)amino-1H-1,2,4-triazole (compound #120);

5-amino-1-(4-(iso-propoxy)phenyl)carbonyl-3-[3-(methoxy)phenylamino]-1H-1,2,4-triazole (compound #121);

5-amino-3-[3-(iso-propoxy)phenylamino]-1-(4-(iso-propoxy)phenyl)carbonyl-1H-1,2,4-triazole (compound #122);

5-amino-3-[4-(fluoro)phenylamino]-1-(4-(methyl)phenyl)carbonyl-1H-1,2,4-triazole (compound #123);

5-amino-3-[3-(fluoro)phenylamino]-1-(4-(methyl)phenyl)carbonyl-1H-1,2,4-triazole (compound #124);

5-amino-3-[3-(ethoxy)phenylamino]-1-(4-(iso-propoxy)phenyl)carbonyl-1H-1,2,4-triazole (compound #125);

5-amino-3-(1,4-benzodioxan-6-yl)amino-1-[4-(methoxycarbonylmethoxy)phenyl)carbonyl-1H-1,2,4-triazole (compound #126);

5-amino-1-(3-(cyclopentoxy)phenyl)carbonyl-3-(1,4-benzodioxan-6-yl)amino-1H-1,2,4-triazole (compound #127);

5-amino-1-(3-(ethoxy)phenyl)carbonyl-3-(1,4-benzodioxan-6-yl)amino-1H-1,2,4-triazole (compound #128);

5-amino-3-[2-(fluoro)phenylamino]-1-(4-(methyl)phenyl)carbonyl-1H-1,2,4-triazole (compound #129);

5-amino-3-[N-(2-(tetrahydropyran-2-yloxy)methylbenzofuran-5-yl)-amino]-1-(3-(methyl)phenyl)carbonyl-1H-1,2,4-triazole (compound #130);

5-amino-3-[4-(methyl)phenylamino]-1-(4-(methyl)phenyl)carbonyl-1H-1,2,4-triazole (compound #131);

5-amino-3-[4-(methoxy)phenylamino]-1-(4-(methyl)phenyl)carbonyl-1H-1,2,4-triazole (compound #132);

5-amino-3-[3-(methyl)phenylamino]-1-(4-(methyl)phenyl)carbonyl-1H-1,2,4-triazole (compound #133);

5-amino-3-[3-(methoxy)phenylamino]-1-(4-(methyl)phenyl)carbonyl-1H-1,2,4-triazole (compound #134);

5-amino-1-(4-(iso-propoxy)phenyl)carbonyl-3-[3-(methoxycarbonylmethoxy)phenylamino]-1H-1,2,4-triazole (compound #135);

5-amino-3-(2-(hydroxymethyl)benzofuran-5-yl)amino-1-(3-(methyl)phenyl)carbonyl-1H-1,2,4-triazole (compound #136);

5-amino-1-(4-(methyl)phenyl)carbonyl-3-phenylamino-1H-1,2,4-triazole (compound #137);

5-amino-3-(1,4-benzodioxan-6-yl)amino-1-[3-(methoxycarbonylmethoxy)phenyl)carbonyl-1H-1,2,4-triazole (compound #138);

5-amino-1-(4-(iso-propoxy)phenyl)carbonyl-3-[3-(2,2,2-trifluoroethoxy)phenylamino]-1H-1,2,4-triazole (compound #139);

3-amino-5-phenylamino-1-(trans-2-(furan-2-yl)ethenyl)carbonyl-1H-1,2,4-triazole (compound #140); mp 190-193° C.; $^1$H NMR (300 MHz, DMSO-d$_6$) δ 10.04 (s, 1H), 7.94 (s, 1H), 7.76-7.66 (m, 3H), 7.39-7.30 (m, 3H), 7.10 (m, 2H), 6.71 (m, 2H), 6.15 (br s, 2H); $^{13}$C NMR (75 MHz, DMSO-d$_6$) δ 163.5, 160.9, 152.7, 150.1, 146.2, 137.5, 131.5, 128.4, 122.4, 118.2, 117.3, 113.5, 112.6; IR (ATR) 3193, 1598, 1527 cm$^{-1}$; ESI MS m/z 296 [C$_{16}$H$_{13}$N$_6$O$_2$+H]$^+$; HPLC (Method 1)>99% (AUC), t$_R$=14.22 min.

5-amino-3-phenylamino-1-(trans-2-(furan-2-yl)ethenyl)carbonyl-1H-1,2,4-triazole (compound #141); mp 212-216° C.; $^1$H NMR (300 MHz, DMSO-d$_6$) δ 9.30 (s, 1H), 7.97 (s, 1H), 7.72-7.57 (m, 5H), 7.34-7.25 (m, 3H), 7.11 (d, J=3.3 Hz, 1H), 6.88 (m, 1H), 6.71 (m, 1H); $^{13}$C NMR (75 MHz, DMSO-d$_6$) δ 162.2, 156.6, 154.9, 149.1, 145.2, 139.5, 130.5, 127.2, 118.6, 116.3, 115.2, 112.3, 111.6; IR (ATR) 3334, 1674, 1642, 1609 cm$^{-1}$; ESI MS m/z 296 [C$_{16}$H$_{13}$N$_5$O$_2$+H]$^+$; HPLC (Method 1)>99% (AUC), t$_R$=13.38 min.

5-amino-1-(4-(benzyloxy)phenyl)carbonyl-3-(1,4-benzodioxan-6-yl)amino-1H-1,2,4-triazole (compound #142);

5-amino-3-[2-(methoxy)phenylamino]-1-(4-(methyl)phenyl)carbonyl-1H-1,2,4-triazole (compound #143);

5-amino-3-[2-(methyl)phenylamino]-1-(4-(methyl)phenyl)carbonyl-1H-1,2,4-triazole (compound #144);

5-amino-3-[-[2-(hydroxyl)ethoxy]phenylamino]-1-(3-(methyl)phenyl)carbonyl-1H-1,2,4-triazole (compound #145);

5-amino-3-[3-(methylaminocarbonylmethoxy)phenylamino]-1-(3-(methyl)phenyl)carbonyl-1H-1,2,4-triazole (compound #146);

5-amino-3-[3-(methoxycarbonylmethoxy)phenylamino]-1-(3-(methyl)phenyl)carbonyl-1H-1,2,4-triazole (compound #147);

5-amino-3-[3-(N-(2,2-dimethyl-1,3-dioxolan-4-yl)methyl) aminocarbonylmethoxy)phenylamino]-1-(3-(methyl)phenyl)carbonyl-1H-1,2,4-triazole (compound #148);

5-amino-3-(1,4-benzodioxan-6-yl)amino-1-[4-[2-(morpholin-4-yl)ethoxy]phenyl]carbonyl-1H-1,2,4-triazole (compound #149);

5-amino-3-(1,4-benzodioxan-6-yl)amino-1-[3-[2-(morpholin-4-yl)ethoxy]phenyl]carbonyl-1H-1,2,4-triazole (compound #150);

5-amino-3-[4-(cyclopentoxy)phenylamino]-1-(4-(iso-propoxy)phenyl)carbonyl-1H-1,2,4-triazole (compound #151);

5-amino-1-(4-(iso-propoxy)phenyl)carbonyl-3-[4-(2,2,2-trifluoroethoxy)phenylamino]-1H-1,2,4-triazole (compound #152);

5-amino-3-[3-(N-(2,3-dihydroxypropyl)amino)carbonylmethoxy]-phenylamino-1-(3-(methyl)phenyl)carbonyl-1H-1,2,4-triazole (compound #153);

5-amino-3-(indazol-5-yl)amino-1-(3-(methyl)phenyl)carbonyl-1H-1,2,4-triazole (compound #154);

3-amino-1-(3-(benzyloxy)phenyl)carbonyl-5-(1,4-benzodioxan-6-yl)amino-1H-1,2,4-triazole (compound #155);

5-amino-1-(3-(benzyloxy)phenyl)carbonyl-3-(1,4-benzodioxan-6-yl)amino-1H-1,2,4-triazole (compound #156);

5-amino-1-(4-(iso-propoxy)phenyl)carbonyl-3-[4-(methoxycarbonylmethoxy)phenylamino]-1H-1,2,4-triazole (compound #157);

5-amino-3-[4-[2-(1,3-dioxolan-2-yl)ethoxy]phenylamino]-1-(4-(iso-propoxy)phenyl)carbonyl-1H-1,2,4-triazole (compound #158);

5-amino-1-(4-(iso-propoxy)phenylcarbonyl-3-[4-[2-(morpholin-4-yl)ethoxy]phenylamino]-1H-1,2,4-triazole (compound #159);

5-amino-3-(indazol-6-yl)amino-1-(3-(methyl)phenyl)carbonyl-1H-1,2,4-triazole (compound #160);

5-amino-3-(benzo[b][1,4]oxazin-3(4H)-on-6-yl)amino-1-(3-(methyl)phenyl)carbonyl-1H-1,2,4-triazole (compound #161);

5-amino-3-(1,4-benzodioxan-6-yl)amino-1-(4-(hydroxy)phenyl)carbonyl-1H-1,2,4-triazole (compound #162);

5-amino-1-(4-(iso-propoxy)phenylcarbonyl-3-[4-[2-(piperidin-1-yl)ethoxy]phenylamino]-1H-1,2,4-triazole (compound #163);

3-amino-5-[3-[cyclohexylaminocarbonylmethoxy]phenylamino]-1-(3-(methyl)phenyl)carbonyl-1H-1,2,4-triazole (compound #164);

5-amino-3-[3-[cyclohexylaminocarbonylmethoxy]phenylamino]-1-(3-(methyl)phenyl)carbonyl-1H-1,2,4-triazole (compound #165);

5-amino-3-(1,4-benzodioxan-6-yl)-amino-1-(3-(hydroxy)phenyl)carbonyl-1H-1,2,4-triazole (compound #166);

3-amino-5-[(2H,3H-4-tert-butoxycarbonylbenzo[1,4]oxazin-6-yl)-[(2H,3H-4-tert-butoxycarbonylbenzo[1,4]oxazin-6-yl)amino]-1-(3-(methyl)phenyl)carbonyl-1H-1,2, 4-triazole (compound #167);

5-amino-1-(3-(iso-propoxy)phenyl)carbonyl-3-[4-[2-(piperidin-1-yl)ethoxy]phenylamino]-1H-1,2,4-triazole (compound #168); off-white solid, ¹H-NMR (DMSO-d₆, 300 MHz) 9.05 (s, 1H), 8.14 (d, J=0.9 Hz, 1H), 7.74 (d, J=8.4 Hz, 2H), 7.63 (d, J=7.4 Hz, 1H), 7.43 (t, J=7.7 Hz, 1H), 7.40 (d, J=8.7 Hz, 2H), 7.17 (dd, J=8.3 Hz, J=2.6 Hz, 1H), 6.76 (d, J=8.7 Hz, 2H), 4.66 (quint, J=6.0 Hz, 1H), 3.97, (t, J=5.9 Hz, 2H), 2.62 (t, J=6.0 Hz, 2H), 2.42 (m, 4H), 1.48 (m, 4H), 1.38-1.35 (m, 2H), 1.29 (d, J=6 Hz, 6H) ppm; MS (ES) 465.57 (M+H), 453.55 (M−H).

5-amino-1-(3-(iso-propoxy)phenyl)carbonyl-3-[4-[2-(morpholin-4-yl)ethoxy]phenylamino]-1H-1,2,4-triazole (compound #169); off-white solid, ¹H-NMR (DMSO-d₆, 300 MHz) 9.05 (s, 1H), 8.12 (d, J=1.5 Hz, 1H), 7.74 (d, J=9.3 Hz, 2H), 7.63 (d, J=7.5 Hz, 1H), 7.46-7.36 (m, 3H), 7.17 (d, J=7.5 Hz, 1H), 6.77 (d, J=8.7 Hz, 2H), 4.66 (quint., J=5.1 Hz, 1H), 3.98 (t, J=5.9 Hz, 1H), 3.55 (t, J=4.5 Hz, 2H), 2.63 (t, J=5.6 Hz, 1H), 2.44 (m, 2H), 1.29 (d, J=5.1 Hz, 6H) ppm; MS (ES) 467.14 (M+H), 465.30 (M−H).

5-amino-1-(3-(iso-propoxy)phenyl)carbonyl-3-[3-(1,3-oxazol-5-yl)phenylamino]-1H-1,2,4-triazole (compound #170); white solid, ¹H-NMR (MeOH-d₄, 300 MHz) 8.18 (s, 1H), 8.13 (m, 1H), 7.78-7.72 (m, 2H), 7.44 (t, J=8.1 Hz, 1H), 7.33-7.19 (m, 5H), 4.63 (quint., J=5.7 Hz, 1H), 1.26 (d, J=5.7 Hz, 6H) ppm; MS (ES) 405.06 (M+H), 403.15 (M−H).

5-amino-1-(3-(iso-propoxy)pyridin-5-yl)carbonyl-3-[4-[2-(morpholin-4-yl)ethoxy]phenylamino]-1H-1,2,4-triazole (compound #171), yellow solid, ¹H-NMR (DMSO-d₆, 300 MHz) 9.09 (s, 1H), 8.74 (d, J=1.8 Hz, 1H), 8.44 (d, J=2.7 Hz, 1H), 8.05 (t, J=1.5 Hz, 1H), 7.79 (br. s, 2H), 7.37 (d, J=8.7 Hz, 2H), 6.76 (d, J=9 Hz, 2H), 4.73 (quint, J=6 Hz, 1H), 3.98 (t, J=5.4 Hz, 2H), 3.55 (m, 4H), 2.63 (t, J=5.7 Hz, 2H), 2.43 (m, 4H), 1.31 (d, J=6 Hz, 6H) ppm; MS (ES) 468.48 (M+H), 466.49 (M−H).

5-amino-N-(4-chlorophenyl)-3-[4-(methoxy)phenylamino]-1H-1,2,4-triazole-1-carboxamide (compound #172);

5-amino-3-(4-methoxyphenyl)amino-1-(tert-butoxycarbonyl)-1H-1,2,4-triazole (compound #173);

3-[4-(acetyl(methyl)amino)phenyl]amino-5-amino-N-(4-chlorophenyl)-1H-1,2,4-triazole-1-carboxamide (compound #174);

3-[4-(acetyl(methyl)amino)phenyl]amino-5-amino-N-(1,3-benzodioxol-5-yl)-1H-1,2,4-triazole-1-carboxamide (compound #175);

5-[4-(acetyl(methyl)amino)phenyl]amino-3-amino-N-(1,3-benzodioxol-5-yl)-1H-1,2,4-triazole-1-carboxamide (compound #176);

3-[4-(acetyl(methyl)amino)phenyl]amino-5-amino-N-cyclopentyl-1H-1,2,4-triazole-1-carboxamide (compound #177);

5-[4-(acetyl(methyl)amino)phenyl]amino-3-amino-N-cyclopentyl-1H-1,2,4-triazole-1-carboxamide (compound #178);

3-[4-(acetyl(methyl)amino)phenyl]amino-5-amino-N-(4-(iso-propyl)phenyl)-1H-1,2,4-triazole-1-carboxamide (compound #179);

3-[4-(acetyl(methyl)amino)phenyl]amino-5-amino-N-(4-(butoxy)phenyl)-1H-1,2,4-triazole-1-carboxamide (compound #180);

3-amino-N-(4-(butoxy)phenyl)-5-[4-[2-(piperidin-1-yl)ethoxy]phenylamino]-1H-1,2,4-triazole-1-carboxamide (compound #182);

3-amino-N-(4-(methyl)phenyl)-5-[4-[2-(piperidin-1-yl)ethoxy]phenylamino]-1H-1,2,4-triazole-1-carboxamide (compound #183);

3-amino-N-(4-(methoxy)phenyl)-5-[4-[2-(piperidin-1-yl)ethoxy]phenylamino]-1H-1,2,4-triazole-1-carboxamide (compound #184);

3-[4-(acetyl(methyl)amino)phenyl]amino-5-amino-N-cyclohexyl-1H-1,2,4-triazole-1-carboxamide (compound #185);

3-[4-(acetyl(methyl)amino)phenyl]amino-3-amino-N-cyclohexyl-1H-1,2,4-triazole-1-carboxamide (compound #186);

3-amino-N-(3-(methyl)phenyl)-5-[4-[2-(piperidin-1-yl)ethoxy]phenylamino]-1H-1,2,4-triazole-1-carboxamide (compound #187);

3-amino-N-(3,5-dimethoxyphenyl)-5-[4-[2-(piperidin-1-yl)ethoxy]phenylamino]-1H-1,2,4-triazole-1-carboxamide (compound #188);

3-amino-N-cyclohexyl-5-[4-[2-(piperidin-1-yl)ethoxy]phenylamino]-1H-1,2,4-triazole-1-carboxamide (compound #189);

3-amino-N-cyclopentyl-5-[4-[2-(piperidin-1-yl)ethoxy]phenylamino]-1H-1,2,4-triazole-1-carboxamide (compound #190);

3-amino-1-(4-iso-propoxyphenyl)carbonyl-5-[4-[2-(pyrrolidin-1-yl)ethoxy]phenylamino]-1H-1,2,4-triazole (compound #191);

3-amino-1-(4-(iso-propoxy)phenyl)carbonyl-5-[4-(piperidin-1-yl)phenylamino]-1H-1,2,4-triazole (compound #192);

3-amino-N-(1,3-benzodioxol-5-yl)-5-[4-[2-(piperidin-1-yl)ethoxy]phenylamino]-1H-1,2,4-triazole-1-carboxamide (compound #193);

5-amino-N-(4-cyanophenyl)-3-[4-[2-(piperidin-1-yl)ethoxy]phenylamino]-1H-1,2,4-triazole-1-carboxamide (compound #194);

5-amino-1-[2-(bicyclo[2.2.1]hept-5-ene)carbonyl]-3-[4-[2-(pyrrolidin-1-yl)ethoxy]phenylamino]-1H-1,2,4-triazole (compound #196);

5-amino-1-(3-(dimethylamino)phenyl)carbonyl-3-[4-[2-(pyrrolidin-1-yl)ethoxy]phenylamino]-1H-1,2,4-triazole (compound #197);

5-amino-1-(3,4-(dimethoxy)phenyl)carbonyl-3-[4-[2-(pyrrolidin-1-yl)ethoxy]phenylamino]-1H-1,2,4-triazole (compound #198);

5-amino-N-(3,5-(dimethyl)phenyl)-3-[4-[2-(piperidin-1-yl)ethoxy]phenylamino]-1H-1,2,4-triazole-1-carboxamide (compound #199);

5-amino-1-[2-(bicyclo[2.2.1]heptane)carbonyl]-3-[4-[2-(pyrrolidin-1-yl)ethoxy]phenylamino]-1H-1,2,4-triazole (compound #200);

5-amino-3-[4-(piperidin-1-yl)phenylamino]-1-(tert-butoxycarbonyl)-1H-1,2,4-triazole (compound #201);

3-amino-1-(1H-indol-5-yl)carbonyl-5-[4-[2-(pyrrolidin-1-yl)ethoxy]phenylamino]-1H-1,2,4-triazole (compound #202);

5-amino-1-(pyridin-2-yl)carbonyl-3-[4-[2-(pyrrolidin-1-yl)ethoxy]phenylamino]-1H-1,2,4-triazole (compound #203);

5-amino-1-(pyridin-4-yl)carbonyl-3-[4-[2-(pyrrolidin-1-yl)ethoxy]phenylamino]-1H-1,2,4-triazole (compound #204);

5-amino-3-[(2H,3H-4-tert-butoxycarbonylbenzo[1,4]oxazin-6-yl)amino]-1-(3-methylphenyl)carbonyl-1,2,4-triazole (compound #206);

5-amino-1-(3-methylphenyl)carbonyl-3-[2-[N-[2-(tetrahydropyran-2-yloxy)ethyl]amino]carbonylbenzofuran-5-yl]amino-1H-1,2,4-triazole (compound #207);

5-amino-3-[2-[2-hydroxyethylaminocarbonyl]benzofuran-5-yl]amino-1-(3-methylphenyl)carbonyl-1H-1,2,4-triazole (compound #208);

3-amino-1-[3-[2-(1,3-dioxolan-2-yl)ethoxy]phenylcarbonyl-5-(1,4-benzodioxan-6-yl)amino-1H-1,2,4-triazole (compound #209);

5-amino-1-[3-[2-(1,3-dioxolan-2-yl)ethoxy]phenylcarbonyl-3-(1,4-benzodioxan-6-yl)amino-1H-1,2,4-triazole (compound #210);

5-amino-3-[2-(hydroxyl)phenylamino]-1-(4-methylphenyl)carbonyl-1H-1,2,4-triazole (compound #211);

5-amino-1-(3-methylphenyl)carbonyl-3-[3-[(2-methoxyethoxy)methoxy]phenylamino]-1H-1,2,4-triazole (compound #212);

3-amino-1-[4-[2-(1,3-dioxolan-2-yl)ethoxy]phenylcarbonyl-5-(1,4-benzodioxan-6-yl)amino-1H-1,2,4-triazole (compound #213);

5-amino-1-[4-[2-(1,3-dioxolan-2-yl)ethoxy]phenylcarbonyl-3-(1,4-benzodioxan-6-yl)amino-1H-1,2,4-triazole (compound #214);

5-amino-3-[(3,4-dihydrobenzo[1,4]oxazin-6-yl)amino]-1-(3-methylphenyl)carbonyl-1H-1,2,4-triazole (compound #215);

5-amino-3-(3-methoxymethoxy)phenylamino-1-(3-methylphenyl)carbonyl-1H-1,2,4-triazole (compound #216);

5-amino-3-(4-chlorophenyl)amino-1-(4-chlorophenyl)carbonyl-1H-1,2,4-triazole (compound #217);

5-amino-3-(4-bromophenyl)amino-1-(4-chlorophenyl)carbonyl-1H-1,2,4-triazole (compound #218);

5-amino-3-[2-(ethoxycarbonyl)benzofuran-5-yl]amino-1-(3-methylphenyl)carbonyl-1H-1,2,4-triazole (compound #219);

5-amino-1-(3-methylphenyl)carbonyl-3-(pyridin-3-yl)amino-1H-1,2,4-triazole (compound #220);

5-amino-1-(3-methylphenyl)carbonyl-3-[(3-tert-butoxycarbonylmethoxy)phenyl]amino-1H-1,2,4-triazole (compound #221);

5-amino-3-(2-methyl-2H-indazol-5yl)amino-1-(3-methylphenyl)carbonyl-1H-1,2,4-triazole (compound #222);

5-amino-1-(3-methylphenyl)carbonyl-3-[3-[2-(tetrahydropyran-2-yl)ethoxyaminocarbonyl]methoxy]phenylamino-1H-1,2,4-triazole (compound #223);

5-amino-3-(3-hydroxycarbonylmethoxy)phenylamino-1-(3-methylphenyl)carbonyl-1H-1,2,4-triazole (compound #224);

5-amino-3-[3-((2-hydroxyethyl)aminocarbonylmethoxy)phenyl]amino-1-(3-methylphenyl)carbonyl-1H-1,2,4-triazole (compound #225);

5-amino-3-(1,4-benzodioxan-6-yl)amino-1-[4-[2-(piperidin-1-yl)ethoxy]phenylcarbonyl-1H-1,2,4-triazole (compound #226);

5-amino-3-[1-methyl-1H-indazol-5-yl]amino-1-(3-methylphenyl)carbonyl-1H-1,2,4-triazole (compound #227);

5-amino-3-(1,4-benzodioxan-6-yl)amino-1-(3-(2,2,2-trifluoroethoxy)phenyl)carbonyl-1H-1,2,4-triazole (compound #228);

5-amino-3-(benzofuran-5-yl)amino-1-(3-methylphenyl)carbonyl-1H-1,2,4-triazole (compound #229);

5-amino-3-(1,4-benzodioxan-6-yl)amino-1-(4-(2,2,2-trifluoroethoxy)phenyl)carbonyl-1H-1,2,4-triazole (compound #230);

5-amino-1-(3-aminocarbonylmethoxy)phenylcarbonyl-3-(1,4-benzodioxan-6-yl)amino-1H-1,2,4-triazole (compound #231);

5-amino-3-(1,4-benzodioxan-6-yl)amino-1-(4-iso-propylphenyl)carbonyl-1H-1,2,4-triazole (compound #232);

3-amino-5-(1,4-benzodioxan-6-yl)amino-1-(4-iso-propylphenyl)carbonyl-1H-1,2,4-triazole (compound #233);

5-amino-1-(3,4-dimethylphenyl)carbonyl-3-(1,4-benzodioxan-6-yl)amino-1H-1,2,4-triazole (compound #234);

5-amino-1-(3-methylphenyl)carbonyl-3-[3-(methylsulfonylmethoxy)phenyl]amino-1H-1,2,4-triazole (compound #235);

3-amino-1-(3,4-dimethylphenyl)carbonyl-5-(1,4-benzodioxan-6-yl)amino-1H-1,2,4-triazole (compound #236);

5-amino-3-(1,4-benzodioxan-6-yl)amino-1-(4-thiomethylphenyl)carbonyl-1H-1,2,4-triazole (compound #237);

3-amino-5-(1,4-benzodioxan-6-yl)amino-1-(4-thiomethylphenyl)carbonyl-1H-1,2,4-triazole (compound #238);

5-amino-3-(1,4-benzodioxan-6-yl)amino-1-(3,5-dimethylphenyl)carbonyl-1H-1,2,4-triazole (compound #239);

5-amino-3-(1,4-benzodioxan-6-yl)amino-1-(4-nitrophenyl)carbonyl-1H-1,2,4-triazole (compound #240);

3-amino-5-(1,4-benzodioxan-6-yl)amino-1-[(4-fluoro-3-methyl)phenyl]carbonyl-1H-1,2,4-triazole (compound #241);

5-amino-3-(1,4-benzodioxan-6-yl)amino-1-[(4-fluoro-3-methyl)phenyl]carbonyl-1H-1,2,4-triazole (compound #242);

5-amino-1-(4-aminophenyl)carbonyl-3-(1,4-benzodioxan-6-yl)amino-1H-1,2,4-triazole (compound #243);

5-amino-3-(1,4-benzodioxan-6-yl)amino-1-[(4-trifluoromethyl)phenyl]carbonyl-1H-1,2,4-triazole (compound #244);

5-amino-1-(4-cyanophenyl)carbonyl-3-(1,4-benzodioxan-6-yl)amino-1H-1,2,4-triazole (compound #245);

1-[(4-Acetylamino)phenyl]carbonyl-5-amino-3-(1,4-benzodioxan-6-yl)-amino-1H-1,2,4-triazole (compound #246);

5-amino-1-[(4-dimethylamino)phenyl]carbonyl-3-(1,4-benzodioxan-6-yl)amino-1H-1,2,4-triazole (compound #247);

5-amino-3-(1,4-benzodioxan-6-yl)amino-1-[(4-methylsulfonyl)phenyl]carbonyl-1H-1,2,4-triazole (compound #248);

5-amino-1-[(3-chloro-4-methyl)phenyl]carbonyl-3-(1,4-benzodioxan-6-yl)-amino-1H-1,2,4-triazole (compound #249);

5-amino-3-(benzothiazol-6-yl)amino-1-(3-methylphenyl)carbonyl-1H-1,2,4-triazole (compound #250);

5-amino-1-(3-methylphenyl)carbonyl-3-(6-quinolinyl)amino-1H-1,2,4-triazole (compound #251);

5-amino-3-(1H-indol-5-yl)amino-1-(3-methylphenyl)carbonyl-1H-1,2,4-triazole (compound #252);

5-amino-3-(1H-2-methyl-indazol-6-yl)amino-1-(3-methylphenyl)carbonyl-1H-1,2,4-triazole (compound #253);

5-amino-3-(1H-1-methyl-indazol-6-yl)amino-1-(3-methylphenyl)carbonyl-1H-1,2,4-triazole (compound #254);

5-amino-3-(1H-2-methyl-indol-5-yl)amino-1-(3-methylphenyl)carbonyl-1H-1,2,4-triazole (compound #255);

5-amino-3-(benzothiazol-2-yl)amino-1-(3-methylphenyl)carbonyl-1H-1,2,4-triazole (compound #256);

5-amino-3-(1,4-benzodioxan-6-yl)amino-1-(3-methyl-4-methoxy)phenylcarbonyl-1H-1,2,4-triazole (compound #257);

5-amino-3-(1,4-benzodioxan-6-yl)amino-1-(3-methyl-4-iso-propoxy)phenylcarbonyl-1H-1,2,4-triazole (compound #258);

5-amino-3-(1,2-benzisothiazol-5-yl)amino-1-(3-methylphenyl)carbonyl-1H-1,2,4-triazole (compound #259);

5-amino-3-(3-methyl-1,2-benzisothiazol-5-yl)amino-1-(3-methylphenyl)carbonyl-1H-1,2,4-triazole (compound #260);

1-Acetyl-5-amino-3-(1,4-benzodioxan-6-yl)amino-1H-1,2,4-triazole (compound #261);

5-amino-3-[4-[2-(pyrrolidin-1-yl)ethoxy]-3-fluorophenyl]amino-1-[4-(morpholin-4-yl)phenyl]carbonyl-1H-1,2,4-triazole (compound #262), $^1$H-NMR (DMSO-d$_6$, 300 MHz) 9.21 (s, 1H), 8.20 (d, J=0.9 Hz, 1H), 7.75 (m, 2H), 6.80-7.60 (m, 4H), 4.10 (m, 1H), 3.75 (m, 4H), 3.30 (m, 5H), 3.20 (m, 2H), 2.95 (m, 2H), 2.85 (m, 1H), 2.40-2.60 (m, 5H), 1.65 (m, 2H) ppm.

5-amino-1-(4-(tert-butyl)phenyl)carbonyl-3-[3-(1,3-oxazol-5-yl)phenylamino]-1H-1,2,4-triazole (compound #263), tan solid; $^1$H-NMR (DMSO-d$_6$, 300 MHz) 9.48 (s, 1H), 8.39 (s, 1H), 8.14 (d, J=8.4 Hz, 2H), 8.08 (s, 1H), 7.82 (s, 2H), 7.57 (d, J=8.4 Hz, 2H), 7.36 (s, 1H), 7.32-7.28 (m, 2H), 1.35 (s, 9H) ppm; MS (ES) 403.07 (M+H), 401.24 (M−H).

5-amino-1-(4-(tert-butoxy)phenyl)carbonyl-3-[3-(1,3-oxazol-5-yl)phenylamino]-1H-1,2,4-triazole (compound #264), off-white solid; $^1$H-NMR (DMSO-d$_6$, 300 MHz) 8.33 (dt, J=9.0 Hz, 2.1 Hz, 2H), 8.03 (t, J=1.8 Hz, 1H), 7.89 (s, 1H), 7.32 (t, J=7.5 Hz, 2H), 7.25 (s, 1H), 7.11-7.08 (m, 3H), 6.72 (s, 2H), 1.48 (s, 9H) ppm; MS (ES) 419.04 (M+H), 417.18 (M−H).

5-amino-1-(1H-indol-6-yl)carbonyl-3-[4-[2-(morpholin-4-yl)ethoxy]phenylamino]-1H-1,2,4-triazole (compound #265), off-white solid; $^1$H-NMR (DMSO-d$_6$, 300 MHz) 11.59 (s, 1H), 9.02 (s, 1H), 8.52 (s, 1H), 8.12 (s, 1H), 7.85-7.59 (m, 6H), 7.46 (d, J=9.0 Hz, 2H), 6.83 (d, J=9.0 Hz, 2H), 6.55-6.54 (m, 1H), 3.99 (t, J=5.7 Hz, 2H), 3.56 (t, J=4.5 Hz, 4H), 2.64 (t, J=5.7 Hz, 2H), 2.45 (t, J=4.5 Hz, 4H) ppm; MS (ES) 448.108 (M+H), 446.23 (M−H).

5-amino-1-(4-(tert-butyl)phenyl)carbonyl-3-[4-[2-(morpholin-4-yl)ethoxy]phenylamino]-1H-1,2,4-triazole (compound #266), yellow solid; $^1$H-NMR (DMSO-d$_6$, 300 MHz) 9.02 (s, 1H), 8.16-8.12 (m, 3H), 7.74 (s, 2H), 7.56 (d, J=8.7 Hz, 2H), 7.41 (d, J=8.7 Hz, 2H), 6.82 (d, J=8.7 Hz, 2H), 4.00 (t, J=5.7 Hz, 2H), 3.56 (t, J=4.5 Hz, 4H), 2.64 (t, J=5.7 Hz, 2H), 2.45 (t, J=4.5 Hz, 4H), 1.34 (s, 9H) ppm; MS (ES) 465.15 (M+H), 463.29 (M−H).

5-amino-1-(4-(tert-butoxy)phenyl)carbonyl-3-[4-[2-(morpholin-4-yl)ethoxy]phenylamino]-1H-1,2,4-triazole (compound #267), off-white solid; $^1$H-NMR (DMSO-d$_6$, 300 MHz) 9.02 (s, 1H), 8.18 (d, J=8.7 Hz, 2H), 8.11 (s, 1H), 7.71 (s, 2H), 7.41 (d, J=8.7 Hz, 2H), 7.32 (d, J=8.7 Hz, 2H), 6.82 (d, J=8.7 Hz, 2H), 4.00 (t, J=4.2 Hz, 2H), 3.56 (t, J=3.6 Hz, 4H), 2.64 (t, J=5.7 Hz, 2H), 2.45 (t, J=4.5 Hz, 4H), 1.42 (s, 9H) ppm; MS (ES) 481.18 (M+H), 479.25 (M−H).

5-amino-1-(4-(imidazol-1-yl)phenyl)carbonyl-3-[4-[2-(pyrrolidin-1-yl)ethoxy]phenylamino]-1H-1,2,4-triazole (compound #268), yellow solid; $^1$H-NMR (DMSO-d$_6$, 300 MHz) 9.09 (s, 1H), 8.44 (s, 1H), 8.32 (d, J=9.0 Hz, 2H), 8.14 (s, 3H), 7.91 (s, 1H), 7.87 (d, J=8.7 Hz, 2H), 7.78 (m, 2H), 7.42 (d, J=9.0 Hz, 2H), 7.15 (s, 1H), 6.83 (d, J=9.3 Hz, 2H), 3.98 (t, J=6.7 Hz, 2H), 2.79 (t, J=6.7 Hz, 2H), 2.55 (m, 4H), 1.68 (m, 4H) ppm; MS (ES) 459.08 (M+H), 457.22 (M−H).

5-amino-1-(4-(phenoxy)phenyl)carbonyl-3-[4-[2-(pyrrolidin-1-yl)ethoxy]phenylamino]-1H-1,2,4-triazole (compound #269), pale yellow solid; $^1$H-NMR (DMSO-d$_6$, 300 MHz) 9.04 (s, 1H), 8.25 (d, J=9.0 Hz, 2H), 8.17 (s, 1H), 7.74 (s, 1H), 7.49-7.39 (m, 4H), 7.24 (t, J=7.2 Hz, 1H), 7.15 (d, J=8.7 Hz, 2H), 7.09 (d, J=7.2 Hz, 2H), 6.81 (d, J=6.6 Hz, 2H), 3.99 (t, J=6.0 Hz, 2H), 2.81 (t, J=6.0 Hz, 2H), 2.58 (m, 4H), 1.69 (m, 4H) ppm; MS (ES) 485.07 (M+H), 483.30 (M−H).

5-amino-1-(4-(tert-butoxycarbonylamino)phenyl)carbonyl-3-[4-[2-(pyrrolidin-1-yl)ethoxy]phenylamino]-1H-1,2,4-triazole (compound #270), yellow solid; $^1$H-NMR (DMSO-d$_6$, 300 MHz) 9.78 (s, 1H), 9.02 (s, 1H), 8.18-8.14 (m, 3H), 7.70 (s, 2H), 7.59 (d, J=9.0 Hz, 2H), 7.41 (d, J=9.0

Hz, 2H), 6.81 (d, J=9.0 Hz, 2H), 4.00 (t, J=6.0 Hz, 2H), 2.82 (t, J=6.0 Hz, 2H), 2.58 (m, 4H), 1.69 (m, 4H), 1.50 (s, 9H) ppm; MS (ES) 508.13 (M+H), 506.27 (M−H).

5-amino-1-(benzo[d]thiazol-6-yl)carbonyl-3-[4-[2-(pyrrolidin-1-yl)ethoxy]phenylamino]-1H-1,2,4-triazole (compound #271), off-white solid; pale yellow solid; $^1$H-NMR (DMSO-d$_6$, 300 MHz) 9.60 (s, 1H), 9.06 (d, J=9.0 Hz, 2H), 8.24 (q, J=8.4 Hz, 3H), 8.14 (d, J=9.0 Hz, 1H), 7.80 (s, 2H), 7.41 (d, J=9.0 Hz, 2H), 6.78 (d, J=9.0 Hz, 2H), 3.97 (t, J=6.0 Hz, 2H), 2.78 (m, 2H), 1.68 (m, 4H) ppm; MS (ES) 450.04 (M+H), 448.22 (M−H).

5-amino-1-(4-(tert-butoxy)phenyl)carbonyl-3-[4-[2-(pyrrolidin-1-yl)ethoxy]phenyl][methyl]amino-1H-1,2,4-triazole (compound #272), off-white solid; $^1$H-NMR (DMSO-d$_6$, 300 MHz) 8.19 (d, J=8.7 Hz, 2H), 7.71 (s, 2H), 7.29 (d, J=8.7 Hz, 2H), 7.07 (d, J=8.7 Hz, 2H), 6.88 (d, J=8.7 Hz, 2H), 4.04 (t, J=6.0 Hz, 2H), 3.29 (s, 3H), 2.78 (t, J=6.0 Hz, 2H), 2.53 (m, 4H), 1.68 (m, 4H), 1.40 (s, 9H) ppm; MS (ES) 479.13 (M+H).

5-amino-1-(4-(tert-butyl)phenyl)carbonyl-3-[4-((tert-butoxycarbonyl)aminochroman-6-yl]amino-1H-1,2,4-triazole (compound #273), off-white solid; $^1$H-NMR (DMSO-d$_6$, 300 MHz) 8.97 (s, 1H), 8.14 (d, J=8.4 Hz, 2H), 7.75 (m, 2H), 7.62 (d, J=8.4 Hz, 2H), 7.33-7.27 (m, 3H), 6.62 (d, J=9.0 Hz, 1H), 6.78 (d, J=9.0 Hz, 2H), 4.64 (m, 1H), 4.10 (t, J=5.3 Hz, 2H), 1.98 (m, 1H), 1.85 (m, 1H), 1.38 (s, 9H), 1.34 (s, 9H) ppm; MS (ES) 507.70 (M+H), 505.73 (M−H).

5-amino-1-(4-(iso-propoxy)phenyl)carbonyl-3-[4-((tert-butoxycarbonyl)aminochroman-6-yl]amino-1H-1,2,4-triazole (compound #274), off-white solid; $^1$H-NMR (DMSO-d$_6$, 300 MHz) 8.97 (s, 1H), 8.28 (d, J=9.3 Hz, 2H), 7.72 (s, 2H), 7.38-7.25 (m, 3H), 7.08 (d, J=9.3 Hz, 2H), 6.64 (d, J=8.7 Hz, 1H), 4.81 (quint., J=6.0 Hz, 1H), 4.65 (m, 1H), 4.10 (t, J=5.7 Hz, 2H), 1.98 (m, 1H), 1.85 (m, 1H), 1.32 (m, 15H) ppm; MS (ES) 509.64 (M+H), 507.62 (M−H).

5-amino-1-(4-(tert-butoxy)phenyl)carbonyl-3-[4-((tert-butoxycarbonyl)aminochroman-6-yl]amino-1H-1,2,4-triazole (compound #275), off-white solid; $^1$H-NMR (DMSO-d$_6$, 300 MHz) 8.97 (s, 1H), 8.19 (d, J=9.0 Hz, 2H), 7.73 (s, 2H), 7.33-7.27 (m, 3H), 7.17 (d, J=8.7 Hz, 1H), 6.62 (d, J=9.0 Hz, 2H), 4.64 (m, 1H), 4.10 (t, J=4.8 Hz, 2H), 1.98 (m, 1H), 1.84 (m, 1H), 1.40 (m, 18H) ppm; MS (ES) 523.70 (M+H), 521.59 (M−H).

5-amino-1-(1H-indol-6-yl)carbonyl-3-[4-((tert-butoxycarbonyl)aminochroman-6-yl]amino-1H-1,2,4-triazole (compound #276), off-white solid; $^1$H-NMR (DMSO-d$_6$, 300 MHz) 11.53 (s, 1H), 8.97 (s, 1H), 8.47 (s, 1H), 7.91 (d, J=7.5 Hz, 2H), 7.73 (s, 2H), 7.66 (d, J=8.4 Hz, 1H) 7.61 (m, 1H), 7.49 (dd, J=8.7, 2.7 Hz, 1H), 7.32 (d, J=8.7 Hz, 1H), 7.21 (s, 1H), 6.54 (d, J=8.7 Hz, 1H), 6.52 (s, 1H), 4.64 (m, 1H), 4.10 (m, 2H), 1.98 (m, 1H), 1.85 (m, 1H), 1.39 (m, 9H) ppm; MS (ES) 490.61 (M+H), 488.55 (M−H).

5-amino-1-(4-(phenyl)phenyl)carbonyl-3-[4-[2-(pyrrolidin-1-yl)ethoxy]phenylamino]-1H-1,2,4-triazole (compound #277), yellow solid; $^1$H-NMR (DMSO-d$_6$, 300 MHz) 9.08 (s, 1H), 8.28 (d, J=8.7 Hz, 2H), 8.16 (s, 1H), 7.86 (d, J=8.7 Hz, 2H), 7.80 (m, 4H), 7.51 (t, J=7.2 Hz, 2H), 7.45-7.40 (m, 3H), 6.83 (d, J=9.3 Hz, 2H), 3.99 (t, J=6.0 Hz, 2H), 2.80 (t, J=6.0 Hz, 2H), 2.56 (m, 4H), 1.68 (m, 4H) ppm; MS (ES) 469.10 (M+H), 467.29 (M−H).

5-amino-1-[4-((tert-butoxycarbonyl)aminomethyl)phenyl]carbonyl-3-[4-[2-(pyrrolidin-1-yl)ethoxy]phenylamino]-1H-1,2,4-triazole (compound #278), yellow solid; $^1$H-NMR (DMSO-d$_6$, 300 MHz) 9.05 (s, 1H), 8.17 (s, 1H), 8.11 (d, J=8.1 Hz, 2H), 7.75 (s, 1H), 7.39 (t, J=6.0 Hz, 4H), 6.79 (d, J=9.3 Hz, 2H), 4.21 (d, J=6.0 Hz, 2H), 4.00 (t, J=6.0 Hz, 2H), 2.85 (t, J=6.0 Hz, 2H), 2.62 (m, 4H), 1.71 (m, 4H), 1.41 (s, 9H) ppm; MS (ES) 522.65 (M+H), 520.59 (M−H).

5-amino-1-(2,3-dihydrobenzofuran-5-yl)carbonyl-3-[4-[2-(pyrrolidin-1-yl)ethoxy]phenylamino]-1H-1,2,4-triazole (compound #279), yellow solid; $^1$H-NMR (DMSO-d$_6$, 300 MHz) 9.04 (s, 1H), 8.17 (m, 2H), 8.08 (dd, J=8.6, 2.0 Hz, 1H), 7.70 (s, 1H), 7.43 (d, J=9.3 Hz, 2H), 6.94-6.82 (m, 3H), 4.67 (t, J=9.0 Hz, 2H), 4.00 (t, J=6.0 Hz, 2H), 3.28 (t, J=8.7 Hz, 2H), 2.84 (t, J=6.0 Hz, 2H), 2.60 (m, 4H), 1.70 (m, 4H) ppm; MS (ES) 435.58 (M+H), 433.46 (M−H).

5-amino-1-(4-(1,2,3-thiadiazol-4-yl)phenyl)carbonyl-3-[4-[2-(pyrrolidin-1-yl)ethoxy]phenylamino]-1H-1,2,4-triazole (compound #280), off-white solid; $^1$H-NMR (DMSO-d$_6$, 300 MHz) 9.81 (s, 1H), 9.10 (s, 1H), 8.33 (s, 4H), 8.17 (s, 1H), 7.80 (s, 2H), 7.42 (d, J=9.0 Hz, 2H), 6.82 (d, J=9.0 Hz, 2H), 3.97 (t, J=6.0 Hz, 2H), 2.77 (t, J=6.0 Hz, 2H), 2.53 (m, 4H), 1.67 (m, 4H) ppm; MS (ES) 477.51 (M+H), 475.47 (M−H).

5-amino-1-(1H-benzo[d][1,2,3]triazol-5-yl)carbonyl-3-[4-[2-(pyrrolidin-1-yl)ethoxy]phenylamino]-1H-1,2,4-triazole (compound #281), yellow solid; $^1$H-NMR (DMSO-d$_6$, 300 MHz) 9.09 (s, 1H), 8.93 (s, 1H), 8.16 (s, 1H), 8.11 (dd, J=8.7, 1.2 Hz, 1H), 7.97 (d, J=8.4 Hz, 2H), 6.79 (d, J=9.0 Hz, 1H), 3.99 (t, J=5.7 Hz, 2H), 2.83 (t, J=5.7 Hz, 2H), 2.60 (m, 4H), 1.70 (m, 4H) ppm; MS (ES) 434.56 (M+H), 432.51 (M−H).

5-amino-1-(4-(pyrrol-1-yl)phenyl)carbonyl-3-[4-[2-(pyrrolidin-1-yl)ethoxy]phenylamino]-1H-1,2,4-triazole (compound #282), pale yellow solid; $^1$H-NMR (DMSO-d$_6$, 300 MHz) 9.09 (s, 1H), 8.32 (d, J=9.0 Hz, 2H), 8.18 (s, 1H), 7.77 (m, 4H), 7.56 (m, 2H), 7.43 (d, J=9.3 Hz, 2H), 6.85 (d, J=9.0 Hz, 2H), 4.01 (t, J=6.0 Hz, 2H), 2.63 (m, 4H), 1.71 (m, 4H) ppm; MS (ES) 458.56 (M+H), 456.55 (M−H).

5-amino-1-(3-methylthien-2-yl)carbonyl-3-[4-[2-(pyrrolidin-1-yl)ethoxy]phenylamino]-1H-1,2,4-triazole (compound #283), off-white solid; $^1$H-NMR (DMSO-d$_6$, 300 MHz), 9.80 (s, 1H), 9.21 (s, 1H), 7.95 (d, J=5.4 Hz, 1H), 7.75 (s, 2H), 7.61 (d, J=9.0 Hz, 2H), 7.13 (d, J=5.4 Hz, 1H), 6.97 (d, J=9.0 Hz, 2H), 4.24 (t, J=5.1 Hz, 2H), 3.13 (m, 2H), 2.62 (s, 2H), 2.52 (s, 2H), 2.04-1.87 (m, 4H) ppm; MS (ES) 413.03 (M+H).

5-amino-1-(5-methylthien-2-yl)carbonyl-3-[4-[2-(pyrrolidin-1-yl)ethoxy]phenylamino]-1H-1,2,4-triazole (compound #284), pale yellow solid; $^1$H-NMR (DMSO-d$_6$, 300 MHz), 9.63 (s, 1H), 9.24 (s, 1H), 8.11 (d, J=3.9 Hz, 1H), 7.75 (s, 2H), 7.60 (d, J=9.0 Hz, 2H), 7.03 (d, J=3.9 Hz, 1H), 6.99 (d, J=9.0 Hz, 2H), 4.25 (t, J=5.1 Hz, 2H), 3.57 (m, 2H), 3.14 (m, 2H), 2.58 (s, 2H), 2.04-1.87 (m, 4H) ppm; MS (ES) 413.03 (M+H).

5-amino-1-(thien-2-yl)carbonyl-3-[4-[2-(pyrrolidin-1-yl)ethoxy]phenylamino]-1H-1,2,4-triazole (compound #285), pale yellow solid; $^1$H-NMR (DMSO-d$_6$, 300 MHz), 8.50 (s, 1H), 8.35 (dd, J=3.6, 1.2 Hz, 1H), 7.95 (dd, J=5.1, 1.2 Hz, 1H), 7.62 (d, J=9.0 Hz, 2H), 7.25 (dd, J=5.1, 3.6 Hz, 1H), 7.01 (d, J=9.0 Hz, 2H), 4.30 (t, J=5.4 Hz, 2H), 3.58 (t, J=5.4 Hz, 2H), 3.40 (m, 4H), 2.10 (m, 4H) ppm; MS (ES) 399.03 (M+H), 397.04 (M−H).

5-amino-1-(4-(methylamino)phenyl)carbonyl-3-[4-[2-(pyrrolidin-1-yl)ethoxy]phenylamino]-1H-1,2,4-triazole (compound #286), off-white solid; $^1$H-NMR (DMSO-d$_6$, 300 MHz) 8.48 (s, 1H), 8.27-8.23 (m, 2H), 7.51 (d, J=9.0 Hz, 2H), 6.94 (d, J=9.0 Hz, 2H), 6.61 (d, J=9.0 Hz, 2H), 4.27 (t, J=5.1 Hz, 2H), 3.56 (t, J=5.1 Hz, 2H), 3.40 (s, 4H), 2.79 (s, 3H), 2.10 (m, 4H) ppm; MS (ES) 422.07 (M+H), 420.24 (M−H).

5-amino-1-(4-(methylthio)phenyl)carbonyl-3-[4-[2-(pyrrolidin-1-yl)ethoxy]phenylamino]-1H-1,2,4-triazole (compound #287), off-white solid; $^1$H-NMR (DMSO-d$_6$, 300 MHz) 9.05 (s, 1H), 8.16 (m, 2H), 7.74 (s, 2H), 7.40 (m, 3H), 6.83 (d, J=9.0 Hz, 2H), 3.99 (t, J=6.0 Hz, 2H), 2.79 (t, J=6.0 Hz, 2H), 2.57 (m, 7H), 1.69 (m, 4H) ppm; MS (ES) 439.02 (M+H), 437.22 (M−H).

5-amino-1-(quinolin-6-yl)carbonyl-3-[4-[2-(pyrrolidin-1-yl)ethoxy]phenylamino]-1H-1,2,4-triazole (compound #288), yellow solid; $^1$H-NMR (DMSO-d$_6$, 300 MHz) 9.11 (s, 1H), 9.03 (dd, J=3.9, 1.2 Hz, 1H), 8.90 (d, J=1.5 Hz, 1H), 8.54 (d, J=9.0 Hz, 1H), 8.38 (dd, J=9.0, 1.5 Hz, 1H), 8.17 (s, 1H), 8.13 (d, J=9.0 Hz, 1H), 7.84 (s, 2H), 7.65 (dd, J=7.8, 3.9 Hz, 1H), 7.42 (d, J=9.0 Hz, 2H), 6.79 (d, J=9.0 Hz, 2H), 4.00 (t, J=5.7 Hz, 2H), 2.86 (t, J=5.7 Hz, 2H), 2.63 (m, 4H), 1.70 (m, 4H) ppm; MS (ES) 444.04 (M+H), 442.29 (M–H).

5-amino-1-(2,6-difluorophenyl)carbonyl-3-[4-[2-(pyrrolidin-1-yl)ethoxy]phenylamino]-1H-1,2,4-triazole (compound #289), off-white solid; $^1$H-NMR (DMSO-d$_6$, 300 MHz) 9.09 (s, 1H), 8.16 (s, 1H), 7.86 (s, 2H), 7.66 (m, 2H), 7.29 (d, J=8.4 Hz, 2H), 7.22 (d, J=9.0 Hz, 1H), 6.70 (d, J=9.0 Hz, 2H), 3.96 (t, J=6.0 Hz, 2H), 2.80 (t, J=6.0 Hz, 2H), 2.58 (m, 4H), 1.69 (m, 4H) ppm; MS (ES) 429.06 (M+H), 427.18 (M–H).

5-amino-1-(4-(tert-butylcarbonylamino)phenyl)carbonyl-3-[4-[2-(pyrrolidin-1-yl)ethoxy]phenylamino]-1H-1,2,4-triazole (compound #290), pale yellow solid; $^1$H-NMR (DMSO-d$_6$, 300 MHz) 9.52 (s, 1H), 9.03 (s, 1H), 8.21 (d, J=9.0 Hz, 2H), 8.60 (s, 1H), 7.83 (d, J=8.4 Hz, 2H), 7.72 (s, 2H), 7.42 (d, J=8.7 Hz, 2H), 6.81 (d, J=8.7 Hz, 2H), 3.99 (t, J=5.7 Hz, 2H), 2.78 (t, J=6.0 Hz, 2H), 2.54 (m, 4H), 1.68 (m, 4H), 1.25 (s, 9H) ppm; MS (ES) 492.13 (M+H), 490.30 (M–H).

5-amino-1-(4-(tert-butoxy)phenyl)carbonyl-3-[4-(pyrrolidin-1-yl)phenylamino]-1H-1,2,4-triazole (compound #291), yellow solid; $^1$H-NMR (DMSO-d$_6$, 300 MHz) 8.74 (s, 1H), 8.18 (d, J=8.7 Hz, 2H), 7.67 (s, 2H), 7.33 (d, J=8.7 Hz, 2H), 7.11 (d, J=8.7 Hz, 2H), 6.44 (d, J=9.0 Hz, 2H), 3.14 (m, 4H), 1.91 (m, 4H), 1.41 (s, 9H) ppm; MS (ES) 421.15 (M+H), 419.20 (M–H).

3-amino-1-(4-(tert-butoxy)phenyl)carbonyl-5-(4-(pyrrolidin-1-yl)phenylamino)-1H-1,2,4-triazole (compound #292), yellow solid; $^1$H-NMR (DMSO-d$_6$, 300 MHz) 9.88 (s, 1H), 8.15 (d, J=9.0 Hz, 2H), 7.50 (d, J=9.0 Hz, 2H), 7.07 (d, J=8.7 Hz, 2H), 6.52 (d, J=9.0 Hz, 2H), 5.98 (s, 2H), 3.20 (m, 4H), 1.94 (m, 4H), 1.39 (s, 9H) ppm; MS (ES) 421.13 (M+H).

5-amino-1-(4-(iso-propoxy)phenyl)carbonyl-3-[4-(pyrrolidin-1-yl)phenylamino]-1H-1,2,4-triazole (compound #293), yellow solid; $^1$H-NMR (DMSO-d$_6$, 300 MHz) 8.74 (s, 1H), 8.24 (d, J=9.0 Hz, 2H), 7.66 (s, 2H), 7.34 (d, J=9.0 Hz, 2H), 7.04 (d, J=9.3 Hz, 2H), 6.46 (d, J=8.7 Hz, 2H), 4.78 (sept., J=6.0 Hz, 1H), 3.15 (m, 4H), 1.91 (m, 4H), 1.31 (d, 6.0 Hz, 6H) ppm; MS (ES) 407.10 (M+H), 405.06 (M–H).

3-amino-1-(4-(iso-propoxy)phenyl)carbonyl-5-(4-(pyrrolidin-1-yl)phenylamino)-1H-1,2,4-triazole (compound #294), yellow solid; $^1$H-NMR (DMSO-d$_6$, 300 MHz) 9.91 (s, 1H), 8.22 (d, J=8.7 Hz, 2H), 7.49 (d, J=8.7 Hz, 2H), 7.01 (d, J=8.7 Hz, 2H), 6.51 (d, J=9.3 Hz, 2H), 5.97 (s, 2H), 4.75 (sept., 6.0 Hz, 1H), 3.20 (m, 4H), 1.94 (m, 4H), 1.30 (d, 5.7 Hz, 6H) ppm; MS (ES) 407.10 (M+H).

5-amino-1-(2,2-dimethyl-2H-benzo[b][1,4]oxazin-3(4H)-on-6-yl)carbonyl-3-[4-(pyrrolidin-1-yl)phenylamino]-1H-1,2,4-triazole (compound #295), yellow solid; $^1$H-NMR (DMSO-d$_6$, 300 MHz) 8.74 (s, 1H), 7.98 (dd, J=8.7, 2.1 Hz, 1H), 7.67 (m, 3H), 7.33 (d, J=9.0 Hz, 2H), 7.07 (d, J=8.4 Hz, 1H), 6.44 (d, J=9.0 Hz, 2H), 3.14 (m, 4H), 1.91 (m, 4H), 1.45 (s, 6H) ppm; MS (ES) 448.06 (M+H), 446.15 (M–H).

3-amino-1-(2,2-dimethyl-2H-benzo[b][1,4]oxazin-3(4H)-on-6-yl)carbonyl-5-[4-(pyrrolidin-1-yl)phenylamino]-1H-1,2,4-triazole (compound #296), yellow solid; $^1$H-NMR (DMSO-d$_6$, 300 MHz) 10.83 (s, 1H), 9.84 (s, 1H), 7.91 (dd, J=8.4, 2.1 Hz, 1H), 7.68 (d, J=2.1 Hz, 1H), 7.49 (d, J=9.0 Hz, 2H), 7.03 (d, J=8.7 Hz, 1H), 6.52 (d, J=9.0 Hz, 2H), 5.98 (s, 2H), 3.20 (m, 4H), 1.94 (m, 4H), 1.44 (s, 6H) ppm; MS (ES) 448.12 (M+H), 446.16 (M–H).

5-amino-1-(4-(tert-butyl)phenyl)carbonyl-3-[4-(pyrrolidin-1-yl)phenylamino]-1H-1,2,4-triazole (compound #297), yellow solid; $^1$H-NMR (DMSO-d$_6$, 300 MHz) 8.74 (s, 1H), 8.15 (d, J=8.7 Hz, 2H), 7.70 (s, 2H), 7.55 (d, J=8.7 Hz, 2H), 7.32 (d, J=8.7 Hz, 2H), 6.44 (d, J=9.0 Hz, 2H), 3.14 (m, 4H), 1.91 (m, 4H), 1.34 (s, 9H) ppm; MS (ES) 404.13 (M+H).

3-amino-1-(4-(tert-butyl)phenyl)carbonyl-5-[4-(pyrrolidin-1-yl)phenylamino]-1H-1,2,4-triazole (compound #298), yellow solid; $^1$H-NMR (DMSO-d$_6$, 300 MHz) 9.84 (s, 1H), 8.03 (d, J=8.4 Hz, 2H), 7.51 (dd, J=8.7, 2.7 Hz, 4H), 6.52 (d, J=9.0 Hz, 2H), 5.96 (s, 2H), 3.20 (m, 4H), 1.94 (m, 4H), 1.31 (s, 9H) ppm; MS (ES) 404.15 (M+H).

5-amino-1-(4-(dimethylamino)phenyl)carbonyl-3-[4-(pyrrolidin-1-yl)phenylamino]-1H-1,2,4-triazole (compound #299), yellow solid; $^1$H-NMR (DMSO-d$_6$, 300 MHz) 8.68 (s, 1H), 8.26 (d, J=9.0 Hz, 2H), 7.59 (s, 2H), 7.37 (d, J=9.0 Hz, 2H), 6.76 (d, J=9.3 Hz, 2H), 6.47 (d, J=9.0 Hz, 2H), 3.16 (m, 4H), 3.04 (s, 6H), 1.92 (m, 4H) ppm; MS (ES) 392.12 (M+H), 393.11 (M–H).

5-amino-1-(4-(methyl)phenyl)carbonyl-3-[4-(pyrrolidin-1-yl)phenylamino]-1H-1,2,4-triazole (compound #300), yellow solid; $^1$H-NMR (DMSO-d$_6$, 300 MHz) 8.76 (s, 1H), 8.04 (s, 1H), 7.92 (m, 1H), 7.69 (s, 2H), 7.43-7.41 (m, 2H), 7.33 (d, J=8.7 Hz, 2H), 6.42 (d, J=8.7 Hz, 2H), 3.13 (m, 4H), 2.41 (s, 3H), 1.91 (m, 4H) ppm; MS (ES) 363.10 (M+H), 361.17 (M–H).

3-amino-1-(4-methylphenyl)carbonyl-5-(4-(pyrrolidin-1-yl)phenylamino)-1H-1,2,4-triazole (compound #301), yellow solid; $^1$H-NMR (DMSO-d$_6$, 300 MHz) 9.82 (s, 1H), 7.88-7.84 (m, 2H), 7.50 (d, J=8.7 Hz, 2H), 7.40-7.37 (m, 2H), 6.50 (d, J=9.0 Hz, 2H), 5.98 (s, 2H), 3.20 (m, 4H), 2.37 (s, 3H), 1.94 (m, 4H) ppm; MS (ES) 363.10 (M+H), 361.29 (M–H).

5-amino-1-(4-(tert-butyl)phenyl)carbonyl-3-[4-[2-(pyrrolidin-1-yl)ethoxy]phenylamino]-1H-1,2,4-triazole (compound #302), yellow solid; $^1$H-NMR (DMSO-d$_6$, 300 MHz) 9.03 (s, 1H), 8.13 (d, J=8.4 Hz, 2H), 7.75 (s, 2H), 7.56 (d, J=8.4 Hz, 2H), 7.40 (d, J=8.7 Hz, 2H), 6.81 (d, J=9.0 Hz, 2H), 3.96 (t, J=5.7 Hz, 2H), 2.59 (t, J=5.7 Hz, 2H), 2.40 (m, 4H), 1.48 (m, 4H), 1.40-1.30 (m, 2H), 1.34 (s, 9H) ppm; MS (ES) 463.15 (M+H), 461.22 (M–H).

3-amino-1-(4-(tert-butyl)phenyl)carbonyl-5-[4-[2-(pyrrolidin-1-yl)ethoxy]phenylamino]-1H-1,2,4-triazole (compound #303), yellow solid; $^1$H-NMR (DMSO-d$_6$, 300 MHz) 9.96 (s, 1H), 8.02 (d, J=8.7 Hz, 2H), 7.64 (d, J=8.7 Hz, 2H), 7.52 (d, J=8.7 Hz, 2H), 6.92 (d, J=9.0 Hz, 2H), 6.03 (s, 2H), 4.03 (t, J=6.0 Hz, 2H), 2.62 (t, J=6.0 Hz, 2H), 2.41 (m, 4H), 1.49 (m, 4H), 1.38 (m, 2H), 1.31 (s, 9H) ppm; MS (ES) 463.15 (M+H), 461.34 (M–H).

3-amino-1-(4-(morpholin-4-yl)phenyl)carbonyl-5-[3-fluoro-4-[2-(pyrrolidin-1-yl)ethoxy]phenylamino]-1H-1,2,4-triazole (compound #304), yellow solid; $^1$H-NMR (DMSO-d$_6$, 300 MHz) 10.17 (s, 1H), 8.22 (d, J=9.0 Hz, 2H), 7.86 (dd, J=13.8, 3.0 Hz, 1H), 7.40 (d, J=7.2 Hz, 1H), 7.15 (t, J=9.1 Hz, 1H), 6.99 (d, J=9.3 Hz, 2H), 6.04 (s, 2H), 4.14 (t, J=5.7 Hz, 2H), 3.73 (m, 4H), 3.33 (m, 4H), 2.91 (s, 2H), 2.64 (s, 4H), 1.72 (m, 4H) ppm; MS (ES) 496.94 (M+H), 494.56 (M–H).

5-amino-1-(4-(tert-butoxy)phenyl)carbonyl-3-[3-fluoro-4-[2-(pyrrolidin-1-yl)ethoxy]phenylamino]-1H-1,2,4-triazole (compound #305), yellow solid; $^1$H-NMR (DMSO-d$_6$, 300 MHz) 9.26 (s, 1H), 8.12 (d, J=9.0 Hz, 2H), 7.74 (s, 2H), 7.49 (dd, J=13.8, 2.1 Hz, 1H), 7.16-6.98 (m, 4H), 4.03 (t, J=6.0 Hz, 2H), 2.76 (t, J=5.7 Hz, 2H), 2.51 (m, 4H), 1.67 (m, 4H), 1.41 (s, 9H) ppm; MS (ES) 483.14 (M+H), 481.30 (M–H).

5-amino-1-(4-(1,2,3-thiadiazol-4-yl)phenyl)carbonyl-3-[3-fluoro-4-[2-(pyrrolidin-1-yl)ethoxy]phenylamino]-1H-1,2,4-triazole (compound #306), yellow solid; $^1$H-NMR (DMSO-d$_6$, 300 MHz) 9.81 (d, J=1.2 Hz, 1H), 9.31 (s, 1H), 8.30 (s, 4H), 8.14 (d, J=1.5 Hz, 1H), 7.83 (s, 2H), 7.44 (dd, J=14.1, 1.8 Hz, 1H), 7.17 (d, J=10.2 Hz, 1H), 7.03 (t, J=9.1 Hz, 1H), 4.02 (t, J=6.0 Hz, 2H), 2.75 (t, J=6.0 Hz, 2H), 2.51 (m, 4H), 1.65 (m, 4H) ppm; MS (ES) 495.05 (M+H), 493.14 (M–H).

5-amino-1-(4-(iso-propoxy)phenyl)carbonyl-3-[3-fluoro-4-[2-(pyrrolidin-1-yl)ethoxy]phenylamino]-1H-1,2,4-triazole (compound #307), yellow solid; ¹H-NMR (DMSO-d₆, 300 MHz) 9.25 (s, 1H), 8.18 (d, J=8.7 Hz, 2H), 7.73 (s, 2H), 7.47 (dd, J=14.4, 2.4 Hz, 1H), 7.17 (d, J=11.7 Hz, 1H), 7.08-7.02 (m, 3H), 4.76 (sept., J=6.1 Hz, 1H), 4.04 (t, J=6.0 Hz, 2H), 2.77 (t, J=5.7 Hz, 2H), 2.53 (m, 4H), 1.67 (m, 4H), 1.31 (d, J=5.7 Hz, 6H) ppm; MS (ES) 469.12 (M+H), 467.25 (M−H).

5-amino-1-(phenyl)carbonyl-3-[3-fluoro-4-[2-(pyrrolidin-1-yl)ethoxy]phenylamino]-1H-1,2,4-triazole (compound #308), yellow solid; ¹H-NMR (DMSO-d₆, 300 MHz) 9.27 (s, 1H), 8.13-8.08 (m, 2H), 7.78 (s, 2H), 7.66-7.42 (m, 4H), 7.12-6.98 (m, 2H), 4.03 (t, J=6.0 Hz, 2H), 2.76 (t, J=6.0 Hz, 2H), 2.51 (m, 4H), 1.67 (m, 4H) ppm; MS (ES) 411.10 (M+H), 409.20 (M−H).

5-amino-1-(1H-indol-6-yl)carbonyl-3-[3-fluoro-4-[2-(pyrrolidin-1-yl)ethoxy]phenylamino]-1H-1,2,4-triazole (compound #309), yellow solid; ¹H-NMR (DMSO-d₆, 300 MHz) 11.55 (s, 1H), 9.25 (s, 1H), 8.41 (s, 1H), 8.14 (s, 1H), 7.82 (dd, J=8.1, 1.2 Hz, 1H), 7.74 (s, 2H), 7.65-7.60 (m, 2H), 7.47 (dd, J=14.1, 2.1 Hz, 1H), 7.20 (d, J=9.9 Hz, 1H), 7.04 (t, J=9.45 Hz, 1H), 6.54 (s, 1H), 4.03 (t, J=6.0 Hz, 2H), 2.77 (t, J=6.0 Hz, 2H), 2.52 (m, 4H), 1.67 (m, 4H) ppm; MS (ES) 450.09 (M+H), 448.24 (M−H).

5-amino-1-(3-(thiazol-2-yl)phenyl)carbonyl-3-[4-[2-(pyrrolidin-1-yl)ethoxy]phenylamino]-1H-1,2,4-triazole (compound #310), yellow solid; ¹H-NMR (DMSO-d₆, 300 MHz) 9.12 (s, 1H), 8.90 (s, 1H), 8.22-8.13 (m, 3H), 7.98 (d, J=3.0 Hz, 1H), 7.87-7.80 (m, 3H), 7.68 (t, J=7.8 Hz, 1H), 7.44 (d, J=8.7 Hz, 2H), 6.69 (d, J=8.7 Hz, 2H), 3.98 (t, J=5.7 Hz, 2H), 2.88 (t, J=5.7 Hz, 2H), 2.66 (m, 4H), 1.72 (m, 4H) ppm; MS (ES) 476.01 (M+H), 474.17 (M−H).

5-amino-1-(4-(thien-2-yl)phenyl)carbonyl-3-[4-[2-(pyrrolidin-1-yl)ethoxy]phenylamino]-1H-1,2,4-triazole (compound #311), yellow solid; ¹H-NMR (DMSO-d₆, 300 MHz) 9.07 (s, 1H), 8.23 (d, J=8.4 Hz, 2H), 7.84 (d, J=8.4 Hz, 2H), 7.77 (s, 2H), 7.69 (m, 1H), 7.42 (d, J=9.0 Hz, 2H), 7.19 (m, 1H), 6.83 (d, J=9.0 Hz, 2H), 3.99 (t, J=6.0 Hz, 2H), 2.79 (t, J=6.0 Hz, 2H), 2.55 (m, 4H), 1.68 (m, 4H) ppm; MS (ES) 475.04 (M+H), 473.20 (M−H).

5-amino-1-(1,2,3-thiadiazol-4-yl)carbonyl-3-[4-[2-(pyrrolidin-1-yl)ethoxy]phenylamino]-1H-1,2,4-triazole (compound #312), pale yellow solid; ¹H-NMR (DMSO-d₆, 300 MHz), 8.15 (s, 1H), 7.46 (d, J=8.7 Hz, 2H), 6.98 (d, J=8.7, 2H), 5.11 (s, 1H), 4.08 (t, J=5.7 Hz, 2H), 2.86 (t, J=5.7 Hz, 2H), 2.60 (m, 4H), 1.70 (m, 4H) ppm; MS (ES) 373.03 (M+H), 371.22 (M−H).

5-amino-1-(3-(thien-2-yl)phenyl)carbonyl-3-[4-[2-(pyrrolidin-1-yl)ethoxy]phenylamino]-1H-1,2,4-triazole (compound #313), off-white solid; ¹H-NMR (DMSO-d₆, 300 MHz) 8.88 (s, 1H), 8.32 (s, 1H), 7.76-7.70 (m, 2H), 7.59 (s, 2H), 7.40-7.22 (m, 2H), 7.21 (d, J=9.0 Hz, 2H), 6.96-6.94 (m, 1H), 6.46 (d, J=9.0 Hz, 2H), 3.74 (t, J=5.7 Hz, 2H), 2.64 (t, J=5.7 Hz, 2H), 2.41 (m, 4H), 1.49 (m, 4H) ppm; MS (ES) 475.04 (M+H), 473.14 (M−H).

5-amino-1-(4-(thien-3-yl)phenyl)carbonyl-3-[4-[2-(pyrrolidin-1-yl)ethoxy]phenylamino]-1H-1,2,4-triazole (compound #314), pale yellow solid; ¹H-NMR (DMSO-d₆, 300 MHz) 9.07 (s, 1H), 8.23 (d, J=8.4 Hz, 2H), 8.10 (t, J=2.1 Hz, 1H), 7.91 (d, J=8.7 Hz, 2H), 7.77 (s, 2H), 7.69 (m, 1H), 7.42 (d, J=8.7 Hz, 2H), 6.83 (d, J=8.7 Hz, 2H), 3.99 (t, J=6.0 Hz, 2H), 2.80 (t, J=6.0 Hz, 2H), 2.56 (m, 4H), 1.68 (m, 4H) ppm; MS (ES) 475.04 (M+H), 473.24 (M−H).

5-amino-1-(4-(tert-butyl)phenyl)carbonyl-3-[3-methoxy-4-[2-(pyrrolidin-1-yl)ethoxy]phenylamino]-1H-1,2,4-triazole (compound #315), off-white solid; ¹H-NMR (DMSO-d₆, 300 MHz) 9.10 (s, 1H), 8.08 (d, J=8.1 Hz, 2H), 7.77 (s, 2H), 7.51 (d, J=8.1 Hz, 2H), 7.50 (s, 1H), 6.85-6.77 (m, 2H), 3.98 (t, J=6.0 Hz, 2H), 3.62 (s, 3H), 2.89 (t, J=6.0 Hz, 2H), 2.69 (m, 4H), 1.73 (m, 4H), 1.31 (s, 9H) ppm; MS (ES) 479.13 (M+H), 477.30 (M−H).

5-amino-1-(4-(iso-propoxy)phenyl)carbonyl-3-[3-methoxy-4-[2-(pyrrolidin-1-yl)ethoxy]phenylamino]-1H-1,2,4-triazole (compound #316), off-white solid; ¹H-NMR (DMSO-d₆, 300 MHz) 9.06 (s, 1H), 8.22 (d, J=8.4 Hz, 2H), 7.71 (s, 2H), 7.42 (d, J=1.8 Hz, 1H), 7.01 (d, J=8.7 Hz, 2H), 6.85-6.77 (m, 2H), 4.75 (sept., J=2.7 Hz, 1H), 3.97 (t, J=6.0 Hz, 2H), 3.68 (s, 3H), 2.82 (t, J=6.0 Hz, 2H), 2.60 (m, 4H), 1.70 (m, 4H), 1.31 (d, J=2.7 Hz, 6H) ppm; MS (ES) 481.08 (M+H).

5-amino-1-(4-(tert-butoxy)phenyl)carbonyl-3-[3-methoxy-4-[2-(pyrrolidin-1-yl)ethoxy]phenylamino]-1H-1,2,4-triazole (compound #317), off-white solid; ¹H-NMR (DMSO-d₆, 300 MHz) 9.10 (s, 1H), 8.22 (s, 1H), 8.18 (d, J=8.7 Hz, 2H), 7.77 (s, 2H), 7.51 (d, J=8.1 Hz, 2H), 7.45 (s, 1H), 7.08 (d, J=8.7 Hz, 2H), 6.84 (s, 2H), 3.99 (t, J=6.0 Hz, 2H), 3.67 (s, 3H), 2.91 (t, J=6.0 Hz, 2H), 2.69 (m, 4H), 1.73 (m, 4H), 1.31 (s, 9H) ppm; MS (ES) 495.11 (M+H), 493.29 (M−H).

5-amino-1-(1H-indol-6-yl)carbonyl-3-[3-methoxy-4-[2-(pyrrolidin-1-yl)ethoxy]phenylamino]-1H-1,2,4-triazole (compound #318), pale yellow solid; ¹H-NMR (DMSO-d₆, 300 MHz) 11.54 (s, 1H), 9.06 (s, 1H), 8.42 (s, 1H), 8.20 (s, 1H), 7.84 (d, J=7.5 Hz, 1H), 7.72-7.59 (m, 4H), 7.43 (d, J=2.1 Hz, 1H), 6.91 (dd, J=7.5, 2.1 Hz, 1H), 6.84 (d, J=9.0 Hz, 1H), 6.53 (s, 1H), 3.97 (t, J=6.0 Hz, 2H), 3.51 (s, 3H), 2.86 (t, J=6.0 Hz, 2H), 2.65 (m, 4H), 1.71 (m, 4H) ppm; MS (ES) 462.08 (M+H), 460.22 (M−H).

5-amino-1-(4-(1,2,3-thiadiazol-4-yl)phenyl)carbonyl-3-[3-methoxy-4-[2-(pyrrolidin-1-yl)ethoxy]phenylamino]-1H-1,2,4-triazole (compound #319);

5-amino-1-(4-(tert-butyl)phenyl)carbonyl-3-[4-[2-(azepan-1-yl)ethoxy]phenylamino]-1H-1,2,4-triazole (compound #320), off-white solid; ¹H-NMR (DMSO-d₆, 300 MHz) 9.03 (s, 1H), 8.17 (s, 1H), 8.14 (d, J=8.4 Hz, 2H), 7.75 (s, 2H), 7.56 (d, J=8.4 Hz, 1H), 7.41 (d, J=9.0 Hz, 2H), 6.81 (d, J=8.7 Hz, 2H), 3.98 (t, J=6.0 Hz, 2H), 2.88 (t, J=6.0 Hz, 2H), 2.74 (m, 4H), 1.59-1.54 (m, 8H), 1.33 (s, 9H) ppm; MS (ES) 477.18 (M+H), 475.33 (M−H).

5-amino-1-(4-(iso-propoxy)phenyl)carbonyl-3-[4-[2-(azepan-1-yl)ethoxy]phenylamino]-1H-1,2,4-triazole (compound #321), pale yellow solid; ¹H-NMR (DMSO-d₆, 300 MHz) 9.03 (s, 1H), 8.24 (d, J=9.0 Hz, 2H), 8.17 (s, 1H), 7.71 (s, 2H), 7.42 (d, J=9.0 Hz, 2H), 7.05 (d, J=9.0 Hz, 2H), 6.83 (d, J=9.0 Hz, 2H), 4.77 (sept., J=6.0 Hz, 1H), 3.98 (t, J=6.0 Hz, 2H), 2.87 (t, J=6.0 Hz, 2H), 2.73 (t, J=5.1 Hz, 4H), 1.59-1.54 (m, 8H), 1.31 (d, J=6.0 Hz, 6H) ppm; MS (ES) 479.13 (M+H), 477.28 (M−H).

5-amino-1-(4-(tert-butoxy)phenyl)carbonyl-3-[4-[2-(azepan-1-yl)ethoxy]phenylamino]-1H-1,2,4-triazole (compound #322), pale yellow solid; ¹H-NMR (DMSO-d₆, 300 MHz) 9.03 (s, 1H), 8.17 (s, 1H), 8.16 (d, J=8.4 Hz, 2H), 7.72 (s, 2H), 7.42 (d, J=8.7 Hz, 1H), 7.12 (d, J=8.1 Hz, 2H), 6.82 (d, J=8.7 Hz, 2H), 3.98 (t, J=6.0 Hz, 2H), 2.88 (t, J=6.0 Hz, 2H), 2.74 (t, J=5.3 Hz, 4H), 1.59-1.54 (m, 8H), 1.42 (s, 9H) ppm; MS (ES) 493.16 (M+H), 491.33 (M−H).

5-amino-1-(1H-indol-6-yl)carbonyl-3-[4-[2-(azepan-1-yl)ethoxy]phenylamino]-1H-1,2,4-triazole (compound #323), off-white solid; ¹H-NMR (DMSO-d₆, 300 MHz) 11.60 (s, 1H), 9.02 (s, 1H), 8.51 (s, 1H), 8.14 (s, 1H), 7.84 (dd, J=8.1, 1.5 Hz, 1H), 7.72 (s, 2H), 7.63-7.60 (m, 2H), 7.46 (d, J=9.0 Hz, 2H), 6.83 (d, J=9.0 Hz, 2H), 6.54 (s, 1H), 3.96 (t, J=6.0 Hz, 2H), 2.84 (t, J=6.0 Hz, 2H), 2.70 (t, J=5.3 Hz, 4H), 1.59-1.54 (m, 8H) ppm; MS (ES) 460.10 (M+H), 458.34 (M−H).

5-amino-1-(4-(1,2,3-thiadiazol-4-yl)phenyl)carbonyl-3-[4-[2-(azepan-1-yl)ethoxy]phenylamino]-1H-1,2,4-triazole (compound #324), off-white solid; ¹H-NMR (DMSO-d₆, 300

MHz) 9.81 (s, 1H), 9.09 (s, 1H), 8.33 (s, 4H), 7.80 (s, 2H), 7.42 (d, J=8.7 Hz, 2H), 6.82 (d, J=8.7 Hz, 2H), 3.96 (t, J=6.0 Hz, 2H), 2.85 (t, J=6.0 Hz, 2H), 2.71 (t, J=5.1 Hz, 4H), 1.59-1.54 (m, 8H) ppm; MS (ES) 505.05 (M+H), 503.23 (M−H).

5-amino-N-(2,4,6-trifluorophenyl)-3-[4-[2-(pyrrolidin-1-yl)ethoxy]phenylamino]-1H-1,2,4-triazole-1-carbothioamide (compound #325), off-white solid; $^1$H-NMR (DMSO-d$_6$, 300 MHz) 9.14 (s, 1H), 8.35 (s, 2H), 8.14 (s, 1H), 7.60 (d, J=9.0 Hz, 2H) 7.39-7.32 (m, 2H), 6.81 (d, J=9.0 Hz, 2H), 4.01 (t, J=6.0 Hz, 2H), 2.84 (t, J=6.0 Hz, 2H), 2.60 (m, 4H), 1.71 (m, 4H) ppm; MS (ES) 478.02 (M+H), 476.25 (M−H).

5-amino-N-(2,6-difluorophenyl)-3-[4-[2-(pyrrolidin-1-yl)ethoxy]phenylamino]-1H-1,2,4-triazole-1-carbothioamide (compound #326), off-white solid; $^1$H-NMR (DMSO-d$_6$, 300 MHz) 9.13 (s, 1H), 8.35 (s, 2H), 8.16 (s, 1H), 7.60 (d, J=9.0 Hz, 2H) 7.47-7.36 (m, 2H), 7.22 (t, J=8.0 Hz, 2H), 6.80 (d, J=9.0 Hz, 2H), 4.00 (t, J=6.0 Hz, 2H), 2.81 (t, J=6.0 Hz, 2H), 2.57 (m, 4H), 1.69 (m, 4H) ppm; MS (ES) 460.03 (M+H).

5-amino-1-(4-(morpholin-4-yl)phenyl)carbonyl-3-[4-[2-(isoindolin-1-yl)ethoxy]phenylamino]-1H-1,2,4-triazole (compound #327), yellow solid; $^1$H-NMR (DMSO-d$_6$, 300 MHz) 9.00 (s, 1H), 8.25 (d, J=9.3 Hz, 2H), 8.14 (s, 1H), 7.66 (s, 2H), 7.47 (d, J=9.0 Hz, 2H), 7.23-7.14 (m, 4H), 7.03 (d, J=9.0 Hz, 2H), 6.88 (d, J=9.3 Hz, 2H), 4.07 (t, J=5.7 Hz, 2H), 3.93 (s, 4H), 3.74 (t, J=4.8 Hz, 4H), 3.33 (t, J=4.8 Hz, 4H), 3.04 (t, J=5.7 Hz, 2H) ppm; MS (ES) 526.10 (M+H).

5-amino-1-(4-(iso-propoxy)phenyl)carbonyl-3-[4-[2-(isoindolin-1-yl)ethoxy]phenylamino]-1H-1,2,4-triazole (compound #328), off-white solid; $^1$H-NMR (DMSO-d$_6$, 300 MHz) 9.03 (s, 1H), 8.24 (d, J=9.0 Hz, 2H), 8.14 (s, 1H), 7.70 (s, 2H), 7.44 (d, J=9.0 Hz, 2H), 7.22-7.17 (m, 4H), 7.06 (d, J=9.0 Hz, 2H), 6.88 (d, J=9.0 Hz, 2H), 4.77 (sept., J=6.0 Hz, 1H), 4.07 (t, J=5.7 Hz, 2H), 3.94 (s, 4H), 3.04 (t, J=5.7 Hz, 2H), 1.31 (d, J=6.0 Hz, 6H) ppm; MS (ES) 499.08 (M+H), 497.37 (M−H).

5-amino-1-(4-(tert-butoxy)phenyl)carbonyl-3-[4-[2-(isoindolin-1-yl)ethoxy]phenylamino]-1H-1,2,4-triazole (compound #329), off-white solid; $^1$H-NMR (DMSO-d$_6$, 300 MHz) 9.03 (s, 1H), 8.18 (d, J=8.7 Hz, 2H), 8.13 (s, 1H), 7.72 (s, 2H), 7.43 (d, J=9.0 Hz, 2H), 7.20-7.11 (m, 6H), 6.85 (d, J=9.0 Hz, 2H), 4.07 (t, J=5.7 Hz, 2H), 3.94 (s, 4H), 3.04 (t, J=5.7 Hz, 2H), 1.41 (s, 9H) ppm; MS (ES) 513.11 (M+H), 511.27 (M−H).

5-amino-1-(1H-indol-6-yl)carbonyl-3-[4-[2-(isoindolin-1-yl)ethoxy]phenylamino]-1H-1,2,4-triazole (compound #330), off-white solid; $^1$H-NMR (DMSO-d$_6$, 300 MHz) 11.61 (s, 1H), 9.02 (s, 1H), 8.52 (s, 1H), 8.18 (s, 2H), 7.84 (dd, J=8.3, 1.4 Hz, 1H), 7.72 (s, 2H), 7.66-7.42 (m, 4H), 7.22-7.14 (m, 2H), 6.87 (d, J=8.7 Hz, 2H), 6.54 (s, 1H), 4.07 (t, J=5.7 Hz, 2H), 3.93 (s, 4H), 3.03 (t, J=5.7 Hz, 2H), 2.97 (s, 4H) ppm; MS (ES) 480.04 (M+H), 478.25 (M−H).

5-amino-1-(3-(morpholin-4-yl)phenyl)carbonyl-3-[4-[2-(pyrrolidin-1-yl)ethoxy]phenylamino]-1H-1,2,4-triazole (compound #331), off-white solid; $^1$H-NMR (DMSO-d$_6$, 300 MHz) 9.06 (s, 1H), 8.19 (s, 2H), 7.77 (d, J=12.0, 2H), 7.65-7.21 (m, 4H), 6.77 (d, J=9.0 Hz, 2H), 3.97 (t, J=5.7 Hz, 2H), 3.73 (m, 4H), 3.16 (m, 4H), 2.76 (t, J=5.7 Hz, 2H), 2.53 (m, 4H), 1.67 (m, 4H) ppm; MS (ES) 478.08 (M+H), 476.31 (M−H).

5-amino-1-[4-(2-(morpholin-4-yl)ethoxy)phenyl]carbonyl-3-[4-[2-(pyrrolidin-1-yl)ethoxy]phenylamino]-1H-1,2,4-triazole (compound #332), off-white solid; $^1$H-NMR (DMSO-d$_6$, 300 MHz) 9.06 (s, 1H), 8.25 (d, J=9.0 Hz, 2H), 7.72 (s, 2H), 7.44 (d, J=9.0 Hz, 2H), 7.09 (d, J=9.0 Hz, 2H), 6.85 (d, J=9.0 Hz, 2H), 4.20 (t, J=5.6 Hz, 2H), 4.06 (t, J=5.7 Hz, 2H), 3.57 (m, 4H), 3.00 (t, J=5.6 Hz, 2H), 2.78-2.69 (m, 6H), 1.76 (m, 4H) ppm; MS (ES) 522.08 (M+H), 520.22 (M−H).

5-amino-1-(4-(iso-propoxy)phenyl)carbonyl-3-(phenylamino)-1H-1,2,4-triazole (compound #333), off-white solid; $^1$H-NMR (DMSO-d$_6$, 300 MHz) 9.25 (s, 1H), 8.23 (d, J=8.7 Hz, 2H), 7.74 (s, 2H), 7.52 (d, J=8.4 Hz, 2H), 7.22 (t, J=5.1 Hz, 2H), 7.06 (d, J=8.7 Hz, 2H), 6.83 (t, J=7.5 Hz, 1H), 4.79 (sept., J=6.0 Hz, 1H), 1.32 (d, J=6.0 Hz, 6H) ppm; MS (ES) 338.05 (M+H).

5-amino-1-(4-(1,2,3-thiadiazol-4-yl)phenyl)carbonyl-3-(phenylamino)-1H-1,2,4-triazole (compound #334), off-white solid; off-white solid; $^1$H-NMR (DMSO-d$_6$, 300 MHz) 9.83 (s, 1H), 9.31 (s, 1H), 8.33 (s, 4H), 7.84 (s, 2H) 7.51 (d, J=8.1 Hz, 2H), 7.20 (t, J=7.7 Hz, 2H), 6.82 (t, J=7.7 Hz, 1H) ppm; MS (ES) 364.02 (M+H), 362.07 (M−H).

5-amino-1-(4-(morpholin-4-yl)phenyl)carbonyl-3-(phenylamino)-1H-1,2,4-triazole (compound #335), off-white solid; $^1$H-NMR (DMSO-d$_6$, 300 MHz) 9.23 (s, 1H), 8.24 (d, J=9.3 Hz, 2H), 7.71 (s, 2H), 7.53 (d, J=7.8 Hz, 2H), 7.23 (t, J=8.0 Hz, 2H), 7.04 (d, J=9.0 Hz, 2H), 6.83 (t, J=7.4 Hz, 1H), 3.75 (t, J=4.8 Hz, 4H), 3.34 (t, J=4.8 Hz, 4H) ppm; MS (ES) 365.08 (M+H).

5-amino-1-(3-(morpholin-4-yl)phenyl)carbonyl-3-(phenylamino)-1H-1,2,4-triazole (compound #336), off-white solid; $^1$H-NMR (DMSO-d$_6$, 300 MHz) 9.28 (s, 1H), 7.79 (s, 2H), 7.58-7.25 (m, 6H), 7.17 (t, J=8.0 Hz, 2H), 6.83 (t, J=7.2 Hz, 1H), 3.74 (m, 4H), 3.18 (m, 4H) ppm; MS (ES) 365.07 (M+H), 363.26 (M−H).

5-amino-1-(4-(iso-propoxy)phenyl)carbonyl-3-[4-[2-(pyrrolidin-2-on-1-yl)ethoxy]phenylamino]-1H-1,2,4-triazole (compound #337), off-white solid; $^1$H-NMR (DMSO-d$_6$, 300 MHz) 9.05 (s, 1H), 8.24 (d, J=9.0 Hz, 2H), 7.72 (s, 2H), 7.43 (d, J=9.0 Hz, 2H), 7.08 (d, J=9.0 Hz, 2H), 6.84 (d, J=9.0 Hz, 2H), 4.79 (sept., J=6.0 Hz, 1H), 4.00 (t, J=5.6 Hz, 2H), 3.50 (t, J=5.7 Hz, 2H), 3.41 (t, J=6.9 Hz, 2H), 2.21 (t, J=8.1 Hz, 2H), 1.91 (t, J=7.7 Hz, 2H), 1.32 (d, J=6.0 Hz, 6H) ppm; MS (ES) 465.07 (M+H).

5-amino-1-(4-(1,2,3-thiadiazol-4-yl)phenyl)carbonyl-3-[4-[2-(pyrrolidin-2-on-1-yl)ethoxy]phenylamino]-1H-1,2,4-triazole (compound #338), off-white solid; $^1$H-NMR (DMSO-d$_6$, 300 MHz) 9.82 (s, 1H), 9.12 (s, 1H), 8.33 (s, 4H), 7.82 (s, 2H), 7.43 (d, J=9.0 Hz, 2H), 6.83 (d, J=9.0 Hz, 2H), 3.98 (t, J=5.4 Hz, 2H), 3.48 (t, J=5.6 Hz, 2H), 3.41 (t, J=6.9 Hz, 2H), 2.20 (t, J=8.1 Hz, 2H), 1.89 (quint., J=7.5 Hz, 2H) ppm; MS (ES) 491.01 (M+H), 489.18 (M−H).

5-amino-1-(4-(morpholin-4-yl)phenyl)carbonyl-3-[4-[2-(pyrrolidin-2-on-1-yl)ethoxy]phenylamino]-1H-1,2,4-triazole (compound #339), off-white solid; $^1$H-NMR (DMSO-d$_6$, 300 MHz) 9.03 (s, 1H), 8.25 (d, J=8.4 Hz, 2H), 7.68 (s, 2H), 7.46 (d, J=8.7 Hz, 2H), 7.04 (d, J=8.7 Hz, 2H), 6.86 (d, J=8.4 Hz, 2H), 4.00 (t, J=5.4 Hz, 2H), 3.75 (m, 4H), 3.51 (t, J=5.6 Hz, 2H), 3.44 (t, J=6.9 Hz, 2H), 3.32 (m, 4H), 2.22 (m, 2H), 1.91 (m, 2H) ppm; MS (ES) 492.07 (M+H), 490.13 (M−H).

5-amino-1-(3-(morpholin-4-yl)phenyl)carbonyl-3-[4-[2-(pyrrolidin-2-on-1-yl)ethoxy]phenylamino]-1H-1,2,4-triazole (compound #340), off-white solid; $^1$H-NMR (DMSO-d$_6$, 300 MHz) 9.08 (s, 1H), 7.77 (s, 2H), 7.51 (d, J=8.4 Hz, 1H), 7.44-7.39 (m, 3H), 7.23 (d, J=8.4 Hz, 1H), 6.78 (d, J=9.0 Hz, 2H), 3.99 (t, J=5.1 Hz, 2H), 3.74 (m, 4H), 3.50 (t, J=5.1 Hz, 2H), 3.43 (t, J=6.9 Hz, 2H), 3.17 (m, 4H), 2.21 (t, J=8.1 Hz, 2H), 1.90 (quint., J=7.5 Hz, 2H) ppm; MS (ES) 492.06 (M+H).

5-amino-1-(4-(tert-butoxy)phenyl)carbonyl-3-(phenylamino)-1H-1,2,4-triazole (compound #341), pale yellow solid; $^1$H-NMR (DMSO-d$_6$, 300 MHz) 10.17 (s, 1H), 9.25 (s, 1H), 8.16 (d, J=8.0 Hz, 2H), 7.75 (s, 2H), 7.51 (d, J=7.5 Hz, 2H), 7.20 (t, J=8.0 Hz, 2H), 7.13 (d, J=9.0 Hz, 2H), 6.82 (t, J=7.4 Hz, 1H), 1.41 (s, 9H) ppm; MS (ES) 352.08 (M+H), 350.16 (M−H).

5-amino-1-(4-(tert-butoxy)phenyl)carbonyl-3-[4-[2-(pyrrolidin-2-on-1-yl)ethoxy]phenylamino]-1H-1,2,4-triazole (compound #342), off-white solid; $^1$H-NMR (DMSO-d$_6$, 300

MHz) 9.06 (s, 1H), 8.18 (d, J=8.4 Hz, 2H), 7.73 (s, 2H), 7.42 (d, J=8.7 Hz, 2H), 7.12 (d, J=9.0 Hz, 2H), 6.83 (d, J=8.7 Hz, 2H), 3.99 (t, J=5.6 Hz, 2H), 3.50 (t, J=5.4 Hz, 2H), 3.43 (t, J=6.9 Hz, 2H), 2.21 (t, J=8.0 Hz, 2H), 1.91 (t, J=7.5 Hz, 2H), 1.42 (s, 9H) ppm; MS (ES) 479.07 (M+H), 477.25 (M−H).

5-amino-1-(4-(morpholin-4-yl)phenyl)carbonyl-3-[3-methoxy-4-[2-(pyrrolidin-1-yl)ethoxy]phenylamino]-1H-1,2,4-triazole (compound #343), off-white solid; $^1$H-NMR (DMSO-d$_6$, 300 MHz) 9.06 (s, 1H), 8.26-8.21 (m, 2H), 7.69 (s, 2H), 7.46-7.36 (m, 1H), 6.99 (d, J=8.7 Hz, 2H), 6.87-6.84 (m, 1H), 3.99 (m, 2H), 3.75 (m, 4H), 3.70 (s, 3H), 3.31 (t, J=4.7 Hz, 4H), 2.89 (t, J=6.0 Hz, 2H), 2.68 (m, 4H), 1.73 (m, 4H) ppm; MS (ES) 441.07 (M+H), 439.25 (M−H).

5-amino-1-(3-(morpholin-4-yl)phenyl)carbonyl-3-[3-methoxy-4-[2-(pyrrolidin-1-yl)ethoxy]phenylamino]-1H-1,2,4-triazole (compound #344), off-white solid; $^1$H-NMR (DMSO-d$_6$, 300 MHz) 9.10 (s, 1H), 8.22 (s, 1H), 7.76 (s, 2H), 7.62 (s, 1H), 7.55 (d, J=7.5 Hz, 1H), 7.43-7.14 (m, 1H), 6.98-6.91 (m, 2H), 6.81 (d, J=8.7 Hz, 2H), 4.00 (t, J=6.8 Hz, 2H), 3.73 (m, 4H), 3.60 (s, 3H), 3.14 (m, 4H), 2.96 (m, 2H), 2.76 (m, 4H), 1.75 (m, 4H) ppm; MS (ES) 441.07 (M+H), 439.26 (M−H).

3-amino-1-(4-(tert-butoxy)phenyl)carbonyl-5-[(3-(aminocarbonyl)bicyclo[2.2.1]hept-5-en-2-yl)amino]-1H-1,2,4-triazole (compound #345), off-white solid; $^1$H-NMR (DMSO-d$_6$, 300 MHz) 8.69 (d, J=8.4 Hz, 1H), 8.08 (d, J=8.7 Hz, 2H), 7.59 (br. s, 1H), 7.08 (br. s, 1H), 7.04 (d, J=8.7 Hz, 2H), 6.30-6.28 (m, 1H), 6.23-6.20 (m, 1H), 5.86 (br. s, 2H), 3.91 (t, J=8.1 Hz, 1H), 2.80 (d, J=8.1 Hz, 2H), 2.46-2.40 (m, 1H), 2.15 (d, J=8.1 Hz, 1H), 1.45-1.40 (m, 1H), 1.38 (s, 9H) ppm; MS (ES) 411.14 (M+H), 409.16 (M−H).

5-amino-1-(4-(tert-butoxy)phenyl)carbonyl-3-[(5-(aminocarbonyl)bicyclo[2.2.1]hept-2-en-6-yl)amino]-1H-1,2,4-triazole (compound #346), off-white solid; $^1$H-NMR (DMSO-d$_6$, 300 MHz) 8.16 (d, J=8.7 Hz, 2H), 7.65 (br. s, 2H), 7.54 (br. s, 1H), 7.07 (d, J=8.4 Hz, 2H), 7.04 (br. s, 1H), 6.25-6.21 (m, 1H), 6.20-6.14 (m, 1H), 5.83 (d, J=8.7 Hz, 2H), 3.64 (t, J=8.1 Hz, 1H), 2.80 (d, J=12.9 Hz, 2H), 2.44-2.40 (m, 1H), 2.11 (d, J=9.0 Hz, 1H), 1.39 (s, 9H), 1.36-1.32 (m, 1H) ppm; MS (ES) 411.23 (M+H), 409.16 (M−H).

3-amino-1-(3-(tert-butoxy)phenyl)carbonyl-5-[(3-(aminocarbonyl)bicyclo[2.2.1]hept-5-en-2-yl)amino]-1H-1,2,4-triazole (compound #347), off-white solid; $^1$H-NMR (DMSO-d$_6$, 300 MHz) 8.71 (d, J=8.4 Hz, 1H), 7.73 (d, J=7.2 Hz, 1H), 7.60 (br. s, 2H), 7.36 (t, J=7.8 Hz, 1H), 7.16 (d, J=8.4 Hz, 2H), 7.10 (br. s, 1H), 6.30-6.28 (m, 1H), 6.23-6.20 (m, 1H), 5.88 (br. s, 2H), 3.90 (t, J=8.1 Hz, 1H), 2.82 (br. s, 2H), 2.46-2.40 (m, 1H), 2.16 (d, J=7.8 Hz, 1H), 1.42 (d, J=8.7 Hz, 1H), 1.30 (s, 9H) ppm; MS (ES) 411.20 (M+H), 409.14 (M−H).

5-amino-1-(3-(tert-butoxy)phenyl)carbonyl-3-[(5-(aminocarbonyl)bicyclo[2.2.1]hept-2-en-6-yl)amino]-1H-1,2,4-triazole (compound #348), off-white solid; $^1$H-NMR (DMSO-d$_6$, 300 MHz) 7.84 (s, 1H), 7.76 (d, J=7.2 Hz, 1H), 7.68 (br. s, 2H), 7.51 (br. s, 1H), 7.41 (t, J=7.8 Hz, 2H), 7.19 (d, J=7.8 Hz, 1H), 7.04 (br. s, 1H), 6.25-6.20 (m, 1H), 6.16-6.12 (m, 1H), 5.88 (d, J=9.0 Hz, 2H), 3.63 (t, J=8.1 Hz, 1H), 2.77 (d, J=17.7 Hz, 2H), 2.41 (d, J=8.1 Hz, 1H), 2.09 (d, J=8.4 Hz, 1H), 1.40-1.35 (m, 1H), 1.32 (s, 9H) ppm; MS (ES) 411.18 (M+H), 409.16 (M−H).

3-amino-1-(4-(dimethylamino)phenyl)carbonyl-5-[(3-(aminocarbonyl)bicyclo[2.2.1]hept-5-en-2-yl)amino]-1H-1,2,4-triazole (compound #349), pale yellow solid; $^1$H-NMR (DMSO-d$_6$, 300 MHz) 8.65 (d, J=8.4 Hz, 1H), 8.17 (d, J=9.0 Hz, 2H), 7.55 (br. s, 1H), 7.05 (br. s, 1H), 6.68 (d, J=9.3 Hz, 2H), 6.29 (dd, J=5.4, 2.1 Hz, 1H), 6.21 (dd, J=5.4, 2.1 Hz, 1H), 5.77 (br. s, 2H), 3.92 (t, J=8.4 Hz, 1H), 3.00 (s, 6H), 2.78 (d, J=12.6 Hz, 2H), 2.49-2.47 (m, 2H), 2.15 (d, J=9.0 Hz, 1H), 1.41 (d, J=9.0 Hz, 1H) ppm; MS (ES) 382.15 (M+H), 380.13 (M−H).

5-amino-1-(4-(dimethylamino)phenyl)carbonyl-3-[(5-(aminocarbonyl)bicyclo[2.2.1]hept-2-en-6-yl)amino]-1H-1,2,4-triazole (compound #350), off-white solid; $^1$H-NMR (DMSO-d$_6$, 300 MHz) 8.22 (d, J=8.7 Hz, 2H), 7.55 (br. s, 2H), 7.54 (br. s, 1H), 7.03 (br. s, 1H), 6.72 (d, J=9.0 Hz, 2H), 6.22 (br. s, 2H), 5.74 (d, J=9.3 Hz, 1H), 3.66 (t, J=9.0 Hz, 1H), 3.01 (s, 6H), 2.75 (d, J=9.6 Hz, 2H), 2.44 (d, J=8.4 Hz, 1H), 2.11 (d, J=8.4 Hz, 1H), 1.35 (d, J=8.4 Hz, 9H) ppm; MS (ES) 382.16 (M+H), 380.23 (M−H).

3-amino-1-(3-(dimethylamino)phenyl)carbonyl-5-[(3-(aminocarbonyl)bicyclo[2.2.1]hept-5-en-2-yl)amino]-1H-1,2,4-triazole (compound #351), yellow solid; $^1$H-NMR (DMSO-d$_6$, 300 MHz) 8.69 (d, J=8.4 Hz, 1H), 7.60 (br. s, 1H), 7.33 (d, J=8.1 Hz, 1H), 7.26 (s, 1H), 7.22 (d, J=8.7 Hz, 1H), 7.09 (br. s, 1H), 6.89 (dm, J=7.2 Hz, 1H), 7.10 (br. s, 1H), 6.31 (dd, J=8.4, 3.3 Hz, 1H), 6.22 (dd, J=8.4, 3.0 Hz, 1H), 5.83 (br. s, 2H), 3.90 (t, J=7.5 Hz, 1H), 2.91 (s, 6H), 2.80 (d, J=6.3 Hz, 2H), 2.49-2.47 (m, 1H), 2.16 (d, J=8.7 Hz, 1H), 1.42 (d, J=6.3 Hz, 1H) ppm; MS (ES) 382.16 (M+H), 380.25 (M−H).

5-amino-1-(3-(dimethylamino)phenyl)carbonyl-3-[(5-(aminocarbonyl)bicyclo[2.2.1]hept-2-en-6-yl)amino]-1H-1,2,4-triazole (compound #352), pale yellow solid; $^1$H-NMR (DMSO-d$_6$, 300 MHz) 7.65 (br. s, 2H), 7.59 (s, 1H), 7.52 (br. s, 1H), 7.35 (d, J=8.1 Hz, 1H), 7.28 (t, J=7.8 Hz, 1H), 7.04 (br. s, 1H), 6.94 (d, J=8.4 Hz, 1H), 6.23 (dd, J=5.4, 2.7 Hz, 1H), 6.11 (dd, J=5.4, 3.0 Hz, 1H), 5.86 (d, J=9.0 Hz, 1H), 3.61 (t, J=9.6 Hz, 1H), 2.93 (s, 6H), 2.74 (d, J=8.4 Hz, 2H), 2.41 (d, J=7.2 Hz, 1H), 2.08 (d, J=8.4 Hz, 1H), 1.35 (d, J=9.0 Hz, 1H) ppm; MS (ES) 382.23 (M+H), 380.55 (M−H).

3-amino-1-(4-(iso-propoxy)phenyl)carbonyl-5-[(3-(aminocarbonyl)bicyclo[2.2.1]hept-5-en-2-yl)amino]-1H-1,2,4-triazole (compound #353), off-white solid; $^1$H-NMR (DMSO-d$_6$, 300 MHz) 8.68 (d, J=8.7 Hz, 1H), 8.15 (d, J=8.7 Hz, 2H), 7.58 (br. s, 1H), 7.07 (br. s, 1H), 6.96 (d, J=8.7 Hz, 2H), 6.30-6.24 (m, 1H), 6.24-6.17 (m, 1H), 5.85 (br. s, 2H), 4.72 (quint. J=5.4 Hz, 1H), 3.92 (t, J=7.2 Hz, 1H), 2.79 (d, J=8.7 Hz, 2H), 2.50-2.46 (m, 1H), 2.15 (d, J=8.7 Hz, 1H), 1.41 (d, J=7.2 Hz, 1H), 1.28 (d, J=5.4 Hz, 6H) ppm; MS (ES) 397.15 (M+H), 395.15 (M−H).

5-amino-1-(4-(iso-propoxy)phenyl)carbonyl-3-[(5-(aminocarbonyl)bicyclo[2.2.1]hept-2-en-6-yl)-amino]-1H-1,2,4-triazole (compound #354), off-white solid; $^1$H-NMR (DMSO-d$_6$, 300 MHz) 8.21 (d, J=8.7 Hz, 1H), 7.63 (br. s, 2H), 7.53 (br. s, 1H), 7.03 (br. s, 1H), 7.01 (d, J=9.0 Hz, 2H), 6.24-6.16 (m, 2H), 5.82 (d, J=9.0 Hz, 2H), 4.74 (quint. J=6.0 Hz, 1H), 3.64 (t, J=8.1 Hz, 1H), 2.74 (d, J=9.3 Hz, 2H), 2.43 (d, J=8.7 Hz, 1H), 2.10 (d, J=7.5 Hz, 1H), 1.35 (d, J=9.4 Hz, 1H), 1.29 (d, J=5.7 Hz, 6H) ppm; MS (ES) 397.23 (M+H), 395.08 (M−H).

3-amino-1-(1H-indol-6-yl)carbonyl-5-[(3-(aminocarbonyl)bicyclo[2.2.1]hept-5-en-2-yl)amino]-1H-1,2,4-triazole (compound #355), off-white solid; $^1$H-NMR (DMSO-d$_6$, 300 MHz) 11.49 (s, 1H), 8.72 (d, J=8.7 Hz, 1H), 8.37 (s, 1H), 7.74 (d, J=8.1 Hz, 1H), 7.57 (d, J=7.8 Hz, 2H), 7.56 (s, 1H), 7.09 (br. s, 1H), 6.49 (br. s, 1H), 6.32-6.27 (m, 1H), 6.26-6.20 (m, 1H), 5.82 (br. s, 2H), 3.94 (t, J=9.0 Hz, 1H), 2.82 (br. s, 2H), 2.52 (br. s, 1H), 2.18 (d, J=8.7 Hz, 1H), 1.43 (d, J=8.1 Hz, 1H) ppm; MS (ES) 377.98 (M+H), 376.09 (M−H).

5-amino-1-(1H-indol-6-yl)carbonyl-3-[(5-(aminocarbonyl)bicyclo[2.2.1]hept-2-en-6-yl)amino]-1H-1,2,4-triazole (compound #356), pale yellow solid; $^1$H-NMR (DMSO-d$_6$, 300 MHz) 11.54 (s, 1H), 8.52 (s, 1H), 7.77 (d, J=8.4 Hz, 1H), 7.66 (br. s, 2H), 7.62-7.55 (m, 3H), 7.05 (br. s, 1H), 6.51 (br. s, 1H), 6.21 (s, 2H), 5.80 (d, J=9.3 Hz, 1H), 3.67 (t, J=9.3 Hz, 1H), 2.76 (br. s, 2H), 2.44 (d, J=8.7 Hz, 1H), 2.12 (d, J=8.7 Hz, 1H), 1.36 (d, J=8.7 Hz, 1H) ppm; MS (ES) 378.16 (M+H), 376.15 (M−H).

5-amino-1-(4-(tert-butoxy)phenyl)carbonyl-3-[4-(4-methylpiperazin-1-yl)phenylamino]-1H-1,2,4-triazole (compound #357), pale yellow solid; ¹H-NMR (DMSO-d₆, 300 MHz) 8.95 (s, 1H), 8.18 (d, J=9.0 Hz, 2H), 7.71 (br. s, 2H), 7.37 (d, J=8.4 Hz, 2H), 7.12 (d, J=9.0 Hz, 2H), 6.82 (d, J=8.7 Hz, 2H), 3.05-2.95 (m, 4H), 2.45-2.40 (m, 4H), 2.21 (s, 3H), 1.42 (s, 9H) ppm; MS (ES) 450.27 (M+H), 448.07 (M−H).

5-amino-1-(3-(tert-butoxy)phenyl)carbonyl-3-[4-(4-methylpiperazin-1-yl)phenylamino]-1H-1,2,4-triazole (compound #358), pale yellow solid; ¹H-NMR (DMSO-d₆, 300 MHz) 8.99 (s, 1H), 7.84 (d, J=7.5 Hz, 1H), 7.79 (s, H), 7.75 (br. s, 2H), 7.45 (t, J=8.1 Hz, 1H), 7.36 (d, J=9.0 Hz, 2H), 7.25 (dm, J=8.1 Hz, 1H), 6.79 (d, J=9.0 Hz, 2H), 3.02 (t, J=4.8 Hz, 4H), 2.56 (t, J=4.5 Hz, 4H), 2.29 (s, 3H), 1.33 (s, 9H) ppm; MS (ES) 450.39 (M+H), 448.52 (M−H).

5-amino-1-(4-(iso-propoxy)phenyl)carbonyl-3-[4-(4-methylpiperazin-1-yl)phenylamino]-1H-1,2,4-triazole (compound #359), pale yellow solid; ¹H-NMR (DMSO-d₆, 300 MHz) 8.99 (s, 1H), 8.24 (d, J=9.3 Hz, 2H), 7.70 (br. s, 2H), 7.40 (d, J=8.4 Hz, 2H), 7.05 (d, J=9.0 Hz, 2H), 6.87 (d, J=9.0 Hz, 2H), 4.78 (quint. J=6.0 Hz, 1H), 3.13 (br. s, 4H), 2.85 (br. s, 4H), 2.53 (s, 3H), 1.32 (d, J=6.0 Hz, 6H) ppm; MS (ES) 436.63 (M+H), 434.71 (M−H).

3-amino-1-(4-(iso-propoxy)phenyl)carbonyl-5-(4-(4-methylpiperazin-1-yl)phenylamino]-1H-1,2,4-triazole (compound #360), pale yellow solid; ¹H-NMR (DMSO-d₆, 300 MHz) 10.01 (s, 1H), 8.22 (d, J=8.7 Hz, 2H), 7.56 (d, J=8.7 Hz, 2H), 7.02 (d, J=8.7 Hz, 2H), 6.92 (d, J=8.7 Hz, 2H), 4.76 (quint. J=6.0 Hz, 1H), 3.09 (br. s, 4H), 2.44 (br. s, 4H), 2.21 (s, 3H), 1.30 (d, J=6.0 Hz, 6H) ppm; MS (ES) 436.63 (M+H).

5-amino-1-(4-(dimethylamino)phenyl)carbonyl-3-[4-(4-methylpiperazin-1-yl)phenylamino]-1H-1,2,4-triazole (compound #361), pale yellow solid; ¹H-NMR (DMSO-d₆, 300 MHz) 8.90 (s, 1H), 8.26 (d, J=7.8 Hz, 2H), 7.63 (br. s, 2H), 7.41 (d, J=8.4 Hz, 2H), 6.85 (d, J=8.4 Hz, 2H), 6.77 (d, J=8.7 Hz, 2H), 3.03-2.98 (m, 4H), 2.94 (s, 3H), 2.93 (s, 3H), 2.50-2.42 (m, 4H), 2.21 (s, 3H) ppm; MS (ES) 421.67 (M+H), 419.62 (M−H).

3-amino-1-(4-(dimethylamino)phenyl)carbonyl-5-(4-(4-methylpiperazin-1-yl)phenylamino]-1H-1,2,4-triazole (compound #362), yellow solid; ¹H-NMR (DMSO-d₆, 300 MHz) 10.12 (s, 1H), 8.25 (d, J=9.0 Hz, 2H), 7.55 (d, J=8.1 Hz, 2H), 6.91 (d, J=9.0 Hz, 2H), 6.72 (d, J=9.0 Hz, 2H), 5.95 (br. s, 2H), 3.12-3.04 (m, 4H), 3.03 (s, 6H), 2.48-2.40 (m, 4H), 2.21 (s, 3H) ppm; MS (ES) 421.65 (M+H).

5-amino-1-(3-(dimethylamino)phenyl)carbonyl-3-[4-(4-methylpiperazin-1-yl)phenylamino]-1H-1,2,4-triazole (compound #363), pale yellow solid; ¹H-NMR (DMSO-d₆, 300 MHz) 8.97 (s, 1H), 7.73 (br. s, 2H), 7.58 (s, 1H), 7.38 (d, J=8.7 Hz, 2H), 7.31 (d, J=7.5 Hz, 1H), 7.19 (t, J=8.4 Hz, 1H), 6.98 (d, J=8.4 Hz, 1H), 6.77 (d, J=8.7 Hz, 2H), 3.04-2.96 (m, 4H), 2.96 (s, 6H), 2.50-2.46 (m, 4H), 2.23 (s, 3H) ppm; MS (ES) 421.79 (M+H), 419.62 (M−H).

3-amino-1-(3-(dimethylamino)phenyl)carbonyl-5-(4-(4-methylpiperazin-1-yl)phenylamino]-1H-1,2,4-triazole (compound #364), pale yellow solid; ¹H-NMR (DMSO-d₆, 300 MHz) 10.30 (s, 1H), 7.30-7.25 (m, 2H), 7.20-7.15 (m, 4H), 6.90 (dm, J=8.4 Hz, 2H), 6.51 (s, 2H), 3.36-3.30 (m, 4H), 2.94 (s, 6H), 2.53 (s, 3H), 2.50-2.46 (m, 4H) ppm; MS (ES) 421.73 (M+H).

5-amino-1-(bicyclo[2.2.1]heptan-2-yl)carbonyl-3-[4-(4-methylpiperazin-1-yl)phenylamino]-1H-1,2,4-triazole (compound #365), pale yellow solid; ¹H-NMR (DMSO-d₆, 300 MHz) 9.67 (s, 1H), 8.21 (br. s, 2H), 7.53 (d, J=8.7 Hz, 2H), 6.88 (d, J=8.7 Hz, 2H), 3.12-3.04 (m, 4H), 2.45-2.37 (m, 4H), 2.30-2.26 (m, 1H), 2.20 (s, 3H), 1.68-1.24 (m, 10H) ppm; MS (ES) 396.69 (M+H), 394.65 (M−H).

5-amino-1-(1H-indol-3-yl)carbonyl-3-[4-[2-(pyrrolidin-1-yl)ethoxy]phenylamino]-1H-1,2,4-triazole (compound #366), off-white solid; ¹H-NMR (DMSO-d₆, 300 MHz) 11.76 (br. s, 3H), 8.00-7.90 (m, 4H), 7.42 (d, J=7.2 Hz, 2H), 7.20-7.05 (m, 4H), 4.10-4.06 (m, 2H), 3.06 (br. s, 2H), 2.52 (br. s, 4H), 1.70-1.62 (m, 4H) ppm; MS (ES) 432.10 (M+H), 430.25 (M−H).

5-amino-1-(benzo[b]thiophen-2-yl)carbonyl-3-[4-[2-(pyrrolidin-1-yl)ethoxy]phenylamino]-1H-1,2,4-triazole (compound #367), yellow solid; ¹H-NMR (DMSO-d₆, 300 MHz) 9.28 (s, 1H), 8.70 (s, 1H), 8.15 (d, J=8.1 Hz, 1H), 8.11 (d, J=7.8 Hz, 1H), 7.87 (br. s, 2H), 7.63 (d, J=9.3 Hz, 2H), 7.56 (t, J=7.2 Hz, 1H), 7.48 (t, J=7.2 Hz, 1H), 7.01 (d, J=9.0 Hz, 2H), 4.14 (t, J=5.7 Hz, 2H), 3.10 (br. s, 2H), 2.86 (br. s, 4H), 1.86-1.75 (m, 4H) ppm; MS (ES) 449.10 (M+H), 447.18 (M−H).

3-amino-1-(benzo[b]thiophen-2-yl)carbonyl-5-[4-[2-(pyrrolidin-1-yl)ethoxy]phenylamino]-1H-1,2,4-triazole (compound #368), yellow solid; ¹H-NMR (DMSO-d₆, 300 MHz) 9.97 (br. s, 1H), 8.81 (s, 1H), 8.10-8.02 (m, 2H), 7.64 (d, J=9.0 Hz, 2H), 7.60-7.45 (m, 2H), 6.93 (d, J=9.9 Hz, 2H), 6.27 (br. s, 2H), 4.04 (t, J=5.7 Hz, 2H), 2.77 (t, J=5.7 Hz, 2H), 2.60-2.50 (m, 4H), 1.70-1.62 (m, 4H) ppm; MS (ES) 449.05 (M+H), 447.23 (M−H).

5-amino-1-(benzo[b]thiophen-5-yl)carbonyl-3-[4-[2-(pyrrolidin-1-yl)ethoxy]phenylamino]-1H-1,2,4-triazole (compound #369), pale yellow solid; ¹H-NMR (DMSO-d₆, 300 MHz) 9.06 (br. s, 1H), 8.78 (s, 1H), 8.17-8.09 (m, 2H), 7.89 (d, J=4.5 Hz, 1H), 7.78 (br. s, 2H), 7.62 (d, J=4.5 Hz, 1H), 7.42 (d, J=8.7 Hz, 2H), 7.78 (d, J=8.1 Hz, 2H), 3.97 (t, J=5.7 Hz, 2H), 2.77 (t, J=5.7 Hz, 2H), 2.53 (br. s, 4H), 1.68 (br. s, 4H) ppm; MS (ES) 449.05 (M+H), 447.26 (M−H).

5-amino-1-(4-(tert-butoxy)phenyl)carbonyl-3-[4-[2-(imidazol-1-yl)ethoxy]phenylamino]-1H-1,2,4-triazole (compound #370), pale yellow solid; ¹H-NMR (DMSO-d₆, 300 MHz) 9.05 (br. s, 1H), 8.16 (d, J=8.7 Hz, 2H), 7.72 (br. s, 2H), 7.65 (s, 1H), 7.41 (d, J=9.0 Hz, 2H), 7.21 (s, 1H), 7.11 (d, J=8.4 Hz, 2H), 6.84 (s, 1H), 6.80 (d, J=8.7 Hz, 2H), 4.30 (t, J=4.5 Hz, 2H), 4.17 (t, J=4.5 Hz, 2H), 1.41 (s, 9H) ppm; MS (ES) 462.05 (M+H), 460.24 (M−H).

5-amino-1-(3-(tert-butoxy)phenyl)carbonyl-3-[4-[2-(imidazol-1-yl)ethoxy]phenylamino]-1H-1,2,4-triazole (compound #371), yellow solid; ¹H-NMR (DMSO-d₆, 300 MHz) 9.07 (br. s, 1H), 7.82 (d, J=7.2 Hz, 1H), 7.75 (br. s, 2H), 7.65 (s, 1H), 7.44 (t, J=7.5 Hz, 1H), 7.38 (d, J=8.7 Hz, 2H), 7.24 (d, J=7.5 Hz, 1H), 7.20 (s, 1H), 6.86 (s, 1H), 6.75 (d, J=8.4 Hz, 2H), 4.49 (t, J=4.5 Hz, 2H), 4.14 (t, J=4.5 Hz, 2H), 1.32 (s, 9H) ppm; MS (ES) 462.05 (M+H), 460.21 (M−H).

5-amino-1-(4-(iso-propoxy)phenyl)carbonyl-3-[4-[2-(imidazol-1-yl)ethoxy]phenylamino]-1H-1,2,4-triazole (compound #372), off-white solid; ¹H-NMR (DMSO-d₆, 300 MHz) 9.05 (br. s, 1H), 6.22 (d, J=9.0 Hz, 2H), 7.71 (br. s, 2H), 7.65 (s, 1H), 7.42 (d, J=9.3 Hz, 2H), 7.21 (s, 1H), 7.05 (d, J=8.7 Hz, 2H), 6.86 (s, 1H), 6.82 (d, J=9.3 Hz, 2H), 4.78 (quint. J=6.0 Hz, 1H), 4.30 (t, J=5.1 Hz, 2H), 4.16 (t, J=5.1 Hz, 2H), 1.32 (d, J=6.0 Hz, 6H) ppm; MS (ES) 448.06 (M+H), 446.22 (M−H).

5-amino-1-(4-(dimethylamino)phenyl)carbonyl-3-[4-[2-(imidazol-1-yl)ethoxy]phenylamino]-1H-1,2,4-triazole (compound #373), yellow solid; ¹H-NMR (DMSO-d₆, 300 MHz) 9.00 (br. s, 1H), 8.24 (d, J=9.0 Hz, 2H), 7.67 (s, 1H), 7.63 (br. s, 2H), 7.44 (d, J=8.7 Hz, 2H), 7.22 (s, 1H), 6.88 (s, 1H), 6.82 (d, J=9.3 Hz, 2H), 6.76 (d, J=8.7 Hz, 2H), 4.31 (t, J=4.5 Hz, 2H), 4.16 (t, J=4.8 Hz, 2H), 3.04 (s, 6H) ppm; MS (ES) 433.02 (M+H), 431.21 (M−H).

5-amino-1-(3-(dimethylamino)phenyl)carbonyl-3-[4-[2-(imidazol-1-yl)ethoxy]phenylamino]-1H-1,2,4-triazole (compound #374), pale yellow solid; ¹H-NMR (DMSO-d₆, 300 MHz) 9.07 (br. s, 1H), 7.73 (s, 1H), 7.64 (br. s, 2H), 7.55 (s, 1H), 7.42 (d, J=8.4 Hz, 2H), 7.36-7.32 (m, 2H), 7.20 (s, 1H), 6.98-6.90 (s, 1H), 6.75 (d, J=8.1 Hz, 2H), 4.29 (t, J=4.5 Hz, 2H), 4.14 (t, J=4.5 Hz, 2H), 2.95 (s, 6H) ppm; MS (ES) 433.02 (M+H), 431.23 (M−H).

5-amino-1-(1H-indol-6-yl)carbonyl-3-[4-[2-(imidazol-1-yl)ethoxy]phenylamino]-1H-1,2,4-triazole (compound #375), pale brown solid; $^1$H-NMR (DMSO-d$_6$, 300 MHz) 11.60 (br. s, 1H), 9.05 (s, 1H), 8.50 (s, 1H), 7.82 (d, J=8.4 Hz, 1H), 7.72 (br. s, 2H), 7.69-7.62 (m, 2H), 7.45 (d, J=8.7 Hz, 2H), 7.22 (s, 1H), 6.88 (s, 1H), 6.81 (d, J=8.4 Hz, 2H), 6.54 (s, 1H), 4.30 (t, J=4.5 Hz, 2H), 4.15 (t, J=4.8 Hz, 2H) ppm; MS (ES) 429.00 (M+H), 427.18 (M−H).

3-amino-1-(1H-indol-6-yl)carbonyl-5-[4-[2-(imidazol-1-yl)ethoxy]phenylamino]-1H-1,2,4-triazole (compound #376), pale yellow solid; $^1$H-NMR (DMSO-d$_6$, 300 MHz) 11.61 (br. s, 1H), 10.10 (br. s, 1H), 9.05 (s, 1H), 8.50 (s, 1H), 7.81 (m, 1H), 7.72-7.63 (m, 2H), 7.45 (d, J=8.4 Hz, 2H), 7.21 (d, J=8.1 Hz, 1H), 6.92 (d, J=9.0 Hz, 1H), 6.81 (d, J=8.4 Hz, 2H), 6.54 (br. s, 1H), 6.00 (br. s, 2H), 4.22 (t, J=4.5 Hz, 2H), 4.14 (t, J=4.8 Hz, 2H) ppm; MS (ES) 429.00 (M+H), 427.17 (M−H).

5-amino-1-(benzo[b]thiophen-5-yl)carbonyl-3-[4-[2-(imidazol-1-yl)ethoxy]phenylamino]-1H-1,2,4-triazole (compound #377), yellow solid; $^1$H-NMR (DMSO-d$_6$, 300 MHz) 9.09 (br. s, 1H), 8.77 (s, 1H), 8.18-8.06 (m, 3H), 7.89 (br. s, 1H), 7.78 (br. s, 2H), 7.64 (br. s, 2H), 7.41 (d, J=8.4 Hz, 2H), 7.20 (s, 1H), 6.86 (s, 1H), 6.77 (d, J=7.8 Hz, 2H), 4.29 (br. s, 2H), 4.14 (br. s, 2H) ppm; MS (ES) 445.95 (M+H), 444.15 (M−H).

3-amino-1-(benzo[b]thiophen-5-yl)carbonyl-5-[4-[2-(imidazol-1-yl)ethoxy]phenylamino]-1H-1,2,4-triazole (compound #378), yellow solid; $^1$H-NMR (DMSO-d$_6$, 300 MHz) 9.09 (br. s, 1H), 8.78 (s, 1H), 8.18-8.08 (m, 2H), 7.90 (d, J=5.4 Hz, 1H), 7.78 (br. s, 2H), 7.69 (s, 1H), 7.62 (d, J=5.4 Hz, 1H), 7.42 (d, J=9.0 Hz, 2H), 7.22 (s, 1H), 6.89 (s, 1H), 6.77 (d, J=8.7 Hz, 2H), 4.30 (t, J=5.1 Hz, 2H), 4.15 (t, J=5.1 Hz, 2H) ppm; MS (ES) 445.96 (M+H), 444.14 (M−H).

5-amino-1-(benzo[b]thiophen-2-yl)carbonyl-3-[4-[2-(imidazol-1-yl)ethoxy]phenylamino]-1H-1,2,4-triazole (compound #379), yellow solid; $^1$H-NMR (DMSO-d$_6$, 300 MHz) 9.27 (br. s, 1H), 8.69 (s, 1H), 8.15 (d, J=7.8 Hz, 1H), 8.10-8.08 (m, 1H), 7.86 (br. s, 2H), 7.71 (s, 1H), 7.61 (d, J=9.0 Hz, 2H), 7.56 (t, J=7.8 Hz, 1H), 7.48 (t, J=8.1 Hz, 1H), 7.25 (s, 1H), 6.96 (d, J=8.4 Hz, 2H), 6.90 (s, 1H), 4.34 (t, J=5.1 Hz, 2H), 4.23 (t, J=5.1 Hz, 2H) ppm; MS (ES) 445.95 (M+H), 444.13 (M−H).

5-amino-1-(4-(tert-butoxy)phenyl)carbonyl-3-[4-[2-(pyrrolidin-1-yl)ethoxy]phenylamino]-1H-1,2,4-triazole (compound #380), pale yellow solid; $^1$H-NMR (DMSO-d$_6$, 300 MHz) 10.05 (br. s, 1H), 9.09 (br. s, 1H), 8.17 (d, J=7.1 Hz, 2H), 7.71 (br. s, 2H), 7.45 (d, J=6.9 Hz, 2H), 7.11 (d, J=7.1 Hz, 2H), 6.90 (d, J=7.1 Hz, 2H), 4.22 (br. s, 2H), 3.53 (br. s, 4H), 3.10 (br. s, 2H), 1.97-1.88 (m, 4H), 1.41 (s, 9H) ppm; MS (ES) 465.40 (M+H).

5-amino-1-(3-fluoro-4-methoxyphenyl)carbonyl-3-[4-[2-(pyrrolidin-1-yl)ethoxy]phenylamino]-1H-1,2,4-triazole (compound #381), pale yellow solid; $^1$H-NMR (DMSO-d$_6$, 300 MHz) 9.17 (br. s, 1H), 8.20 (d, J=13.2 Hz, 1H), 8.07 (d, J=8.4 Hz, 1H), 7.77 (br. s, 2H), 7.46 (d, J=8.7 Hz, 2H), 7.34 (t, J=8.4 Hz, 1H), 6.90 (d, J=8.7 Hz, 2H), 4.21 (t, J=5.1 Hz, 2H), 3.95 (s, 3H), 3.60-3.50 (br. s, 2H), 3.05-3.15 (m, 4H), 2.02-1.88 (m, 4H) ppm; MS (ES) 441.05 (M+H), 439.20 (M−H).

5-amino-1-(4-(morpholin-4-yl)phenyl)carbonyl-3-[4-[2-(pyrrolidin-1-yl)ethoxy]phenylamino]-1H-1,2,4-triazole (compound #382), pale yellow solid; $^1$H-NMR (DMSO-d$_6$, 300 MHz) 9.10 (br. s, 1H), 8.23 (d, J=8.1 Hz, 2H), 7.68 (br. s, 2H), 7.48 (d, J=9.3 Hz, 2H), 7.03 (d, J=8.4 Hz, 2H), 6.92 (t, J=8.1 Hz, 2H), 4.21 (br. s, 2H), 3.75 (br. s, 4H), 3.33 (br. s, 4H), 3.30-3.20 (m, 2H), 3.20-3.05 (m, 4H), 2.02-1.88 (m, 4H) ppm; MS (ES) 478.37 (M+H).

5-amino-1-(4-(4-methylpiperazin-1-yl)phenyl)carbonyl-3-[4-[2-(pyrrolidin-1-yl)ethoxy]phenylamino]-1H-1,2,4-triazole (compound #383), pale yellow solid; $^1$H-NMR (DMSO-d$_6$, 300 MHz) 9.11 (br. s, 1H), 8.25 (d, J=8.4 Hz, 2H), 7.71 (br. s, 2H), 7.48 (d, J=8.4 Hz, 2H), 7.11 (d, J=8.4 Hz, 2H), 6.91 (t, J=8.7 Hz, 2H), 4.21-4.12 (m, 4H), 3.55 (br. s, 4H), 3.14 (br. s, 4H), 2.87 (s, 3H), 2.53 (br. s, 4H), 2.02-1.88 (m, 4H) ppm; MS (ES) 491.15 (M+H).

5-amino-1-(4-(tert-butoxy)phenyl)carbonyl-3-[4-[2-((S)-3-fluoropyrrolidin-1-yl)ethoxy]phenylamino]-1H-1,2,4-triazole (compound #384), pale yellow solid; $^1$H-NMR (DMSO-d$_6$, 300 MHz) 9.02 (br. s, 1H), 8.17 (d, J=8.1 Hz, 2H), 7.74 (br. s, 2H), 7.41 (d, J=8.4 Hz, 2H), 7.11 (d, J=8.1 Hz, 2H), 6.82 (d, J=8.7 Hz, 2H), 3.99 (t, J=5.7 Hz, 2H), 3.00-2.58 (m, 6H), 2.17-2.04 (m, 1H), 1.98-1.65 (m, 2H), 1.41 (s, 9H) ppm; MS (ES) 483.35 (M+H), 481.47 (M−H).

5-amino-1-(4-(dimethylamino)phenyl)carbonyl-3-[4-[2-((S)-3-fluoropyrrolidin-1-yl)ethoxy]phenylamino]-1H-1,2,4-triazole (compound #385), pale yellow solid; $^1$H-NMR (DMSO-d$_6$, 300 MHz) 8.97 (br. s, 1H), 8.25 (d, J=9.0 Hz, 2H), 7.63 (br. s, 2H), 7.45 (d, J=8.7 Hz, 2H), 6.85 (d, J=8.7 Hz, 2H), 6.76 (d, J=9.0 Hz, 2H), 4.00 (t, J=5.7 Hz, 2H), 3.05 (s, 6H), 3.00-2.70 (m, 6H), 2.26-2.06 (m, 1H), 1.98-1.78 (m, 2H) ppm; MS (ES) 454.16 (M+H).

5-amino-1-(1,4-benzodioxan-6-yl)carbonyl-3-[4-[2-((S)-3-fluoropyrrolidin-1-yl)ethoxy]phenylamino]-1H-1,2,4-triazole (compound #386), pale yellow solid; $^1$H-NMR (DMSO-d$_6$, 300 MHz) 9.03 (br. s, 1H), 7.82 (s, 1H), 7.79 (br. s, 1H), 7.71 (br. s, 2H), 7.42 (d, J=9.0 Hz, 2H), 7.00 (d, J=8.7 Hz, 1H), 6.81 (d, J=8.4 Hz, 2H), 4.33 (d, J=6.3 Hz, 4H), 3.99 (t, J=6.0 Hz, 2H), 2.98-2.68 (m, 6H), 2.26-2.06 (m, 1H), 1.93-1.78 (m, 2H) ppm; MS (ES) 469.33 (M+H), 467.06 (M−H).

3-amino-1-(1,4-benzodioxan-6-yl)carbonyl-5-[4-[2-((S)-3-fluoropyrrolidin-1-yl)ethoxy]phenylamino]-1H-1,2,4-triazole (compound #387), pale yellow solid; $^1$H-NMR (DMSO-d$_6$, 300 MHz) 10.01 (br. s, 1H), 8.18 (s, 1H), 7.84 (d, J=8.4 Hz, 1H), 7.79 (br. s, 1H), 7.63 (d, J=9.0 Hz, 2H), 7.92 (d, J=8.7 Hz, 2H), 6.06 (br. s, 2H), 4.33-4.30 (m, 4H), 4.04 (t, J=5.4 Hz, 2H), 2.94-2.71 (m, 6H), 2.18-2.05 (m, 1H), 1.92-1.76 (m, 2H) ppm; MS (ES) 469.19 (M+H), 466.86 (M−H).

5-amino-1-(1H-indol-6-yl)carbonyl-3-[4-[2-((S)-3-fluoropyrrolidin-1-yl)ethoxy]phenylamino]-1H-1,2,4-triazole (compound #388), pale yellow solid; $^1$H-NMR (DMSO-d$_6$, 300 MHz) 11.59 (br. s, 1H), 9.01 (br. s, 1H), 8.51 (s, 1H), 7.83 (d, J=8.4 Hz, 1H), 7.71 (br. s, 2H), 7.66-7.61 (m, 2H), 7.46 (d, J=8.4 Hz, 2H), 6.82 (d, J=8.1 Hz, 2H), 6.54 (s, 1H), 3.97 (t, J=5.7 Hz, 2H), 2.94-2.65 (m, 6H), 2.16-2.05 (m, 1H), 1.91-1.76 (m, 2H) ppm; MS (ES) 450.41 (M+H), 448.13 (M−H).

3-amino-1-(1H-indol-6-yl)carbonyl-5-[4-[2-((S)-3-fluoropyrrolidin-1-yl)ethoxy]phenylamino]-1H-1,2,4-triazole (compound #389), pale yellow solid; $^1$H-NMR (DMSO-d$_6$, 300 MHz) 11.54 (br. s, 1H), 9.02 (br. s, 1H), 8.44 (s, 1H), 7.84-7.80 (m, 1H), 7.68 (d, J=9.0 Hz, 2H), 7.46 (d, J=8.7 Hz, 1H), 6.94 (d, J=9.0 Hz, 2H), 6.82 (d, J=8.7 Hz, 1H), 6.54-6.52 (m, 1H), 6.00 (br. s, 2H), 4.97 (t, J=5.7 Hz, 2H), 2.94-2.65 (m, 6H), 2.30-2.00 (m, 1H), 1.93-1.80 (m, 2H) ppm; MS (ES) 450.14 (M+H), 448.12 (M−H).

5-amino-1-(3,5-difluoro-4-methoxyphenyl)carbonyl-3-[4-[2-(pyrrolidin-1-yl)ethoxy]phenylamino]-1H-1,2,4-triazole (compound #390), pale yellow solid; $^1$H-NMR (DMSO-d$_6$, 300 MHz) 9.10 (br. s, 1H), 8.03 (d, J=9.6 Hz, 2H), 7.80 (br. s, 2H), 7.39 (d, J=8.7 Hz, 1H), 6.80 (d, J=8.7 Hz, 2H), 4.08 (s, 3H), 3.98 (t, J=5.7 Hz, 2H), 2.76 (t, J=5.7 Hz, 2H), 2.49 (br. s, 4H), 1.67 (br. s, 4H) ppm; MS (ES) 459.08 (M+H), 457.22 (M−H).

3-amino-1-(2,6-difluorophenyl)carbonyl-5-(1-methylsulfonylpiperidin-4-yl)amino-1H-1,2,4-triazole (compound #391), off-white solid; $^1$H-NMR (DMSO-d$_6$, 300 MHz) 7.64-7.54 (m, 1H), 7.23 (t, J=8.1 Hz, 2H), 6.50 (d, J=7.5 Hz, 1H), 6.02 (br. s, 2H), 3.80-3.65 (m, 1H), 3.59-3.55 (m, 2H), 2.87 (s, 3H), 2.82-2.72 (m, 3H), 2.04-2.01 (m, 2H), 1.87-1.78 (m, 2H) ppm; MS (ES) 401.03 (M+H).

5-amino-1-(2,6-difluorophenyl)carbonyl-3-(1-methylsulfonylpiperidin-4-yl)amino-1H-1,2,4-triazole (compound #392), off-white solid; $^1$H-NMR (DMSO-d$_6$, 300 MHz) 7.74 (br. s, 2H), 7.64-7.52 (m, 1H), 7.23 (t, J=8.7, 7.8 Hz, 2H), 6.50 (d, J=7.2 Hz, 1H), 3.74-3.41 (m, 2H), 2.80 (s, 3H), 2.76-2.73 (m, 3H), 1.87-1.82 (m, 2H), 1.50-1.36 (m, 2H) ppm; MS (ES) 401.03 (M+H).

5-amino-1-(4-(tert-butoxy)phenyl)carbonyl-3-(1-methylsulfonylpiperidin-4-yl)amino-1H-1,2,4-triazole (compound #393), off-white solid; $^1$H-NMR (DMSO-d$_6$, 300 MHz) 8.12 (t, J=8.4, 7.5 Hz, 3H), 7.62 (br. s, 2H), 7.05 (d, J=8.4 Hz, 2H), 3.56-3.44 (m, 2H), 2.84 (s, 3H), 2.85-2.78 (m, 3H), 2.05-1.90 (m, 2H), 1.60-1.45 (m, 2H), 1.39 (s, 9H) ppm; MS (ES) 437.09 (M+H), 435.08 (M–H).

5-amino-1-(4-(iso-propoxy)phenyl)carbonyl-3-(1-methylsulfonylpiperidin-4-yl)amino-1H-1,2,4-triazole (compound #394), off-white solid; $^1$H-NMR (DMSO-d$_6$, 300 MHz) 8.18 (d, J=8.4 Hz, 2H), 7.82 (br. s, 1H), 7.60 (br. s, 2H), 6.98 (d, J=7.5 Hz, 2H), 4.74 (quint. J=5.4 Hz, 1H), 3.58-3.40 (m, 2H), 2.84 (s, 3H), 2.85-2.78 (m, 3H), 2.05-1.90 (m, 2H), 1.80-1.60 (m, 1H), 1.60-1.42 (m, 1H), 1.29 (s, J=5.4 Hz, 6H) ppm; MS (ES) 423.06 (M+H), 421.06 (M–H).

5-amino-1-(4-(dimethylamino)phenyl)carbonyl-3-(1-methylsulfonylpiperidin-4-yl)amino-1H-1,2,4-triazole (compound #395), off-white solid; $^1$H-NMR (DMSO-d$_6$, 300 MHz) 8.20 (d, J=8.7 Hz, 2H), 7.53 (br. s, 2H), 6.70 (d, J=8.7 Hz, 2H), 6.26 (d, J=7.2 Hz, 1H), 3.52-3.42 (m, 2H), 3.01 (s, 6H), 2.88-2.78 (m, 3H), 2.84 (s, 3H), 2.00-1.95 (m, 2H), 1.58-1.52 (m, 2H) ppm; MS (ES) 408.08 (M+H), 406.22 (M–H).

3-amino-1-(4-(dimethylamino)phenyl)carbonyl-5-(1-methylsulfonylpiperidin-4-yl)amino-1H-1,2,4-triazole (compound #396), off-white solid; $^1$H-NMR (DMSO-d$_6$, 300 MHz) 8.20 (d, J=9.0 Hz, 2H), 7.86 (d, J=7.5 Hz, 1H), 6.70 (d, J=8.7 Hz, 2H), 5.78 (br. s, 2H), 3.54-3.45 (m, 2H), 3.01 (s, 6H), 2.90-2.80 (m, 3H), 2.88 (s, 3H), 2.05-1.96 (m, 2H), 1.76-1.50 (m, 2H) ppm; MS (ES) 408.08 (M+H), 406.22 (M–H).

5-amino-1-(1,4-benzodioxan-6-yl)carbonyl-3-(1-methylsulfonylpiperidin-4-yl)amino-1H-1,2,4-triazole (compound #397), off-white solid; $^1$H-NMR (DMSO-d$_6$, 300 MHz) 7.79 (s, 1H), 7.62 (br. s, 2H), 6.93 (d, J=8.7 Hz, 2H), 6.37 (d, J=8.1 Hz, 1H), 4.26 (dm, J=7.5 Hz, 4H), 3.55-3.44 (m, 2H), 2.88-2.80 (m, 3H), 2.84 (s, 3H), 2.06-1.93 (m, 2H), 1.80-1.65 (m, 1H), 1.58-1.45 (m, 1H) ppm; MS (ES) 423.02 (M+H), 421.07 (M–H).

5-amino-1-(1H-indol-6-yl)carbonyl-3-(1-methylsulfonylpiperidin-4-yl)amino-1H-1,2,4-triazole (compound #398), off-white solid; $^1$H-NMR (DMSO-d$_6$, 300 MHz) 11.50 (br. s, 1H), 8.42 (d, J=9.0 Hz, 1H), 7.87 (d, J=7.5 Hz, 1H), 7.58 (d, J=8.7 Hz, 1H), 7.57 (br. s, 1H), 6.50 (s, 1H), 3.56-3.46 (m, 2H), 2.86-2.79 (m, 3H), 2.83 (s, 3H), 2.10-1.97 (m, 2H), 1.80-1.68 (m, 1H), 1.60-1.46 (m, 1H) ppm; MS (ES) 404.06 (M+H), 402.14 (M–H).

5-amino-1-(4-(morpholin-4-yl)phenyl)carbonyl-3-(1-methylsulfonylpiperidin-4-yl)amino-1H-1,2,4-triazole (compound #399), off-white solid; $^1$H-NMR (DMSO-d$_6$, 300 MHz) 8.18 (d, J=8.4 Hz, 2H), 7.56 (br. s, 2H), 6.96 (d, J=8.7 Hz, 2H), 6.30 (d, J=7.2 Hz, 1H), 3.72 (br. s, 4H), 3.50-3.40 (m, 2H), 2.88-2.80 (m, 3H), 2.85 (s, 3H), 2.04-1.92 (m, 2H), 1.60-1.46 (m, 2H) ppm; MS (ES) 450.04 (M+H), 448.21 (M–H).

5-amino-1-(4-(1,1-dioxo-thiomorpholin-4-yl)phenyl)carbonyl-3-[4-[2-(pyrrolidin-1-yl)ethoxy]phenylamino]-1H-1,2,4-triazole (compound #400), pale yellow solid; $^1$H-NMR (DMSO-d$_6$, 300 MHz) 9.01 (br. s, 1H), 8.23 (d, J=6.0 Hz, 2H), 7.68 (br. s, 2H), 7.44 (d, J=8.1 Hz, 2H), 7.13 (d, J=8.1 Hz, 2H), 6.83 (d, J=6.0 Hz, 2H), 3.97 (br. s, 4H), 3.15 (br. s, 6H), 2.85-2.75 (m, 2H), 2.52 (br. s, 4H), 1.68 (br. s, 4H) ppm; MS (ES) 526.04 (M+H), 524.13 (M–H).

5-amino-1-(4-(piperidin-1-yl)phenyl)carbonyl-3-[4-[2-(pyrrolidin-1-yl)ethoxy]phenylamino]-1H-1,2,4-triazole (compound #401), pale yellow solid; $^1$H-NMR (DMSO-d$_6$, 300 MHz) 8.97 (br. s, 1H), 8.22 (d, J=9.0 Hz, 2H), 7.63 (br. s, 2H), 7.44 (d, J=9.0 Hz, 2H), 6.98 (d, J=9.3 Hz, 1H), 6.84 (d, J=8.7 Hz, 2H), 3.99 (t, J=6.0 Hz, 4H), 3.40 (br. s, 4H), 2.77 (t, J=5.7 Hz, 2H), 2.53 (br. s, 4H), 1.68 (br. s, 4H), 1.60 (br. s, 6H) ppm; MS (ES) 476.95 (M+H), 474.62 (M–H).

5-amino-3-[3-chloro-4-[2-(pyrrolidin-1-yl)ethoxy]phenylamino]-1-(3,5-dichlorophenyl)carbonyl-1H-1,2,4-triazole (compound #402); $^1$H-NMR (DMSO-d$_6$) δ 8.18 (d, 1H), 7.90 (m, 3H), 7.19 (d, 2H), 4.20 (t, 2H), 2.93 (m, 2H), 2.69 (m, 4H), 1.72 (s, 4H) ppm; MS (ES) 496 (M+H).

5-amino-3-[N-(3-(4-(2-chloro-6-fluorophenyl)piperazin-1-yl)prop-1-yl)-N-((3-methylphenyl)carbonyl)amino]-1-(3-methylphenyl)carbonyl-1H-1,2,4-triazole (compound #403); mp 109-113° C.; $^1$H-NMR (300 MHz, DMSO-d$_6$) δ 7.90 (br s, 2H), 7.40-7.08 (m, 10H), 6.92 (d, J=7.8 Hz, 1H), 3.81 (m, 2H), 3.55 (br s, 2H), 2.50-2.20 (m, 14H), 1.74 (m, 2H); IR (ATR) 2813, 1663, 1549, 1440 cm$^{-1}$; ESI MS m/z 605 [C$_{32}$H$_{36}$ClFN$_7$O$_2$+H]$^+$; HPLC (Method 1) 91.9% (AUC), t$_R$=11.56 min.

3-amino-5-[3-(4-(2-chloro-6-fluorophenyl)piperazin-1-yl)prop-1-yl]amino-1-(3-methylphenyl)carbonyl-1H-1,2,4-triazole (compound #404); mp 86-92° C.; $^1$H NMR (300 MHz, DMSO-d$_6$) δ 8.13 (m, 1H), 7.87-7.82 (m, 2H), 7.40-7.30 (m, 4H), 7.21 (m, 1H), 5.84 (br s, 2H), 3.59 (br s, 2H), 3.39 (m, 2H), 2.37-2.30 (m, 13H), 1.74 (m, 2H); $^{13}$C NMR (75 MHz, DMSO-d$_6$) δ 164.6, 160.4, 158.2, 156.4, 135.3, 134.0, 133.9, 131.4, 130.9, 128.6, 128.4, 128.3, 126.0, 125.6, 123.8, 122.0, 121.7, 112.8, 122.5, 54.2, 51.1, 50.6, 50.3, 40.3, 23.8, 19.3; IR (ATR) 2814, 1669, 1630, 1650, 1573 cm$^{-1}$; ESI MS m/z 486 [C$_{24}$H$_{29}$ClFN$_7$O+H]$^+$; HPLC (Method 1) 96.7% (AUC), t$_R$=9.55 min.

5-amino-3-[3-(4-(2-chloro-6-fluorophenyl)piperazin-1-yl)prop-1-yl]amino-1-(3-methylphenyl)carbonyl-1H-1,2,4-triazole (compound #405); mp 62-69° C.; $^1$H NMR (300 MHz, DMSO-d$_6$) δ 7.90 (m, 2H), 7.63 (br s, 2H), 7.40-7.32 (m, 4H), 7.22 (m, 1H), 6.29 (m, 1H), 3.57 (m, 2H), 3.03 (m, 2H), 2.40-2.20 (m, 8H), 2.36 (s, 3H), 1.63 (m, 2H); $^{13}$C NMR (75 MHz, DMSO-d$_6$) δ 166.7, 163.5, 162.5, 160.2, 158.4, 137.3, 135.9, 133.7, 133.3, 133.1, 131.1, 130.5, 130.3, 130.1, 128.8, 128.0, 127.9, 126.8, 125.9, 123.9, 123.7, 114.8, 114.5, 55.9, 53.0, 52.8, 52.3, 26.6, 22.0; IR (ATR) 2938, 1672, 1587, 1347 cm$^{-1}$; ESI MS m/z 486 [C$_{24}$H$_{29}$ClFN$_7$O+H]$^+$; HPLC (Method 1) 95.8% (AUC), t$_R$=9.91 min.

All compounds of the invention which exist in free base or acid form can be converted to their pharmaceutically acceptable salts by treatment with the appropriate inorganic or organic base or acid by methods known to one of ordinary skill in the art. Salts of the compounds of the invention can be converted to their free base or acid form by standard techniques known to one skilled in the art.

Testing of the Compounds of the Invention

The compounds of the invention were tested in the following assay for their ability to inhibit Axl activity.

Phospho-Akt in-Cell Western Assay

Reagents and Buffers:

Cell culture plate: 96 well assay plate (Corning 3610), white, clear bottom, tissue-culture treated.

Cells: Hela cells.

Starvation medium: For Axl stimulation: 0.5% FCS (fetal calf serum) in DMEM, plus Axl/Fc (extracellular domain of AXL fused to immunoglobulin Fc region) (R&D, 154-AL) 500 ng/mL.

For EGF (epidermal growth factor) stimulation: 0.5% FCS in DMEM (Dulbecco's modified Eagles medium).

Poly-L-Lysine 0.01% solution (the working solution): 10 µg/ml, dilute In PBS (phosphate buffered saline).

Axl antibody cross-linking:

$1^{st}$: Mouse anti-Axl (R&D, MAB154).

$2^{nd}$: Biotin-SP-conjugated AffiniPure goat anti-mouse IgG (H+L) (Jackson ImmunoResearch #115-065-003).

Fixing buffer: 4% formaldehyde in PBS.

Wash buffer: 0.1% TritonX-100 in PBS.

Quenching buffer: 3% $H_2O_2$, 0.1% Azide in wash buffer, Azide and hydrogen peroxide ($H_2O_2$) are added fresh.

Blocking buffer: 5% BSA in TBST (tris buffered saline plus 0.1% Tween 20).

Primary antibody: Rabbit anti-human Phospho-Akt antibody (Cell Signaling 9271): 1×250 diluted in blocking buffer.

Secondary antibody: HRP (horse radish peroxidase)-conjugated Goat anti-Rabbit secondary, stock solution: Jackson ImmunoResearch (Goat anti-Rabbit HRP, #111-035-144) 1:1 diluted in glycerol, store at −20° C. The working solution: 1×2000 dilution of stock in blocking buffer.

Chemiluminescent working solution (Pierce, 37030): SuperSignal ELISA (enzyme linked immunosorbant assay) Pico Chemiluminescent substrate.

Crystal Violet solution: Stock: 2.5% Crystal violet in methanol, filtered and kept at ambient temperature. The working solution: dilute the stock 1:20 with PBS immediately before use.

10% SDS: working solution: 5% SDS (sodium dodecylsulfate), diluted in PBS

Methods:

Day 1:

A 96 well TC (tissue culture treated) plate was coated with 10 µg/mL poly-L-Lysine at 37° C. for 30 min, washed twice with PBS, and air-dried for 5 minutes before cells were added. Hela cells were seeded at 10,000 cells/well and the cells were starved in 100 µL starvation medium containing Axl/Fc for 24 hrs.

Day 2:

The cells were pre-treated with test compounds by adding 100 µL of 2× test compound to the starvation medium on the cells. The cells were incubated at 37° C. for 1 hr before stimulation.

The cells were stimulated by Axl-antibody cross-linking as follows: A 5×$1^{st}$/$2^{nd}$ Axl antibody mixture was made (37.5 µg/mL $1^{st}$/100 µg/mL $2^{nd}$) in starvation medium and nutatedat 4° C. with thorough mixing for 1-2 hours for clustering. The resulting mix was warmed to 37° C. 50 µL of 5× Axl $1^{st}$/$2^{nd}$ of antibody cluster was added to the cells and the cells were incubated at 37° C. for 5 min.

After 5 minutes stimulation, the plate was flicked to remove medium and the plate was tapped onto paper towels. Formaldehyde (4.0% in PBS, 100 µL) was added to fix the cells and the cells were incubated at ambient temperature for 20 min without shaking.

The cells were washed with a plate washer buffer to remove the formaldehyde solution. The plate was flicked to removed excess wash buffer and tapped onto paper towels. Quenching buffer (100 µL) was added to each well and the cells were incubated at ambient temperature for 20 minutes without shaking.

The cells were washed with a plate washer buffer to remove the quenching buffer. Blocking buffer (100 µL) was added and the cells were incubated at ambient temperature for at least an hour with gentle shaking.

The cells were washed with a plate washer buffer and diluted primary antibody (50 µL) was added to each well (blocking buffer was added to the negative control wells instead). The plates were incubated overnight at 4° C. with gentle shaking.

Day 3:

The wash buffer was removed, diluted secondary antibody (100 µL) was added, and the cells were incubated at ambient temperature for 1 hour with gentle shaking. During the incubation, the chemiluminescent reagent was brought to ambient temperature.

The secondary antibody was removed by washing the cells 1× with wash buffer, 1× with PBS by plate washer. The PBS was removed from the plate and the chemiluminescent reagent (80 µL: 40 µL A and 40 µL B) was added to each well at ambient temperature.

The resulting chemiluminescence was read with a Luminomitor within 10 minutes to minimize changes in signal intensity. After reading the chemiluminescence, the cells were washed 1× with wash buffer and 1× with PBS by plate washer. The plate was tapped onto paper towels to remove excess liquid from wells and air-dried at ambient temperature for 5 minutes.

Crystal Violet working solution (60 µL) was added to each well and the cells were incubated at ambient temperature for 30 min. The crystal violet solution was removed, and the wells were rinsed with PBS, then washed 3× with PBS (200 µL) for 5 minutes each.

5% SDS solution (70 µL) was added to each well and the cells were incubated on a shaker for 30 min at ambient temperature.

The absorbance was read at 590 nM on a Wallac photospec. The 590 nM readings indicated the relative cell number in each well. This relative cell number was then used to normalize each luminescence reading.

The results of the ability of the compounds of the invention to inhibit Axl activity, when tested in the above assay, are shown in the following Tables 1-10 wherein the level of activity (i.e., the $IC_{50}$) for each compound is indicated in each Table. The compound numbers in the Tables referred to the compounds disclosed herein as being prepared by the methods disclosed herein:

TABLE 1

| Cpd # | Compound Name | R1b | R1c | R1d | R4 | R3b | R3c | R3d | R3e | R3f | IC50 |
|---|---|---|---|---|---|---|---|---|---|---|---|
| 168 | 5-amino-1-(3-(iso-propoxy)phenyl)carbonyl-3-[4-[2-(piperidin-1-yl)ethoxy]phenylamino]-1H-1,2,4-triazole | ~O\~N(piperidine) | H | H | H | H | isopropoxy (O-iPr) | H | H | H | A |
| 169 | 5-amino-1-(3-(iso-propoxy)phenyl)carbonyl-3-[4-[2-(morpholin-4-yl)ethoxy]phenylamino]-1H-1,2,4-triazole | ~O\~N(morpholine) | H | H | H | H | isopropoxy (O-iPr) | H | H | H | A |
| 170 | 5-amino-1-(3-(iso-propoxy)phenyl)carbonyl-3-[3-(1,3-oxazol-5-yl)phenylamino]-1H-1,2,4-triazole | H | oxazol-5-yl | H | H | H | isopropoxy (O-iPr) | H | H | H | B |

TABLE 1-continued

| Cpd # | Compound Name | R1b | R1c | R1d | R4 | R3b | R3c | R3d | R3e | R3f | IC50 |
|---|---|---|---|---|---|---|---|---|---|---|---|
| 94 | 5-amino-1-(2-(chlorophenyl)carbonyl-3-(1,4-benzodioxan-6-yl)amino-1H-1,2,4-triazole | | -O-CH2-CH2-O- | —H | —H | —H | —H | —Cl | —H | —H | D |
| 95 | 5-amino-1-(4-(chlorophenyl)carbonyl-3-(1,4-benzodioxan-6-yl)amino-1H-1,2,4-triazole | | -O-CH2-CH2-O- | —H | —H | —Cl | —H | —H | —H | —H | B |
| 96 | 5-amino-3-(1,4-benzodioxan-6-yl)amino-1-(3-(methyl)phenyl)carbonyl-1H-1,2,4-triazole | | -O-CH2-CH2-O- | —H | —H | —H | —CH3 | —H | —H | —H | B |
| 97 | 5-amino-3-(1,4-benzodioxan-6-yl)amino-1-(2-(methyl)phenyl)carbonyl-1H-1,2,4-triazole | | -O-CH2-CH2-O- | —H | —H | —H | —H | —CH3 | —H | —H | C |
| 98 | 5-amino-3-(1,4-benzodioxan-6-yl)amino-1-(3-(methoxy)phenyl)carbonyl-1H-1,2,4-triazole | | -O-CH2-CH2-O- | —H | —H | —H | —OCH3 | —H | —H | —H | B |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 99 | 5-amino-3-(1,4-benzodioxan-6-yl)amino-1-(2-(fluoro)phenyl) carbonyl-1H-1,2,4-triazole | | —O–CH$_2$–CH$_2$–O— | | —H | —H | —H | —F | —H | —H | C |
| 100 | 5-amino-3-(1,4-benzodioxan-6-yl)amino-1-(4-(fluoro)phenyl) carbonyl-1H-1,2,4-triazole | | —O–CH$_2$–CH$_2$–O— | | —H | —F | —H | —H | —H | —H | D |
| 101 | 5-amino-1-(3-(chloro)phenyl) carbonyl-3-(1,4-benzodioxan-6-yl) amino-1H-1,2,4-triazole | | —O–CH$_2$–CH$_2$–O— | | —H | —H | —Cl | —H | —H | —H | B |
| 102 | 5-amino-3-(1,4-benzodioxan-6-yl)amino-1-(4-(methyloxy)phenyl) carbonyl-1H-1,2,4-triazole | | —O–CH$_2$–CH$_2$–O— | | —H | —OCH$_3$ | —H | —H | —H | —H | B |
| (Ia-15) | 5-amino-3-[3-(hydroxy)phenyl]amino]-1-(4-(methyl)phenyl) carbonyl-1H-1,2,4-triazole | —H | —OH | | —H | —CH$_3$ | —H | —H | —H | —H | C |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| (Ia-4) | 5-amino-3-[4-(hydroxy)phenylamino]-1-(4-(methyl)phenyl)carbonyl-1H-1,2,4-triazole | —OH | —H | —H | —H | —CH$_3$ | —H | —H | —H | —H | D |
| 104 | 5-amino-3-(1,4-benzodioxan-6-yl)amino-1-(4-(methyl)phenyl)carbonyl-1H-1,2,4-triazole | —O-CH$_2$-CH$_2$-O— | | —H | —H | —CH$_3$ | —H | —H | —H | —H | B |
| 105 | 5-amino-3-(1,4-benzodioxan-6-yl)amino-1-(3-(fluoro)phenyl)carbonyl-1H-1,2,4-triazole | —O-CH$_2$-CH$_2$-O— | | —H | —H | —H | —F | —H | —H | —H | D |
| 106 | 5-amino-3-(1,4-benzodioxan-6-yl)amino-1-(2-(methyloxyphenyl)carbonyl-1H-1,2,4-triazole | —O-CH$_2$-CH$_2$-O— | | —H | —H | —H | —H | —OCH$_3$ | —H | —H | D |
| (Ia-6) | 5-amino-3-[3-(hydroxyphenyl-amino)]-1-(2-(methyl)phenyl)carbonyl-1H-1,2,4-triazole | —H | —OH | —H | —H | —H | —H | —CH$_3$ | —H | —H | D |
| (Ia-7) | 5-amino-3-[3-(hydroxy)phenylamino]-1-(3-(methyl)phenyl)carbonyl-1H-1,2,4-triazole | —H | —OH | —H | —H | —H | —CH$_3$ | —H | —H | —H | B |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| (Ia-5) | 5-amino-3-[3-(cyanomethoxy)phenylamino]-1-(4-(methyl)phenyl)carbonyl-1H-1,2,4-triazole | —H | —OCH$_2$CN | —H | —H | —CH$_3$ | —H | —H | —H | —H | D |
| (Ia-10) | 5-amino-3-[4-(benzyloxy)phenylamino]-1-(4-(iso-propoxy)phenyl)carbonyl-1H-1,2,4-triazole | —OCH$_2$—Ph | —H | —H | —H | ⟨isopropoxy⟩ | —H | —H | —H | —H | D |
| 109 | 1-(4-(acetoxy)phenyl)carbonyl-5-amino-3-(1,4-benzodioxan-6-yl)amino-1H-1,2,4-triazole | ⟨-OCH$_2$CH$_2$O-⟩ | | —H | —OC(O)CH$_3$ | —H | —H | —H | —H | B | |
| 110 | 1-(3-(acetoxy)phenyl)carbonyl-5-amino-3-(1,4-benzodioxan-6-yl)amino-1H-1,2,4-triazole | ⟨-OCH$_2$CH$_2$O-⟩ | | —H | —H | —OC(O)CH$_3$ | —H | —H | —H | B | |
| (Ia-8) | 5-amino-3-[3-(cyanomethoxy)phenylamino]-1-(2-(methyl)phenyl)carbonyl-1H-1,2,4-triazole | —H | —OCH$_2$CN | —H | —H | —H | —H | —CH$_3$ | —H | —H | D |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| (Ia-9) | 5-amino-3-[3-(cyanomethoxy)phenylamino]-1-(3-(methyl)phenyl)carbonyl-1H-1,2,4-triazole | H | —OCH$_2$CN | H | H | H | —CH$_3$ | H | H | H | D |
| (Ia-17) | 5-amino-3-[3-(benzyloxy)phenylamino]-1-(3-(isopropoxy)phenyl)carbonyl-1H-1,2,4-triazole | H | —OCH$_2$—Ph | H | H | H | isopropoxy | H | H | H | D |
| 111 | 5-amino-3-[4-(isopropoxy)phenylamino]-1-(4-(isopropoxy)phenyl)carbonyl-1H-1,2,4-triazole | isopropoxy | H | H | H | H | H | H | H | H | B |
| 112 | 5-amino-3-(1,4-benzodioxan-6-yl)amino-1-(3-(isopropoxy)phenyl)carbonyl-1H-1,2,4-triazole | | OCH$_2$CH$_2$O | | H | H | isopropoxy | H | H | H | B |
| 113 | 5-amino-3-(1,4-benzodioxan-6-yl)amino-1-(4-(isopropoxy)phenyl)carbonyl-1H-1,2,4-triazole | | OCH$_2$CH$_2$O | | H | isopropoxy | H | H | H | H | B |

TABLE 1-continued

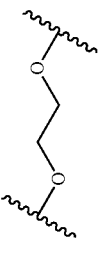

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 114 | 5-amino-1-(4-ethoxyphenyl) carbonyl-3-(1,4-benzodioxan-6-yl) amino-1H-1,2,4-triazole | —H | 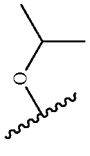 | —H | —H | —OCH$_2$CH$_3$ | —H | —H | —H | —H | B |
| (Ia-16) | 5-amino-3-[3-(hydroxy) phenylamino]-1-(3-(iso-propoxy)phenyl) carbonyl-1H-1,2,4-triazole | —H | —OH | —H | —H | —H | 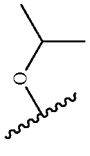 | —H | —H | —H | B |
| (Ia-13) | 5-amino-3-[3-(hydroxy) phenylamino]-1-(4-(iso-propoxy)phenyl) carbonyl-1H-1,2,4-triazole | —H | —OH | —H | —H | 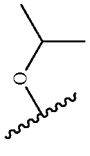 | —H | —H | —H | —H | B |
| (Ia-25) | 5-amino-3-[3-(benzyloxy) phenylamino]-1-(4-(iso-propoxy)phenyl) carbonyl-1H-1,2,4-triazole | —H | —OCH$_2$—Ph | —H | —H | 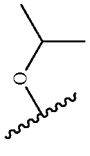 | —H | —H | —H | —H | D |
| 116 | 5-amino-3-[3-(cyclopentoxy) phenylamino]-1-(4-(iso-propoxy) phenyl)carbonyl-1H-1,2,4-triazole | —H |  | —H | —H |  | —H | —H | —H | —H | D |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| (Ia-11) | 5-amino-3-[4-(hydroxy)phenylamino]-1-(4-(iso-propoxy)phenyl)carbonyl-1H-1,2,4-triazole | —OH | H | H | H | iso-propoxy | H | H | H | H | B |
| 117 | 5-amino-1-(4-(iso-propoxy)phenyl)carbonyl-3-[4-(methoxy)phenylamino]-1H-1,2,4-triazole | —OCH$_3$ | H | H | H | iso-propoxy | H | H | H | H | B |
| 118 | 5-amino-3-[4-(ethoxy)phenylamino]-1-(4-(iso-propoxy)phenyl)carbonyl-1H-1,2,4-triazole | —OCH$_2$CH$_3$ | H | H | H | iso-propoxy | H | H | H | H | B |
| 119 | 1-(2-(acetoxy)phenyl)carbonyl-5-amino-3-(1,4-benzodioxan-6-yl)amino-1H-1,2,4-triazole | -OCH$_2$CH$_2$O- | | H | H | H | H | acetoxy | H | H | B |
| 120 | 5-amino-1-(4-(cyclopentoxy)phenyl)carbonyl-3-(1,4-benzodioxan-6-yl)amino-1H-1,2,4-triazole | -OCH$_2$CH$_2$O- | | H | H | cyclopentoxy | H | H | H | H | D |

TABLE 1-continued

| Cpd # | Compound Name | R1b | R1c | R1d | R4 | R3b | R3c | R3d | R3e | R3f | IC50 |
|---|---|---|---|---|---|---|---|---|---|---|---|
| 121 | 5-amino-1-(4-(iso-propoxy)phenyl) carbonyl]-3-[3-(methoxy) phenylamino]-1H-1,2,4-triazole | —H | —OCH₃ | —H | —H | —O-iPr | —H | —H | —H | —H | B |
| 122 | 5-amino-3-[3-(iso-propoxy)phenylamino)-1-(4-iso-propoxy)phenyl) carbonyl-1H-1,2,4-triazole | —H | —O-iPr | —H | —H | —O-iPr | —H | —H | —H | —H | B |
| 123 | 5-amino-3-[4-(fluoro)phenylamino]-1-(4-(methyl)phenyl) carbonyl-1H-1,2,4-triazole | —F | —H | —H | —H | —CH₃ | —H | —H | —H | —H | C |
| 124 | 5-amino-3-[3-(fluoro)phenylamino)-1-(4-(methyl)phenyl) carbonyl-1H-1,2,4-triazole | —H | —F | —H | —H | —CH₃ | —H | —H | —H | —H | C |
| (Ia-26) | 5-amino-3-[3-[2-(morpholin-4-yl)ethoxy] phenylamino]-1-phenylcarbonyl-1H-1,2,4-triazole | —H | —O(CH₂)₂-morpholine | —H | —H | —H | —H | —H | —H | —H | D |

TABLE 1-continued
| Cpd # | Compound Name | R1b | R1c | R1d | R4 | R3b | R3c | R3d | R3e | R3f | IC50 |
|---|---|---|---|---|---|---|---|---|---|---|---|
| (Ia-27) | 5-amino-1-(3-(methyl) phenyl)carbonyl-3-[3-[2-(morpholin-4-yl)ethoxy] phenylamino]-1H-1,2,4-triazole | —H |  | —H | —H | —H | —CH3 | —H | —H | —H | B |
| (Ia-22) | 5-amino-1-(4-(iso-propoxy) phenyl)carbonyl-3-[3-[2-(morpholin-4-yl)ethoxy] phenylamino]-1H-1,2,4-triazole | —H |  | —H | —H |  | —H | —H | —H | —H | B |
| 125 | 5-amino-3-[3-(ethoxyphenylamino]-1-(4-(iso-propoxy)phenyl) carbonyl-1H-1,2,4-triazole | —H | —OCH2CH3 | —H | —H |  | —H | —H | —H | —H | B |

TABLE 1-continued

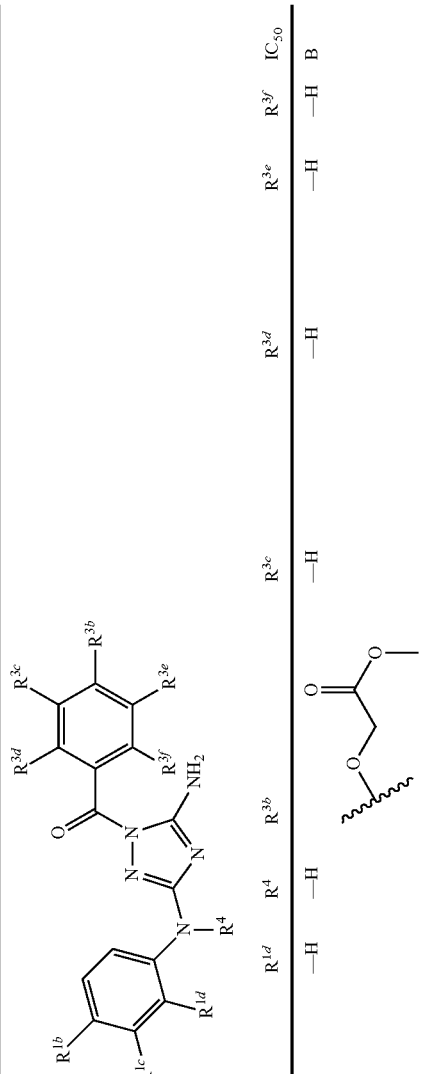

| Cpd # | Compound Name | R1b | R1c | R1d | R4 | R3b | R3c | R3d | R3e | R3f | IC50 |
|---|---|---|---|---|---|---|---|---|---|---|---|
| 126 | 5-amino-3-(1,4-benzodioxan-6-yl)amino-1-[4-(methoxy-carbonylmethoxy)phenyl)-carbonyl]-1H-1,2,4-triazole | | 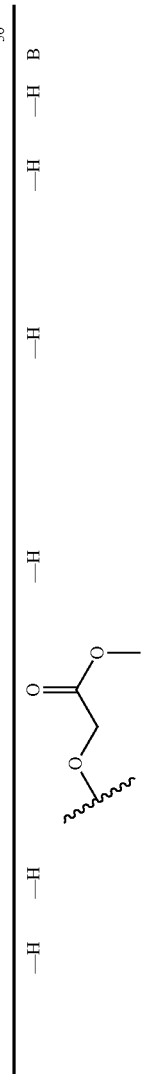 | | H | (methoxycarbonylmethoxy) | H | H | H | H | B |
| 127 | 5-amino-1-(3-(cyclopentoxy)phenyl)carbonyl-3-(1,4-benzodioxan-6-yl)amino-1H-1,2,4-triazole | | | | H | H | cyclopentoxy | H | H | H | B |
| 128 | 5-amino-1-(3-(ethoxyphenyl)carbonyl-3-(1,4-benzodioxan-6-yl)amino-1H-1,2,4-triazole | | | | H | H | —OCH2CH3 | H | H | H | D |
| 129 | 5-amino-3-[2-(fluoro)phenylamino]-1-(4-(methyl)phenyl)carbonyl-1H-1,2,4-triazole | —H | | —F | H | —CH3 | H | H | H | H | D |
| 131 | 5-amino-3-[4-(methyl)phenylamino]-1-(4-(methyl)phenyl)carbonyl-1H-1,2,4-triazole | —CH3 | | —H | H | —CH3 | H | H | H | H | D |
| 132 | 5-amino-3-[4-(methoxy)phenylamino]-1-(4-(methyl)phenyl)carbonyl-1H-1,2,4-triazole | —OCH3 | | —H | H | —CH3 | H | H | H | H | B |

TABLE 1-continued

| Cpd # | Compound Name | $R^{1b}$ | $R^{1c}$ | $R^{1d}$ | $R^4$ | $R^{3b}$ | $R^{3c}$ | $R^{3d}$ | $R^{3e}$ | $R^{3f}$ | $IC_{50}$ |
|---|---|---|---|---|---|---|---|---|---|---|---|
| 133 | 5-amino-3-[3-(methyl)phenylamino]-1-(4-(methyl)phenyl)carbonyl-1H-1,2,4-triazole | —H | —CH₃ | —H | —H | —CH₃ | —H | —H | —H | —H | B |
| 134 | 5-amino-3-[3-(methoxy)phenylamino]-1-(4-(methyl)phenyl)carbonyl-1H-1,2,4-triazole | —H | —OCH₃ | —H | —H | —CH₃ | —H | —H | —H | —H | B |
| 135 | 5-amino-1-(4-(iso-propoxy)phenyl)carbonyl-3-[3-(methoxy-carbonylmethoxy)phenyl-amino]-1H-1,2,4-triazole | —H | —OCH₂C(O)OCH₃ | —H | —H | —OCH(CH₃)₂ | —H | —H | —H | —H | B |
| (Ia-23) | 5-amino-1-(4-(iso-propoxy)phenyl)carbonyl-3-[3-(piperidin-1-yl)phenylamino]-1H-1,2,4-triazole | —H | —OCH₂CH₂-(piperidin-1-yl) | —H | —H | —OCH(CH₃)₂ | —H | —H | —H | —H | B |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| (Ia-24) | 5-amino-3-[3-[2-(1,3-dioxolan-2-yl)ethoxy]phenyl]amino]-1-(4-(isopropoxy)phenyl)carbonyl]-1H-1,2,4-triazole | —H |  | —H | —H | 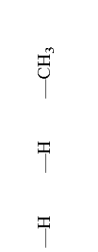 | —H | —H | —H | —H | B |
| 137 | 5-amino-1-(4-(methyl)phenyl)carbonyl-3-phenylamino-1H-1,2,4-triazole | —H | —H | —H | —H | —CH$_3$ | —H | —H | —H | —H | D |
| 138 | 5-amino-3-(1,4-benzodioxan-6-yl)amino-1-[3-(methoxycarbonylmethoxy)phenyl]carbonyl-1H-1,2,4-triazole | —H |  | —H | —H | —H | 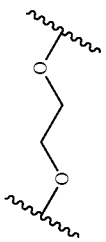 | —H | —H | —H | B |
| 139 | 5-amino-1-(4-(isopropoxy)phenyl)carbonyl-3-[3-(2,2,2-trifluoroethoxy)phenylamino]-1H-1,2,4-triazole | —H | —OCH$_2$CF$_3$ | —H | —H | 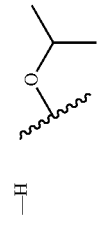 | —H | —H | —H | —H | D |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| (Ia-12) | 5-amino-3-[4-(cyanomethoxy)phenylamino]-1-(4-(iso-propoxy)phenyl)carbonyl-1H-1,2,4-triazole | —OCH$_2$CN | —H | —H | —H | —O-iPr | —H | —H | —H | —H | B |
| (Ia-21) | 5-amino-3-[3-(cyanomethoxy)phenylamino]-1-(4-(iso-propoxy)phenyl)carbonyl-1H-1,2,4-triazole | —H | —OCH$_2$CN | —H | —H | —O-iPr | —H | —H | —H | —H | B |
| 142 | 5-amino-1-(4-(benzyloxy)phenyl)carbonyl-3-(1,4-benzodioxan-6-ylamino-1H-1,2,4-triazole | —H | —OCH$_2$CH$_2$O— | | —H | —OCH$_2$Ph | —H | —H | —H | —H | B |
| 143 | 5-amino-3-[2-(methoxy)phenylamino]-1-(4-(methyl)phenyl)carbonyl-1H-1,2,4-triazole | —H | —H | —OCH$_3$ | —H | —CH$_3$ | —H | —H | —H | —H | D |
| 144 | 5-amino-3-[2-(methyl)phenylamino]-1-(4-(methyl)phenyl)carbonyl-1H-1,2,4-triazole | —H | —H | —CH$_3$ | —H | —CH$_3$ | —H | —H | —H | —H | D |

TABLE 1-continued

| Cpd # | Compound Name | R1b | R1c | R1d | R4 | R3b | R3c | R3d | R3e | R3f | IC50 |
|---|---|---|---|---|---|---|---|---|---|---|---|
| 145 | 5-amino-3-[2-(hydroxy)ethoxy]phenylamino]-1-(3-(methyl)phenyl)carbonyl-1H-1,2,4-triazole | —H | —O-CH2CH2-OH | —H | —H | —CH3 | —H | —H | —H | —H | B |
| 146 | 5-amino-3-[3-(methyl-aminocarbonylmethoxy)phenylamino]-1-(3-(methyl)phenyl)carbonyl-1H-1,2,4-triazole | —H | —O-CH2-C(=O)-NH-CH3 | —H | —H | —H | —CH3 | —H | —H | —H | B |
| 147 | 5-amino-3-[3-(methoxy-carbonylmethoxy)phenylamino]-1-(3-(methyl)phenyl)carbonyl-1H-1,2,4-triazole | —H | —O-CH2-C(=O)-O-CH3 | —H | —H | —H | —CH3 | —H | —H | —H | B |
| 148 | 5-amino-3-[3-(N-(2,2-dimethyl-1,3-dioxolan-4-yl)methyl)aminocarbonylmethoxy)phenylamino]-1-(3-(methyl)phenyl)carbonyl-1H-1,2,4-triazole | —H | —O-CH2-C(=O)-NH-CH2-(2,2-dimethyl-1,3-dioxolan-4-yl) | —H | —H | —H | —CH3 | —H | —H | —H | B |

TABLE 1-continued

| Cpd # | Compound Name | R$^{1b}$ | R$^{1c}$ | R$^{1d}$ | R$^{4}$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 149 | 5-amino-3-(1,4-benzodioxan-6-yl)amino-1-[4-[2-(morpholin-4-yl)ethoxy]phenyl]carbonyl-1H-1,2,4-triazole | 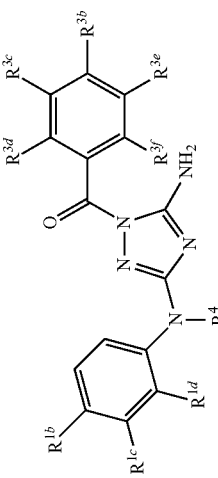 | | H | H | 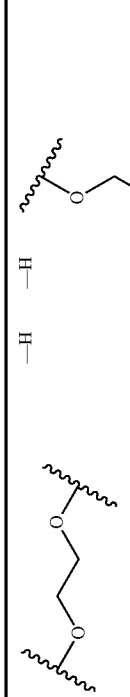 | H | H | H | H | B |
| 150 | 5-amino-3-(1,4-benzodioxan-6-yl)amino-1-[3-[2-(morpholin-4-yl)ethoxy]phenyl]carbonyl-1H-1,2,4-triazole | 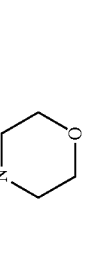 | | H | H | H |  | H | H | H | D |
| 151 | 5-amino-3-[4-(cyclopentoxy)phenylamino]-1-(4-(iso-propoxy)phenyl)carbonyl-1H-1,2,4-triazole |  | H | H | H |  | H | H | H | H | D |
| 152 | 5-amino-1-(4-(iso-propoxy)phenyl)carbonyl-3-[4-(2,2,2-trifluoroethoxy)phenylamino]-1H-1,2,4-triazole | —OCH$_2$CF$_3$ | H | H | H | 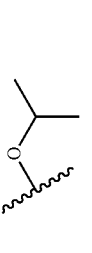 | H | H | H | H | D |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 153 | 5-amino-3-[3-(N-(2,3-dihydroxypropyl amino)carbonyl-methoxy]-phenylamino-1-(3-(methyl)phenyl)carbonyl-1H-1,2,4-triazole | —H | [-OCH$_2$C(O)NHCH$_2$CH(OH)CH$_2$OH] | —H | —H | —H | —CH$_3$ | —H | —H | —H | B |
| 156 | 5-amino-1-(3-(benzyloxy)phenyl)carbonyl-3-[4-(1,4-benzodioxan-6-yl)amino]-1H-1,2,4-triazole | —H | [-OCH$_2$CH$_2$OCH$_2$Ph] | —H | —H | —H | —OCH$_2$Ph | —H | —H | —H | C |
| 157 | 5-amino-1-(4-(iso-propoxy)phenyl)carbonyl-3-[4-(methoxy-carbonylmethoxy)phenyl-amino]-1H-1,2,4-triazole | —H | [-OCH$_2$C(O)OCH$_3$] | —H | —H | [-O-iPr] | —H | —H | —H | —H | B |
| 158 | 5-amino-3-[4-[2-(1,3-dioxolan-2-yl)ethoxy]phenylamino]-1-(4-(iso-propoxy)phenyl)carbonyl-1H-1,2,4-triazole | —H | [-OCH$_2$CH$_2$-(1,3-dioxolan-2-yl)] | —H | —H | [-O-iPr] | —H | —H | —H | —H | B |

TABLE 1-continued
| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 159 | 5-amino-1-(4-(iso-propoxy)phenylcarbonyl-3-[4-[2-(morpholin-4-yl)ethoxy]phenylamino]-1H-1,2,4-triazole |  | —H | —H | —H |  | —H | —H | —H | —H | A |
| 162 | 5-amino-3-(1,4-benzodioxan-6-yl)amino-1-(4-(hydroxy)phenyl)carbonyl-1H-1,2,4-triazole |  | —H | —H | —H | —OH | —H | —H | —H | —H | B |
| 163 | 5-amino-1-(4-(iso-propoxy)phenylcarbonyl-3-[4-[2-(piperidin-1-yl)ethoxy]phenylamino]-1H-1,2,4-triazole |  | —H | —H | —H |  | —H | —H | —H | —H | A |

TABLE 1-continued

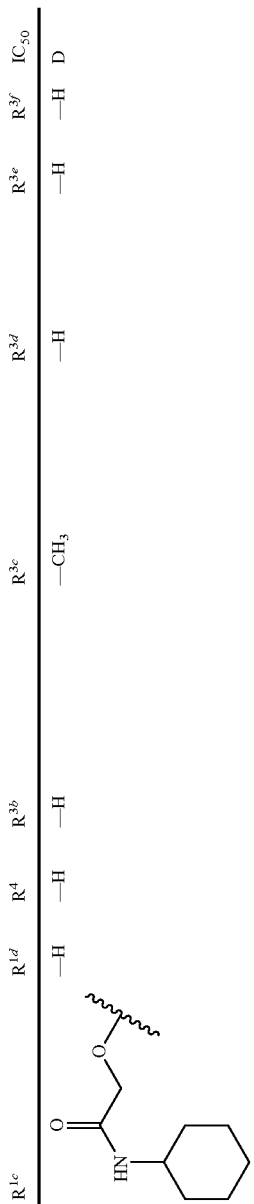

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 165 | 5-amino-3-[3-[cyclohexyl-aminocarbonylmethoxy]-phenyl]amino]-1-(3-(methyl)phenyl)carbonyl-1H-1,2,4-triazole | —H | 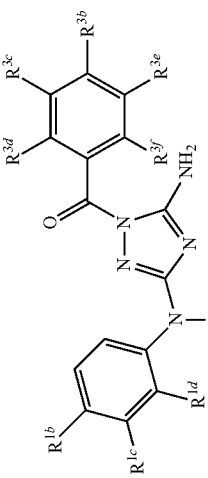 | —H | —H | —H | —CH$_3$ | —H | —H | —H | D |
| 166 | 5-amino-3-(1,4-benzodioxan-6-yl)amino-1-(3-(hydroxy)phenyl)carbonyl-1H-1,2,4-triazole | | 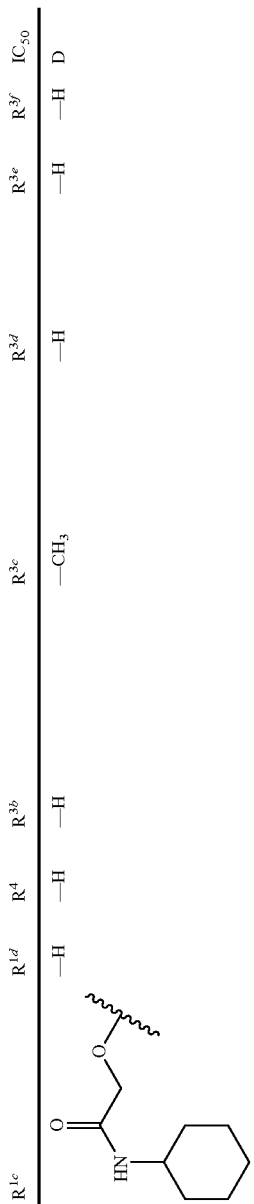 | —H | —H | —H | —OH | —H | —H | —H | B |
| 210 | 5-amino-1-[3-[2-(1,3-dioxolan-2-yl)ethoxy]phenyl]carbonyl-3-(1,4-benzodioxan-6-yl)amino-1H-1,2,4-triazole | | 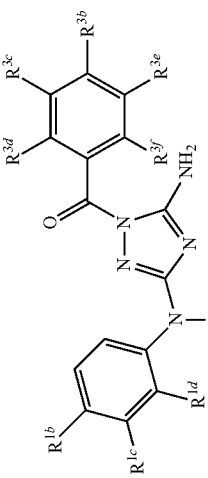 | —H | —H | —H | 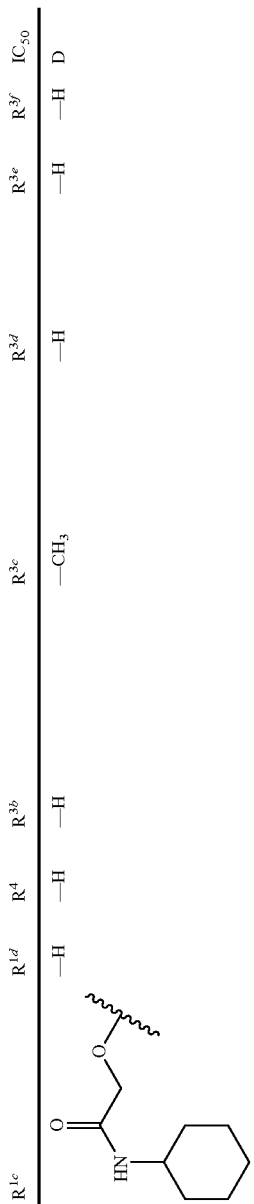 | —H | —H | —H | B |
| 211 | 5-amino-3-[2-(hydroxy)phenyl]amino]-1-(4-methylphenyl)carbonyl-1H-1,2,4-triazole | —H | —H | —OH | —H | —CH$_3$ | —H | —H | —H | —H | D |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 212 | 5-amino-1-(3-methylphenyl)carbonyl-3-[3-[(2-methoxyethoxy)methoxy]phenylamino]-1H-1,2,4-triazole | —H | (2-methoxyethoxy)methoxy group | —H | —H | —H | —CH$_3$ | —H | —H | —H | B |
| 214 | 5-amino-1-[4-[2-(1,3-dioxolan-2-yl)ethoxy]phenyl]carbonyl-3-(1,4-benzodioxan-6-yl)amino-1H-1,2,4-triazole | —H | 1,4-benzodioxan-6-yl group | —H | —H | 2-(1,3-dioxolan-2-yl)ethoxy group | —H | —H | —H | —H | B |
| 216 | 5-amino-3-(3-methoxymethoxy)phenylamino-1-(3-methylphenyl)carbonyl-1H-1,2,4-triazole | —H | methoxymethoxy group | —H | —H | —H | —CH$_3$ | —H | —H | —H | D |
| 217 | 5-amino-3-(4-chlorophenyl)amino-1-(4-chlorophenyl)carbonyl-1H-1,2,4-triazole | —Cl | —H | —H | —H | —Cl | —H | —H | —H | —H | D |
| 218 | 5-amino-3-(4-bromophenyl)amino-1-(4-chlorophenyl)carbonyl-1H-1,2,4-triazole | —Br | —H | —H | —H | —Cl | —H | —H | —H | —H | B |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 221 | 5-amino-1-(3-methylphenyl)carbonyl-3-[(3-tert-butoxycarbonylmethoxy)phenyl]amino-1H-1,2,4-triazole | —H | *tert-butyl ester of oxyacetyl group* | —H | —H | —H | —CH$_3$ | —H | —H | —H | B |
| 223 | 5-amino-1-(3-methylphenyl)carbonyl-3-[3-[2-(tetrahydropyran-2-yl)ethoxyaminocarbonyl]methoxy]phenylamino-1H-1,2,4-triazole | —H | *THP-ethoxyaminocarbonylmethoxy group* | —H | —H | —H | —CH$_3$ | —H | —H | —H | B |
| 224 | 5-amino-3-(3-hydroxycarbonylmethoxy)phenylamino-1-(3-methylphenyl)carbonyl-1H-1,2,4-triazole | —H | *carboxymethoxy group* | —H | —H | —H | —CH$_3$ | —H | —H | —H | D |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 225 | 5-amino-3-[3-((2-hydroxyethyl)aminocarbonylmethoxy)phenyl]amino-1-(3-methylphenyl)carbonyl-1H-1,2,4-triazole | —H | 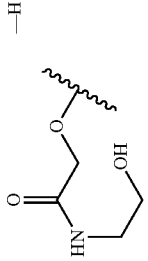 | —H | —H | —H | —CH$_3$ | —H | —H | —H | B |
| 226 | 5-amino-3-(1,4-benzodioxan-6-yl)amino-1-[4-[2-(piperidin-1-yl)ethoxy]phenylcarbonyl]-1H-1,2,4-triazole | —H | 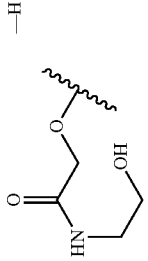 | —H | —H | 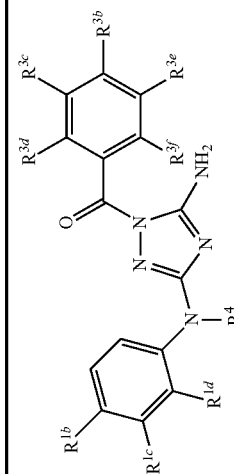 | —H | —H | —H | —H | B |
| (Ia-18) | 5-amino-1-(3-methylphenyl)carbonyl-3-[2-(4-morpholinyl)ethylaminocarbonyl)methoxy]phenyl]amino-1H-1,2,4-triazole | —H |  | —H | —H | —H | —CH$_3$ | —H | —H | —H | B |

TABLE 1-continued

| Cpd # | Compound Name | $R^{1b}$ | $R^{1c}$ | $R^{1d}$ | $R^4$ | $R^{3b}$ | $R^{3c}$ | $R^{3d}$ | $R^{3e}$ | $R^{3f}$ | $IC_{50}$ |
|---|---|---|---|---|---|---|---|---|---|---|---|
| (Ia-19) | 5-amino-1-(3-methylphenyl)carbonyl-3-[3-(N-tert-butoxycarbonyl)piperazin-4-ylcarbonylmethoxy)phenyl]amino-1H-1,2,4-triazole | —H |  | —H | —H | —H | —CH$_3$ | —H | —H | —H | D |
| 228 | 5-amino-3-(1,4-benzodioxan-6-yl)amino-1-(3-(2,2,2-trifluoroethoxy)phenyl)carbonyl-1H-1,2,4-triazole | |  | | —H | —H | —OCH$_2$CF$_3$ | —H | —H | —H | D |
| (Ia-20) | 5-amino-1-(3-methylphenyl)carbonyl-3-[3-(piperazin-4-ylcarbonylmethoxy)phenyl]amino-1H-1,2,4-triazole | —H |  | —H | —H | —H | —CH$_3$ | —H | —H | —H | B |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 230 | 5-amino-3-(1,4-benzodioxan-6-yl)amino-1-(4-(2,2,2-trifluoroethoxy)phenyl)carbonyl-1H-1,2,4-triazole | —O-CH$_2$CH$_2$-O— | | | —H | —OCH$_2$CF$_3$ | —H | —H | —H | —H | D |
| 231 | 5-amino-1-(3-aminocarbonylmethoxyphenyl)carbonyl-3-(1,4-benzodioxan-6-yl)amino-1H-1,2,4-triazole | —O-CH$_2$CH$_2$-O— | | | —H | —H | —OCH$_2$C(O)NH$_2$ | —H | —H | —H | D |
| 232 | 5-amino-3-(1,4-benzodioxan-6-yl)amino-1-(4-isopropylphenyl)carbonyl-1H-1,2,4-triazole | —O-CH$_2$CH$_2$-O— | | | —H | —CH(CH$_3$)$_2$ | —H | —H | —H | —H | B |
| 234 | 5-amino-1-(3,4-dimethylphenyl)carbonyl-3-(1,4-benzodioxan-6-yl)amino-1H-1,2,4-triazole | —O-CH$_2$CH$_2$-O— | | | —H | —CH$_3$ | —CH$_3$ | —H | —H | —H | B |
| 237 | 5-amino-3-(1,4-benzodioxan-6-yl)amino-1-(4-thiomethylphenyl)carbonyl-1H-1,2,4-triazole | —O-CH$_2$CH$_2$-O— | | | —H | —SCH$_3$ | —H | —H | —H | —H | B |
| 240 | 5-amino-3-(1,4-benzodioxan-6-yl)amino-1-(4-nitrophenyl)carbonyl-1H-1,2,4-triazole | —O-CH$_2$CH$_2$-O— | | | —H | —NO$_2$ | —H | —H | —H | —H | D |

TABLE 1-continued

| Cpd # | Compound Name | R1b | R1c | R1d | R4 | R3b | R3c | R3d | R3e | R3f | IC50 |
|---|---|---|---|---|---|---|---|---|---|---|---|
| 242 | 5-amino-3-(1,4-benzodioxan-6-yl)amino-1-[(4-fluoro-3-methyl)phenyl]carbonyl-1H-1,2,4-triazole | | *~O~\~~O~\* | —H | —H | —F | —CH₃ | —H | —H | —H | D |
| 243 | 5-amino-1-(4-aminophenyl)carbonyl-3-(1,4-benzodioxan-6-yl)amino-1H-1,2,4-triazole | | *~O~\~~O~\* | —H | —H | —NH₂ | —H | —H | —H | —H | B |
| 235 | 5-amino-1-(3-methylphenyl)carbonyl-3-[3-(methylsulfonyl methoxy)phenyl]amino-1H-1,2,4-triazole | —H | *CH₃SO₂CH₂O~\* | | —H | —H | —CH₃ | —H | —H | —H | B |
| 244 | 5-amino-3-(1,4-benzodioxan-6-yl)amino-1-[(4-trifluoromethyl)phenyl]carbonyl-1H-1,2,4-triazole | | *~O~\~~O~\* | —H | —H | —CF₃ | —H | —H | —H | —H | D |
| 245 | 5-amino-1-(4-cyanophenyl)carbonyl-3-(1,4-benzodioxan-6-yl)amino-1H-1,2,4-triazole | | *~O~\~~O~\* | —H | —H | —CN | —H | —H | —H | —H | D |

TABLE 1-continued

| Cpd # | Compound Name | R$^{1b}$ | R$^{1c}$ | R$^{1d}$ | R$^{4}$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 246 | 1-[(4-acetylamino)phenyl]carbonyl-5-amino-3-(1,4-benzodioxan-6-yl)amino-1H-1,2,4-triazole | | —O–CH$_2$CH$_2$–O— | —H | —H | —NHC(O)CH$_3$ | —H | —H | —H | —H | B |
| 247 | 5-amino-1-[(4-dimethylamino)phenyl]carbonyl-3-(1,4-benzodioxan-6-yl)amino-1H-1,2,4-triazole | | —O–CH$_2$CH$_2$–O— | —H | —H | —N(CH$_3$)$_2$ | —H | —H | —H | —H | B |
| 248 | 5-amino-3-(1,4-benzodioxan-6-yl)amino-1-[(4-methylsulfonyl)phenyl]carbonyl-1H-1,2,4-triazole | | —O–CH$_2$CH$_2$–O— | —H | —H | —SO$_2$CH$_3$ | —H | —H | —H | —H | D |
| 249 | 5-amino-1-[(3-chloro-4-methyl)phenyl]carbonyl-3-(1,4-benzodioxan-6-yl)amino-1H-1,2,4-triazole | | —O–CH$_2$CH$_2$–O— | —H | —H | —CH$_3$ | —Cl | —H | —H | —H | D |
| 257 | 5-amino-3-(1,4-benzodioxan-6-yl)amino-1-(3-methyl-4-methoxy)phenyl-carbonyl-1H-1,2,4-triazole | | —O–CH$_2$CH$_2$–O— | —H | —H | —OCH$_3$ | —CH$_3$ | —H | —H | —H | B |

TABLE 1-continued

| Cpd # | Compound Name | R1b | R1c | R1d | R4 | R3b | R3c | R3d | R3e | R3f | IC50 |
|---|---|---|---|---|---|---|---|---|---|---|---|
| 258 | 5-amino-3-(1,4-benzodioxan-6-yl)amino-1-(3-methyl-4-iso-propoxy)phenyl]carbonyl-1H-1,2,4-triazole | 1,4-benzodioxan-6-yl (via O-CH2-CH2-O) | — | H | H | isopropoxy | —CH3 | —H | —H | —H | B |
| 48 | 5-amino-1-(4-(iso-propoxy)phenyl)carbonyl-3-(4-(morpholin-4-yl)phenylamino]-1H-1,2,4-triazole | morpholin-4-yl | —H | H | H | isopropoxy | —H | —H | —H | —H | A |
| 50 | 5-amino-3-[4-[2-(piperidin-1-yl)ethoxy]phenylamino]-1-(4-(tert-butoxy)phenyl)carbonyl-1H-1,2,4-triazole | 2-(piperidin-1-yl)ethoxy | —H | H | H | tert-butoxy | —H | —H | —H | —H | A |

TABLE 1-continued

| Cpd # | Compound Name | R1b | R1c | R1d | R4 | R3b | R3c | R3d | R3e | R3f | IC50 |
|---|---|---|---|---|---|---|---|---|---|---|---|
| 51 | 5-amino-1-(4-(iso-propyl)phenyl)carbonyl-3-[4-[2-(piperidin-1-yl)ethoxy]phenylamino]-1H-1,2,4-triazole | 4-[2-(piperidin-1-yl)ethoxy] | H | H | H | —CH(CH$_3$)$_2$ | H | H | H | H | A |
| 52 | 5-amino-1-(4-(iso-propyl)phenyl)carbonyl-3-(4-(morpholin-4-yl)phenylamino]-1H-1,2,4-triazole | 4-(morpholin-4-yl) | H | H | H | —CH(CH$_3$)$_2$ | H | H | H | H | A |
| 53 | 5-amino-1-(4-(methyl)phenyl)carbonyl-3-[4-[2-(piperidin-1-yl)ethoxy]phenylamino]-1H-1,2,4-triazole | 4-[2-(piperidin-1-yl)ethoxy] | H | H | H | —CH$_3$ | H | H | H | H | A |
| 54 | 5-amino-1-(4-(methyl)phenyl)carbonyl-3-(4-(morpholin-4-yl)phenylamino]-1H-1,2,4-triazole | 4-(morpholin-4-yl) | H | H | H | —CH$_3$ | H | H | H | H | A |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 55 | 5-amino-3-[4-(iso-propoxy)phenylamino]-1-(4-(methyl)phenyl)carbonyl-1H-1,2,4-triazole | isopropoxy | —H | —H | —H | —CH$_3$ | —H | —H | —H | —H | A |
| 57 | 5-amino-3-(4-(morpholin-4-yl)phenylamino)-1-(4-(tert-butoxy)phenyl)carbonyl-1H-1,2,4-triazole | morpholin-4-yl | —H | —H | —H | tert-butoxy | —H | —H | —H | —H | A |
| 59 | 5-amino-1-(3-(methyl)phenyl)carbonyl-3-[4-[2-(piperidin-1-yl)ethoxy]phenylamino]-1H-1,2,4-triazole | 2-(piperidin-1-yl)ethoxy | —H | —H | —H | —H | —CH$_3$ | —H | —H | —H | A |
| 60 | 5-amino-1-(4-(iso-propoxy)phenylcarbonyl-3-[4-[2-(thiomorpholin-4-yl)ethoxy]phenylamino]-1H-1,2,4-triazole | 2-(thiomorpholin-4-yl)ethoxy | —H | —H | —H | isopropoxy | —H | —H | —H | —H | A |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 61 | 5-amino-1-(3-(methyl) phenyl]carbonyl-3-[4-[2-(thiomorpholin-4-yl)ethoxy] phenylamino]-1H-1,2,4-triazole | (2-(thiomorpholin-4-yl)ethoxy) | —H | —H | —H | —H | —CH$_3$ | —H | —H | —H | B |
| 62 | 5-amino-1-(4-(cyclohexyl) phenyl)carbonyl]-3-[4-[2-(piperidin-1-yl) ethoxy]phenylamino]-1H-1,2,4-triazole | (2-(piperidin-1-yl)ethoxy) | —H | —H | —H | cyclohexyl | —H | —H | —H | —H | B |
| 67 | 5-amino-1-(3-(hydroxyphenyl) carbonyl]-3-(4-(morpholin-4-yl) phenylamino)-1H-1,2,4-triazole | (morpholin-4-yl) | —H | —H | —H | —H | —OH | —H | —H | —H | B |
| 70 | 5-amino-1-(4-(aminosulfonyl) phenyl]carbonyl-3-(4-(morpholin-4-yl)phenylamino)-1H-1,2,4-triazole | (morpholin-4-yl) | —H | —H | —H | —SO$_2$NH$_2$ | —H | —H | —H | —H | D |

TABLE 1-continued

| Cpd # | Compound Name | R1b | R1c | R1d | R4 | R3b | R3c | R3d | R3e | R3f | IC50 |
|---|---|---|---|---|---|---|---|---|---|---|---|
| 71 | 5-amino-3-[4-(iso-propoxy)phenylamino]-1-(3-(nitro)phenyl)carbonyl]-1H-1,2,4-triazole | iso-propoxy | —H | —H | —H | —H | —NO₂ | —H | —H | —H | B |
| 72 | 5-amino-3-(4-(morpholin-4-yl)phenylamino)-1-(3-(nitro)phenyl)carbonyl]-1H-1,2,4-triazole | morpholin-4-yl | —H | —H | —H | —H | —NO₂ | —H | —H | —H | B |
| 73 | 5-amino-1-(3-(hydroxy)phenyl)carbonyl]-3-[4-(iso-propoxy)phenylamino]-1H-1,2,4-triazole | iso-propoxy | —H | —H | —H | —H | —OH | —H | —H | —H | B |
| 74 | 5-amino-1-(3-(chloro)phenyl)carbonyl]-3-[4-(morpholin-4-yl)phenylamino]-1H-1,2,4-triazole | morpholin-4-yl | —H | —H | —H | —H | —Cl | —H | —H | —H | B |
| 76 | 5-amino-1-(3-(chloro)phenyl)carbonyl]-3-[4-(iso-propoxy)phenylamino]-1H-1,2,4-triazole | iso-propoxy | —H | —H | —H | —H | —Cl | —H | —H | —H | D |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 77 | 5-amino-3-[4-(iso-propoxy)phenylamino]-1-[4-[2-(piperidin-1-yl)ethoxy]phenyl)carbonyl]-1H-1,2,4-triazole | -O-iPr | H | H | H | -OCH$_2$CH$_2$-piperidine | H | H | H | H | B |
| 79 | 5-amino-1-(3-(methoxycarbonyl)phenyl)carbonyl]-3-[4-[2-(piperidin-1-yl)ethoxy]phenylamino]-1H-1,2,4-triazole | -OCH$_2$CH$_2$-piperidine | H | H | H | H | -CO$_2$CH$_3$ | H | H | H | B |
| 80 | 5-amino-1-(3-(methoxyphenyl)carbonyl]-3-[4-[2-(piperidin-1-yl)ethoxy]phenylamino]-1H-1,2,4-triazole | -OCH$_2$CH$_2$-piperidine | H | H | H | H | -OCH$_3$ | H | H | H | A |

TABLE 1-continued

| Cpd # | Compound Name | R¹ᵇ | R¹ᶜ | R¹ᵈ | R⁴ | R³ᵇ | R³ᶜ | R³ᵈ | R³ᵉ | R³ᶠ | IC₅₀ |
|---|---|---|---|---|---|---|---|---|---|---|---|
| 81 | 5-amino-1-(3-(methoxyphenyl)carbonyl-3-(4-(morpholin-4-yl)phenylamino)-1H-1,2,4-triazole | (morpholin-4-yl) | —H | —H | —H | —H | —OCH₃ | —H | —H | —H | B |
| 82 | 5-amino-3-[4-[2-(dimethylamino)ethoxy]phenylamino]-1-(4-(methyl)phenyl)carbonyl-1H-1,2,4-triazole | (2-dimethylaminoethoxy) | —H | —H | —H | —CH₃ | —H | —H | —H | —H | |
| 83 | 5-amino-3-[4-[2-(dimethylamino)ethoxy]phenylamino]-1-(4-(tert-butoxy)phenyl)carbonyl-1H-1,2,4-triazole | (2-dimethylaminoethoxy) | —H | —H | H | (tert-butoxy) | —H | —H | —H | —H | A |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 84 | 5-amino-3-[4-[2-(dimethylamino)propoxy]phenyl-amino]-1-(4-(iso-propoxy)phenyl)carbonyl-1H-1,2,4-triazole | ~O(CH$_2$)$_3$N(CH$_3$)$_2$ | H | H | H | isopropoxy | H | H | H | H | A |
| 85 | 5-amino-3-[4-[2-(dimethylamino)ethoxy]phenyl-amino]-1-(4-(iso-propoxy)phenyl)carbonyl-1H-1,2,4-triazole | ~O(CH$_2$)$_2$N(CH$_3$)$_2$ | H | H | H | isopropoxy | H | H | H | H | A |
| 87 | 5-amino-3-[4-[2-(dimethylamino)ethoxy]phenylamino]-1-(4-(dimethylamino)phenyl)carbonyl-1H-1,2,4-triazole | ~O(CH$_2$)$_2$N(CH$_3$)$_2$ | H | H | H | —N(CH$_3$)$_2$ | H | H | H | H | A |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 88 | 5-amino-1-(4-(dimethylamino)phenyl)carbonyl-3-[4-[2-(dimethylamino)propoxy]phenyl-amino]-1H-1,2,4-triazole | ~O~N(CH$_3$)$_2$ | —H | —H | —H | —N(CH$_3$)$_2$ | —H | —H | —H | —H | A |
| 89 | 5-amino-3-[4-[2-(dimethylamino)propoxy]phenyl-amino]-1-(4-(tert-butoxy)phenyl)carbonyl-1H-1,2,4-triazole | ~O~N(CH$_3$)$_2$ | —H | —H | —H | —OC(CH$_3$)$_3$ | —H | —H | —H | —H | B |
| 91 | 5-amino-3-[4-[3-(dimethylamino)propoxy]phenyl-amino]-1-(4-(methyl)phenyl)carbonyl-1H-1,2,4-triazole | ~O~N(CH$_3$)$_2$ | —H | —H | —H | —CH$_3$ | —H | —H | —H | —H | B |

TABLE 1-continued

| Cpd # | Compound Name | R1b | R1c | R1d | R4 | R3b | R3c | R3d | R3e | R3f | IC50 |
|---|---|---|---|---|---|---|---|---|---|---|---|
| (Ia-2) | 5-amino-1-(4-(iso-propoxy)phenyl)carbonyl-3-[4-[2-(pyrrolidin-1-yl)ethoxy]phenyl]amino]-1H-1,2,4-triazole | —O-CH₂CH₂-N(pyrrolidine) | H | H | H | —O-CH(CH₃)₂ | H | H | H | H | A |
| 26 | 5-amino-1-(4-(iso-propoxy)phenyl)carbonyl-3-[4-(piperidin-1-yl)phenylamino]-1H-1,2,4-triazole | —N(piperidine) | H | H | H | —O-CH(CH₃)₂ | H | H | H | H | B |
| 13 | 5-amino-1-(1,3-benzodioxol-5-yl)carbonyl-3-[4-[2-(piperidin-1-yl)ethoxy]phenylamino]-1H-1,2,4-triazole | —O-CH₂CH₂-N(piperidine) | H | H | H | —O-CH₂-O— (benzodioxole) | | H | H | H | A |

TABLE 1-continued

| Cpd # | Compound Name | R¹ᵇ | R¹ᶜ | R¹ᵈ | R⁴ | R³ᵇ | R³ᶜ | R³ᵈ | R³ᵉ | R³ᶠ | IC₅₀ |
|---|---|---|---|---|---|---|---|---|---|---|---|
| 21 | 5-amino-1-(3,4-dimethoxyphenyl)carbonyl-3-[4-[2-(piperidin-1-yl)ethoxy]phenylamino]-1H-1,2,4-triazole | –O-CH₂CH₂-N(piperidinyl) | —H | —H | —H | —OCH₃ | —OCH₃ | —H | —H | —H | A |
| 19 | 5-amino-1-(3,5-dimethoxyphenyl)carbonyl-3-[4-[2-(piperidin-1-yl)ethoxy]phenylamino]-1H-1,2,4-triazole | –O-CH₂CH₂-N(piperidinyl) | —H | —H | —H | —H | —OCH₃ | —H | —OCH₃ | —H | A |
| 239 | 5-amino-3-(1,4-benzodioxan-6-yl)amino-1-(3,5-dimethylphenyl)carbonyl-1H-1,2,4-triazole | –O–CH₂CH₂–O– (fused benzodioxan) | | —H | —H | —H | —CH₃ | —H | —CH₃ | —H | B |

TABLE 1-continued

| Cpd # | Compound Name | R1b | R1c | R1d | R4 | R3b | R3c | R3d | R3e | R3f | IC50 |
|---|---|---|---|---|---|---|---|---|---|---|---|
| 11 | 5-amino-1-(3-(dimethylamino)phenyl)carbonyl-3-[4-[2-(piperidin-1-yl)ethoxy]phenylamino]-1H-1,2,4-triazole | ~O~N(piperidine) | —H | —H | —H | —H | —N(CH₃)₂ | —H | —H | —H | A |
| 2 | 5-amino-1-(4-(dimethylamino)phenyl)carbonyl-3-[4-[2-(piperidin-1-yl)ethoxy]phenylamino]-1H-1,2,4-triazole | ~O~N(piperidine) | —H | —H | —H | —N(CH₃)₂ | —H | —H | —H | —H | A |
| 16 | 5-amino-1-(1,3-benzodioxol-5-yl)carbonyl-3-[4-[2-(pyrrolidin-1-yl)ethoxy]phenylamino]-1H-1,2,4-triazole | ~O~N(pyrrolidine) | —H | —H | —H | —H | -OCH₂O- (methylenedioxy) | | —H | —H | A |

TABLE 1-continued

| Cpd # | Compound Name | R¹ᵇ | R¹ᶜ | R¹ᵈ | R⁴ | R³ᵇ | R³ᶜ | R³ᵈ | R³ᵉ | R³ᶠ | IC₅₀ |
|---|---|---|---|---|---|---|---|---|---|---|---|
| 9 | 5-amino-1-(3-methylphenyl)carbonyl-3-[4-[2-(pyrrolidin-1-yl)ethoxy]phenyl]amino]-1H-1,2,4-triazole | ~O~CH₂CH₂-N(pyrrolidine) | —H | —H | —H | —H | —CH₃ | —H | —H | —H | A |
| 22 | 5-amino-1-(3,5-(dimethoxy)phenyl)carbonyl-3-[4-[2-(pyrrolidin-1-yl)ethoxy]phenyl]amino]-1H-1,2,4-triazole | ~O~CH₂CH₂-N(pyrrolidine) | —H | —H | —H | —H | —OCH₃ | —H | —OCH₃ | —H | A |
| 12 | 5-amino-1-(4-methylphenyl)carbonyl-3-[4-[2-(pyrrolidin-1-yl)ethoxy]phenyl]amino]-1H-1,2,4-triazole | ~O~CH₂CH₂-N(pyrrolidine) | —H | —H | —H | —CH₃ | —H | —H | —H | —H | A |

TABLE 1-continued

| Cpd # | Compound Name | R<sup>1b</sup> | R<sup>1c</sup> | R<sup>1d</sup> | R<sup>4</sup> | R<sup>3b</sup> | R<sup>3c</sup> | R<sup>3d</sup> | R<sup>3e</sup> | R<sup>3f</sup> | IC$_{50}$ |
|---|---|---|---|---|---|---|---|---|---|---|---|
| 17 | 5-amino-1-(1,4-benzodioxan-6-yl)carbonyl-3-[4-[2-(pyrrolidin-1-yl)ethoxy]phenyl]amino]-1H-1,2,4-triazole | ~O~CH₂CH₂-N(pyrrolidine) | —H | —H | —H | —H | -O-CH₂CH₂-O- (fused) | —H | —H | —H | A |
| 1 | 5-amino-3-[4-[2-(pyrrolidin-1-yl)ethoxy]phenylamino]-1-(4-(tert-butoxy)phenyl)carbonyl-1H-1,2,4-triazole | ~O~CH₂CH₂-N(pyrrolidine) | —H | —H | —H | —H | —O-C(CH₃)₃ | —H | —H | —H | A |
| 14 | 5-amino-1-(3-(methoxy)phenyl)carbonyl-3-[4-[2-(pyrrolidin-1-yl)ethoxy]phenylamino]-1H-1,2,4-triazole | ~O~CH₂CH₂-N(pyrrolidine) | —H | —H | —H | —H | —OCH₃ | —H | —H | —H | A |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 4 | 5-amino-1-(4-(dimethylamino)phenyl)carbonyl-3-[4-[2-(pyrrolidin-1-yl)ethoxy]phenyl]amino]-1H-1,2,4-triazole | ⤳O⌒⌒N(pyrrolidine) | —H | —H | —H | —N(CH$_3$)$_2$ | —H | —H | —H | —H | A |
| 197 | 5-amino-1-(3-(dimethylamino)phenyl)carbonyl-3-[4-[2-(pyrrolidin-1-yl)ethoxy]phenyl]amino]-1H-1,2,4-triazole | ⤳O⌒⌒N(pyrrolidine) | —H | —H | —H | —H | —N(CH$_3$)$_2$ | —H | —H | —H | D |
| 198 | 5-amino-1-(3,4-(dimethoxyphenyl)carbonyl-3-[4-[2-(pyrrolidin-1-yl)ethoxy]phenyl]amino]-1H-1,2,4-triazole | ⤳O⌒⌒N(pyrrolidine) | —H | —H | —H | —OCH$_3$ | —OCH$_3$ | —H | —H | —H | D |

TABLE 1-continued

| Cpd # | Compound Name | $R^{1b}$ | $R^{1c}$ | $R^{1d}$ | $R^4$ | $R^{3b}$ | $R^{3c}$ | $R^{3d}$ | $R^{3e}$ | $R^{3f}$ | $IC_{50}$ |
|---|---|---|---|---|---|---|---|---|---|---|---|
| 18 | 5-amino-3-[4-[2-(pyrrolidin-1-yl)ethoxy]phenylamino]-1-(3-(tert-butoxy)phenyl)carbonyl-1H-1,2,4-triazole | ⟞O⟝(CH₂)₂-pyrrolidine | H | H | H | H | —O-tBu | H | H | H | A |
| 7 | 5-amino-3-[4-[2-(pyrrolidin-1-yl)ethoxy]phenylamino]-1-(3-(trifluoromethoxy)phenyl)carbonyl-1H-1,2,4-triazole | ⟞O⟝(CH₂)₂-pyrrolidine | H | H | H | H | —OCF₃ | H | H | H | A |
| 23 | 5-amino-3-[4-[2-(pyrrolidin-1-yl)ethoxy]phenylamino]-1-(4-(trifluoromethoxy)phenyl)carbonyl-1H-1,2,4-triazole | ⟞O⟝(CH₂)₂-pyrrolidine | H | H | H | —OCF₃ | H | H | H | H | A |

TABLE 1-continued

| Cpd # | Compound Name | R1b | R1c | R1d | R4 | R3b | R3c | R3d | R3e | R3f | IC50 |
|---|---|---|---|---|---|---|---|---|---|---|---|
| 15 | 5-amino-3-[4-[3-(pyrrolidin-1-yl)propoxy]phenyl]amino]-1-(4-(tert-butoxy)phenyl) carbonyl]-1H-1,2,4-triazole | ~O-CH2CH2CH2-N(pyrrolidine) | H | H | H | O-tBu | H | H | H | H | |
| 24 | 5-amino-3-[4-[3-(pyrrolidin-1-yl)propoxy]phenyl]amino]-1-(3-(tert-butoxy)phenyl) carbonyl]-1H-1,2,4-triazole | ~O-CH2CH2CH2-N(pyrrolidine) | H | H | H | H | O-tBu | H | H | H | A |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 10 | 5-amino-1-(4-(iso-propoxy)phenyl)carbonyl-3-[4-[3-(pyrrolidin-1-yl)propoxy]phenylamino]-1H-1,2,4-triazole | ~O~N(pyrrolidine) | —H | —H | —H | isopropoxy | —H | —H | —H | —H | A |
| 8 | 5-amino-1-(4-(dimethylamino)phenyl)carbonyl-3-[4-[3-(pyrrolidin-1-yl)propoxy]phenylamino]-1H-1,2,4-triazole | ~O~N(pyrrolidine) | —H | —H | —H | —N(CH$_3$)$_2$ | —H | —H | —H | —H | A |

TABLE 1-continued

| Cpd # | Compound Name | R$^{1b}$ | R$^{1c}$ | R$^{1d}$ | R$^{4}$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 20 | 5-amino-1-(3-(dimethylamino)phenyl)carbonyl-3-[4-[3-(pyrrolidin-1-yl)propoxy]phenyl]amino]-1H-1,2,4-triazole | *~O~*~~~N-pyrrolidine (propoxy) | —H | —H | —H | —H | —N(CH$_3$)$_2$ | —H | —H | —H | A |
| 262 | 5-amino-3-[4-[2-(pyrrolidin-1-yl)ethoxy]-3-fluorophenyl]amino-1-[4-(morpholin-4-yl)phenyl]carbonyl-1H-1,2,4-triazole | *~O~*~~~N-pyrrolidine (ethoxy) | —F | —H | —H | morpholine | —H | —H | —H | —H | A |
| 263 | 5-amino-1-(4-(tert-butyl)phenyl)carbonyl-3-[3-(1,3-oxazol-5-yl)phenyl]amino]-1H-1,2,4-triazole | —H | oxazol-5-yl | —H | —H | —C(CH$_3$)$_3$ | —H | —H | —H | —H | B |
| 264 | 5-amino-1-(4-(tert-butoxy)phenyl)carbonyl-3-[3-(1,3-oxazol-5-yl)phenyl]amino]-1H-1,2,4-triazole | —H | oxazol-5-yl | —H | —H | —OC(CH$_3$)$_3$ | —H | —H | —H | —H | B |

TABLE 1-continued

| Cpd # | Compound Name | R1b | R1c | R1d | R4 | R3b | R3c | R3d | R3e | R3f | IC50 |
|---|---|---|---|---|---|---|---|---|---|---|---|
| 266 | 5-amino-1-(4-(tert-butyl)phenyl) carbonyl-3-[4-[2-(morpholin-4-yl)ethoxy]phenylamino]-1H-1,2,4-triazole | ~O-CH2CH2-N(morpholine) | —H | —H | —H | —C(CH3)3 | —H | —H | —H | —H | A |
| 267 | 5-amino-1-(4-(tert-butoxy)phenyl) carbonyl-3-[4-[2-(morpholin-4-yl)ethoxy]phenylamino]-1H-1,2,4-triazole | ~O-CH2CH2-N(morpholine) | —H | —H | —H | —OC(CH3)3 | —H | —H | —H | —H | A |
| 268 | 5-amino-1-(4-(imidazol-1-yl)phenyl)carbonyl-3-[4-[2-(pyrrolidin-1-yl)ethoxy]phenylamino]-1H-1,2,4-triazole | ~O-CH2CH2-N(pyrrolidine) | —H | —H | —H | N-imidazolyl | —H | —H | —H | —H | A |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 269 | 5-amino-1-(4-(phenoxyphenyl)carbonyl-3-[4-[2-(pyrrolidin-1-yl)ethoxy]phenyl]amino]-1H-1,2,4-triazole | ~O~N (pyrrolidinylethoxy) | H | H | H | phenoxy-tBu | H | H | H | H | A |
| 270 | 5-amino-1-(4-(tert-butoxycarbonylamino)phenyl)-carbonyl-3-[4-[2-(pyrrolidin-1-yl)ethoxy]phenylamino]-1H-1,2,4-triazole | ~O~N (pyrrolidinylethoxy) | H | H | H | NHC(O)OC(CH$_3$)$_3$ | H | H | H | H | A |
| 272 | 5-amino-1-(4-(tert-butoxyphenyl)carbonyl-3-[4-[2-(pyrrolidin-1-yl)ethoxy]phenyl][methyl]amino-1H-1,2,4-triazole | ~O~N (pyrrolidinylethoxy) | H | H | —CH$_3$ | —OC(CH$_3$)$_3$ | H | H | H | H | D |

TABLE 1-continued

| Cpd # | Compound Name | R1b | R1c | R1d | R4 | R3b | R3c | R3d | R3e | R3f | IC50 |
|---|---|---|---|---|---|---|---|---|---|---|---|
| 277 | 5-amino-1-(4-(phenyl)phenyl)carbonyl-3-[4-[2-(pyrrolidin-1-yl)ethoxy]phenylamino]-1H-1,2,4-triazole | *O-CH2CH2-N(pyrrolidine) | H | H | H | phenyl | H | H | H | H | A |
| 278 | 5-amino-1-[4-((tert-butoxycarbonyl)aminomethyl)phenyl]carbonyl-3-[4-[2-(pyrrolidin-1-yl)ethoxy]phenylamino]-1H-1,2,4-triazole | *O-CH2CH2-N(pyrrolidine) | H | H | H | CH2-NH-C(O)-O-tBu | H | H | H | H | A |
| 280 | 5-amino-1-(4-(1,2,3-thiadiazol-4-yl)phenyl)carbonyl-3-[4-[2-(pyrrolidin-1-yl)ethoxy]phenylamino]-1H-1,2,4-triazole | *O-CH2CH2-N(pyrrolidine) | H | H | H | 1,2,3-thiadiazol-4-yl | H | H | H | H | A |

TABLE 1-continued

| Cpd # | Compound Name | R1b | R1c | R1d | R4 | R3b | R3c | R3d | R3e | R3f | IC50 |
|---|---|---|---|---|---|---|---|---|---|---|---|
| 282 | 5-amino-1-(4-(pyrrol-1-yl)phenyl)carbonyl-3-[4-[2-(pyrrolidin-1-yl)ethoxy]phenylamino]-1H-1,2,4-triazole | ~O~N(pyrrolidine) | —H | —H | —H | pyrrol-1-yl | —H | —H | —H | —H | A |
| 286 | 5-amino-1-(4-(methylamino)phenyl)carbonyl-3-[4-[2-(pyrrolidin-1-yl)ethoxy]phenylamino]-1H-1,2,4-triazole | ~O~N(pyrrolidine) | —H | —H | —H | —N(CH3)H | —H | —H | —H | —H | A |
| 287 | 5-amino-1-(4-(methylthio)phenyl)carbonyl-3-[4-[2-(pyrrolidin-1-yl)ethoxy]phenylamino]-1H-1,2,4-triazole | ~O~N(pyrrolidine) | —H | —H | —H | —S—CH3 | —H | —H | —H | —H | A |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 289 | 5-amino-1-(2,6-difluorophenyl)carbonyl-3-[4-[2-(pyrrolidin-1-yl)ethoxy]phenylamino]-1H-1,2,4-triazole | ~O~CH₂CH₂-pyrrolidinyl | —H | —H | —H | —H | —H | —F | —H | —F | D |
| 290 | 5-amino-1-(4-(tert-butylcarbonylamino)phenyl)carbonyl-3-[4-[2-(pyrrolidin-1-yl)ethoxy]phenylamino]-1H-1,2,4-triazole | ~O~CH₂CH₂-pyrrolidinyl | —H | —H | —H | —NHC(O)C(CH₃)₃ | H | —H | —H | —H | C |
| 291 | 5-amino-1-(4-(tert-butoxy)phenyl)carbonyl-3-[4-(pyrrolidin-1-yl)phenylamino]-1H-1,2,4-triazole | N-pyrrolidinyl | —H | —H | —H | —OC(CH₃)₃ | —H | —H | —H | —H | D |
| 293 | 5-amino-1-(4-(isopropoxy)phenyl)carbonyl-3-[4-(pyrrolidin-1-yl)phenylamino]-1H-1,2,4-triazole | N-pyrrolidinyl | —H | —H | —H | —OCH(CH₃)₂ | —H | —H | —H | —H | B |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 297 | 5-amino-1-(4-(tert-butyl)phenyl)carbonyl-3-[4-(pyrrolidin-1-yl)phenylamino]-1H-1,2,4-triazole | pyrrolidin-1-yl | —H | —H | —H | —C(CH$_3$)$_3$ | —H | —H | —H | —H | D |
| 299 | 5-amino-1-(4-(dimethylamino)phenyl)carbonyl-3-[4-(pyrrolidin-1-yl)phenylamino]-1H-1,2,4-triazole | pyrrolidin-1-yl | —H | —H | —H | —N(CH$_3$)$_2$ | —H | —H | —H | —H | B |
| 300 | 5-amino-1-(4-(methyl)phenyl)carbonyl-3-[4-(pyrrolidin-1-yl)phenylamino]-1H-1,2,4-triazole | pyrrolidin-1-yl | —H | —H | —H | —CH$_3$ | —H | —H | —H | —H | B |
| 302 | 5-amino-1-(4-(tert-butyl)phenyl)carbonyl-3-[4-[2-(pyrrolidin-1-yl)ethoxy]phenylamino]-1H-1,2,4-triazole | 2-(pyrrolidin-1-yl)ethoxy | —H | —H | —H | —C(CH$_3$)$_3$ | —H | —H | —H | —H | A |

TABLE 1-continued

| Cpd # | Compound Name | R$^{1b}$ | R$^{1c}$ | R$^{1d}$ | R$^{4}$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 305 | 5-amino-1-(4-(tert-butoxy)phenyl)carbonyl-3-[3-fluoro-4-[2-(pyrrolidin-1-yl)ethoxy]phenyl]amino]-1H-1,2,4-triazole | ~O~N(pyrrolidine) | —F | —H | —H | —OC(CH$_3$)$_3$ | —H | —H | —H | —H | A |
| 306 | 5-amino-1-(4-(1,2,3-thiadiazol-4-yl)phenyl)carbonyl-3-[3-fluoro-4-[2-(pyrrolidin-1-yl)ethoxy]phenyl]amino]-1H-1,2,4-triazole | ~O~N(pyrrolidine) | —F | —H | —H | thiadiazolyl | —H | —H | —H | —H | A |
| 307 | 5-amino-1-(4-(isopropoxy)phenyl)carbonyl-3-[3-fluoro-4-[2-(pyrrolidin-1-yl)ethoxy]phenyl]amino]-1H-1,2,4-triazole | ~O~N(pyrrolidine) | —F | —H | —H | —OCH(CH$_3$)$_2$ | —H | —H | —H | —H | A |

TABLE 1-continued

| Cpd # | Compound Name | $R^{1b}$ | $R^{1c}$ | $R^{1d}$ | $R^4$ | $R^{3b}$ | $R^{3c}$ | $R^{3d}$ | $R^{3e}$ | $R^{3f}$ | $IC_{50}$ |
|---|---|---|---|---|---|---|---|---|---|---|---|
| 308 | 5-amino-1-(phenyl)carbonyl-3-[3-fluoro-4-[2-(pyrrolidin-1-yl)ethoxy]phenyl]amino]-1H-1,2,4-triazole | ~O-CH2CH2-N(pyrrolidine) | F | H | H | H | H | H | H | H | A |
| 310 | 5-amino-1-(3-(thiazol-2-yl)phenyl)carbonyl-3-[4-[2-(pyrrolidin-1-yl)ethoxy]phenyl]amino]-1H-1,2,4-triazole | ~O-CH2CH2-N(pyrrolidine) | H | H | H | 2-thiazolyl | H | H | H | H | A |
| 311 | 5-amino-1-(4-(thien-2-yl)phenyl)carbonyl-3-[4-[2-(pyrrolidin-1-yl)ethoxy]phenyl]amino]-1H-1,2,4-triazole | ~O-CH2CH2-N(pyrrolidine) | H | H | H | 2-thienyl | H | H | H | H | A |

TABLE 1-continued

| Cpd # | Compound Name | R¹ᵇ | R¹ᶜ | R¹ᵈ | R⁴ | R³ᵇ | R³ᶜ | R³ᵈ | R³ᵉ | R³ᶠ | IC₅₀ |
|---|---|---|---|---|---|---|---|---|---|---|---|
| 313 | 5-amino-1-(3-(thien-2-yl)phenyl)carbonyl-3-[4-[2-(pyrrolidin-1-yl)ethoxy]phenylamino]-1H-1,2,4-triazole | ~O~N(pyrrolidine) | —H | —H | —H | —H | thien-2-yl | —H | —H | —H | A |
| 314 | 5-amino-1-(4-(thien-3-yl)phenyl)carbonyl-3-[4-[2-(pyrrolidin-1-yl)ethoxy]phenylamino]-1H-1,2,4-triazole | ~O~N(pyrrolidine) | —H | —H | —H | —H | —H | thien-3-yl | —H | —H | A |
| 315 | 5-amino-1-(4-(tert-butyl)phenyl)carbonyl-3-[3-methoxy-4-[2-(pyrrolidin-1-yl)ethoxy]phenylamino]-1H-1,2,4-triazole | ~O~N(pyrrolidine) | —OCH₃ | —H | —H | —C(CH₃)₃ | —H | —H | —H | —H | A |

TABLE 1-continued

| Cpd # | Compound Name | R[1b] | R[1c] | R[1d] | R[4] | R[3b] | R[3c] | R[3d] | R[3e] | R[3f] | IC$_{50}$ |
|---|---|---|---|---|---|---|---|---|---|---|---|
| 316 | 5-amino-1-(4-(iso-propoxy)phenyl)carbonyl-3-[3-methoxy-4-[2-(pyrrolidin-1-yl)ethoxy]phenylamino]-1H-1,2,4-triazole | 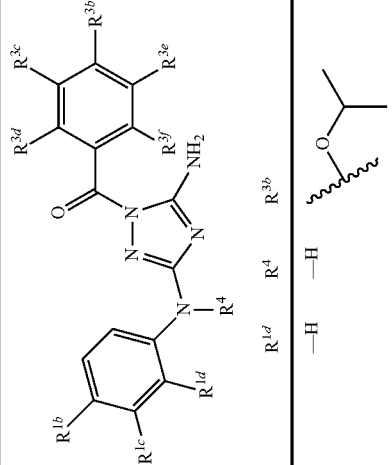 | —OCH$_3$ | —H | —H | 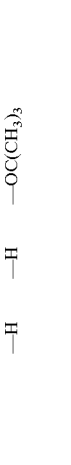 | —H | —H | —H | —H | A |
| 317 | 5-amino-1-(4-(tert-butoxy)phenyl)carbonyl-3-[3-methoxy-4-[2-(pyrrolidin-1-yl)ethoxy]phenylamino]-1H-1,2,4-triazole | 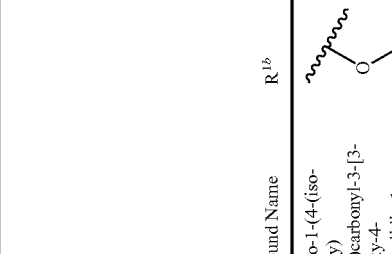 | —OCH$_3$ | —H | —H | —OC(CH$_3$)$_3$ | —H | —H | —H | —H | A |
| 319 | 5-amino-1-(4-(1,2,3-thiadiazol-4-yl)phenyl)carbonyl-3-[3-methoxy-4-[2-(pyrrolidin-1-yl)ethoxy]phenylamino]-1H-1,2,4-triazole |  | —OCH$_3$ | —H | —H |  | —H | —H | —H | —H | A |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 320 | 5-amino-1-(4-(tert-butyl)phenyl)carbonyl-3-[4-[2-(azepan-1-yl)ethoxy]phenyl]amino]-1H-1,2,4-triazole | ~O~CH₂CH₂-azepanyl | —H | —H | —H | —C(CH₃)₃ | —H | —H | —H | —H | A |
| 321 | 5-amino-1-(4-(iso-propoxy)phenyl)carbonyl-3-[4-[2-(azepan-1-yl)ethoxy]phenyl]amino]-1H-1,2,4-triazole | ~O~CH₂CH₂-azepanyl | —H | —H | —H | —OCH(CH₃)₂ | —H | —H | —H | —H | A |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 322 | 5-amino-1-(4-(tert-butoxy)phenyl)carbonyl-3-[4-[2-(azepan-1-yl)ethoxy]phenylamino]-1H-1,2,4-triazole | ~O~N(azepane) | —H | —H | —H | —OC(CH$_3$)$_3$ | —H | —H | —H | —H | A |
| 324 | 5-amino-1-(4-(1,2,3-thiadiazol-4-yl)phenyl)carbonyl-3-[4-[2-(azepan-1-yl)ethoxy]phenylamino]-1H-1,2,4-triazole | ~O~N(azepane) | —H | —H | —H | (1,2,3-thiadiazol-4-yl) | —H | —H | —H | —H | A |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 327 | 5-amino-1-(4-(morpholin-4-yl)phenyl)carbonyl-3-[4-[2-(isoindolin-1-yl)ethoxy]phenyl]amino]-1H-1,2,4-triazole | ~O-CH₂CH₂-N(isoindoline) | —H | —H | —H | morpholin-4-yl | —H | —H | —H | —H | A |
| 328 | 5-amino-1-(4-(iso-propoxyphenyl)carbonyl-3-[4-[2-(isoindolin-1-yl)ethoxy]phenyl]amino]-1H-1,2,4-triazole | ~O-CH₂CH₂-N(isoindoline) | —H | —H | —H | isopropoxy | —H | —H | —H | —H | B |

TABLE 1-continued

| Cpd # | Compound Name | R^{1b} | R^{1c} | R^{1d} | R^4 | R^{3b} | R^{3c} | R^{3d} | R^{3e} | R^{3f} | IC_{50} |
|---|---|---|---|---|---|---|---|---|---|---|---|
| 329 | 5-amino-1-(4-(tert-butoxy)phenyl)carbonyl-3-[4-[2-(isoindolin-1-yl)ethoxy]phenyl]amino]-1H-1,2,4-triazole | ~O~CH2CH2-isoindolinyl | —H | —H | —H | —OC(CH3)3 | —H | —H | —H | —H | B |
| 331 | 5-amino-1-(3-(morpholin-4-yl)phenyl)carbonyl-3-[4-[2-(pyrrolidin-1-yl)ethoxy]phenyl]amino]-1H-1,2,4-triazole | ~O~CH2CH2-pyrrolidinyl | —H | —H | —H | —H | morpholinyl | —H | —H | —H | A |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 332 | 5-amino-1-[4-(2-(morpholin-4-yl)ethoxy)phenyl]carbonyl-3-[4-[2-(pyrrolidin-1-yl)ethoxy]phenylamino]-1H-1,2,4-triazole | -O-CH₂CH₂-N(pyrrolidine) | H | H | H | -O-CH₂CH₂-N(morpholine) | H | H | H | H | A |
| 333 | 5-amino-1-(4-(iso-propoxy)phenyl)carbonyl-3-(phenylamino)-1H-1,2,4-triazole | H | H | H | H | -O-CH(CH₃)₂ | H | H | H | H | B |
| 334 | 5-amino-1-(4-(1,2,3-thiadiazol-4-yl)phenyl)carbonyl-3-(phenylamino)-1H-1,2,4-triazole | H | H | H | H | 1,2,3-thiadiazol-4-yl | H | H | H | H | D |
| 335 | 5-amino-1-(4-(morpholin-4-yl)phenyl)carbonyl-3-(phenylamino)-1H-1,2,4-triazole | H | H | H | H | -N(morpholine) | H | H | H | H | D |
| 336 | 5-amino-1-(3-(morpholin-4-yl)phenyl)carbonyl-3-(phenylamino)-1H-1,2,4-triazole | H | H | H | H | H | -N(morpholine) | H | H | H | C |

TABLE 1-continued

| Cpd # | Compound Name | R1b | R1c | R1d | R4 | R3b | R3c | R3d | R3e | R3f | IC50 |
|---|---|---|---|---|---|---|---|---|---|---|---|
| 337 | 5-amino-1-(4-(iso-propoxy)phenyl)carbonyl-3-[4-[2-(pyrrolidin-2-on-1-yl)ethoxy]phenylamino]-1H-1,2,4-triazole | ~O~N(pyrrolidinone) | H | H | H | isopropoxy | H | H | H | H | A |
| 338 | 5-amino-1-(4-(1,2,3-thiadiazol-4-yl)phenyl)carbonyl-3-[4-[2-(pyrrolidin-2-on-1-yl)ethoxy]phenylamino]-1H-1,2,4-triazole | ~O~N(pyrrolidinone) | H | H | H | 1,2,3-thiadiazol-4-yl | H | H | H | H | B |
| 339 | 5-amino-1-(4-(morpholin-4-yl)phenyl)carbonyl-3-[4-[2-(pyrrolidin-2-on-1-yl)ethoxy]phenylamino]-1H-1,2,4-triazole | ~O~N(pyrrolidinone) | H | H | H | morpholin-4-yl | H | H | H | H | B |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 340 | 5-amino-1-(3-(morpholin-4-yl)phenyl)carbonyl-3-[4-[2-(pyrrolidin-2-on-1-yl)ethoxy]phenylamino]-1H-1,2,4-triazole | ~O-CH2CH2-N(pyrrolidinone) | H | H | H | H | morpholin-N-yl | H | H | H | B |
| 341 | 5-amino-1-(4-(tert-butoxy)phenyl)carbonyl-3-(phenylamino)-1H-1,2,4-triazole | H | H | H | H | —OC(CH$_3$)$_3$ | H | H | H | H | B |
| 342 | 5-amino-1-(4-(tert-butoxy)phenyl)carbonyl-3-[4-[2-(pyrrolidin-2-on-1-yl)ethoxy]phenylamino]-1H-1,2,4-triazole | ~O-CH2CH2-N(pyrrolidinone) | H | H | H | —OC(CH$_3$)$_3$ | H | H | H | H | A |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 343 | 5-amino-1-(4-(morpholin-4-yl)phenyl)carbonyl-3-[3-methoxy-4-[2-(pyrrolidin-1-yl)ethoxy]phenylamino]-1H-1,2,4-triazole | ~O~CH$_2$CH$_2$-N(pyrrolidine) | —OCH$_3$ | —H | —H | N-morpholinyl | —H | —H | —H | —H | A |
| 344 | 5-amino-1-(3-(morpholin-4-yl)phenyl)carbonyl-3-[3-methoxy-4-[2-(pyrrolidin-1-yl)ethoxy]phenylamino]-1H-1,2,4-triazole | ~O~CH$_2$CH$_2$-N(pyrrolidine) | —OCH$_3$ | —H | —H | —H | N-morpholinyl | —H | —H | —H | A |
| 357 | 5-amino-1-(4-(tert-butoxy)phenyl carbonyl-3-[4-(4-methyl-piperazin-1-yl)phenylamino]-1H-1,2,4-triazole | 4-methylpiperazin-1-yl | —H | —H | —H | —OC(CH$_3$)$_3$ | —H | —H | —H | —H | A |
| 358 | 5-amino-1-(3-(tert-butoxy)phenyl carbonyl-3-[4-(4-methylpiperazin-1-yl)phenylamino]-1H-1,2,4-triazole | 4-methylpiperazin-1-yl | —H | —H | —H | —H | —OC(CH$_3$)$_3$ | —H | —H | —H | A |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 359 | 5-amino-1-(4-(iso-propoxy)phenyl)carbonyl-3-[4-(4-methylpiperazin-1-yl)phenylamino]-1H-1,2,4-triazole | 4-methylpiperazin-1-yl | H | H | H | isopropoxy | H | H | H | H | A |
| 361 | 5-amino-1-(4-(dimethylamino)phenyl)carbonyl-3-[4-(4-methylpiperazin-1-yl)phenylamino]-1H-1,2,4-triazole | 4-methylpiperazin-1-yl | H | H | H | —N(CH$_3$)$_2$ | H | H | H | H | A |
| 363 | 5-amino-1-(3-(dimethylamino)phenyl)carbonyl-3-[4-(4-methylpiperazin-1-yl)phenylamino]-1H-1,2,4-triazole | 4-methylpiperazin-1-yl | H | H | H | H | —N(CH$_3$)$_2$ | H | H | H | A |
| 370 | 5-amino-1-(4-(tert-butoxy)phenyl)carbonyl-3-[4-[2-(imidazol-1-yl)ethoxy]phenylamino]-1H-1,2,4-triazole | 2-(imidazol-1-yl)ethoxy | H | H | H | —OC(CH$_3$)$_3$ | H | H | H | H | A |

TABLE 1-continued

| Cpd # | Compound Name | R^{1b} | R^{1c} | R^{1d} | R^4 | R^{3b} | R^{3c} | R^{3d} | R^{3e} | R^{3f} | IC_{50} |
|---|---|---|---|---|---|---|---|---|---|---|---|
| 371 | 5-amino-1-(3-(tert-butoxy)phenyl)carbonyl-3-[4-[2-(imidazol-1-yl)ethoxy]phenylamino]-1H-1,2,4-triazole | —O-CH₂CH₂-imidazole | —H | —H | —H | —H | —OC(CH₃)₃ | —H | —H | —H | B |
| 372 | 5-amino-1-(4-(iso-propoxy)phenyl)carbonyl-3-[4-[2-(imidazol-1-yl)ethoxy]phenylamino]-1H-1,2,4-triazole | —O-CH₂CH₂-imidazole | —H | —H | —H | —OCH(CH₃)₂ | —H | —H | —H | —H | A |
| 373 | 5-amino-1-(4-(dimethylamino)phenyl)carbonyl-3-[4-[2-(imidazol-1-yl)ethoxy]phenylamino]-1H-1,2,4-triazole | —O-CH₂CH₂-imidazole | —H | —H | —H | —N(CH₃)₂ | —H | —H | —H | —H | A |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 374 | 5-amino-1-(3-(dimethylamino)phenyl)carbonyl-3-[4-[2-(imidazol-1-yl)ethoxy]phenylamino]-1H-1,2,4-triazole | ⟨imidazolylethoxy⟩ | —H | —H | —H | —H | —N(CH$_3$)$_2$ | —H | —H | —H | B |
| 380 | 5-amino-1-(4-(tert-butoxy)phenyl)carbonyl-3-[4-[2-(pyrrolidin-1-yl)ethoxy]phenylamino]-1H-1,2,4-triazole | ⟨pyrrolidinylethoxy⟩ | —H | —H | —H | —H | —OC(CH$_3$)$_3$ | —H | —H | —H | A |
| 381 | 5-amino-1-(3-fluoro-4-methoxyphenyl)carbonyl-3-[4-[2-(pyrrolidin-1-yl)ethoxy]phenylamino]-1H-1,2,4-triazole | ⟨pyrrolidinylethoxy⟩ | —H | —H | —H | —OCH$_3$ | —F | —H | —H | —H | A |

TABLE 1-continued
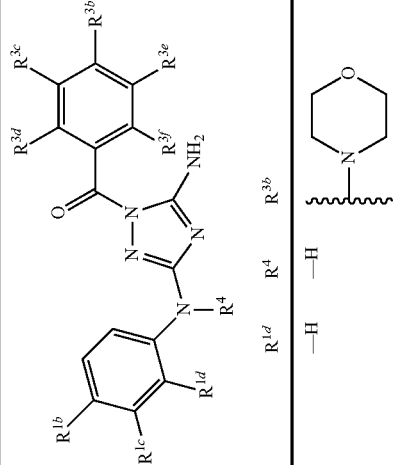
| Cpd # | Compound Name | R1b | R1c | R1d | R4 | R3b | R3c | R3d | R3e | R3f | IC50 |
|---|---|---|---|---|---|---|---|---|---|---|---|
| 382 | 5-amino-1-(4-(morpholin-4-yl)phenyl)carbonyl-3-[4-[2-(pyrrolidin-1-yl)ethoxy]phenylamino]-1H-1,2,4-triazole | 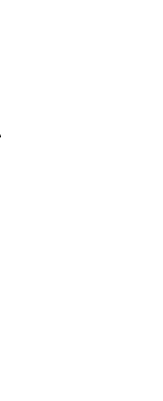 | H | H | H | 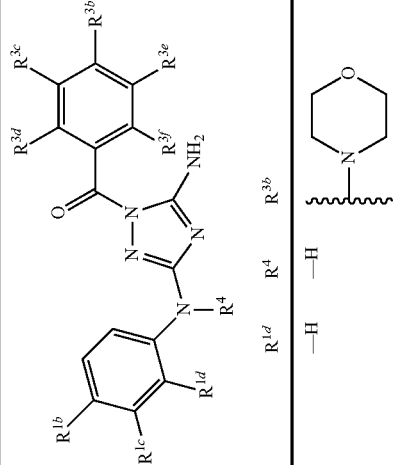 | H | H | H | H | A |
| 383 | 5-amino-1-(4-(4-methylpiperazin-1-yl)phenyl)carbonyl-3-[4-[2-(pyrrolidin-1-yl)ethoxy]phenylamino]-1H-1,2,4-triazole | 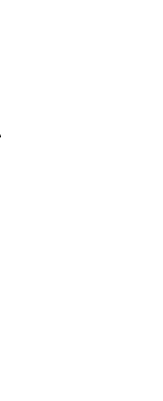 | H | H | H | 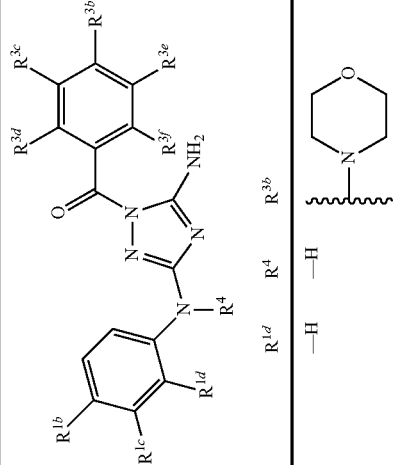 | H | H | H | H | A |
| 384 | 5-amino-1-(4-(tert-butoxy)phenyl)carbonyl-3-[4-[2-((S)-3-fluoropyrrolidin-1-yl]ethoxy]phenylamino]-1H-1,2,4-triazole | 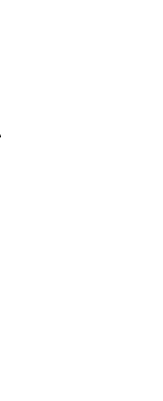 | H | H | H | —OC(CH3)3 | H | H | H | H | A |

TABLE 1-continued

| Cpd # | Compound Name | R$^{1b}$ | R$^{1c}$ | R$^{1d}$ | R$^4$ | R$^{3b}$ | R$^{3c}$ | R$^{3d}$ | R$^{3e}$ | R$^{3f}$ | IC$_{50}$ |
|---|---|---|---|---|---|---|---|---|---|---|---|
| 385 | 5-amino-1-(4-(dimethylamino)phenyl)carbonyl-3-[4-[2-((S)-3-fluoropyrrolidin-1-yl)ethoxy]phenylamino]-1H-1,2,4-triazole | ~O~N~F (S)-3-fluoropyrrolidinyl-ethoxy | —H | —H | —H | —N(CH$_3$)$_2$ | —H | —H | —H | —H | A |
| 390 | 5-amino-1-(3,5-difluoro-4-methoxyphenyl)carbonyl-3-[4-[2-(pyrrolidin-1-yl)ethoxy]phenylamino]-1H-1,2,4-triazole | ~O~N pyrrolidinyl-ethoxy | —H | —H | —H | —OCH$_3$ | —F | —H | —F | —H | A |
| 400 | 5-amino-1-(4-(1,1-dioxothiomorpholin-4-yl)phenyl)carbonyl-3-[4-[2-(pyrrolidin-1-yl)ethoxy]phenylamino]-1H-1,2,4-triazole | ~O~N pyrrolidinyl-ethoxy | —H | —H | —H | 1,1-dioxothiomorpholin-4-yl | —H | —H | —H | —H | A |

TABLE 1-continued

| Cpd # | Compound Name | R¹ᵇ | R¹ᶜ | R¹ᵈ | R⁴ | R³ᵇ | R³ᶜ | R³ᵈ | R³ᵉ | R³ᶠ | IC₅₀ |
|---|---|---|---|---|---|---|---|---|---|---|---|
| 401 | 5-amino-1-(4-(piperidin-1-yl)phenyl)carbonyl-3-[4-[2-(pyrrolidin-1-yl)ethoxy]phenylamino]-1H-1,2,4-triazole | —O-CH₂CH₂-N(pyrrolidine) | —H | —H | —H | piperidin-1-yl-methyl | —H | —H | —H | —H | A |
| 402 | 5-amino-3-[3-chloro-4-[2-(pyrrolidin-1-yl)ethoxy]phenylamino]-1-(3,5-dichlorophenyl)carbonyl-1H-1,2,4-triazole | —O-CH₂CH₂-N(pyrrolidine) | —Cl | —H | —H | —H | —Cl | —H | —Cl | —H | D |

IC₅₀ activity:
A = <1 μM
B = 1 to 10 μM
C = >10 to 20 μM
D = >20 μM

TABLE 2

[Structure: central 1H-1,2,4-triazole with 3-amino (H₂N), 5-position NH-linked to phenyl ring bearing R^1b, R^1c, R^1d, and 1-position linked via carbonyl (C=O) to phenyl ring bearing R^3b, R^3c, R^3d, R^3e]

| Cpd # | Compound Name | R^1b | R^1c | R^1d | R^3b | R^3c | R^3d | R^3e | IC₅₀ |
|---|---|---|---|---|---|---|---|---|---|
| 92 | 3-amino-5-(1,4-benzodioxan-6-yl)amino-1-phenylcarbonyl-1H-1,2,4-triazole | \[–O–CH₂CH₂–O– (R^1b and R^1c joined, forming 1,4-benzodioxan)\] | | —H | —H | —H | —H | —H | B |
| 155 | 3-amino-1-(3-(benzyloxy)phenyl)carbonyl-5-(1,4-benzodioxan-6-yl)amino-1H-1,2,4-triazole | \[–O–CH₂CH₂–O–\] | | —H | —H | —OCH₂Ph | —H | —H | D |
| 164 | 3-amino-5-[3-[cyclohexyl-aminocarbonyl-methoxy]phenylamino]-1-(3-(methyl)phenyl)carbonyl-1H-1,2,4-triazole | —H | \[cyclohexyl-NH-C(=O)-CH₂-O–\] | —H | —H | —CH₃ | —H | —H | D |
| 209 | 3-amino-1-[3-[2-(1,3-dioxolan-2-yl)ethoxy]phenylcarbonyl-5-(1,4-benzodioxan-6-yl)amino-1H-1,2,4-triazole | \[–O–CH₂CH₂–O–\] | | —H | —H | \[–O–CH₂CH₂–(1,3-dioxolan-2-yl)\] | —H | —H | D |
| 213 | 3-amino-1-[4-[2-(1,3-dioxolan-2-yl)ethoxy)phenyl-carbonyl-5-(1,4-benzodioxan-6-yl)amino-1H-1,2,4-triazole | \[–O–CH₂CH₂–O–\] | | —H | \[–O–CH₂CH₂–(1,3-dioxolan-2-yl)\] | —H | —H | —H | D |
| 233 | 3-amino-5-(1,4-benzodioxan-6-yl)amino-1-(4-isopropylphenyl)carbonyl-1H-1,2,4-triazole | \[–O–CH₂CH₂–O–\] | | —H | —CH(CH₃)₂ | —H | —H | —H | D |

TABLE 2-continued

[Structure diagram showing a 1H-1,2,4-triazole core with R1b, R1c, R1d substituents on one phenyl ring (attached via NH), H2N group on triazole, and R3b, R3c, R3d, R3e substituents on a benzoyl group]

| Cpd # | Compound Name | R1b | R1c | R1d | R3b | R3c | R3d | R3e | IC50 |
|---|---|---|---|---|---|---|---|---|---|
| 236 | 3-amino-1-(3,4-dimethylphenyl)carbonyl-5-(1,4-benzodioxan-6-yl)amino-1H-1,2,4-triazole | -O-CH2-CH2-O- (benzodioxan) | | —H | —CH3 | —CH3 | —H | —H | D |
| 238 | 3-amino-5-(1,4-benzodioxan-6-yl)amino-1-(4-thiomethylphenyl)carbonyl-1H-1,2,4-triazole | -O-CH2-CH2-O- (benzodioxan) | | —H | —SCH3 | —H | —H | —H | D |
| 241 | 3-amino-5-(1,4-benzodioxan-6-yl)amino-1-[(4-fluoro-3-methyl)phenyl]carbonyl-1H-1,2,4-triazole | -O-CH2-CH2-O- (benzodioxan) | | —H | —F | —CH3 | —H | —H | D |
| 47 | 3-amino-1-(4-(iso-propoxy)phenyl)carbonyl-5-[4-[2-(piperidin-1-yl)ethoxy]phenylamino]-1H-1,2,4-triazole | -O-CH2-CH2-O- (benzodioxan) | | —H | —O-iPr | —H | —H | —H | D |
| 49 | 3-amino-1-(4-(iso-propoxy)phenyl)carbonyl-5-(4-(morpholin-4-yl)phenylamino]-1H-1,2,4-triazole | morpholin-4-yl | —H | —H | —O-iPr | —H | —H | —H | D |
| 56 | 3-amino-5-[4-(iso-propoxy)phenylamino]-1-(4-(methyl)phenyl)carbonyl-1H-1,2,4-triazole | —O-iPr | —H | —H | —CH3 | —H | —H | —H | D |
| 58 | 3-amino-5-(4-(morpholin-4-yl)phenylamino)-1-(4-(tert-butoxy)phenyl)carbonyl-1H-1,2,4-triazole | morpholin-4-yl | —H | —H | —O-tBu | —H | —H | —H | D |

TABLE 2-continued

[Structure: phenyl-NH-triazole(3-amino)-N1-C(=O)-phenyl with substituents R^1b, R^1c, R^1d on left phenyl and R^3b, R^3c, R^3d, R^3e on right phenyl]

| Cpd # | Compound Name | R^1b | R^1c | R^1d | R^3b | R^3c | R^3d | R^3e | IC$_{50}$ |
|---|---|---|---|---|---|---|---|---|---|
| 75 | 3-amino-1-(3-(chloro)phenyl)carbonyl-5-(4-(morpholin-4-yl)phenylamino)-1H-1,2,4-triazole | morpholin-4-yl | —H | —H | —H | —Cl | —H | —H | D |
| 191 | 3-amino-1-(4-iso-propoxyphenyl)carbonyl-5-[4-[2-(pyrrolidin-1-yl)ethoxy)phenylamino]-1H-1,2,4-triazole | 2-(pyrrolidin-1-yl)ethoxy | —H | —H | —O-iPr | —H | —H | —H | B |
| 192 | 3-amino-1-(4-(iso-propoxy)phenyl)carbonyl-5-[4-(piperidin-1-yl)phenylamino]-1H-1,2,4-triazole | piperidin-1-yl | —H | —H | —O-iPr | —H | —H | —H | C |
| 292 | 3-amino-1-(4-(tert-butoxy)phenyl)carbonyl-5-(4-(pyrrolidin-1-yl)phenylamino]-1H-1,2,4-triazole | pyrrolidin-1-yl | —H | —H | —OC(CH$_3$)$_3$ | —H | —H | —H | D |
| 294 | 3-amino-1-(4-(iso-propoxy)phenyl)carbonyl-5-(4-(pyrrolidin-1-yl)phenylamino]-1H-1,2,4-triazole | pyrrolidin-1-yl | —H | —H | —O-iPr | —H | —H | —H | D |
| 298 | 3-amino-1-(4-(tert-butyl)phenyl)carbonyl-5-[4-(pyrrolidin-1-yl)phenylamino]-1H-1,2,4-triazole | pyrrolidin-1-yl | —H | —H | —C(CH$_3$)$_3$ | —H | —H | —H | D |

TABLE 2-continued

| Cpd # | Compound Name | R^1b | R^1c | R^1d | R^3b | R^3c | R^3d | R^3e | IC_50 |
|---|---|---|---|---|---|---|---|---|---|
| 301 | 3-amino-1-(4-methylphenyl)carbonyl-5-(4-(pyrrolidin-1-yl)phenyl-amino]-1H-1,2,4-triazole | pyrrolidin-1-yl | —H | —H | —CH₃ | —H | —H | —H | D |
| 303 | 3-amino-1-(4-(tert-butyl)phenyl)carbonyl-5-[4-[2-(pyrrolidin-1-yl)ethoxy]phenyl-amino]-1H-1,2,4-triazole | 2-(pyrrolidin-1-yl)ethoxy | —H | —H | —C(CH₃)₃ | —H | —H | —H | B |
| 304 | 3-amino-1-(4-(morpholin-4-yl)phenyl)carbonyl-5-[3-fluoro-4-[2-(pyrrolidin-1-yl)ethoxy)phenyl-amino]-1H-1,2,4-triazole | 2-(pyrrolidin-1-yl)ethoxy | —F | —H | morpholin-4-yl | —H | —H | —H | C |
| 360 | 3-amino-1-(4-(iso-propoxy)phenyl)carbonyl-5-(4-(4-methylpiperazin-1-yl)phenylamino]-1H-1,2,4-triazole | 4-methylpiperazin-1-yl | —H | —H | —O-iPr | —H | —H | —H | B |
| 362 | 3-amino-1-(4-(dimethylamino)phenyl)carbonyl-5-(4-(4-methylpiperazin-1-yl)phenyl-amino]-1H-1,2,4-triazole | 4-methylpiperazin-1-yl | —H | —H | —N(CH₃)₂ | —H | —H | —H | B |

TABLE 2-continued

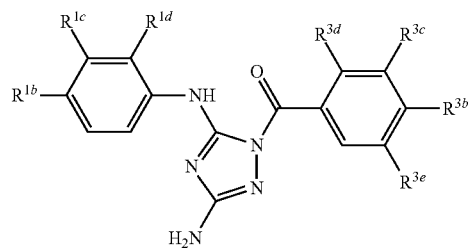

| Cpd # | Compound Name | $R^{1b}$ | $R^{1c}$ | $R^{1d}$ | $R^{3b}$ | $R^{3c}$ | $R^{3d}$ | $R^{3e}$ | $IC_{50}$ |
|---|---|---|---|---|---|---|---|---|---|
| 364 | 3-amino-1-(3-(dimethyl-amino)phenyl)carbonyl-5-(4-(4-methyl-piperazin-1-yl)phenyl-amino]-1H-1,2,4-triazole | 4-methylpiperazin-1-yl | —H | —H | —H | —N(CH$_3$) | —H | —H | B |

$IC_{50}$ activity:
A = <1 μM
B = 1 to 10 μM
C = >10 to 20 μM
D = >20 μM

TABLE 3

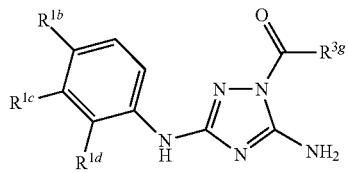

| Cpd # | Compound Name | $R^{1b}$ | $R^{1c}$ | $R^{1d}$ | $R^{3g}$ | $IC_{50}$ |
|---|---|---|---|---|---|---|
| 171 | 5-amino-1-(3-(iso-propoxy)pyridin-5-yl)carbonyl-3-[4-[2-(morpholin-4-yl)ethoxy]phenylamino]-1H-1,2,4-triazole | 2-(morpholin-4-yl)ethoxy | —H | —H | 3-(iso-propoxy)pyridin-5-yl | B |
| 261 | 1-acetyl-5-amino-3-(1,4-benzodioxan-6-yl)amino-1H-1,2,4-triazole | (benzodioxan ring) | (benzodioxan ring) | —H | —CH$_3$ | D |
| 141 | 5-amino-3-phenylamino-1-(trans-2-(furan-2-yl)ethenyl)carbonyl-1H-1,2,4-triazole | —H | —H | —H | trans-2-(furan-2-yl)ethenyl | B |
| 65 | 5-amino-1-(2,2-dimethyl-2H-benzo[b][1,4]oxazin-3(4H)-on-6-yl)carbonyl-3-(4-(iso-propoxy)phenyl)amino-1H-1,2,4-triazole | iso-propoxy | —H | —H | 2,2-dimethyl-2H-benzo[b][1,4]oxazin-3(4H)-on-6-yl | B |

TABLE 3-continued

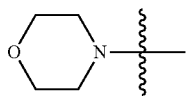

| Cpd # | Compound Name | R$^{1b}$ | R$^{1c}$ | R$^{1d}$ | R$^{3g}$ | IC$_{50}$ |
|---|---|---|---|---|---|---|
| 68 | 5-amino-1-(2,2-dimethyl-2H-benzo[b][1,4]oxazin-3(4H)-on-6-yl)carbonyl-3-(4-(morpholin-4-yl)phenylamino)-1H-1,2,4-triazole | 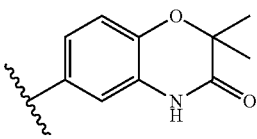 [SMILES: *c1ccc2c(c1)NC(=O)C(C)(C)O2] | —H | —H | 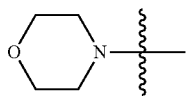 | B |
| 78 | 5-amino-1-(2,2-dimethyl-2H-benzo[b][1,4]oxazin-3(4H)-on-6-yl)carbonyl-3-[4-[2-(piperidin-1-yl)ethoxy]phenylamino]-1H-1,2,4-triazole | 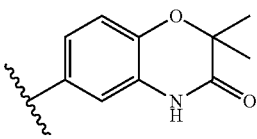 [SMILES: *c1ccc2c(c1)NC(=O)C(C)(C)O2] | —H | —H | 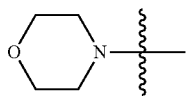 | A |
| 86 | 5-amino-3-[4-[2-(dimethylamino)ethoxy)phenylamino]-1-(2,2-dimethyl-2H-benzo[b][1,4]oxazin-3(4H)-on-6-yl)carbonyl-1H-1,2,4-triazole | 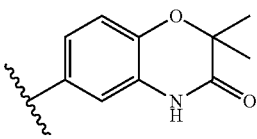 [SMILES: *c1ccc2c(c1)NC(=O)C(C)(C)O2] | —H | —H | 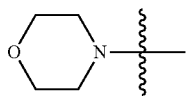 | A |
| 90 | 5-amino-3-[4-[2-(dimethylamino)propoxy)phenylamino]-1-(2,2-dimethyl-2H-benzo[b][1,4]oxazin-3(4H)-on-6-yl)carbonyl-1H-1,2,4-triazole | 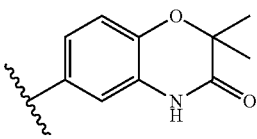 [SMILES: *c1ccc2c(c1)NC(=O)C(C)(C)O2] | —H | —H | 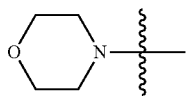 | B |
| 196 | 5-amino-1-[2-(bicyclo[2.2.1]hept-5-ene)carbonyl]-3-[4-[2-(pyrrolidin-1-yl)ethoxy]phenylamino]-1H-1,2,4-triazole | 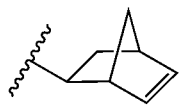 | —H | —H | 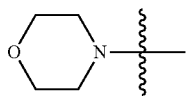 | D |
| 27 | 5-amino-1-(4-(methoxy)cyclohexyl)carbonyl-3-[4-[2-(piperidin-1-yl)ethoxy)phenylamino]-1H-1,2,4-triazole |  | —H | —H |  | B |

TABLE 3-continued

| Cpd # | Compound Name | R$^{1b}$ | R$^{1c}$ | R$^{1d}$ | R$^{3g}$ | IC$_{50}$ |
|---|---|---|---|---|---|---|
| 200 | 5-amino-1-[2-(bicyclo[2.2.1]heptane)carbonyl]-3-[4-[2-(pyrrolidin-1-yl)ethoxy)phenylamino]-1H-1,2,4-triazole | 2-(pyrrolidin-1-yl)ethoxy | —H | —H | bicyclo[2.2.1]heptanyl | D |
| 3 | 5-amino-1-(1H-indol-5-yl)carbonyl-3-[4-[2-(pyrrolidin-1-yl)ethoxy]phenylamino]-1H-1,2,4-triazole | 2-(pyrrolidin-1-yl)ethoxy | —H | —H | 1H-indol-5-yl | A |
| 5 | 5-amino-1-(1H-indol-6-yl)carbonyl-3-[4-[2-(pyrrolidin-1-yl)ethoxy]phenylamino]-1H-1,2,4-triazole | 2-(pyrrolidin-1-yl)ethoxy | —H | —H | 1H-indol-6-yl | A |
| 6 | 5-amino-1-(1H-indol-2-yl)carbonyl-3-[4-[2-(pyrrolidin-1-yl)ethoxy]phenylamino]-1H-1,2,4-triazole | 2-(pyrrolidin-1-yl)ethoxy | —H | —H | 1H-indol-2-yl | A |
| 25 | 5-amino-1-(benzimidazol-6-yl)carbonyl-3-[4-[2-(pyrroldiin-1-yl)ethoxy]phenylamino]-1H-1,2,4-triazole | 2-(pyrrolidin-1-yl)ethoxy | —H | —H | benzimidazol-6-yl | B |

TABLE 3-continued

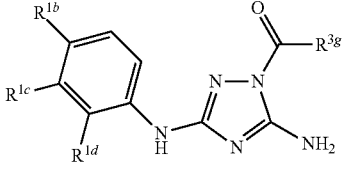

| Cpd # | Compound Name | R$^{1b}$ | R$^{1c}$ | R$^{1d}$ | R$^{3g}$ | IC$_{50}$ |
|---|---|---|---|---|---|---|
| 28 | 5-amino-1-(6-(methyl)pyridin-3-yl)carbonyl-3-[4-[2-(pyrrolidin-1-yl)ethoxy]phenylamino]-1H-1,2,4-triazole | 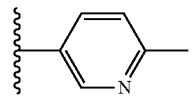 | —H | —H | 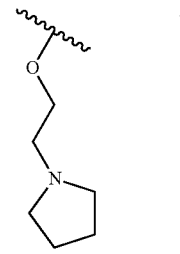 [SMILES: *OCCN1CCCC1] | B |
| 203 | 5-amino-1-(pyridin-2-yl)carbonyl-3-[4-[2-(pyrrolidin-1-yl)ethoxy]phenylamino]-1H-1,2,4-triazole | 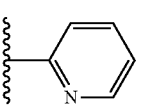 | —H | —H | 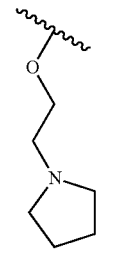 [SMILES: *OCCN1CCCC1] | D |
| 204 | 5-amino-1-(pyridin-4-yl)carbonyl-3-[4-[2-(pyrrolidin-1-yl)ethoxy]phenylamino]-1H-1,2,4-triazole | 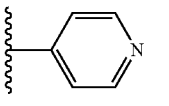 | —H | —H | 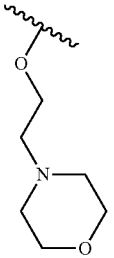 [SMILES: *OCCN1CCOCC1] | D |
| 265 | 5-amino-1-(1H-indol-6-yl)carbonyl-3-[4-[2-(morpholin-4-yl)ethoxy)phenylamino]-1H-1,2,4-triaozle | 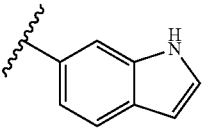 [SMILES: *c1ccc2cc[nH]c2c1] | —H | —H | 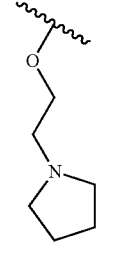 | A |
| 271 | 5-amino-1-(benzo[d]thiazol-6-yl)carbonyl-3-[4-(2-(pyrrolidin-1-yl)ethoxy]phenylamino]-1H-1,2,4-triazole | 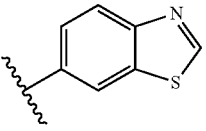 [SMILES: *c1ccc2ncsc2c1] | —H | —H | | B |

TABLE 3-continued

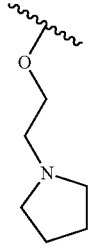 [SMILES: *OCCN1CCCC1]

| Cpd # | Compound Name | R$^{1b}$ | R$^{1c}$ | R$^{1d}$ | R$^{3g}$ | IC$_{50}$ |
|---|---|---|---|---|---|---|
| 279 | 5-amino-1-(2,3-dihydrobenzofuran-5-yl)carbonyl-3-[4-[2-(pyrrolidin-1-yl)ethoxy]phenylamino]-1H-1,2,4-triazole | 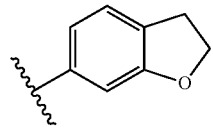 [SMILES: *c1ccc2c(c1)OCC2] | —H | —H | 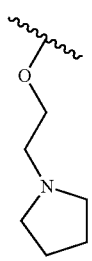 | A |
| 281 | 5-amino-1-(1H-benzo[d][1,2,3]triazol-5-yl)carbonyl-3-[4-[2-(pyrrolidin-1-yl)ethoxy]phenylamino]-1H-1,2,4-triazole | 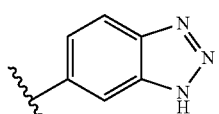 | —H | —H | 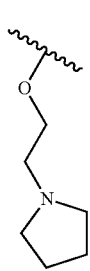 [SMILES: *OCCN1CCCC1] | C |
| 283 | 5-amino-1-(3-methylthien-2-yl)carbonyl-3-[4-[2-(pyrrolidin-1-yl)ethoxy]phenylamino]-1H-1,2,4-triazole | 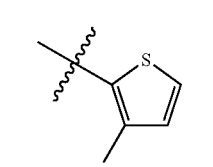 [SMILES: *c1sccc1C] | —H | —H |  | A |
| 284 | 5-amino-1-(5-methylthien-2-yl)carbonyl-3-[4-[2-(pyrrolidin-1-yl)ethoxy]phenylamino]-1H-1,2,4-triazole | 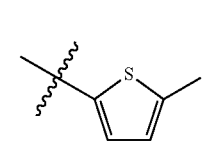 [SMILES: *c1ccc(C)s1] | —H | —H |  | A |
| 285 | 5-amino-1-(thien-2-yl)carbonyl-3-[4-[2-(pyrrolidin-1-yl)ethoxy]phenylamino]-1H-1,2,4-triazole | 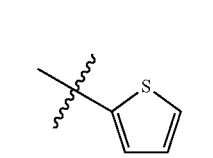 [SMILES: *c1cccs1] | —H | —H | | A |

TABLE 3-continued

| Cpd # | Compound Name | R$^{1b}$ | R$^{1c}$ | R$^{1d}$ | R$^{3g}$ | IC$_{50}$ |
|---|---|---|---|---|---|---|
| 288 | 5-amino-1-(quinolin-6-yl)carbonyl-3-[4-[2-(pyrrolidin-1-yl)ethoxy]phenylamino]-1H-1,2,4-triazole | 2-(pyrrolidin-1-yl)ethoxy | —H | —H | quinolin-6-yl | A |
| 295 | 5-amino-1-(2,2-dimethyl-2H-benzo[b][1,4]oxazin-3(4H)-on-6-yl)carbonyl-3-[4-(pyrrolidin-1-yl)phenylamino]-1H-1,2,4-triazole | pyrrolidin-1-yl | —H | —H | 2,2-dimethyl-2H-benzo[b][1,4]oxazin-3(4H)-on-6-yl | B |
| 309 | 5-amino-1-(1H-indol-6-yl)carbonyl-3-[3-fluoro-4-[2-(pyrrolidin-1-yl)ethoxy]phenylamino]-1H-1,2,4-triazole | 2-(pyrrolidin-1-yl)ethoxy | —F | —H | 1H-indol-6-yl | A |
| 312 | 5-amino-1-(1,2,3-thiadiazol-4-yl)carbonyl-3-[4-[2-(pyrrolidin-1-yl)ethoxy]phenylamino]-1H-1,2,4-triazole | 2-(pyrrolidin-1-yl)ethoxy | —H | —H | 1,2,3-thiadiazol-4-yl | D |
| 318 | 5-amino-1-(1H-indol-6-yl)carbonyl-3-[3-methoxy-4-[2-(pyrrolidin-1-yl)ethoxy]phenylamino]-1H-1,2,4-triazole | 2-(pyrrolidin-1-yl)ethoxy | —OCH$_3$ | —H | 1H-indol-6-yl | A |

TABLE 3-continued

| Cpd # | Compound Name | R¹ᵇ | R¹ᶜ | R¹ᵈ | R³ᵍ | IC₅₀ |
|---|---|---|---|---|---|---|
| 323 | 5-amino-1-(1H-indol-6-yl)carbonyl-3-[4-[2-(azepan-1-yl)ethoxy]phenylamino]-1H-1,2,4-triazole | 2-(azepan-1-yl)ethoxy | —H | —H | 1H-indol-6-yl | A |
| 330 | 5-amino-1-(1H-indol-6-yl)carbonyl-3-[4-[2-(isoindolin-1-yl)ethoxy]phenylamino]-1H-1,2,4-triazole | 2-(isoindolin-2-yl)ethoxy | —H | —H | 1H-indol-6-yl | A |
| 365 | 5-amino-1-(bicyclo[2.2.1]heptan-2-yl)carbonyl-3-[4-(4-methylpiperazin-1-yl)phenylamino]-1H-1,2,4-triazole | 4-methylpiperazin-1-yl | —H | —H | bicyclo[2.2.1]heptan-2-yl | D |
| 366 | 5-amino-1-(1H-indol-3-yl)carbonyl-3-[4-[2-(pyrrolidin-1-yl)ethoxy]phenylamino]-1H-1,2,4-triazole | 2-(pyrrolidin-1-yl)ethoxy | —H | —H | 1H-indol-3-yl | B |
| 367 | 5-amino-1-(benzo[b]thiophen-2-yl)carbonyl-3-[4-[2-(pyrrolidin-1-yl)ethoxy]phenylamino]-1H-1,2,4-triazole | 2-(pyrrolidin-1-yl)ethoxy | —H | —H | benzo[b]thiophen-2-yl | A |

TABLE 3-continued

| Cpd # | Compound Name | R[1b] | R[1c] | R[1d] | R[3g] | IC$_{50}$ |
|---|---|---|---|---|---|---|
| 369 | 5-amino-1-(benzo[b]thiophen-5-yl)carbonyl-3-[4-[2-(pyrrolidin-1-yl)ethoxy]phenylamino]-1H-1,2,4-triazole |  | —H | —H | 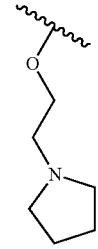 | A |
| 375 | 5-amino-1-(1H-indol-6-yl)carbonyl-3-[4-[2-(imidazol-1-yl)ethoxy]phenylamino]-1H-1,2,4-triazole | 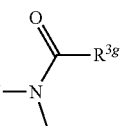 | —H | —H | 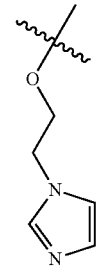 [SMILES: *OCCn1ccnc1] | A |
| 377 | 5-amino-1-(benzo[b]thiophen-5-yl)carbonyl-3-[4-[2-(imidazol-1-yl)ethoxy]phenylamino]-1H-1,2,4-triazole | 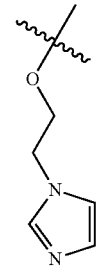 [SMILES: *OCCn1ccnc1] | —H | —H |  | A |
| 379 | 5-amino-1-(benzo[b]thiophen-2-yl)carbonyl-3-[4-[2-(imidazol-1-yl)ethoxy]phenylamino]-1H-1,2,4-triazole | 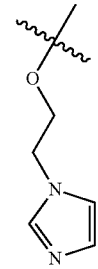 [SMILES: *OCCn1ccnc1] | —H | —H | 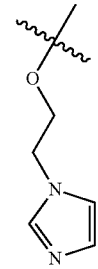 [SMILES: *OCCn1ccnc1] | A |
| 386 | 5-amino-1-(1,4-benzodioxan-6-yl)carbonyl-3-[4-[2-((S)-3-fluoropyrrolidin-1-yl)ethoxy]phenylamino]-1H-1,2,4-triazole |  | —H | —H | 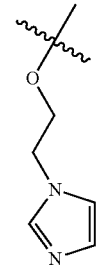 | A |

TABLE 3-continued

| Cpd # | Compound Name | $R^{1b}$ | $R^{1c}$ | $R^{1d}$ | $R^{3g}$ | IC$_{50}$ |
|---|---|---|---|---|---|---|
| 388 | 5-amino-1-(1H-indol-6-yl)carbonyl-3-[4-[2-((S)-3-fluoropyrrolidin-1-yl)ethoxy]phenylamino]-1H-1,2,4-triazole | (2-((S)-3-fluoropyrrolidin-1-yl)ethoxy) | —H | —H | 1H-indol-6-yl | A |

IC$_{50}$ activity:

A = <1 μM

B = 1 to 10 μM

C = >10 to 20 μM

D = >20 μM

TABLE 4

| Cpd # | Compound Name | $R^{1b}$ | $R^{1c}$ | $R^{1d}$ | $R^{3g}$ | IC$_{50}$ |
|---|---|---|---|---|---|---|
| 140 | 3-amino-5-phenylamino-1-(trans-2-(furan-2-yl)ethenyl)carbonyl-1H-1,2,4-triazole | —H | —H | —H | trans-2-(furan-2-yl)ethenyl | D |
| 66 | 3-amino-1-(2,2-dimethyl-2H-benzo[b][1,4]oxazin-3(4H)-on-6-yl)carbonyl-5-(4-(iso-propoxy)phenyl)amino-1H-1,2,4-triazole | isopropoxy | —H | —H | 2,2-dimethyl-2H-benzo[b][1,4]oxazin-3(4H)-on-6-yl | B |
| 69 | 3-amino-1-(2,2-dimethyl-2H-benzo[b][1,4]oxazin-3(4H)-on-6-yl)carbonyl-5-(4-(morpholin-4-yl)phenylamino)-1H-1,2,4-triazole | morpholin-4-yl | —H | —H | 2,2-dimethyl-2H-benzo[b][1,4]oxazin-3(4H)-on-6-yl | B |

TABLE 4-continued

| Cpd # | Compound Name | R$^{1b}$ | R$^{1c}$ | R$^{1d}$ | R$^{3g}$ | IC$_{50}$ |
|---|---|---|---|---|---|---|
| 202 | 3-amino-1-(1H-indol-5-yl)carobnyl-5-[4-[2-(pyrrolidin-1-yl)ethoxy)phenylamino]-1H-1,2,4-triazole | 2-(pyrrolidin-1-yl)ethoxy | —H | —H | 1H-indol-5-yl | B |
| 296 | 3-amino-1-(2,2-dimethyl-2H-benzo[b][1,4]oxazin-3(4H)-on-6-yl)carbonyl-5-[4-(pyrrolidin-1-yl)phenylamino]-1H-1,2,4-triazole | pyrrolidin-1-yl | —H | —H | 2,2-dimethyl-benzo[1,4]oxazin-3(4H)-on-6-yl | C |
| 368 | 3-amino-1-(benzo[b]thiophen-2-yl)carbonyl-5-[4-[2-(pyrrolidin-1-yl)ethoxy]phenylamino]-1H-1,2,4-triazole | 2-(pyrrolidin-1-yl)ethoxy | —H | —H | benzo[b]thiophen-2-yl | B |
| 376 | 3-amino-1-(1H-indol-6-yl)carbonyl-5-[4-[2-(imidazol-1-yl)ethoxy]phenylamino]-1H-1,2,4-triazole | 2-(imidazol-1-yl)ethoxy | —H | —H | 1H-indol-6-yl | A |
| 378 | 3-amino-1-(benzo[b]thiophen-5-yl)carbonyl-5-[4-[2-(imidazol-1-yl)ethoxy]phenylamino]-1H-1,2,4-triazole | 2-(imidazol-1-yl)ethoxy | —H | —H | benzo[b]thiophen-5-yl | A |

TABLE 4-continued

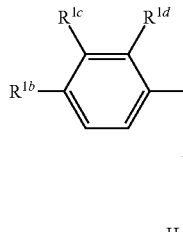

| Cpd # | Compound Name | R$^{1b}$ | R$^{1c}$ | R$^{1d}$ | R$^{3g}$ | IC$_{50}$ |
|---|---|---|---|---|---|---|
| 387 | 3-amino-1-(1,4-benzodioxan-6-yl)carbonyl-5-[4-[2-((S)-3-fluoropyrrolidin-1-yl)ethoxy]phenylamino]-1H-1,2,4-triazole | 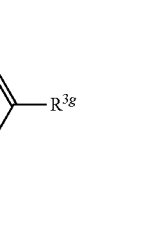 | —H | —H |  | A |
| 389 | 3-amino-1-(1H-indol-6-yl)carbonyl-5-[4-[2-((S)-3-fluoropyrrolidin-1-yl)ethoxy]phenylamino]-1H-1,2,4-triazole | 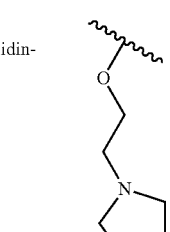 | —H | —H | 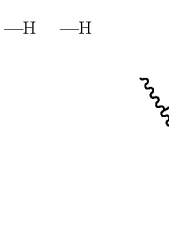 | A |

IC$_{50}$ activity:
A = <1 μM
B = 1 to 10 μM
C = >10 to 20 μM
D = >20 μM

TABLE 5

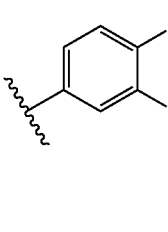

| Cpd # | Compound Name | R$^{1}$ | R$^{3b}$ | R$^{3c}$ | R$^{3d}$ | R$^{3e}$ | R$^{3f}$ | R$^{2}$ | IC$_{50}$ |
|---|---|---|---|---|---|---|---|---|---|
| 103 | 5-amino-3-(2-(ethoxycarbonyl)benzo-furan-5-yl)amino-1-(3-(iso-propoxy)phenyl)carbonyl-1H-1,2,4-triazole | 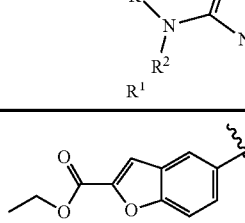 | —H | 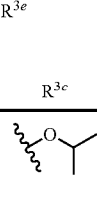 | —H | —H | —H | —H | D |
| 130 | 5-amino-3-[N-(2-(tetra-hydropy-ran-2-yloxy) methylbenzo-furan-5-yl) amino]-1-(3-(methyl)phenyl)carbonyl-1H-1,2,4-triazole | 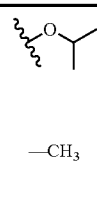 | —H | —CH$_3$ | —H | —H | —H | —H | B |

TABLE 5-continued

| Cpd # | Compound Name | R¹ | R³ᵇ | R³ᶜ | R³ᵈ | R³ᵉ | R³ᶠ | R² | IC₅₀ |
|---|---|---|---|---|---|---|---|---|---|
| 136 | 5-amino-3-(2-(hydroxymethyl)benzo-furan-5-yl)amino-1-(3-(methyl)phenyl)carbonyl-1H-1,2,4-triazole | 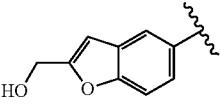 [SMILES: *c1ccc2oc(CO)cc2c1] | —H | —CH₃ | —H | —H | —H | —H | B |
| 154 | 5-amino-3-(indazol-5-yl)amino-1-(3-(methyl)phenyl)carbonyl-1H-1,2,4-triazole | 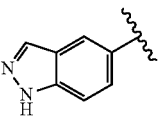 [SMILES: *c1ccc2[nH]ncc2c1] | —H | —CH₃ | —H | —H | —H | —H | B |
| 160 | 5-amino-3-(indazol-6-yl)amino-1-(3-(methyl)phenyl)carbonyl-1H-1,2,4-triazole | 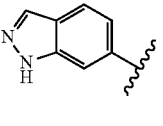 [SMILES: *c1ccc2cn[nH]c2c1] | —H | —CH₃ | —H | —H | —H | —H | B |
| 161 | 5-amino-3-(benzo[b][1,4]oxazin-3(4H)-on-6-yl)amino-1-(3-(methylphenyl)carbonyl-1H-1,2,4-triazole | 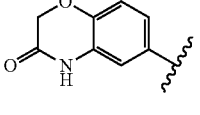 | —H | —CH₃ | —H | —H | —H | —H | D |
| 206 | 5-amino-3-[(2H,3H-4-tert-butoxycarbonylbenzo[1,4]oxazin-6-yl)amino]-1-(3-methylphenyl)carbonyl-1,2,4-triazole | 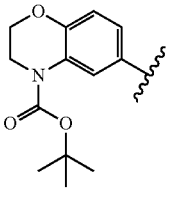 [SMILES: *c1ccc2c(c1)N(C(=O)OC(C)(C)C)CCO2] | —H | —CH₃ | —H | —H | —H | —H | D |
| 207 | 5-amino-1-(3-methylphenyl)carbonyl-3-[2-[N-[2-(tetrahydropyran-2-yloxy)ethyl]amino]carbonyl-benzofuran-5-yl]amino-1H-1,2,4-triazole | 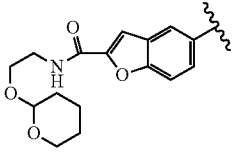 [SMILES: *c1ccc2oc(C(=O)NCCOC3CCCCO3)cc2c1] | —H | —CH₃ | —H | —H | —H | —H | B |
| 208 | 5-amino-3-[2-[2-hydroxyethyl-aminocarbonyl]-benzofuran-5-yl]amino-1-(3-methylphenyl)carbonyl-1H-1,2,4-triazole | 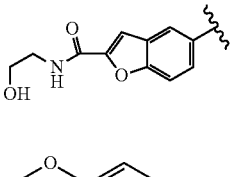 | —H | —CH₃ | —H | —H | —H | —H | B |
| 215 | 5-amino-3-[(3,4-dihydrobenzo[1,4]oxazin-6-yl)amino]-1-(3-methylphenyl)carbonyl-1H-1,2,4-triazole | 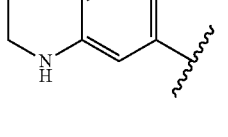 | —H | —CH₃ | —H | —H | —H | —H | D |
| 219 | 5-amino-3-[2-(ethoxycarbonyl)benzo-furan-5-yl]amino-1-(3-methylphenyl)carbonyl-1H-1,2,4-triazole | 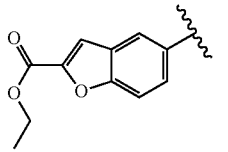 [SMILES: *c1ccc2oc(C(=O)OCC)cc2c1] | —H | —CH₃ | —H | —H | —H | —H | B |

TABLE 5-continued

| Cpd # | Compound Name | R¹ | R³ᵇ | R³ᶜ | R³ᵈ | R³ᵉ | R³ᶠ | R² | IC₅₀ |
|---|---|---|---|---|---|---|---|---|---|
| 220 | 5-amino-1-(3-methylphenyl)carbonyl-3-(pyridin-3-yl)amino-1H-1,2,4-triazole | 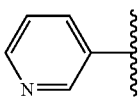 | —H | —CH₃ | —H | —H | —H | —H | D |
| 222 | 5-amino-3-(2-methyl-2H-indazol-5yl)amino-1-(3-methylphenyl)carbonyl-1H-1,2,4-triazole | 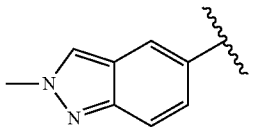 [SMILES: *c1ccc2nn(C)cc2c1] | —H | —CH₃ | —H | —H | —H | —H | D |
| (Ia-28) | 5-amino-3-(2-((allyl(methyl)amino)methyl)-benzofuran-5-yl)amino-1-(3-methyl-phenyl)carbonyl-1H-1,2,4-triazole | 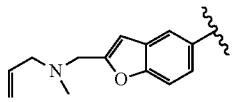 [SMILES: *c1ccc2oc(CN(C)CC=C)cc2c1] | —H | —CH | —H | —H | —H | —H | B |
| 227 | 5-amino-3-[1-methyl-1H-indazol-5-yl]amino-1-(3-methylphenyl)carbonyl-1H-1,2,4-triazole | 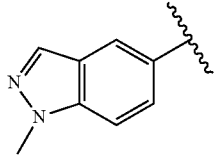 [SMILES: *c1ccc2c(cnn2C)c1] | —H | —CH₃ | —H | —H | —H | —H | B |
| (Ia-29) | 5-amino-3-(2-((methylamino)methyl)benzo-furan-5-yl)amino-1-(3-methylphenyl)carbonyl-1H-1,2,4-triazole | 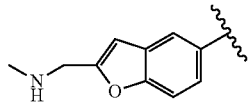 [SMILES: *c1ccc2oc(CNC)cc2c1] | —H | —CH₃ | —H | —H | —H | —H | A |
| 229 | 5-amino-3-(benzofuran-5-yl)amino-1-(3-methyl-phenyl)carbonyl-1H-1,2,4-triazole | 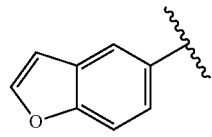 [SMILES: *c1ccc2occc2c1] | —H | —CH₃ | —H | —H | —H | —H | B |
| 250 | 5-amino-3-(benzothiazol-6-yl)amino-1-(3-methyl-phenyl)carbonyl-1H-1,2,4-triazole | 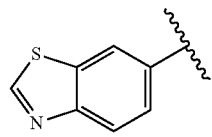 [SMILES: *c1ccc2ncsc2c1] | —H | —CH₃ | —H | —H | —H | —H | B |
| 251 | 5-amino-1-(3-methylphenyl)carbonyl-3-(6-quinolinyl)aminio-1H-1,2,4-triazole | 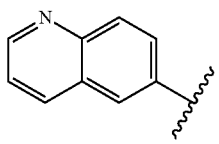 [SMILES: *c1ccc2ncccc2c1] | —H | —CH₃ | —H | —H | —H | —H | B |
| 252 | 5-amino-3-(1H-indol-5-yl)amino-1-(3-methyl-phenyl)-carbonyl-1H-1,2,4-triazole | 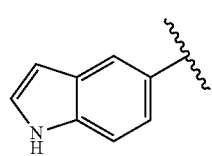 [SMILES: *c1ccc2[nH]ccc2c1] | —H | —CH₃ | —H | —H | —H | —H | B |

TABLE 5-continued

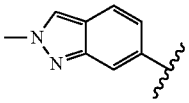 [SMILES: *c1ccc2cn(C)nc2c1]

| Cpd # | Compound Name | R¹ | R³ᵇ | R³ᶜ | R³ᵈ | R³ᵉ | R³ᶠ | R² | IC₅₀ |
|---|---|---|---|---|---|---|---|---|---|
| 253 | 5-amino-3-(1H-2-methyl-indazol-6-yl)amino-1-(3-methylphenyl)carbonyl-1H-1,2,4-triazole | 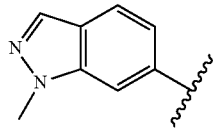 | —H | —CH₃ | —H | —H | —H | —H | B |
| 254 | 5-amino-3-(1H-1-methyl-indazol-6-yl)amino-1-(3-methylphenyl)carbonyl-1H-1,2,4-triazole | 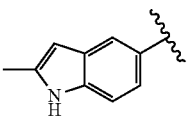 [SMILES: *c1ccc2[nH]c(C)cc2c1] | —H | —CH₃ | —H | —H | —H | —H | D |
| 255 | 5-amino-3-(1H-2-methyl-indol-5-yl)amino-1-(3-methylphenyl)carbonyl-1H-1,2,4-triazole | 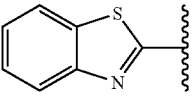 [SMILES: *c1nc2ccccc2s1] | —H | —CH₃ | —H | —H | —H | —H | B |
| 256 | 5-amino-3-(benzothiazol-2-yl)amino-1-(3-methyl-phenyl)carbonyl-1H-1,2,4-triazole | 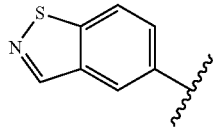 [SMILES: *c1ccc2sncc2c1] | —H | —CH₃ | —H | —H | —H | —H | D |
| 259 | 5-amino-3-(1,2-benziso-thiazol-5-yl)amino-1-(3-methylphenyl)carbonyl-1H-1,2,4-triazole | 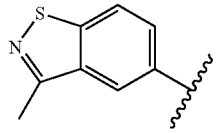 [SMILES: *c1ccc2snc(C)c2c1] | —H | —CH₃ | —H | —H | —H | —H | D |
| 260 | 5-amino-3-(3-methyl-1,2-benzisothiazol-5-yl)amino-1-(3-methylphenyl)carbonyl-1H-1,2,4-triazole | 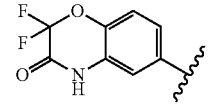 [SMILES: *c1ccc2c(c1)NC(=O)C(F)(F)O2] | —H | —CH₃ | —H | —H | —H | —H | D |
| 63 | 5-amino-3-(2,2-difluoro-2H-benzo[b][1,4]oxazin-3(4H)-on-6-yl)amino-1-(4-(iso-propoxy)phenyl)carbonyl-1H-1,2,4-triazole |  | 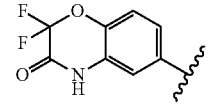 [SMILES: *c1ccc2c(c1)NC(=O)C(F)(F)O2] | —H | —H | —H | —H | —H | D |
| 64 | 5-amino-3-(2,2-difluoro-2H-benzo[b][1,4]oxazin-3(4H)-on-6-yl)amino-1-(3-(methyl)phenyl)carbonyl-1H-1,2,4-triazole |  | —H | —CH₃ | —H | —H | —H | —H | D |
| 273 | 5-amino-1-(4-(tert-butyl)phenyl)carbonyl-3-[4-((tert-butoxycarbonyl)amino-chroman-6-yl]amino-1H-1,2,4-triazole | 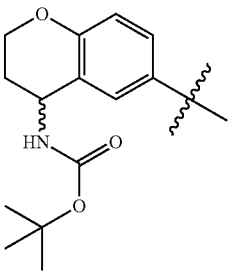 [SMILES: *c1ccc2c(c1)C(NC(=O)OC(C)(C)C)CCO2] | —C(CH₃)₃ | —H | —H | —H | —H | —H | D |

TABLE 5-continued

| Cpd # | Compound Name | R¹ | R³ᵇ | R³ᶜ | R³ᵈ | R³ᵉ | R³ᶠ | R² | IC$_{50}$ |
|---|---|---|---|---|---|---|---|---|---|
| 274 | 5-amino-1-(4-(iso-propoxy)phenyl)carbonyl-3-[4-((tert-butoxycarbonyl)amino-chroman-6-yl]amino-1H-1,2,4-triazole | (tert-butoxycarbonylamino-chroman-6-yl) | —O-iPr | —H | —H | —H | —H | —H | D |
| 275 | 5-amino-1-(4-(tert-butoxy)phenyl)carbonyl-3-[4-((tert-butoxycarbonyl)amino-chroman-6-yl]amino-1H-1,2,4-triazole | (tert-butoxycarbonylamino-chroman-6-yl) | —OC(CH$_3$)$_3$ | —H | —H | —H | —H | —H | D |
| 346 | 5-amino-1-(4-(tert-butoxy)phenyl)carbonyl-3-[(5-(aminocarbonyl)bicyclo[2.2.1]-hept-2-en-6-yl)amino]-1H-1,2,4-triazole | (5-(aminocarbonyl)bicyclo[2.2.1]hept-2-en-6-yl) | —OC(CH$_3$)$_3$ | —H | —H | —H | —H | —H | D |
| 348 | 5-amino-1-(3-(tert-butoxy)phenyl)carbonyl-3-[(5-(aminocarbonyl)bicyclo[2.2.1]-hept-2-en-6-yl)amino]-1H-1,2,4-triazole | (5-(aminocarbonyl)bicyclo[2.2.1]hept-2-en-6-yl) | —H | —OC(CH$_3$)$_3$ | —H | —H | —H | —H | D |
| 350 | 5-amino-1-(4-(dimethyl-amino)phenyl)carbonyl-3-[(5-(aminocarbonyl)-bicyclo[2.2.1]hept-2-en-6-yl)amino]-1H-1,2,4-triazole | (5-(aminocarbonyl)bicyclo[2.2.1]hept-2-en-6-yl) | —N(CH$_3$)$_3$ | —H | —H | —H | —H | —H | D |
| 352 | 5-amino-1-(3-(dimethyl-amino)phenyl)carbonyl-3-[(5-(aminocarbonyl)-bicyclo[2.2.1]hept-2-en-6-yl)amino]-1H-1,2,4-triazole | (5-(aminocarbonyl)bicyclo[2.2.1]hept-2-en-6-yl) | —H | —N(CH$_3$)$_3$ | —H | —H | —H | —H | D |

TABLE 5-continued

| Cpd # | Compound Name | R¹ | R³ᵇ | R³ᶜ | R³ᵈ | R³ᵉ | R³ᶠ | R² | IC₅₀ |
|---|---|---|---|---|---|---|---|---|---|
| 354 | 5-amino-1-(4-(iso-propoxy)phenyl)carbonyl-3-[(5-(aminocarbonyl)bicyclo[2.2.1]-hept-2-en-6-yl)amino]-1H-1,2,4-triazole | (5-(aminocarbonyl)bicyclo[2.2.1]hept-2-en-6-yl) | —O-iPr | —H | —H | —H | —H | —H | D |
| 392 | 5-amino-1-(2,6-difluorophenyl)carbonyl-3-(1-methylsulfonylpiperidin-4-yl)amino-1H-1,2,4-triazole | 1-methylsulfonylpiperidin-4-yl | —H | —H | —F | —H | —F | —H | D |
| 393 | 5-amino-1-(4-(tert-butoxy)phenyl)carbonyl-3-(1-methylsulfonylpiperidin-4-yl)amino-1H-1,2,4-triazole | 1-methylsulfonylpiperidin-4-yl | —OC(CH₃)₃ | —H | —H | —H | —H | —H | D |
| 394 | 5-amino-1-(4-(tert-butoxy)phenyl)carbonyl-3-(1-methylsulfonylpiperidin-4-yl)amino-1H-1,2,4-triazole | 1-methylsulfonylpiperidin-4-yl | —O-iPr | —H | —H | —H | —H | —H | D |
| 395 | 5-amino-1-(4-(dimethylamino)phenyl)carbonyl-3-(1-methylsulfonyl-piperidin-4-yl)amino-1H-1,2,4-triazole | 1-methylsulfonylpiperidin-4-yl | —N(CH₃)₂ | —H | —H | —H | —H | —H | -D |
| 399 | 5-amino-1-(4-(morpholin-4-yl)phenyl)carbonyl-3-(1-methylsulfonylpiperidin-4-yl)amino-1H-1,2,4-triazole | 1-methylsulfonylpiperidin-4-yl | —N(morpholin-4-yl) | —H | —H | —H | —H | —H | D |
| 403 | 5-amino-3-[N-(3-(4-(2-chloro-6-fluorophenyl)piperazin-1-yl)prop-1-yl)-N-((3-methylphenyl)carbonyl)amino]-1-(3-methylphenyl)carbonyl-1H-1,2,4-triazole | 3-(4-(2-chloro-6-fluorobenzyl)piperazin-1-yl)propyl | —H | —CH₃ | —H | —H | —H | (3-methylphenyl)carbonyl | D |

TABLE 5-continued

| Cpd # | Compound Name | R¹ | R³ᵇ | R³ᶜ | R³ᵈ | R³ᵉ | R³ᶠ | R² | IC₅₀ |
|---|---|---|---|---|---|---|---|---|---|
| 405 | 5-amino-3-[3-(4-(2-chloro-6-fluorophenyl)piperazin-1-yl)prop-1-yl]amino-1-(3-methylphenyl)carbonyl-1H-1,2,4-triazole | 3-(4-(2-chloro-6-fluorobenzyl)piperazin-1-yl)propyl group | —H | —CH₃ | —H | —H | —H | —H | D |

IC₅₀ activity:
A = <1 μM
B = 1 to 10 μM
C = >10 to 20 μM
D = >20 μM

TABLE 6

| Cpd # | Compound Name | R¹ᵉ | R³ᵇ | R³ᶜ | R³ᵈ | R³ᵉ | R³ᶠ | IC₅₀ |
|---|---|---|---|---|---|---|---|---|
| 167 | 3-amino-5-[(2H,3H-4-tert-butoxycarbonylbenzo[1,4]oxazin-6-yl)amino]-1-(3-(methyl)phenyl)carbonyl-1H-1,2,4-triazole | 4-tert-butoxycarbonyl-2H,3H-benzo[1,4]oxazin-6-yl | —H | —CH₃ | —H | —H | | D |
| 345 | 3-amino-1-(4-(tert-butoxy)phenyl)carbonyl-5-[(3-(aminocarbonyl)bicyclo[2.2.1]hept-5-en-2-yl)amino]-1H-1,2,4-triazole | 3-(aminocarbonyl)bicyclo[2.2.1]hept-5-en-2-yl | —OC(CH₃)₃ | —H | —H | —H | | D |

TABLE 6-continued

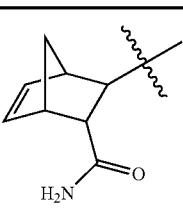

| Cpd # | Compound Name | R$^{1e}$ | R$^{3b}$ | R$^{3c}$ | R$^{3d}$ | R$^{3e}$ | R$^{3f}$ | IC$_{50}$ |
|---|---|---|---|---|---|---|---|---|
| 347 | 3-amino-1-(3-(tert-butoxy)phenyl)carbonyl-5-[(3-(aminocarbonyl)bicyclo[2.2.1]hept-5-en-2-yl)amino]-1H-1,2,4-triazole | 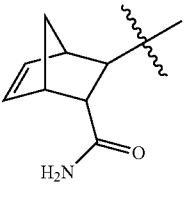 | —H | —OC(CH$_3$)$_3$ | —H | —H | | D |
| 349 | 3-amino-1-(4-(dimethylamino)phenyl)carbonyl-5-[(3-(aminocarbonyl)bicyclo[2.2.1]hept-5-en-2-yl)amino]-1H-1,2,4-triazole | 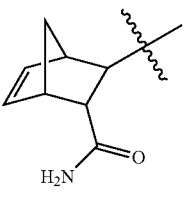 [SMILES: *C1C2C=CC(C2)C1C(N)=O] | —N(CH$_3$)$_2$ | —H | —H | —H | | D |
| 351 | 3-amino-1-(3-(dimethylamino)phenyl)carbonyl-5-[(3-(aminocarbonyl)bicyclo[2.2.1]hept-5-en-2-yl)amino]-1H-1,2,4-triazole | 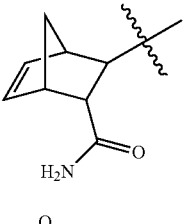 | —H | —N(CH$_3$)$_2$ | —H | —H | | D |
| 353 | 3-amino-1-(4-(iso-propoxy)phenyl)carbonyl-5-[(3-(aminocarbonyl)bicyclo[2.2.1]hept-5-en-2-yl)amino]-1H-1,2,4-triazole | 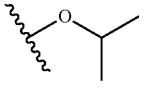 | —H | 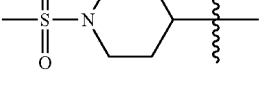 | —H | —H | —H | D |
| 391 | 3-amino-1-(2,6-difluorophenyl)carbonyl-5-(1-methylsulfonylpiperidin-4-yl)amino-1H-1,2,4-triazole | 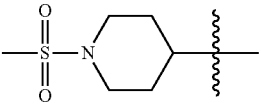 [SMILES: *C1CCN(S(C)(=O)=O)CC1] | —H | —H | —F | —H | —F | D |
| 396 | 3-amino-1-(4-(dimethylamino)phenyl)carbonyl-5-(1-methylsulfonylpiperidin-4-yl)amino-1H-1,2,4-triazole | 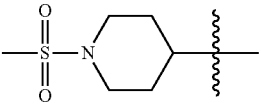 [SMILES: *C1CCN(S(C)(=O)=O)CC1] | —N(CH$_3$)$_2$ | —H | —H | —H | —H | D |

TABLE 6-continued

| Cpd # | Compound Name | R$^{1e}$ | R$^{3b}$ | R$^{3c}$ | R$^{3d}$ | R$^{3e}$ | R$^{3f}$ | IC$_{50}$ |
|---|---|---|---|---|---|---|---|---|
| 404 | 3-amino-5-[3-(4-(2-chloro-6-fluorophenyl)piperazin-1-yl)prop-1-yl]amino-1-(3-methylphenyl)carbonyl-1H-1,2,4-triazole | [3-(4-(2-chloro-6-fluorobenzyl)piperazin-1-yl)propyl] | —H | —CH$_3$ | —H | —H | —H | D |

IC$_{50}$ activity:
A = <1 µM
B = 1 to 10 µM
C = >10 to 20 µM
D = >20 µM

TABLE 7

| Cpd # | Compound Name | R$^{1b}$ | R$^{1c}$ | R$^{1d}$ | Y | Z | R$^{3g}$ | IC$_{50}$ |
|---|---|---|---|---|---|---|---|---|
| 172 | 5-amino-N-(4-chlorophenyl)-3-[4-(methoxy)phenylamino]-1H-1,2,4-triazole-1-carboxamide | —OCH$_3$ | —H | —H | O | —N(H)— | 4-chlorophenyl | D |
| 174 | 3-[4-(acetyl(methyl)amino)phenyl]amino-5-amino-N-(4-chlorophenyl)-1H-1,2,4-triazole-1-carboxamide | N(CH$_3$)C(O)CH$_3$ | —H | —H | O | —N(H)— | 4-chlorophenyl | D |
| 175 | 3-[4-(acetyl(methyl)amino)phenyl]amino-5-amino-N-(1,3-benzodioxol-5-yl)-1H-1,2,4-triazole-1-carboxamide | N(CH$_3$)C(O)CH$_3$ | —H | —H | O | —N(H)— | 1,3-benzodioxol-5-yl | B |

TABLE 7-continued

| Cpd # | Compound Name | R$^{1b}$ | R$^{1c}$ | R$^{1d}$ | Y | Z | R$^{3g}$ | IC$_{50}$ |
|---|---|---|---|---|---|---|---|---|
| 177 | 3-[4-(acetyl(methyl)amino)phenyl]amino-5-amino-N-cyclopentyl-1H-1,2,4-triazole-1-carboxamide | N-methyl acetamide | —H | —H | O | —N(H)— | cyclopentyl | D |
| 179 | 3-[4-(acetyl(methyl)amino)phenyl]amino-5-amino-N-(4-(iso-propyl)phenyl)-1H-1,2,4-triazole-1-carboxamide | N-methyl acetamide | —H | —H | O | —N(H)— | 4-isopropylphenyl | B |
| 180 | 3-[4-(acetyl(methyl)amino)phenyl]amino-5-amino-N-(4-(butoxy)phenyl)-1H-1,2,4-triazole-1-carboxamide | N-methyl acetamide | —H | —H | O | —N(H)— | 4-butoxyphenyl | B |
| 41 | 5-amino-N-(4-(iso-propyl)phenyl)-3-[4-[2-(piperidin-1-yl)ethoxy]phenylamino]-1H-1,2,4-triazole-1-carboxamide | 2-(piperidin-1-yl)ethoxy | —H | —H | O | —N(H)— | 4-isopropylphenyl | B |
| 46 | 5-amino-N-(4-butoxyphenyl)-3-[4-[2-(piperidin-1-yl)ethoxy]phenylamino]-1H-1,2,4-triazole-1-carboxamide | 2-(piperidin-1-yl)ethoxy | —H | —H | O | —N(H)— | 4-butoxyphenyl | B |
| 39 | 5-amino-N-(4-methylphenyl)-3-[4-[2-(piperidin-1-yl)ethoxy]phenylamino]-1H-1,2,4-triazole-1-carboxamide | 2-(piperidin-1-yl)ethoxy | —H | —H | O | —N(H)— | 4-methylphenyl | B |

TABLE 7-continued

| Cpd # | Compound Name | R$^{1b}$ | R$^{1c}$ | R$^{1d}$ | Y | Z | R$^{3g}$ | IC$_{50}$ |
|---|---|---|---|---|---|---|---|---|
| 40 | 5-amino-N-(4-(methoxy)phenyl)-3-[4-[2-(piperidin-1-yl)ethoxy]phenylamino]-1H-1,2,4-triazole-1-carboxamide | 4-[2-(piperidin-1-yl)ethoxy] | —H | —H | O | —N(H)— | 4-methoxyphenyl | B |
| 185 | 3-[4-(acetyl(methyl)amino)phenyl]amino-5-amino-N-cyclohexyl-1H-1,2,4-triazole-1-carboxamide | 4-(acetyl(methyl)amino) | —H | —H | O | —N(H)— | cyclohexyl | D |
| 35 | 5-amino-N-(1,3-benzodioxol-5-yl)-3-[4-[2-(piperidin-1-yl)ethoxy]phenylamino]-1H-1,2,4-triazole-1-carboxamide | 4-[2-(piperidin-1-yl)ethoxy] | —H | —H | O | —N(H)— | 1,3-benzodioxol-5-yl | B |
| 29 | 5-amino-N-(3-methylphenyl)-3-[4-[2-(piperidin-1-yl)ethoxy]phenylamino]-1H-1,2,4-triazole-1-carboxamide | 4-[2-(piperidin-1-yl)ethoxy] | —H | —H | O | —N(H)— | 3-methylphenyl | A |
| 30 | 5-amino-N-(3-methoxyphenyl)-3-[4-[2-(piperidin-1-yl)ethoxy]phenylamino]-1H-1,2,4-triazole-1-carboxamide | 4-[2-(piperidin-1-yl)ethoxy] | —H | —H | O | —N(H)— | 3-methoxyphenyl | A |

TABLE 7-continued

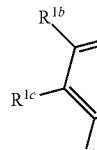

| Cpd # | Compound Name | $R^{1b}$ | $R^{1c}$ | $R^{1d}$ | Y | Z | $R^{3g}$ | $IC_{50}$ |
|---|---|---|---|---|---|---|---|---|
| 33 | 5-amino-N-(3,5-(dimethoxy)phenyl)-3-[4-[2-(piperidin-1-yl)ethoxy]phenylamino]-1H-1,2,4-triazole-1-carboxamide | 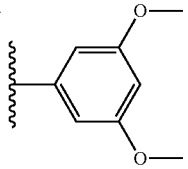 | —H | —H | O | —N(H)— | 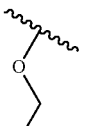 | A |
| 42 | 5-amino-N-cyclohexyl-3-[4-[2-(piperidin-1-yl)ethoxy]phenylamino]-1H-1,2,4-triazole-1-carboxamide | 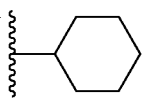 | —H | —H | O | —N(H)— | 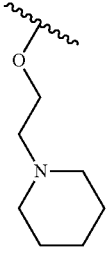 [SMILES: *OCCN1CCCCC1] | B |
| 45 | 5-amino-N-cyclopentyl-3-[4-[2-(piperidin-1-yl)ethoxy]phenylamino]-1H-1,2,4-triazole-1-carboxamide | 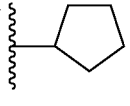 | —H | —H | O | —N(H)— | 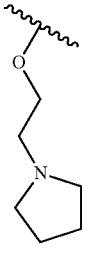 [SMILES: *OCCN1CCCC1] | B |
| 37 | 5-amino-N-(4-methylphenyl)-3-[4-[2-(pyrrolidin-1-yl)ethoxy]phenylamino]-1H-1,2,4-triazole-1-carboxamide | 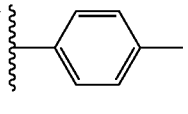 | —H | —H | O | —N(H)— | 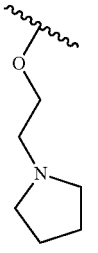 [SMILES: *OCCN1CCCC1] | B |
| 32 | 5-amino-N-(3-methoxyphenyl)-3-[4-[2-(pyrrolidin-1-yl)ethoxy]phenylamino]-1H-1,2,4-triazole-1-carboxamide | 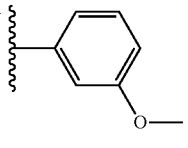 | —H | —H | O | —N(H)— | | A |

TABLE 7-continued

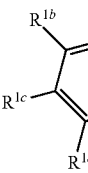

| Cpd # | Compound Name | R$^{1b}$ | R$^{1c}$ | R$^{1d}$ | Y | Z | R$^{3g}$ | IC$_{50}$ |
|---|---|---|---|---|---|---|---|---|
| 194 | 5-amino-N-(4-cyanophenyl)-3-[4-[2-(piperidin-1-yl)ethoxy]phenylamino]-1H-1,2,4-triazole-1-carboxamide | 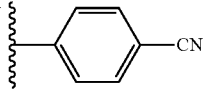 | —H | —H | O | —N(H)— |  | D |
| 36 | 5-amino-N-(1,3-benzodioxol-5-yl)-3-[4-[2-(pyrrolidin-1-yl)ethoxy]phenylamino]-1H-1,2,4-triazole-1-carboxamide | 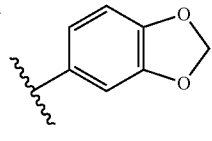 [SMILES: *c1ccc2c(c1)OCO2] | —H | —H | O | —N(H)— | 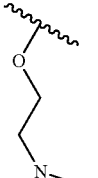 | B |
| 31 | 5-amino-N-(3-methylphenyl)-3-[4-[2-(pyrrolidin-1-yl)ethoxy]phenylamino]-1H-1,2,4-triazole-1-carboxamide | 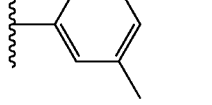 | —H | —H | O | —N(H)— |  | A |
| 34 | 5-amino-N-(3,5-(dimethoxy)phenyl)-3-[4-[2-(pyrrolidin-1-yl)ethoxy]phenylamino]-1H-1,2,4-triazole-1-carboxamide | 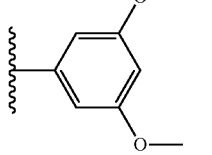 | —H | —H | O | —N(H)— |  | A |
| 43 | 5-amino-N-(3,4-(dimethoxy)phenyl)-3-[4-[2-(piperidin-1-yl)ethoxy]phenylamino]-1H-1,2,4-triazole-1-carboxamide | 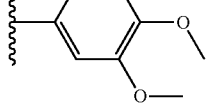 | —H | —H | O | —N(H)— | | B |

TABLE 7-continued

| Cpd # | Compound Name | $R^{1b}$ | $R^{1c}$ | $R^{1d}$ | Y | Z | $R^{3g}$ | $IC_{50}$ |
|---|---|---|---|---|---|---|---|---|
| 38 | 5-amino-N-(3,4-(dimethyl)phenyl)-3-[4-[2-(piperidin-1-yl)ethoxy]phenylamino]-1H-1,2,4-triazole-1-carboxamide | 2-(piperidin-1-yl)ethoxy | —H | —H | O | —N(H)— | 3,4-dimethylphenyl | B |
| 199 | 5-amino-N-(3,5-(dimethyl)phenyl)-3-[4-[2-(piperidin-1-yl)ethoxy]phenylamino]-1H-1,2,4-triazole-1-carboxamide | 2-(piperidin-1-yl)ethoxy | —H | —H | O | —N(H)— | 3,5-dimethylphenyl | D |
| 44 | 5-amino-N-(4-(dimethylamino)phenyl)-3-[4-[2-(piperidin-1-yl)ethoxy]phenylamino]-1H-1,2,4-triazole-1-carboxamide | 2-(piperidin-1-yl)ethoxy | —H | —H | O | —N(H)— | 4-(dimethylamino)phenyl | B |
| 201 | 5-amino-3-[4-(piperidin-1-yl)phenylamino]-1-(tert-butoxycarbonyl)-1H-1,2,4-triazole | piperidin-1-yl | —H | —H | O | O | tert-butyl | D |
| 325 | 5-amino-N-(2,4,6-trifluorophenyl)-3-[4-[2-(pyrrolidin-1-yl)ethoxy]phenylamino]-1H-1,2,4-triazole-1-carbothioamide | 2-(pyrrolidin-1-yl)ethoxy | —H | —H | S | —N(H)— | 2,4,6-trifluorophenyl | B |
| 326 | 5-amino-N-(2,6-difluorophenyl)-3-[4-[2-(pyrrolidin-1-yl)ethoxy]phenylamino]-1H-1,2,4-triazole-1-carbothioamide | 2-(pyrrolidin-1-yl)ethoxy | —H | —H | S | —N(H)— | 2,6-difluorophenyl | A |

TABLE 7-continued

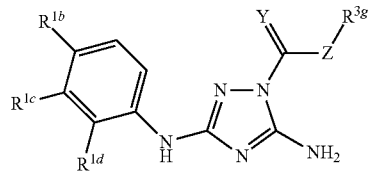

| Cpd # | Compound Name | $R^{1b}$ | $R^{1c}$ | $R^{1d}$ | Y | Z | $R^{3g}$ | $IC_{50}$ |
|---|---|---|---|---|---|---|---|---|

$IC_{50}$ activity:

A = <1 µM

B = 1 to 10 µM

C = >10 to 20 µM

D = >20 µM

TABLE 8

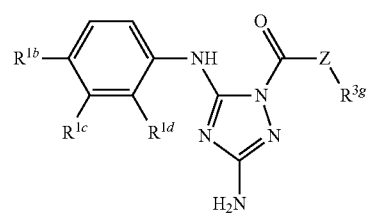

| Cpd # | Compound Name | $R^{1b}$ | $R^{1c}$ | $R^{1d}$ | Z | $R^{3g}$ | $IC_{50}$ |
|---|---|---|---|---|---|---|---|
| 93 | 3-amino-5-(1,4-benzodioxan-6-yl)amino-1-methoxycarbonyl-1H-1,2,4-triazole | (ethylenedioxy bridge to $R^{1c}$) | | —H | O | —CH$_3$ | D |
| 173 | 5-amino-3-(4-methoxyphenyl)amino-1-(tert-butoxycarbonyl)-1H-1,2,4-triazole | —OCH$_3$ | —H | —H | O | —C(CH$_3$)$_3$ | D |
| 176 | 5-[4-(acetyl(methyl)amino)phenyl]amino-3-amino-N-(1,3-benzodioxol-5-yl)-1H-1,2,4-triazole-1-carboxamide | N(CH$_3$)C(O)CH$_3$ | —H | —H | —N(H)— | 1,3-benzodioxol-5-yl | D |
| 178 | 5-[4-(acetyl(methyl)amino)phenyl]amino-3-amino-N-cyclopentyl-1H-1,2,4-triazole-1-carboxamide | N(CH$_3$)C(O)CH$_3$ | —H | —H | —N(H)— | cyclopentyl | D |
| 182 | 3-amino-N-(4-(butoxy)phenyl)-5-[4-[2-(piperidin-1-yl)ethoxy]phenylamino]-1H-1,2,4-triazole-1-carboxamide | —O-CH$_2$CH$_2$-piperidin-1-yl | —H | —H | —N(H)— | 4-butoxyphenyl | D |

TABLE 8-continued

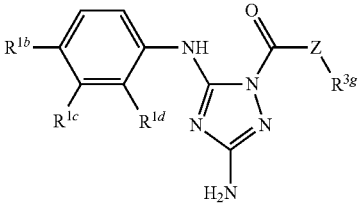

| Cpd # | Compound Name | R¹ᵇ | R¹ᶜ | R¹ᵈ | Z | R³ᵍ | IC₅₀ |
|---|---|---|---|---|---|---|---|
| 183 | 3-amino-N-(4-(methyl)phenyl)-5-[4-[2-(piperidin-1-yl)ethoxy]phenylamino]-1H-1,2,4-triazole-1-carboxamide | 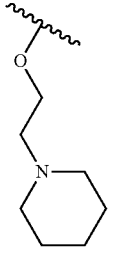 [SMILES: *OCCN1CCCCC1] | —H | —H | —N(H)— | 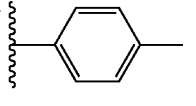 [SMILES: *c1ccc(C)cc1] | B |
| 184 | 3-amino-N-(4-(methoxy)phenyl)-5-[4-[2-(piperidin-1-yl)ethoxy]phenylamino]-1H-1,2,4-triazole-1-carboxamide | 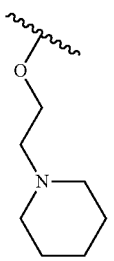 [SMILES: *OCCN1CCCCC1] | —H | —H | —N(H)— | 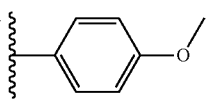 | B |
| 186 | 3-[4-(acetyl(methyl)amino)phenyl]amino-3-amino-N-cyclohexyl-1H-1,2,4-triazole-1-carboxamide | 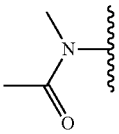 [SMILES: *N(C)C(C)=O] | —H | —H | —N(H)— | 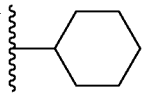 | D |
| 187 | 3-amino-N-(3-(methyl)phenyl)-5-[4-[2-(piperidin-1-yl)ethoxy]phenylamino]-1H-1,2,4-triazole-1-carboxamide | 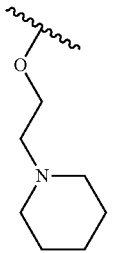 [SMILES: *OCCN1CCCCC1] | —H | —H | —N(H)— | 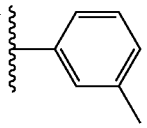 | B |
| 188 | 3-amino-N-(3,5-dimethoxyphenyl)-5-[4-[2-(piperidin-1-yl)ethoxy]phenylamino]-1H-1,2,4-triazole-1-carboxamide | 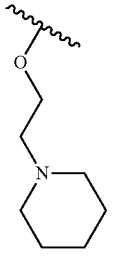 [SMILES: *OCCN1CCCCC1] | —H | —H | —N(H)— | 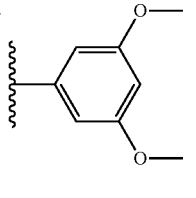 [SMILES: *c1cc(OC)cc(OC)c1] | B |

TABLE 8-continued
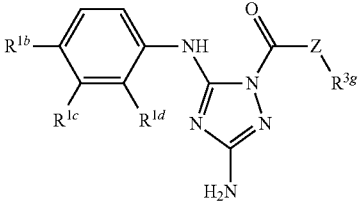
| Cpd # | Compound Name | R^{1b} | R^{1c} | R^{1d} | Z | R^{3g} | IC_{50} |
|---|---|---|---|---|---|---|---|
| 189 | 3-amino-N-cyclohexyl-5-[4-[2-(piperidin-1-yl)ethoxy]phenylamino]-1H-1,2,4-triazole-1-carboxamide |  | —H | —H | —N(H)— | 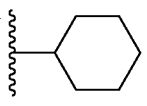 | B |
| 190 | 3-amino-N-cyclopentyl-5-[4-[2-(piperidin-1-yl)ethoxy]phenylamino]-1H-1,2,4-triazole-1-carboxamide | 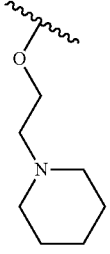 [SMILES: *OCCN1CCCCC1] | —H | —H | —N(H)— | 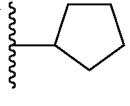 | D |
| 193 | 3-amino-N-(1,3-benzodioxol-5-yl)-5-[4-[2-(piperidin-1-yl)ethoxy]phenylamino]-1H-1,2,4-triazole-1-carboxamide | 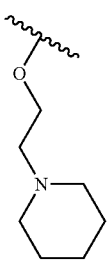 [SMILES: *OCCN1CCCCC1] | —H | —H | —N(H)— | 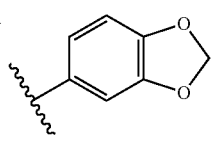 | B |
IC_{50} activity:
A = <1 μM
B = 1 to 10 μM
C = >10 to 20 μM
D = >20 μM

TABLE 9

| Cpd # | Compound Name | R$^{1e}$ | R$^{3g}$ | IC$_{50}$ |
|---|---|---|---|---|
| 276 | 5-amino-1-(1H-indol-6-yl)carbonyl-3-[4-((tert-butoxycarbonyl)aminochroman-6-yl]amino-1H-1,2,4-triazole | chroman-6-yl with 4-NHBoc substituent | 1H-indol-6-yl | B |
| 356 | 5-amino-1-(1H-indol-6-yl)carbonyl-3-[(5-(aminocarbonyl)bicyclo[2.2.1]hept-2-en-6-yl)amino]-1H-1,2,4-triazole | 5-(aminocarbonyl)bicyclo[2.2.1]hept-2-en-6-yl | 1H-indol-6-yl | D |
| 397 | 5-amino-1-(1,4-benzodioxan-6-yl)carbonyl-3-(1-methylsulfonylpiperidin-4-yl)amino-1H-1,2,4-triazole | 1-methylsulfonylpiperidin-4-yl | 1,4-benzodioxan-6-yl | D |
| 398 | 5-amino-1-(1H-indol-6-yl)carbonyl-3-(1-methylsulfonylpiperidin-4-yl)amino-1H-1,2,4-triazole | 1-methylsulfonylpiperidin-4-yl | 1H-indol-6-yl | D |

IC$_{50}$ activity:
A = <1 μM
B = 1 to 10 μM
C = >10 to 20 μM
D = >20 μM

TABLE 10

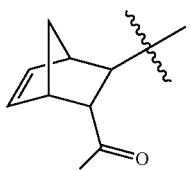

| Cpd # | Compound Name | $R^{1e}$ | $R^{3g}$ | $IC_{50}$ |
|---|---|---|---|---|
| 355 | 3-amino-1-(1H-indol-6-yl)carbonyl-5-[(3-(aminocarbonyl)bicyclo[2.2.1]hept-5-en-2-yl)amino]-1H-1,2,4-triazole | 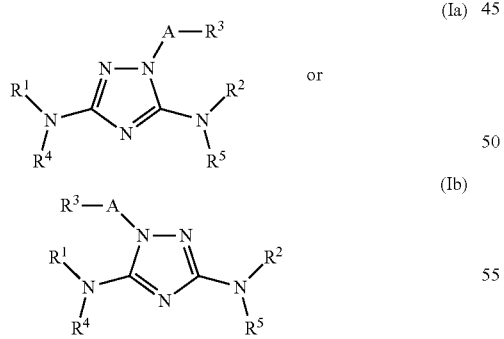 | | D |

$IC_{50}$ activity:
A = <1 μM
B = 1 to 10 μM
C = >10 to 20 μM
D = >20 μM

All of the U.S. patents, U.S. patent application publications, U.S. patent applications, foreign patents, foreign patent applications and non-patent publications referred to in this specification and/or listed in the Application Data Sheet are incorporated herein by reference, in their entireties.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of treating a disease or condition associated with Axl catalytic activity in a mammal, wherein the method comprises administering to the mammal a therapeutically effective amount of a compound of formula (Ia) or formula (Ib):

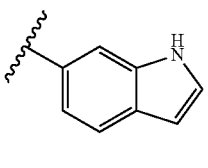

wherein, independently at each occurrence:
A is —C(O)— or —C(S)—;
$R^1$ is aryl substituted with at least one of —$R^8$—$OR^{10}$ or —$R^8$—O—$R^9$—CN, where each $R^8$ is a direct bond and $R^{10}$ is selected from the group consisting of optionally substituted heterocyclylalkyl, optionally substituted heteroarylalkyl and optionally substituted aralkyl, and optionally substituted with one or more substituents selected from the group consisting of halo, haloalkyl, alkyl, optionally substituted heteroaryl, optionally substituted heterocyclyl, and alkoxy;
$R^2$, $R^4$ and $R^5$ are each independently hydrogen, alkyl, aryl, aralkyl, —C(O)$R^{10}$ or —C(O)N($R^6$)$R^7$;
$R^3$ is one of the following:
a) aryl optionally substituted with one or more substituents selected from the group consisting of alkyl, halo; haloalkyl, nitro, cycloalkyl, cycloalkylalkyl, optionally substituted aryl, optionally substituted heteroaryl, optionally substituted heterocyclyl, —$R^8$—$OR^{10}$, —$R^8$—C(O)$OR^{10}$, —$R^8$—OC(O)$R^{10}$, —$R^8$—O—$R^9$—C(O)$OR^{10}$, —$R^8$—O—$R^9$—C(O)N($R^6$)$R^7$, —S(O)$_p R^6$ (where p is 0, 1 or 2), —S(O)$_t$N($R^6$)$R^7$ (where t is 1 or 2), —$R^8$—N($R^6$)$R^7$, —$R^8$—N($R^6$)C(O)$R^{10}$, —$R^8$—N($R^6$)C(O)$OR^{10}$ and —$R^8$—CN; or
b) optionally substituted heteroaryl;
$R^6$ and $R^7$ are each independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^9$—CN, —$R^9$—NO$_2$, —$R^9$—N($R^{10}$)$_2$, —$R^9$—C(O)$OR^{10}$ and —$R^9$—C(O)N($R^{10}$)$_2$;
optionally, $R^6$ and $R^7$, together with the nitrogen to which they are attached, form an optionally substituted N-heteroaryl or an optionally substituted N-heterocyclyl;
each $R^8$ present in a $R^3$ substituent is independently selected from the group consisting of a direct bond, an optionally substituted straight or branched alkylene chain, an optionally substituted straight or branched alkenylene chain and an optionally substituted straight or branched alkynylene chain;
each $R^9$ is independently selected from the group consisting of an optionally substituted straight or branched alkylene chain, an optionally substituted straight or branched alkenylene chain and an optionally substituted straight or branched alkynylene chain; and $R^{10}$ present in the $R^2$, $R^4$ and $R^5$ substituents and each $R^{10}$ present in a $R^3$ substituent, a $R^6$ substituent or a $R^7$ substituent is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

as an isolated stereoisomer or tautomer thereof or mixtures thereof, or a pharmaceutically acceptable salt or N-oxide thereof.

2. The method of claim 1 wherein the disease or condition associated with Axl catalytic activity is selected from the group consisting of endometriosis, rheumatoid arthritis, psoriasis, visual impairment due to macular degeneration, diabetic retinopathy, retinopathy of prematurity, osteoarthritis, cataracts, vascular diseases selected from the group consisting of restenosis, atherosclerosis, and thrombosis, vascular injury, kidney diseases selected from the group consisting of glomerulonephritis, diabetic nephropathy and renal transplant rejection, solid tumors selected from the group consisting of breast carcinoma, renal carcinoma, endometrial carcinoma, ovarian carcinoma, thyroid carcinoma, non-small cell lung carcinoma, prostate carcinoma, gastric cancer and uveal melanoma, and liquid tumors selected from the group consisting of myeloid leukemia and lymphoma.

3. The method of claim 2 wherein the disease or condition is selected from the group consisting of rheumatoid arthritis, vascular disease selected from the group consisting of restenosis, atherosclerosis and thrombosis, and vascular injury, psoriasis, visual impairment due to macular degeneration, diabetic retinopathy, retinopathy of prematurity, kidney disease selected from the group consisting of glomerulonephritis, diabetic nephropathy and renal transplant rejection, osteoarthritis, and cataracts.

4. The method of claim 2, wherein the disease or condition is solid tumors selected from the group consisting of breast carcinoma, renal carcinoma, endometrial carcinoma, ovarian carcinoma, thyroid carcinoma, non-small cell lung carcinoma, prostate carcinoma, gastric cancer and uveal melanoma.

5. The method of claim 2, wherein the disease or condition is liquid tumors selected from the group consisting of leukemia and lymphoma.

6. The method of claim 2 wherein the disease or condition is endometriosis.

\* \* \* \* \*

UNITED STATES PATENT AND TRADEMARK OFFICE
CERTIFICATE OF CORRECTION

PATENT NO.        : 8,389,557 B2
APPLICATION NO.   : 12/965545
DATED             : March 5, 2013
INVENTOR(S)       : Singh et al.

Page 1 of 1

It is certified that error appears in the above-identified patent and that said Letters Patent is hereby corrected as shown below:

In the Claims

Column 370, Lines 55-56, Claim 1:
"heteroarylalkynyl, -$R^9$-CN, -$R^9$-NO$_2$, -$R^9$-N($R^{10}$)$_2$, -$R^9$-C(O)O$R^{10}$ and –$R^9$-C(O)N($R^{10}$)$_2$;" should read, --heteroarylalkynyl, -$R^9$-O$R^{10}$, -$R^9$-CN, -$R^9$-NO$_2$, -$R^9$-N($R^{10}$)$_2$, -$R^9$-C(O)O$R^{10}$ and –$R^9$-C(O)N($R^{10}$)$_2$;--.

Signed and Sealed this
Twenty-eighth Day of January, 2014

Michelle K. Lee
*Deputy Director of the United States Patent and Trademark Office*